US012458604B2

(12) United States Patent
Buschmann et al.

(10) Patent No.: US 12,458,604 B2
(45) Date of Patent: Nov. 4, 2025

(54) METHODS OF LIPID NANOPARTICLE MANUFACTURE AND COMPOSITIONS DERIVED THEREFROM

(71) Applicants: George Mason Research Foundation, Inc., Fairfax, VA (US); The Trustees of the University of Pennsylvania, Philadelphia, PA (US)

(72) Inventors: Michael Daro Buschmann, Fairfax, VA (US); Mikell Paige, Fairfax, VA (US); Suman Alishetty, Fairfax, VA (US); Manuel Carrasco, Fairfax, VA (US); Mohamad Gabriel Alameh, Fairfax, VA (US); Drew Weissman, Fairfax, VA (US)

(73) Assignees: The Trustees of the University of Pennsylvania, Philadelphia, PA (US); George Mason Research Foundation, Inc., Fairfax, VA (US)

( * ) Notice: Subject to any disclaimer, the term of this patent is extended or adjusted under 35 U.S.C. 154(b) by 761 days.

(21) Appl. No.: 17/500,491

(22) Filed: Oct. 13, 2021

(65) Prior Publication Data

US 2022/0235377 A1 Jul. 28, 2022

Related U.S. Application Data

(60) Provisional application No. 63/179,885, filed on Apr. 26, 2021, provisional application No. 63/179,872, filed on Apr. 26, 2021, provisional application No. 63/091,616, filed on Oct. 14, 2020, provisional application No. 63/091,603, filed on Oct. 14, 2020.

(51) Int. Cl.

| | |
|---|---|
| ***A61K 9/51*** | (2006.01) |
| ***A61K 9/127*** | (2006.01) |
| ***A61K 31/7088*** | (2006.01) |
| ***A61K 31/7105*** | (2006.01) |
| ***A61K 47/18*** | (2017.01) |
| ***A61K 47/28*** | (2006.01) |
| ***A61P 37/04*** | (2006.01) |
| ***B82Y 5/00*** | (2011.01) |
| ***C07C 229/16*** | (2006.01) |
| ***C07D 207/09*** | (2006.01) |
| ***C07D 211/26*** | (2006.01) |
| ***C07D 295/13*** | (2006.01) |
| ***C12N 15/88*** | (2006.01) |
| *A61K 48/00* | (2006.01) |

(52) U.S. Cl.

CPC ............ *A61K 9/5123* (2013.01); *A61K 9/127* (2013.01); *A61K 31/7088* (2013.01); *A61K 31/7105* (2013.01); *A61K 47/18* (2013.01); *A61K 47/28* (2013.01); *A61P 37/04* (2018.01); *B82Y 5/00* (2013.01); *C07C 229/16* (2013.01); *C07D 207/09* (2013.01); *C07D 211/26* (2013.01); *C07D 295/13* (2013.01); *C12N 15/88* (2013.01); *A61K 48/00* (2013.01)

(58) Field of Classification Search

None

See application file for complete search history.

(56) References Cited

U.S. PATENT DOCUMENTS

| | | | |
|---|---|---|---|
| 4,987,071 A | 1/1991 | Cech et al. | |
| 5,589,332 A | 12/1996 | Shih et al. | |
| 5,741,679 A | 4/1998 | George et al. | |
| 5,834,186 A | 11/1998 | George et al. | |
| 5,837,282 A | 11/1998 | Fenske et al. | |
| 5,849,902 A | 12/1998 | Arrow et al. | |
| 5,871,914 A | 2/1999 | Nathan | |
| 5,989,912 A | 11/1999 | Arrow et al. | |
| 6,197,553 B1 | 3/2001 | Lee et al. | |
| 7,074,596 B2 | 7/2006 | Darzynkiewicz et al. | |
| 7,745,651 B2 | 6/2010 | Heyes et al. | |
| 7,811,602 B2 | 10/2010 | Cullis et al. | |

(Continued)

FOREIGN PATENT DOCUMENTS

| | | |
|---|---|---|
| AU | 2010326132 A1 | 7/2012 |
| AU | 2012267531 A1 | 12/2013 |

(Continued)

OTHER PUBLICATIONS

Abdelaal et al., "Ligand-mediated delivery of RNAi-based therapeutics for the treatment of oncological diseases", NAR Cancer, Jul. 2021, pp. 1-23, vol. 3, No. 3.

(Continued)

*Primary Examiner* — Celeste A Roney

(74) *Attorney, Agent, or Firm* — Choate, Hall & Stewart LLP; Brenda Herschbach Jarrell; Michael A. Shinall

(57) ABSTRACT

Disclosed herein are methods of increasing the potency of nucleic acid loaded lipid nanoparticles (naLNPs) through certain novel and surprisingly superior LNP manufacturing techniques. Also disclosed are pharmaceutical compositions containing naLNPs manufactured according to the manufacturing methods described herein. The methods disclosed herein overcome major technical difficulties and high costs associated with previous LNP manufacturing techniques. The methods disclosed herein, therefore, greatly improve the industrial production of LNPs in unexpected ways thereby providing more potent naLNPs for nucleic acid delivery. Specifically, the invention disclosed herein are methods that show increased potency naLNPs due to increased mixing concentration of the lipids and mRNA during assembly.

45 Claims, 137 Drawing Sheets

Specification includes a Sequence Listing.

(56) References Cited

U.S. PATENT DOCUMENTS 8,058,069 B2 11/2011 Yaworski et al.
8,278,036 B2 10/2012 Kariko et al.
8,329,070 B2 12/2012 MaClachlan et al.
8,569,256 B2 10/2013 Heyes et al.
8,702,942 B2 4/2014 Corbett et al.
8,754,062 B2 6/2014 De Fougerolles et al.
8,853,377 B2 10/2014 Guild et al.
8,936,942 B2 1/2015 Heyes et al.
9,018,187 B2 4/2015 Heyes et al.
9,061,021 B2 6/2015 Guild et al.
9,139,554 B2 9/2015 Hope et al.
9,181,321 B2 11/2015 Heartlein et al.
9,227,917 B2 1/2016 Anderson et al.
9,308,281 B2 4/2016 Guild et al.
9,352,042 B2 5/2016 Heyes et al.
9,364,435 B2 6/2016 Yaworski et al.
9,428,751 B2 8/2016 MacDonald et al.
9,439,968 B2 9/2016 Anderson et al.
9,522,176 B2 12/2016 DeRosa et al.
9,567,296 B2 2/2017 Payne et al.
9,580,708 B2 2/2017 Uhlmann et al.
9,597,413 B2 3/2017 Guild et al.
9,629,804 B2 4/2017 Heartlein et al.
9,668,980 B2 6/2017 DeRosa et al.
9,713,626 B2 7/2017 Heartlein et al.
9,717,690 B2 8/2017 Guild et al.
9,732,340 B2 8/2017 Uhlmann et al.
9,732,341 B2 8/2017 Uhlmann et al.
9,738,593 B2 8/2017 Ansell et al.
9,790,494 B2 10/2017 Uhlmann et al.
9,850,269 B2 12/2017 DeRosa et al.
9,868,692 B2 1/2018 Benenato
9,872,900 B2 1/2018 Ciaramella et al.
9,925,277 B2 3/2018 Almarsson et al.
9,926,560 B2 3/2018 MacLachlan et al.
9,943,595 B2 4/2018 DeRosa et al.
9,950,068 B2 4/2018 De Fougerolles et al.
9,956,271 B2 5/2018 Guild et al.
9,957,499 B2 5/2018 Heartlein et al.
9,970,047 B2 5/2018 Heartlein et al.
10,022,455 B2 7/2018 DeRosa et al.
10,041,074 B2 8/2018 Ozsolak
10,041,091 B2 8/2018 Cullis et al.
10,052,284 B2 8/2018 Heartlein et al.
10,058,623 B2 8/2018 Krieg et al.
10,059,941 B2 8/2018 Krieg et al.
10,064,959 B2 9/2018 Schrum et al.
10,072,057 B2 9/2018 Hoge et al.
10,093,924 B2 10/2018 Uhlmann et al.
10,106,490 B2 10/2018 Du
10,137,087 B2 11/2018 DeRosa et al.
10,138,213 B2 11/2018 DeRosa et al.
10,143,758 B2 12/2018 Guild et al.
10,144,942 B2 12/2018 Strack-Logue et al.
10,155,785 B2 12/2018 DeRosa et al.
10,172,924 B2 1/2019 DeRosa et al.
10,174,315 B2 1/2019 Krieg et al.
10,174,323 B2 1/2019 Krieg et al.
10,174,328 B2 1/2019 Krieg et al.
10,208,295 B2 2/2019 DeRosa et al.
10,221,127 B2 3/2019 Du et al.
10,232,055 B2 3/2019 Kariko et al.
10,238,754 B2 3/2019 Guild et al.
10,245,229 B2 4/2019 Heartlein et al.
10,258,698 B2 4/2019 Hoge et al.
10,266,485 B2 4/2019 Benenato
10,266,559 B2 4/2019 DeRosa et al.
10,266,843 B2 4/2019 DeRosa et al.
10,286,082 B2 5/2019 DeRosa et al.
10,286,083 B2 5/2019 DeRosa et al.
10,293,057 B2 5/2019 DeRosa et al.
10,350,303 B1 7/2019 Guild et al.
10,413,618 B2 9/2019 Guild et al.
10,420,791 B2 9/2019 Heartlein et al.
10,428,349 B2 10/2019 DeRosa et al.
10,442,756 B2 10/2019 Benenato et al.
10,471,153 B2 11/2019 DeRosa et al.
10,485,885 B2 11/2019 Besin et al.
10,493,031 B2 12/2019 Heartlein et al.
10,493,166 B2 12/2019 DeRosa et al.
10,507,183 B2 12/2019 Guild et al.
10,507,249 B2 12/2019 Guild et al.
10,556,855 B1 2/2020 Angel et al.
10,561,732 B2 2/2020 Heyes et al.
10,576,166 B2 3/2020 DeRosa et al.
10,577,403 B2 3/2020 De Fougerolles et al.
10,584,165 B2 3/2020 Heartlein et al.
10,626,393 B2 4/2020 Lee et al.
10,646,504 B2 5/2020 DeRosa et al.
10,653,767 B2 5/2020 Ciaramella et al.
10,702,600 B1 7/2020 Ciaramella et al.
10,703,789 B2 7/2020 De Fougerolles et al.
2002/0182643 A1 12/2002 Marks et al.
2003/0077829 A1 4/2003 MaClachlan
2003/0236266 A1 12/2003 Friebe et al.
2005/0118253 A1 6/2005 MaClachlan et al.
2006/0051405 A1 3/2006 MaClachlan et al.
2007/0042031 A1 2/2007 MaClachlan et al.
2007/0049581 A1 3/2007 Mueller et al.
2010/0021713 A1 1/2010 Lane et al.
2010/0055169 A1 3/2010 Dande et al.
2010/0166714 A1 7/2010 Chien et al.
2011/0003327 A1 1/2011 Chien et al.
2011/0033430 A1 2/2011 Chien et al.
2011/0244026 A1 10/2011 Guild et al.
2012/0009222 A1 1/2012 Nguyen
2012/0142756 A1 6/2012 Guild et al.
2012/0251618 A1 10/2012 Schrum et al.
2012/0276209 A1 11/2012 Cullis et al.
2013/0017223 A1 1/2013 Hope et al.
2013/0079383 A1 3/2013 Bennett et al.
2013/0090372 A1 4/2013 Budzik et al.
2013/0195967 A1 8/2013 Guild et al.
2014/0045913 A1 2/2014 Kuboyama et al.
2014/0206753 A1 7/2014 Guild et al.
2014/0288160 A1 9/2014 Guild et al.
2014/0294938 A1 10/2014 Guild et al.
2014/0294939 A1 10/2014 Guild et al.
2014/0294940 A1 10/2014 Guild et al.
2014/0371302 A1 12/2014 Afeyan et al.
2015/0004217 A1 1/2015 Guild et al.
2015/0030576 A1 1/2015 Bancel
2015/0038556 A1 2/2015 Heartlein et al.
2015/0099791 A1 4/2015 Krieg et al.
2015/0110857 A1 4/2015 DeRosa et al.
2015/0110858 A1 4/2015 DeRosa et al.
2015/0110859 A1 4/2015 Heartlein et al.
2015/0133362 A1 5/2015 Krieg et al.
2015/0133528 A1 5/2015 Krieg et al.
2015/0140070 A1 5/2015 Heartlein et al.
2015/0157565 A1 6/2015 Heartlein et al.
2015/0159160 A1 6/2015 Krieg et al.
2015/0218560 A1 8/2015 Krieg et al.
2015/0232858 A1 8/2015 Ozsolak
2015/0239926 A1 8/2015 Payne et al.
2015/0247141 A1 9/2015 Uhlmann et al.
2015/0252364 A1 9/2015 Krieg et al.
2015/0267192 A1 9/2015 Heartlein et al.
2015/0299695 A1 10/2015 Uhlmann et al.
2015/0315585 A1 11/2015 Uhlmann et al.
2015/0315586 A1 11/2015 Uhlmann et al.
2015/0315587 A1 11/2015 Uhlmann et al.
2015/0315588 A1 11/2015 Uhlmann et al.
2015/0366997 A1 12/2015 Guild et al.
2015/0376144 A1 12/2015 DeRosa et al.
2015/0376220 A1 12/2015 DeRosa et al.
2016/0002705 A1 1/2016 Heartlein et al.
2016/0031928 A1 2/2016 DeRosa et al.
2016/0032356 A1 2/2016 Heartlein et al.
2016/0038612 A1 2/2016 Hoge et al.
2016/0040154 A1 2/2016 Heartlein et al.
2016/0101160 A1 4/2016 Guild et al.
2016/0106772 A1 4/2016 Heartlein et al.
2016/0122727 A1 5/2016 Heartlein et al.

(56) References Cited

U.S. PATENT DOCUMENTS

2016/0158354 A1 6/2016 DeRosa et al.
2016/0184458 A1 6/2016 Heartlein
2016/0222391 A1 8/2016 Krieg et al.
2016/0243259 A1 8/2016 Almarsson et al.
2016/0287725 A1 10/2016 DeRosa et al.
2016/0324940 A1 11/2016 DeRosa et al.
2016/0376224 A1 12/2016 Du et al.
2017/0073648 A1 3/2017 DeRosa et al.
2017/0143848 A1 5/2017 Calias et al.
2017/0159093 A1 6/2017 Strack-Logue et al.
2017/0210697 A1 7/2017 Benenato et al.
2017/0211065 A1 7/2017 Uhlmann et al.
2017/0239371 A1 8/2017 Guild et al.
2017/0246319 A1 8/2017 DeRosa et al.
2017/0281542 A1 10/2017 Heartlein et al.
2017/0314041 A1 11/2017 DeRosa et al.
2018/0008543 A1 1/2018 Guild et al.
2018/0008680 A1 1/2018 DeRosa et al.
2018/0015116 A1 1/2018 Heartlein et al.
2018/0028445 A1 2/2018 DeRosa et al.
2018/0028557 A1 2/2018 Ozsolak
2018/0030444 A1 2/2018 Uhlmann et al.
2018/0030452 A1 2/2018 Ozsolak
2018/0085474 A1 3/2018 Almarsson et al.
2018/0092971 A1 4/2018 Manoharan et al.
2018/0112234 A9 4/2018 Dombrowski et al.
2018/0125937 A1 5/2018 De Fougerolles et al.
2018/0125989 A1 5/2018 DeRosa et al.
2018/0127449 A1 5/2018 DeRosa et al.
2018/0148719 A1 5/2018 Lee et al.
2018/0153822 A1 6/2018 Karve et al.
2018/0169020 A1 6/2018 Guild et al.
2018/0185516 A1 7/2018 Ansell et al.
2018/0214579 A1 8/2018 Almarsson et al.
2018/0236047 A1 8/2018 Guild et al.
2018/0237766 A1 8/2018 Heartlein et al.
2018/0251754 A1 9/2018 DeRosa et al.
2018/0251755 A1 9/2018 Abysalh et al.
2018/0256741 A1 9/2018 Dias et al.
2018/0256750 A1 9/2018 Butora et al.
2018/0271938 A1 9/2018 Bancel et al.
2018/0272002 A1 9/2018 DeRosa et al.
2018/0272003 A1 9/2018 DeRosa et al.
2018/0272004 A1 9/2018 DeRosa et al.
2018/0272005 A1 9/2018 DeRosa et al.
2018/0291425 A1 10/2018 Heartlein et al.
2018/0298384 A1 10/2018 Krieg et al.
2018/0311176 A1 11/2018 Ozsolak et al.
2018/0311336 A1 11/2018 Ciaramella et al.
2018/0312839 A1 11/2018 Bhat et al.
2018/0333457 A1 11/2018 Heartlein et al.
2018/0353616 A1 12/2018 Guild et al.
2018/0360961 A1 12/2018 DeRosa et al.
2018/0369144 A1 12/2018 Heartlein et al.
2018/0369413 A1 12/2018 Heartlein et al.
2018/0369419 A1 12/2018 Benenato et al.
2019/0000932 A1 1/2019 Martini et al.
2019/0000933 A1 1/2019 Martini et al.
2019/0002890 A1 1/2019 Martini et al.
2019/0015501 A1 1/2019 Ciaramella et al.
2019/0022247 A1 1/2019 Ansell et al.
2019/0032087 A1 1/2019 Cullis et al.
2019/0054112 A1 2/2019 Gregoire
2019/0055553 A1 2/2019 Barsoum et al.
2019/0062743 A1 2/2019 Uhlmann et al.
2019/0100753 A1 4/2019 Heartlein et al.
2019/0111153 A1 4/2019 Stephan et al.
2019/0127708 A1 5/2019 Heartlein et al.
2019/0134164 A1 5/2019 DeRosa et al.
2019/0142971 A1 5/2019 Hoge et al.
2019/0144480 A1 5/2019 DeRosa et al.
2019/0151461 A1 5/2019 Brown et al.
2019/0175517 A1 6/2019 Martini et al.
2019/0175761 A1 6/2019 Guild et al.
2019/0185435 A1 6/2019 DeRosa et al.
2019/0192688 A1 6/2019 Askew et al.
2019/0192689 A1 6/2019 Guild et al.
2019/0192690 A1 6/2019 Guild et al.
2019/0211314 A1 7/2019 DeRosa et al.
2019/0216730 A1 7/2019 Heartlein et al.
2019/0216843 A1 7/2019 DeRosa et al.
2019/0224326 A1 7/2019 Bhat et al.
2019/0240339 A1 8/2019 Yaworski et al.
2019/0249191 A1 8/2019 DeRosa et al.
2019/0263850 A1 8/2019 DeRosa et al.
2019/0274968 A1 9/2019 Weissman et al.
2019/0298657 A1 10/2019 Martini et al.
2019/0298755 A1 10/2019 Karve et al.
2019/0314284 A1 10/2019 Guild et al.
2019/0314291 A1 10/2019 Besin et al.
2019/0314527 A1 10/2019 De Fougerolles et al.
2019/0316121 A1 10/2019 Smith et al.
2019/0321489 A1 10/2019 Guild et al.
2019/0359556 A1 11/2019 Du et al.
2019/0388562 A1 12/2019 Payne et al.
2019/0388563 A1 12/2019 Heartlein
2020/0016274 A1 1/2020 Karve et al.
2020/0022921 A1 1/2020 Karve et al.
2020/0032274 A1 1/2020 Mauger et al.
2020/0038515 A1 2/2020 DeRosa et al.
2020/0040333 A9 2/2020 Krieg et al.
2020/0046752 A1 2/2020 Heartlein et al.
2020/0046830 A1 2/2020 Hooper et al.
2020/0069599 A1 3/2020 Smith et al.
2020/0078299 A1 3/2020 Heartlein et al.
2020/0078313 A1 3/2020 Roy et al.
2020/0085973 A1 3/2020 Guild et al.
2020/0093936 A1 3/2020 Muzykantov et al.
2020/0109113 A1 4/2020 Payne et al.
2020/0113832 A1 4/2020 Yaworski et al.
2020/0121809 A1 4/2020 Hope et al.
2020/0129445 A1 4/2020 Patel et al.
2020/0155691 A1 5/2020 DeRosa et al.
2020/0157157 A1 5/2020 Karve et al.
2020/0157205 A1 5/2020 Heartlein et al.
2020/0163878 A1 5/2020 Baumhof et al.
2020/0172472 A1 6/2020 Du
2020/0206362 A1 7/2020 Besin et al.
2020/0237671 A1 7/2020 Guild et al.
2020/0247861 A1 8/2020 De Fougerolles et al.
2020/0254086 A1 8/2020 Hoge et al.
2020/0283372 A1 9/2020 Du
2020/0306191 A1 10/2020 Schariter et al.
2020/0385721 A1 12/2020 Lee et al.
2021/0161818 A1 6/2021 Haas et al.
2021/0169804 A1 6/2021 Patwardhan et al.
2021/0222173 A1 7/2021 Dymek et al.
2021/0230112 A1 7/2021 Hamilton et al.
2021/0236647 A1 8/2021 Wu et al.
2021/0244675 A1 8/2021 Landfester et al.
2021/0252163 A1 8/2021 Payne et al.
2021/0254097 A1 8/2021 O'Dea et al.
2021/0290756 A1 9/2021 Sullivan et al.
2021/0292303 A1 9/2021 Brown
2021/0299172 A1 9/2021 Getts et al.
2021/0299261 A1 9/2021 Rajeev et al.
2021/0317468 A1 10/2021 Limphong et al.
2022/0218612 A1* 7/2022 Karve .................... A61K 9/127
2022/0218622 A1 7/2022 Buschmann et al.
2022/0235377 A1 7/2022 Buschmann et al.

FOREIGN PATENT DOCUMENTS

AU 2010326132 B2 8/2014
AU 2010326132 B9 10/2014
AU 2014250713 A1 11/2014
AU 2013262649 A1 1/2015
AU 2013262656 A1 1/2015
AU 2013262663 A1 1/2015
AU 2013262699 A1 1/2015
AU 2013262700 A1 1/2015
AU 2013271392 A1 1/2015
AU 2014239250 A1 8/2015
AU 2014239264 A1 8/2015

(56) References Cited

FOREIGN PATENT DOCUMENTS

| | | | |
|---|---|---|---|
| AU | 2014340149 | A1 | 5/2016 |
| AU | 2014340155 | A1 | 5/2016 |
| AU | 2014250713 | B2 | 7/2016 |
| AU | 2016250459 | A1 | 11/2016 |
| AU | 2015279968 | A1 | 1/2017 |
| AU | 2012267578 | B2 | 4/2017 |
| AU | 2012267531 | B2 | 6/2017 |
| AU | 2015357562 | A1 | 6/2017 |
| AU | 2017204509 | A1 | 7/2017 |
| AU | 2012308320 | B2 | 2/2018 |
| AU | 2013271392 | B2 | 2/2018 |
| AU | 2016338559 | A1 | 5/2018 |
| AU | 2014239562 | B2 | 7/2018 |
| AU | 2013315225 | B2 | 11/2018 |
| AU | 2014340155 | B2 | 11/2018 |
| AU | 2017266932 | A1 | 11/2018 |
| AU | 2017266948 | A1 | 12/2018 |
| AU | 2017268396 | A1 | 12/2018 |
| AU | 2017283479 | A1 | 12/2018 |
| AU | 2014236305 | B2 | 1/2019 |
| AU | 2019200474 | A1 | 2/2019 |
| AU | 2017204509 | B2 | 4/2019 |
| AU | 2019201924 | A1 | 4/2019 |
| AU | 2017356190 | A1 | 5/2019 |
| AU | 2017357748 | A1 | 6/2019 |
| AU | 2017204509 | C1 | 7/2019 |
| AU | 2014340083 | B2 | 8/2019 |
| AU | 2017266932 | A9 | 8/2019 |
| AU | 2014340092 | B2 | 9/2019 |
| AU | 2018203985 | B2 | 9/2019 |
| AU | 2018224318 | A1 | 9/2019 |
| AU | 2018224326 | A1 | 9/2019 |
| AU | 2019240643 | A1 | 10/2019 |
| AU | 2015266764 | B2 | 11/2019 |
| AU | 2015279968 | B2 | 11/2019 |
| AU | 2018268859 | A1 | 12/2019 |
| AU | 2020200489 | A1 | 2/2020 |
| AU | 2020200576 | A1 | 2/2020 |
| AU | 2020202322 | A1 | 4/2020 |
| AU | 2018203310 | B2 | 5/2020 |
| AU | 2018202634 | B2 | 10/2020 |
| AU | 2017248189 | B2 | 4/2021 |
| AU | 2019200789 | B2 | 4/2021 |
| AU | 2021201646 | A1 | 4/2021 |
| AU | 2019202582 | B2 | 5/2021 |
| AU | 2015249312 | B2 | 7/2021 |
| AU | 2016233135 | B2 | 7/2021 |
| AU | 2016219052 | B2 | 6/2022 |
| BR | 112014028634 | A2 | 6/2017 |
| BR | 112016009014 | A2 | 9/2017 |
| BR | 112014028631 | A2 | 10/2017 |
| BR | 112015022505 | A2 | 10/2017 |
| BR | 112015022507 | A2 | 10/2017 |
| BR | 112015022660 | A2 | 10/2017 |
| BR | 112015022868 | A2 | 11/2017 |
| BR | 112016024632 | A2 | 1/2018 |
| BR | 112016027705 | A2 | 1/2018 |
| BR | 112016030292 | A2 | 1/2018 |
| BR | 112014030677 | A2 | 7/2022 |
| CA | 2782676 | A1 | 6/2011 |
| CA | 2838063 | A1 | 12/2012 |
| CA | 2838069 | A1 | 12/2012 |
| CA | 2873766 | A1 | 11/2013 |
| CA | 2873769 | A1 | 11/2013 |
| CA | 2873794 | A1 | 11/2013 |
| CA | 2873797 | A1 | 11/2013 |
| CA | 2873809 | A1 | 11/2013 |
| CA | 2876155 | A1 | 12/2013 |
| CA | 2884608 | A1 | 3/2014 |
| CA | 2853689 | * | 4/2014 |
| CA | 2902892 | A1 | 9/2014 |
| CA | 2903487 | A1 | 9/2014 |
| CA | 2903488 | A1 | 9/2014 |
| CA | 2904151 | A1 | 9/2014 |
| CA | 2921459 | A1 | 2/2015 |
| CA | 2928040 | A1 | 4/2015 |
| CA | 2928078 | A1 | 4/2015 |
| CA | 2928186 | A1 | 4/2015 |
| CA | 2928188 | A1 | 4/2015 |
| CA | 2944800 | A1 | 10/2015 |
| CA | 2949106 | A1 | 12/2015 |
| CA | 2952824 | A1 | 12/2015 |
| CA | 2976576 | A1 | 8/2016 |
| CA | 2979695 | A1 | 9/2016 |
| CA | 3001852 | A1 | 4/2017 |
| CA | 3020343 | A1 | 10/2017 |
| CA | 3024507 | A1 | 11/2017 |
| CA | 3024624 | A1 | 11/2017 |
| CA | 3024625 | A1 | 11/2017 |
| CA | 3027312 | A1 | 12/2017 |
| CA | 3034681 | A1 | 1/2018 |
| CA | 3041350 | A1 | 5/2018 |
| CA | 3043033 | A1 | 5/2018 |
| CA | 3054062 | A1 | 8/2018 |
| CA | 3054321 | A1 | 8/2018 |
| CA | 3054323 | A1 | 8/2018 |
| CA | 3063531 | A1 | 11/2018 |
| CA | 3063989 | A1 | 12/2018 |
| CA | 2902884 | C | 5/2021 |
| CA | 2848753 | C | 7/2022 |
| CN | 102525926 | A | 7/2012 |
| CN | 103906527 | A | 7/2014 |
| CN | 104519915 | A | 4/2015 |
| CN | 104540946 | A | 4/2015 |
| CN | 104540947 | A | 4/2015 |
| CN | 104583398 | A | 4/2015 |
| CN | 104583399 | A | 4/2015 |
| CN | 104583401 | A | 4/2015 |
| CN | 105026411 | A | 11/2015 |
| CN | 105051190 | A | 11/2015 |
| CN | 105051213 | A | 11/2015 |
| CN | 105209633 | A | 12/2015 |
| CN | 105658242 | A | 6/2016 |
| CN | 105658800 | A | 6/2016 |
| CN | 105813656 | A | 7/2016 |
| CN | 103748078 | B | 11/2016 |
| CN | 106413811 | A | 2/2017 |
| CN | 106659731 | A | 5/2017 |
| CN | 106795142 | A | 5/2017 |
| CN | 107095849 | A | 8/2017 |
| CN | 109312313 | A | 2/2019 |
| CN | 110114058 | A | 8/2019 |
| CN | 106164248 | B | 10/2019 |
| CN | 110511927 | A | 11/2019 |
| CN | 105142676 | B | 6/2022 |
| CN | 108473969 | B | 9/2022 |
| CN | 109072223 | B | 10/2022 |
| EP | 0250358 | A2 | 12/1987 |
| EP | 1781593 | B1 | 12/2011 |
| EP | 2506857 | A1 | 10/2012 |
| EP | 2506857 | A4 | 4/2014 |
| EP | 2717893 | A1 | 4/2014 |
| EP | 2858679 | A1 | 4/2015 |
| EP | 2929035 | A1 | 10/2015 |
| EP | 2850185 | A4 | 12/2015 |
| EP | 2850182 | A4 | 1/2016 |
| EP | 2850188 | A4 | 1/2016 |
| EP | 2970940 | A1 | 1/2016 |
| EP | 2971010 | A1 | 1/2016 |
| EP | 3008191 | A2 | 4/2016 |
| EP | 2859102 | A4 | 5/2016 |
| EP | 3043826 | A1 | 7/2016 |
| EP | 3060257 | A1 | 8/2016 |
| EP | 3060258 | A1 | 8/2016 |
| EP | 3060671 | A1 | 8/2016 |
| EP | 3052632 | A4 | 3/2017 |
| EP | 3043826 | A4 | 5/2017 |
| EP | 3160959 | A1 | 5/2017 |
| EP | 3033422 | A4 | 8/2017 |
| EP | 2970351 | B1 | 9/2017 |
| EP | 1937213 | B1 | 10/2017 |
| EP | 3226912 | A1 | 10/2017 |
| EP | 2718269 | B1 | 1/2018 |
| EP | 2506857 | B1 | 2/2018 |

(56) References Cited

FOREIGN PATENT DOCUMENTS

| | | | |
|---|---|---|---|
| EP | 3160959 | A4 | 2/2018 |
| EP | 3318248 | A1 | 5/2018 |
| EP | 2971102 | B1 | 6/2018 |
| EP | 3338765 | A1 | 6/2018 |
| EP | 2968586 | B1 | 7/2018 |
| EP | 2970940 | B1 | 7/2018 |
| EP | 3256591 | A4 | 8/2018 |
| EP | 3354644 | A1 | 8/2018 |
| EP | 3362565 | A1 | 8/2018 |
| EP | 3256592 | A4 | 9/2018 |
| EP | 3368671 | A1 | 9/2018 |
| EP | 3122878 | B1 | 10/2018 |
| EP | 3256590 | A4 | 10/2018 |
| EP | 2850189 | B1 | 11/2018 |
| EP | 2970955 | B1 | 11/2018 |
| EP | 2971098 | B1 | 11/2018 |
| EP | 3060303 | B1 | 11/2018 |
| EP | 3403647 | A1 | 11/2018 |
| EP | 2850186 | B1 | 12/2018 |
| EP | 3338765 | B1 | 12/2018 |
| EP | 3431592 | A1 | 1/2019 |
| EP | 2756080 | B1 | 2/2019 |
| EP | 3446712 | A1 | 2/2019 |
| EP | 3458081 | A1 | 3/2019 |
| EP | 3458104 | A1 | 3/2019 |
| EP | 3458590 | A1 | 3/2019 |
| EP | 3318248 | B1 | 4/2019 |
| EP | 3467108 | A1 | 4/2019 |
| EP | 2717893 | B1 | 5/2019 |
| EP | 3495505 | A1 | 6/2019 |
| EP | 3501605 | A1 | 6/2019 |
| EP | 3148552 | B1 | 7/2019 |
| EP | 3511416 | A1 | 7/2019 |
| EP | 3134506 | B1 | 8/2019 |
| EP | 3533873 | A1 | 9/2019 |
| EP | 3536787 | A1 | 9/2019 |
| EP | 3538068 | A1 | 9/2019 |
| EP | 3538136 | A1 | 9/2019 |
| EP | 2895200 | B1 | 11/2019 |
| EP | 3565535 | A1 | 11/2019 |
| EP | 3567112 | A1 | 11/2019 |
| EP | 3450553 | B1 | 12/2019 |
| EP | 3574923 | A1 | 12/2019 |
| EP | 3586861 | A1 | 1/2020 |
| EP | 3301102 | B1 | 4/2020 |
| EP | 3336082 | B1 | 4/2020 |
| EP | 3558271 | A4 | 7/2020 |
| EP | 3440206 | B1 | 10/2020 |
| EP | 3469074 | B1 | 12/2020 |
| EP | 3362555 | B1 | 1/2021 |
| EP | 2858679 | B1 | 2/2021 |
| EP | 3270894 | B1 | 2/2021 |
| EP | 3585891 | B1 | 10/2021 |
| EP | 3585892 | B1 | 6/2022 |
| EP | 3587409 | B8 | 7/2022 |
| ES | 2647832 | T3 | 12/2017 |
| ES | 2663360 | T3 | 4/2018 |
| ES | 2666559 | T3 | 5/2018 |
| ES | 2680595 | T3 | 9/2018 |
| ES | 2689523 | T3 | 11/2018 |
| ES | 2692363 | T3 | 12/2018 |
| ES | 2707966 | T3 | 4/2019 |
| ES | 2707969 | T3 | 4/2019 |
| ES | 2708561 | T3 | 4/2019 |
| ES | 2708562 | T3 | 4/2019 |
| ES | 2713852 | T3 | 5/2019 |
| ES | 2734973 | T3 | 12/2019 |
| ES | 2740248 | T3 | 2/2020 |
| HK | 1199206 | A1 | 6/2015 |
| HK | 1200484 | A1 | 8/2015 |
| HK | 1208352 | A1 | 3/2016 |
| HK | 1208618 | A1 | 3/2016 |
| HK | 1208700 | A1 | 3/2016 |
| HK | 1218068 | A1 | 2/2017 |
| HK | 1219955 | A1 | 4/2017 |
| HK | 1220137 | A1 | 4/2017 |
| IL | 240982 | B | 11/2018 |
| IL | 276122 | A | 8/2020 |
| IL | 229699 | B | 2/2021 |
| JP | 2014-101357 | A | 6/2014 |
| JP | 2014523411 | A | 9/2014 |
| JP | 2014523870 | A | 9/2014 |
| JP | 2014527819 | A | 10/2014 |
| JP | 2015518710 | A | 7/2015 |
| JP | 2015518713 | A | 7/2015 |
| JP | 2015518714 | A | 7/2015 |
| JP | 2015520195 | A | 7/2015 |
| JP | 2015523853 | A | 8/2015 |
| JP | 2015523854 | A | 8/2015 |
| JP | 2015529469 | A | 10/2015 |
| JP | 2016513470 | A | 5/2016 |
| JP | 2016513973 | A | 5/2016 |
| JP | 2016514970 | A | 5/2016 |
| JP | 2016515216 | A | 5/2016 |
| JP | 2016517437 | A | 6/2016 |
| JP | 2016531570 | A | 10/2016 |
| JP | 6022557 | B2 | 11/2016 |
| JP | 2016534035 | A | 11/2016 |
| JP | 2016534992 | A | 11/2016 |
| JP | 2016535729 | A | 11/2016 |
| JP | 2016535738 | A | 11/2016 |
| JP | 2016539916 | A | 12/2016 |
| JP | 2017014278 | A | 1/2017 |
| JP | 2017019857 | A | 1/2017 |
| JP | 6129844 | B2 | 5/2017 |
| JP | 2017127325 | A | 7/2017 |
| JP | 2017518371 | A | 7/2017 |
| JP | 2017518734 | A | 7/2017 |
| JP | 2017520563 | A | 7/2017 |
| JP | 6184945 | B2 | 8/2017 |
| JP | 2017203045 | A | 11/2017 |
| JP | 2017206567 | A | 11/2017 |
| JP | 2018500303 | A | 1/2018 |
| JP | 6316930 | B2 | 4/2018 |
| JP | 2018511588 | A | 4/2018 |
| JP | 2018100307 | A | 6/2018 |
| JP | 2018115164 | A | 7/2018 |
| JP | 6372042 | B2 | 8/2018 |
| JP | 2018141006 | A | 9/2018 |
| JP | 2018531017 | A | 10/2018 |
| JP | 2018174942 | A | 11/2018 |
| JP | 2019014742 | A | 1/2019 |
| JP | 6463810 | B2 | 2/2019 |
| JP | 2019048900 | A | 3/2019 |
| JP | 6506749 | B2 | 4/2019 |
| JP | 2019065047 | A | 4/2019 |
| JP | 2019065052 | A | 4/2019 |
| JP | 2019073557 | A | 5/2019 |
| JP | 2019513372 | A | 5/2019 |
| JP | 6525435 | B2 | 6/2019 |
| JP | 2019516719 | A | 6/2019 |
| JP | 2019519511 | A | 7/2019 |
| JP | 2019519601 | A | 7/2019 |
| JP | 6557722 | B2 | 8/2019 |
| JP | 6561378 | B2 | 8/2019 |
| JP | 6567494 | B2 | 8/2019 |
| JP | 2019135241 | A | 8/2019 |
| JP | 2019522047 | A | 8/2019 |
| JP | 6571679 | B2 | 9/2019 |
| JP | 2019163322 | A | 9/2019 |
| JP | 6586075 | B2 | 10/2019 |
| JP | 6599373 | B2 | 10/2019 |
| JP | 6608815 | B2 | 11/2019 |
| JP | 2019533708 | A | 11/2019 |
| JP | 2019205472 | A | 12/2019 |
| JP | 2019206545 | A | 12/2019 |
| JP | 6646773 | B2 | 2/2020 |
| KR | 20120138865 | A | 12/2012 |
| KR | 20140044356 | A | 4/2014 |
| KR | 20150030205 | A | 3/2015 |
| KR | 20150127582 | A | 11/2015 |
| KR | 20150128687 | A | 11/2015 |
| KR | 20160010398 | A | 1/2016 |
| KR | 20160073885 | A | 6/2016 |

(56) References Cited

FOREIGN PATENT DOCUMENTS

| | | | |
|---|---|---|---|
| KR | 20160074368 | A | 6/2016 |
| KR | 20160091893 | A | 8/2016 |
| KR | 20160145004 | A | 12/2016 |
| KR | 20170021281 | A | 2/2017 |
| KR | 20190027353 | A | 3/2019 |
| KR | 20190067261 | A | 6/2019 |
| KR | 20190120160 | A | 10/2019 |
| MX | 2013014419 | A | 1/2014 |
| MX | 2014015041 | A | 6/2015 |
| MX | 2015011943 | A | 12/2015 |
| MX | 2015011944 | A | 12/2015 |
| MX | 2015011945 | A | 12/2015 |
| MX | 2015012333 | A | 5/2016 |
| MX | 2015012865 | A | 7/2016 |
| MX | 2016005236 | A | 8/2016 |
| MX | 2016005237 | A | 8/2016 |
| MX | 2016005238 | A | 8/2016 |
| MX | 2016005239 | A | 8/2016 |
| MX | 2016013965 | A | 1/2017 |
| MX | 2017000143 | A | 5/2017 |
| MX | 365409 | B | 5/2019 |
| MX | 367605 | B | 8/2019 |
| NZ | 600616 | A | 11/2014 |
| NZ | 700688 | A | 2/2016 |
| NZ | 618275 | A | 11/2016 |
| NZ | 716192 | A | 7/2017 |
| RU | 2013154295 | A | 7/2015 |
| WO | WO-9508986 | A1 | 4/1995 |
| WO | WO-9512673 | A1 | 5/1995 |
| WO | WO-9521251 | A1 | 8/1995 |
| WO | WO-9521915 | A1 | 8/1995 |
| WO | WO-9827104 | A1 | 6/1998 |
| WO | WO-9929842 | A1 | 6/1999 |
| WO | WO-9932619 | A1 | 7/1999 |
| WO | WO-0024931 | A2 | 5/2000 |
| WO | WO-0026226 | A1 | 5/2000 |
| WO | WO-0044895 | A1 | 8/2000 |
| WO | WO-0129058 | A1 | 4/2001 |
| WO | WO-0202606 | A2 | 1/2002 |
| WO | WO-0234771 | A2 | 5/2002 |
| WO | WO-02098443 | A2 | 12/2002 |
| WO | WO-03018054 | A1 | 3/2003 |
| WO | WO-2005002619 | A2 | 1/2005 |
| WO | WO-2005007196 | A2 | 1/2005 |
| WO | WO-2005032582 | A3 | 11/2005 |
| WO | WO-2005111066 | A2 | 11/2005 |
| WO | WO-2006091517 | A2 | 8/2006 |
| WO | WO-2006110413 | A2 | 10/2006 |
| WO | WO-2006/138380 | A2 | 12/2006 |
| WO | WO-2006138004 | A2 | 12/2006 |
| WO | WO-2007049155 | A2 | 5/2007 |
| WO | WO-2008014979 | A2 | 2/2008 |
| WO | WO-2008016473 | A2 | 2/2008 |
| WO | WO-2008054819 | A2 | 5/2008 |
| WO | WO-2008083949 | A2 | 7/2008 |
| WO | WO-2008157688 | A2 | 12/2008 |
| WO | WO-2009016515 | A2 | 2/2009 |
| WO | WO-2008020330 | A3 | 3/2009 |
| WO | WO-2009031043 | A2 | 3/2009 |
| WO | WO-2009095226 | A2 | 8/2009 |
| WO | WO-2009104092 | A2 | 8/2009 |
| WO | WO-2009109860 | A2 | 9/2009 |
| WO | WO-2009149253 | A2 | 12/2009 |
| WO | WO-2010042856 | A2 | 4/2010 |
| WO | WO-2010042877 | A1 | 4/2010 |
| WO | WO-2010119343 | A2 | 10/2010 |
| WO | WO-2010144678 | A2 | 12/2010 |
| WO | WO-2011005799 | A2 | 1/2011 |
| WO | WO-2011015347 | A1 | 2/2011 |
| WO | WO-2011068810 | A1 | 6/2011 |
| WO | WO-2011076807 | A2 | 6/2011 |
| WO | WO-2012006372 | A1 | 1/2012 |
| WO | WO-2012019780 | A1 | 2/2012 |
| WO | WO-2012075040 | A2 | 6/2012 |
| WO | WO-2012170889 | A1 | 12/2012 |
| WO | WO-2012170930 | A1 | 12/2012 |
| WO | WO-2013040429 | A1 | 3/2013 |
| WO | WO-2013059475 | A1 | 4/2013 |
| WO | WO-2013143700 | A2 | 10/2013 |
| WO | WO-2013149140 | A1 | 10/2013 |
| WO | WO-2013173598 | A1 | 11/2013 |
| WO | WO-2013173599 | A1 | 11/2013 |
| WO | WO-2013173638 | A1 | 11/2013 |
| WO | WO-2013173645 | A1 | 11/2013 |
| WO | WO-2013173652 | A1 | 11/2013 |
| WO | WO-2013185067 | A1 | 12/2013 |
| WO | WO-2013185069 | A1 | 12/2013 |
| WO | WO-2012170930 | A9 | 1/2014 |
| WO | WO-2014/028487 | A1 | 2/2014 |
| WO | WO-2014043544 | A1 | 3/2014 |
| WO | WO-2012075040 | A3 | 4/2014 |
| WO | WO-2014089486 | A1 | 6/2014 |
| WO | WO-2014152211 | A1 | 9/2014 |
| WO | WO-2014152513 | A1 | 9/2014 |
| WO | WO-2014152659 | A1 | 9/2014 |
| WO | WO-2014152673 | A1 | 9/2014 |
| WO | WO-2014152940 | A1 | 9/2014 |
| WO | WO-2014152966 | A1 | 9/2014 |
| WO | WO-2014153052 | A2 | 9/2014 |
| WO | WO-2013173645 | A8 | 12/2014 |
| WO | WO-2015011633 | A1 | 1/2015 |
| WO | WO-2015023941 | A1 | 2/2015 |
| WO | WO-2014201252 | A3 | 3/2015 |
| WO | WO-2015038892 | A1 | 3/2015 |
| WO | WO-2015051283 | A1 | 4/2015 |
| WO | WO-2015061461 | A1 | 4/2015 |
| WO | WO-2015061467 | A1 | 4/2015 |
| WO | WO-2015061491 | A1 | 4/2015 |
| WO | WO-2015061500 | A1 | 4/2015 |
| WO | WO-2014153052 | A9 | 8/2015 |
| WO | WO-2015148247 | A1 | 10/2015 |
| WO | WO-2015164773 | A1 | 10/2015 |
| WO | WO-2015184256 | A2 | 12/2015 |
| WO | WO-2015199952 | A1 | 12/2015 |
| WO | WO-2015200465 | A1 | 12/2015 |
| WO | WO-2015184256 | A3 | 1/2016 |
| WO | WO-2016090262 | A1 | 6/2016 |
| WO | WO-2016097065 | A1 | 6/2016 |
| WO | WO-2016130929 | A1 | 8/2016 |
| WO | WO-2016130943 | A1 | 8/2016 |
| WO | WO-2016130963 | A1 | 8/2016 |
| WO | WO-2016149508 | A1 | 9/2016 |
| WO | WO-2016176330 | A1 | 11/2016 |
| WO | WO-2016197133 | A1 | 12/2016 |
| WO | WO-2017004143 | A1 | 1/2017 |
| WO | WO-2017/049245 | A2 | 3/2017 |
| WO | WO-2017049074 | A1 | 3/2017 |
| WO | WO-2017066573 | A1 | 4/2017 |
| WO | WO-2017066594 | A1 | 4/2017 |
| WO | WO-2017075030 | A1 | 5/2017 |
| WO | WO-2017075531 | A1 | 5/2017 |
| WO | WO-2017177169 | A1 | 10/2017 |
| WO | WO-2017181026 | A1 | 10/2017 |
| WO | WO-2017182524 | A1 | 10/2017 |
| WO | WO-2017186928 | A1 | 11/2017 |
| WO | WO-2017201317 | A1 | 11/2017 |
| WO | WO-2017201328 | A1 | 11/2017 |
| WO | WO-2017201332 | A1 | 11/2017 |
| WO | WO-2017201346 | A1 | 11/2017 |
| WO | WO-2017201349 | A1 | 11/2017 |
| WO | WO-2017218524 | A1 | 12/2017 |
| WO | WO-2018031871 | A1 | 2/2018 |
| WO | WO-2018078053 | A1 | 5/2018 |
| WO | WO-2018081480 | A1 | 5/2018 |
| WO | WO-2018081638 | A1 | 5/2018 |
| WO | WO-2018089790 | A1 | 5/2018 |
| WO | WO-2018089801 | A1 | 5/2018 |
| WO | WO-2018089846 | A1 | 5/2018 |
| WO | WO-2018157133 | A1 | 8/2018 |
| WO | WO-2018157141 | A1 | 8/2018 |
| WO | WO-2018157153 | A1 | 8/2018 |
| WO | WO-2018165257 | A1 | 9/2018 |
| WO | WO-2018170336 | A1 | 9/2018 |
| WO | WO-2018157154 | A3 | 10/2018 |

(56) References Cited

FOREIGN PATENT DOCUMENTS

| | | | | |
|---|---|---|---|---|
| WO | WO-2018191719 A1 | 10/2018 | | |
| WO | WO-2018213476 A1 | 11/2018 | | |
| WO | WO-2018231709 A1 | 12/2018 | | |
| WO | WO-2018236849 A1 | 12/2018 | | |
| WO | WO-2019036028 A1 | 2/2019 | | |
| WO | WO-2019036030 A1 | 2/2019 | | |
| WO | WO-2019040590 A1 | 2/2019 | | |
| WO | WO-2019046809 A1 | 3/2019 | | |
| WO | WO-2019056098 A1 | 3/2019 | | |
| WO | WO-2019077053 A1 | 4/2019 | | |
| WO | WO-2019089828 A1 | 5/2019 | | |
| WO | WO-2019126593 A1 | 6/2019 | | |
| WO | WO-2019131839 A1 | 7/2019 | | |
| WO | WO-2019137999 A1 | 7/2019 | | |
| WO | WO-2019140102 A1 | 7/2019 | | |
| WO | WO-2019140102 A8 | 8/2019 | | |
| WO | WO-2019152802 A1 | 8/2019 | | |
| WO | WO-2019154985 A1 | 8/2019 | | |
| WO | WO-2019191780 A1 | 10/2019 | | |
| WO | WO-2019213308 A1 | 11/2019 | | |
| WO | WO-2019222277 A1 | 11/2019 | | |
| WO | WO-2019222424 A1 | 11/2019 | | |
| WO | WO-2019226925 A1 | 11/2019 | | |
| WO | WO-2019232095 A1 | 12/2019 | | |
| WO | WO-2019232097 A1 | 12/2019 | | |
| WO | WO-2019232103 A1 | 12/2019 | | |
| WO | WO-2019232208 A1 | 12/2019 | | |
| WO | WO-2020002540 A1 | 1/2020 | | |
| WO | WO-2020002598 A1 | 1/2020 | | |
| WO | WO-2020035609 A2 | 2/2020 | | |
| WO | WO-2020041793 A1 | 2/2020 | | |
| WO | WO-2020047061 A1 | 3/2020 | | |
| WO | WO-2020051223 A1 | 3/2020 | | |
| WO | WO-2020061332 A1 | 3/2020 | | |
| WO | WO-2020061367 A1 | 3/2020 | | |
| WO | WO-2020061426 A2 | 3/2020 | | |
| WO | WO-2020061457 A1 | 3/2020 | | |
| WO | WO-2020061426 A3 | 4/2020 | | |
| WO | WO-2020072605 A1 | 4/2020 | | |
| WO | WO-2020081938 A1 | 4/2020 | | |
| WO | WO-2020093061 A1 | 5/2020 | | |
| WO | WO-2020097493 A1 | 5/2020 | | |
| WO | WO-2020097540 A1 | 5/2020 | | |
| WO | WO-2020097548 A1 | 5/2020 | | |
| WO | WO-2020118041 A1 | 6/2020 | | |
| WO | WO-2020121273 A1 | 6/2020 | | |
| WO | WO-2020128012 A1 | 6/2020 | | |
| WO | WO-2020144295 A1 | 7/2020 | | |
| WO | WO-2020146805 A1 | 7/2020 | | |
| WO | WO-2020160397 A1 | * | 8/2020 | ......... A61K 31/7105 |
| WO | WO-2020161224 A1 | 8/2020 | | |
| WO | WO-2020191103 A1 | 9/2020 | | |
| WO | WO-2020201383 A1 | 10/2020 | | |
| WO | WO-2020214946 A1 | 10/2020 | | |
| WO | WO-2020219876 A1 | 10/2020 | | |
| WO | WO-2020219941 A1 | 10/2020 | | |
| WO | WO-2020247382 A1 | 12/2020 | | |
| WO | WO-2021026358 A1 | 2/2021 | | |
| WO | WO-2021030701 A1 | 2/2021 | | |
| WO | WO-2021123332 A1 | 6/2021 | | |
| WO | WO-2021129945 A1 | 7/2021 | | |
| WO | WO-2021130225 A1 | 7/2021 | | |
| WO | WO-2022081750 A1 | 4/2022 | | |
| WO | WO-2022081752 A1 | 4/2022 | | |
| ZA | 201409228 B | 7/2016 | | |
| ZA | 201409229 B | 7/2016 | | |
| ZA | 201507605 B | 1/2017 | | |

OTHER PUBLICATIONS

ACD/LABS, "ACD/pKa Classic Module Report", Dec. 20, 2020, 4 pages.

Adams, "AstraZeneca's eagerly awaited COVID-19 vaccine passes large test, but confirmation needed," FierceBiotech, Jul. 20, 2020 [online], [retrieved on Mar. 8, 2022]. Retrieved from the Internet URL: https://www.fiercebiotech.com/biotech/astrazeneca-s-eagerly-awaited-covid-vaccine-passes-large-test-but-confirmation-needed, 3 pages.

Adams, B., "China's Sinovac hit by late-stage COVID-19 vaccine halt after reports of a death in Brazilian trial," FierceBiotech, Nov. 10, 2020 [online], [retrieved on Mar. 8, 2022]. Retrieved from the Internet URL: https://www.fiercebiotech.com/biotech/china-s-sinovac-hit-by-late-stage-covd-vaccine-halt-after-reports-a-death-brazilian-trial, 2 pages.

Adams, B., "Pfizer, BioNTech start their COVID-19 vax phase 3, squaring off with Moderna," FierceBiotech, Jul. 28, 2020 [online], [retrieved on Mar. 8, 2022]. Retrieved from the Internet URL: https://www.fiercebiotech.com/biotech/pfizer-biontech-start-their-covid-vax-phase-3-squaring-off-moderna, 5 pages.

Adams, B., "Pfizer, Under pressure, Pfizer, Moderna (and soon AstraZeneca) publish COVID-19 vaccine protocols," FierceBiotech, Sep. 18, 2020 [online], [retrieved on Mar. 8, 2022]. Retrieved from the Internet URL: https://www.fiercebiotech.com/biotech/under-pressure-pfizer-moderna-and-soon-astrazeneca-publish-covid-vaccine-protocols, 2 pages.

Adams, Pfizer, "BioNTech nab fast track tag, prep for major phase 3 COVID-19 vax test this month," FierceBiotech, Jul. 13, 2020 [online], [retrieved on Mar. 8, 2022]. Retrieved from the Internet URL: https://www.fiercebiotech.com/biotech/pfizer-biontech-nab-fast-track-tag-preps-for-major-phase-3-covid-vax-test-month, 2 pages.

Addison, et al., Extracellular matrix mineralization in murine MC3T3-E1 osteoblast cultures: An ultrastructural, compositional and comparative analysis with mouse bone, Bone, Feb. 2015, pp. 244-256, vol. 71.

Ahmad et al., "New multivalent cationic lipids reveal bell curve for transfection efficiency versus membrane charge density: lipid-DNA complexes for gene delivery," The Journal of Gene Medicine, 2005, pp. 739-748, vol. 7.

Ahmed et al., "Preliminary Identification of Potential Vaccine Targets for the COVID-19 Coronavirus (SARS-CoV-2) Based on SARS-CoV Immunological Studies," Viruses 12(3):254, pp. 1-15 (2020).

Akinc, et al., Targeted delivery of RNAi therapeutics with endogenous and exogenous ligand-based mechanisms, Molecular Therapy, Jul. 1, 2010, pp. 1357-1364, vol. 18, No. 7.

Al Idrus, "CanSino adds mRNA to COVID-19 vaccine efforts with Precision NanoSystems deal," FierceBiotech, May 20, 2020 [online], [retrieved on Mar. 8, 2022]. Retrieved from the Internet URL: https://www.fiercebiotech.com/biotech/cansino-adds-mrna-to-covid-19-vaccine-efforts-precision-nanosystems-deal, 2 pages.

Al Idrus, "Moderna's COVID-19 vaccine triggers immune response in older adults," FierceBiotech, Aug. 26, 2020 [online], [retrieved on Mar. 8, 2022]. Retrieved from the Internet URL: https://www.fiercebiotech.com/biotech/moderna-s-covid-19-vaccine-triggers-immune-response-older-adults, 4 pages.

Alabi, et al., "Multiparametric approach for the evaluation of lipid nanoparticles for SIRNA delivery, Supporting Information", Applied Biological Sciences, Jul. 23, 2013, 4 pages.

Alameh, et al., "siRNA delivery with chitosan: Influence of chitosan molecular weight, degree of deacetylation, and amine to phosphate ratio on in vitro silencing efficiency, hemocompatibility, biodistribution, and in vivo efficacy", Biomacromolecules, 2018, pp. 112-131, vol. 19.

Alameh et al., "Lipid nanoparticles enhance the efficacy of mRNA and protein subunit vaccines by inducing robust T follicular helper cell and humoral responses," Immunity, 2021, pp. 2877-2892, vol. 54, No. 12.

Alameh et al., "Messenger RNA-Based Vaccines Against Infectious Diseases," Current Topics in Microbiology and Immunology, Apr. 17, 2020, pp. 1-35.

Alberer et al., "Safety and immunogenicity of a mRNA rabies vaccine in healthy adults: an open-label, non-randomised, prospective, first-in-human phase 1 clinical trial", Lancet, Sep. 23, 2017, pp. 1511-1520, vol. 390.

Alberts et al., Cell biology: the endless frontier, Molecular Biology of the Cell, Nov. 15, 2010, pp. 3785-3785, vol. 21, No. 22.

(56) References Cited

OTHER PUBLICATIONS

Aldrich et al., "Proof-of-concept of a low-dose unmodified mRNA-based rabies vaccine formulated with lipid nanoparticles in human volunteers: a phase 1 trial", Vaccine, 2021, pp. 1310-1318, vol. 39.
Ali et al., "Design of a new cell penetrating peptide for DNA, siRNA and mRNA delivery", The Journal of Gene Medicine, 2022, pp. 1-31, vol. 24, No. 3.
Alishetty, et al., "Novel lipid nanoparticle provides potent SARS-CoV-2 mRNA vaccine at low dose with low local reactogenicity, high thermostability and limited systemic biodistribution", 2021, 55 pages.
Allen et al., "Efficient Delivery of Macromolecules into Human Cells by Improving the Endosomal Escape Activity of Cell-Penetrating Peptides: Lessons Learned from dfTAT and its Analogs", Biomolecules, 2018, pp. 1-13, vol. 8.
Allen, et al., Liposomal drug delivery systems: from concept to clinical applications, Advanced Drug Delivery Reviews, Jan. 1, 2013, pp. 36-48, vol. 65, No. 1.
Amanat et al., "SARS-CoV-2 Vaccines: Status Report," Immunity, vol. 52, Apr. 14, 2020, pp. 583-589.
An, et al., "Systematic Messenger RNA Therapy as a Treatment for Methylmalonic Acidemia", Cell Reports, Dec. 19, 2017, pp. 3548-3558, vol. 21.
Anderson, B.R. et al., "Incorporation of pseudouridine into mRNA enhances translation by diminishing PKR activation," Nucleic Acids Research, vol. 38(17):5884-5892 (2010).
Anderson, et al., Safety and immunogenicity of SARS-CoV-2 mRNA-1273 vaccine in older adults, Supplemental Appendix, N Engl J Med., 2020, pp. 1-63.
Ando et al., "Enzymatic litigation of an antibody and arginine 9 peptide for efficient and cell-specific siRNA delivery", Scientific Reports, 2021, pp. 1-11, vol. 11.
Armbruster et al., "Advances in RNA Vaccines for Preventative Indications: A Case Study of a Vaccine against Rabies", Vaccines, 2019, pp. 1-12, vol. 7.
Armen et al., "Phospholipid Component Volumes. Determination and Application to Bilayer Structure Calculations," Biophysical Journal, Aug. 1998, pp. 734-744, vol. 75.
Arteta et al., "Supporting Information," PNAS, 2 pages.
Arteta, M.Y., et al., "Successful Reprogramming of Cellular Protein Production Through Mrna Delivered by Functionalized Lipid Nanoparticles," Proceedings of the National Academy of Sciences of the United States of America, 2018, vol. 115(15), pp. E3351-E3360.
Attia, et al., "Modification of Nanoparticles with Transferrin for Targeting Brain Tissues", Peptide Conjugation, Methods in Molecular Biology, 2021, pp. 49-56.
Avanti Polar Lipids, 18:0 PC-d83, No Date, 1 page.
Avanti Polar Lipids, cholesterol-d6, No Date, 1 page.
Avanti Polar Lipids, cholesterol-d7, No Date, 1 page.
Avanti Polar Lipids, "Storage & Handling of Lipids", Oct. 4, 2019, 3 pages. Retrieved from https://avantilipids.com/tech-support/storage-handling-of-lipids#:~:text=SATURATED%20LIPIDS&text=These%20lipids%20should%20be%20stored,temperature%20before%20opening%20the%20bottle.
Awasthi et al., "Antibody responses to crucial functional epitopes as a novel approach to assess immunogenicity of vaccine adjuvants", Vaccine, May 2019, pp. 3770-3778, vol. 37, No. 29.
Bachmann et al., "Vaccine delivery: a matter of size, geometry, kinetics and molecular patterns", Nature Reviews, Immunology, Nov. 2010, pp. 787-796, vol. 10.
Baden et al., "A Phase3, Randomized, Stratified, Observer-Blind, Placebo-Controlled Study to Evaluate the Efficacy, Safety, and Immunogenicity of mRNA-1273 SARS CoV-2 Vaccine in Adults Aged 18 Years and Older", Statistical Analysis Plan, Version 1.0, Sep. 10, 2020, pp. 1-307.
Bahl et al., "Preclinical and Clinical demonstration of Immunogenicity by mRNA Vaccines against H10N8 and H7N9 Influenza Viruses", Molecular Therapy, Jun. 2017, pp. 1316-1327, vol. 25, No. 6.
Baiersdorfer et al., "A Facile Method for the Removal of dsRNA Contaminant from In Vitro-Transcribed RNA," Moleculary Therapy Nucleic Acids, Apr. 2019, pp. 26-35, vol. 15.
Baladi et al., "Stealth fluorescence labeling for live microscopy imaging of mRNA delivery", BioRxiv, 2020, pp. 1-45.
Ball et al., "Oral delivery of siRNA lipid nanoparticles: Fate in the GI tract", Scientific Reports, 2018, pp. 1-12, vol. 8.
Bangham, The action of steroids and streptolysin S on the permeability of phospholipid structures to cations, J. Mol. Biol. Aug. 1, 1965, pp. 238-252, vol. 13, No. 1.
Barda et al., "Safety of the BNT162b2 mRNA Covid-19 Vaccine in a Nationwide Setting," The New England Journal of Medicine, Aug. 25, 2021, pp. 1-14.
Barichello, et al., "Complexation of siRNA and pDNA with Cationic Liposomes: The Important Aspects in Lipoplex Preparation," Methods in Molecular Biology, 2010, pp. 461-472, vol. 605.
Bar-On et al., "Protection of BNT162b2 Vaccine Booster against Covid-19 in Israel," The New England Journal of Medicine, Sep. 15, 2021, pp. 1-8.
Bar-Zeev et al., "Encouraging results from phase 1/2 COVID-19 vaccine trials," The Lancet, Jul. 20, 2020, URL https://doi.org/10.1016/S0140-6736(20)31611-1 pp. 1-2.
Basha, et al., Influence of cationic lipid composition on gene silencing properties of lipid nanoparticle formulations of siRNA in antigen-presenting cells, Molecular Therapy, Dec. 1, 2011, pp. 2186-2200, vol. 19, No. 12.
Beckert, Synthesis of RNA by In Vitro Transcription in RNA in Methods in Molecular Biology, InRna, 2011, pp. 29-41.
Belliveau et al., "Microfluidic Synthesis of Highly Potent Limit-size Lipid Nanoparticles for In Vivo Delivery of siRNA," Molecular Therapy-Nucleic Acids, 2012, 1, e37, 9 pages.
Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).
Bernstein, P. et al., Poly(A), poly(A) binding protein and the regulation of mRNA stability. Trends Biochem Sci. Sep. 14, 198S(9):373-7.
Berthub et al., "The CureVac Vaccine, and a brief tour through some of the wonders of nature", Mar. 8, 2021, 12 pages.
Bhattacharjee, "DLS and zeta potential—What they are and what they are not?", Journal of Controlled Release, 2016, pp. 337-351, vol. 235.
Bhattacharya et al., "Development of epitope-based peptide vaccine against novel coronavirus 2019 (SARS-CoV-2): Immunoinformatics approach," Journal of Medical Virology, 2020, pp. 618-631, vol. 92.
Binder, R. et al., Evidence that the pathway of transferrin receptor mRNA degradation involves an endonucleolytic cleavage within the 3' UTR and does not involve poly(A) tail shortening. EMBO J. Apr. 15, 1994;13(8):1969-80.
Binette, et al., "Tetrapolar measurement of electrical conductivity and thickness of articular cartilage", J. Biomech. Eng., Aug. 2004, pp. 475-484, vol. 126.
Biontech, "Study to Describe the Safety, Tolerability, Immunogenicity, and Potential Efficacy of RNA Vaccine Candidates Against COVID-19 in Healthy Adults," ClinicalTrials, 2020, 2 Pages. Retrieved from the Internet URL: https://clinicaltrials.gov/ct2/show/NCT04368728, pp. 1-16.
Bisht et al., "Severe acute respiratory syndrome coronavirus spike protein expressed by attenuated vaccinia virus protectively immunizes mice," PNAS, Apr. 27, 2004, pp. 6641-6646, vol. 101, No. 17.
Bizet, et al., "The TGF-β co-receptor, CD109, promotes internalization and degradation of TGF-β receptors", Biochimica et Biophysica Acta 1813, Feb. 2, 2011, pp. 742-753.
Blakcenship, "CureVac ties up Wacker to churn out more than 100M does of mRNA coronavirus vaccine", Nov. 25, 2020, 2 pages.
Blanc et al., "Optimal Processing Method to Obtain Four-color Confocal Fluorescent Images of the Cytoskeleton and Nucleus in Three-dimensional Chondrocyte Cultures", Journal of Histochemistry and Cytochemistry, May 11, 2005, pp. 1171-1175, vol. 53, No. 9.

(56) References Cited

OTHER PUBLICATIONS

Bnyan et al., "Surfactant effects on Lipid-Based Vesicles Properties", Journal of Pharmaceutical Sciences, Jan. 2018, pp. 1237-1246, vol. 107.
Boada et al., "LDL-Based Lipid Nanoparticle Derived for Blood Plasma Accumulates Preferentially in Atherosclerotic Plaque", Frontiers in Bioengineering and Biotechnoogy, Dec. 2021, p. 1-14, vol. 9.
Bolles et al., "A Double-Inactivated Severe Acute Respiratory Syndrome Coronavirus Vaccine Provides Incomplete Protection in Mice and Induces Increased Eosinophilic Proinflammatory Pulmonary Response upon Challenge," Journal of Virology, Dec. 2011, pp. 12201-12215, vol. 85, No. 23.
Boucher et al., "Human corneal epithelial cell response to epidermal growth factor tethered via coiled-coil interactions", Biomaterials, May 27, 2010, pp. 1-11.
Bour-Jordan, H. et al., "Intrinsic and extrinsic control of peripheral T-cell tolerance by costimulatory molecules of the CD28/ B7 family," Immunol. Rev. 241(1):180-205 (2011).
Bourquin et al., "Biodistribution, Clearance, and Long-Term Fate of Clinically Relevant Nanomaterials", Advanced Materials, 2018, pp. 1-31, vol. 30.
Bowman et al., "Lack of effects on female fertility and prenatal and postnatal offspring development in rats with BNT162b2, a mRNA-based COVID-19 vaccine," Reproductive Toxicology, 2021, pp. 28-35, vol. 103.
Brader et al., "Encapsulation state of messenger RNA inside lipid nanoparticles", Biophysical Journal, 2021, pp. 1-2, vol. 120.
Brahmer et al., "Safety and Activity of Anti-PD-L1 Antibody in Patients with Advanced Cancer," N Engl J Med., 366:2455-2465 (2012).
Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-75.
Braun et al., "Supplementary Table," 2020, 7 pages.
Brighman et al., Rapid communication: In vivo transfection of murine lungs with a functioning prokaryotic gene using a liposome vehicle, Am. J. Med. Sci., 2 Oct. 1, 1989, pp. 278-281, vol. 298, No. 4.
Brunelle, et al., In vitro transcription from plasmid or PCR-amplified DNA, InMethods in Enzymology, Jan. 1, 2013, pp. 101-114, vol. 530.
Bulik, B. S., "Pfizer lays out COVID-19 vaccine commercial strategy for pandemic and beyond," FiercePharma, Jul. 29, 2020 [online], [retrieved on Mar. 8, 2022]. Retrieved from the Internet URL: https://www.fiercepharma.com/marketing/pfizer-lays-out-commercial-strategy-for-covid-19-vaccine-during-pandemic-and-beyond, 2 pages.
Buschmann et al., "A Method of Quantitative Autoradiography for the Spatial Localization of Proteoglycan Synthesis Rates in Cartilage", The Journal of Histochemistry and Cytochemistry, Dec. 28, 1995, pp. 423-431, vol. 44 No. 5.
Buschmann et al., "A Molecular Model of Proteoglycan-Associated Electrostatic Forces in Cartilage Mechanics", Journal of Biomechanical Engineering, May 1995, pp. 179-192, vol. 117.
Buschmann et al., "Altered aggrecan synthesis correlates with cell and nucleus structure in statically compressed cartilage", Journal of Cell Science, Nov. 15, 1995, pp. 499-508, vol. 109.
Buschmann et al., "Cartilage Repair with Chitosan-Glycerol Phosphate-Stabilized Blood Clots", Cartilage Repair Strategies, 2007, 85-104.
Buschmann et al., "Chitosans for delivery of nucleic acids", Advanced Drug Delivery Reviews, Jul. 18, 2013, pp. 1234-1270, vol. 65.
Buschmann et al., "Chondrocytes in Agarose Culture Synthesize a Mechanically functional Extracellular Matrix", Journal of Orthopedic Research, 1992, pp. 745-758, vol. 10.
Buschmann et al., "Confined compression of articular cartilage: Linearity in ramp and sinusoidal tests and the importance of interdigitation and incomplete confinement", Journal of Biomechanics, 1998, pp. 171-178, vol. 31.
Buschmann et al., "Mechanical compression modulates matrix biosynthesis in Chondrocyte/agarose culture", Journal of Cell Science, Jan. 6, 1995, pp. 1497-1508, vol. 108.
Buschmann et al., "Nanomaterial Delivery Systems for mRNA Vaccines", Vaccines, Jan. 19, 2021, pp. 1-30, vol. 9, No. 65.
Buschmann et al., "Numerical Conversion of Transient to Harmonic Response Functions for Linear Viscoelastic Materials", Biomechanics, 1997, pp. 197-202, vol. 30 No. 2.
Buschmann et al., "Ruthenium Hexammine Trichloride Chemography for Aggrecan Mapping in Cartilage is a Sensitive Indicator of Matrix Degradation", Journal of Histochemistry and Cytochemistry, 2000, 81-88, vol. 48, No. 1.
Buschmann et al., "Stimulation of Aggrecan Synthesis in Cartilage Explants by Cyclic Loading is Localized to Regions of High Interstitial Fluid Flow", Biochemistry and Biophysics, Feb. 22, 1999, pp. 1-7, vol. 366.
Callow et al., "The time course of the immune response to experimental coronavirus infection of man," Epidemiol. Infect., 1990, pp. 435-446, vol. 105.
Caput, D. et al., Identification of a common nucleotide sequence in the 3'-untranslaled region of mRNA molecules specifying inflammatory mediators. Proc Natl Acad Sci US A. Mar. 1986;83(6):1670-4.
Carrasco et al., "Ionization and Structural Properties of mRNA Lipid Nanoparticles that Influence Expression in Intramuscular and Intravascular Administration", Communications Biology, 2021, pp. 1-36, vol. 4.
Cech et al., Ribozymes and their medical implications, JAMA, Nov. 25, 1988, pp. 3030-3034.
Cevaal et al., "In Vivo T Cell-Targeting Nanoparticle Drug Delivery Systems: Considerations for Rational Design", ACS Nano, 2021, pp. 3736-3753, vol. 15.
Chandrashekar et al., "SARS-CoV-2 infection protects against rechallenge in rhesus macaques," Science, May 20, 2020, DOI: 10.1126/science.abc4776, pp. 1-12.
Changoor et al. "A polarized light microscopy method for accurate and reliable grading of collagen organization in cartilage repair", Osteoarthritis and Cartilage, Oct. 2, 2010, pp. 126-135, vol. 19.
Changoor et al., "Effects of Refrigeration and Freezing on the Electromechanical and Biomechanical Properties of Articular Cartilage", Journal of Biomechanical Engineering, Jun. 2010, pp. 1-6, vol. 132.
Changoor et al., "Streaming Potential-Based Arthroscopic Device is Sensitive to Cartilage Changes Immediately Post-Impact in an Equine Cartilage Injury Model", Journal of Biomechanical Engineering, Jun. 2011, pp. 1-9, vol. 133.
Changoor et al., "Structural characteristics of the collagen network in human normal, degraded and repair articular cartilages observed in polarized light and scanning electron microscopies", Osteoarthritis and Cartilage, Sep. 23, 2011, pp. 1458-1468, vol. 19.
Charlebois et al., "Nonlinear Tensile Properties of Bovine Articular Cartilage and their Variation with Age and Depth", Journal of Biomechanical Engineering, Apr. 2004, pp. 129-137, vol. 26.
Chaudhary et al., "mRNA vaccines for infectious diseases: principles, delivery and clinical translation," Nature Reviews, Aug. 25, 2021, pp. 817-838, vol. 20, No. 11.
Chen et al., "Acute Osteoclast Activity following Subchondral Drilling is Promoted by Chitosan and Associated with Improved Cartilage Repair Tissue Integration", Cartilage, Oct. 11, 2010, pp. 1-14, vol. 2, No. 2.
Chen et al., "Bone marrow stimulation induces greater chondrogenesis in trochlear vs condylar cartilage defects in skeletally mature rabbits", Osteoarthritis and Cartilage, Apr. 14, 2013, pp. 999-1007, vol. 21.
Chen et al., "Bone Marrow Stimulation of the Medial Femoral Condyle Produces Inferior Cartilage and Bone Repair Compared to the Trochlea in a rabbit Surgical Model", Journal of Orthopedic Research, Jul. 10, 2013, pp. 1757-1764, vol. 31, No. 11.
Chen et al., "Characterization of Subchondral Bone Repair for Marrow-Stimulated Chondral Defects and its Relationship to Articular Cartilage Resurfacing", The American Journal of Sports Medicine, May 31, 2011, pp. 1731-1740, vol. 39 No. 8.

(56) References Cited

OTHER PUBLICATIONS

Chen et al., "Depth of Subchondral Perforation Influences the Outcome of Bone Marrow Stimulation Cartilage Repair", Journal of Orthopedic Research, Feb. 24, 2011, pp. 1178-1184, vol. 29, No. 8.
Chen et al., "Drilling and Microfracture Lead to Different Bone Structure and Necrosis during Bone-Marrow Stimulation for Cartilage Repair", Journal of Orthopedic Research, Nov. 2009, pp. 1432-1438, vol. 27, No. 11.
Chen et al., "Influence of particle size on the in vivo potency of lipid nanoparticle formulations of siRNA," Journal of Controlled Release, Aug. 10, 2016, pp. 236-244, vol. 235.
Chen et al., "Nanoparticles targeting tumor-associated macrophages: A novel anti-tumor therapy", Nano Research, Jul. 2021, pp. 1-19.
Cheng et al., "Small Angle Neutron Scattering Study of Conformation of Oligo(ethylene glycol)-Grafted Polystyrene in Dilute Solutions: Effect of the Backbone Length," Macromolecules, 2008, pp. 9831-9836, vol. 41.
Cheng et al., "The role of helper lipids in lipid nanoparticles (LNPs) designed for oligonucleotide delivery", Advanced Drug Delivery Reviews, 2016, pp. 129-137, vol. 99.
Chenite et al., "Monolithic gelation of chitosan solutions via enzymatic hydrolysis of urea", Carbohydrate Polymers, Jan. 20, 2006, pp. 419-424, vol. 64.
Chenite et al., "Novel injectable neutral solutions of chitosan form biodegradable gels in situ", Biomaterials, Apr. 7, 2000, pp. 2155-2161, vol. 21.
Chenite et al., "Rheological characterization of thermogelling chitosan/glycerol-phosphate solutions", Carbohydrate Polymers, Jul. 28, 2000, pp. 39-47, vol. 46.
Chevrier et al., "Chitosan-glycerol phosphate/blood implants increase cell recruitment, transient vascularization and subchondral bone remodeling in drilled cartilage defects", Osteoarthritis and Cartilage, Aug. 10, 2006, pp. 316-327, vol. 15, No. 3.
Chevrier et al., "Injectable chitosan-platelet-rich plasma implants to promote tissue regeneration: in vitro properties, in vivo residence, degradation, cell recruitment and vascularization", Journal of Tissue Engineering and Regenerative Medicine, 2017, pp. 1-12.
Chevrier et al., "Injectable chitosan-platelet-rich plasma implants to promote tissue regeneration: In vitro properties, in vivo residence, degradation cell recruitment and vascularization" Journal of Tissue Engineering and Regenerative Medicine, 2018, pp. 217-228, vol. 12.
Chevrier et al., "Interspecies Comparison of Subchondral Bone Properties Important for Cartilage Repair", Journal of Orthopedic Research, Aug. 25, 2014, pp. 1-8, vol. 33, No. 1.
Chevrier et al., "Meniscus Structure in Human, Sheep, Rabbit, for Animal Models of Meniscus Repair", Journal of Orthopedic Research, Feb. 25, 2009, pp. 1197-1203, vol. 27.
Chevrier et al., "Soluble Recombinant Neprilysin Induces Aggrecanase-Mediated Cleavage of Aggrecan in Cartilage Explant Cultures", Archives of Biochemistry and Biophysics, 2001, pp. 1-9.
Chevrier et al., "Optimization of Histoprocessing Methods to Detect Glycosaminoglycan, Collagen Type II, and Collagen Type I in Decalcified Rabbit Osteochondral Sections", The Journal of Histotechnology, Sep. 2005, pp. 165-175, vol. 28, No. 3.
Chevrier et al., "Temporal and spatial modulation of chondrogenic foci in subchondral microdrill holes by chitosan-glycerol phosphate/blood implants", Osteoarthritis and Cartilage, Jan. 2011, pp. 136-144, vol. 19.
Chibowksi et al., "Zeta potential and surface charge of DPPC and DOPC liposomes in the presence of PLC enzyme", Adsorption, 2016, pp. 755-765, vol. 22.
Chithrani et al., "Polyethylene Glycol Density and Length Affects Nanoparticle Uptake by Cancer Cells", Journal of nanomedicine Research, Oct. 18, 2014, pp. 1-6, vol. 1, Issue 1.
Choi et al., "Safety and immunogenicity of SARS-CoV-2 variant mRNA vaccine boosters in healthy adults: an interim analysis," Nature Medicine, 2021, https://doi.org/10.1038/s41591-021-01527-y, 13 pages.
Clarke, "Characterizing the Zeta Potential & Isoelectric Point of Nanomaterials | Malvern Panalytical," 2013, 195 pages.
Clarke, "Development of Hierarchical Magnetic Nanocomposite Material for Biomedical Applications", Dublin City University, Jan. 2013, pp. 1-195.
Clayton et al., "Physical characterization of nanoparticle size and surface modification using particle scattering diffusometry", Biomicrofluidics, 2016, pp. 1-14, vol. 10.
clinicaltrials.gov, "Safety and Immunogenicity Study of 2019-nCoV Vaccine (mRNA-1273) for Prophylaxis Sars CoV-2 Infection (COVID-19)", 2019, 10 pages.
Cohen, "Vaccine designers take first shots at COVID-19," Science Mag, Apr. 3, 2020, pp. 14-16, vol. 368, Issue 6486.
Cohen, "What went wrong with the CureVac's mRNA vaccine", Science Magazine, 2021, p. 1381, vol. 372, No. 6549,.
Collier et al., "SARS-CoV-2 B.1.1.7 escape from mRNA vaccine-elicited neutralizing antibodies," MedRxiv, Feb. 2, 2021, 32 pages. Retrieved from the internet https://doi.org/10.1101/2021.01.19.21249840.
Collins, F., "Meet the Researcher Leading NIH's COVID-19 Vaccine Development Effort,". NIH Director's Blog, Jul. 9, 2020 [online], [retrieved on Mar. 8, 2022]. Retrieved from the Internet URL: https://directorsblog.nih.gov/2020/07/09/meet-the-researcher-leading-nihs-covid-19-vaccine-development-efforts/, 6 pages.
Collins, "Researchers Publish Encouraging Early Data on COVID-19 Vaccine: NIH Director's Blog", Jul. 16, 2020, 6 pages. Retrieved from the Internet URL: https://directorsblog.nih.gov/2020/07/16/researchers-publish-encouraging-early-data-on-covid-19-vaccine/.
Coon, et al. "Nitinol thin films functionalized with CAR-T cells for the treatment of solid tumours." Nature Biomedical Engineering 4.2, 2020, pp. 95-206.
Corbett et al., "SARS-CoV-2 mRNA vaccine design enabled by prototype pathogen preparedness", Nature, Aug. 5, 2020, pp. 567-571, vol. 586, No. 7830.
Corbett et al., "SARS-COV-2 mRNA Vaccine Development Enabled by Prototype Pathogen Preparedness," bioRxiv, Jun. 11, 2020, retrieved from the internet https://doi.org/10.1101/2020.06.11.145920, 39 pages.
Corbett, et al., "Evaluation of the mRNA-1273 Vaccine against SARS-CoV-2 in Nonhuman Primate", The New England Journal of Medicine, Jul. 28, 2020, pp. 1-12, vol. 383, No. 16.
Corbett et al., "Evaluation of the mRNA-1273 vaccine against SARS-CoV-2 in nonhuman primates, Supplementary Appendix", The New England Journal of Medicine, Jul. 28, 2020, pp. 1-24.
Corey et al., "A strategic approach to COVID-19 vaccine R&D," Science, May 11, 2020, DOI: 10.1126/science.abc5312, pp. 1-6.
Cott, E. et al., "How Pfizer Makes Its Covid-19 Vaccine," The New York Times, Apr. 28, 2021 [online], [retrieved on Mar. 8, 2022]. Retrieved from the Internet URL: https://www.nytimes.com/interactive/2021/health/pfizer-coronavirus-vaccine.html, 25 pages.
Crobett et al., "Advances in the measurement of protein mobility using laser Doppler electrophoresis—the diffusion barrier technique", Electrophoresis, 2011, pp. 1787-1794, vol. 32.
Cross, Chemical & Engineering News, Aug. 25, 7 pages. Retrieved from the Internet URL: https://cen.acs.org/pharmaceuticals/drug-discovery/Michelle-Lynn-Hall/97/i33.
Cross, "Modeling mastermind is using computational chemistry to help scientists craft mRNA therapies", Drug Discovery, Aug. 25, 2019, 7 pages, vol. 97, Issue 33.
Cugia et al., "Interplay of ion specificity, pH, and buffers: insights from electrophoretic mobility and pH measurements of lysozyme solutions", The Royal Society of Chemistry Advances, 2013, pp. 5882-5888, vol. 3.
Curevac, "About CureVac's activities regarding an mRNA-based vaccine against COVID-19", Apr. 8, 2020, 5 pages.
Curevac, "CureVac Announces Financial Results and Business Updates for the Third Quarter and First Nine Months of 2020", 9 pages.
Curevac, "CureVac Provides Update on Phase 2b/3 Trial of First-Generation COVID-19 Vaccine Candidate, CVnCoV", Jun. 16, 2021, 4 pages.

(56) References Cited

OTHER PUBLICATIONS

Dahlman, James E. et al., In vivo endothelial siRNA delivery using polymeric nanoparticles with low molecular weight, Nature Nanotechnology, 2014, No vol.#, pp. 1-8.
Dammes et al., "Conformation-sensitive targeting of lipid nanoparticles for RNA therapeutics", nature nanotechnology, Nature nanotechnology, 2021, pp. 1030-1038, vol. 16, No. 9.
Danaei et al., "Impact of particle Size and Polydispersity Index on the Clinical Applications of Lipidic nanocarrier Systems", Pharmaceutics, 2018, pp. 1-17, vol. 10.
Danaei et al., "Probing nanoliposomes using single particle analytical techniques: effect of excipients, solvents, phase transition and zeta potential", Heliyon, Dec. 2018, pp. 1-32.
Darras et al., "Chitosan modified with gadolinium diethylenetriaminepentaacetic acid for magnetic resonance imaging of DNA/chitosan nanoparticles", Carbohydrate Polymers, Jan. 22, 2010, pp. 1137-1146, vol. 80.
Davidson et al., "Fibroblast Growth Factor (FGF) 18 Signals through FGF Receptor 3 to Promote Chondrogenesis", The Journal of Biological Chemistry, Mar. 21, 2005, pp. 20509-20515, vol. 280, No. 21.
Dedeudis, "Learned a lot last year': After Covid-19 success, Moderna's Stéphane Bancel plans to give rest of pipeline a big push", Endpoint News, 2021, 29 pages.
Demolliens et al., "Tyrosinase-Catalyzed Synthesis of a Universal Coil-Chitosan Bioconjugate for Protein immobilization", Bioconjugate Chemistry, Aug. 14, 2008, pp. 1849-1854, vol. 19, No. 9.
Deng et al., "Primary exposure to SARS-CoV-2 protects against reinfection in rhesus macaques," Science, Jul. 2, 2020, pp. 1-10, DOI: 10.1126/science.abc5343.
Deprés-Tremblay et al., "Chitosan inhibits platelet-mediated clot retraction, increases platelet-derived growth factor release, and increases residence time and bioactivity of platelet-rich plasma in vivo", Biomedical Materials, Nov. 10, 2017, pp. 1-11, vol. 13.
Deprés-Tremblay et al., "Freeze-Dried Chitosan-Platelet-Rich Plasma Implants for Rotator Cuff Tear repair: Pilot Ovine Studies" ACS Biomaterials Science and Engineering, Oct. 13, 2017, pp. 1-10, vol. 4, No. 11.
Deprés-Tremblay et al., "Rotator cuff repair: a review of surgical techniques, animal models, and new technologies under development", Journal of Shoulder and Elbow Surgery, 2016, pp. 2078-2085, vol. 25.
DeRosa et al., "Improved Efficacy in a Fabry Disease Model Using a Systemic mRNA Liver Depot System as Compared to Enzyme Replacement Therapy," Molecular Therapy, Apr. 2019, pp. 878-889, vol. 27, Issue No. 4.
Di et al., "When liposomes met antibodies: Drug delivery and beyond", Advanced Drug Delivery Reviews, Sep. 2020, pp. 151-162, vol. 154-155.
Dinnon, "SARS-CoV-2 mRNA Vaccine Design Enabled by Prototype Pathogen Preparedness, Peer review File", Natureresearch, 2020, pp. 12 pages.
Dinpajooh et al., "Mobility of nanometer-size solutes in water riven by electric field", Arizona State University, Jun. 7, 2016, pp. 1-10.
Dipiazza et al., "COVID-19 vaccine mRNA-1273 elicits a protective immune profile in mice that is not associated with vaccine-enhanced disease upon SARS-CoV-2 challenge", Immunity, Jun. 2021, pp. 1869-1882, vol. 54, No. 8.
Doane et al., "Nanoparticle Potentials", Accounts of Chemical Research, 2012, pp. 317-326, vol. 45, No. 3.
Dold et al., "A poly (beta-amino ester) activates macrophages independent of NF-KB signaling", Acta Biomaterialia, 2018, pp. 168-177, vol. 68.
Dolsten, "COVID-19 R&D," Pfizer, No. Date, 30 pages.
Doremalen et al., "ChAdOx1 nCoV-19 vaccination prevents SARS-CoV-2 pneumonia in rhesus macaques," bioRxiv, May 13, 2020, retrieved from the internet https://doi.org/10.1101/2020.05.13.093195, 23 pages.
Dreyfus, et al., 2002, The poly(A) tail of mRNAs: Bodyguard in eukaryotes, scavenger in bacteria, Cell, Nov. 27, 2002, pp. 611-613.
Drzymala et al., "Ice/Water interface: Zeta Potential, Point of Zero Charge, and Hydrophobicity", Journal of Colloid and Interface Science, 1999, pp. 229-234, vol. 220.
Dudek et al., "Knockdown of B-catenin with Dicer-Substrate sirRNAs Reduces Liver Tumor Burden in vivo", Molecular Therapy, Jan. 2014, pp. 92-101, vol. 22, No. 1.
Duguay et al., "Lipofection of plasmid DNA into human mast cell lines using lipid nanoparticles generated by microfluidic mixing", Journal of Leukocyte Biology, Mar. 2018, pp. 587-596, vol. 104.
Dumont et al., "Mature Full-thickness Articular Cartilage Explants Attached to Bone are Physiologically Stable over Long-term Culture in Serum-free Media", Connective Tissue Research, Apr. 29, 1999, pp. 259-272, vol. 40, No. 4.
Duval-Valentin et al, "Specific Inhibition of Transcription by Triple Helix-Forming Oligonucleotides," Proc. Natl. Acad. Sci. USA, 89:504-508 (1992).
Dwivedi et al., "Bone Marrow Progenitor Cells Isolated from Young Rabbit Trochlea are More Numerous and Exhibit Greater Clonogenic, Chondrogenic, and Osteogenic Potential than Cells Isolated from Condyles", Cartilage, 2018, pp. 378-390, vol. 9, No. 4.
Dwivedi et al., "Injectable freeze-dried chitosan-platelet-rich-plasma implants improve marrow-stimulated cartilage repair in a chronic-defect rabbit model", Journal of Tissue Engineering and Regenerative Medicine, Jan. 14, 2019, pp. 599-611, vol. 13.
Efrati et al., "Safety and humoral responses to BNT162b2 mRNA vaccination of SARS-CoV-2 previously infected and naïve populations," Scientific Repports, 2021, 7 pages, vol. 11, No. 16543. https://doi.org/10.1038/s41598-021-96129-6.
Egawa et al., "Liposome Adhesion on Mica Surface Studied by Atomic Force Microscopy", Langmuir, Dec. 18, 1998, pp. 1660-1666, vol. 15.
Egholm, et al., PNA hybridizes to complementary oligonucleotides obeying the Watson-Crick hydrogen-bonding rules, Nature, Oct. 1993, pp. 566-568.
Elbashir, et al., Duplexes of 21-nucleotide RNAs mediate RNA interference in cultured mammalian cells, Nature, May 2001, pp. 494-498, vol. 411.
El-Bikai et al., "Perturbation of adhesion molecule-mediated chondrocyte-matrix interactions by 4-hydroxynonenal binding: implication in osteoarthritis pathogenesis", Arthritis research and Therapy, 2010, pp. 1-14, vol. 12.
EMA, "Assessment Report: COVID-19 Vaccine Moderna", European Medicines Agency, Mar. 11, 2021, pp. 1-169.
Espeseth, Supplementary Files, "Supplementary Figure 1. Flow Cytometry of RSV F constructs containing an intact transmembrane domain expressed in Expi293F cells", No Date, 14 pages.
Evans et al., "Endosomolytic Nano-Polyplex Platform Technology for Cytosolic Peptide Delivery to Inhibit Pathological Vasoconstriction", ACS Nano, 2015, pp. 5893-5907, vol. 9 No. 6.
Everton et al., "Transient yet Robust Expression of Proteins in the Mouse Liver via Intravenous Injection of Lipid Nanoparticle-encapsulated Nucleoside-modified mRNA," Bio-protocol, Oct. 15, 2021, pp. 1-15, vol. 11, No. 19.
Ewert et al., "Lipoplex Structures and their Distinct cellular Pathways", Advanced in Genetics, 2005, pp. 119-155, vol. 53.
Fairhurst, "An Overview of the Zeta Potential—Part 2: Measurement," American Pharmaceutical Review, Apr. 1, 2013, 6 pages.
Falsey, et al., "SARS-CoV-2 Neutralization with BNT162b2 Vaccine Dose 3," N Engl J Med, 2021, pp. 1-3.
Falsini, Advances in Lipid-Based Platforms for RNAi Therapeutics, J. Med. Chem., Sep. 18, 2013, pp. 1138-1146, vol. 57, No. 4.
Fan et al., "Analytical characterization of liposomes and other lipid nanoparticles for drug delivery", Journal of Pharmaceutical and Biomedical Analysis, 2021, pp. 1-21, vol. 192.
Fang et al., "Evidence of the adsorption of hydroxide ion at hexadecane/water interface from second harmonic generation study", The Royal Society of Chemistry Advances, 2015, pp. 23578-23585, vol. 5.
Fehring et al., "Delivery of Therapeutic siRNA to the Lung Endothelium via Novel Lipoplex Formulation DACC", Molecular Therapy, Apr. 2014, pp. 811-820, vol. 22 No. 4.
Feldman et al., "mRNA vaccines against H10N8 and H7N9 influenza viruses of pandemic potential are immunogenic and well

(56) References Cited

OTHER PUBLICATIONS tolerated in healthy adults in phase 1 randomized clinical trials", Vaccine, May 2019, pp. 3326-3334, vol. 37.
Felgner, PL Cationic lipid/polynucleotide condensates for in vitro and in vivo polynucleotide delivery—the cytofectins. J. of Liposome Research. 1993; 3(1): 3-16.
Felgner P.L., et al., "Lipofection: A Highly Efficient, Lipid-Mediated DNA-Transfection Procedure," Proceedings of the National Academy of Sciences USA, vol. 84 (21), Nov. 1987, pp. 7413-7417.
Felgner, Pl Particulate systems and polymers for in vitro and in vivo delivery of polynucleotides. Adv. Drug Delivery Rev. 1990; 5(3): 163-187.
Fenton et al., "Synthesis and biological Evaluation of Ionizable Lipid Materials for the In Vivo Delivery of Messenger RNA to B Lymphocytes", Advanced Materials, Supporting Information, 2017, pp. 1-17.
Ferretti, et al., "COVID-19 Patients Form Memory CD8+ T Cells that Recognize a Small Set of Shared Immunodominant Epitopes in SARS-CoV-2," medRxiv, Jul. 29, 2020, pp. 1-21. retrieved from URL https://doi.org/10.1101/2020.07.24.20161653.
Filion et al., "Chitosan-glycerol-phosphate (GP) gels release freely diffusible GP and possess titratable fixed charge", Carbohydrate Polymers, Jul. 4, 2013, pp. 813-819, vol. 98.
Filion et al., "Ionization and Solubility of Chitosan Solutions related to Thermosensitive Chitosan/Glycerol-Phosphate Systems", Biomacromolecules, Jul. 12, 2007, pp. 3224-3234, vol. 8.
Finn et al., "A Single Administration of CRISPR/Cas9 Lipid Nanoparticles Achieves Robus and Persistent In Vivo Genome Editing", Cell Reports, 2018, pp. 2227-2235, vol. 22, No. 9.
Fish et al., "Deformable microparticles for shuttling nanoparticles to the vascular wall", Science Advances, Apr. 2021, pp. 1-11, vol. 7.
Fleischmann et al., "General Sites of Nanoparticle Biodistribution as a Novel Opportunity for Nanomedicine", European Journal of Pharmaceutics and Biopharmaceutics, May 2021, pp. 44-60, vol. 166.
Fobian et al., "Smart Lipid-Based Nanosystems for Therapeutic Immune Induction against Cancers: perspectives and Outlooks", Pharmaceutics, Dec. 2021, pp. 1-43, vol. 14.
Fohse et al., "The BNT162b2 mRNA vaccine against SARS-CoV-2 reprograms both adaptive and innate immune responses," medRxiv, May 6, 2021, pp. 1-21. retrieved from URL https://doi.org/10.1101/2021.05.03.2125650.
Folegatti, et al., "Safety and immunogenicity of the ChAdOx1 nCoV-19 vaccine against SARS-CoV-2: a preliminary report of a phase 1/2, single-blind, randomised controlled trial," The Lancet, Jul. 20, 2020, pp. 1-13. retrieved from URL https://doi.org/10.1016/S0140-6736(20)31604-4.
Fong et al., "Biodegradable chitosan microparticles induce delayed STAT-1 activation and lead to distinct cytokine responses in differently polarized human macrophages in vitro", Acta Biomaterialia, Oct. 25, 2014, pp. 183-194, vol. 12.
Food and Drug Administration, "Fact sheet for healthcare providers administering vaccine (vaccination providers): Emergency Use Authorization (EUA) of the Pfizer-BioNTech COVID-19 vaccine to prevent coronavirus disease 2019 (COVID-19), Silver Spring, MD: US Department of Health and Human Services." Food and Drug Administration, 2021, 30 pages.
Fornaguera et al., "mRNA Delivery System for targeting Antigen-Presenting Cells In Vivo", Advanced Healthcare Materials, 2018, pp. 1-11, vol. 7.
Fortin et al., "Dynamic measurement of internal solid displacement in articular cartilage using ultrasound backscatter", Journal of biomechanics, 2003, pp. 443-447, vol. 36.
Fortin et al., "Unconfined Compresion of Articular Cartilage: Nonlinear behavior and Comparison with a Fibril-Reinforced Biphasic Model", Journal of Biomechanical Engineering, Apr. 2000, pp. 189-195, vol. 122.
Foster et al., "Development of GPC2-directed chimeric antigen receptors using mRNA for pediatric brain tumors," bioRxiv, Jul. 7, 2021, 40 pages. retrived from URL https://doi.org/10.1101/2021.07.06.451385.
Foster et al., "Purification of mRNA Encoding Chimeric Antigen Receptor Is Critical for Generation of a Robust T-Cell Response," Human Gene Therapy, 2019, pp. 168-178, vol. 30, No. 2.
Fotin-Mleczek, M., et al., "Messenger RNA-Based Vaccines with Dual Activity Induce Balanced TLR-7 Dependent Adaptive Immune Responses and Provide Antitumor Activity," Journal of Immunotherapy 34(1 ): 1-15, Informa Healthcare, England (2011 ).
Fox, Targeting DNA with triplexes, Current medicinal chemistry, Jan. 1, 2000, pp. 17-37, vol. 7, No. 1.
Franklin et al., "Internal Electrostatic Potentials in Bilayers: Measuring and Controlling Dipole Potentials in Lipid vesicles", Biophysical Journal, Jul. 1993, pp. 289-299, vol. 65.
Freichel et al., "Effects of Linker and Liposome Anchoring on Lactose-functionalized Glycomacromolecules as Multivalent Ligands for Binding Galectin-3", The Royal Society of Chemistry, Supporting Information, 2019, 56 pages.
Friedman, "membrane-Ion Interactions", The Journal of Membrane Biology, 2018, pp. 453-460, vol. 251.
Fuchs et al., "Lipid analysis by thin-layer chromatography—A review of the current state", Journal of Chromatography A, 2011, pp. 2754-2774, vol. 1218.
Gallas, Chemistry and formulations for siRNA therapeutics, Chem. Soci. Rev., 2013, pp. 7983-7997, vol. 42, No. 20.
Gan et al., "The behavior of hydroxide and hydronium ions at the hexadecane-water interface studied with second harmonic generation and zeta potential measurements", Soft Matter, Apr. 2017, pp. 7962-7968, vol. 13.
Ganesh et al., "Direct Pharmacological Inhibition of β-Catenin by RNA Interference in Tumors of Diverse Origin", Molecular Cancer Therapeutics, Sep. 2016, pp. 2143-2154, vol. 15, No. 9.
Gao et al., "Development of an inactivated vaccine candidate for SARS-CoV-2," Science, May 6, 2020, pp. 1-10.
Gao et al., "Mesenchymal Stem Cell Transplantation to Promote Bone Healing", Journal of Orthopedic Research, Jan. 6, 2012, pp. 1183-1189, vol. 30, No. 8.
Garon et al., "Streaming potentials maps are spatially resolved indicators of amplitude frequency and ionic strength dependent response of articular cartilage to load", Journal of Biomechanics, 2002, pp. 207-216, vol. 35.
Gauthier et al., "Degree of crosslinking and mechanical properties of crosslinked poly (vinyl alcohol) beads for use in solid-phase organic synthesis", Polymer, Oct. 12, 2004, pp. 8201-8210, vol. 45.
Geall et al., RNA: the new revolution in nucleic acid vaccines, InSeminars in immunology, Apr. 1, 2013, pp. 152-159, vol. 25, No. 2.
Gessner, "Optimizing nanoparticle design and surface modification toward clinical translation", MRS Bulletin, Jul. 2021, pp. 1-7, vol. 6.
Ghazi et al., "Freeze-Dried Chitosan-PRP Injectable Surgical Implants for Meniscus Repair: Pilot Feasibility Studies in Ovine Models", Regenerative Medicine and Therapeutics, 2017, pp. 16-29, vol. No. 1,.
Ghazi et al., "Freeze-dried chitosan-PRP injectable surgical implants for meniscus repair: Pilot feasibility studies in ovine models", The Open Orthopedics Journal, No Date, pp. 1-31.
Ghazi et al., "Multiple platelet-rich plasma preparations can solubilize freeze-dried chitosan formulations t form injectable implants for orthopedic indications", Bio-Medical Materials and Engineering, 2019, pp. 349-364, vol. 30.
Gigout et a., "Chondrocyte Aggregation in Suspension Culture is GFOGER-GPP- and β1 Integrin-dependent", The Journal of Biological Chemistry, Nov. 14, 2008, pp. 31522-31530, vol. 283, No. 46.
Gigout et al., "CHO Cells Adhering to Nitrogen-Rich Plasma-Polymerised Ethylene Exhibit High Production of a Specific Recombinant Protein", Macromolecular Bioscience, 2009, pp. 979-988, vol. 9.
Gigout et al., "Chondrocytes Cultured in Stirred Suspension with Serum-Free Medium Containing Pluronic-68 Aggregate and Prolif-

(56) References Cited

OTHER PUBLICATIONS erate While Maintaining their Differentiated Phenotype", Tissue Engineering, 2009, pp. 1-12, vol. 15 No. 8.
Gigout et al., "Low calcium levels in serum-free media maintain chondrocyte phenotype in monolayer culture and reduce chondrocyte aggregation in suspension culture", Osteoarthritis and Cartilage, 2005, pp. 1012-1024, vol. 13.
Gigout et al., "The Fate of Pluronic F-68 in Chondrocytes and CHO Cells", Biotechnology and Bioengineering, Aug. 1, 2008, pp. 975-987, vol. 100, No. 5.
Gilleron et al., "Image-based analysis of lipid nanoparticle-mediated siRNA delivery, intracellular trafficking and endosomal escape", Nature Biotechnology, Jul. 2013, pp. 638-670, vol. 13, No. 7.
Gindy et al., "Challenges in the pharmaceutical development of lipid-based short interfering ribonucleic acid therapeutics", Taylor Francis Online, Feb. 1, 2012, pp. 171-182, vol. 9, Issue 2.
Gindy et al., "Stabilization of Ostwald Ripening in Low Molecular Weight Amino Lipid Nanoparticles for Systemic delivery of siRNA Therapeutics, Supporting Information", Molecular Pharmaceutics, 2014, pp. 4143-4153, vol. 11.
Giuliani, et al., A universal vaccine for serogroup B meningococcus, Proc Natl Acad Sci., Jul. 18, 2006, pp. 10834-9, vol. 103, No. 29.
Glaszlou, "Waste in covid-19 research," BMJ, May 12, 2020, pp. 1-2, vol. 369, No. m1847.
Graham et al., "Evaluation of the immunogenicity of prime-boost vaccination with the replication-deficient viral vectored COVID-19 vaccine candidate ChAdOx1 nCoV-19," bioRxiv, Jun. 20, 2020, pp. 1-11. retrieved from URL https://doi.org/10.1101/2020.06.20.159715.
Graham et al., "Rapid COVID-19 vaccine development," Science, May 8, 2020, 5 pages. DOI: 10.1126/science.abb8923.
Graham et al., "Structure-Based Vaccine Antigen Design," Annual Review of Medicine, 2019, pp. 91-104, vol. 70.
Granot-Matok et al., "Therapeutic mRNA delivery to leukocytes", Journal of Controlled Release, May 2019, pp. 165-175, vol. 305.
Greenwood et al., "Partial molecular vols. of lipids and cholesterol", Chemistry and Physics of Lipids, 2006, pp. 1-10, vol. 143.
Grifoni et al., "Targets of T Cell Responses to SARS-CoV-2 Coronavirus in Humans with COVID-19 Disease and Unexposed Individuals," Cell, Supplemental Information, Jun. 25, 2020, 6 pages.
Grit et al., "Determination of phosphatidylcholine, phosphatidylglycerol and their lyso forms from liposome dispersions by high-performance liquid chromatography using high-sensitivity refractive index detection" Journal of Chromatography, May 1991, pp. 239-246, vol. 585.
Grudzien-Nogalska et al., Synthetic mRNAss with superior translation and stability properties in Synthetic Messenger RNA and Cell Metabolism Modulation in Methods in Molecular Biology, 2013, pp. 55-72.
Gubernatorova et al., "IL-6: Relevance for immunopathology of SARS-CoV-2," Cytokine and Growth Factor Reviews, May 20, 2020, pp. 13-24, vol. 53.
Guhaniyogi, J. et al., Regulation of mRNA stability in mammalian cells. Gene. Mar. 7, 2001;265(1-2):11-23.
Guyon et al., "Relevant Physiochemical Methods to Functionalize, Purify, and Characterize Surface-Decorated Lipid-Based Nanocarriers", Molecular Pharmaceutics, 2021, pp. 44-64, vol. 18.
Guzmám-Morales et al., "Subchondral chitosan/blood implant-guided bone plate resorption and woven bone repair is coupled to hyaline cartilage regeneration from microdrill holes in aged rabbit knees", Osteoarthritis and Cartilage, 2014, pp. 323-333, vol. 22.
Hadjab et al., "Electromechanical properties of human osteoarthritic and asymptomatic articular cartilage are sensitive and earl detectors of degeneration", Osteoarthritis and Cartilage, 2018, pp. 405-413, vol. 26.
Hafez, et al., Gene Ther 8:1188-1196, 2001.
Hafez et al., "Tunable pH-Sensitive Liposomes Composed of Mixtures of Cationic and Anionic Lipids", Biophysical Journal, Sep. 2000, pp. 1438-1446, vol. 79.
Hajj et al., "A Potent Branched-Tail Lipid Nanoparticle Enables Multiplexed mRNA Delivery and Gene Editing In Vivo," Nano Letters, 2020, pp. 5167-5175, vol. 20.
Hajj et al., "Branched-Tail Lipid Nanoparticles Potently Deliver mRNA In Vivo due to Enhanced Ionization at Endosomal pH," Small, 2019, pp. 1-16, vol. 10.
Hajj et al., "Tools for translation: non-viral materials for therapeutic mRNA delivery," Nature Reviews Material, Sep. 12, 2017, pp. 1-17, vol. 2.
Hamman, et al., Length variation of helix III in a hammerhead ribozyme and its influence on cleavage activity, Antisense and Nucleic Acid Drug Dev., Feb. 1999, pp. 25-31, vol. 9, No. 1.
Han et al., "The Forward Problem of Electroarthrography: Modeling Load-Induced electrical Potentials at the Surface of the Knee", IEEE Transactions on Biomedical Engineering, Jul. 2014, pp. 2020-2027, vol. 61, No. 7.
Hassett et al., "Optimization of Lipid Nanoparticles for Intramuscular Administration of mRNA Vaccines", OMTN, 2019, pp. 1-7, vol. 15.
Heerklotz, "Interactions of surfactants with lipid membranes", Quarterly Reviews of Biophysics, 2008, p. 205-264, vol. 41.
Heilig et al., Large-Scale Preparation of Plasmid DNA, Current Protocols in Molecular Biology, Jan. 1998, pp. 1-7.
Helfand, C., "JPM: How did Pfizer up its COVID-19 vaccine capacity? 'Out of the box manufacturing,' CEO says," FiercePharma, Jan. 13, 2021, 5 pages [online], [retrieved on Mar. 8, 2022]. Retrieved from the Internet URL: https://www.fiercepharma.com/pharma/jpm-how-did-pfizer-up-its-covid-19-vaccine-capacity-out-box-manufacturing-ceo-says.
Heyes, et al., "Genevant Keto Intermediate", American Chemical Society, 2020, 3 pages.
Heyes, et al., Genevant Tail Procedure, American Chemical Society, 2020, 3 pages.
Heyes, J. et al. (2005), "Cationic lipid saturation influences intracellular delivery of encapsulated nucleic acids," Journal of Controlled Release, 107:276-287.
Hill et al., "Electrophoretic Interpretation of PEGylated NP Structure with and without Peripheral Charge", Langmuir, Sep. 2, 2015, pp. 10246-10253, vol. 31.
Hinton et al., "Letter in response to a request from Pfizer Inc. tthat the Food and Drug Administration (FDA) issue an Emergency Use Authorization for emergency use of Pfizer-BioNTech COVID-19 Vaccine," US FDA, Dec. 11, 2020, 9 pages.
Hinton, Letter to Moderna from the Food and Drug Administration, Dec. 18, 2020, 9 pages.
Hoemann et al., "A Multivalent Assay to Detect Glycosaminoglycan, Protein, Collagen, RNA, and DNA Content in Milligram Samples of Cartilage or Hydrogel-based Repair Cartilage", Analytical Biochemistry, 2001, pp. 1-10, vol. 300, No. 1.
Hoemann et al. Appendix to "Chondroinduction is the Main Cartilage Repair Response to Microfracture and Microfracture with BST-CarGel", The American Journal of Sports Medicine, Aug. 10, 2015, 4 pages.
Hoemann et al., "Scaffold-Guided Subchondral Bone Repair", The American Journal of Sports Medicine, 2010, pp. 1-13, vol. 38, No. 9.
Hoemann et al., "Characterization of Initial Microfracture Defects in Human Condyles", The Journal of Knee Surgery, 2013, pp. 1-10, vol. 26, No. 5.
Hoemann et al., "Chitosan Rate of Uptake in HEK293 Cells is Influenced by Soluble versus Microparticle State and Enhanced by Serum-Induced Cell Metabolism and Lactate-Based Media Acidification", Molecules, 2013, pp. 1-21, vol. 18.
Hoemann et al., "Chitosan-glycerol phosphate/blood implants elicit hyaline cartilage repair integrated with porous subchondral bone in microdrilled rabbit defects", osteoarthritis and Cartilage, 2007, pp. 78-89, vol. 15.

(56) References Cited

OTHER PUBLICATIONS

Hoemann et al., "Chitosan-Glycerol Phosphate/Blood Implants Improve Hyaline Cartilage Repair in Ovine Microfracture Defects", The Journal of Bone and Joint Surgery, Dec. 2005, pp. 2671-2686, vol. 87, No. 12.
Hoemann et al., "Chondroinduction is the Main Cartilage Repair Response to Microfracture and Microfracture with BST-CarGel", The American Journal of Sports Medicine, Aug. 10, 2015, pp. 1-12, vol. XX, No. X.
Hoemann et al., "Cytocompatible gel formation of Chitosan-glycerol phosphate solutions supplemented with hydroxyl ethyl cellulose is due to the presence of glyoxal", Journal of Biomedical Materials Research Part A, Feb. 27, 2007, pp. 521-529, vol. 83, No. 2.
Hoemann et al., "In vitro osteogenesis assays: Influence of the primary cell source on alkaline phosphatase activity and mineralization", Pathologie Biologie, 2008, pp. 1-6, vol. 57, No. 4.
Hoemann et al., "International Cartilage Repair Society (ICRS) Recommended Guidelines for Histological Endpoints for Cartilage Repair Studies in Animal Models and Clinical Trials", Cartilage, 2011, pp. 153-172, vol. 2, No. 2.
Hoemann et al., "The Cartilage-Bone Interface", The Journal of Knee Surgery, 2012, pp. 1-13, vol. 25, No. 2.
Hoemann et al., "Tissue engineering of cartilage using and injectable and adhesive chitosan-based cell delivery vehicle", Osteoarthritis and Cartilage, 2005, pp. 318-329, vol. 13.
Hoemann et al., "Two Distinct Notch1 Mutant Alleles are Involved in the Induction of T-Cell Leukemia in c-myc Transgenic Mice", Molecular and Cellular Biology, Jun. 2000, pp. 3831-3842, vol. 20 No. 11.
Hoemann, "Molecular and Biochemical Assays of Cartilage Components", Cartilage and Osteoarthritis, 2004, pp. 127-156.
Hoerr, I. et al., In vivo application of RNA leads to induction of specific cytotoxic T lymphocytes and antibodies. EurJ Immunol. Jan. 2000;30(1): 1-7.
Hoffman et al., "Age- and Sex-Graded Data Evaluation of Vaccination Reactions after Initial Injection of the BNT162b2 mRNA Vaccine in a Local Vaccination Center in Germany," Vaccines, Aug. 16, 2021, pp. 1-10, vol. 9, No. 911.
Hoffmann et al., CnCoV protects human ACE2 trangenic mice from ancestral B PavPat1 and emerging B.1.351 SARS-CoV-2, Cell Rep Med, 2021, pp. 1-16, vol. 2.
Hotz et al., "Local delivery of mRNA-encoding cytokines promotes antitumor immunity and tumor eradication across multiple preclinical tumor models," Science Translational Medicine, Sep. 8, 2021, pp. 1-13, vol. 13.
Hu et al., "Polysarcosine as an Alternative to PEG for Therapeutic Protein Conjugation," Bioconjugate Chem, 2018, pp. 2232-2238, vol. 29.
Huang et al., "Priming with SARS CoV S DNA and boosting with SARS CoV S epitopes specific for CD4+ and CD8+ T cells," Vaccine, Jul. 16, 2007, pp. 6981-6991, vol. 25.
Huotari et al., "Endosome Maturation", The EMBO Journal, 2011, pp. 3481-3500, vol. 30.
Hurtig et al., "Preclinical Studies for Cartilage Repair: Recommendations from the International Cartilage Repair Society", Cartilage, 2011, pp. 137-152, vol. 2, No. 2.
Idrus, "Moderna's COVID-19 jab spurs 'robust' immune response in first published data", FierceBiotech, Jul. 14, 2020, 5 Pages. Retrieved from the Internet URL: https://www.fiercebiotech.com/biotech/moderna-s-covid-19-jab-spurs-immune-response-first-published-data.
Idrus, "Moderna COVID-19 vaccine passes FDA reviewers' test, but shares drop anyway", FierceBiotech, Dec. 15, 2020, 7 pages. Retrieved from the Internet URL: https://www.fiercebiotech.com/biotech/moderna-covid-19-shot-passes-muster-at-fda-but-shares-dip.
Iliescu et al., "Ultrastructure of Hybrid Chitosan-Glycerol Phosphate Blood Clots by Environmental Scanning Electron Microscopy", Microscopy Research and Technique, 2008, pp. 236-247, vol. 71.
International Organization for Standardazation, "Particle size analysis—Dynamic light scattering (DLS)," International Organization for Standardization, Feb. 2017, 3 pages.
International Search Report and Written Opinion for Application No. PCT/US2021/054837, mailed Mar. 18, 2022, 12 pages.
International Search Report and Written Opinion for International Application No. PCT/US2021/054839, mailed Feb. 8, 2022, 14 pages.
Invitation to Pay Additional Fees for International Application No. PCT/US2021/054837, mailed Jan. 13, 2022, 2 pages.
Ishida T et al., "A combinatorial approach to producing sterically stabilized (Stealth) immunoliposomal drugs." FEBS Letters, vol. 460, 1999, pp. 129-133. (Year: 1999).
Isho, B. et al., "Persistence of serum and saliva antibody responses to SARS-CoV-2 spike antigens in COVID-19 patients," Science Immunology, Oct. 8, 2020, pp. 1-21. [online], [retrieved on Mar. 8, 2022]. Retrieved from the Internet URL: https://www.science.org/doi/10.1126/sciimmunol.abe5511.
Iyer et al., "Persistence and decay of human antibody responses to the receptor binding domain of SARS-CoV-2 spike protein in COVID-19 patients," Science Immunology, Oct. 8, 2020, pp. 1-13, DOI: 10.1126/sciimmunol.abe0367.
Jackson, et al., "An mRNA Vaccine against SARS-CoV-2—Preliminary Report", The New England Journal of Medicine, Nov. 12, 2020, 6 pages. Retrieved from the Internet URL: https://doi.org/10.1056/NEJMoa2022483.
Jackson, et al., "Experimental COVID-19 vaccine safe, generates immune response", Jul. 14, 2020, 4 pages. Retrieved from the Internet URL: https://www.nih.gov/news-events/news-releases/experimental-covid-19-vaccine-safe-generates-immune-response.
Jackson et al., "The promise of mRNA vaccines: a biotech and industrial perspective," npj Vaccines, Feb. 4, 2020, pp. 1-6, vol. 11.
Jackson et al., "An mRNA Vaccine against SARS-CoV-2 Preliminary Report," The New England Journal of Medicine, pp. 1-12 (2020).
Jahn et al., "Microfluidic Mixing and the Formation of Nanoscale Lipid Vesicles", ACS Nano, Mar. 31, 2010, pp. 2077-2087, vol. 4, No. 4.
Janowski et al., Inhibiting gene expression at transcription start sites in chromosomal DNA with antigene RNAs, Nature Chemical Biology, Sep. 1, 2005, pp. 216-222.
Jansig et al., "Viromers as carriers for mRNA-mediated expression of therapeutic molecules under inflammatory conditions," Scientific Reports, Sep. 15, 2020, 3 pages, vol. 10, retrieved from URL https://doi.org/10.1038/s41598-020-72004-8.
Jarry et al., "Effects of Steam Sterilization on Thermogelling Chitosan-Based Gels", 2000, pp. 127-135, vol. 58, No. 1.
Jayaraman et al., "Maximizing the Potency of siRNA Lipid Nanoparticles for Hepatic Gene Silencing In Vivo," Angew. Chem. Int. Ed. 2012, 51, 8529-8533.
Jean et al., "Chitosan-based therapeutic nanoparticles for combination gene therapy and gene silencing of in vitro cell lines relevant to type 2 diabetes", European Journal of Pharmaceutical Sciences, 2012, pp. 138-149, vol. 45.
Jean et al., "Chitosan-plasmid nanoparticle formulations for IM and SC delivery of recombinant FGF-2 and PDGF-BB or generation of antibodies", Gene Therapy, 2009, pp. 1097-1110, vol. 16.
Jean et al., "Effective and safe gene-based delivery of GLP-1 using chitosan/plasmid-DNA therapeutics nanocomplexes in an animal model of type 2 diabetes", Gene Therapy, 2011, pp. 807-816, vol. 18.
Jeong et al., "Assemblies of putative SARS-CoV-2-spike-enconding mRNA Sequences for Vaccines BNT-162b2 and mRNA-1273", Version 0.1beta, Mar. 23, 2021, pp. 1-4.
Jiang et al., "Identification of murine antigen-specific T follicular helper cells using an activation-induced marker assay," Journal of Immunological Methods, Feb. 22, 2019, pp. 48-57, vol. 467.

(56) References Cited

OTHER PUBLICATIONS

Jiang et al., "Quantitating endosomal Escape of a Library of Polymers for mRNA Delivery", Nano Letters, 2020, pp. 1117-1123, vol. 20.
Jimeno, et al., "Abstract CT032: A phase 1/2, open-label, multi-center, dose escalation and efficacy study of mRNA-2416, a lipid nanoparticle encapsulated mRNA encoding human OX40L, for intratumoral injection alone or in combination with durvalumab for patients with advanced malignancies. AACR", Aug. 2020, 4 pages. Retrieved from the Internet URL: https://cancerres.aacrjournals.org/content/80/16_Supplement/CT032.
Johnson et al., "CureVac, latest experimental coronavirus vaccine, proved just 47 percent effective amid spread of variants, preliminary analysis shows", The Washington Post, 2021, pp. 1-7.
Jorge et al., "Lipid Nanocarriers for Oligonucleotide Delivery to the Brian", Nanoparticles for Brain Drug Delivery, Chapter 8, 2021, pp. 258-287.
Joshi et al., "Microfluidics based manufacture of liposomes simultaneously entrapping hydrophilic and lipophilic drugs", International Journal of Pharmaceutics, Jul. 2016, pp. 160-168, vol. 514.
Jurvelin et al., "Mechanical anisotropy of the human knee articular cartilage in compression", Journal of engineering in Medicine, 2003, pp. 215-219, vol. 217.
Jurvelin et al., Optical and Mechanical Determination of Poisson's Ratio of Adult Bovine Humeral Articular Cartilage, Journal of Biomechanics, 1997, pp. 335-241, vol. 30 No. 3.
Kaczmarek et al., "Polymer-Lipid Nanoparticles for Systemic Delivery of mRNA to the Lungs", Angewandte Chemical International Edition, 2016, pp. 13808-13812, vol. 55.
Kaczmarek et al., "Systemic Delivery of mRNA and DNA to the Lung using Polymer-Lipid Nanoparticles", Biomaterials, Journal Pre-Proof, Jun. 2021, pp. 1-25,.
Kallen et al., "A novel, disruptive vaccination technology", Human Vaccines and Immunotherapeutics, 2013, pp. 2263-2276, vol. 9.
Kalnin et al., "Immunogenicity of novel mRNA COVID-19 vaccine MRT5500 in mice and non-human primates," bioXriv, Oct. 14, 2020, pp. 1-28. retrieved from URL https://doi.org/10.1101/2020.10.14.337535.
Kamakaka, In Vitro Transcription, Current Protocols in Cell Biology, Apr. 1999, pp. 11-16, vol. 2, No. 1.
Kansteiner, F., "JPM: BioNTech hikes COVID-19 vaccine output to 2B doses in 2021—and plans a bigger label, too," FiercePharma, Jan. 11, 2021, 2 pages. [online], [retrieved on Mar. 8, 2022]. Retrieved from the Internet URL: https://www.fiercepharma.com/manufacturing/jpm-biontech-raises-covid-19-vaccine-output-to-2b-eyeing-label-extensions-and-higher.
Kapadia et al., "Long-term protection from SARS coronavirus infection conferred by a single immunization with an attenuated VSV-based vaccine," Virology, Jul. 25, 2005, pp. 174-182, vol. 340.
Kariko et al., "Generating the optimal mRNA for therapy: HPLC purification eliminates immune activation and improves translation of nucleoside-modified, protein-encoding mRNA", Nucleic Acids Research, Oxford University Press, GB, vol. 39, No. 21, Nov. 1, 2011 (Nov. 1, 2011), pp. e142-1.
Kariko et al., "Increased Erythropoiesis in Mice Injected With Submicrogram Quantities of Pseudouridine-containing mRNA Encoding Erythropoietin," Molecular Therapy, May 2012, pp. 948-953, vol. 20, No. 5.
Kariko et al., "What does the success of mRNA vaccines tell us about the future of biological therapeutics?" Cell Systems, Aug. 18, 2021, pp. 757-758, vol. 12.
Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).
Kariko, K. et al., "Suppression of RNA Recognition by Toll-like Receptors: The Impact of Nucleoside Modification and the Evolutionary Origin of RNA," Immunity, vol. 23: 165-175 (2005).
Kariko, Katalin, et al. Naturally occurring nucleoside modifications suppress the immunostimulatory activity of RNA: Implication for therapeutic RNA development. Current Opinion in Drug Discovery & Development 2007 10(5) 523-532; The Thomson Corporation ISSN 1367-6733.
Karlin S., et al., "Applications and Statistics For Multiple High-scoring Segments In Molecular Sequences," Proceedings of National Academy of Sciences, Jun. 15, 1993, vol. 90, No. 12, pp. 5873-5877.
Kasiewicz et al., "Lipid nanoparticles incorporating a GalNAc ligand enable in vivo liver ANGPTL3 editing in wild-type and somatic LDLR knockout non-human primates", bioRxiv, Nov. 2021, pp. 1-7.
Kaszuba, "How to Obtain better Data from Zetasizer Measurements", PowerPoint slides, 2017, 22 pages.
Katnelson, "Preventative Cancer Vaccine Based on Neoantigens Gets Put to the Test," ACS Central Science, 2021, 4 pages. retrieved from URL https://doi.org/10.1021/ascsentsci.1c00936.
Kazemi et al., "Greep behavior of the intact and meniscectomy knee joints", Journal of the Mechanical behavior of Biomedical Materials, 2011, pp. 1351-1358, vol. 4.
Kazemi et al., "Partial Meniscectomy Changes Fluid Pressurization in Articular cartilage in Human Knees", Journal of Biomechanical Engineering, Feb. 2012, pp. 1-10, vol. 134.
Ke et al., "Surface-Functionalized PEGylated Nanoparticles Deliver Messenger RNA to Pulmonary Immune Cells", ACS Applied Materials Interfaces, 2020, pp. 35835-35844, vol. 12.
Kedmi et al., "A modular platform for targeted RNAi therapeutics", Nature Nanotechnology, Supplementary Information, 2018, 13 pages.
Keech et al., "Phase 1-2 Trial of a SARS-COV-2 Recombinant Spike Protein Nanoparticle Vaccine," N Engl J Med, Sep. 2, 2020, pp. 1-13.
Kenworthy et al., "Range and Magnitude of the Steric Pressure Between Bilayers Containing Phospholipids with Covalently Attached Poly (ethylene glycol)", Biophysical Journal, May 1995, pp. 1921-1936, vol. 68.
Khalil et al., "Phosphonodithioformate-amine coupling reaction: from basic discovery to application for the functionalization of liposomes", Taylor Francis Online, Dec. 2021, 4 pages.
Khalil et al., "Recent Advances in Research on Particulate Formulations such as Lipoproteins, Liposomes, Extracellular Vesicles, and iPS-Derived Cells", Biol. Pharm. Bulletin, 2020, pp. 584-595, vol. 43, No. 4.
Khillari, "mRNA Vaccine and Therapeutics Market Growth, Trends and Forecast Report", from the SelectedWorks of Shweta Khillari, 2020, pp. 1-3.
Kilchrist et al., "Gal8 Visualization of Endosome disruption Predicts Carrier-Mediated Biologic Drug Intracellular Bioavailability", ACS Nano, 2019, pp. 1136-1152, vol. 13.
Kim et al., "Cuboplexes: topologically Active siRNA Delivery", ACS Nano, 2015, pp. 10214-10226, vol. 9 No. 10.
Kim et al., "Microfluidics Synthesis of gene Silencing Cubosomes", ACS Nano, 2018, pp. 9196-9205, vol. 12.
Kirk et al., "Electrophoretic mobility of weakly-charged (dipolar) hydrogels in water: Contribution of hydrogen-bonding in the solvent dipole layer", Journal of Colloid and Interface Science, 2014, pp. 294-305, vol. 416.
Klasczyk et al., "Interactions of alkali metal chlorides with phosphatidylcholine vesicles", Supporting Information, 2010, 1 page.
Klauda, "Considerations of Recent All-Atom Lipid Force Field Development", The Journal of Physical Chemistry, May 28, 2021, pp. 5676-5682, vol. 125, No. 22.
Knecht et al., "Electrophoresis of neutral oil in water", Journal of Colloid and Interface Science, 2010, pp. 223-231, vol. 352.
Knecht et al., "Electrophoretic mobility does not always reflect the charge on an oil droplet", Journal of Colloid and Interface Science, 2008, pp. 477-486, vol. 318.
Knudson, et al., "Lipid-nanoparticle encapsulated mRNA vaccines induce protective memory CD8 T cells against a lethal viral infection", ScienceDirect, May 14, 2021. 5 pages. Retrieved from the Internet: URL: https://www.sciencedirect.com/science/article/pii/S152500162100263X.

(56) References Cited

OTHER PUBLICATIONS

Knudson et al., "Lipid-nanoparticle-encapsulated mRNA vaccines induce protective memory Cds T cells against a lethal viral infection," Molecular Therapy, Sep. 2021, pp. 1-13, vol. 29, No. 9.
Koerner et al., "Electrodynamics of Lipid Membrane Interactions in the Presence of Zwitterionic Buffers", Biophysical Journal, Jul. 2011, pp. 362-369, vol. 101.
Kore, A.R. et al., "Synthesis and biological validation of N7 -(4-chlorophenoxyethyl) substituted dinucleotide cap analogs for mRNA translation," Bioorganic & Medicinal Chemistry, vol. 21:4570-4574 (2013).
Kose et al., "A Lipid-encapsulated mRNA Encoding a Potently Neutralizing Human Monoclonal Antibody Protects Against Chikungunya Infection," Science Immunology (2019) 4(35): eaaw6647, 28 pages.
Kowalski et al., "ionizable Amino-Polyesters Synthesized via Ring Opening Polymerization of Tertiary Amino-Alcohols for Tissue Selective mRNA Delivery", Advanced Materials, 2018, pp. 1-10, vol. 30.
Kranz, et al., RNA delivery to dendritic cells exploits antiviral defence for cancer immunotherapy, Nature, Jun. 2016, pp. 396-401.
Kremsner et al., "Phase 1 Assessment of the Safety and Immunogenicity of an mRNA-Lipid Nanoparticle Vaccine Candidate Against SARS-VoV-2 in Human Volunteers", MedRxiv, 2020, pp. 1-38.
Krienke et al., "A noninflammatory mRNA vaccine for treatment of experimental autoimmune encephalomyelitis," Science, Jan. 8, 2021, pp. 1-9, vol. 371.
Kuhn et al., "Phosphorothioate cap analogs increase stability and translational efficiency of RNA vaccines in immature dendritic cells and induce superior immune reponses in vivo," Gene Therapy, Apr. 22, 2010, pp. 961-971, vol. 17.
Kulkarni et al., "Lipid Nanoparticle Technology for Clinical Translation of siRNA Therapeutics", Accounts of Chemical Research, 2019, pp. 2435-2444, vol. 52.
Laczko et al., "A Single Immunization with Nucleoside-Modified mRNA Vaccines Elicits Strong Cellular and Humoral Immune Responses against SARS-CoV-2 in Mice," Immunity, Oct. 13, 2020, pp. 724-732, vol. 53.
Lafantaisie-Favreau et al., "Subchondral pre-solidified chitosan/ blood implants elicit reproducible early osteochondral wound-repair responses including neutrophil and stromal cell chemotaxis, bone resorption and repair, enhanced repair tissue integration and delayed matrix deposition", BMC Musculoskeletal Disorders, 2013, pp. 1-16, vol. 14.
Lakdawala et al., "The search for a COVID-19 animal model," Science, May 29, 2020, pp. 942-943, vol. 368, Issue 6494.
Langelier et al., "Increasing strain and strain rate strengthen transient stiffness but weaken the response to subsequent compression for articular cartilage in unconfined compression", Journal of Biomechanics, 2003, pp. 853-859, vol. 36.
Langelier et al., "The Chondrocyte Cytoskeleton in Mature Articular Cartilage: Structure and Distribution of Actin, Tubulin, and Vimentin Filaments", The Journal of Histochemistry and Cytochemistry, 2000, pp. 1307-1320, vol. 48, No. 10.
Latourette, II et al., "Protection against herpes simplex virus type 2 infection in a neonatal murine model using a trivalent nucleoside-modified mRNA in lipid nanoparticle vaccine," Vaccine, 2020, pp. 7409-7413, vol. 38.
Lavertu et al., "A validated 1H NMR method for the determination o the degree of deacetylation of chitosan", Journal of Pharmaceuticals and Biomedical Analysis, 2003, pp. 1149-1158, vol. 32.
Lavertu et al., "Heat-Induced Transfer of Protons from Chitosan to Glycerol Phosphate Produces Chitosan Precipitation and Gelation" Biomacromolecules, 2008, pp. 640-650, vol. 9.
Lavertu et al., "High efficiency gene transfer using chitosan/DNA nanoparticles with specific combinations of molecular weight and degree of deacetylation", Biomaterials, 2006, pp. 4815-4824, vol. 27.
Lavertu et al., "Kinetics and efficiency of chitosan reacetylation", Carbohydrate Polymers, 2012, pp. 1192-1198, vol. 87.
Le Bert et al., "SARS-CoV-2-specific T cell immunity in cases of COVID-19 and SARS, and uninfected controls," Nature, Jul. 15, 2020, 25 pages. retrieved from URL https://doi.org/10.1038/ss41586-020-2550-z.
Le et al., "The COVID-19 vaccine development landscape," Nature Reviews Drug Delivery, May 2020, pp. 305-306, vol. 19.
Lederer et al., "SARS-CoV-2 mRNA Vaccines Foster Potent Antigen-Specific Germinal Center Responses Associated with Neutralizing Antibody Generation," Immunity, Dec. 15, 2020, pp. 1281-1295, vol. 53.
Lee, Justin B. et al., Lipid Nanoparticle siRNA Systems for Silencing the Androgen Receptor in Human Prostate Cancer in Vivo, International Journal of Cancer, 2012, vol. 131, pp. 781-790.
Leslie, "T cells found in coronavirus patients 'bode well' for long-term immunity," Science, May 22, 2020, pp. 809-810, vol. 368, Issue 6493.
Leung et al., "Lipid Nanoparticles Containing siRNA Synthesized by Microfluidic Mixing Exhibit an Electron-Dense Nanostructured Core," The Journal of Physical Chemistry C, 2012, 116:18440-18450.
Leung et al., "Microfluidic Mixing: A General Method for Encapsulating macromolecules in Lipid Nanoparticle Systems", The Journal of Physical Chemistry, Jun. 18, 2015, pp. 8698-8706, vol. 8.
Legare et al., "Detection and analysis of cartilage degeneration by spatially resolved streaming potentials", Journal of Orthopedic Research, 2002, pp. 819-826, vol. 20.
Li et al., "A fibril reinforced nonhomogeneous poroelastic model for articular cartilage: inhomogeneous response in unconfined compression", Journal of Biomechanics, 2000, pp. 1533-1541, vol. 33.
Li et al., "BBB pathophysiology-independent delivery of siRNA in traumatic brain injury", Science Advances, Jan. 2021, pp. 1-16, vol. 7.
Li et al., "Simultaneous separation of small interfering RNA and lipids sing ion-pair reversed-phase liquid chromatography", Journal of Chromatography A, Apr. 2019, pp. 145-154, vol. 1601.
Li et al., "Investigation of mechanical behavior of articular cartilage by fibril reinforced poroelastic models", Biorheology, pp. 227-233, vol. 40.
Li et al., "Nonlinear analysis of cartilage in unconfined ramp compression using a fibril reinforced poroelastic model", Clinical Biomechanics, 1999, pp. 673-682, vol. 14.
Li et al., "The Asymmetry of transient Response in Compression Versus Release for Cartilage in Unconfined Compression", Journal of Biomechanical Engineering, Oct. 2001, pp. 519-522, vol. 123.
Li et al., "The role of fibril reinforcement in the mechanical behavior of cartilage", Biorheology, 2002, pp. 89-96, vol. 39.
Li et al., "Strain-rate Dependent Stiffness of Articular Cartilage in Unconfined Compression", Journal of Biomechanical Engineering, Apr. 2003, pp. 161-168, vol. 125.
Liang et al, Design and Synthesis of Lipidic Organoalkoxysilanes for the Self-Assembly of Liposomal Nanohybrid Cerasomes with Controlled Drug Release Properties, Chemistry: A European Journal, 2013, pp. 16113-16121, vol. 19.
Liang et al., "Dissociation of skeletal muscle for flow cytometric characterization of immune cell in macaques", Journal of Immunological Methods, 2015, pp. 69-78, vol. 425.
Liang et al., "Efficient targeting and Activation of Antigen-Presenting Cells in Vivo after Modified mRNA Vaccine Administration in Rhesus Macaques", Molecular Therapy, Dec. 2017, pp. 1-13, vol. 25 No. 12.
Lin et al., "Three-Dimensional Imaging of Lipid Gene-Carriers: Membrane Charge Density Controls Universal Transfection Behavior in Lamellar Cationic Liposome-DNA Complexes," Biophysical Journal, May 2003, pp. 3307-3316, vol. 84, No. 5.
Linpinsel, et al., General protocols for preparation of plasmid DNA template, RNA in vitro transcription, and RNA purification by denaturing p. InRecombinant and in vitro RNA synthesis, 2013, pp. 43-58.
Liu et al., "BNT162b2-Elicited Neutralization against New SARS-CoV-2 Spike Variants," N Engl J Med, May 12, 2021, pp. 1-2.
Liu et al., "BNT162b2-elicited neutralization of B.1.617 and other SARS-CoV-2 variants," Nature, Jun. 10, 2021, 12 pages. retrived from URL https://doi.org/10.1038/s41586-021-03693-y.

(56) References Cited

OTHER PUBLICATIONS

Liu et al., "Chimeric severe acute respiratory syndrome coronavirus (SARS-CoV) S glycoprotein and influenza matrix 1 efficiently form virus-like particles (VLPs) that protect mice against challenge with SARS-COV," Vaccine, Jul. 14, 2011, pp. 6606-6613, vol. 29.
Liu et al., "Neutralizing Activity of BNT162b2-Elicited Serum—Preliminary Report," N Engl J Med, Feb. 19, 2021, pp. 1-3.
Liu et al., "Two-Year Prospective Study of the Humoral Immune Response of Patients with Severe Acute Respiratory Syndrome," JID, Mar. 15, 2006, pp. 792-795, vol. 193.
Liu, "Feds consider half-doses of Moderna COVID-19 vaccine to stretch supplies, as U.K. spaces out Pfizer, AstraZeneca shots", FiercePharma, Jan. 4, 2021, 4 pages. Retrieved from the Internet URL: https://www.fiercepharma.com/pharma/feds-consider-half-dose-moderna-covid-19-vaccine-as-u-k-spaces-out-pfizer-astrazeneca-shots.
Liu, "mRNA Latecomer CureVac recruits Bayer to speed COVID-19 vaccine to market", FiercePharma, 2021, pp. 1-2.
Lonn et al., "Enhancing Endosomal Escape for Intracellular Delivery of Macromolecular Biologic Therapeutics", Scientific Reports, Sep. 2016, pp. 1-9, vol. 6.
Lo et al., "Evaluation of a Single-Dose Nucleoside-Modified Messenger RNA Vaccine Encoding Hendra Virus-Soluble Glycoprotein Against Lethal Nipah virus Challenge in Syrian Hamsters," The Journal of Infectious Diseases, Supplemental 4, 2020, pp. S493-S498.
Loftus, "Moderna Vows to Not Enforce Covid-19 Vaccine Patents During Pandemic", The Wall Street Journal, Oct. 8, 2020, 2 pages. Retrieved from the Internet URL: https://www.wsj.com/articles/moderna-vows-to-not-enforce-covid-19-vaccine-patents-during-pandemic-11602154805.
Lood et al., "TLR7/8 activation in neutrophils impairs immune complex phagocytosis through shedding of FcgRIIA", The Journal of Experimental Medicine, pp. 2103-2119, vol. 214, No. 7.
Lopes De Menezes et al., "Cellular Trafficking and Cytotoxicity of Anti-CD19-Targeted Liposomal Doxorubicin in B Lymphoma Cells", Journal of Liposome Research, 1999, pp. 199-228, vol. 9, No. 2.
Losick, In vitro transcription, Ann Rev Biochem., Jul. 1972, pp. 409-446.
Lou et al., "mRNA Polyplexes with Post-Conjugated GALA Peptides Efficiently Target, Transfect, and Activate Antigen Presenting Cells", Bioconjugate Chemistry, 2019, pp. 461-475, vol. 30.
Loughrey et al., "Non-liver mRNA Delivery", Accounts of Chemical Research, Sep. 2021, pp. 13-23, vol. 55.
Lovelace, Moderna says new data shows its Covid vaccine is more than 90% effective against virus six months after second shot:, CNBC, Apr. 13, 2021, 9 pages. Retrieved from the Internet URL: https://www.cnbc.com/2021/04/13/covid-vaccine-moderna-says-new-data-shows-its-90percent-effective-six-months-after-second-dose.html.
Lowry et al., "Guidance to improve the scientific value of zeta-potential measurements in nanoEHS", Environmental Science Nano, 2016, pp. 953-965, vol. 3.
López-Vidal et al., "Deep Learning Enables Discovery of a Short Nuclear Targeting Peptide for efficient Delivery of Antisense Oligomers", An Open Access Journal of the American Chemical Society, Oct. 6, 2021, pp. 1-12, vol. 1, No. 11.
Lu et al., "Chemical Conjugation Strategies for the Development of Protein-Based Subunit Nanovaccines", Vaccines, 2021, pp. 1-24, vol. 9, No. 563.
Lu et al., "Genomic characterisation and epidemiology of 2019 novel coronavirus: implications for virus origins and receptor binding," The Lancet, Jan. 29, 2020, retrieved from URL https://doi.org/10.1016/S0140-6736(20)30251-8, pp. 1-10.
Luksasky, et al., Large-scale preparation and purification of polyacrylamide-free RNA oligonucleotides, RNA, May 1, 2004, pp. 889-893.
Lutz, "Supplementary Figure 1", No Date, 1 page.
Ma et al., "Complete Physiochemical Characterization of DNA/Chitosan Complexes by Multiple Detection Using Asymmetrical Flow Field-Flow Fractionation", Analytical Chemistry, Dec. 10, 2010, pp. 9636-9643, vol. 82 No. 23.
Ma et al., "New Insights into Chitosan—DNA Interactions Using isothermal Titration Microcalorimetry", Biomacromolecules, 2009, pp. 1490-1499, vol. 10.
Ma et al., "One-Step Analysis of DNA/Chitosan Complexes by Field-Flow Fractionation Reveals Particle Size and Free Chitosan Content", Biomacromolecules, 2010, pp. 549-554, vol. 11.
Ma et al., "Precise derivatization of structurally distinct chitosans with rhodamine B isothiocyanate", Carbohydrate Polymers, 2008, pp. 616-624, vol. 72.
Ma et al., "Stability and binding affinity of DNA/Chitosan complexes by polyanion competition", Carbohydrate Polymers, 2017, pp. 167-176, vol. 176.
Maass et al., "The Effect of Radiofrequency Energy in Tissue", Histologic Technical Bulletin for Histotechnology, 2005, pp. 21-40, vol. 38.
Macqueen et al., "Electro-manipulation of Biological Cells in Microdevices", IEEE Transactions on Dielectrics and Electrical Insulation, Aug. 2012, pp. 1261-1268, vol. 19 No. 4.
Macqueen et al., "Electromechanical deformation of mammalian cells in suspension depends on their cortical actin thickness", Journal of Biometrics, 2012, pp. 2797-2803, vol. 45.
Macqueen et al., "Gene delivery by electroporation after dielectrophoretic positioning of cells in a non-uniform electric field", Bioelectrochemistry, 2008, pp. 141-148, vol. 72.
Macqueen et al., "Mechanical properties of mammalian cells in suspension measured by electro-deformation", Journal of Micromechanics and Microengineering, 2010, pp. 1-11, vol. 20.
Madrigal et al., "Biomaterial-Guided gene delivery for Musculoskeletal Tissue Repair", Tissue Engineering: Part B, 2017, pp. 347-361, vol. 23, No. 4.
Maeki et al., "Understanding the formation mechanism of lipid nanoparticles in microfluidic devices with chaotic micromixers", PLOS One, 2017, pp. 1-16, vol. 12, No. 11.
Mai et al., "Advances in engineering and synthetic biology toward improved therapeutic immune cells", Current Opinion in Biomedical Engineering, 2021, 9 pages.
Maier, et al., Biodegradable lipids enabling rapidly eliminated lipid nanoparticles for systemic delivery of RNAi therapeutics, Molecular Therapy, Aug. 1, 2013, pp. 1570-1578, vol. 21, No. 8.
Majzoub et al., "Quantitative intracellular localization of cationic lipid-nucleic acid nanoparticles with fluorescence microscopy", Methods of Molecular Biology, Jan. 2017, pp. 1-32.
Makino, et al., "Temperature- and ionic strength-induced conformational changes in the lipid head group region of liposomes as suggested by zeta potential data," ScienceDirect, Nov. 1991, 2 pages.
Makino et al., "Temperature-and-ionic strength-induced confrontational changes in the lipid head group region of liposomes as suggested by zeta potential data", Biophysical Chemistry, Nov. 1991, pp. 175-183, vol. 41, No. 2.
Malven Instruments Limited, "Dynamic light Scattering: an introduction," 2017, 17 pages.
Malvern Instruments, "How is the frequency shift measured in electrophoretic light scattering?", No Date, 3 pages.
Malvern Instruments, "What is a Frequency Plot?", No Date, 2 pages.
Malvern Instruments, "What is a Voltage and Current Plot?", No Date, 3 pages.
Malvern Instruments, "What is the Wall Zeta Potential?", No Date, 2 pages.
Malvern Instruments, "What is Zeta Potential and what value is it?", No Date, 1 pages.
Malvern Instruments Worldwide, "Zetasizer nano series, user manual," 2017, 4 pages.
Malvern Instruments Worldwide, "Zetasizer Nano Specifications Zeta Potential Mximum Concentration Limit 40% with v, Technical Note," 2017, 4 pages.
Malvern, The diffusion barrier technique, Practical aspects and data interpretation, 2017, 5 pages.
Malvern, Zetasizer Nano Series User Manual, Apr. 2013, 250 pages, Issue 1.1.

(56) References Cited

OTHER PUBLICATIONS

Manolova et al., "Nanoparticles target distinct dendritic cell populations according to their size", European Journal of Immunology, 2008, pp. 1404-1413, vol. 38.
Marchand et al., "C3, C5, and factor B bind to Chitosan without Complement Activation", Journal of Biomedical Materials Research Part A, 2009, pp. 1429-1441, vol. 93, No. 4.
Marchand et al., "Microdrilled Cartilage Defects treated with Thrombin-Solidified Chitosan/Blood Implant Regenerate a more Hyaline, Stable, and Structurally Integrated Osteochondral Unit Compared to Drilled Controls", Tissue Engineering, 2011, pp. 1-12, vol. 18.
Marchand et al., "Solidification mechanisms of chitosan-glycerol phosphate/blood implant for articular cartilage repair", Osteoarthritis and Cartilage, 2009, pp. 950-960, vol. 17.
Marcos-Contreras et al., "Selective targeting of nanomedicine to inflamed cerebral vasculature to enhance the blood-brain barrier," PNAS, 2020, pp. 1-23, vol. 117, No. 7.
Marsh et al., "Lipid membranes with grafted polymers: physicochemical aspects," Biochimica et Biophysica Acta, 2003, pp. 33-59, vol. 1615.
Maruggi, et al., "mRNA as a Transformative Technology for Vaccine Development to Control Infectious Diseases," Molecular Therapy, Apr. 2019, pp. 757-772, vol. 27.
Mattern-Schain et al., "Cell mimetic liposomal nanocarriers for tailored delivery of vascular therapeutics", Chemistry and Physics of Lipids, 2019, pp. 149-157, vol. 218.
Matyushov, "Electrophoretic mobility without charge driven by polarization of the nanoparticle - water interface", Molecular Physics, 2014, pp. 2029-2039, vol. 112, No. 15.
Maugeri et al., "Linkage between endosomal escape of LNP-mRNA and loading into Evs for transport to other cells," Nature Communications, 2019, pp. 1-15, with supplemental data, vol. 10, No. 4333.
Mcdaniel et al., "Electrostatic potential distribution of a soft spherical particle with a charged core and pH-dependent charge density", Colloids and Surfaces B: Biointerfaces, 2015, pp. 143-147, vol. 127.
Mckay et al., "Self-amplifying Rna SARS-CoV-2 lipid nanoparticle vaccine candidate induces high neutralizing antibody titers in mice," Nature Communications, 2020, pp. 1-7, vol. 11, No. 3523.
Mckay et al., "Self-amplifying Rna SARS-CoV-2 lipid nanoparticle vaccine induces equivalent preclinical antibody titers and viral neutralization to recovered COVID-19 patients," bioRxiv, Apr. 25, 2020, pp. 1-14. retrieved from URL https://doi.org/10.1101/2020.04.22.055608.
Mercado, et al., "Single-shot Ad26 vaccine protects against SARS-CoV-2 in rhesus macaques," Nature, Jul. 30, 2020, 27 pages. retrieved from URL https://doi.org/10.1038/s41586-020-2607-z.
Merzouki et al., "Adva-27a, a Novel Podophyllotoxin Derivative Found to be Effective against Multidrug Resistant Human Cancer Cells", Anticancer Research, 2012, pp. 4423-4432, vol. 32.
Merzouki et al., "Chitosanase-based method for RNA isolation form cells transfected with chitosan/siRNA nanocomplexes for real-time RT-PCR in gene silencing", International Journal of Nanomedicine, 2010 pp. 473-481, vol. 5.
Merzouki et al., "Low Molecular Weight Chitosan Nanoparticulate System at Low N:P Ratio for Nontoxic Polynucleotide Delivery", International Journal of Nanomedicine, 2012, pp. 1399-1414, vol. 7.
Milicevic et al., "Establishing conditions for simulating hydrophobic solutes in electric fields by molecular dynamics", Journal of Molecular Model, Aug. 2014, pp. 1-11, vol. 20.
Miller, "mRNA-1273 Clinical Development Program" Moderna, Aug. 26, 2020, pp. 1-18.
Šmisterová et al., "Molecular Shape of the Cationic Lipid Controls the Structure of Cationic Lipid/Dioleylphosphatidylethanolamine-DNA Complexes and the Efficiency of Gene Delivery", The Journal of Biological Chemistry, Dec. 2001, pp. 47615-47622, vol. 276, No. 50.
Miyoshi et al., "A detailed analysis of partial molecular volumes in DPPC/cholesterol binary bilayers", Biochimica et Biophysica Acta, 2014, pp. 3069-3077, vol. 1838.
Modern Instruments Limited, Comparisons between the Folded Capillary Cell (DTS1060/DTS1061), the 'dip' cell (ZEN1002) and the high concentration cell (ZEN1010), 2017, 3 pages.
Modern Instruments Limited, "Dynamic light scattering—definition of terms", 2017, 17 pages.
Moderna, I. "Safety, Tolerability, and Immunogenicity of VAL-506440 in Healthy Adult Subjects", Dec. 2015, 6 pages. Retrieved from the Internet URL: https://clinicaltrials.gov/ct2/show/NCT03076385.
Moderna, "Moderna Advances Late-Stage Development of its Vaccine (mRNA-1273) Against COVID-19," Jun. 11, 2020, 7 pages. Retrieved from the Internet URL: https://investors.modernatx.com/news-releases/news-release-details/moderna-advances-late-stage-development-its-vaccine-mrna-1273/.
Moderna, "Moderna Announces First Participants in Each Age Cohort Dosed in Phase 2 Study of mRNA Vaccine (mRNA-1273) Against Novel Coronavirus", Yahoo Business, May 29, 2020, 11 pages. Retrieved from the Internet URL: https://ca.finance.yahoo.com/quote/MRNA/.
Moderna, "Moderna Announces Positive Interim Phase 1 Data for its mRNA Vaccine (mRNA-1273) Against Novel Coronavirus", May 18, 2020, 7 pages. Retrieved from the Internet URL: https://investors.modernatx.com/news-releases/news-release-details/moderna-announces-positive-interim-phase-1-data-its-mrna-vaccine/.
Moderna, "Moderna's COVID-19 Vaccine Candidate Meets its Primary Efficacy Endpoint in the First Interim Analysis of the Phase 3 COVE Study", Nov. 16, 2020, 6 pages. Retrieved from the Internet URL: https://investors.modernatx.com/news-releases/news-release-details/modernas-covid-19-vaccine-candidate-meets-its-primary-efficacy/.
Moderna, "Moderna Provides COVID-19 Vaccine Supply Update", Jan. 4, 2021, 5 pages. Retrieved from the Internet URL: https://investors.modernatx.com/news-releases/news-release-details/moderna-provides-covid-19-vaccine-supply-update/.
Mole, "Shkreli Award" goes to Moderna for "blatantly greedy" COVID vaccine price Ars Technica, Jan. 6, 2021 5 pages. Retrieved from the Internet URL: https://arstechnica.com/science/2021/01/moderna-shamed-with-shkreli-award-over-high-covid-vaccine-prices/.
Monslow et al., "Immunogenicity generated by mRNA vaccine encoding VZV gE antigen is comparable to adjuvanted subunit vaccine and better than live attenuated vaccine in nonhuman primates", Vaccine, Jul. 2020, pp. 5793-5802, vol. 38.
Moore, L., "Pfizer ramps up vaccine production to 2 billion doses for 2021," MLive [online], [retrieved on Mar. 8, 2022]. Retrieved from the Internet URL: https://www.mlive.com/coronavirus/2021/01/pfizer-ramps-up-vaccine-production-to-2-billion-doses-for-2021.html, 3 pages.
Morrissey, et al., Potent and persistent in vivo anti-HBV activity of chemically modified siRNAs, Nat. Biotech., Aug. 2005, pp. 1002-1007, vol. 23, No. 8.
Moyo et al., "Tetravalent Immunogen Assembled from Conserved Regions of HIV-1 and Delivered as mRNA Demonstrates Potent Preclinical T-Cell Immunogenicity and Breadth", Vaccines, 2020, pp. 1-10, vol. 8.
Mèthot et al., "Osteochondral Biopsy Analysis Demonstrates that BST-CarGel treatment Improves Structural and Cellular Characteristics of Cartilage repair Tissue Compared with Microfracture", Cartilage, 2015, pp. 1-13, vol. 7, No. 1.
Mui, et al., Influence of polyethylene glycol lipid desorption rates on pharmacokinetics and pharmacodynamics of siRNA lipid nanoparticles, Molecular Therapy-Nucleic Acids, Jan. 1, 2013, e139.
Mulligan et al., "Phase 1/2 Study to Describe the Safety and Immunogenicity of a COVID-19 RNA Vaccine Candidate (BNT162b1) in Adults 18 to 55 Years of Age: Interim Report," medRxiv, Jul. 1, 2020, pp. 1-16. retrieved from URL https://doi.org/10.1101/2020.06.03.20142570.
Mulligan et al., "Phase I/II study of COVID-19 Rna vaccine BNT162b1 in adults," Nature Research Supplementary Information, PF-07302048 (BNT162 RNA-Based COVID-19 Vaccines), Protocol C4591001, Protocol Amendment 3, Jun. 10, 2020, 131 pages.

(56) References Cited

OTHER PUBLICATIONS

Naito et al., "Real-world evidence for the effectiveness and breakthrough of BNT162b2 mRNA COVID-19 vaccine at a medical center in Japan," Human Vaccines & Immunotherapeutics, Oct. 6, 2021, retrieved from URL https://doi.org/10.1080/21645515.2021.1984124, pp. 1-2.
National Institutes of Health, "Safety and Immunogenicity Study of 2019-nCoV Vaccine (mRNA-1273) for Prophylaxis Sars CoV-2 Infection (COVID-19)", ClinicalTrials, Apr. 13, 2020, 19 pages. Retrieved from the Internet URL: https://clinicaltrials.gov/ct2/show/NCT04283461.
National Institutes of Health, "Phase 3 clinical trial of investigational vaccine for COVID-19 begins", NIH, Jul. 27, 2020, 3 pages. Retrieved from the Internet URL: https://www.nih.gov/news-events/news-releases/phase-3-clinical-trial-investigational-vaccine-covid-19-begins.
National Institutes of Health, "Promising Interim Results from Clinical Trial of NIH-Moderna COVID-19 Vaccine", Nov. 16, 2020, 6 pages. Retrieved from the Internet URL: https://www.nih.gov/news-events/news-releases/promising-interim-results-clinical-trial-nih-moderna-covid-19-vaccine.
Ndeupen et al., "The mRNA-LNP platform's lipid nanoparticle component ussed in preclinical vaccine studies is highly inflammatory," bioRxiv, Mar. 4, 2021, pp. 1-24.
Neidleman et al., "mRNA vaccine-induced SARS-CoV-2-specific T cells recognize B.1.1.7 and B.1.351 variants but differ in longevity and homing properties depending on prior infection status", bioRxiv, May 12, 2021 pp. 1-62.
Nelson et al., "Human Cytomegalovirus Glycoprotein B Nucleoside-Modified mRNA Vaccine Elicits Antibody Responses with Greater Durability and Breadth than MF59-Adjuvanted GB Protein Immunization," Journal of Virology, Apr. 16, 2020, pp. 1-19, vol. 94, No. 9.
Nelson et al., "Impact of mRNA chemistry and manufacturing process on innate immune activation", Science Advances, 2020, pp. 1-13, vol. 6.
Netea et al., "Trained Immunity: a Tool for Reducing Susceptibility to and the Severity of SARS-CoV-2 Infection," Cell, May 28, 2020, pp. 969-977, vol. 181.
Nguyen et al., "Fractionation and characterization of chitosan by analytical SEC and 1H NMR after semi-preparative SEC", Carbohydrate Polymers, 2009, pp. 636-645, vol. 75.
Nguyen et al., "Improved reproducibility in the determination of the molecular weight of chitosan by analytical size exclusion chromatography", Carbohydrate Polymers, 2009, pp. 528-533, vol. 75.
Nguyen et al., "Lipid-derived nanoparticles for immunostimulatory RNA adjuvent delivery," Proc. Natl. Acad. Sci., Mar. 15, 2012, pp. E797-E803, vol. 109, No. 14.
Nimesh et al., "Enhanced Gene Delivery Mediated by Low Molecular Weight Chitosan/DNA Complexes: effect of pH and Serum", Molecular Biotechnology, 2010, pp. 182-196, vol. 46.
Nittner-Marszalska et al., "Pfizer-BioNTech COVID-19 Vaccine Tolerance in Allergic versus Non-Allergic Individuals," Vaccines, May 25, 2021, 8 pages, vol. 9, No. 553.
No Author, "Example for Diffusion Barrier Method SOP," No Date, 1 page.
No Author, "Vaccines and Related Biological Advisory Committee Meeting, FDA Briefing Document, Pfizer-BioNTech COVID-19 Vaccine", Dec. 10, 2020, 53 pages.
Nogueira et al., "Polysarcosine-Functionalized Lipid Nanoparticles for Therapeutic mRNA Delivery," ACS Appl. Nano Mater., Sep. 25, 2020, pp. 10634-10645, vol. 3.
O'Brien et al., "The electrophoretic mobility of an uncharged particle", Journal of Colloid and Interface Science, 2014, pp. 70-73, vol. 420.
O'Callaghan et al., "Developing a SARS-CoV-2 Vaccine at Warp Speed," JAMA, Aug. 4, 2020, pp. 437-438, vol. 324, No. 5.
Oesterhelt et al., S4 Appendix, Estimating the contour lengths of PEG and ddFLN4, No Date, 1 page.
Ohshima, "A Simple Expression for Henry's Function for the Retardation Effect in Electrophoresis of Spherical Colloidal Particles", Journal of Colloid and Interface Science, Nov. 1994, pp. 269-271, vol. 168, Issue 1.
Ohshima, "Donnan potential and surface potential of a spherical soft particle in an electrolyte solution", Journal of Colloid and Interface Science, 2008, pp. 92-97, vol. 323.
Ohshima et al., "Donnan Potential and Surface Potential of a Charged Membrane", Biophysical Journal, May 1985, pp. 673-678, vol. 47.
Ohshima, "Limiting electrophoretic mobility of a highly charged soft particle in an electrolyte solution; solidification effect", Journal of Colloid and Interface Science, 2010, pp. 641-644, vol. 349.
Ohshima, "Theory of electrostatics and electrokinetics of soft particles", Science and technology of Advanced Materials, 2009, pp. 1-13, vol. 10.
Oswald et al., "HPLC analysis as a tool for assessing targeted liposome composition", International Journal of Pharmaceutics, 2016, pp. 293-300, vol. 497.
Pallesen et al., "Immunogenicity and structures of a rationally designed prefusion MERS-CoV spike antigen," PNAS E7348-E7357 (2017).
Parayath et al., "In vitro-transcribed antigen receptor mRNA nanocarriers for transient expression in circulating T cells in vivo", Supplementary Information, 2020, 9 pages.
Pardi et al., "Administration of nucleoside-modified mRNA encoding broadly neutralizing antibody protects humanized mice from HIV-1 challenge," Nature Communications, Mar. 2, 2017, pp. 1-8, vol. 8, Article No. 14630.
Pardi et al., "Expression kinetics of nucleoside-modified mRNA delivered in lipid nanoparticles to mice by various routes," Journal of Controlled Release, 217, 2015, 345-351.
Pardi et al., In vitro transcription of long RNA containing modified nucleosides in Synthetic Messenger RNA and Cell Metabolism Modulation in Methods in Molecular Biology, 2013, pp. 29-42.
Pardi et al., "mRNA vaccines—a new era in vaccinology," Nature Reviews, 2018, pp. 261-279, vol. 17.
Pardi et al., "Nucleoside-modified mRNA immunization elicits influenza virus hemagglutinin stalk-specific antibodies," Nature Communications, Aug. 22, 2018, pp. 1-12, vol. 9, Article No. 3361.
Pardi et al., "Nucleoside-modified mRNA vaccines induce potent T follicular helper and germinal center B cell responses," Journal of Experimental Medicine, May 8, 2018, pp. 1571-1588, vol. 215, No. 6.
Pardi et al., "Zika virus protection by a single low-dose nucleoside-modified mRNA vaccination," Nature, May 9, 2017, pp. 248-251, vol. 543.
Parhiz et al., "Added to pre-existing inflammation, mRNA-lipid nanoparticles induce inflammation exacerbation (IE)," Journal of Controlled Release, 2022, pp. 50-61, vol. 344.
Parhiz et al., "PECAM-1 directed re-targeting of exogenous mRNA providing two orders of magnitude enhancement of vascular delivery an expression in lungs independent of apolipoprotein E-mediated uptake", Journal of Controlled Release, 2018, pp. 106-115, vol. 291.
Park et al., "Endocytosis and exocytosis of nanoparticles in mammalian cells", International Journal of Nanomedicine, 2014, pp. 51-63, vol. 201.
Patel et al., "Boosting Intracellular Delivery of Lipid Nanoparticle-Encapsulated mRNA", Nano Letters, 2017, pp. 5711-5718, vol. 17.
Patel et al., "Brief update on endocytosis of nanomedicines", Advanced Drug Delivery Reviews, 2019, pp. 90-111, vol. 144.
Patel et al., "Naturally-occurring cholesterol analogues in lipid nanoparticles induce polymorphic shape and enhance intracellular delivery of mRNA", Nature Communications, 2020, pp. 1-13.
Pepini et al., "Induction of an IFN-Mediated Antiviral Response by a Self-Amplifying RNA Vaccine: Implications for Vaccine Design," The Journal of Immunology, 2017, pp. 4012-4024, vol. 198.
Perche, et al., "Selective gene delivery in dendritic cells with mannosylated and histidylated lipopolyplexes", Journal of Drug Targeting, 2011, pp. 315-325, vol. 19, No. 5.

(56) References Cited

OTHER PUBLICATIONS

Perche et al., "Selective gene delivery in dendritic cells with mannosylated and histidylated lipopolyplexes", Journal on Drug Targeting, Jul. 2010, 3 pages.
Perche, F., et al., Enhancement of dendritic cells transfection in vivo and of vaccination against B16F10 melanoma with mannosylated histidylated lipopolyplexes loaded with tumor antigen messenger RNA. Nanomed: Nanotech, Bio, and Med. Aug. 2011; 7(4): 445-453.
Pfizer, "BNT162b2 VRBPAC Briefing Document," Sep. 17, 2021, 53 pages.
Pfizer, et al., "Vaccines and Related Biological Products Advisory Committee Dec. 17, 2020 Meeting Announcement", U.S. Food & Drug Administration, Dec. 17, 2020, 53 pages. Retrieved from the Internet URL: https://www.fda.gov/advisory-committees/advisory-committee-calendar/vaccines-and-related-biological-products-advisory-committee-december-17-2020-meeting-announcement.
Pfizer, "Pfizer-BioNTech COVID-19 Vaccine: VRBPAC Briefing Document," Dec. 10, 2020, pp. 1-92.
Philipse et al., "The Donnan Equilibrium: I. On the Thermodynamic Foundation of the Donnan Equation of State", Journal of Physics: Condensed Matter, 2011, pp. 1-12, vol. 23.
Pickenhahn et al., "Regioselective thioacetylation of chitosan end-groups for nanoparticle gene delivery system", Chemical Science, 2015, pp. 4650-4664, vol. 6.
Pincet et al., "Bilayers of neutral lipids bear a small but significant charge", The European Physical Journal B, 1999, pp. 127-130, vol. 11.
Player et al., The 2-5 A system: Modulation of viral and cellular processes through acceleration of RNA degradation, Pharmacology & therapeutics, May 1, 1998, pp. 55-113, vol. 78, No. 2.
Polack et al., "Safety and Efficacy of the BNT162b2 mRNA Covid-19 Vaccine," N Engl J Med, Dec. 31, 2020, pp. 2603-2615, vol. 383, No. 27.
Polack et al., "Safety and Efficacy of the BNT162b2 mRNA Covid-19 Vaccine, " N Engl J Med, Dec. 10, 2020, pp. 1-13.
Polvere et al., "A Peptide-Based Assay Discriminates Individual Antibody Response to the COVID-19 Pfizer/BioNTech mRNA Vaccine," Vaccines, Sep. 3, 2021, 8 pages, vol. 9, No. 987.
Poole et al., "Recommendations for the use of preclinical models in the study and treatment of osteoarthritis", osteoarthritis and Cartilage, 2010, pp. 510-516, vol. 18.
Pozzi et al., "Transfection efficiency boost of Cholesterol-containing lipoplexes", Biochimica et Biophysica Acta, 2012, pp. 2335-2343, vol. 1818.
Praseuth, et al., Triple helix formation and the antigene strategy for sequence- specific control of gene expression, Biochim Biophys Acta., Dec. 10, 1999, pp. 181-206, vol. 1489, No. 1.
Prompetchara et al., "Immune responses in COVID-19 and potential vaccines: Lessons learned from SARS and MERS epidemic," Asian Pacific Journal of Allergy and Immunology, 2020, pp. 1-9, vol. 38.
Preville et al., "Electroarthrography: a novel method to assess articular cartilage and diagnose osteoarthritis by non-invasive measurement of load-induced electrical potentials at the surface of the knee", Osteoarthritis and Cartilage, 2013, pp. 1731-1737, vol. 21.
Pu et al., "An in-depth investigation of the safety and immunogenicity of an inactivated SARS-CoV-2 vaccine," medRxiv, Oct. 6, 2020, pp. 1-27. retrieved from URL https://doi.org/10.1101/2020.09.27.20189548.
Puranik et al., "Comparison of two highly-effective mRNA vaccines for COVID-19 during periods of Alpha and Delta variant prevalence," medRxiv, Aug. 8, 2021, pp. 1-29. retrieved from URL https://doi.org/10.1101/2021.08.06.21261707.
Quenneville et al., "A transport model of electrolyte convection through a charged membrane predicts generation of net charge at membrane/electrolyte interfaces", Journal of Membrane Science, 2005, pp. 60-73, vol. 265.
Quenneville et al., "Fabrication and Characterization on Nonplanar Microelectrode Array Circuits for Use in Arthroscopic Diagnosis of Cartilage Diseases", IEEE Transactions on Biomedical Engineering, Dec. 2004, pp. 2164-2173, vol. 51 No. 12.
Quinn et al., "Mechanical compression alters proteoglycan deposition and matrix deformation around individual cells in cartilage explants", Journal of Cell Science, 1998, pp. 573-583, vol. 111.
Rajappan et al., "Property-Driven Design and Development of Lipids for Efficient Delivery of siRNA," Journal of Medicinal Chemistry, Oct. 29, 2020, pp. 12992-13012, vol. 63.
Rajesh, et al., "Dramatic Influence of the Orientation of Linker between Hydrophilic and Hydrophobic Lipid Moiety in Liposomal Gene Delivery," J. Am. Chem. Soc., 2007, pp. 11408-11420, vol. 129.
Ramaswamy et al., "Systemic delivery of factor IX messenger RNA for protein replacement therapy," PNAS, Feb. 15, 2017, pp. E1941-E1950.
Ramishett et al., "A Combinatorial Library of Lipid Nanoparticles for RNA Delivery to Leukocytes", Advanced Materials, 2020, pp. 1-8, vol. 32.
Ramishetti et al., "Systemic Gene Silencing in Primary T Lymphocytes Using Targeted Lipid Nanoparticles", ACS Nano, 2015, pp. 6706-6716, vol. 9, No. 7.
Rauch et al., "mRNA-based SARS-CoV-2 vaccine candidate CVnCoV induces high levels of virus neutralizing antibodies and mediates protection in rodents", BioRxiv, 2020, pp. 1-18, vol. 6, No. 1.
Rauch, "Supplementary Materials", No Date, 2 pages.
Reddy et al., "In vivo targeting of dendritic cells in lymph nodes with poly (propylene sulfide) nanoparticles", Journal of Controlled Release, 2006, pp. 26-34, vol. 112.
Regalado, "What are the ingredients of Pfizer's Covid-19 vaccine?" MIT Technology Review, Dec. 9, 2020, pp. 1-5.
Rehman et al., "Mechanism of Polyplex-and Lipoplex-Mediated delivery of Nucleic Acids: Real-Time Visualization of Transient Membrane Destabilization without Endosomal Lysis", ACS Nano, 2013, pp. 3767-3777, vol. 7 No. 5.
Reichmuth, et al., "mRNA Vaccine Delivery Using Lipid Nanoparticles," Therapeutic Delivery (2016), v. 7, No. 5, pp. 319-334.
Reinhard et al., "Carriers for Nucleic Acid Delivery to the Brain", Nanoparticles for Brain Drug Delivery, Chapter 9, 2021, pp. 289-316.
Restrepo et al., "Challenges in Designing randomized Clinical Trials for Cartilage Repair: the BST-CarGel Experience", Osteoarthritis and Cartilage, Supplement 1, 2009, pp. S177-S178, vol. 17.
Rheosense, Inc., "Viscosity of Two Component Mixtures", 2020, 5 pages.
Ribeiro et al., "Use of nanoparticle concentration as a tool to understand the structural properties of colloids" Scientific Reports, 2018, pp. 1-8, vol. 8.
Richard et al., "Ionization Behavior of Chitosan and Chitosan-DNA Polyplexes Indicate that Chitosan has a Similar Capability to Induce a proton-Sponge Effect as PEI", Biomacromolecules,2013, pp. 1732-1740, vol. 14.
Richner et al., "Modified mRNA Vaccines Protect against Zika Virus Infection", Cell, 2017, pp. 1-23.
Rizvi et al., "Murine liver repair via transient activation of regenerative pathways in hepatocytes using lipid nanoparticle-complexed nucleoside-modified mRNA," Nature Communications, Jan. 27, 2021, pp. 1-10, vol. 12, Article No. 613.
Rockx et al., "Comparative Pathogenesis of COVID-19, MERS, and SARS in a nonhuman primate model," Science, Apr. 17, 2020, pp. 1-10.
Roltgen et al., "mRNA vaccination compared to infection elicits an IgG-predominant response with greater SARS-CoV-2 specificity and similar decrease in variant spike recognition," medRxiv, Apr. 7, 2021, pp. 1-33. retrieved from URL https://doi.org/10.1101/2021.04.05.21254952.
Rossomacha et al., "Simple Methods for Staining Chitosan in Biotechnological Applications", Biosyntech Canada Inc., 2004, pp. 1-19, vol. 27, No. 1.
Rothgangl et al., "In vivo adenine base editing of PCSK9 in macaques reduces LDL cholesterol levels," Nature Biotechnology, May 19, 2021, pp. 949-957, vol. 39.

(56) References Cited

OTHER PUBLICATIONS

Rothwell, et al., "The mRNA IP and Competitive Landscape: Translate BIO; Arcturus; eTheRNA and Other Startups; and LNP Technology (Part II)," JDSUPRA, May 3, 2021, 10 pages.
Roughley et al., "The potential of chitosan-based gels containing intervertebral disc cells for nucleus pulposus supplementation", Biomaterials, 2006, pp. 388-396, vol. 27.
Rowland, C. et al., "Drug companies defend vaccine monopolies in face of global outcry," The Washington Post, Mar. 20, 2021 [online], [retrieved on Mar. 8, 2022]. Retrieved from the Internet URL: https://www.washingtonpost.com/business/2021/03/20/covid-vaccine-global-shortages/, 13 pages.
Rowland, C., "Inside Pfizer's race to produce the world's biggest supply of covid vaccine." The Washington Post, Jun. 16, 2021 [online], [retrieved on Mar. 8, 2022]. Retrieved from the Internet URL: https://www.washingtonpost.com/business/2021/06/16/pfizer-vaccine-engineers-supply/, 15 pages.
Rowland, C., "Why grandparents can't find vaccines: Scarcity of niche biotech ingredients," The Washington Post, Feb. 18, 2021 [online], [retrieved on Mar. 8, 2022]. Retrieved from the Internet URL: https://www.washingtonpost.com/business/2021/02/18/vaccine-fat-lipids-supply/, 10 pages.
Rozkov et al., Large-scale production of endotxoin-frree plasmids for transient expression in mammalian cell culture, Biotechnol. Bioeng., 2008, pp. 557-566.
Rurik et al., "Car T cells produced in vivo to treat cardiac injury," Science, Jan. 7, 2022, pp. 91-96, vol. 375.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Sadoff et al., "Safety and immunogenicity of the Ad26.COV2.S COVID-19 vaccine candidate: interim results of a phase 1/2a, double-blind, randomized, placebo-controlled trial," medRxiv, Sep. 25, 2020, pp. 1-28. retrieved from URL https://doi.org/10.1101/2020.09.23.20199604.
Sago et al., "High-throughput in vivo screen of functional mRNA delivery identifies nanoparticles for endothelial cell gene editing", PNAS, Oct. 16, 2018, pp. 1-10, vol. 115, No. 42.
Sagonowsky, "Bio: Moderna, Merck execs see possible speed bumps in COVID-19 vaccine manufacturing. FiercePharma", Jun. 11, 2020, 5 pages. Retrieved from the Internet URL: https://www.fiercepharma.com/manufacturing/bio-moderna-merck-execs-see-possible-speed-bumps-covid-19-vaccine-manufacturing.
Sagonowsky, "CureVac's mRNA coronavirus shot boasts one advantage over Pfizer and Moderna counterparts-refrigerated storage," FiercePharma, Nov. 12, 2020 [online], [retrieved on Mar. 8, 2022]. Retrieved from the Internet URL: https://www.fiercepharma.com/pharma/curevac-s-mrna-coronavirus-shot-holds-edge-over-pfizer-and-moderna-counterparts-refrigerated, 3 pages.
Sagonowsky, E., "Pfizer and BioNTech, scaling up for 2B coronavirus vaccine doses, temporarily cut deliveries in EU, Canada," FiercePharma, Jan. 19, 2021 [online], [retrieved on Mar. 8, 2022]. Retrieved from the Internet URL: https://www.fiercepharma.com/pharma/pfizer-and-biontech-pushing-for-2b-coronavirus-vaccine-doses-2021-temporarily-reduce, 3 pages.
Sagonowsky, "FDA will require 50% efficacy for COVID-19 vaccines, WSJ says. How high is that bar?" FiercePharma, Jun. 30, 2020, 3 pages. [online], [retrieved on Mar. 8, 2022]. Retrieved from the Internet URL: https://www.fiercepharma.com/vaccines/fda-to-require-at-least-50-efficacy-for-covid-19-vaccines-wsj.
Sagonowsky, "Johnson & Johnson gears up for 60,000-person COVID-19 vaccine trial, the industry's biggest yet," FiercePharma, Aug. 21, 2020 [online], [retrieved on Mar. 8, 2022]. Retrieved from the Internet URL: https://www.fiercepharma.com/vaccines/johnson-johnson-gears-up-for-60-000-person-covid-vaccine-trial-next-month, 2 pages.
Sahin et al., "BNT162b2 vaccine induces neutralizing antibodies and poly-specific T cells in humans," Nature, May 27, 2021, 30 pages. retrieved from URL https://doi.org/10.1038/s41586-021-03653-6.
Sahin et al., "Concurrent human anitbody and TH1 type T-cell responses elicited by a COVID-19 RNA vaccine," medRxiv, Jul. 20, 2020, pp. 1-27. retrieved from URL https://doi.org/10.1101/2020.07.17.20140533.
Sahin, "Reporting Summary," Nature Research, Dec. 30, 2020, pp. 1-6.
Sahin, U. et al., "mRNA-based therapeutics—developing a new class of drugs," Nature Reviews Drug Discovery, vol. 13(10)759-780 (2014).
Samanovic et al., "Poor antigen-specific responses to the second BNT162b2 mRNA vaccine dose in SARS-CoV-2-experienced individuals," medRxiv, Feb. 9, 2021, retrieved from URL https://doi.org/10.1101/2021.02.07.21251311, 9 pages.
Samaridou, et al., "Lipid nanoparticles for nucleic acid delivery: Current perspectives." Advanced drug delivery reviews, 2020, pp. 37-63, vol. 154.
Sample, "Delay in giving second jabs of Pfizer vaccine improves immunity," The Guardian, May 13, 2021, 4 pages. [online], [retrieved on Mar. 8, 2022]. Retrieved from the Internet URL: http://www.theguardian.com/science/2021/may/14/delay-in-giving-second-jabs-of-pfizer-vaccine-improves-immunity.
Samsa et al., "Self-Amplifying RNA Vaccines for Venezuelan Equine Encephalitis Virus Induce Robust Protective Immunogenicity in Mice," Molecular Therapy, Apr. 2019, pp. 850-865, vol. 27.
Saslow, "We're all starved for hope", The Washington Post, Jul. 6, 2020.
Satapathy et al., "Solid Lipid Nanoparticles (SLNs): An Advanced Drug Delivery System Targeting Brain Through BBB", Pharmaceutics, 2021, pp. 1-36, vol. 13.
Sato et al., "Highly specific delivery of siRNA to hepatocytes circumvents endothelial cell-mediated lipid nanoparticle-associated toxicity leading to the safe and efficacious decrease on the hepatitis B virus", Journal of Controlled Release, Nov. 2017, pp. 216-225, vol. 266.
Sato et al., "Relationship Between the Physicochemical Properties of Lipid Nanoparticles and the Quality of siRNA Delivery to Liver Cells", Molecular Therapy, Apr. 2016, pp. 788-795, vol. 24, No. 4.
Sato, et al., "Understanding structure-activity relationships of pH-sensitive cationic lipids facilitates the rational identification of promising lipid nanoparticles for delivering siRNAs in vivo", Journal of Controlled Release, 2019 pp. 140-152, vol. 295.
Saunders et al., "A Nanoprimer to Improve the Systemic Delivery of siRNA and mRNA", Nano Letters, 2020, pp. 4264-4269, vol. 20.
Saunders et al., "Neutralizing antibody vaccine for pandemic and pre-emergent coronaviruses," Supplementary Figures, Nature, May 10, 2021, 28 pages.
Scheel et al., "Immunostimulating capacities of stabilized RNA molecules", Immunology, 2004, pp. 537-547, vol. 34.
Schlothauer et al., "Novel human IgG1 and IgG4 Fc-engineered antibodies with completely abolished immune effector functions", Protein Engineering Design and Selection, 2016, pp. 457-466, vol. 29, No. 10.
Schmidt et al., "Prevalence of serum IgG antibodies against SARS-CoV-2 among clinic staff," PLOS One, Jun. 25, 2020, pp. 1-8, vol. 15, No. 6.
Schnee et al., "An mRNA Vaccine Encoding Rabies Virus Glycoprotein Induces Protection against Lethal Infection in Mice and Correlates of Protection in Adult and Newborn Pigs", PLOS Neglected Tropical Diseases, 2016, pp. 1-20, vol. 10, No. 6.
Schulze et al., "A Liposomal Platform for Delivery of a Protein Antigen to Langerin- Expressing Cells", Supporting Information, May 2019, pp. 2576-80, vol. 58, No. 21.
Sciex, "Thousands of Lipids. One name to remember: Lipidyzer" Broucher, 2016, 8 pages.
Scudellari, "Attack of the killer clones: the next generation of modified T-cell therapies is taking on solid tumors—but it's an uphill fight", Nature, Dec. 2017, pp. 1-3, vol. 552.

(56) References Cited

OTHER PUBLICATIONS

Sedic et al., "Safety Evauation of Lipid Nanoaprticle-Formulated Midfied mRNA in the Sprague-Dawley Rat and Cynomolgus Monkey", Veterinary Pathology, 2017, pp. 341-354, vol. 55, No. 2.
Self et al., "Comparative Effectiveness of Moderna, Pfizer-BioNTech, and Janssen (Johnson & Johnson) Vaccines in Preventing COVID-19 Hospitalizations Among Adults Without Immunocompromising Conditions—United States, Mar.-Aug. 2021," Morbidity and Mortality Weekly Report, Sep. 24, 2021, pp. 1337-1343, vol. 70, No. 38.
Semple, et al., Interactions of liposomes and lipid-based carrier systems with blood proteins: Relation to clearance behaviour in vivo, Advanced drug delivery reviews, Jun. 8, 1998, pp. 3-17, vol. 32.
Semple, S.C., et al., "Rational design of cationic lipids for siRNA delivery", Nature Biotechnology, 2010, vol. 28, No. 2, 172-176.
Seow et al., "Longitudinal evaluation and decline of antibody responses in SARS-CoV-2 infection," medRxiv, Jul. 11, 2020, pp. 1-24. retrieved from URL https://doi.org/10.1101/2020.07.09.20148429.
Shahzad et al., "Drug Delivery Using Nanomaterials", Emerging Materials and Technologies, 2021, pp. 1-431.
Shang et al., "The outbreak of SARS-CoV-2 pneumonia calls for viral vaccines," npj Vaccines, Mar. 6, 2020, pp. 1-3, vol. 5, No. 18.
Shaw et al., "Safety and immunogenicity of a mRNA-based chikungunya in a phase 1 dose-ranging trial", International Journal of Infectious Diseases (Abstracts), 2019, pp. 1, vol. 79, No. S1.
Shimizu et al., "Simultaneous quantification of components of neoglycolipid-coated liposomes using high-performance liquid chromatography with evaporative light scattering detection", Journal of Chromatography B, 2001, pp. 127-133, vol. 754.
Shin et al., "COVID-19 vaccine development and a potential nanomaterial path forward," Nature Nanotechnology, Aug. 2020, pp. 646-655, vol. 15.
Shive et al., "BST-CarGel: In Situ ChondroInduction for Cartilage Repair", Operative Techniques in Orthapedics, 2006, pp. 271-278, vol. 16, No. 4.
Shobaki et al., "Mixing lipids to manipulate the ionization status of lipid nanoparticles for specific tissue targeting", International Journal of Nanomedicine, 2018, pp. 8395-8410, vol. 13.
Shrock et al., Viral epitope profiling of COVID-19 patients reveals cross-reactivity and correlates of severity, Science, Nov. 27, 2020, vol. 370, No. 6520.
Si et al., "Targeted Exosomes for Drug Delivery: Biomanufacturing, Surface Tagging, and Validation", Biotechnology Journal, 2019, pp. 1-12, vol. 15, No. 1.
Siengra et al., "Lipid Nanoparticle Spherical Nucleic Acids for Intracellular DNA and RNA Delivery", Nano Letters, Jul. 21, 2021, pp. 6584-6591, vol. 21, No. 15.
Silverman, et al., Selective RNA cleavage by isolated RNase L activated with 2-5A antisense chimeric oligonucleotides, InMethods in Enzymol., Jan. 1, 2000, pp. 522-533.
Sim et al., "Development of an Electromechanical Grade to Assess Human Knee Articular Cartilage Quality", Annals of Biomedical Engineering, Oct. 2017, pp. 2410-2421, vol. 45 No. 10.
Sim et al., "Electromechanical Probe and Automated Indentation Maps are Sensitive techniques in Assessing Early Degenerated Human Articular Cartilage", Journal of orthopedic Research, 2016, pp. 1-10, vol. 35, No. 4.
Sim et al., "Non-destructive electromechanical assessment (Arthro-BST) of human articular cartilage correlates with histological scores and biomechanical properties", osteoarthritis and Cartilage,2014, pp. 1926-1935, vol. 22.
Singh et al., "A rapid isocratic high-performance liquid chromatography method for determination of cholesterol and 1,2-dioleoyl-sn-glycero-3-phosphocholine in liposome-based drug formulations", Journal of Chromatography A, 2005, pp. 347-353.
Smith et al., "In situ programming of leukemia-specific T cells using synthetic DNA nanocarriers", Nature Nanotechnology, Aug. 2017, pp. 813-823, vol. 12.
Smith, et al., "Tertiary Amine Esters for Carbon Dioxide Based Emulsions", ACS, Mar. 15, 2007, 6 pages. Retrieved from the Internet <url: <a=href=>https://pubs.acs.org/doi/10.1021/ie060934h.</url:>.
Smith et al., "The endosomal Escape of Nanoparticles: Toward More Efficient Cellular Delivery", Bioconjugate Chemistry, 2019, pp. 263-272, vol. 30.
Soulhat et al., "A Fibril-Network-Reinforced Biphasic Model of Cartilage in Unconfined Compression", Journal of Biomechanical Engineering, Jun. 1999, pp. 340-347, vol. 121.
Steensels et al., "Comparison of SARS-CoV-2 Antibody Response Following Vaccination with BNT162b2 and mRNA-1273," JAMA, Aug. 30, 2021, pp. E1-E3.
Stein, et al., Antisense oligonucleotides as therapeutic agents—is the bullet really magical?, Science, Aug. 20, 1993, pp. 1004-1012, vol. 261, No. 5124.
Stetefeld et al., "Dynamic light scattering: a practical guide and applications in biomedical sciences", Biophysics Review, 2016, pp. 409-427, vol. 8.
Studer et al., "Vitrification of articular cartilage by high-pressure freezing", Journal of Microscopy, Pt. 3, Sep. 1995, pp. 321-332, vol. 179.
Subbarao, et al., "Respiratory Virus Infections: Understanding COVID-19," Immunity, vol. 52, Jun. 16, 2020, pp. 905-909.
Sultana et al., "Optimizing Cardiac Delivery of Modified mRNA," Molecular Therapy, Jun. 2017, pp. 1306-1315, vol. 25.
Swaminathan et al., "A novel lipid nanoparticle adjuvant significantly enhances B Cell and T Cell responses to sub-unit vaccine antigens", Vaccine, 2016, pp. 110-119, vol. 34.
Swaminathan et al., "A Tetravalent Sub-Unit Dengue Vaccine Formulated with Ionizable Cationic Lipid Nanoparticle induces Significant Immune Responses in Rodents and Non-Human Primates", Scientific Reports, Oct. 2016, pp. 1-17, vol. 6.
Swan et al., "A simpler expression for henry's function describing the electrophoretic mobility f spherical colloids", Journal of Colloid and interface Science, 2012, pp. 92-94, vol. 388.
Tabernero et al., "First-in-Humans Trial of an RNA Interference Therapeutic Targeting VEGF and KSP in Cancer Patients with Liver Involvement", Cancer Discovery, Jan. 28, 2013, pp. 406-417.
Tam, et al., Small molecule ligands for enhanced intracellular delivery of lipid nanoparticle formulations of siRNA, Nanomedicine: Nanotechnology, Biology and Medicine, Jul. 1, 2013, pp. 665-674, vol. 9, No. 5.
Tanaka et al., "Development of Lipid-like materials for RNA delivery based on intracellular environment-responsive membrane destabilization and spontaneous collapse", Advanced Drug Delivery Reviews, 2020, pp. 1-17, vol. 154.
Tavakoli Naeini, A. et al. (Apr. 7, 2017) "Automated in-line mizing system for large scale produciton of chitosan-based polyplexes" J Colloid Interface Sci, 500:253-263.
Taylor, "CureVac links COVID-19 vaccine to immune response, setting it up to enter pivotal trial" FierceBiotech, 2020, 2 pages.
Taylor, "Moderna finalizes design of phase 3 COVID-19 vaccine trial ahead of July start", FierceBiotech, Jun. 11, 2020, 5 pages. Retrieved from the Internet URL: https://www.fiercebiotech.com/biotech/moderna-finalizes-design-phase-3-covid-19-vaccine-trial-ahead-july-start.
Taylor, N. P., "AstraZeneca's COVID-19 vaccine 70% effective, shares fall," FierceBiotech, Nov. 23, 2020 [online], [retrieved on Mar. 8, 2022]. Retrieved from the Internet URL: https://www.fiercebiotech.com/biotech/astrazeneca-s-covid-19-vaccine-70-effective-phase-3, 2 pages.
Taylor, N. P., "CureVac gets OK to start testing mRNA COVID-19 vaccine in humans," FierceBiotech, Jun. 17, 2020 [online], [retrieved on Mar. 8, 2022]. Retrieved from the Internet URL: https://www.fiercebiotech.com/biotech/curevac-gets-ok-to-start-testing-mrna-covid-19-vaccine-humans, 2 pages.
Taylor, N. P., "Moderna stock sinks as patent case spurs concern for COVID-19 vaccine," FierceBiotech, Jul. 24, 2020 [online], [retrieved on Mar. 8, 2022]. Retrieved from the Internet URL: https://www.fiercebiotech.com/biotech/moderna-stock-sinks-as-patent-case-spurs-concern-for-covid-19-vaccine, 6 pages.

(56) References Cited

OTHER PUBLICATIONS

Taylor, N. P., "Pfizer, BioNTech share clinical data linking favored COVID-19 vaccine to improved tolerability," FierceBiotech, Aug. 21, 2020 [online], [retrieved on Mar. 8, 2022]. Retrieved from the Internet URL: https://www.fiercebiotech.com/biotech/pfizer-biontech-share-clinical-data-linking-favored-covid-19-vaccine-to-improved, 2 pages.

Taylor, N. P., "Pfizer passes COVID-19 vaccine safety milestone, reveals 95% efficacy ahead of EUA," FierceBiotech, Nov. 18, 2020 [online], [retrieved on Mar. 8, 2022]. Retrieved from the Internet URL: https://www.fiercebiotech.com/biotech/pfizer-passes-covid-19-vaccine-safety-milestone-readies-for-eua 2 pages.

Taylor, N. P., "Pfizer reports strong T-cell response to COVID-19 vaccine," FierceBiotech, Jul. 20, 2020 [online], [retrieved on Mar. 8, 2022]. Retrieved from the Internet URL: https://www.fiercebiotech.com/biotech/pfizer-reports-strong-t-cell-response-to-covid-19-vaccine, 2 pages.

Taylor, N. P., "Positive news' on AstraZeneca's COVID-19 vaccine is imminent: report," FierceBiotech, Jul. 15, 2020 [online], [retrieved on Mar. 8, 2022]. Retrieved from the Internet URL: https://www.fiercebiotech.com/biotech/positive-news-astrazeneca-s-covid-19-vaccine-imminent-report, 2 pages.

Taylor, N. P., "Weak clinical data force Sanofi, GSK to delay COVID-19 vaccine," FierceBiotech, Dec. 11, 2020 [online], [retrieved on Mar. 8, 2022]. Retrieved from the Internet URL: https://www.fiercebiotech.com/biotech/weak-clinical-data-force-sanofi-gsk-to-delay-covid-19-vaccine, 3 pages.

Tenchov et al., "Cubic Phases in Phosphatidylcholine-Cholesterol Mixtures: Cholesterol as Membrane 'Fusogen'", Biophysical Journal, Oct. 2006, pp. 2508-2516, vol. 91.

Ter Meulen et al., "Human monoclonal antibody as prophylaxis for SARS coronavirus infection in ferrets," The Lancet, Jun. 26, 2004, pp. 2139-2141, vol. 363.

Thess et al., "Sequence-engineered mRNA Without Chemical Nucleosside Modifications Enables an Effective Protein Therapy in Large Animals," Molecular Therapy, Jun. 30, 2015, pp. 1-9, with supplemental data, vol. 23, No. 9.

Thibault et al., "Cyclic compression of cartilage/bone explants in vitro leads to physical weakening, mechanical breakdown of collagen and release of matrix fragments", Journal of Orthopedic Research, 2002, pp. 1265-1273, vol. 20.

Thibault et al., "Excess Polycation Mediates efficient chitosan-based gene transfer by promoting lysosomal release of the polyplexes", Biomaterials, 2011, pp. 4639-4646, vol. 32.

Thibault et al., "Fibronectin, Vitronectin, and Collagen I Induce Chemotaxis and Haptotaxis of Human and Rabbit Mesenchymal Stem Cells in a Standardized Transmembrane Assay", Stem Cells and Development, 2007, pp. 489-502, vol. 16.

Thibault et al., "Intracellular Trafficking and Decondensation Kinetics of Chitosan-pDNA Polyplexes", Molecular Therapy, Oct. 2010, pp. 1787-1795, vol. 18, No. 10.

Thibault et al., "Migration of Bone Marrow Stromal Cells in 3D: 4 Color Methodology Reveals Spatially and temporally Coordinated Events", Cell Motility and the Cytoskeleton, 2006, pp. 725-740, vol. 63.

Thibault et al., "Structure Dependence of Lysosomal Transit of Chitosan-Based Polyplexes for Gene Delivery", Molecular Biotechnology, 2016, pp. 1-11, vol. 58, No. 10.

Thomas et al., "Safety and Efficacy of the BNT162b2 mRNA Covid-19 Vaccine through 6 Months," N Engl J Med, Sep. 15, 2021, pp. 1-13.

Thran et al., "mRNA mediates passive vaccination against infectious agents, toxins, and tumors", EMBO Molecular Medicine, 2017, pp. 1434-1447, vol. 9, No. 10.

Tombacz et al., "Highly efficient CD4+ T cell targeting and genetic recombination using engineered CD4+ cell-homing mRNA-LNP," Molecular therapy, 2021, pp. 3293-3304, vol. 9, No. 11.

Tombacz et al., "Hughly efficient CD4+ T cell targeting and genetic recombination using engineered CD4+ cell-homing mRNA-LNP", Molecular Therapy, Jun. 3, 2021, pp. 1-28, vol. 29.

Torjesen, "Covid-19: Norway investigates 23 deaths in frail elderly patients after vaccination," BMJ, Jan. 15, 2021, 1 page, vol. 372, No. n149.

Torrence et al., Targeting RNA for degradation with a (2'-5') oligoadenylate- antisense chimera, Proc. Natl. Acad. Sci., Feb. 15, 1993, pp. 1300-1304.

Tran-Khanh et al., "Aged bovine chondrocytes display a diminished capacity to produce a collagen-rich, mechanically functional cartilage extracellular matrix", Journal of orthopedic Research, 2005, pp. 1354-1362, vol. 23.

Tran-Khanh et al., "Young Adult Chondrocytes Proliferate Rapidly and Produce a Cartilaginous Tissue at the Gel-Media Interface in Agarose Cultures", Connective Tissue Research, 2010, pp. 216-223, vol. 51.

Translate Bio, Translate Bio Announces FDA Clearance to Proceed with a Single-ascending Dose (SAD) Phase 1/2 Clinical Trial for Ornithine Transcarbamylase (OTC) Deficiency, Translate Bio, Inc., Jun. 26, 2019, 4 pages. Retrieved from the Internet URL: http://www.globenewswire.com/news-release/2019/06/26/1874354/0/en/Translate-Bio-Announces-FDA-Clearance-to-Proceed-with-a-Single-ascending-Dose-SAD-Phase-1-2-Clinical-Trial-for-Ornithine-Transcarbamylase-OTC-Deficiency.html.

Tureci et al., "Racing for a SARS-CoV-2 vaccine," BioNTech, 2021, 7 pages, DOI: 10.15252/emmm.202115145.

Tuzimski, "Application of different modes of thin-layer chromatography and mass spectrometry for the separation and detection of large and small biomolecules", Journal of Chromatography A, 2011, pp. 8799-8812, vol. 1218.

Uebbing et al., "Investigation of pH-responsiveness inside lipid nanoparticles for parenteral mRNA application using small angle X-ray scattering," Supporting Information, 2020, pp. S1-S11.

United States Patent and Trademark Office, Inter Partes Review of U.S. Pat. No. 9,404,127, Feb. 21, 2018, 75 pages.

United States Securities and Exchange Commission, "Annual Report Pursuant to Section 13 or 15(d) of the Securities Exchange Act of 1934", Dec. 31, 2020, 355 pages. Retrieved from the Internet URL: https://www.sec.gov/ix?doc=/Archives/edgar/data/1682852/000168285221000006/mrn a-20201231.htm.

Unknown Author, 18:1-d7-cholesterol | Avanti Polar Lipids, retrieved on Nov. 2, 2022, 2 pages. https://avantilipids.com/product/791645?utm_source=behavioral-VT.

Unknown Author, Arcturus Therapeutics Announces Positive Interim ARCT-021 (LUNAR-COV19) Phase 1/2 Study Results for Both Single Shot and Prime-boost Regimens, and Up to $220 Million in Additional Financial Commitments from Singapore. MarketWatch, Nov. 9, 2020 [online], 2 pages [retrieved on Mar. 7, 2022]. Retrieved from the Internet <url: <a= href=>https://www.marketwatch.com/press-release/arcturus-therapeutics-announces-positive-interim-arct-021-lunar-cov19-phase-12-study-results-for-both-single-shot-and-prime-boost-regimens-and-up-to-220-million-in-additional-financial-commitments-from-singapore-Nov. 9, 2020 .</url:>.

Unknown Author, Arcturus Therapeutics, "Building the Next Generation of RNA Medicines: Development of a self-transcribing and replicating (STARRtm) mRNA vaccine candidate against SARS-CoV-2," Sep. 2020, 35 pages.

Unknown Author, "Background document on the mRNA vaccine BNT162b2 (Pfizer-BioNTech) against COVID-19," World Health Organization, Jan. 14, 2021, 44 pages.

Unknown Author, BioNTech, "BioNTech and Pfizer announce regulatory approval from German authority Paul-Ehrlich-Institut to commence first clinical trial of COVID-19 vaccine candidates," Apr. 22, 2020, 3 pages.

Unknown Author, BioNTech, Lipid Structures, Dec. 12, 2020, 2 pages.

Unknown Author, BioNTech, "Pfizer and BioNTech Conclude Phase 3 Study of COVID-19 Vaccine Candidate, Meeting All Primary Efficacy Endpoints," Nov. 18, 2020, 3 pages.

Unknown Author, "COVID-19 mRNA Vaccine BNT162b2 (BNT162b2 RNA) concentrate for solution for injection," Medicines & Healthcare products Regulatory Agency, Public Assessment Report, 2020, pp. 1-51.

Unknown Author, "COVID-19 vaccine AZD1222 showed robust immune responses in all participants in Phase I/II trial," AstraZeneca,

(56) References Cited

OTHER PUBLICATIONS

Jul. 20, 2020, 5 pages. [online], [retrieved on Mar. 8, 2022]. Retrieved from the Internet URL: https://www.astrazeneca.com/media-centre/press-releases/2020/covid-19-vaccine-azd1222-showed-robust-immune-responses-in-all-participants-in-phase-i-ii-trial.html.

Unknown Author, Curevac Covid 19 Activities. CureVac, Apr. 8, 2020 [online], [retrieved on Mar. 8, 2022], 5 pages. Retrieved from the Internet <url: <a=href=>https://www.curevac.com/covid-19.</url:>.

Unknown Author, Emergency Use Authorization for Pfizer-BioNTech COVID-19 Vaccine, May 10, 2021 (accessed Dec. 14, 2020), 10 pages.

Unknown Author, European Medicines Agency, Assessment report of COVID-19 mRNA vaccine (nucleoside-modified), Feb. 19, 2021, 140 pages.

Unknown Author, "Imperial College London gets UK funding for Covid-19 vaccine," Clinical Trials Arena, Apr. 23, 2020 [online], [retrieved on Mar. 8, 2022]. Retrieved from the Internet URL: https://www.clinicaltrialsarena.com/news/imperial-covid-19-vaccine-trial/, 9 pages.

Unknown Author, "Industry News: Pfizer and BioNTech to start human trials of COVID-19 vaccine," SelectScience, Apr. 24, 2020 [online], [retrieved on Mar. 8, 2022]. Retrieved from the Internet URL: http://www.selectscience.net/industry-news/pfizer-and-biontech-to-start-human-trials-of-covid-19-vaccine/?artID=51330, 4 pages.

Unknown Author, "Moderna's COVID-19 Vaccine Candidate Meets its Primary Efficacy Endpoint in the First Interim Analysis of the Phase 3 COVE Study," Moderna, Nov. 16, 2020 [online], [retrieved on Mar. 8, 2022]. Retrieved from the Internet URL: https://investors.modernatx.com/news-releases/news-release-details/modernas-covid-19-vaccine-candidate-meets-its-primary-efficacy/, 6 pages.

Unknown Author, "Moderna Loses Challenge of Arbutus Patent on Vaccine Technology," Bloomberg, Jul. 23, 2020, 9 pages.

Unknown Author, "Moderna's Work on a Potential Vaccine Against COVID-19," Moderna, Apr. 16, 2020 [online], [retrieved on Mar. 8, 2022]. Retrieved from the Internet URL: https://www.modernatx.com/modernas-work-potential-vaccine-against-covid-19, 3 pages.

Unknown Author, "Novavax Announces Positive Phase 1 Data for its COVID-19 Vaccine Candidate," Novavax, Aug. 4, 2020 [online], [retrieved on Mar. 8, 2022]. Retrieved from the Internet URL: https://ir.novavax.com/news-releases/news-release-details/novavax-announces-positive-phase-1-data-its-covid-19-vaccine , 5 pages.

Unknown Author "Pfizer and Biontech Announce Vaccine Candidate Against COVID-19 Achieved Success in First Interim Analysis From Phase 3 Study," Pfizer Inc., Nov. 9, 2020 [online], 7 pages. [retrieved on Mar. 8, 2022]. Retrieved from the Internet <url: <a=href=>https://www.pfizer.com/news/press-release/press-release-detail/pfizer-and-biontech-announce-vaccine-candidate-against.</url:>.

Unknown Author, "Start of Production in Record Time: Evonik Delivers First Lipids From German Facility to Biontech," Evonik, , 1 page. [online], [retrieved on Mar. 8, 2022]. Retrieved from the Internet URL: https://corporate.evonik.com/en/start-of-production-in-record-time-evonik-delivers-first-lipids-from-german-facility-to-biontech-157147.html.

Unknown Author, Trilink Biotechnologies CleanCap Technology, 2022, 4 pages. https://www.trilinkbiotech.com/cleancap.

Unknown Author, Which animals are being used to develop a COVID-19 Vaccine? AnimalResearch.info, Jun. 15, 2020 [online], [retrieved on Mar. 8, 2022]. Retrieved from the Internet URL: http://www.animalresearch.info/en/medical-advances/diseases-research/sars-cov-2/, 14 pages.

Unkown Author, "Clinical Trial Protocol Including Amendments Nos. 01 to 04 BNT162-01," BioNTech, Version 7.0, Jun. 26, 2020, pp. 1-137.

US Dept. of Health and Human Services, "Development and Licensure of Vaccines to Prevent COVID-19: Guidance for Industry," Jun. 2020, 24 pages.

Uster et al., "Insertion of poly (ethylene glycol) derivatized phospholipid into pre-formed liposomes results in prolonged in vivo circulation time", FEBS Letters, 1996, pp. 243-246, vol. 386.

Vabret et al., "Immunology of COVID-19: Current State of the Science," Immunity, Jun. 16, 2020, pp. 910-941, vol. 52.

Vacha et al., "The Orientation and Charge of Water at the Hydrophobic Oil droplet—water Interface", The Journal of the American Chemical Society, 2011, pp. 10204-10210, vol. 133.

Valverde-Franco et al., "Defects in articular cartilage metabolism and early arthritis in fibroblast growth factor receptor 3 deficient mice", Human Molecular Genetics, 2006, pp. 1783-1792, vol. 15 No. 11.

Van Der Meel et al., "Nanotechnology for organ-tunable gene editing", Nature Nanotechnology, Apr. 2020, pp. 252-255, vol. 15.

Van Meer et al., "Membrane lipids: where they are and how they behave" Nature, Feb. 2008, pp. 112-124, , vol. 9.

Veiga et al., "Cell Specific delivery of modified mRNA expressing therapeutic proteins to leukocytes", Nature Communications, Oct. 2018, pp. 1-9, vol. 9.

Veilleux et al., "Lyophilisation and concentration of chitosan/siRNA polyplexes: Influence of buffer composition, oligonucleotide sequence, and hyaluronic acid coating", Journal of Colloid and Interface Science, 2018, pp. 335-345, vol. 512.

Veilleux et al., "Preparation of Concentrated Chitosan/DNA Nanoparticle Formulations by Lyophilization for Gene Delivery at Clinically Relevant Dosages", Journal of Pharmaceutical Sciences, 2016, pp. 88-96, vol. 105.

Vermeulen et al., "Endosomal Size and membrane leakiness Influence Proton Sponge-Based Rupture of Endosomal Vesicles, Suporting Information", ACS nano, 2018, 8 pages.

Viger-Gravel et al., "Structure of Lipid Nanoparticles Containing siRNA or mRNA by Dynamic Nuclear Polarization Enhanced NMR Spectroscopy," Supporting Information, 2018, pp. S1-S32.

Villaverde et al., "Targeting strategies for improving the efficacy of nanomedicine in oncology", Journal of Nanotechnology, 2019, pp. 168-181, vol. 10.

Vogel et al., "A prefusion SARS-CoV-2 spike RNA vaccine is highly immunogenic and prevents lung infection in non-human primates," bioRxiv, Sep. 8, 2020, pp. 1-38. retrieved from URL https://doi.org/10.1101/2020.09.08.280818.

Vogel et al., "BNT162b vaccines protect rhesus macaques from SARS-CoV-2," Nature, Apr. 8, 2021, pp. 283-289, vol. 592.

Vogel et al., "Self-Amplifying RNA Vaccines Give Equivalent Protection against Influenza to mRNA Vaccines but at Much Lower Doses," Molecular Therapy, Feb. 2018, pp. 446-455, vol. 26, No. 2.

Vogel et al., "High-Resolution Single Particle Zeta Potential Characterization of Biological Nanoparticles using Tunable Resistive Pulse Sensing", Scientific Reports, Dec. 2017, pp. 1-13, vol. 7.

Voss et al., "Calculation of Standard Atomic Volumes for RNA and Comparison with Proteins: RNA is Packed More Tightly", Journal of Molecular Biology, 2005, pp. 477-492, vol. 346.

Voysey et al., "Single-dose administration and the influence of the timing of the booster dose on immunogenicity and efficacy of ChAdOx1 nCoV-19 (AZD1222) vaccine: a pooled analysis of four randomised trials," The Lancet, Mar. 6, 2021, pp. 881-891, vol. 397.

Vuong et al., "Feline coronavirus drug inhibits the main protease of SARS-CoV-2 and blocks virus replication," Nature Communications, 2020, pp. 1-8, vol. 11, No. 4282.

Wadman et al., "A Rampage through the body: The lungs are ground zero, but COVID-19 also tears through organ systems from brain to blood vessels," Science, Apr. 24, 2020, pp. 356-360, vol. 368, Issue 6489.

Walls et al., "Structure, Function, and Antigenicity of the SARS-COV-2 Spike Glycoprotein," Cell, Mar. 19, 2020, pp. 1-12, vol. 180.

Walsh et al., "Protocol: Safety and Immunogenicity of Two RNA-Based COVID-19 Vaccine Candidates," Pfizer, PF-07302048 (BNT162 RNA-Based COVID-19 Vaccines), Protocol C4591001, Final Protocol, Apr. 15, 2020, 314 pages.

Walsh et al., "RNA-Based COVID-19 Vaccine BNT162b2 Selected for a Pivotal Efficacy Study," medRxiv, Aug. 20, 2020, pp. 1-20. retrieved from URL https://doi.org/10.1101/2020.08.17.20176651.

(56) References Cited

OTHER PUBLICATIONS

Wamhoff et al., "A specific glycomimetic Langerin ligand for human Langerhans cell targeting", Supporting Information, ACS Central Science, 2019, pp. 808-820, vol. 5, No. 5.
Wang et al., "An Evidence Based Perspective on mRNA-SARS-CoV-2 Vaccine Development," Medical Science Monitor, 2020, pp. e924700-1-e924700-8, vol. 26.
Wang et al., Targeting Liver Sinusoidal Endothelial Cells: An Attractive Therapeutic Strategy to Control Inflammation in Nonalcoholic Fatty Liver Disease, Frontiers in Pharmacology, Apr. 5, 2021, pp. 1-16, vol. 12.
Watanabe et al., "Site-Specific glycan analysis of the SARS-CoV-2 spike," Science, May 4, 2020, pp. 1-9, DOI: 10.1126/science. abb9983.
Weber, Immune checkpoint proteins: a new therapeutic paradigm for cancer-preclinical background: CTLA-4 and PD-1 blockade, Semin. Oncol., Oct. 1, 2010, pp. 430-439, . vol. 37, No. 5.
Weinberg et al., Anti-OX40 (CD134) administration to nonhuman primates: immunostimulatory effects and toxicokinetic study, J. Immunother, Nov. 1, 2006, pp. 575-585, vol. 29, No. 6.
Weintraub, A., "It Could Be Several Years for 2 Leading COVID-19 Vaccines to Debut", Wall Street Analysts, Global Research, Apr. 22, 2020, 3 pages. Retrieved from the Internet URL: https://www.globalresearch.ca/it-could-take-5-years-covid-19-vaccines-debut-ai-analysis-finds/5710239.
Weintraub, A., "J&J COVID-19 vaccine candidate protects monkeys after single dose," FiercePharma, Jul. 30, 2020 [online], [retrieved on 2022-03-08]. Retrieved from the Internet URL: https://www.fiercebiotech.com/research/j-j-covid-19-vaccine-candidate-protects-monkeys-after-single-dose, 4 pages.
Weintraub, A., "Pfizer's COVID vaccine data raise some flags, analysts say, but not enough to scuttle an FDA nod," FiercePharma, Dec. 9, 2020 [online], [retrieved on Mar. 8, 2022]. Retrieved from the Internet URL: https://www.fiercepharma.com/pharma/pfizer-s-covid-vaccine-data-raise-some-questions-but-shouldn-t-scuttle-fda-nod-analysts, 2 pages.
Weintraub, "It's too soon to assume success for Moderna's COVID-19 vaccine: analyst", FierceBiotech, May 20, 2020, 5 pages. Retrieved from the Internet URL: https://www.fiercebiotech.com/biotech/it-s-too-soon-to-assume-success-for-moderna-s-covid-19-vaccine-analyst.
Weissman, D., "mRNA transcript therapy," Expert Review of Vaccines, vol. 14(2): 265-281 (2015).
Weissman et al., "D614G Spike Mutation Increases SARS CoV-2 Susceptibility to Neutralization," Cell Host & Microbe, Jan. 13, 2021, pp. 23-31, vol. 29.
Weissman et al., "D614G Spike Mutation Increases SARS CoV-2 Susceptibility to Neutralization," medRxiv, Jul. 24, 2020, pp. 1-16.
Wener, et al., The effect of base mismatches in the substrate recognition helices of hammerhead ribozymes on binding and catalysis, Nucleic Acids Research, Jun. 1995, 2092-2096, vol. 23, No. 12.
Widge, "Durability of responses after SARS-CoV-2 mRNA-1273 Vaccination", The New England Journal of Medicine, Correspondence, Dec. 2020, pp. 1-4.
Willis et al., "Nucleoside-modified mRNA vaccination partially overcomes maternal antibody inhibition of de novo immune responses in mice," Science Translational Medicine, Jan. 8, 2020, pp. 1-12, vol. 12.
Wilson et al., "Biodegradable PLGA-b-PEG Nanoparticles Induce T Helper 2 (Th2) Immune Responses and Sustained Antibody Titers via TLR9 Stimulation", Vaccines, May 29, 2020, pp. 1-14, vol. 8.
Wittrup et al., "Visualizing lipid-formulated siRNA release from endosomes and target gene knockdown", Nature Biotechnology, Aug. 2015, pp. 870-885, vol. 33, No. 8.
Wolfe, "Moderna loses challenge to Arbutus patent on vaccine technology", Jul. 23, 2020, 9 pages. Retrieved from the Internet URL: https://www.reuters.com/article/us-moderna-patent/moderna-loses-challenge-to-arbutus-patent-on-vaccine-technology-idUSKCN2402XY.
Wong et al., "Chondrocyte Biosynthesis Correlates with Local Tissue Strain in Statically Compressed Adult Articular Cartilage", Journal of orthopedic Research, 1997, pp. 186-196, vol. 15.
Wu et al., "Progress and Concept for COVID-19 Vaccine Development," Biotechnology Journal, 2000147, 2020, pp. 1-3.
Xia et al., "Effect of an Inactivated Vaccine Against SARS-CoV-2 on Safety and Immunogenicity Outcomes," JAMA, Aug. 13, 2020, pp. E1-E10.
Xiao et al., "Regulation of microglia polarization via mannose receptor-mediated delivery of siRNA by ligand-functionalized DoGo LNP", Royal Society of Chemistry Advances, 2021, pp. 32549-32558, vol. 11.
Xie et al., "Neutralization of N501Y mutant SARS-CoV-2 by BNT162b2 vaccine-elicited sera," bioRxiv, Jan. 7, 2021, 6 pages. retrieved from URL https://doi.org/10.1101/2021.01.07.425740.
Xu et al., "Cholesterol domains in cationic lipid/DNA complexes improve transfection", Biochimica et Biophysica Acta, Apr. 2008, pp. 2177-2181, vol. 1778.
Yan et al., "Systemic mRNA Delivery to the Lungs by Functional Polyester-based Carriers", Biomacromolecules, 2017, pp. 4307-4315, vol. 18.
Yang et al., "Measurement of the Zeta Potential of Gas Bubbles in Aqueous Solutions by Microelectrophoresis Method", Journal of Colloid and Interface Science, 2001, pp. 128-135, vol. 243.
Yu et al., "DNA vaccine protection against SARS-CoV-2 in rhesus macaques," Science 369(6505) pp. 806-811 (2020).
Yu et al., "Hydrophobic Optimization of Functional Poly (TPAE-co-suberoyl chloride) for Extrahepatic mRNA Delivery following Intravenous Administration", Pharmaceutics, 2021, pp. 1-13, vol. 13.
Zadeh, et al., "Augmentation Techniques for Meniscus Repair", The Journal of Knee Surgery, Mar. 9, 2017, pp. 1-18.
Zagato et al., Quantifying the average number of nucleic acid therapeutics per nanocarrier by single particle tracking microscopy, Supporting Information, Molecular Pharmaceutics, 2018, pp. 1142-1149, vol. 15, No. 3.
Zak et al., "Lipid Nanoparticles for Organ-Specific mRNA Therapeutic Delivery", Pharmaceutics, 2021, pp. 1-13, vol. 13.
Zamore, et al., Ribo-gnome: the big world of small RNAs, Science, Sep. 2, 2005, pp. 1519-1524.
Zamore et al., "RNAi: double-stranded RNA directs the ATP-dependent cleavage of mRNA at 21 to 23 nucleotide intervals," 2000, Cell, 101, 25-33.
Zeng et al., "Scalable Production of Therapeutic protein Nanoparticles Using Flash Nanoprecipitation", Advanced Healthcare Materials, Supporting Information, 2019, 10 pages.
Zeng et al., "Leveraging mRNAs sequences to express SARS-CoV-2 antigens in vivo," bioRxiv, Apr. 5, 2020, 16 pages. retrieved from URL https://doi.org/10.1101/2020.04.01.019877.
Zetaview, Particle Metrix GmbH, Mar. 2014, 132 pages.
Zhang et al., "A thermostable mRNA vaccine against COVID-19," Cell, Journal Pre-proof, 2020, 48 pages.
Zhang et al., "Advances in mRNA Vaccines for Infectious Diseases," Frontiers in Immunology, Mar. 27, 2019, pp. 1-13, vol. 10.
Zhang et al., "Assessing the Heterogeneity Level in Lipid Nanoparticles for siRNA Delivery: Size-Based Separation, Compositional heterogeneity, and Impact of Bioperformance", Molecular Pharmaceutics, 2013, pp. 397-405, vol. 10.
Zhang et al., "Fluorescence Correlation Spectroscopy to find the critical balance between extracellular association and intracellular dissociation of mRNA", Acta Biomaterialia, May 2018, pp. 358-370, vol. 75.
Zhang et al., "In situ repurposing of dendritic cells with CRISPR/Cas9-based nanomedicine to induce transplant tolerance", Biomaterials, Jun. 2019, pp. 1-11, vol. 217.
Zhang et al., "Lipids and Lipid Derivative for RNA Delivery", Chemical Reviews, 2021, pp. 12181-12277, vol. 121,No. 20.
Zhang et al., "Nanoparticles that Reshape the Tumor Milieu Create a Therapeutic Window for Effective T-cell Therapy in Solid Malignancies", Cancer Research, Jul. 1, 2018, pp. 3718-3731, vol. 78, No. 13.

(56) References Cited

OTHER PUBLICATIONS

Zhang et al., "Polydispersity Characterization of Lipid Nanoparticles for siRNA Delivery Using Multiple Detection Size-Exclusion Chromatography", Supporting Information, [figures S1, S2, S3, and S4], Jul. 17, 2012, vol. 84, No. 14.
Zhang et al., "targeted Delivery of mRNA with One-Component Ionizable Amphiphilic Janus Dendrimers", Journal of the American Chemical Society, Oct. 21, 2021, pp. 1-8, vol. 143.
Zhang et al., "The development of an in vitro assay to screen lipid based nanoparticles for siRNA delivery", Journal of Controlled Release, Nov. 2013, pp. 7-14, vol. 174.
Zhang, "What the Vaccine's Side Effects Feel Like", The Atlantic, Dec. 18, 2020, 3 pages. Retrieved from the Internet URL: https://www.theatlantic.com/health/archive/2020/12/what-expect-when-you-get-covid-19-vaccine/617428/.
Zhao, Y., et al., "Lipid Nanoparticles for Gene Delivery," Advances in genetics, 2014, vol. 88, pp. 13-36.
Zheng et al., "Novel antibody epitopes dominate the antigenicity of spike glycoprotein in SARS-CoV-2 compared to SARS-CoV," Cellular & Molecular Immunology, Mar. 4, 2020, pp. 536-538, vol. 17.
Zhou et al., "pH-Sensitive Nanomicelles for High-Efficiency siRNA Delivery in Vitro and in Vivo: An Insight into the Design of Polycations with Robust Cytosolic Release", Nano Letters, 2016, pp. 6916-6923, vol. 16.
Zhu et al., "Decrease of the electrical potentials measured on the surface of the knee produced by cartilage compression during successive loading cycles", Journal of Biomechanics, 2016, pp. 3587-3591, vol. 49.
Zhu et al., "Electrical potentials measured on the surface of the knee reflect the changes of the contact force in the knee joint produced by postural sway", Gait and Posture, 2017, pp. 159-164, vol. 52.
Zhu et al., "Polyelectrolyte Stabilized Drug Nanoparticles via Flash Nanoprecipitation: A Model Study with B-Carotene", Journal of Pharmaceutical Sciences, Oct. 2010, pp. 4295-4306, vol. 99, No. 10.
Zimmer, C et al., "Coronavirus Vaccine Tracker," Nov. 27, 2020 [online], [retrieved on Mar. 8, 2022]. Retrieved from the Internet URL: https://www.nytimes.com/interactive/2020/science/coronavirus-vaccine-tracker.html, 38 pages.
Zimmerman, et al., RNAi-mediated gene silencing in non-human primates, Nature, May 2006, pp. 111-114, vol. 441.
Ziyi et al., "DNA nanotechnology-facilitated ligand manipulation for targeted therapeutics and diagnostics", Journal of Controlled Release, Dec. 10, 2021, pp. 292-307, vol. 340.
Zukancic et al., "The Importance of Poly (ethylene glycol) and Lipid Structure in targeted Gene Delivery to Lymph Nodes by Lipid nanoparticles", Pharmaceutics, Nov. 9, 2020, pp. 1-16, vol. 12.
Extended European Search Report for EP21881024, 138 pages (Jan. 22, 2025).
Hromatka, O., et al., Untersuchungen über Phenthiazinderivate, 19. Mitt. Neue piperazinsubstituierte Phenthiazine, Monatshefte für Chemie und verwandte Teile anderer Wissenschaften, 93: 807-813 (1962) Non-English, English Abstract.
Peeters, A., et al., Carbon dioxide as a reversible amine-protecting agent in selective Michael additions and acylations, Green chemistry 15(6): 1550-1557 (2013).
Alabi, C. et al., Multiparametric approach for the evaluation of lipid nanoparticles for siRNA delivery, Proc Natl Acad Sci USA, 110(32):12881-6 (2013).
Zhu, L. et al., Construction and application of pH-triggered cleavable hyperbranched polyacylhydrazone for drug delivery, Polym. Chem., 2:1761-1768 (2011).

* cited by examiner

Firefly Luciferase Assay formRNA Delivery Efficiency

Ribogreen Assay for mRNA Encapsulation Efficiency

Dynamic Light Scattering for LNP Size (red dots are PDI right y axis).

Firefly Luciferase Assay for mRNA Delivery Efficiency.

Ribogreen Assay for mRNA Encapsulation Efficiency.

Dynamic Light Scattering for LNP Size (red dots are PDI right y axis).

Firefly Luciferase Assay fo r mRNA Delivery Efficiency.

Ribogreen Assay for mRNA Encapsulation Efficiency.

Dynamic Light Scattering for LNP Size (red dots are PDI right y axis).

Toxicity Assay based on Presto Blue HS viability reagent.

Firefly Luciferase Assay fo r mRNA Delivery Efficiency.

Ribogreen Assay for mRNA Encapsulation Efficiency.

Dynamic Light Scattering for LNP Size (red dots are PDI right y axis).

Toxicity Assay based on Presto Blue HS viability reagent.

Ribogreen Assay for mRNA Encapsulation Efficiency.

Dynamic Light Scattering for LNP Size (red dots are PDI right y axis).

Firefly Luciferase Assay fo r mRNA Delivery Efficiency.

Ribogreen Assay for mRNA Encapsulation Efficiency.

Dynamic Light Scattering for LNP Size (red dots are PDI right y axis).

pH measurements.

| Sample | pH before Dialysis | pH after Dialysis |
|---|---|---|
| 1 mg/ml | 6.05 | 7.38 |
| 1.5 mg/ml | 6.43 | 7.32 |
| 2 mg/ml | 6.5 | 7.29 |

Firefly Luciferase Assay for mRNA Delivery Efficiency.

Ribogreen Assay for mRNA Encapsulation Efficiency.

7D: pH measurements.

| Sample | pH before Dialysis | pH after Dialysis |
|---|---|---|
| 1 mg/ml | 5.1 | 7.22 |
| 1.5 mg/ml | 5.29 | 7.31 |
| 2 mg/ml | 5.41 | 7.42 |

Dynamic Light Scattering for LNP Size (red dots are PDI right y axis).

Toxicity Assay based on Presto Blue HS viability reagent.

pH measurements.

| Sample | pH before Dialysis | pH after Dialysis |
|---|---|---|
| 0.05 mg/ml | 6.09 | 7.31 |
| 0.1 mg/ml | 6.12 | 7.35 |
| 0.25 mg/ml | 6.44 | 7.33 |
| 0.5 mg/ml | 6.53 | 7.4 |
| 1 mg/ml | 6.65 | 7.42 |
| 1.5 mg/ml | 6.67 | 7.41 |
| 2 mg/ml | 6.08 | 7.35 |

FIG. 8E

Ribogreen Assay for mRNA Encapsulation Efficiency.

Dynamic Light Scattering for LNP Size (red dots are PDI right y axis).

1. Ex vivo all together

Ribogreen Assay for mRNA Encapsulation Efficiency.

Dynamic Light Scattering for LNP Size (red dots are PDI right y axis).

pH measurements.

| Sample | pH before Dialysis |
|---|---|
| MC3 100% protonation 0.56 mg/ml in water | 7.16 |
| MC3 50% protonation 0.56 mg/ml in water | 7.35 |
| MC3 0% protonation 0.56 mg/ml in water | 7.5 |
| MC3 0.56 mg/ml in 5 mM NaOAc | 7.34 |
| MC3 0.56 mg/ml in 10 mM NaOAc | 7.21 |
| MC3 0.56 mg/ml in 25 mM NaOAc | 6.84 |
| MC3 0.56 mg/ml in 50 mM NaOAc | 6.29 |

FIG. 10C

Firefly Luciferase Assay for mRNA Delivery Efficiency.

Ribogreen Assay for mRNA Encapsulation Efficiency.

Dynamic Light Scattering for LNP Size (red dots are PDI right y axis).

pH measurements.

| Sample | pH before Dialysis after dilution | pH after Dialysis |
|---|---|---|
| LNP 1 mg/ml in 50 mM NaOAc pH4 | 6.09 | 7.51 |
| LNP 2 mg/ml in 50 mM NaOAc pH4 | 6.29 | 7.47 |
| LNP 3 mg/ml in 50 mM NaOAc pH4 | 6.56 | 7.52 |
| LNP 1 mg/ml in 100 mM NaOAc pH4 | 5.14 | 7.5 |
| LNP 2 mg/ml in 100 mM NaOAc pH4 | 5.34 | 7.49 |
| LNP 3 mg/ml in 100 mM NaOAc pH4 | 5.73 | 7.49 |
| LNP 1 mg/ml in 150 mM NaOAc pH4 | 4.79 | 7.45 |
| LNP 2 mg/ml in 150 mM NaOAc pH4 | 4.9 | 7.45 |
| LNP 3 mg/ml in 150 mM NaOAc pH4 | 5.01 | 7.47 |

Firefly Luciferase Assay for mRNA Delivery Efficiency.

Dynamic Light Scattering for LNP Size (red dots are PDI right y axis).

pH measurements. Measurements were taken before (Well1) and after dialysis against 1X DPBS pH7.4 for 4 hours.

| Sample | pH before Dialysis from Well1 | pH after Dialysis |
|---|---|---|
| KC2 1.5 mg/ml in 43 mM NaOAc pH4 | 5.29 | 7.4 |
| MC3 1.5 mg/ml in 43 mM NaOAc pH4 | 5.34 | 7.4 |
| C2C2PipZ 1.5 mg/ml in 43 mM NaOAc pH4 | 5.98 | 7.38 |
| BODC2C4PipZ 1.5 mg/ml in 43 mM NaOAc pH4 | 5.85 | 7.42 |
| KC2 0.25 mg/ml in 43 mM NaOAc pH4 | 4.85 | 7.4 |
| MC3 0.25 mg/ml in 43 mM NaOAc pH4 | 4.84 | 7.38 |
| C2C2PipZ 0.25 mg/ml in 43 mM NaOAc pH4 | 4.84 | 7.39 |
| BODC2C4PipZ 0.25 mg/ml in 43 mM NaOAc pH4 | 4.82 | 7.35 |
| KC2 1.5 mg/ml in 60 mM NaOAc pH4 | 5.09 | 7.4 |
| BODC2C4PipZ 1.5 mg/ml in 60 mM NaOAc pH4 | 5.07 | 7.41 |
| KC2 1.5 mg/ml in 25 mM NaOAc pH4 | 6.33 | 7.35 |
| BODC2C4PipZ 1.5 mg/ml in 25 mM NaOAc pH4 | 6.33 | 7.38 |
| KC2 0.25 mg/ml in 60 mM NaOAc pH4 | 4.64 | 7.31 |
| BODC2C4PipZ 0.25 mg/ml in 60 mM NaOAc pH4 | 4.67 | 7.32 |
| KC2 0.25 mg/ml in 25 mM NaOAc pH4 | 5.45 | 7.35 |
| BODC2C4PipZ 0.25 mg/ml in 25 mM NaOAc pH4 | 5.45 | 7.39 |

FIG. 12D pH measurements.

| Sample | pH before Dialysis after dilution | pH after Dialysis |
|---|---|---|
| KC2 0.25 mg/ml in 5 mM NaOAc pH4 | 7.18 | 7.39 |
| KC2 0.25 mg/ml in 10 mM NaOAc pH4 | 7.04 | 7.4 |
| KC2 0.25 mg/ml in 25 mM NaOAc pH4 | 6.53 | 7.44 |
| KC2 1.5 mg/ml in 12.5 mM NaOAc pH4 | 6.98 | 7.39 |
| KC2 1.5 mg/ml in 25 mM NaOAc pH4 | 6.68 | 7.38 |
| KC2 1.5 mg/ml in 50 mM NaOAc pH4 | 6.03 | 7.32 |
| C2C2PipZ 1.5 mg/ml in 25 mM NaOAc pH4 | 6.88 | 7.4 |
| BODC2C4PipZ 1.5 mg/ml in 25 mM NaOAc pH4 | 6.76 | 7.45 |
| C2C2PipZ 1.5 mg/ml in 25 mM NaOAc pH5 | 7.22 | 7.4 |
| BODC2C4PipZ 1.5 mg/ml in 25 mM NaOAc pH5 | 7.14 | 7.49 |
| C2C2PipZ 1.5 mg/ml in 25 mM NaOAc pH6 | 7.64 | 7.48 |
| BODC2C4PipZ 1.5 mg/ml in 25 mM NaOAc pH6 | 7.38 | 7.46 |

FIG. 13D

Dynamic Light Scattering for LNP Size (red dots are PDI right y axis).

Optimal concentration of Sodium Acetate at pH 4 for highest potency at each mRNA concentration

| mRNA concentration (mg/ml) | Lipid mix concentration (mM) | Sodium Acetate pH 4 concentration (mM) |
|---|---|---|
| 0.1 | 5 | 10 |
| 0.25 | 12.5 | 10 |
| 0.5 | 25 | 20 |
| 1 | 50 | 25 |
| 1.5 | 75 | 25 |
| 2 | 100 | 25 |
| 3 | 150 | 37.5 |

Firefly Luciferase Assay for mRNA Delivery Efficiency

Ribogreen Assay for mRNA Encapsulation Efficiency.

Dynamic Light Scattering for LNP Size (red dots are PDI right y axis).

FIG. 20C
Group1 = 5μg dose (4 hours).
ROI 1=1.998e+08
ROI 2=1.137e+08
ROI 3=2.358e+08
ROI 4=2.306e+08
ROI 5=3.199e+08
ROI 6=1.335e+08
ROI 7=2.172e+08
ROI8=6.452e+07
ROI9=3.785e+08
ROI10=3.046e+07
n=1
ROI 1= 1.781e+08
ROI 11=3.545e+08
ROI 12=1.583e+08
ROI 13=8.496e+07
ROI 14=5.014e+08
ROI 15=1.426e+08
ROI 16=2.341e+07
ROI 17=1.286e+08
ROI 18=3.642e+08
ROI 19=2.436e+07
n=2
ROI 1=1.767e+08
ROI 20=8.395e+07
ROI 21=2.014e+08
ROI 22=1.443e+08
ROI 23=3.088e+08
ROI 24=1.465e+08
ROI 25=1.274e+08
ROI 26=1.568e+08
ROI 27=4.818e+08
ROI 28=4.953e+07
n=3
x10^7
3.0
1.0
Radiance (p/sec/cm^2/sr)
Color Scale Min=1.89e6 Max=3.98e7
4 hr

FIG. 20D
Group1 = 5μg dose (24 hours)
ROI 1= 7.870e+07
ROI 2=5.375e+07
ROI 3= 1.122e+08
ROI 4= 2.876e+08
ROI 5=8.496e+07
ROI 6 =7.854e+07
ROI 7=3.817e+07
ROI 8 =3.884e+07
ROI 9= 9.281e+07
n=1
ROI 1= 6.242e+07
ROI 2=2.314e+08
ROI 3= 4.566e+07
ROI 4 =3.257e+07
ROI 10=1.022e+08
ROI 11=6.722e+07
ROI 12=7.697e+07
ROI 13=1.771e+08
ROI 15=9.977e+07
n=2
ROI 1 = 6.629e+07
ROI 2=2.823e+07
ROI 4= 6.788e+07
ROI 5 = 8.588e+07
ROI 14= 6.707e+07
ROI 15= 4.626e+07
ROI 16= 9.480e+07
ROI 17= 9.935e+07
n=3
24 hr
1.0
0.8
0.6
x10^7
0.4
0.2
Radiance
(p/sec/cm2/sr)
Color Scale
Min=1.00e6
Max=1.00e7

48 hr

Group 1 IM - 1 ug dose (4, 24 hours) - N=1,2,3
Left to Right :
1.1 MC3
1.2 BODD-C2/C2-PipZ
1.3 BODD-C2/C4-PipZ
1.4 BODD-C2/C2-DMA
1.5 BODD-C2/C4-DMA 1 BODDC2C2PipZ 4(1,5)
2 BODDC2C4PipZ 4(1,5)
3 BODDC2C2DMA 4(1,5)
4 BODDC2C4Pyr 4(1,5)
5 BODDC2C2 1Me 2Pyr 4(1,5)

6 BODDC2C0 1Me PipD 4(1,5)
7 SL-C2PipZ 4(1,5)
8 BODDC2C2Pyr 4(1,5)
9 BHDC2C2PipZ 4(1,5)
10 BHDC2C2 1Me 2Pyr 4(1,5)

11 BHDC2C4Pyr 4(1,5)
12 BODDC4C4BA 4(1,5)
13 BODDC2C1 1Me PipD 4(1,5)
14 BODDC2C1 1Me 3PipD 4(1,5)
15 DHC2C4PipZ 4(1,5)

SEQUENCE LISTING

```
<160> NUMBER OF SEQ ID NOS: 4

<210> SEQ ID NO 1
<211> LENGTH: 250
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaaa aaaaaaaaaa     120

aaaaaaaaaa aaaaaaaaaa aaaaaaaaaa aaaaaaaaaa aaaaaaaaaa aaaaaaaaaa     180

aaaaaaaaaa aaaaaaaaaa aaaaaaaaaa aaaaaaaaaa aaaaaaaaaa aaaaaaaaaa     240

aaaaaaaaaa                                                            250


<210> SEQ ID NO 2
<211> LENGTH: 15
<212> TYPE: PRT
<213> ORGANISM: Clostridium tetani

<400> SEQUENCE: 2

Gln Tyr Ile Lys Ala Asn Ser Lys Phe Ile Gly Ile Thr Glu Leu
1               5                   10                  15


<210> SEQ ID NO 3
<211> LENGTH: 16
<212> TYPE: PRT
<213> ORGANISM: Clostridium tetani

<400> SEQUENCE: 3

Ala Gln Tyr Ile Lys Ala Asn Ser Lys Phe Ile Gly Ile Thr Glu Leu
1               5                   10                  15


<210> SEQ ID NO 4
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa a                         101
```

METHODS OF LIPID NANOPARTICLE MANUFACTURE AND COMPOSITIONS DERIVED THEREFROM

CROSS REFERENCE TO RELATED APPLICATIONS

This application claims the benefit of U.S. provisional application No. 63/091,616, which was filed on Oct. 14, 2020; U.S. provisional application No. 63/179,885, which was filed on Apr. 26, 2021; U.S. provisional application No. 63/091,603, which was filed on Oct. 14, 2020; and U.S. provisional application No. 63/179,872, which was filed on Apr. 26, 2021, each of which is incorporate herein by reference in its entirety.

SEQUENCE LISTING

The instant application contains a Sequence Listing which has been submitted electronically in ASCII format and is hereby incorporated by reference in its entirety. Said ASCII copy, created on Dec. 29, 2021, is named AEXR-002-02US-343269-2008_SL.txt and is 1,718 bytes in size.

FIELD OF THE INVENTION

The invention is in the field of nanoparticle manufacturing for the delivery of pharmaceutical nucleic acid payloads.

BACKGROUND OF THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilize specific carrier molecules and carrier compositions, which are allowed selective entry into the cell. Lipid carriers, biodegradable polymers and various conjugate systems can be used to improve delivery of biologically active agents to cells.

One class of biologically active agents that is particularly difficult to deliver to cells is a bio-therapeutic (including peptides, proteins, nucleosides, nucleotides, polynucleotides, nucleic acids and derivatives, such as mRNA, RNAi/siRNA, and self-replicating RNA agents). In general, nucleic acids are stable for only a limited duration in cells or bodily fluids. The development of CRISPR/CAS9, RNA interference, RNAi therapy, mRNA therapy, RNA drugs, antisense therapy, gene therapy, and nucleic acid vaccines (e.g., RNA vaccines), among others, has increased the need for an effective means of introducing active nucleic acid agents into cells. For these reasons, compositions that can stabilize and deliver nucleic acid-based agents into cells are of interest.

The most well-studied approaches for improving the transport of foreign nucleic acids into cells involve the use of viral vectors or formulations with cationic lipids. Viral vectors can be used to transfer genes efficiently into some cell types, but they generally cannot be used to introduce chemically synthesized molecules into cells.

An alternative approach is to use delivery compositions incorporating cationic lipids, which interact with a biologically active agent at one part and interact with a membrane system at another part. Such compositions are reported to provide liposomes, micelles, lipoplexes, or lipid nanoparticles, depending on the composition and method of preparation (for reviews, see Feigner, 1990, Advanced Drug Delivery Reviews, 5, 162-187; Feigner, 1993, J. Liposome Res., 3, 3-16; Gallas, 2013, Chem. Soc. Rev., 42, 7983-7997; Falsini, 2013, J. Med. Chem. dx.doi.org/10.1021/jm400791q; and references therein).

Since the first description of liposomes in 1965 by Bangham (J. Mol. Biol. 13, 238-252), there has been a sustained interest and effort in developing lipid-based carrier systems for the delivery of biologically active agents (Allen, 2013, Advanced Drug Delivery Reviews, 65, 36-48). The process of introducing functional nucleic acids into cultured cells by using positively charged liposomes was first described by Philip Feigner et al. Proc. Natl. Acad. Sci., USA, 84, 7413-7417 (1987). The process was later demonstrated in vivo by K. L. Brigham et al., Am. J. Med. Sci., 298, 278-281 (1989).

More recently, lipid nanoparticle formulations have been developed with demonstrated efficacy in vitro and in vivo. (Falsini, 2013, J. Med. Chem. dx.doi.org/10.1021/jm400791q; Morrissey, 2005, Nat. Biotech., 23, 1002-1007; Zimmerman, 2006, Nature, 441, 111-114; Jayaraman, 2012, Angew. Chem. Int. Ed., 51, 8529-8533.) Lipid formulations are attractive carriers since they can protect biological molecules from degradation while improving their cellular uptake. Out of the various classes of lipid formulations, formulations which contain cationic lipids are commonly used for delivering polyanions (e.g. nucleic acids). Such formulations can be formed using cationic lipids alone and optionally including other lipids and amphiphiles such as phosphatidylethanolamine. It is well known in the art that both the composition of the lipid formulation as well as its method of preparation affect the structure and size of the resultant nanoparticle or aggregate (Leung, 2012, J. Phys Chem. C, 116, 18440-18450).

A variety of methods have been developed to formulate LNP systems containing genetic drugs. These methods include mixing preformed LNPs with nucleic acids in the presence of ethanol or mixing lipid dissolved in ethanol with an aqueous media containing nucleic acids and result in LNPs with diameters of 100 nm or less and nucleic acid encapsulation efficiencies of 65-95%. Both of these methods rely on the presence of cationic lipids to achieve encapsulation of oligonucleotide (OGN) and poly(ethylene glycol) (PEG) to inhibit aggregation and the formation of large structures. The properties of the LNP systems produced, including size and OGN encapsulation efficiency, are sensitive to a variety of formulation parameters such as ionic strength, lipid and ethanol concentration, pH, nucleic acid concentration and mixing rates. In general, parameters such as the relative lipid and nucleic acid concentrations at the time of mixing, as well as the mixing rates are difficult to control using current formulation procedures, resulting in variability in the characteristics of the LNP produced, both within and between preparations.

Of the COVID-19 vaccines, several are based on mRNA-encoded immunogens delivered in lipid nanoparticles (LNPs). This high proportion of mRNA vaccines is due to their rapid implementation and superior efficacy in animal models. In mRNA vaccines, immunogens are encoded in an mRNA sequence often using immunosilencing nucleoside substitutions. In addition to nucleoside substitutions, mRNA design often involves codon optimization, UTR and polyA tail design, 5' cap selection, and purification to remove double stranded RNA contaminants that can activate innate immune sensors to inhibit translation of the delivered mRNA.

Antibody titers in COVID-19 mRNA vaccine vaccinated patients were higher than convalescent sera while neutralizing titers were comparable to convalescent in published trials. There were CD4+ and CD8+ T cell responses in both trials and an absence of a Th2 component, which is important due the potential role of a Th2 response in vaccine-associated enhanced respiratory disease8.

However, local and systemic adverse events were prevalent, and were more frequent with increased severity after the second vaccination. Although there were no serious life-threatening adverse events, the highest doses in some trials were discontinued due to severe local and systemic adverse events. Self-amplifying mRNA LNPs are effective at lower doses but have additional safety concerns.

FDA guidelines suggest success in a phase 3 trial would require 50% protection versus placebo based on an endpoint of severe COVID-19 disease. The vaccine would need to be inexpensively manufactured for potentially 15 billion doses and taken by most people worldwide. The combination of these 3 criteria will be challenging to meet. For example, for 50% protection for 1 year, billions of doses manufactured per year and a worldwide population with access and willingness to be vaccinated.

If current doses succeed in clinical trials, then increased potency would reduce dose and adverse reactions while maintaining efficacy and increase the ability to vaccinate globally by reducing cost and increasing manufacturing capacity. Alternatively, if current doses fail in clinical trials, increased potency at these same doses could increase protection. Accordingly, there is a great need to increase potency by way of payload mRNA expression, immunogenicity, and protection in mRNA vaccines through the control of LNP assembly.

Despite advances in the development of methods for LNP systems containing genetic drugs, a need exists for methods for preparing lipid nanoparticles containing therapeutic materials, as well as improved lipid nanoparticles containing therapeutic materials. The present invention seeks to fulfill this need and provides further related advantages.

SUMMARY OF THE INVENTION

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

One aspect of the invention relates to methods for making a lipid nanoparticle comprising a nucleic acid ("naLNP") providing a nucleic acid solution comprising of at least one nucleic acid at a nucleic acid concentration; providing a lipid solution comprising at least one lipid at a lipid concentration; and combining a portion of the nucleic acid solution and a portion of the lipid solution to create a mixing solution comprising a mixing nitrogen-phosphate ratio and a lipid: nucleic acid ratio; and adjusting the pH in the mixing solution to physiological pH to obtain a pH-adjusted mixing solution; and obtaining the naLNPs from the pH-adjusted mixing solution; and wherein the naLNPs have a greater potency than a reference lipid nanoparticle ("refLNP") wherein the refLNP comprises of at least one lipid and the at least one nucleic acid and is made by a reference LNP manufacturing method.

In one embodiment, the portion nucleic acid solution and the portion of the lipid solution are combined in step (c) in volume ratio selected from the group consisting of 1:1, 2:1, 3:1, 4:1, 5:1, 6:1 and 7:1. In another embodiment, the naLNPs have an average a diameter in the range of about 40 to about 150 nanometers. In a further embodiment, the naLNPs have an average a diameter in the range of about 50 to about 100 nanometers. In still another embodiment, the naLNPs have a nucleic acid encapsulation efficiency of about 40 to about 100%. In yet a further embodiment, the naLNPs have a nucleic acid encapsulation efficiency of about 50% to about 85%. In another embodiment, the naLNPs have a nucleic acid encapsulation efficiency of about 60% to about 85%. In still another embodiment, the naLNPs have a nucleic acid encapsulation efficiency of about 68% to about 83%.

In still another embodiment, the naLNP has a lower nucleic acid encapsulation rate less than the refLNP. In a further embodiment, the at least one nucleic acid is DNA or RNA. In still a further embodiment, the at least one nucleic acid is RNA. In yet another embodiment, the at least one nucleic acid is mRNA. In yet another embodiment, the at least one nucleic acid is mRNA encoding at least one open reading frame. In still another embodiment, the at least one nucleic acid is mRNA encoding at least one open reading frame encoding an immunogen. In a further embodiment, the nucleic acid solution comprises a buffer. In yet another embodiment, the nucleic acid concentration is at least or about 0.21 to about 3 mg/ml. In still another embodiment, the nucleic acid concentration is at least or about 0.23 to about 3 mg/ml. In yet another embodiment, the nucleic acid concentration is at least or about 0.25 to about 3 mg/ml. In another embodiment, the nucleic acid concentration is at least or about 0.28 to about 3 mg/ml. In a further embodiment, the nucleic acid concentration is at least or about 0.29 to about 3 mg/ml. In a further embodiment, the nucleic acid concentration is at least or about 0.30 to about 3 mg/ml. In another embodiment, the nucleic acid concentration is at least or about 0.40 to about 3 mg/ml. In a further embodiment, the nucleic acid concentration is at least or about 0.50 to about 3 mg/ml. In still another embodiment, the nucleic acid concentration is at least or about 0.60 to about 3 mg/ml. In a further embodiment, the nucleic acid concentration is at least or about 0.70 to about 3 mg/ml. In still a further embodiment, the nucleic acid concentration is at least or about 1 to about 3 mg/ml.

In still another embodiment, the lipid solution comprises an organic solvent selected from the group consisting of methanol, ethanol, acetone, benzene and toluene. In a further embodiment, the lipid solution is selected from the group consisting of MC3, KC2, DLin, DODMA, DODAP, Formula I, Formula II, and a combination thereof. In still another embodiment, the at least one lipid in the lipid solution is selected from the group consisting of MC3, KC2, DLin, DODMA, DODAP, and a combination thereof. In still another embodiment, the at least one lipid in the lipid solution is a cationic lipid having a pKa. In yet a further embodiment, the at least one lipid in the lipid solution is an ionizable cationic lipid having a pKa. In still another embodiment, the mixing solution has a pH that is about 0 to about 2 units of pH below the pKa of the lipid in the refLNP. In yet a further embodiment, the mixing solution has a pH that is about 0.5 to about 1.5 units of pH below the pKa of the lipid in the refLNP. In still a further embodiment, the mixing solution has a pH that is about 0.75 to about 1.25 units of pH below the pKa of the lipid in the refLNP. In a further embodiment, the lipid concentration is at least or about 1 mM to about 200 mM. In yet a further embodiment, the lipid concentration is at least or about 10 mM to about 150 mM. In yet another embodiment, the lipid concentration is at least or about 50 mM to about 100 mM. In a further embodiment, the mixing solution nitrogen-phosphate ratio is at least or about 2 to at least or about 10.

In yet a further embodiment, the mixing solution lipid: nucleic acid weight ratio is at least or about 1:0, 2:1, 3:1, 4:1, 5:1, 6:1, 7:1, 8:1, 9:1, 10:1, 11:1, 12:1, 15:1, 17:1, 18:1, 20:1, 25:1, 30:1, 35:1, 40:1 or 50:1. In yet a further embodiment, the refLNP is made using a reference nucleic acid concentration less than 0.21 mg/ml. In another embodiment, the refLNP is made using a reference lipid concentration less than of 10.5 mM. In yet another embodiment, the ref LNP is made using a reference nucleic acid concentration less than 0.21 mg/ml and a reference lipid concentration less than 10.5 mM. In still another embodiment, the potency is about 1.5 times more than the refLNP.

In another embodiment, the potency is about 2 times more than the refLNP. In yet another embodiment, the potency is about 3 times more than the refLNP. In still another embodiment, the potency is about 4 times more than the refLNP. In a further embodiment, the potency is at least or about 5 times more than the refLNP. In yet a further embodiment, the potency is at least or about 6 times more than the refLNP. In still a further embodiment, the potency is at least or about 7 times more than the refLNP. In another embodiment, the potency is at least or about 8 times more than the refLNP. In yet another embodiment, the potency is at least or about 9 times more than the refLNP. In still another embodiment, the potency is at least or about 10 times more than the refLNP. In a further embodiment, the potency is at least or about 11 times more than the refLNP. In still a further embodiment, the potency is at least or about 12 times more than the refLNP. In yet a further embodiment, the potency is at least or about 13 times more than the refLNP. In still another embodiment, the potency is at least or about 14 times more than the refLNP. In yet a further embodiment, the potency is at least or about 15 times more than the refLNP. In another embodiment, the potency is at least or about 20 times more than the refLNP. In still another embodiment, the potency is at least or about 25 times more than the refLNP. In a further embodiment, the potency is at least or about 50 times more than the refLNP.

Another aspect of the invention relates to a solution comprising at least one ionizable lipid at a concentration about, equal to, or greater than 5.25 mM; at least one nucleic acid at a concentration about, equal to, or greater than to 0.21 mg/ml; wherein the acid:lipid ratio is in the range of about 2 to about 10; and nucleic acid carrying lipid nanoparticles ("naLNP") comprising the at least one ionizable lipid and at least one nucleic acid; wherein the naLNPs at physiological pH have a potency greater than a reference lipid nanoparticle formed with the same at least one ionizable lipid and the same at least one nucleic acid in a reference LNP manufacturing method ("refLNP").

In one embodiment of this aspect of the invention, the naLNPs have an average a diameter in the range of about 40 to about 150 nanometers. In another embodiment, the naLNPs have an average a diameter in the range of about 50 to about 100 nanometers. In a further embodiment, the naLNPs have a nucleic acid encapsulation efficiency of about 40 to about 90%. In still another embodiment, the naLNPs have a nucleic acid encapsulation efficiency of about 50% to about 85%. In still another embodiment, the naLNPs have a nucleic acid encapsulation efficiency of about 60% to about 85%. In still a further embodiment, the naLNPs have a nucleic acid encapsulation efficiency of about 68% to about 83%. In yet another embodiment, the naLNPs have a lower nucleic acid encapsulation rate less than the refLNP. In still another embodiment, the at least one nucleic acid is DNA or RNA. In another embodiment, the at least one nucleic acid is RNA. In a further embodiment, the at least one nucleic acid is mRNA. In still another embodiment, the at least one nucleic acid is mRNA encoding at least one open reading frame. In yet a further embodiment, the at least one nucleic acid is mRNA encoding at least one open reading frame encoding an immunogen.

In yet another embodiment, the solution comprises a buffer. In a further embodiment, the nucleic acid concentration is at least or about 0.21 to about 3 mg/ml. In another embodiment, the nucleic acid concentration is at least or about 0.23 to about 3 mg/ml. In still a further embodiment, the nucleic acid concentration is at least or about 0.25 to about 3 mg/ml. In still another embodiment, the nucleic acid concentration is at least or about 0.28 to about 3 mg/ml. In yet a further embodiment, the nucleic acid concentration is at least or about 0.29 to about 3 mg/ml. In yet another embodiment, the nucleic acid concentration is at least or about 0.30 to about 3 mg/ml. In still another embodiment, the nucleic acid concentration is at least or about 0.40 to about 3 mg/ml. In another embodiment, the nucleic acid concentration is at least or about 0.50 to about 3 mg/ml. In a further embodiment, the nucleic acid concentration is at least or about 0.60 to about 3 mg/ml. In still another embodiment, the nucleic acid concentration is at least or about 0.70 to about 3 mg/ml. In still another embodiment, the nucleic acid concentration is at least or about 1 to about 3 mg/ml.

In another embodiment, the solution comprises an organic solvent selected from the group consisting of methanol, ethanol, acetone, benzene and toluene. In another embodiment of this aspect of the invention, the at least one lipid is selected from the group consisting of MC3, KC2, DLin, DODMA, DODAP, Formula I, Formula II, and a combination thereof. In yet a further embodiment, the at least one lipid is selected from the group consisting of MC3, KC2, DLin, DODMA, DODAP, and a combination thereof. In still another embodiment, the at least one lipid is a cationic lipid having a pKa. In yet a further embodiment, the at least one lipid is an ionizable cationic lipid having a pKa. In still another embodiment, the mixing solution has a pH that is about 0 to about 2 units of pH below the pKa of the lipid in the refLNP. In yet a further embodiment, the mixing solution has a pH that is about 0.5 to about 1.5 units of pH below the pKa of the lipid in the refLNP. In still another embodiment, the mixing solution has a pH that is about 0.75 to about 1.25 units of pH below the pKa of the lipid in the refLNP. In yet a further embodiment, the lipid concentration is at least or about 1 mM to about 200 mM. In still another embodiment, the lipid concentration is at least or about 10 mM to about 150 mM. In yet another embodiment, the lipid concentration is at least or about 50 mM to about 100 mM. In yet another embodiment, the mixing solution nitrogen-phosphate ratio is at least or about 2 to at least or about 10. In still another embodiment, the mixing solution lipid:nucleic acid weight ratio is at least or about 1:0, 2:1, 3:1, 4:1, 5:1, 6:1, 7:1, 8:1, 9:1, 10:1, 11:1, 12:1, 15:1, 17:1, 18:1, 20:1, 25:1, 30:1, 35:1, 40:1 or 50:1.

In still another embodiment, the refLNP is made using a reference nucleic acid concentration less than 0.21 mg/ml. In another embodiment, the refLNP is made using a reference lipid concentration less than 10.5 mM. In yet a further embodiment, the refLNP is made using a reference lipid concentration less than 10.5 mM and a reference nucleic acid concentration less than 0.21 mg/ml. In still another embodiment, the potency of the naLNP is about 1.5 times more than the refLNP. In another embodiment, the potency is about 2 times more than the refLNP. In still another embodiment, the potency is about 3 times more than the refLNP. In a further embodiment, the potency is about 4 times more than the refLNP. In still another embodiment, the potency is at least or about 5 times more than the refLNP. In yet a further embodiment, the potency is at least or about 6 times more than the refLNP. In a further embodiment, the potency is at least or about 7 times more than the refLNP. In still a further embodiment, the potency is at least or about 8 times more than the refLNP. In yet a further embodiment, the potency is at least or about 9 times more than the refLNP. In a further embodiment, the potency is at least or about 10 times more than the refLNP. In still another embodiment, the potency is at least or about 11 times more than the refLNP. In yet another embodiment, the potency is at least or about 12 times more than the refLNP. In still a further embodiment, the potency is at least or about 13 times more than the refLNP. In a further embodiment, the potency is at least or about 14 times more than the refLNP. In still another embodiment, the potency is at least or about 15 times more than the refLNP. In a further embodiment, the potency is at least or about 20 times more than the refLNP. In another embodiment, the potency is at least or about 25 times more than the refLNP. In a further embodiment, the potency is at least or about 50 times more than the refLNP.

Another aspect of the invention relates to a pharmaceutical composition comprising the naLNPs made according to the methods described above. In one embodiment, the pharmaceutical composition is a vaccine. In another embodiment, the vaccine is prophylactic. In further embodiment, the vaccines is a therapeutic vaccine. In another embodiment, the vaccine is to treat or prevent an infectious disease. In a further embodiment, the vaccine is to treat or prevent COVID-19. In another embodiment, the vaccine is to treat or prevent a coronavirus infection. In a further embodiment, the composition comprises a bioactive agent selected from the group consisting of a peptide, antibody, antibody fragment, and small molecule therapeutics.

BRIEF DESCRIPTION OF THE FIGURES

A more complete understanding of the presently disclosed subject matter can be obtained by reference to the accompanying Figures, when considered in conjunction with the subsequent detailed description. The embodiments illustrated in the Figures are intended to be exemplary only and should not be construed as limiting the presently disclosed subject matter to the illustrated embodiments. The figures described below are associated with experimental results from the various Examples described below.

FIG. 8E: pH measurements. Measurements were taken before and after dialysis against 1×DPBS pH7.4 for 4 hours. The embodiments illustrated in FIG. 8E correspond to procedure set forth in Example 8E.

FIG. 10C: pH measurements. Measurements were taken before dialysis. The embodiments illustrated in FIG. 10C correspond to procedure set forth in Example 10C.

FIG. 12D: pH measurements. Measurements were taken before (Well1) and after dialysis against 1×DPBS pH7.4 for 4 hours. The embodiments illustrated in FIG. 12D correspond to procedure set forth in Example 12D.

FIG. 13D: pH measurements. Measurements were taken before and after dialysis against 1×DPBS pH7.4 for 4 hours.

FIG.

Figure 27A:
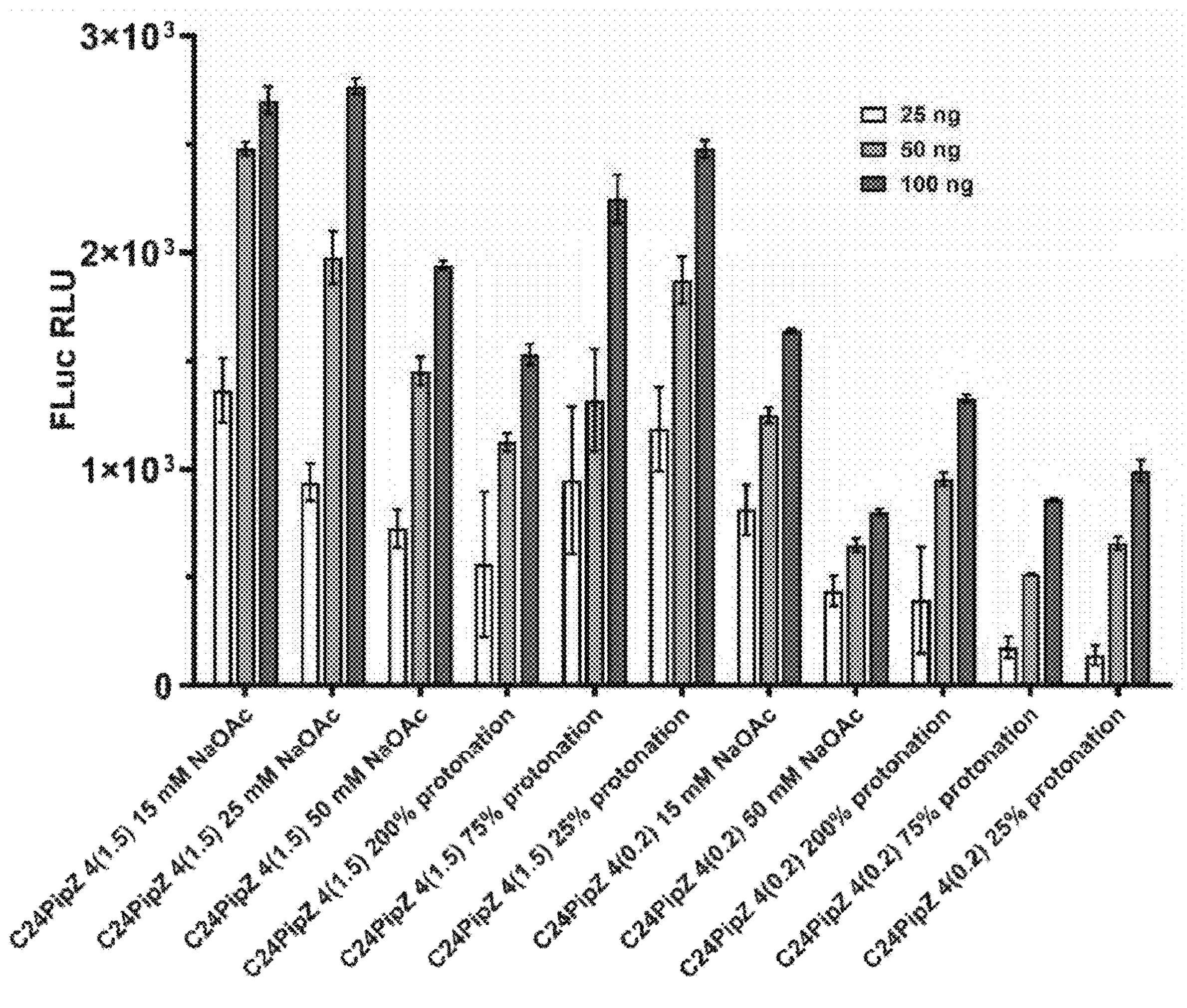
FIG. 27A: Firefly Luciferase Assay for mRNA Delivery Efficiency as set forth in Example 27.
Figure 27B:
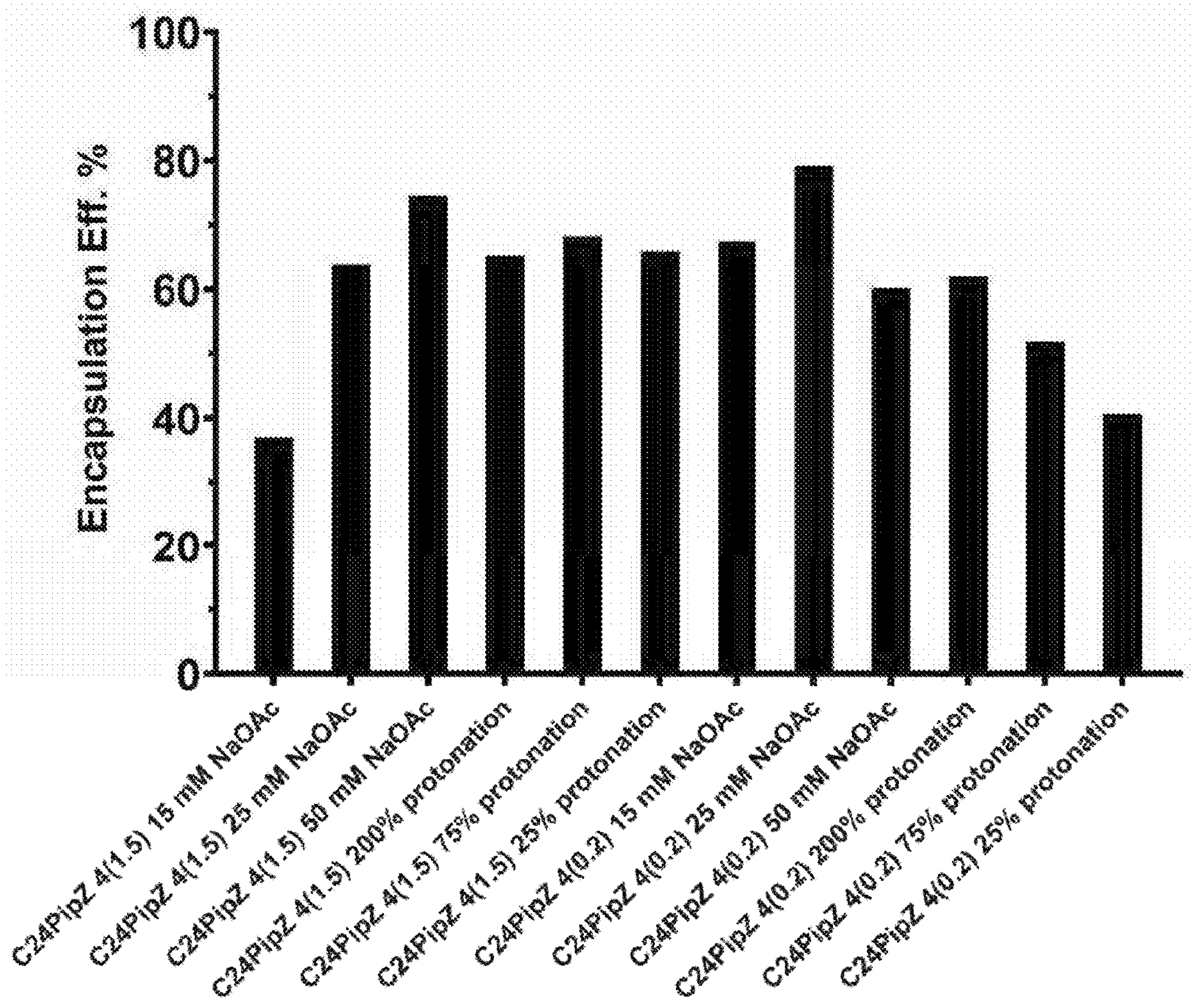
FIG. 27B: Ribogreen Assay for mRNA Encapsulation Efficiency as set forth in Example 27.
Figure 27C:
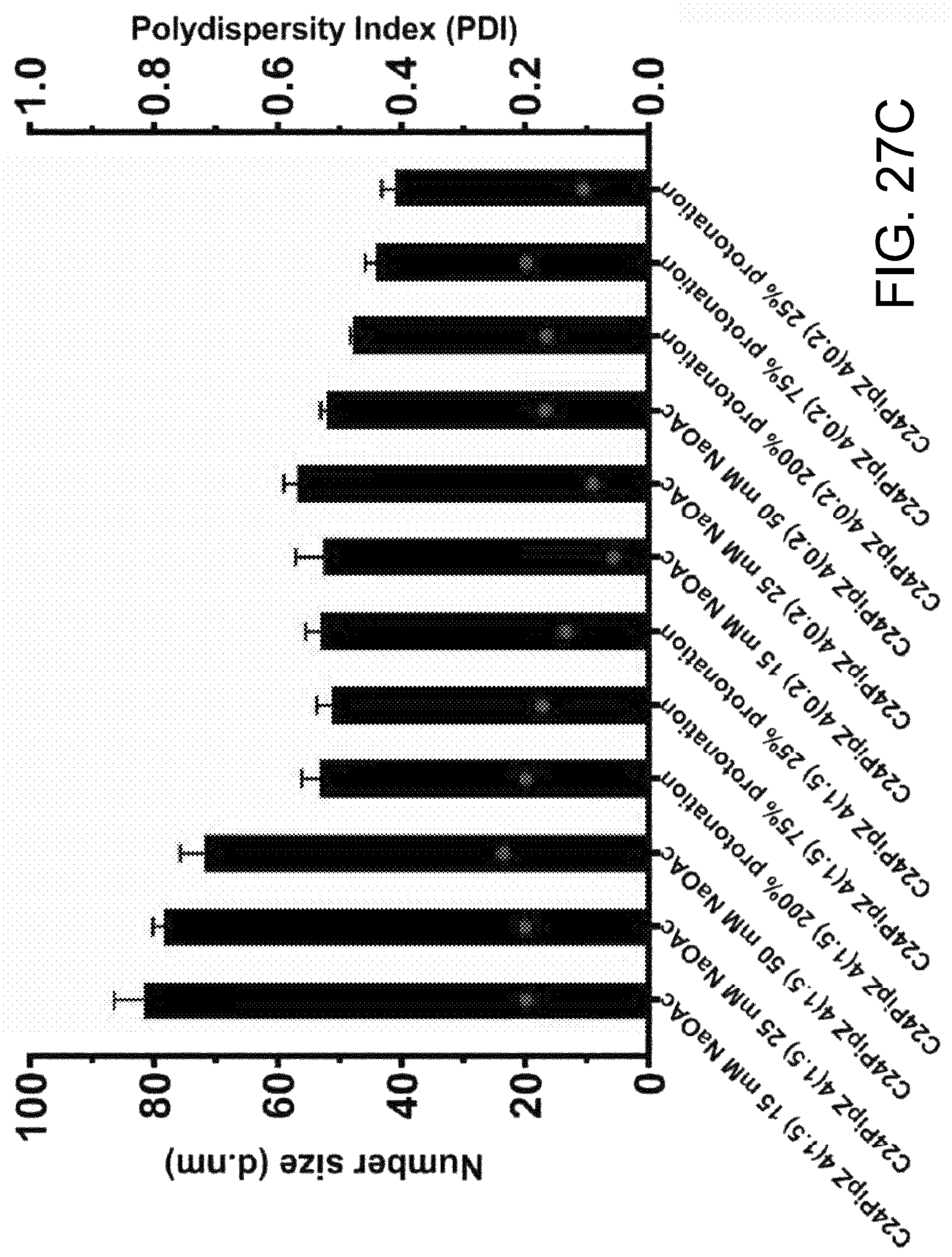

FIG. 27C: Dynamic Light Scattering for LNP Size (white dots are PDI right y axis) as set forth in Example 27.

Figure 27D:
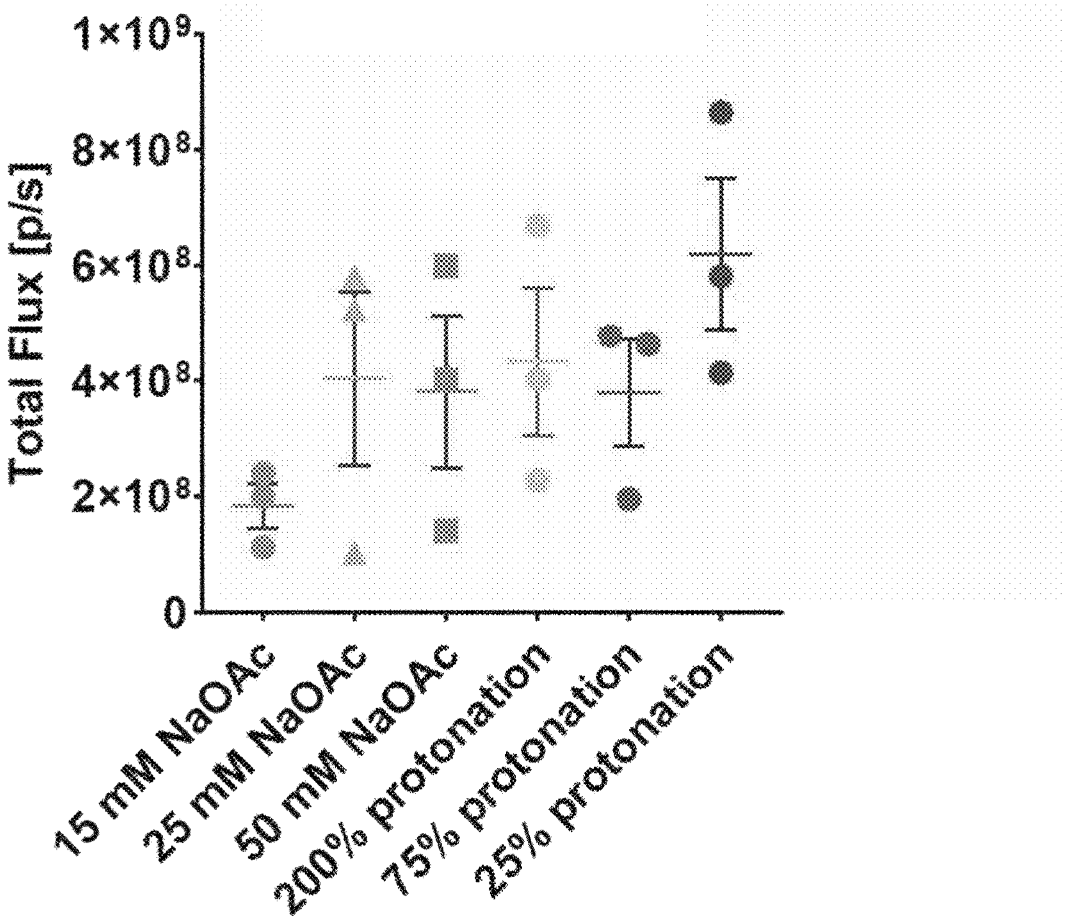
Figure 27D:
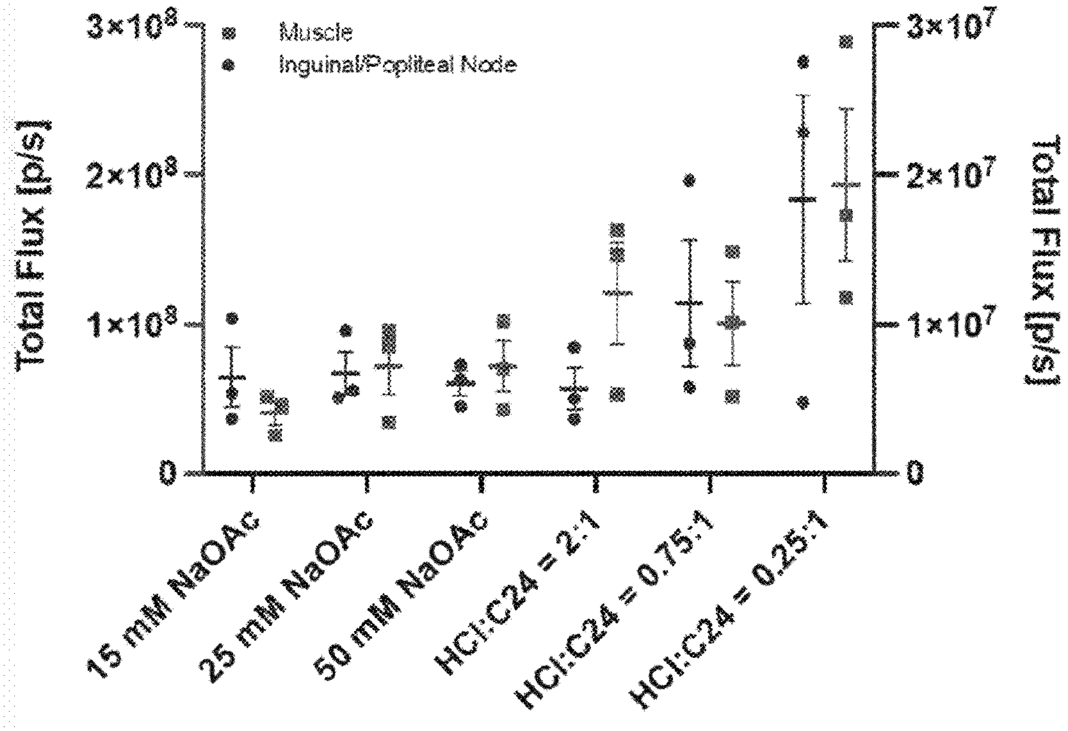

FIG. 27D: In vivo and ex vivo Firefly Luciferase expression in IM administration for LNPs mixed at 1.5 mg/ml as set forth in Example 27.

Figure 27E:
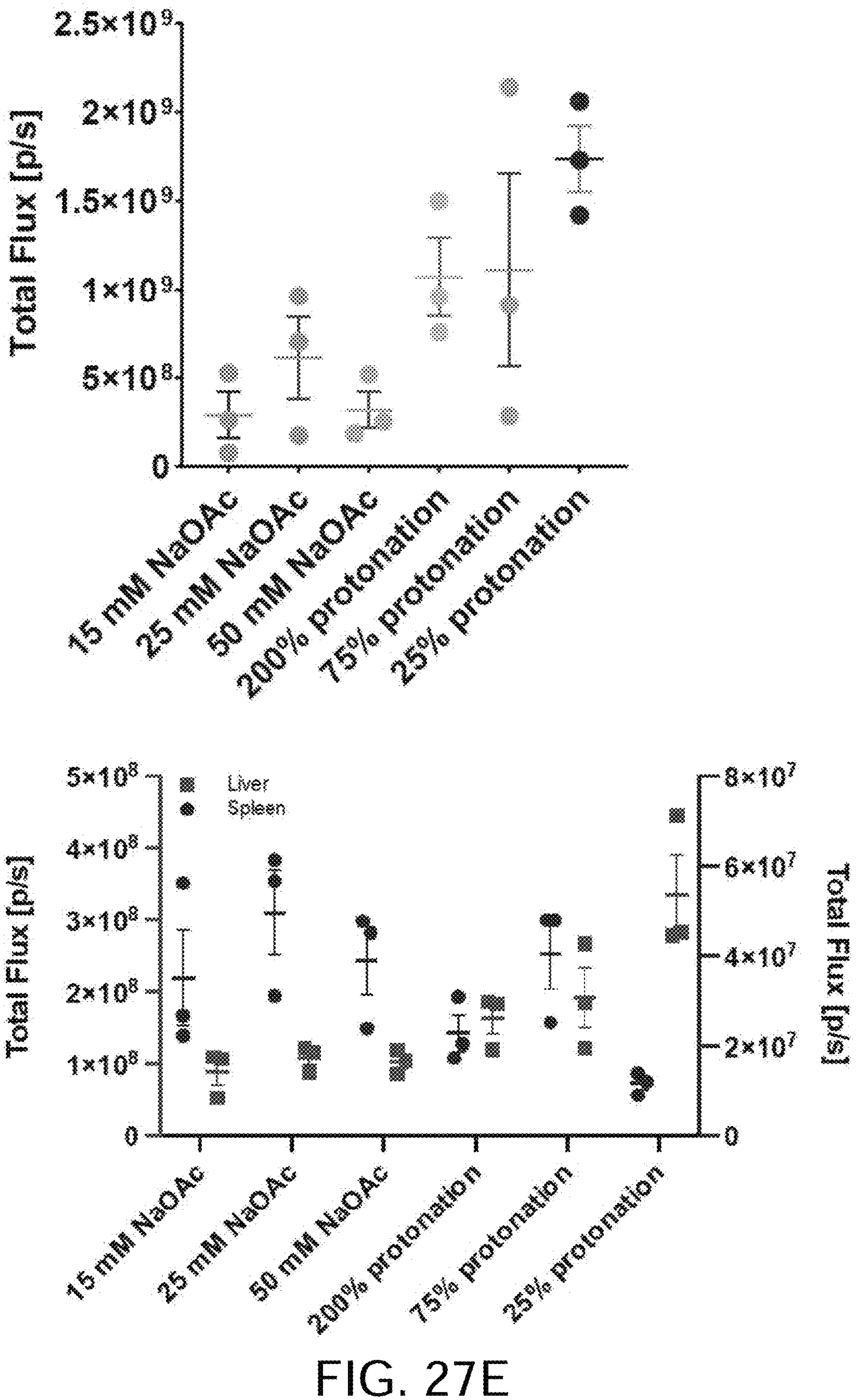

FIG. 27E: In vivo and ex vivo Firefly Luciferase expression in IV administration for LNPs mixed at 1.5 mg/ml as set forth in Example 27.

Figure 28A:
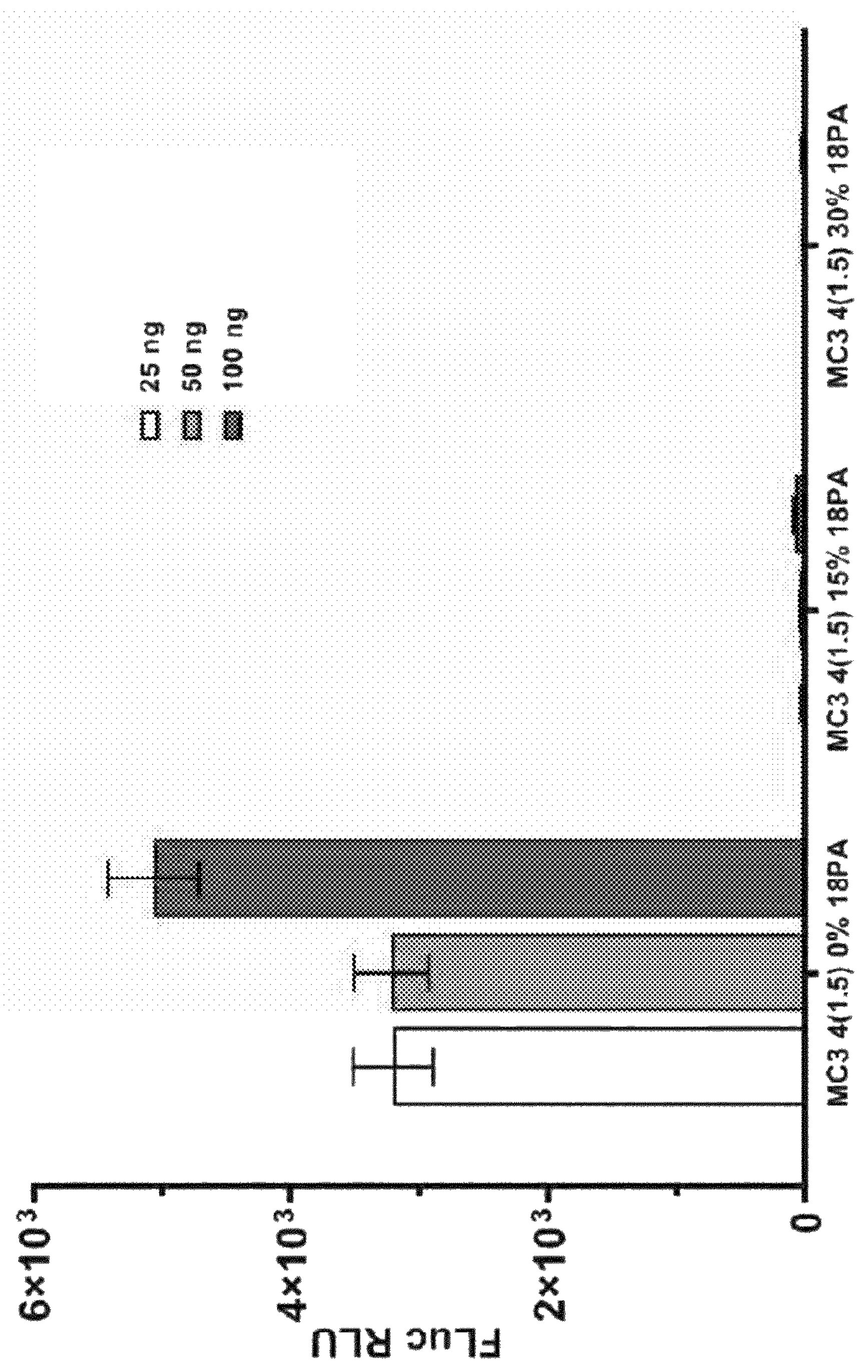

FIG. 28A: Firefly Luciferase Assay for mRNA Delivery Efficiency as set forth in Example 28.

Figure 28B:
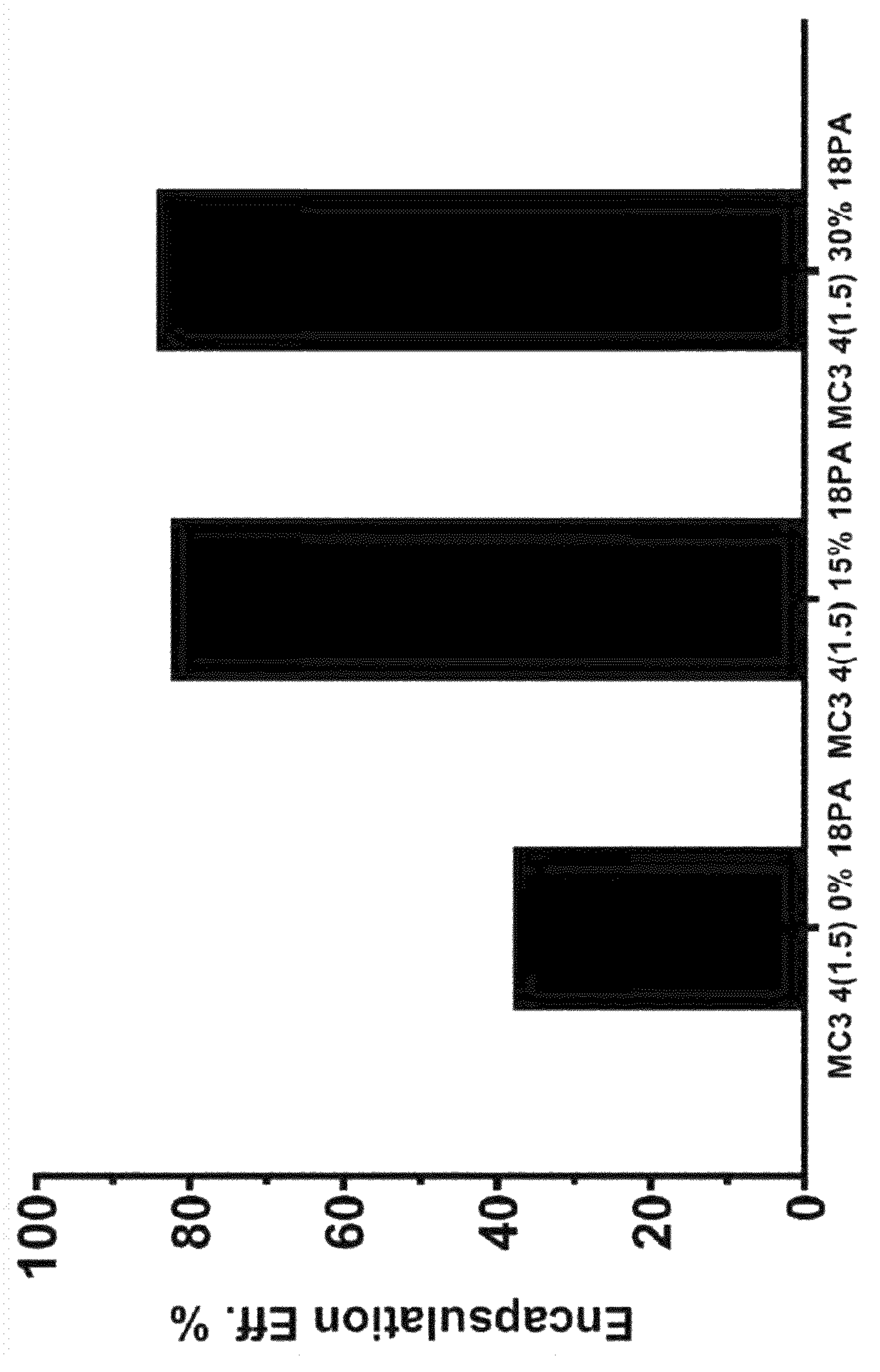

FIG. 28B: Ribogreen Assay for mRNA Encapsulation Efficiency as set forth in Example 28.

Figure 28C:
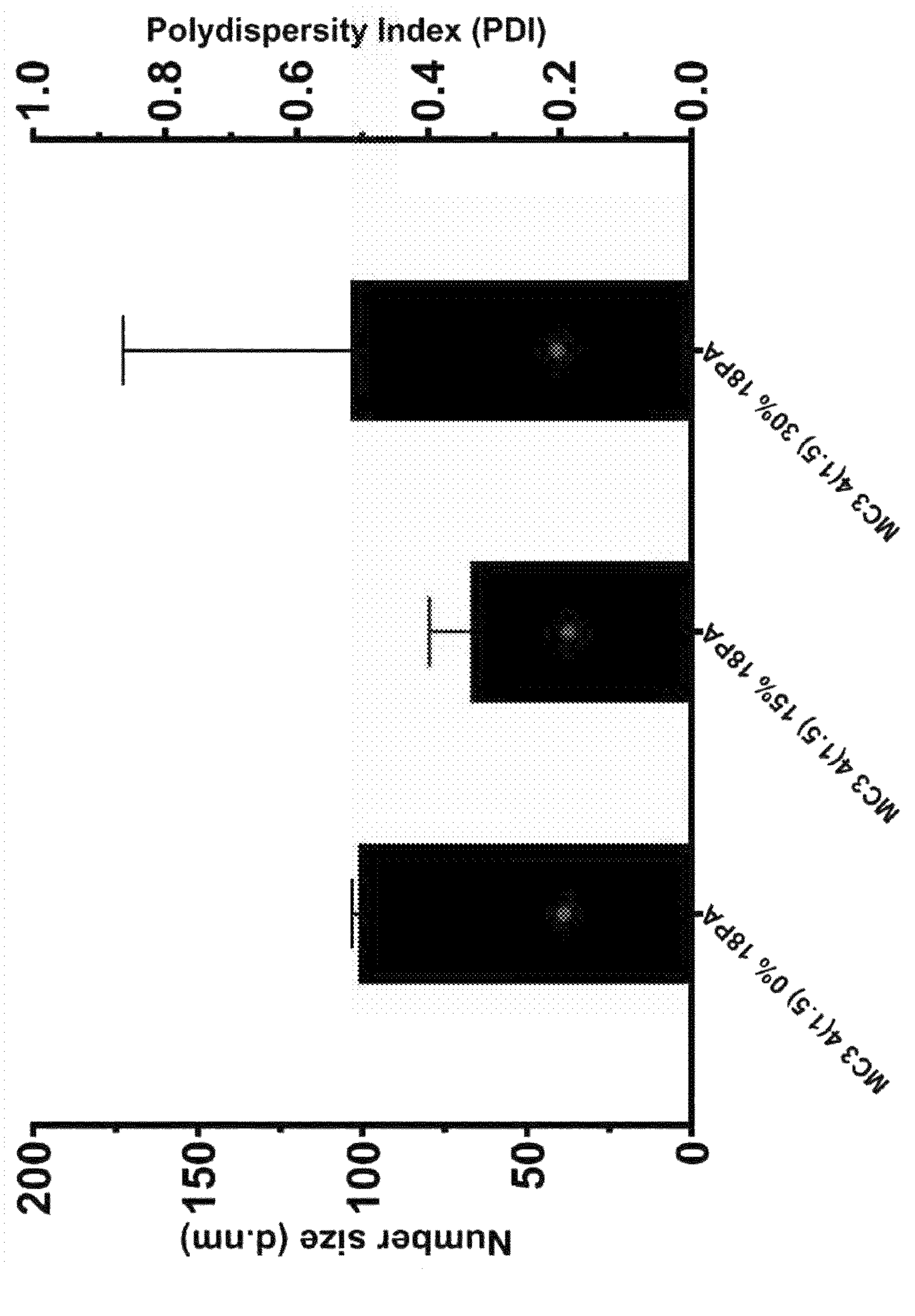

FIG. 28C: Dynamic Light Scattering for LNP Size (white dots are PDI right y axis) as set forth in Example 28.

Figure 28D:
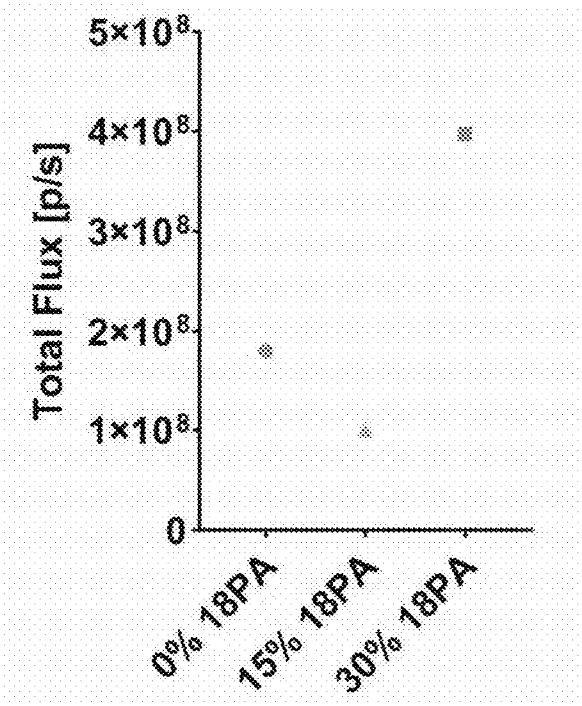
Figure 28E:
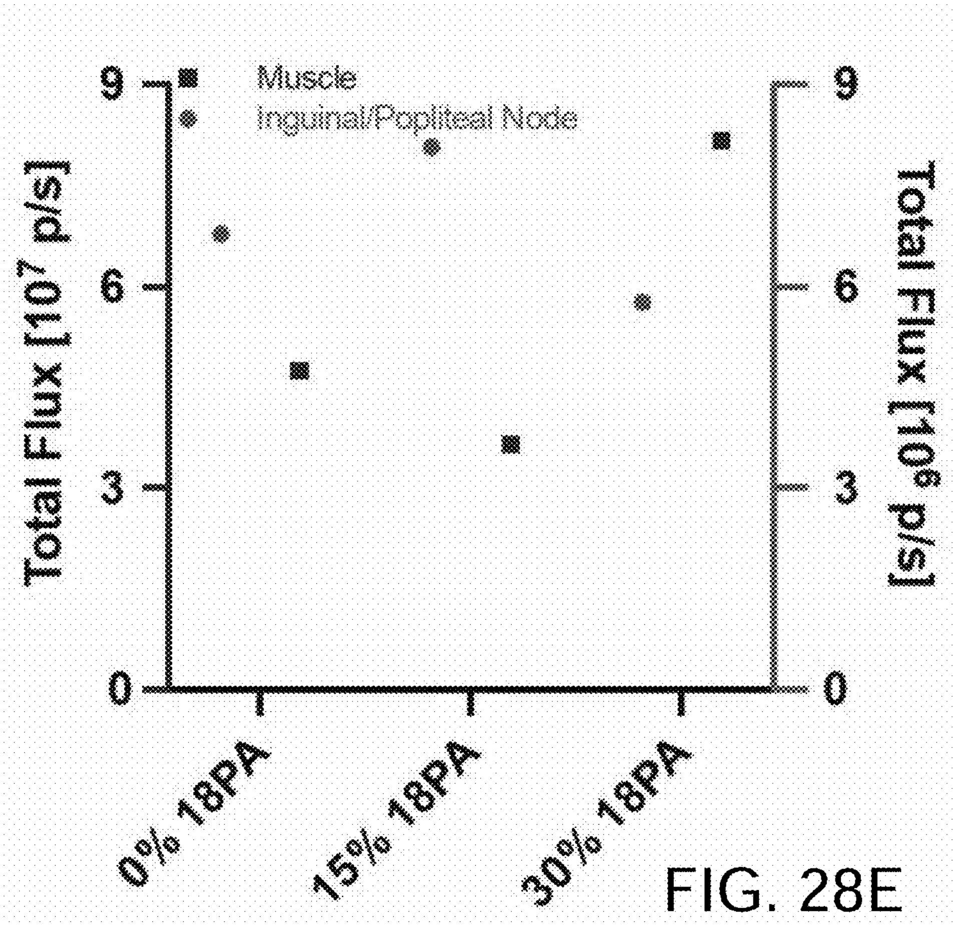
Figure 28F:
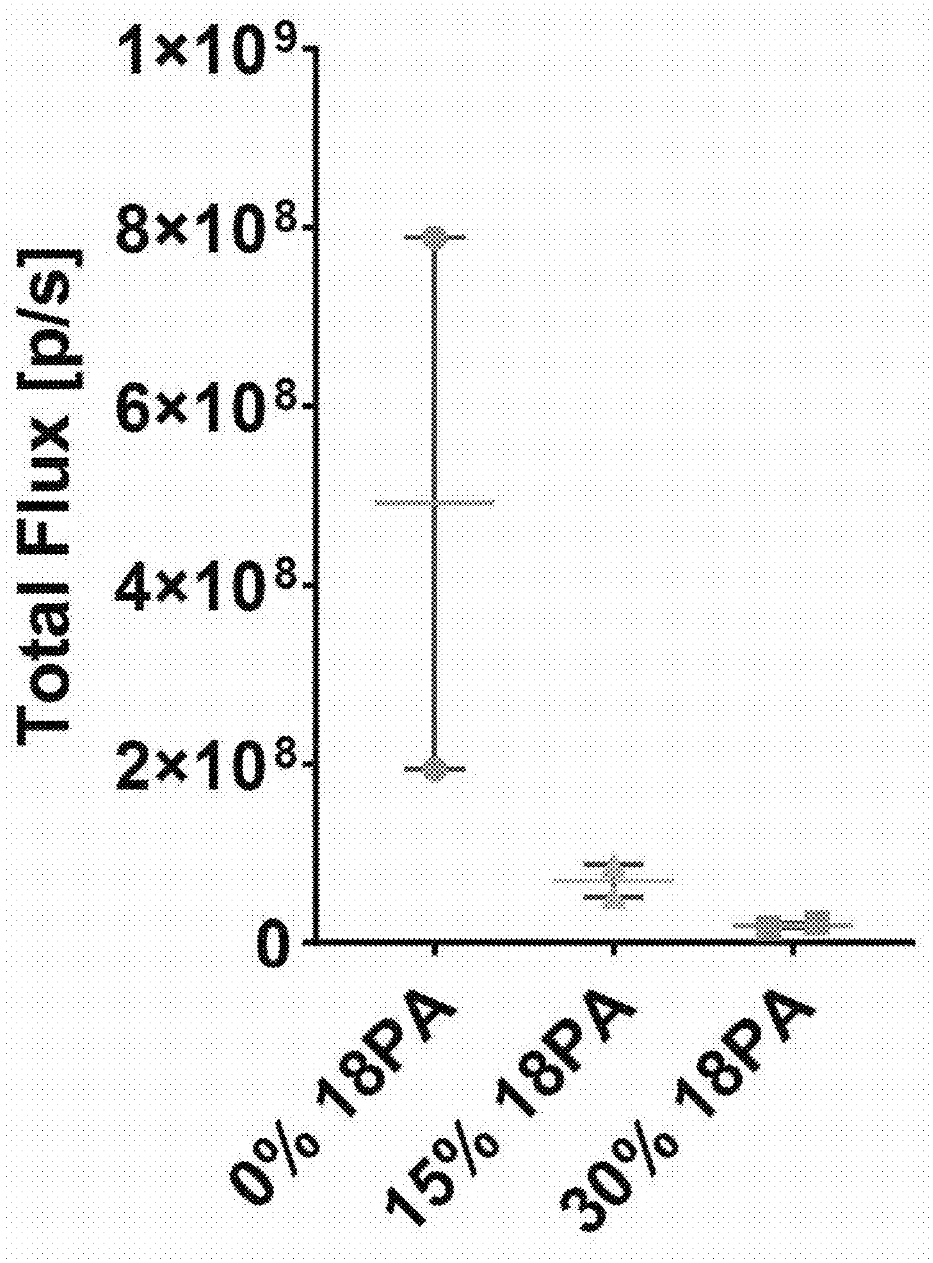
Figure 28G:
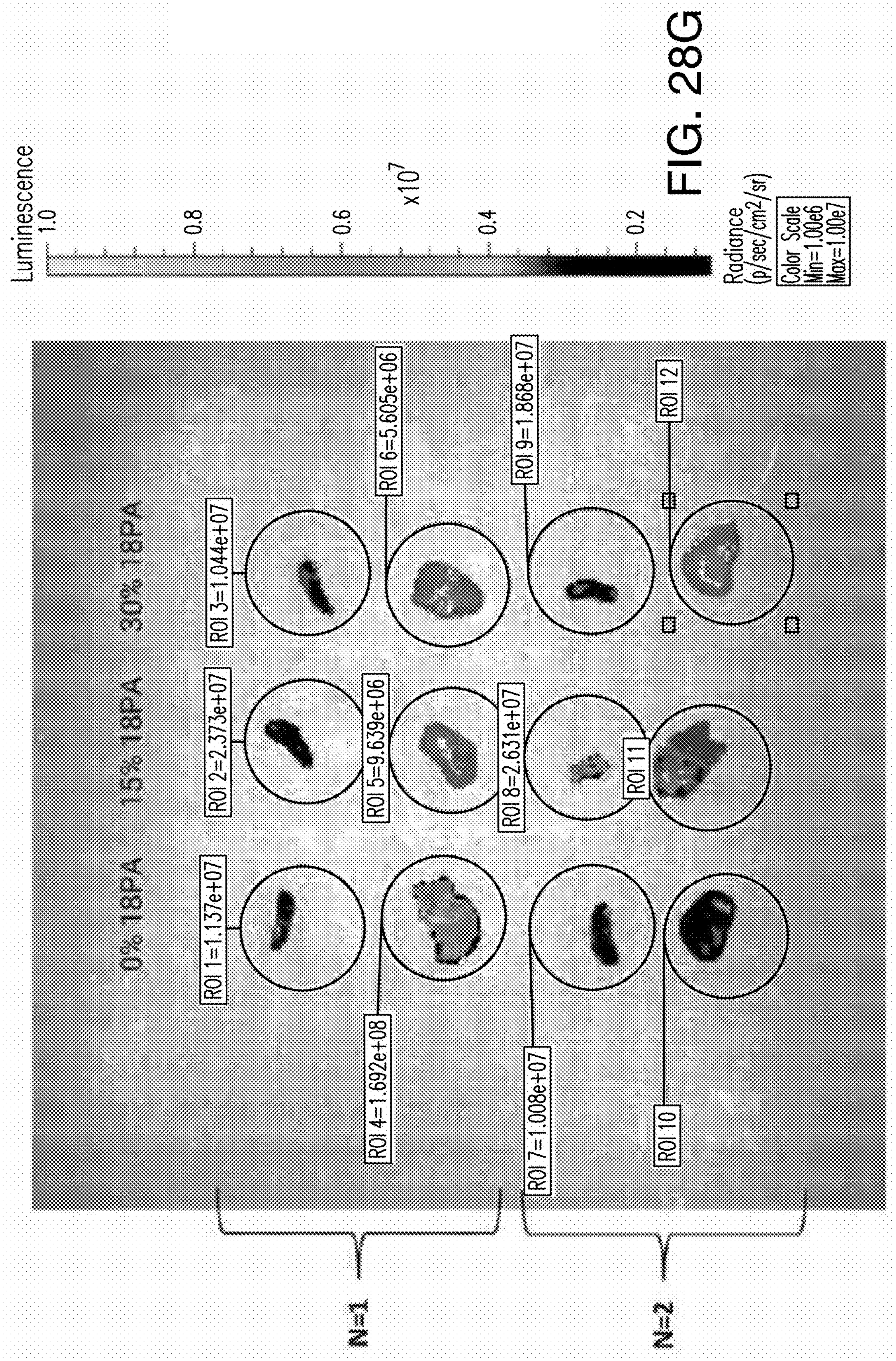
Figure 28H:
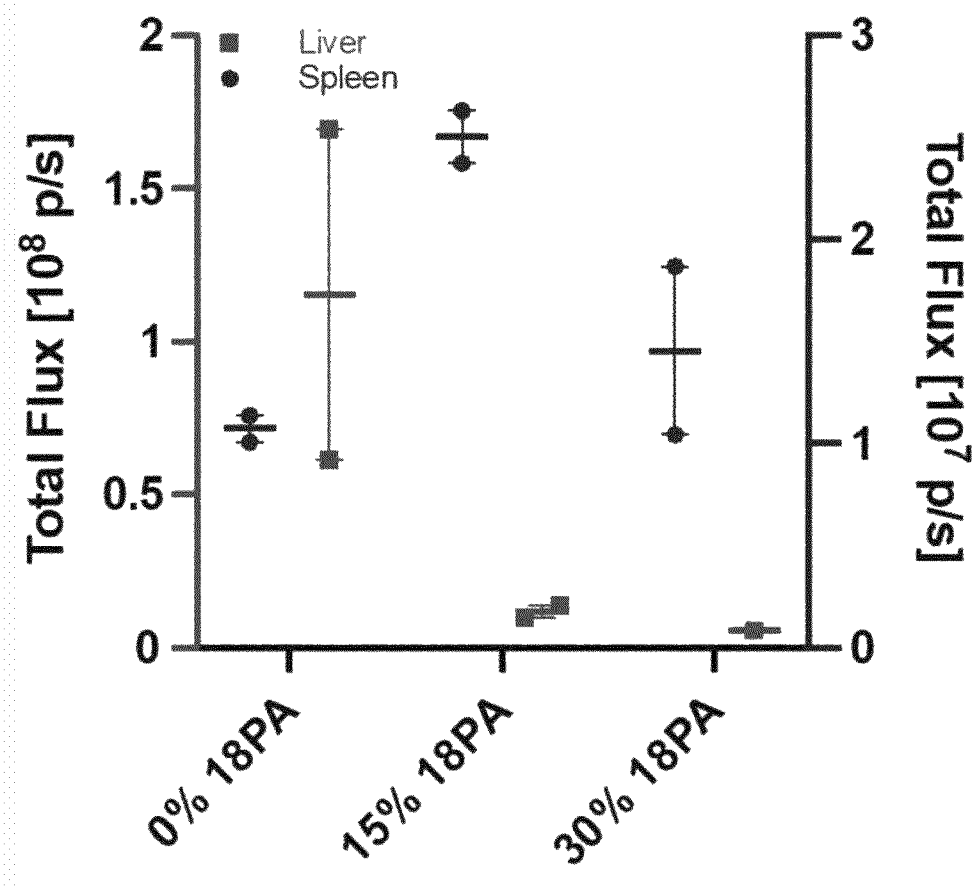
Figure 28I:
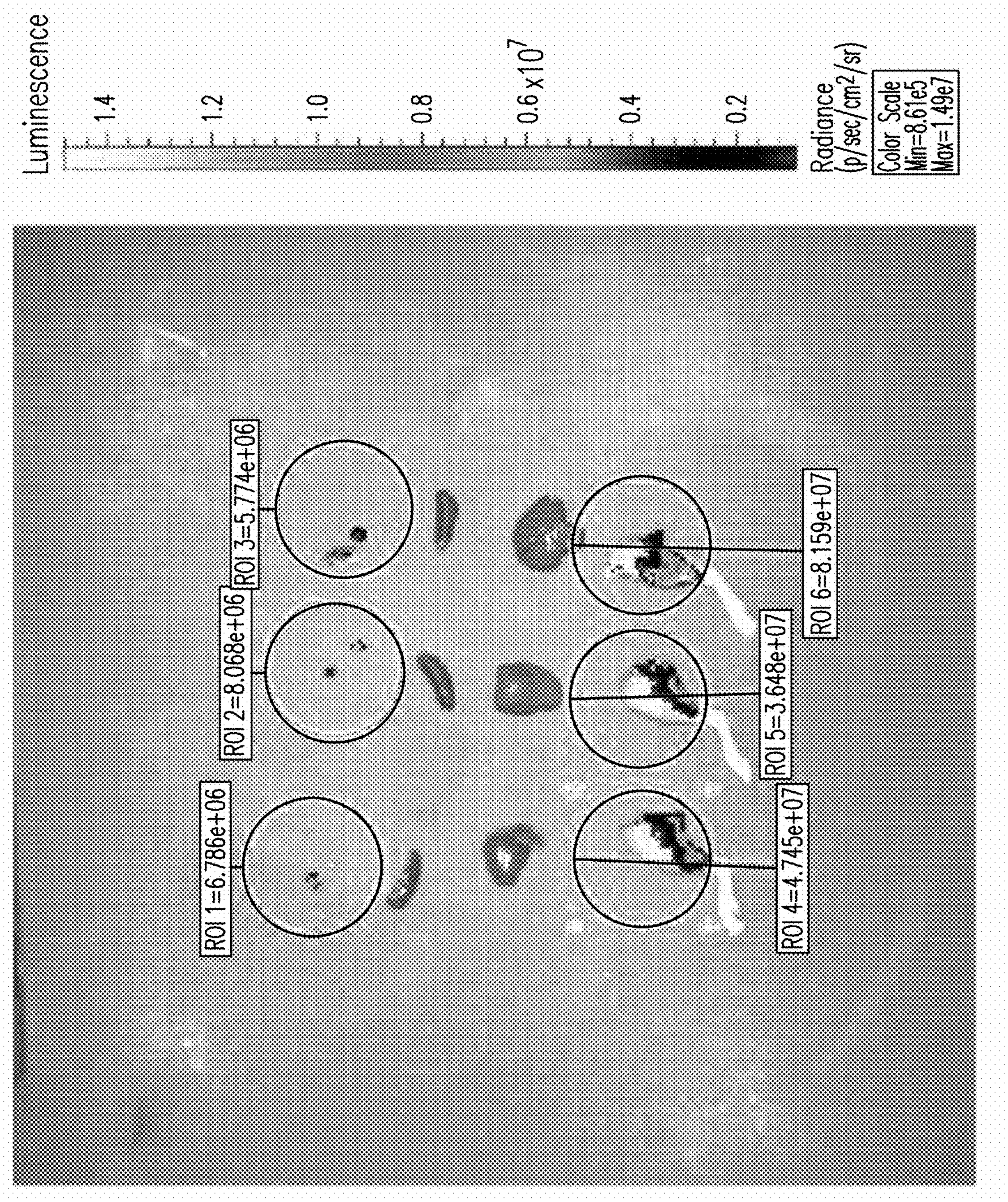

FIG. 28D: In vivo and ex vivo Firefly Luciferase expression in IM administration for LNPs mixed at 1.5 mg/ml as set forth in Example 28.

FIG. 28E to FIG. 28I: In vivo and ex vivo Firefly Luciferase expression in IV administration for LNPs mixed at 1.5 mg/ml as set forth in Example 28.

Figure 29A:
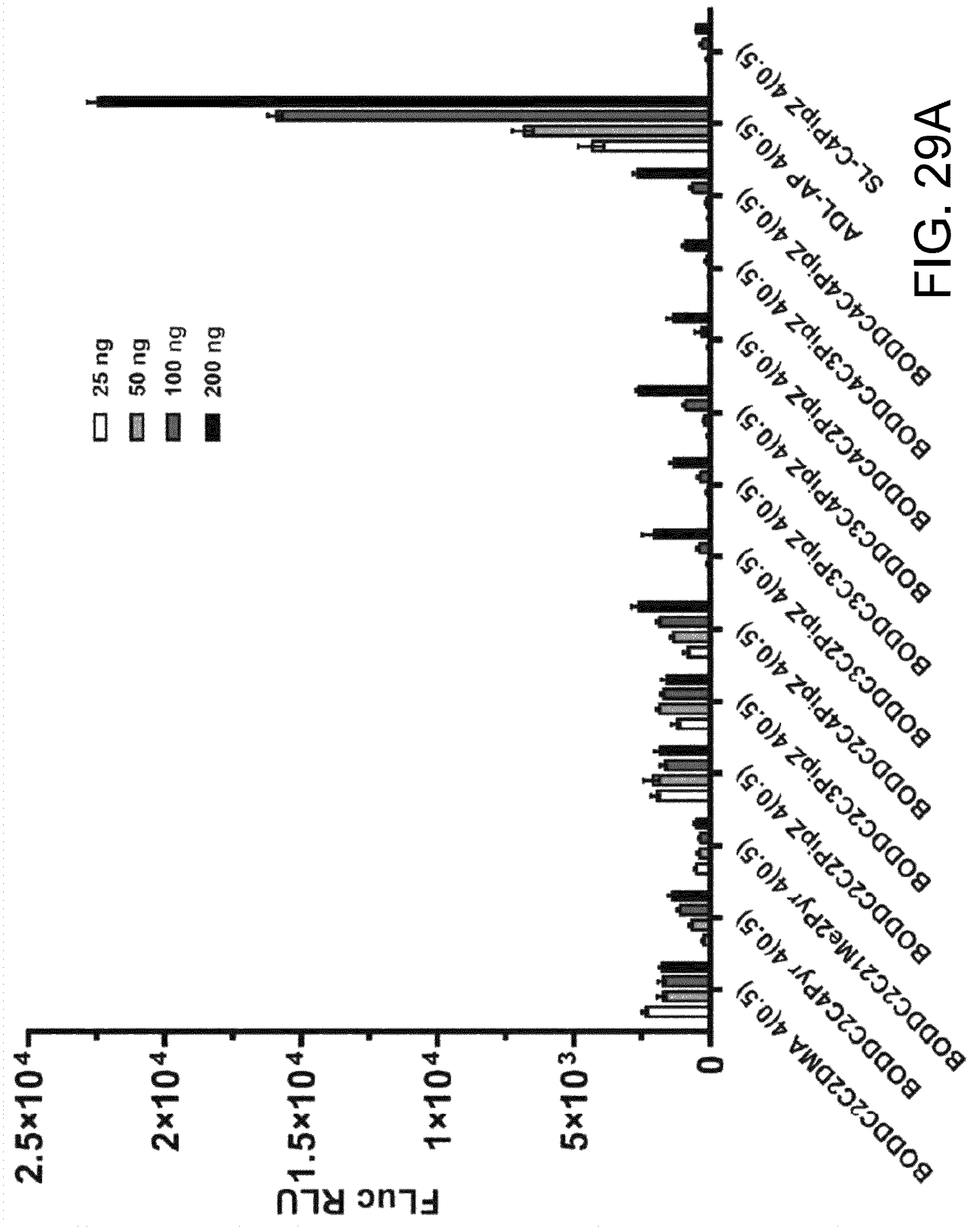

FIG. 29A: Firefly Luciferase Assay for mRNA Delivery Efficiency as set forth in Example 29.

Figure 29B:
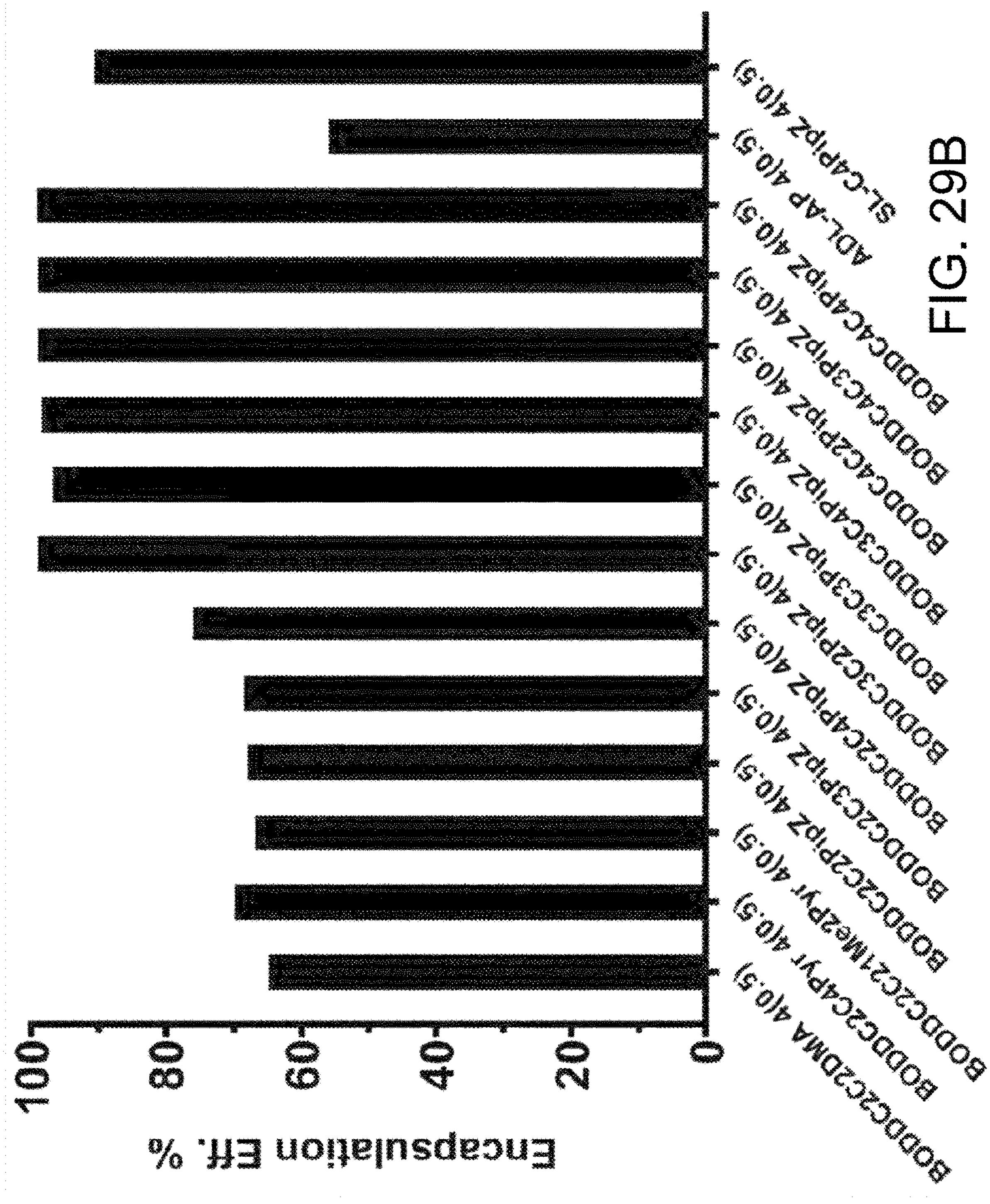

FIG. 29B: Ribogreen Assay for mRNA Encapsulation Efficiency as set forth in Example 29.

Figure 29C:
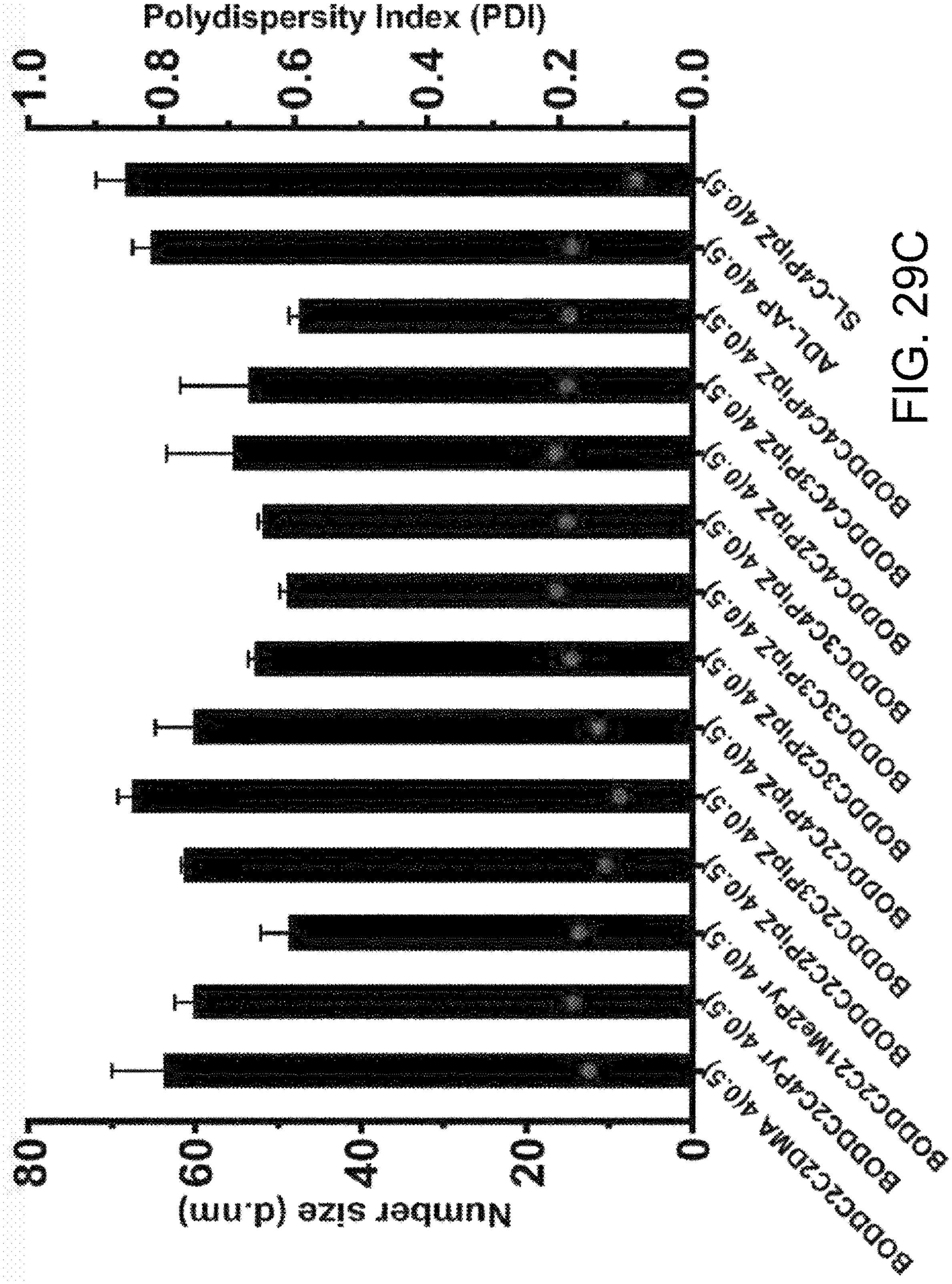

FIG. 29C: Dynamic Light Scattering for LNP Size (white dots are PDI right y axis) as set forth in Example 29.

Figure 30A:
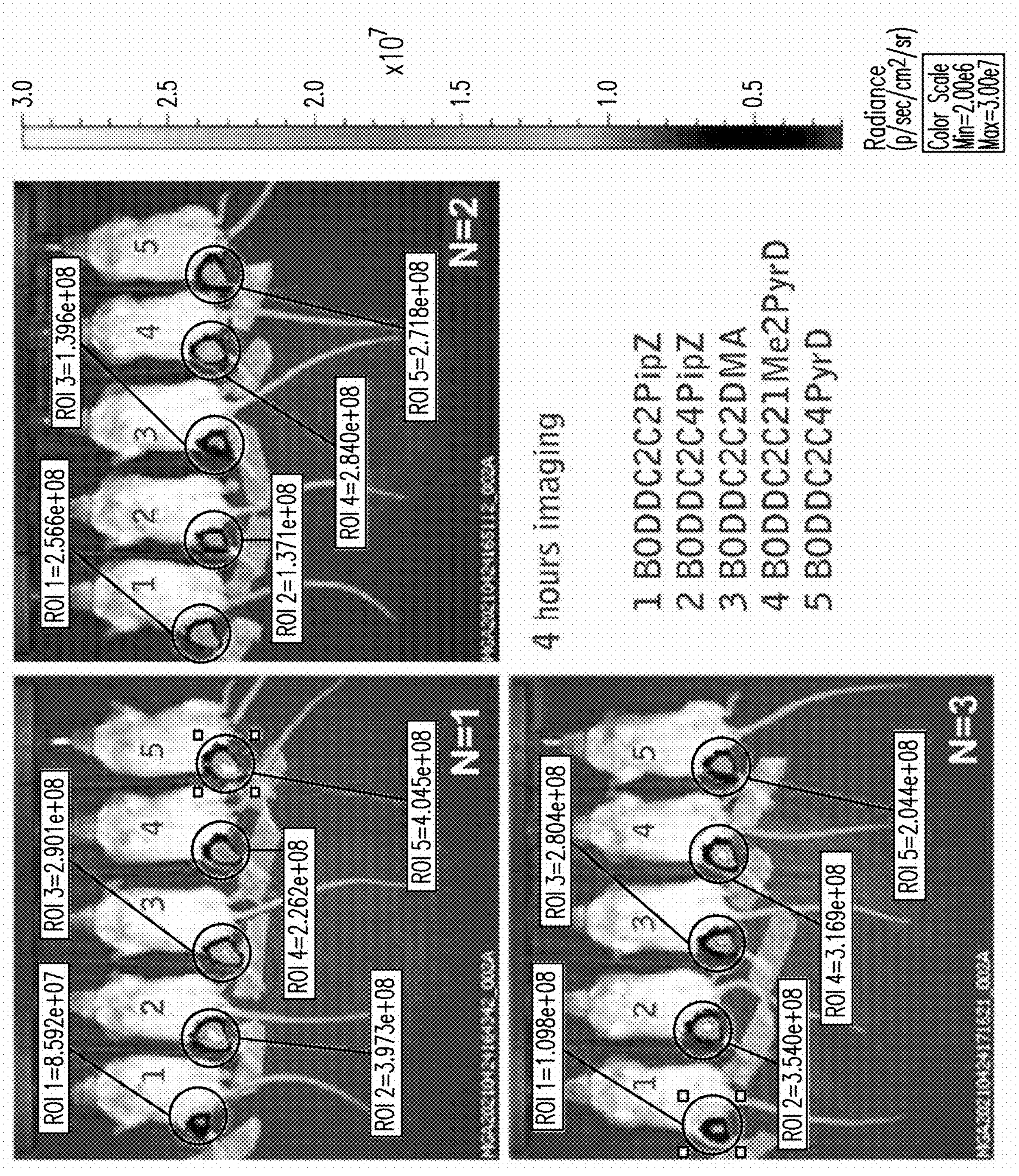

FIG. 30A: In vivo Firefly Luciferase expression of the injection site in IM administration as set forth in Example 30.

Figure 30B:
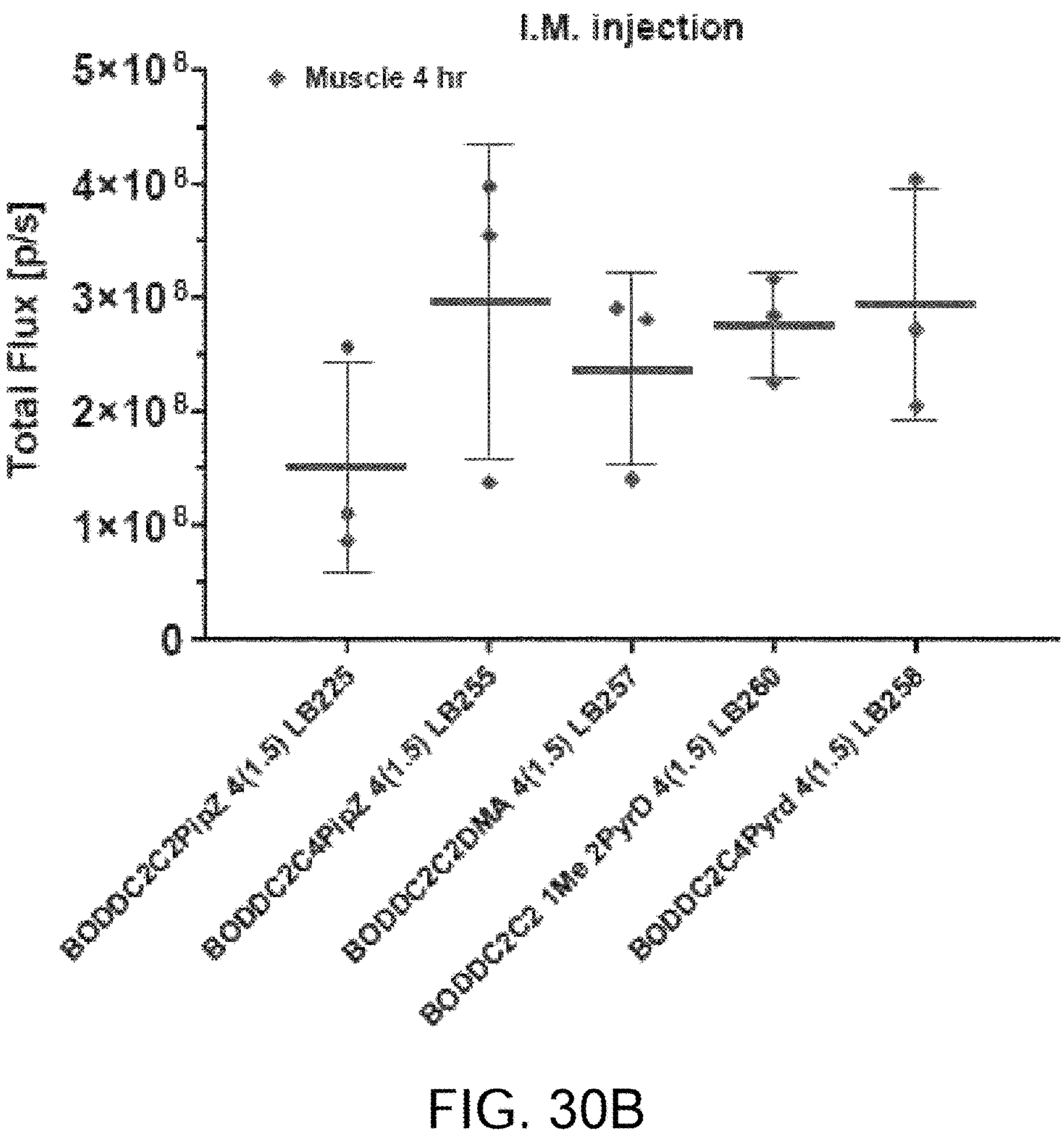

FIG. 30B: In vivo Firefly Luciferase expression of the injection site in IM administration as set forth in Example 30.

Figure 30C:
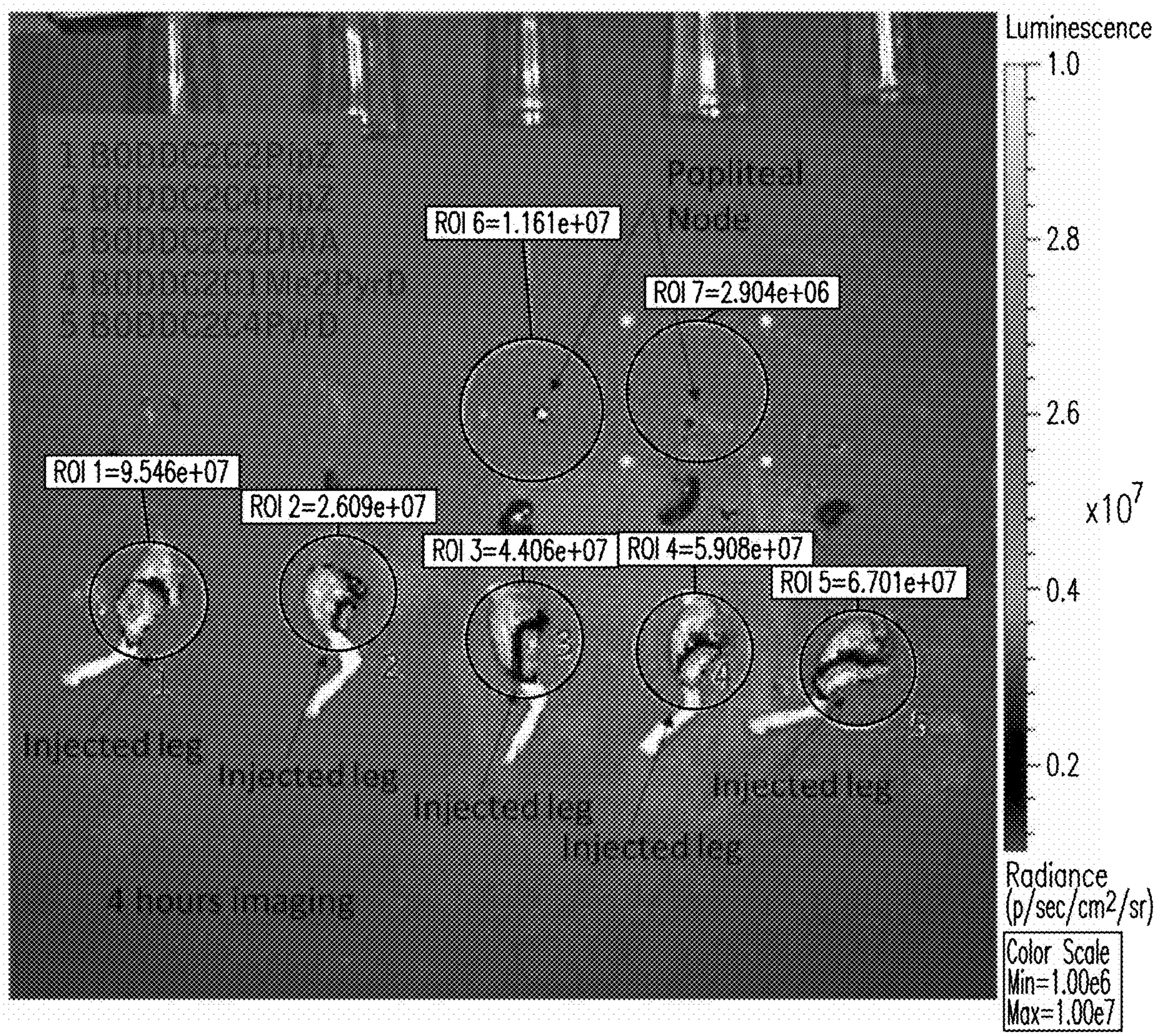

FIG. 30C: Ex vivo Firefly Luciferase expression in IM administration as set forth in Example 30.

Figure 30D:
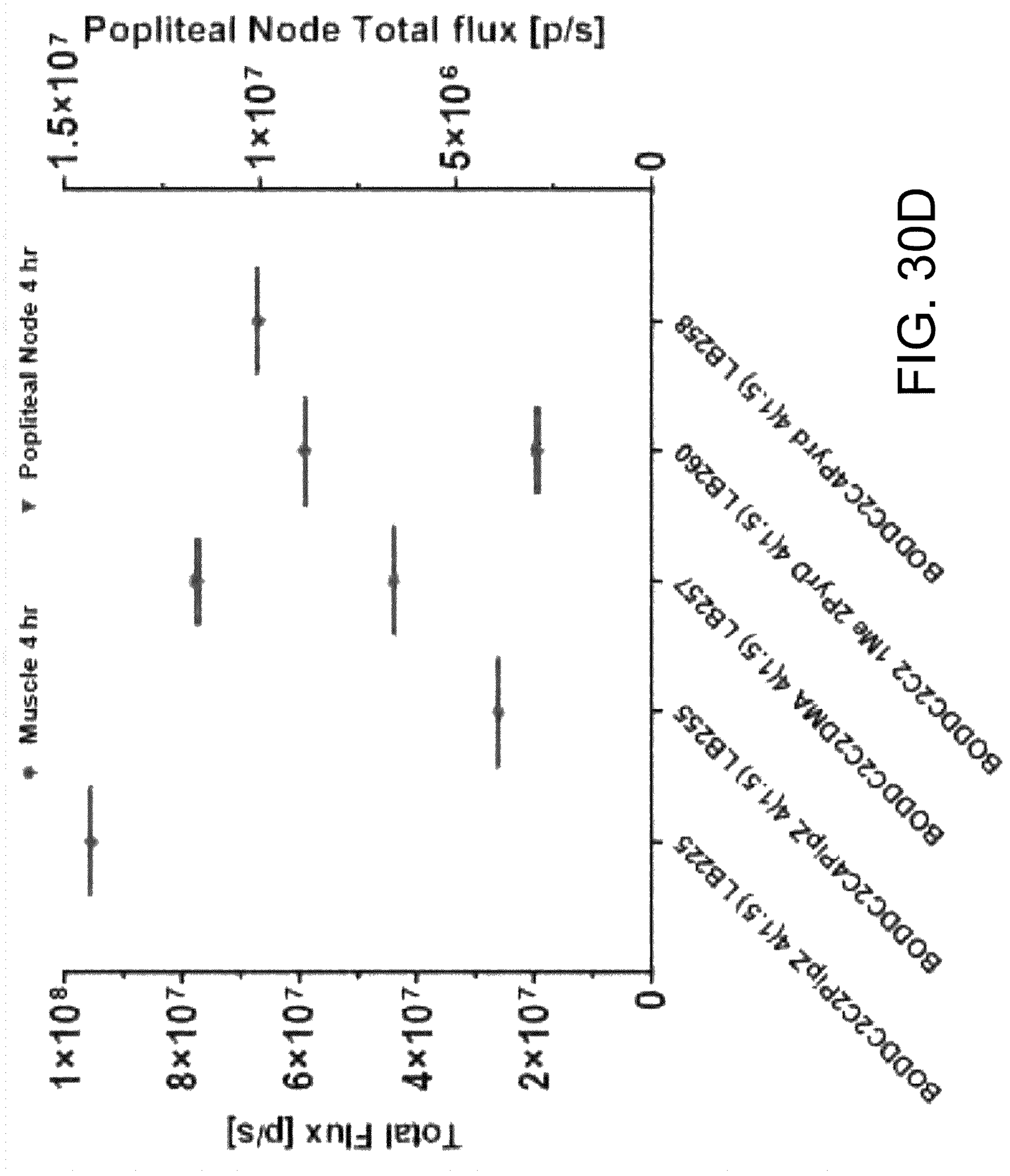

FIG. 30D: Ex vivo Firefly Luciferase expression in IM administration as set forth in Example 30.

Figure 31A:
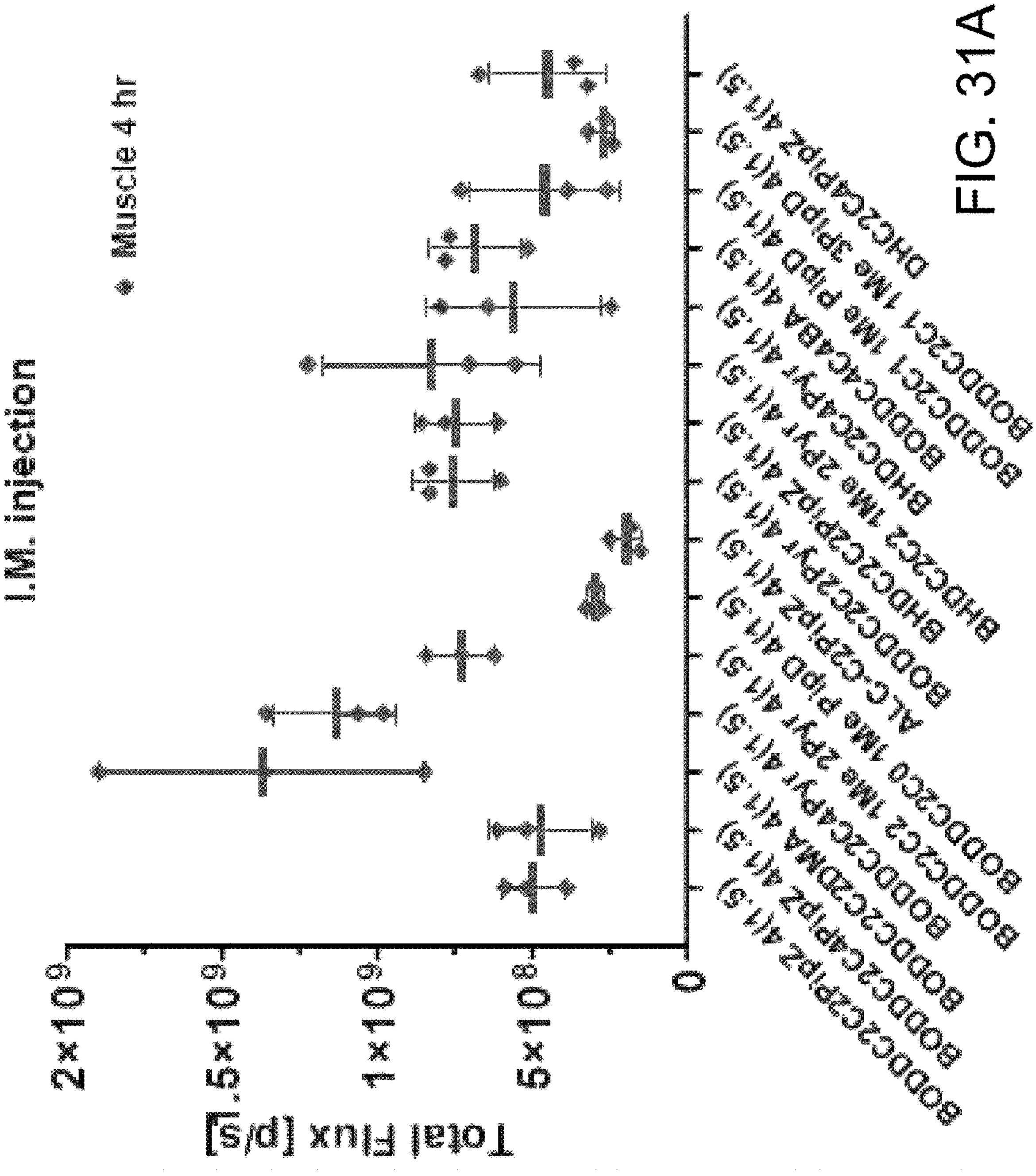

FIG. 31A: In vivo Firefly Luciferase expression of the injection site in IM administration as set forth in Example 31.

Figure 31B:
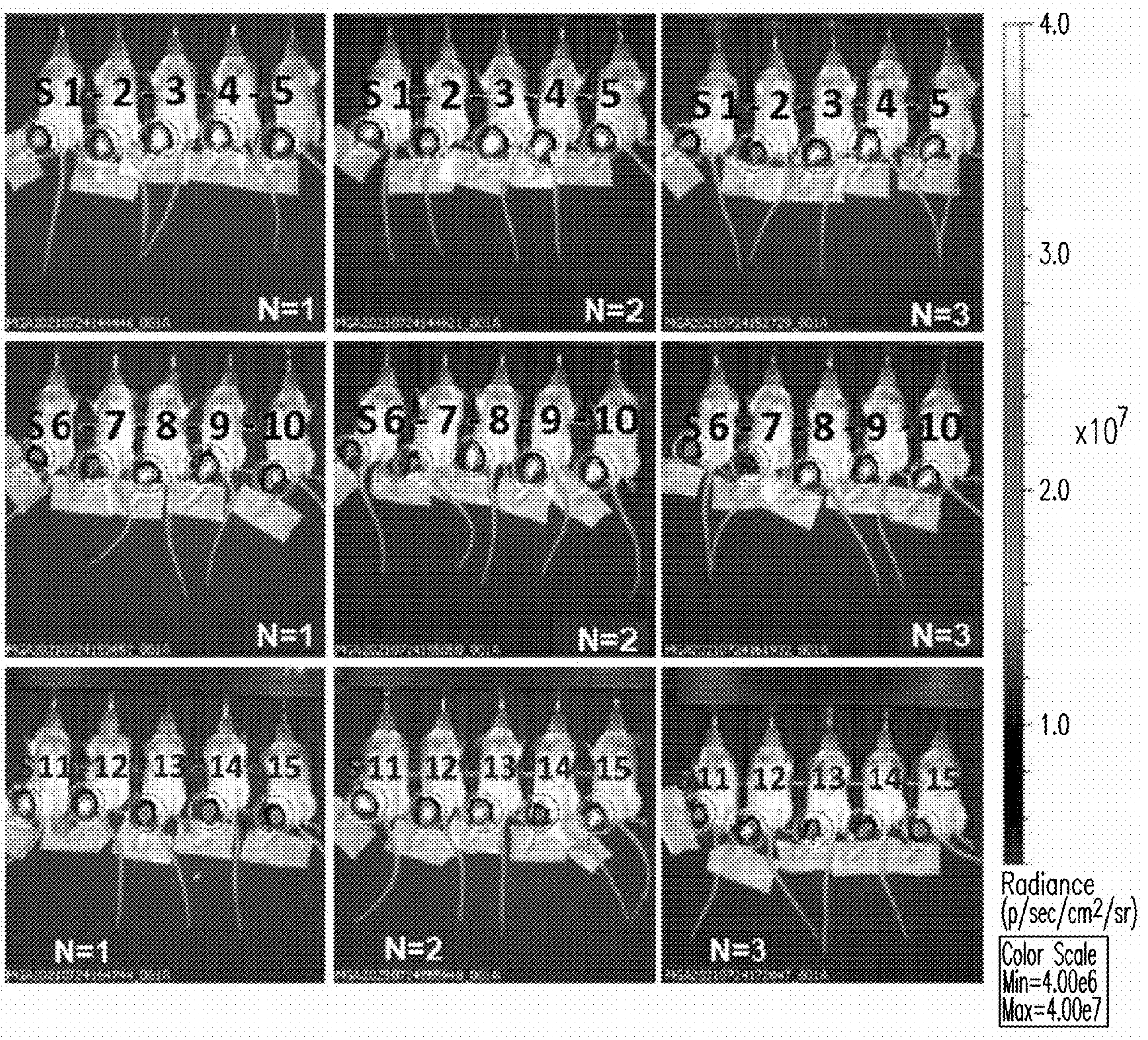

FIG. 31B: In vivo Firefly Luciferase expression of the injection site in IM administration as set forth in Example 31.

Figure 31C:
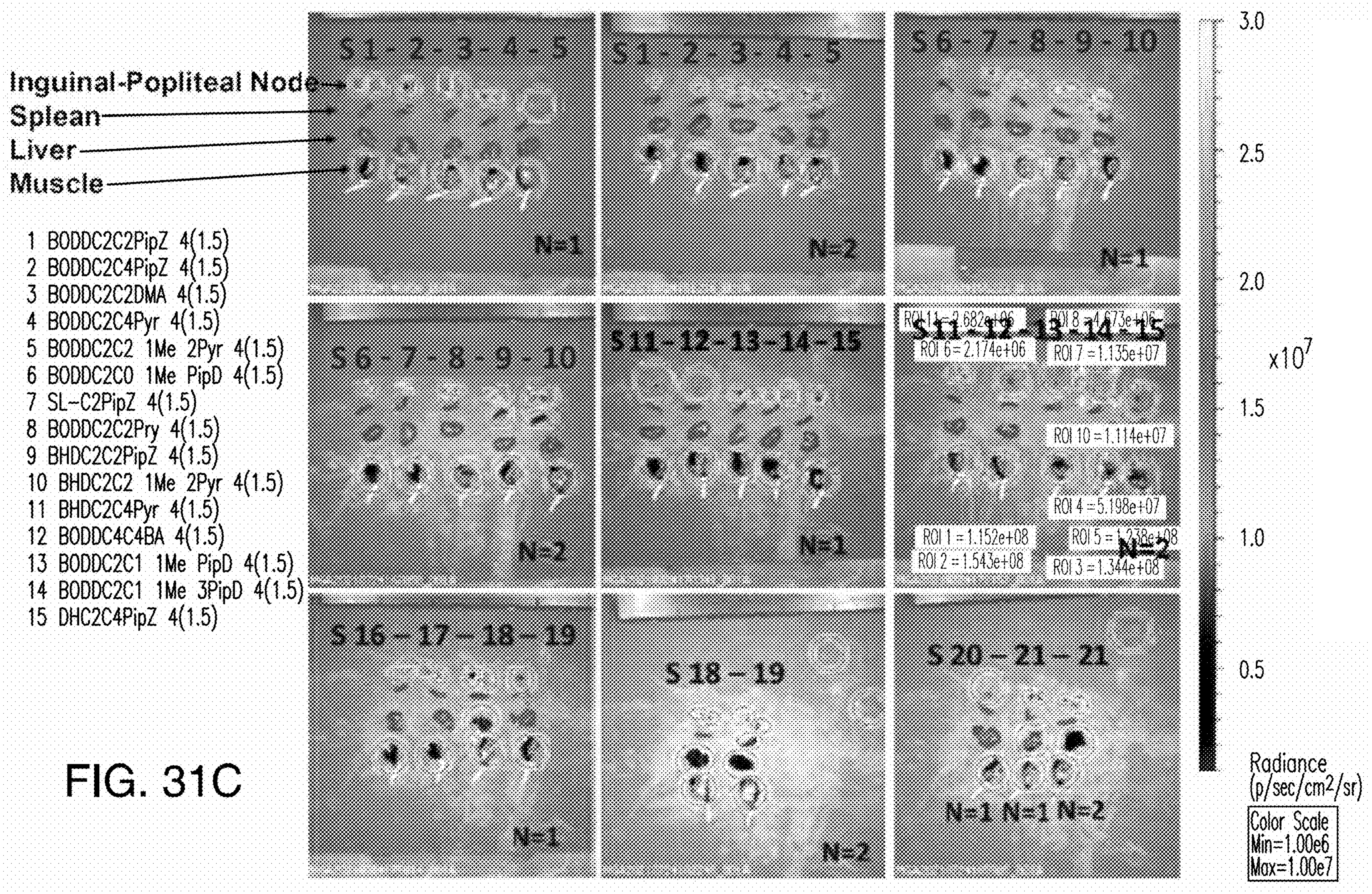

FIG. 31C: Ex vivo Firefly Luciferase expression in IM administration as set forth in Example 31.

Figure 31D:
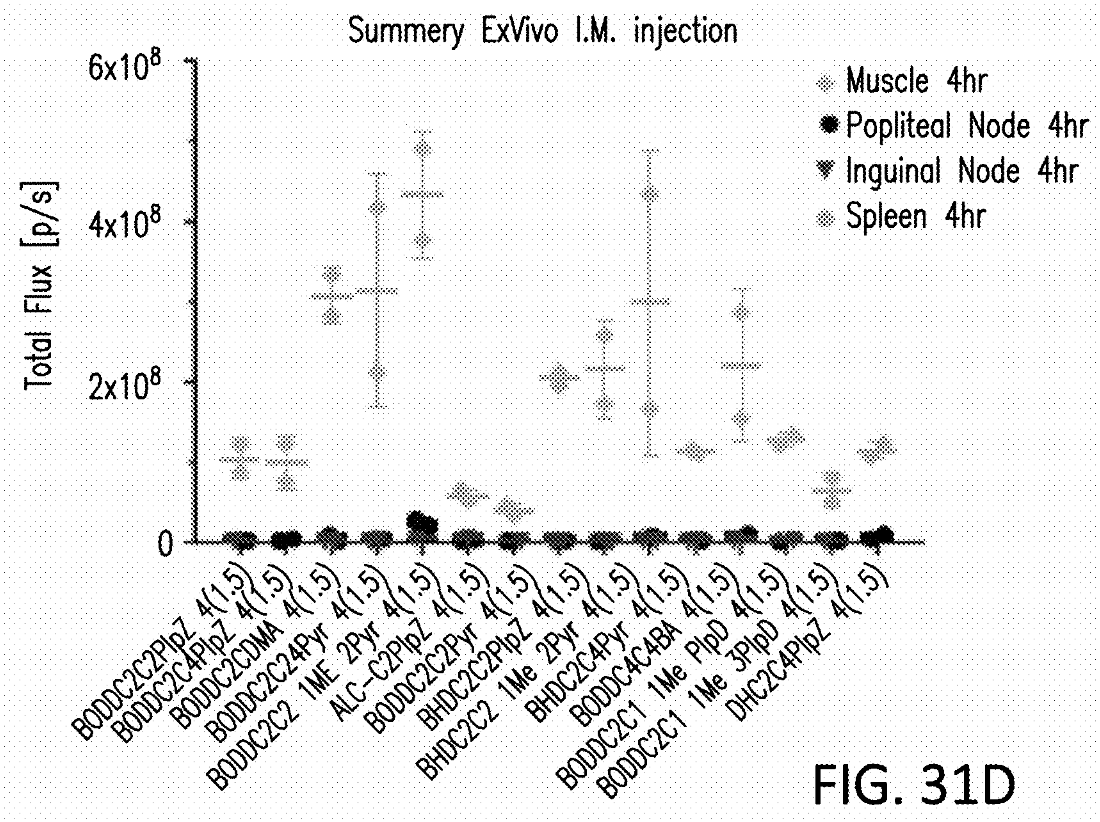

FIG. 31D: Ex vivo Firefly Luciferase expression in IM administration as set forth in Example 31.

Figure 31E:
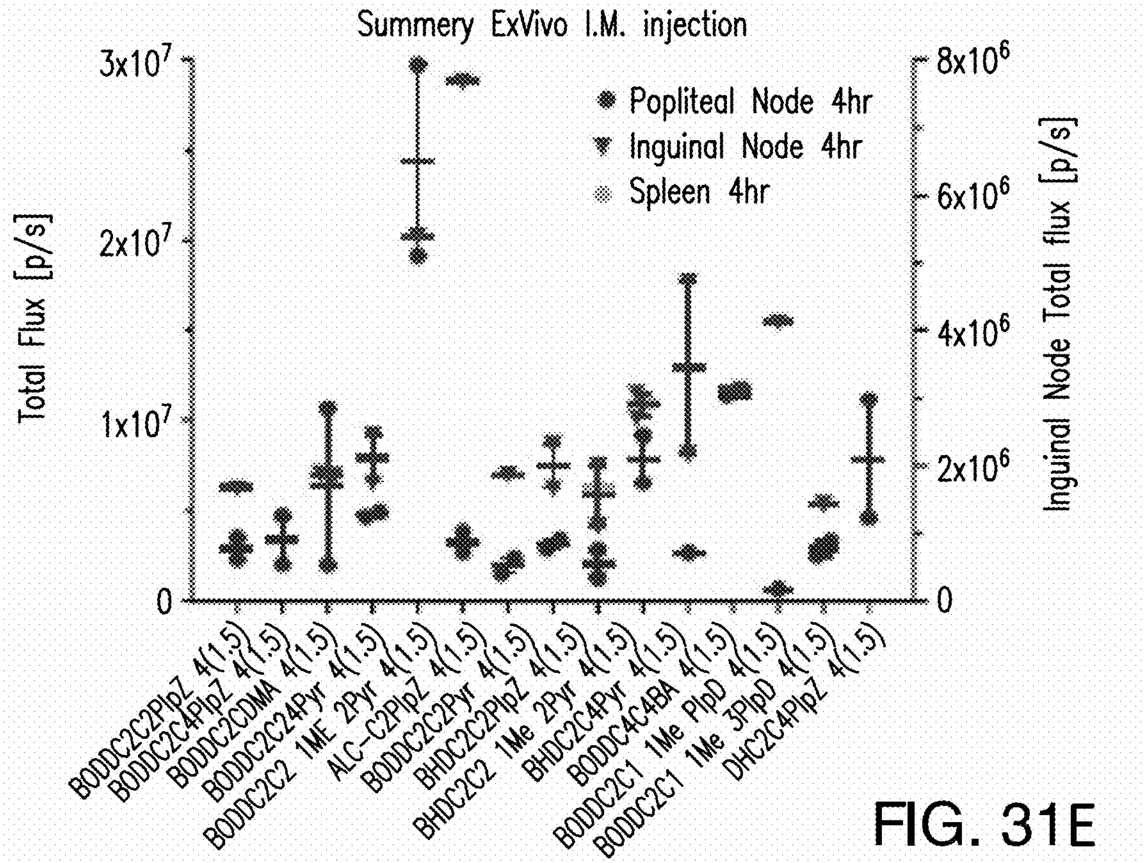

FIG. 31E: Ex vivo Firefly Luciferase expression in IM administration as set forth in Example 31.

Figure 32A:
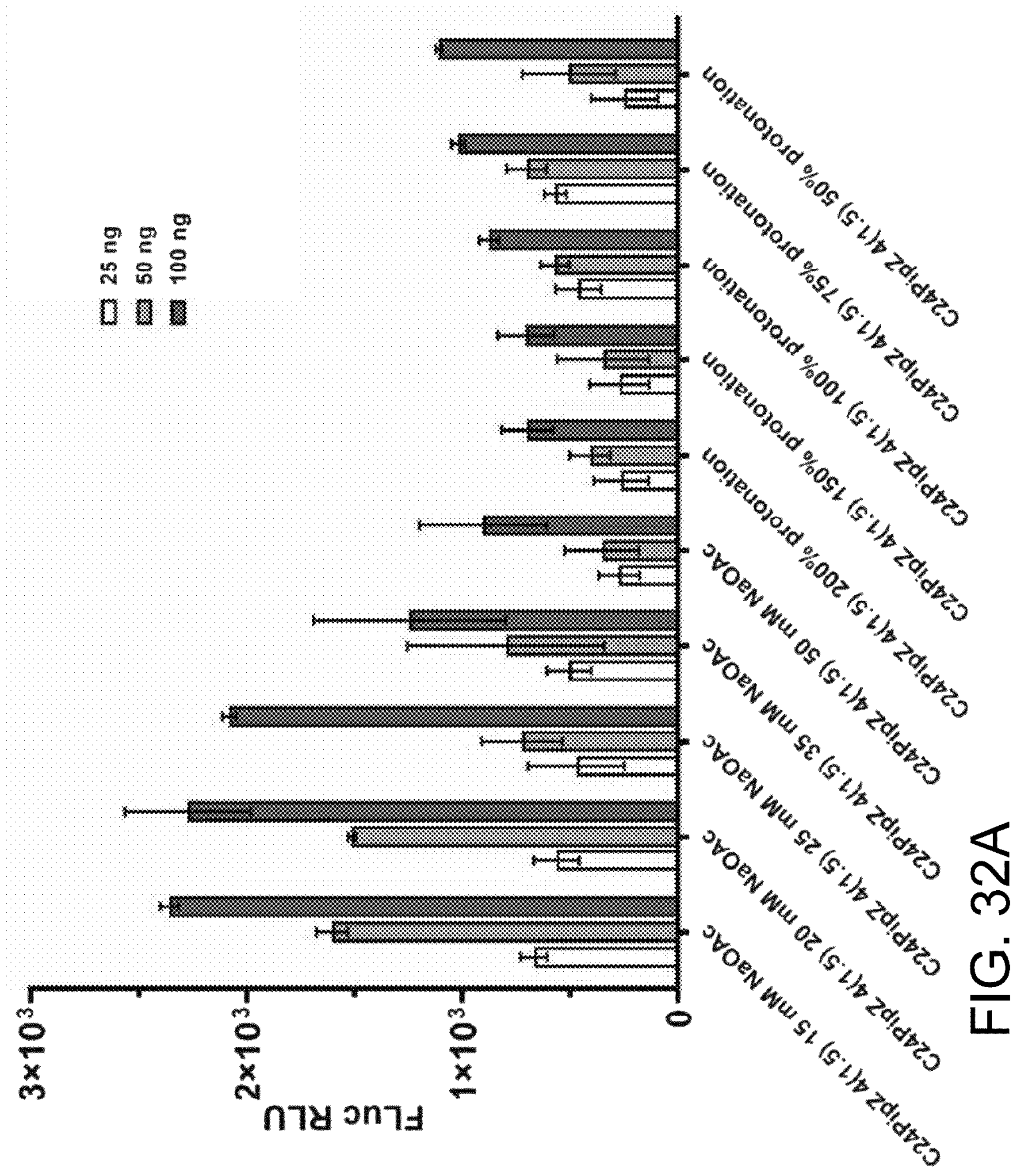

FIG. 32A: Firefly Luciferase Assay for mRNA Delivery Efficiency as set forth in Example 32.

Figure 32B:
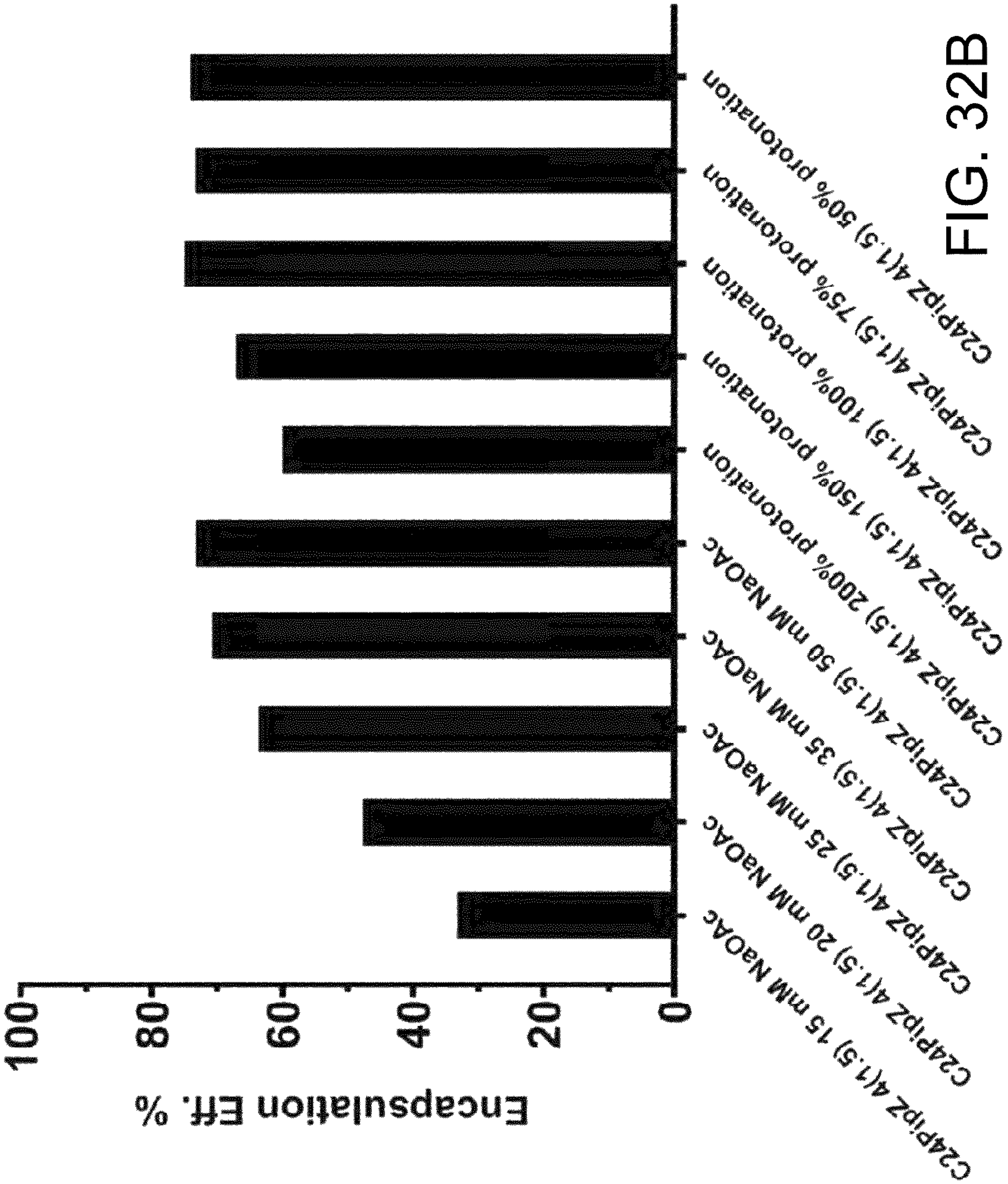

FIG. 32B: Ribogreen Assay for mRNA Encapsulation Efficiency as set forth in Example 32.

Figure 32C:
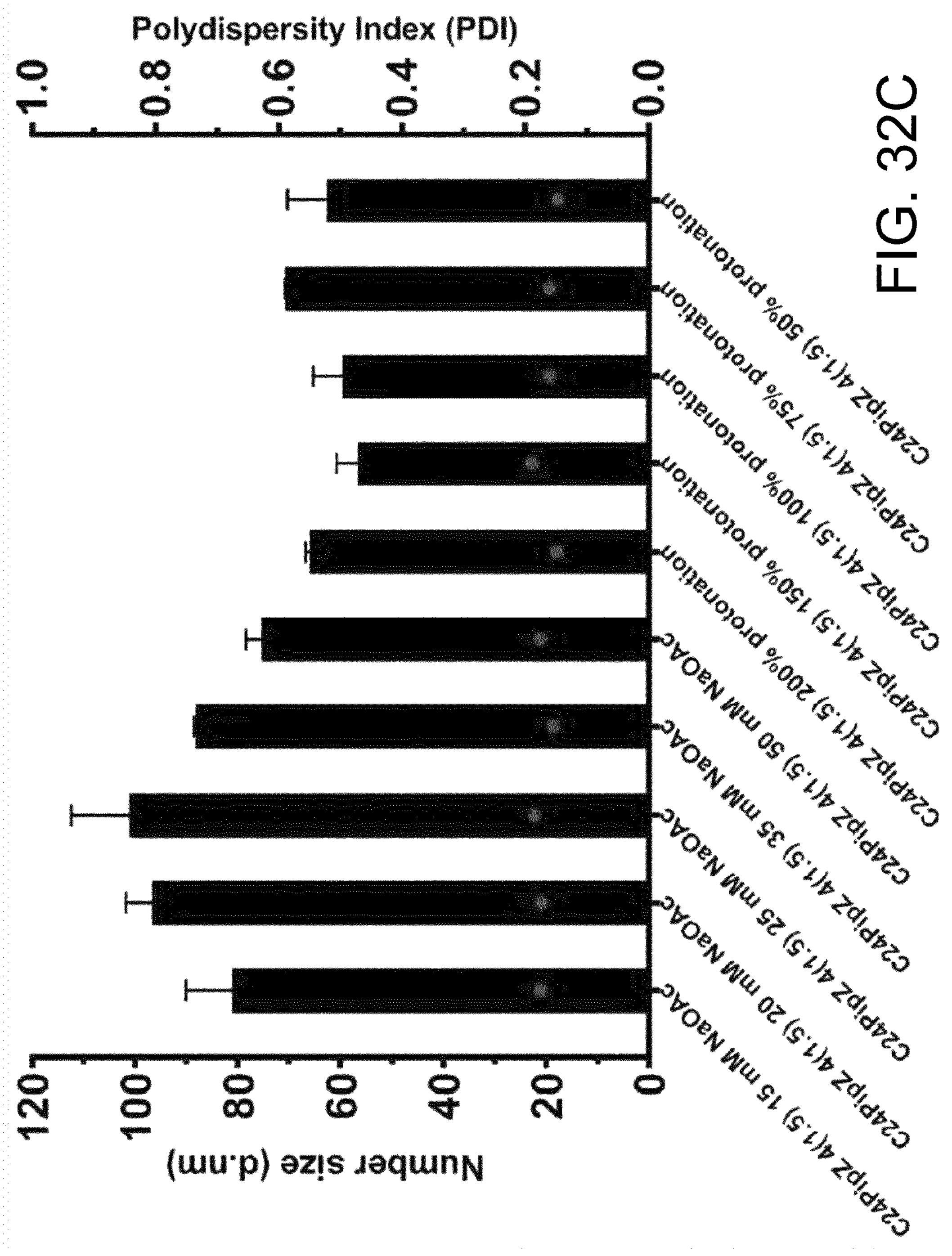

FIG. 32C: Dynamic Light Scattering for LNP Size (white dots are PDI right y axis) as set forth in Example 32.

Figure 33A:
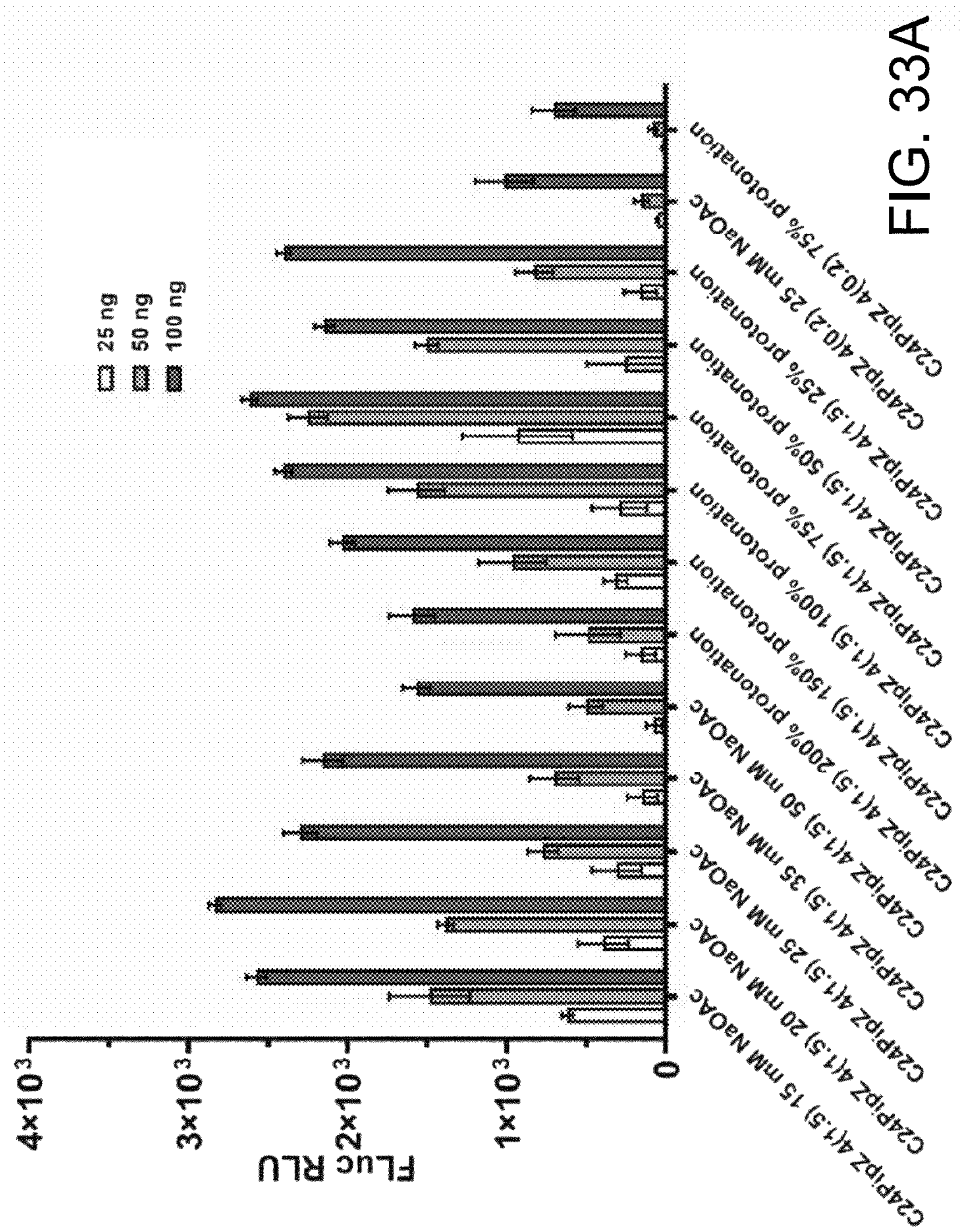

FIG. 33A: Firefly Luciferase Assay for mRNA Delivery Efficiency as set forth in Example 33.

Figure 33B:
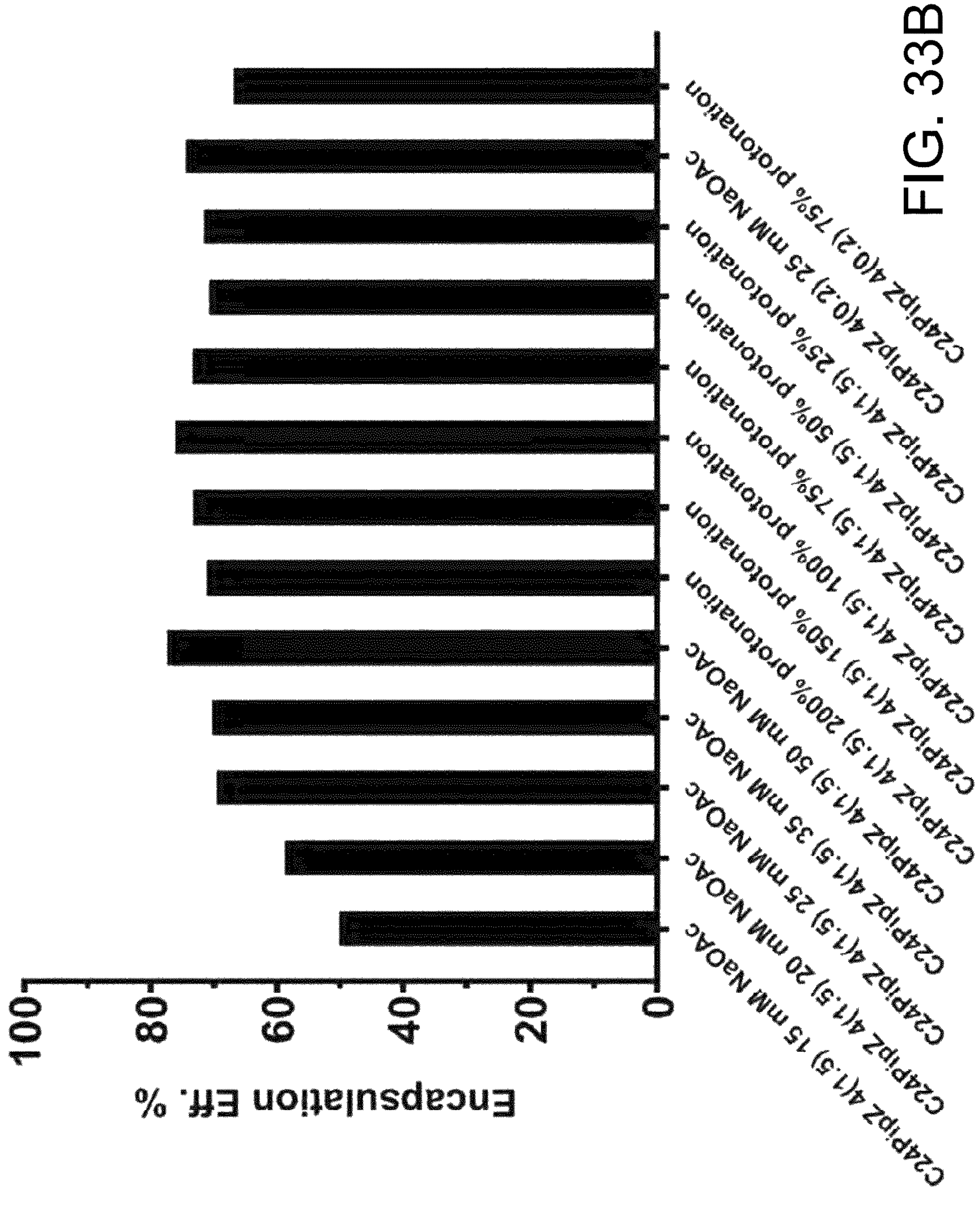

FIG. 33B: Ribogreen Assay for mRNA Encapsulation Efficiency as set forth in Example 33.

Figure 33C:
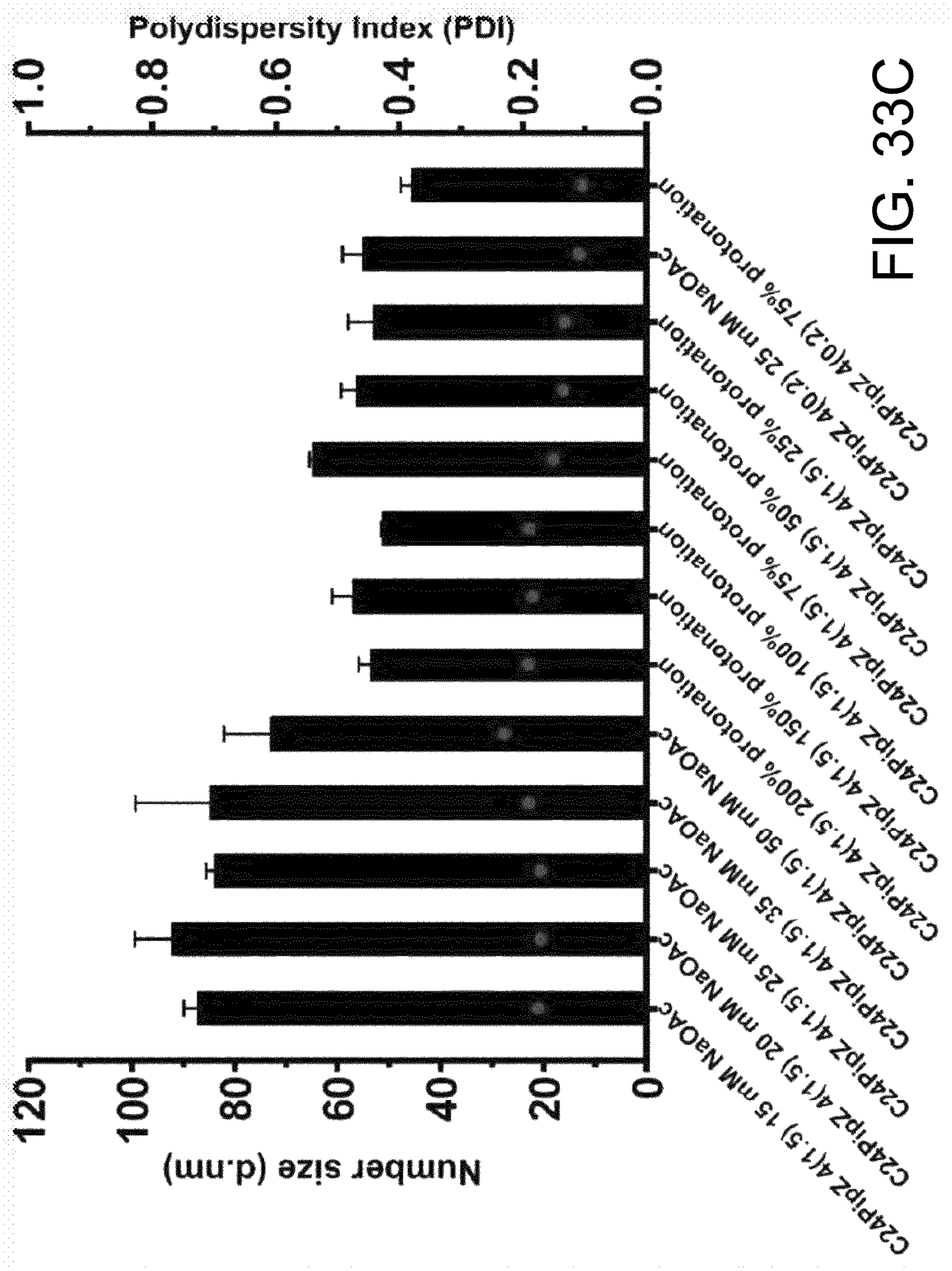

FIG. 33C: Dynamic Light Scattering for LNP Size (dots are PDI right y axis) as set forth in Example 33.

Figure 33D:
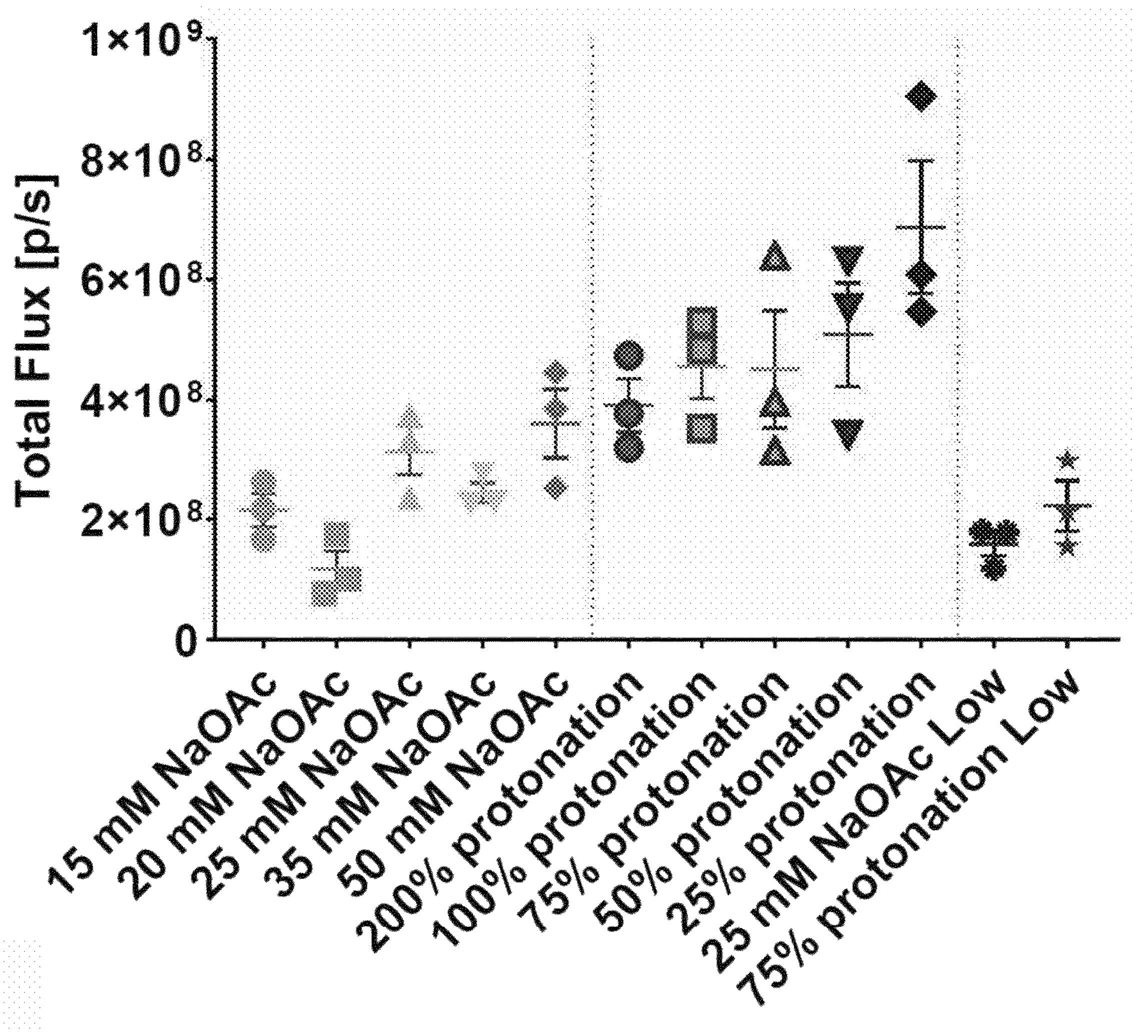

FIG. 33D: In vivo Firefly Luciferase expression in IM administration for LNPs mixed at 1.5 mg/ml as set forth in Example 33.

Figure 33E:
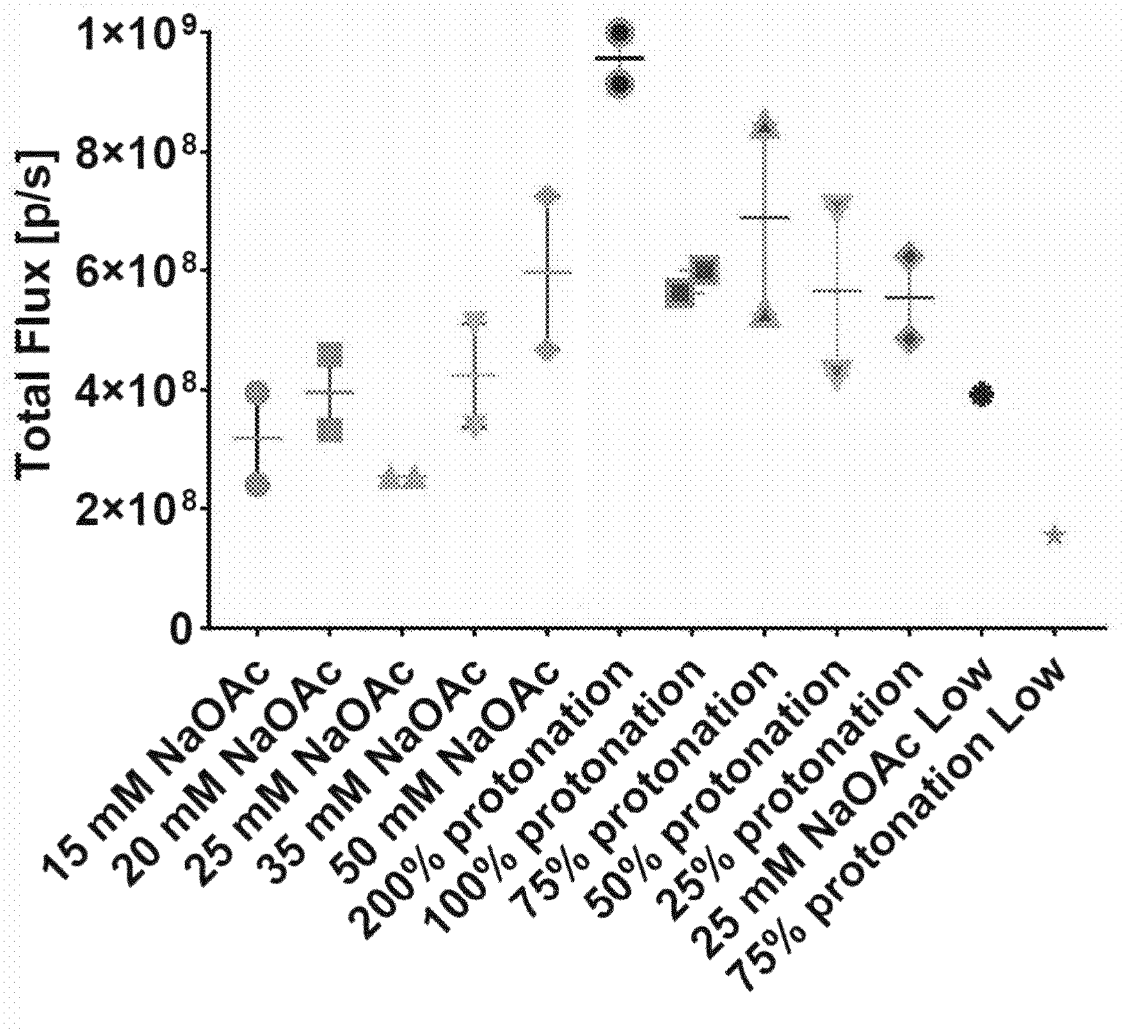

FIG. 33E: Ex vivo Firefly Luciferase expression in IV administration for LNPs mixed at 1.5 mg/ml as set forth in Example 33.

Figure 34A:
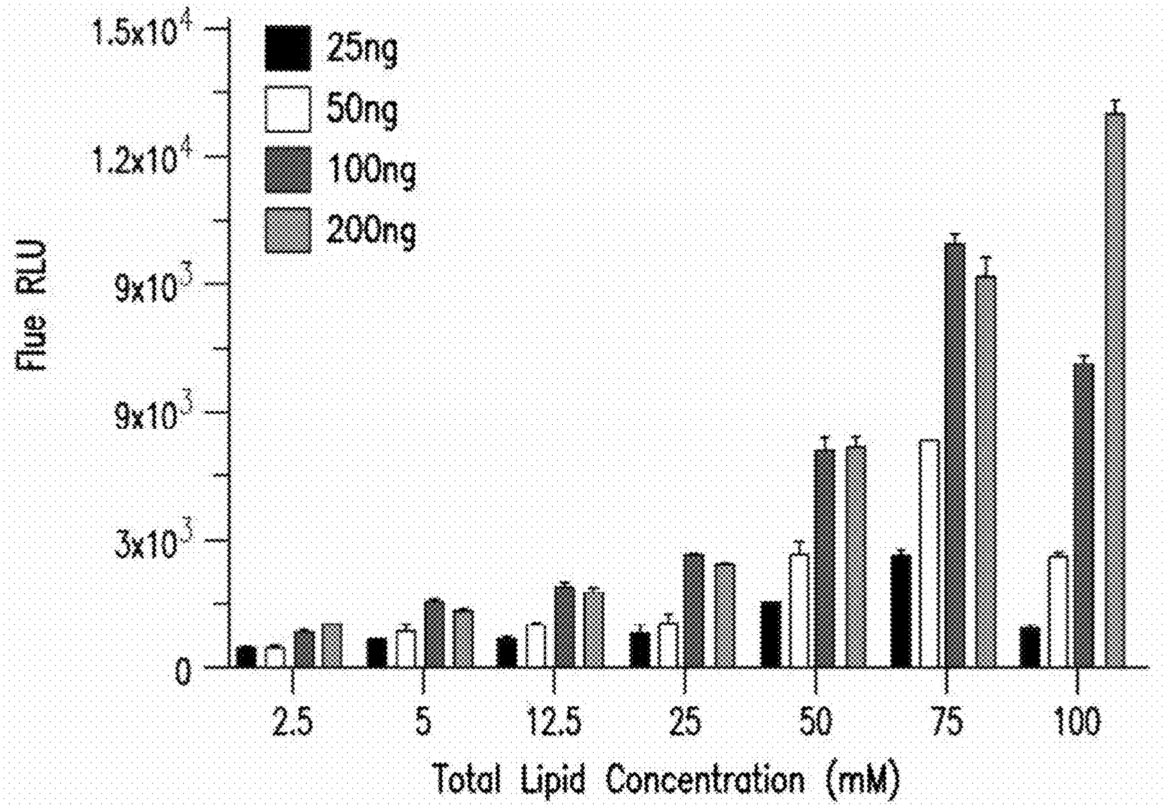
Figure 34B:
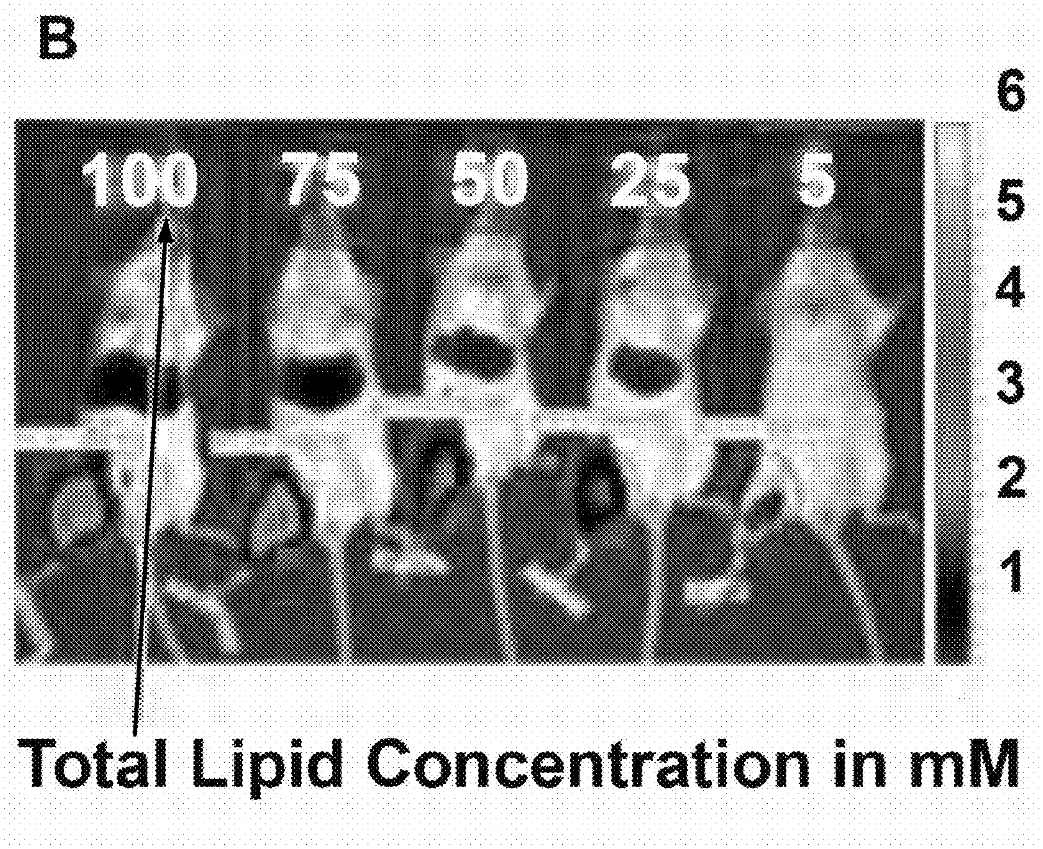
Figure 34C:
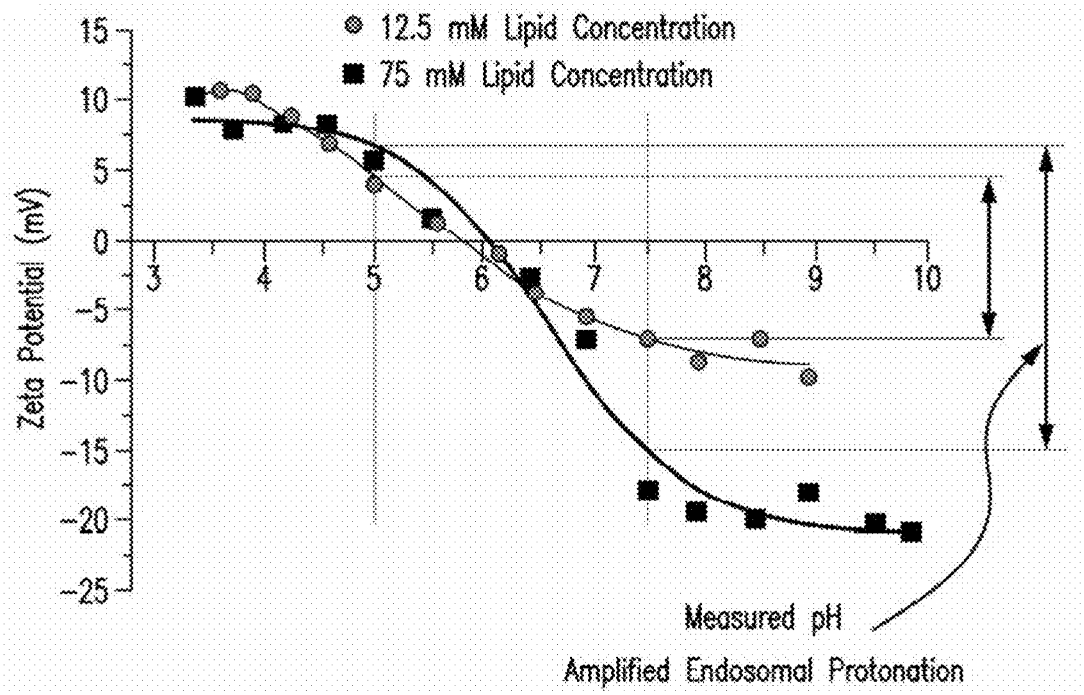

FIG. 34A illustrates KC2 LNPs assembled at higher concentrations produced higher Fluc expression in vitro at the same doses of 25-200 ng per well containing 12 k HEK293 cells. FIG. 34B illustrates LNPs produced at higher mixing concentrations (total lipid concentration in mM at mixing is shown above the animal), and diluted to a constant 5 μg dose in 504, for IM injection, are more potent (color bar is Radiance in 107 p/sec/$cm^2$/sr). FIG. 34C illustrates Zeta potential measurements reveal a greater increase in protonation when pH drops from 7.4 to 5 for the LNP prepared by high concentration mixing, suggesting greater endosomal release.

DETAILED DESCRIPTION

Disclosed herein are methods of increasing the potency of nucleic acid loaded lipid nanoparticles through certain novel and surprisingly superior LNP manufacturing techniques. Also disclosed are pharmaceutical compositions containing LNPs manufactured according to the manufacturing methods described herein.

The methods disclosed herein overcome major technical difficulties and high costs associated with previous LNP manufacturing techniques. The methods disclosed herein, therefore, greatly improve the industrial production of LNPs in unexpected ways thereby providing more potent LNPs for nucleic acid delivery.

One embodiment of the invention disclosed herein are methods that show increased potency LNPs due to increased mixing concentration of the lipids and mRNA during assembly.

The methods disclosed here are applicable to any ionizable lipid and nucleic acid payload. While not desiring to be bound by any particular mechanism of action, increased LNP potency is believed to be mediated through increased endosomal release and subsequent dissociation of mRNA from the ionizable lipid. Furthermore, changes in ultrastructural and ionization properties due to differing mixing concentrations, altered charge state, distribution or the state of the LNP components in a way that promotes endosomal escape and mRNA release (ionizable lipid or cholesterol closer to LNP periphery, altered ionizable lipid-mRNA interaction and internal structure, greater proportion of non-protonated ionizable lipid available for endosomal protonation, multilamellar, faceted structure). Preferably, LNPs delivering nucleic acids, e.g., mRNA encoded immunogens, formed by the methods disclosed herein will be more potent e.g., providing greater protection against viral challenge, compared to those formed at current low concentrations at the same dose.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter. Thus, unless defined otherwise, all technical and scientific terms and any acronyms used herein have the same meanings as commonly understood by one of ordinary skill in the art in the field of the presently disclosed subject matter. Although any compositions, methods, kits, and means for communicating information similar or equivalent to those described herein can be used to practice the presently disclosed subject matter, particular compositions, methods, kits, and means for communicating information are described herein. It is understood that the particular compositions, methods, kits, and means for communicating information described herein are exemplary only and the presently disclosed subject matter is not intended to be limited to just those embodiments.

Following long-standing patent law convention, the terms "a", "an", and "the" refer to "one or more" when used in this application, including the claims. For example, in some embodiments the phrase "an LNP," a "nucleic acid," refers to one or more LNPs or nucleotides, respectively.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

The term "about", as used herein to refer to a measurable value such as an amount of weight, time, dose (e.g., therapeutic dose), etc., is meant to encompass in some embodiments variations of +/−20%, in some embodiments +/−10%, in some embodiments +/−5%, in some embodiments +/−1%, in some embodiments +/−0.1%, in some embodiments +/−0.5%, and in some embodiments +/−0.01% from the specified amount, as such variations are appropriate to perform the disclosed methods.

As used herein, the term "and/or" when used in the context of a list of entities, refers to the entities being present singly or in any and every possible combination and subcombination. Thus, for example, the phrase "A, B, C, and/or D" includes A, B, C, and D individually, but also includes any and all combinations and subcombinations of A, B, C, and D. It is further understood that for each instance wherein multiple possible options are listed for a given element (i.e., for all "Markush Groups" and similar listings of optional components for any element), in some embodiments the optional components can be present singly or in any combination or subcombination of the optional components. It is implicit in these forms of lists that each and every combination and subcombination is envisioned and that each such combination or subcombination has not been listed simply merely for convenience. Additionally, it is further understood that all recitations of "or" are to be interpreted as "and/or" unless the context clearly requires that listed components be considered only in the alternative (e.g., if the components would be mutually exclusive in a given context and/or could not be employed in combination with each other).

I. Definitions

The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

The term "lipid nanoparticle" or "LNP" used herein refers to a particle that comprises a plurality of, i.e. more than one, lipid molecules physically associated with each other by intermolecular forces. In one embodiment, the LNP carries a nucleic acid payload. The LNPs can have one or more different types of lipids. The lipid nanoparticles may be, e.g., microspheres (including unilamellar and multilamellar vesicles, e.g. "liposomes"—lamellar phase lipid bilayers that, in some embodiments are substantially spherical, and, in more particular embodiments can comprise an aqueous core, e.g., comprising a substantial portion of RNA molecules), a dispersed phase in an emulsion, micelles or an internal phase in a suspension.

In some embodiments, the lipid nanoparticles have a size of about 1 to about 2,500 nm, about 10 to about 1,500 nm, about 20 to about 1,000 nm, in one embodiment about 50 to about 600 nm, in a sub-embodiment about 50 to about 400 nm, in a sub-embodiment about 50 to about 250 nm, and in a sub-embodiment about 50 to about 150 nm. Unless indicated otherwise, all sizes referred to herein are the average sizes (diameters) of the fully formed nanoparticle, as measured by dynamic light scattering on a Malvern Zetasizer. The nanoparticle sample is diluted in phosphate buffered saline (PBS) so that the count rate is approximately 200-400 kcts. The data are presented as the number-weighted average obtained by transformation of the intensity-weighted average. The number-weighted average is preferred since it most closely corresponds to the physical diameter of the particle as measured by electron microscopy.

"LNP lipid" as used herein refers to the individual lipid molecules that form an LNP. In certain embodiments, the LNP lipids are ionizable cationic lipids.

As used herein, the term "cationic lipid" refers to a lipid that is cationic or becomes cationic (protonated) as the pH is lowered below the pKa of the ionizable group of the lipid when present in the LNP (i.e. the pKa of the ionizable lipid in the lipid environment of the LNP which is different from the pKa of the ionizable lipid in aqueous media), but is progressively more neutral at higher pH values. At pH values below the pKa, the lipid is then able to associate with negatively charged nucleic acids (e.g., oligonucleotides). As used herein, the term "cationic lipid" includes zwitterionic lipids that assume a positive charge on pH decrease. Notably most helper lipids such as DSPC are zwitterionic but not cationic since they have phosphate groups which balance any cationic charge.

The term "cationic lipid" also refers to any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl) cholesterol (DC-Chol) and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethy-lammonium trifluoroacetate (DOSPA) and (DOPE), from GIBCO/BRL); and TRANSFECTAM®. (Commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In some embodiments, the "LNP lipids" are MC3, DLin, and/or KC2 as shown below. The table highlights the pKa of the ionizable lipid measured in the LNP (TNS pKa) versus the pKa in aqueous medium predicated by a commercial software ACDLabs Percepta.:

TABLE 1

| Published ionizable lipids and pKas | | | | |
|---|---|---|---|---|
| Lipid | Structure | TNS pKa | ACD pKa | DpKa |
| DLin | 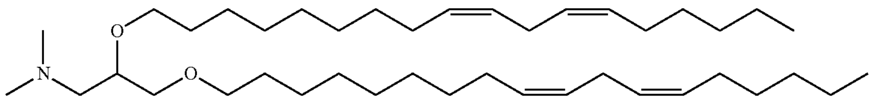 [SMILES: CCCCC/C=C\C/C=C\CCCCCCCCOCC(CN(C)C)OCCCCCCCC/C=C\C/C=C\CCCCC] | 6.8 | 8.6 | 1.8 |

TABLE 1-continued

Published ionizable lipids and pKas

| Lipid | Structure | TNS pKa | ACD pKa | DpKa |
|---|---|---|---|---|
| KC2 | 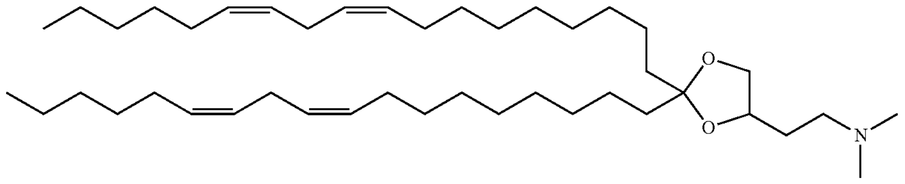 [SMILES: CCCCC/C=C\C/C=C\CCCCCCCCC1(CCCCCCCC/C=C\C/C=C\CCCCC)OCC(CCN(C)C)O1] | 6.7 | 9.3 | 2.6 |
| MC3 | 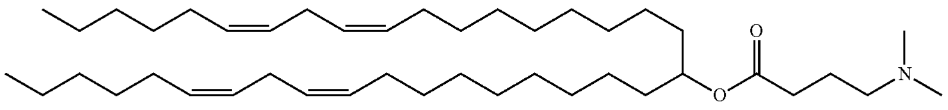 [SMILES: CCCCC/C=C\C/C=C\CCCCCCCCC(CCCCCCCC/C=C\C/C=C\CCCCC)OC(=O)CCCN(C)C] | 6.4 | 9.4 | 3 |

In some embodiments, the invention encompasses a LNP lipid that is a compound encompassed by Formula I*:

Formula I

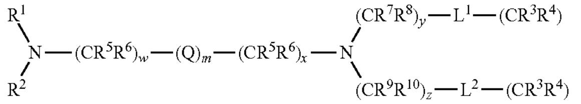

wherein each $R^1$ and each $R^2$ is independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form cycloalkyl or heterocycloalkyl ring, wherein each $R^3$ and $R^4$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl; wherein each $R^5$, $R^6$, $R^7$, $R^8$, $R^9$, and $R^{10}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl; wherein each of w, x, y, and z is independently an integer from 0-10; wherein each Q is independently an atom selected from O, NH, and S; wherein each of m is an integer from 0 to 8; and wherein each of $L^1$ and $L^2$ is independently selected from the group consisting of —C(=O)—; OC(=O); —NH—C(=O)—; —C(=O)NH—; —SO—; —$SO_2$—; —$SO_3$—; —$NSO_2$—; —$SO_2N$—; —NH(($C_1$-$C_8$)alkyl); —N(($C_1$-$C_8$)alkyl)$_2$; —NH(($C_6$)aryl); —N(($C_6$)aryl)$_2$; —C(=O)R'—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In other embodiments, the invention encompasses a LNP lipid that is a compound encompassed by Formula II:

Formula II

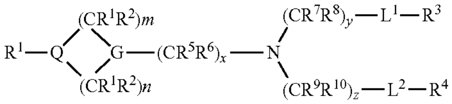

wherein each $R^1$ and each $R^2$ is independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form cycloalkyl or heterocycloalkyl ring, wherein if Q is S or O the $R^1$ attached to the S or O is an electron pair; wherein each $R^3$ and $R^4$ is is independently selected from the group consisting of an optionally substituted $C_1$-$C_{22}$ alkyl, optionally substituted $C_2$-$C_{22}$ alkenyl, optionally substituted $C_2$-$C_{22}$ alkynyl; wherein each $R^5$, $R^6$, $R^7$, $R^8$, $R^9$, and $R^{10}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of x, y, and z is independently an integer from 0-10; wherein G and Q are each independently an atom selected from CH, O, N, and S;

wherein each of m and n is an integer from 0-8; and wherein each of $L^1$ and $L^2$ is independently selected from the group consisting of —C(=O)—; OC(=O)—; —C(=O)O—; —NH—C(=O)—; —C(=O)NH—; —SO—; —$SO_2$—; —$SO_3$—; $NSO_2$—; —$SO_2N$—; —NH(($C_1$-$C_8$)alkyl); —N(($C_1$-$C_8$)alkyl)$_2$; —NH(($C_6$)aryl); —N(($C_6$)aryl)$_2$; —C(=O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In another embodiment, the invention encompasses a LNP lipid that is a compound encompassed by Formula III:

Formula III

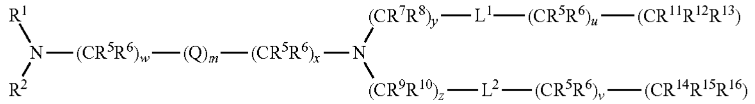

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form cycloalkyl or heterocycloalkyl ring, wherein if Q is S or O the $R^1$ attached to the S or O is an electron pair;

wherein each $R^3$ and $R^4$ is is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, $R^{10}$, $R^{11}$, $R^{12}$, $R^{13}$, $R^{14}$, $R^{15}$, and $R^{16}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, x, y, and z is independently an integer from 0-20;

wherein each Q is independently an atom selected from O, NH, S, or a disulfide bond;

wherein each of m is an integer from 0-4, preferably 0, 1, or 2; and wherein each of $L^1$ and $L^2$ is independently selected from the group consisting of —C(═O)—; OC(═O)—; —OC(═O)O—; —C(═O)O—; —C(═O)O($CR^5R^6R^7$); —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)NR'—; —NHC(═O)O—; —OC(═O)$NR^1$—; —C(═O)R'—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(═O)O—$C_1$-$C_{22}$ alkyl.

In a preferred embodiment, $R^3$ is substituted or unsubstituted —C(═O)O—$C_1$-$C_{22}$ alkenyl.

In a preferred embodiment, $R^3$ is substituted or unsubstituted —C(═O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(═O)O—$C_1$-$C_{22}$ alkyl.

In a preferred embodiment, $R^4$ is substituted or unsubstituted —C(═O)O—$C_1$-$C_{22}$ alkenyl.

In a preferred embodiment, $R^4$ is substituted or unsubstituted —C(═O)O—$C_1$-$C_{22}$ alkynyl.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{12}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, x is 0.

In certain embodiments, x is 1.

In certain embodiments, x is 2.

In certain embodiments, x is 3.

In certain embodiments, x is 4.

In certain embodiments, x is 5.

In certain embodiments, x is 6.

In certain embodiments, x is 7.

In certain embodiments, x is 8.

In certain embodiments, x is 9.

In certain embodiments, x is 10.

In certain embodiments, x is 11.

In certain embodiments, x is 12.

In certain embodiments, x is 13.

In certain embodiments, x is 14.

In certain embodiments, x is 15.

In certain embodiments, x is 16.

In certain embodiments, x is 17.

In certain embodiments, x is 18.

In certain embodiments, x is 19.

In certain embodiments, x is 20.

In certain embodiments, y is 0.

In certain embodiments, y is 1.

In certain embodiments, y is 2.

In certain embodiments, y is 3.

In certain embodiments, y is 4.

In certain embodiments, y is 5.
In certain embodiments, y is 6.
In certain embodiments, y is 7.
In certain embodiments, y is 8.
In certain embodiments, y is 9.
In certain embodiments, y is 10.
In certain embodiments, y is 11.
In certain embodiments, y is 12.
In certain embodiments, y is 13.
In certain embodiments, y is 14.
In certain embodiments, y is 15.
In certain embodiments, y is 16.
In certain embodiments, y is 17.
In certain embodiments, y is 18.
In certain embodiments, y is 19.
In certain embodiments, y is 20.
In certain embodiments, z is 0.
In certain embodiments, z is 1.
In certain embodiments, z is 2.
In certain embodiments, z is 3.
In certain embodiments, z is 4.
In certain embodiments, z is 5.
In certain embodiments, z is 6.
In certain embodiments, z is 7.
In certain embodiments, z is 8.
In certain embodiments, z is 9.
In certain embodiments, z is 10.
In certain embodiments, z is 11.
In certain embodiments, z is 12.
In certain embodiments, z is 13.
In certain embodiments, z is 14.
In certain embodiments, z is 15.
In certain embodiments, z is 16.
In certain embodiments, z is 17.
In certain embodiments, z is 18.
In certain embodiments, z is 19.
In certain embodiments, z is 20.
In certain embodiments $L^1$ is a bond.
In certain embodiments, $L^1$ is —C(═O)—.
In certain embodiments, $L^1$ is —OC(═O)O—.
In certain embodiments, $L^1$ is —NH—C(═O)—.
In certain embodiments, $L^1$ is —SO—.
In certain embodiments, $L^1$ is —$SO_2$—.
In certain embodiments, $L^1$ is OC(═O).
In certain embodiments, $L^1$ is —C(═O)O—.
In certain embodiments, $L^1$ is —C(═O)NH—.
In certain embodiments, $L^1$ is —$SO_3$—.
In certain embodiments, $L^1$ is —$NSO_2$—.
In certain embodiments, $L^1$ is —$SO_2N$.
In certain embodiments, $L^1$ is —NH(($C_1$-$C_{22}$)alkyl).
In certain embodiments, $L^1$ is —N(($C_1$-$C_8$)alkyl)$_2$.
In certain embodiments, $L^1$ is —NH(($C_6$)aryl).
In certain embodiments, $L^1$ is —N(($C_6$)aryl)$_2$.
In certain embodiments, $L^1$ is dioxolopyrrolidine-dione.
In certain embodiments, $L^1$ is —C(═O)$R^1$—.
In certain embodiments, $L^1$ is —CO(($C_1$-$C_{22}$)alkyl).
In certain embodiments, $L^1$ is —CO(($C_6$)aryl).
In certain embodiments, $L^1$ is —$CO_2$(($C_1$-$C_{22}$)alkyl).
In certain embodiments, $L^1$ is —$CO_2$(($C_6$)aryl).
In certain embodiments, $L^1$ is —C(═O)O($CR^1R^2R^3$)
In certain embodiments, $L^1$ is —$SO_2$(($C_1$-$C_{22}$)alkyl).
In certain embodiments, $L^1$ is —$SO_2$(($C_6$)aryl).
In certain embodiments $L^2$ is a bond.
In certain embodiments, $L^2$ is —C(═O)—.
In certain embodiments, $L^2$ is —OC(═O)O—.
In certain embodiments, $L^2$ is —NH—C(═O)—.
In certain embodiments, $L^2$ is —SO—.
In certain embodiments, $L^2$ is —$SO_2$—.
In certain embodiments, $L^2$ is OC(═O).
In certain embodiments, $L^2$ is —C(═O)O—.
In certain embodiments, $L^2$ is —C(═O)NH—.
In certain embodiments, $L^2$ is —$SO_3$—.
In certain embodiments, $L^2$ is —$NSO_2$—.
In certain embodiments, $L^2$ is —$SO_2N$.
In certain embodiments, $L^2$ is —NH(($C_1$-$C_{22}$)alkyl).
In certain embodiments, $L^2$ is —N(($C_1$-$C_8$)alkyl)$_2$.
In certain embodiments, $L^2$ is —NH(($C_6$)aryl).
In certain embodiments, $L^2$ is —N(($C_6$)aryl)$_2$.
In certain embodiments, $L^2$ is dioxolopyrrolidine-dione.
In certain embodiments, $L^2$ is —C(═O)$R^1$—.
In certain embodiments, $L^2$ is —CO(($C_1$-$C_{22}$)alkyl).
In certain embodiments, $L^2$ is —CO(($C_6$)aryl).
In certain embodiments, $L^2$ is —$CO_2$(($C_1$-$C_{22}$)alkyl).
In certain embodiments, $L^2$ is —$CO_2$(($C_6$)aryl).
In certain embodiments, $L^2$ is —$SO_2$(($C_1$-$C_{22}$)alkyl).
In certain embodiments, $L^2$ is —$SO_2$(($C_6$)aryl).
In certain embodiments, Q is CH.
In certain embodiments, Q is O.
In certain embodiments, Q is S.
In certain embodiments, Q is NH.
In certain embodiments, Q is a disulfide bond.
In certain embodiments, m is 0.
In certain embodiments, m is 1.
In certain embodiments, m is 2.
In certain embodiments, m is 3.
In certain embodiments, m is 4.
In certain embodiments, m is 5.
In certain embodiments, m is 6.
In certain embodiments, m is 7.
In certain embodiments, m is 8.
In certain embodiments, m is 9.
In certain embodiments, m is 10.
In certain embodiments, m is 11.
In certain embodiments, m is 12.
In certain embodiments, m is 13.
In certain embodiments, m is 14.
In certain embodiments, m is 15.
In certain embodiments, m is 16.
In certain embodiments, m is 17.
In certain embodiments, m is 18.
In certain embodiments, m is 19.
In certain embodiments, m is 20.

In another embodiment, the invention encompasses a LNP lipid that is a compound encompassed by Formula IV:

Formula IV

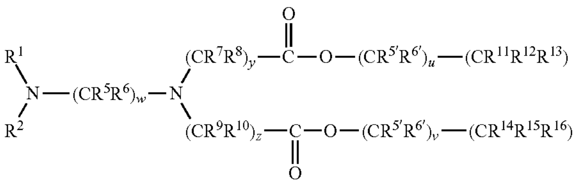

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form cycloalkyl or heterocycloalkyl ring, wherein if Q is S or O the $R^1$ attached to the S or O is an electron pair;

wherein each $R^5$, $R^6$, $R^{5'}$, $R^{6'}$, $R^{5''}$, and $R^{6''}$, is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each $R^5$, $R^6$, $R^7$, $R^8$, $R^9$, $R^{10}$, $R^{11}$, $R^{12}$, $R^{13}$, $R^{14}$, $R^{15}$ and $R^{16}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, y, and z is independently an integer from 0-20;

wherein each Q is independently an atom selected from 0, NH, S, or a disulfide bond; and wherein each of $L^1$ and $L^2$ is independently selected from the group consisting of —C(═O)—; OC(═O)—; —OC(═O)O—; —C(═O)O—; —C(═O)O($CR^5R^6R^7)_m$; —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)NR'—; —NHC(═O)O—; —OC(═O)$NR^1$—; —C(═O)R'—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(═O)—.

In certain embodiments, $L^1$ is —OC(═O)O—.

In certain embodiments, $L^1$ is —NH—C(═O)—.

In certain embodiments, $L^1$ is —SO—.

In certain embodiments, $L^1$ is —$SO_2$—.

In certain embodiments, $L^1$ is OC(═O).

In certain embodiments, $L^1$ is —C(═O)O—.

In certain embodiments, $L^1$ is —C(═O)NH—.

In certain embodiments, $L^1$ is —$SO_3$—.

In certain embodiments, $L^1$ is —$NSO_2$—.

In certain embodiments, $L^1$ is —$SO_2$N.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(═O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(═O)—.

In certain embodiments, $L^2$ is —OC(═O)O—.

In certain embodiments, $L^2$ is —NH—C(═O)—.

In certain embodiments, $L^2$ is —SO—.

In certain embodiments, $L^2$ is —$SO_2$—.

In certain embodiments, $L^2$ is OC(═O).

In certain embodiments, $L^2$ is —C(═O)O—.

In certain embodiments, $L^2$ is —C(═O)NH—.

In certain embodiments, $L^2$ is —$SO_3$—.

In certain embodiments, $L^2$ is —$NSO_2$—.

In certain embodiments, $L^2$ is —$SO_2$N.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(═O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$CO_2$($CR^1R^2R^3$).

In certain embodiments, $L^2$ is —$SO_2$(($C_1$-$C_{22}$)alkyl).

In certain embodiments, $L^2$ is —$SO_2$(($C_6$)aryl).

In certain embodiments, Q is CH.

In certain embodiments, Q is O.

In certain embodiments, Q is S.

In certain embodiments, Q is NH.

In certain embodiments, Q is a disulfide bond.

In certain embodiments, m is 0.

In certain embodiments, m is 1.

In certain embodiments, m is 2.

In certain embodiments, m is 3.

In certain embodiments, m is 4.

In certain embodiments, m is 5.

In certain embodiments, m is 6.

In certain embodiments, m is 7.

In certain embodiments, m is 8.

In certain embodiments, m is 9.

In certain embodiments, m is 10.

In certain embodiments, m is 11.

In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

In certain embodiments, the LNP lipid has the following structure:

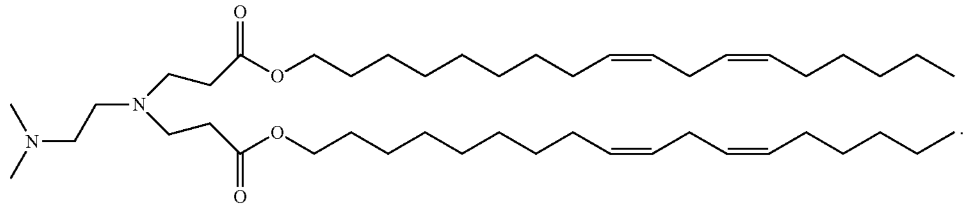 [SMILES: CCCCC/C=C\C/C=C\CCCCCCCCOC(=O)CCN(CCC(=O)OCCCCCCCC/C=C\C/C=C\CCCCC)CCN(C)C]

In certain embodiments, the LNP lipid has the following structure:

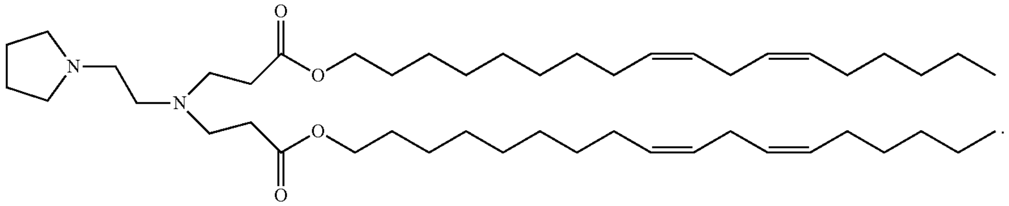 [SMILES: CCCCC/C=C\C/C=C\CCCCCCCCOC(=O)CCN(CCC(=O)OCCCCCCCC/C=C\C/C=C\CCCCC)CCN1CCCC1]

In certain embodiments, the LNP lipid has the following structure:

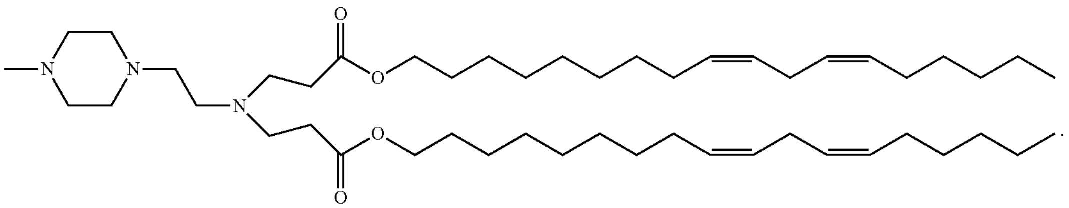 [SMILES: CCCCC/C=C\C/C=C\CCCCCCCCOC(=O)CCN(CCC(=O)OCCCCCCCC/C=C\C/C=C\CCCCC)CCN1CCN(C)CC1]

In certain embodiments, the LNP lipid has the following structure:
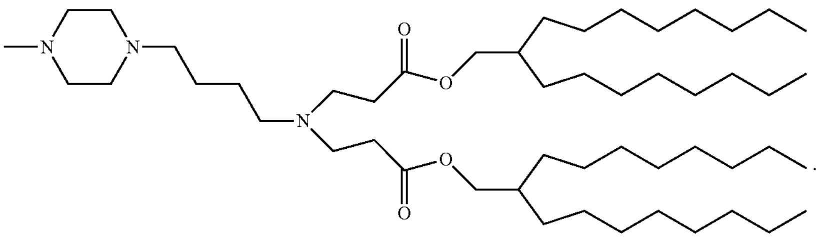 [SMILES: CCCCCCCCC(CCCCCCCC)COC(=O)CCN(CCCCN1CCN(C)CC1)CCC(=O)OCC(CCCCCCCC)CCCCCCCC]
In certain embodiments, the LNP lipid has the following structure:
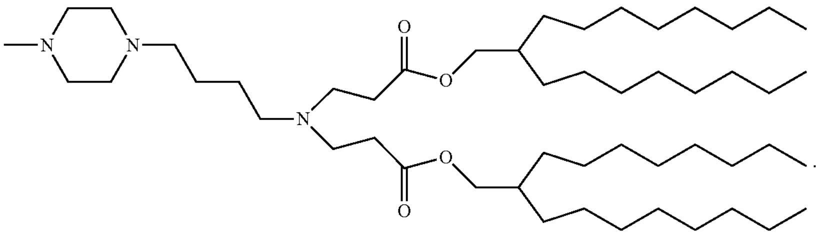 [SMILES: CCCCCCCCC(CCCCCCCC)COC(=O)CCN(CCCCN1CCN(C)CC1)CCC(=O)OCC(CCCCCCCC)CCCCCCCC]
In certain preferred embodiments, the LNP lipid has the following structure:
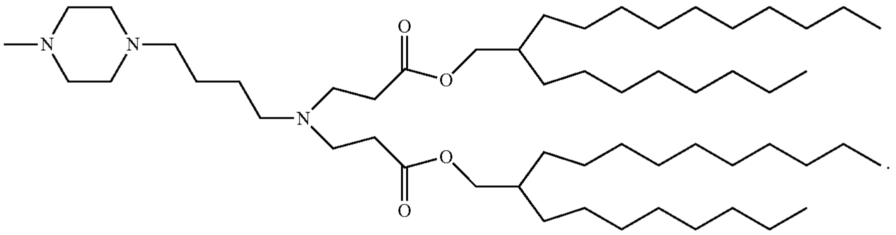 [SMILES: CCCCCCCCCCC(CCCCCCCC)COC(=O)CCN(CCCCN1CCN(C)CC1)CCC(=O)OCC(CCCCCCCC)CCCCCCCCCC]
In certain preferred embodiments, the LNP lipid has the following structure:
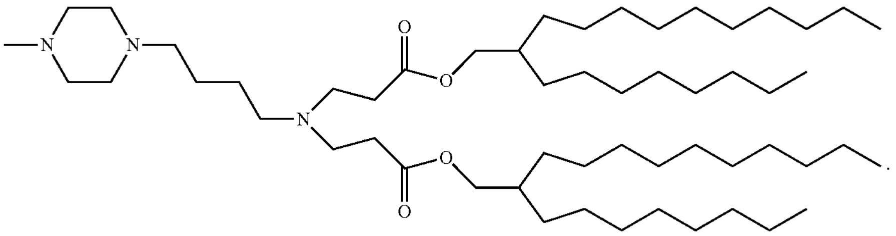 [SMILES: CCCCCCCCCCC(CCCCCCCC)COC(=O)CCN(CCCCN1CCN(C)CC1)CCC(=O)OCC(CCCCCCCC)CCCCCCCCCC]

In certain preferred embodiments, the LNP lipid has the following structure:

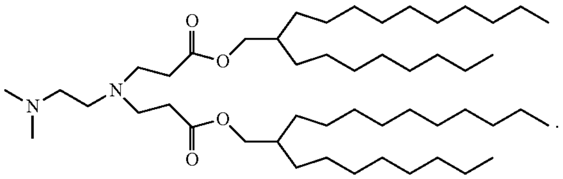 [SMILES: CCCCCCCCCCC(CCCCCCCC)COC(=O)CCN(CCC(=O)OCC(CCCCCCCC)CCCCCCCCCC)CCN(C)C]

In certain preferred embodiments, the LNP lipid has the following structure:

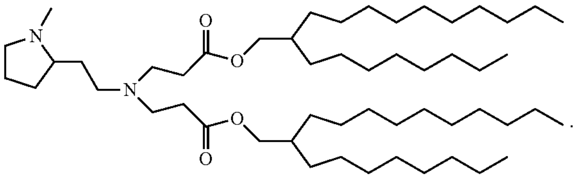 [SMILES: CCCCCCCCCCC(CCCCCCCC)COC(=O)CCN(CCC(=O)OCC(CCCCCCCC)CCCCCCCCCC)CCC1CCCN1C]

In certain preferred embodiments, the LNP lipid has the following structure:

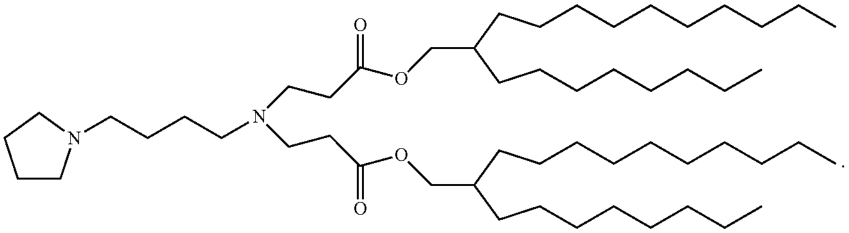 [SMILES: CCCCCCCCCCC(CCCCCCCC)COC(=O)CCN(CCCCN1CCCC1)CCC(=O)OCC(CCCCCCCC)CCCCCCCCCC]

In certain preferred embodiments, the LNP lipid has the following structure:

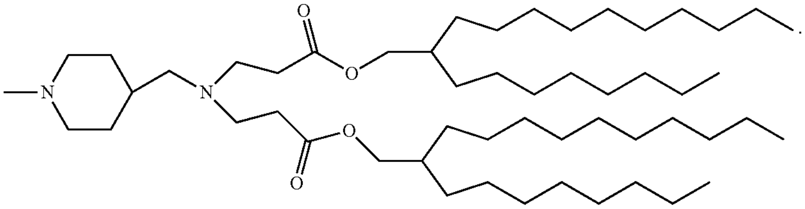

In certain embodiments, the LNP lipids are selected from the structures in Table 2 below:

TABLE 2

| Lipid | Structure | pKa, ACD |
|---|---|---|
| DL-C2/C2-DMA | 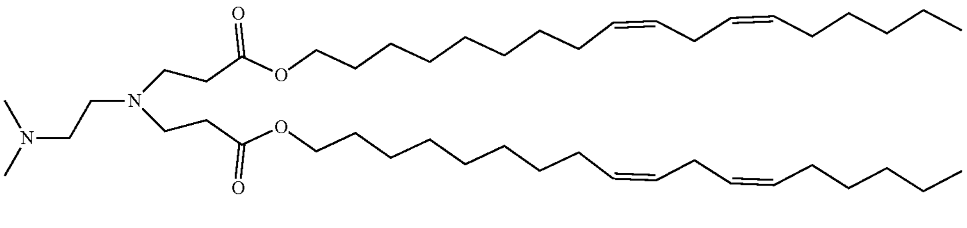 [SMILES: CCCCC/C=C\C/C=C\CCCCCCCCOC(=O)CCN(CCC(=O)OCCCCCCCC/C=C\C/C=C\CCCCC)CCN(C)C] | 8.4, 3.9 |
| DL-C2/C2-Pyr | 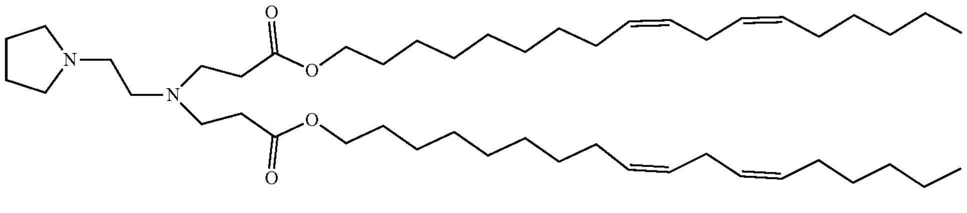 [SMILES: CCCCC/C=C\C/C=C\CCCCCCCCOC(=O)CCN(CCC(=O)OCCCCCCCC/C=C\C/C=C\CCCCC)CCN1CCCC1] | 8.6, 5.9 |

TABLE 2-continued

| Lipid | Structure | pKa, ACD |
|---|---|---|
| DL-C2/C2-PipZ | 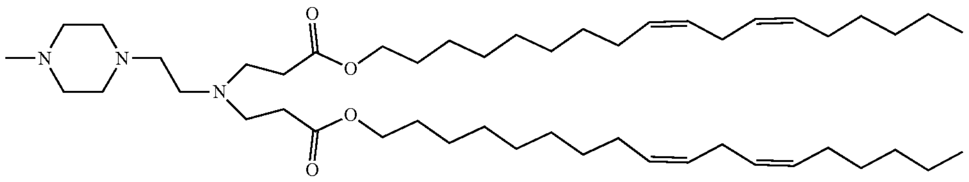 [SMILES: CCCCC/C=C\C/C=C\CCCCCCCCOC(=O)CCN(CCC(=O)OCCCCCCCC/C=C\C/C=C\CCCCC)CCN1CCN(C)CC1] | 7.6, 7.3, 2.4 |
| BOD-C2/C4-PipZ | 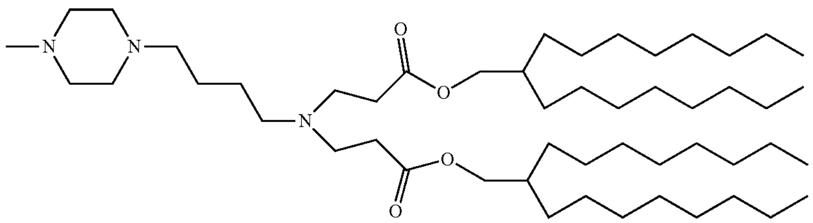 [SMILES: CCCCCCCCC(CCCCCCCC)COC(=O)CCN(CCCCN1CCN(C)CC1)CCC(=O)OCC(CCCCCCCC)CCCCCCCC] | 7.8, 7.7, 4.1 |
| BOD-C2/C2-PipZ | 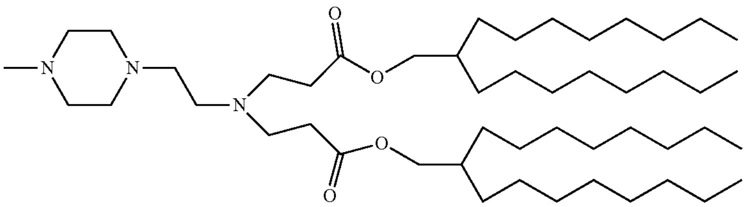 [SMILES: CCCCCCCCC(CCCCCCCC)COC(=O)CCN(CCC(=O)OCC(CCCCCCCC)CCCCCCCC)CCN1CCN(C)CC1] | 7.6, 7.3, 2.4 |

In another embodiment, the invention encompasses Ionizable Lipids of the Invention of Formula V:

Formula V

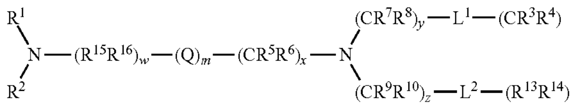

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryl oxy, optionally substituted $C_7$-$C_{10}$ aryl alkyl; optionally substituted $C_5$-$C_{10}$ heteroarylalkyl group, optionally substituted amine; or $R^1$ and $R^2$ can together form cycloalkyl or heterocycloalkyl ring, wherein if Q is S or O the $R^1$ attached to the S or O is an electron pair;

wherein each $R^3$, $R^4$, $R^{13}$, and $R^{14}$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, $R^{10}$, $R^{15}$ and $R^{16}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of w, x, y, and z is independently an integer from 0-10;

wherein each Q is independently an atom selected from 0, NH, S, or a disulfide bond;

wherein each of m is an integer from 0-4, preferably 0, 1, or 2; and wherein each of $L^1$ and $L^2$ is independently selected from the group consisting of —C(═O)—; OC(═O)—; —OC(═O)O—; —C(═O)O—; —C(═O)O(CR$^6$R$^7$)$_m$; —NH—C(═O)—; —C(═O)NH—; —SO—, —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)NR$^1$—; —NHC(═O)O—; —OC(═O)NR$^1$—; —C(═O)R$^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(═O)O—$C_1$-$C_{22}$ alkyl.

In a preferred embodiment, $R^3$ is substituted or unsubstituted —C(═O)O—$C_1$-$C_{22}$ alkenyl.

In a preferred embodiment, $R^3$ is substituted or unsubstituted —C(═O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(═O)O—$C_1$-$C_{22}$ alkyl.

In a preferred embodiment, $R^4$ is substituted or unsubstituted —C(═O)O—$C_1$-$C_{22}$ alkenyl.

In a preferred embodiment, $R^4$ is substituted or unsubstituted —C(═O)O—$C_1$-$C_{22}$ alkynyl.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, x is 0.

In certain embodiments, x is 1.

In certain embodiments, x is 2.

In certain embodiments, x is 3.

In certain embodiments, x is 4.

In certain embodiments, x is 5.

In certain embodiments, x is 6.

In certain embodiments, x is 7.

In certain embodiments, x is 8.

In certain embodiments, x is 9.

In certain embodiments, x is 10.

In certain embodiments, x is 11.

In certain embodiments, x is 12.

In certain embodiments, x is 13.

In certain embodiments, x is 14.

In certain embodiments, x is 15.

In certain embodiments, x is 16.

In certain embodiments, x is 17.

In certain embodiments, x is 18.

In certain embodiments, x is 19.

In certain embodiments, x is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(═O)—.

In certain embodiments, $L^1$ is —OC(═O)O—.

In certain embodiments, $L^1$ is —NH—C(═O)—.

In certain embodiments, $L^1$ is —SO—.

In certain embodiments, $L^1$ is —$SO_2$—.

In certain embodiments, $L^1$ is OC(═O).

In certain embodiments, $L^1$ is —C(═O)O—.

In certain embodiments, $L^1$ is —C(═O)NH—.

In certain embodiments, $L^1$ is —$SO_3$—.

In certain embodiments, $L^1$ is —$NSO_2$—.

In certain embodiments, $L^1$ is —$SO_2N$.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(═O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —C(═O)O($CR^1R^2R^3$)

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(═O)—.

In certain embodiments, $L^2$ is —OC(═O)O—.

In certain embodiments, $L^2$ is —NH—C(═O)—.

In certain embodiments, $L^2$ is —SO—.

In certain embodiments, $L^2$ is —$SO_2$—.

In certain embodiments, $L^2$ is OC(═O).

In certain embodiments, $L^2$ is —C(═O)O—.

In certain embodiments, $L^2$ is —C(═O)NH—.

In certain embodiments, $L^2$ is —$SO_3$—.

In certain embodiments, $L^2$ is —$NSO_2$—.

In certain embodiments, $L^2$ is —$SO_2N$.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(═O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2((C_6)$aryl).

In certain embodiments, $L^2$ is —$SO_2((C_1\text{-}C_{22})$alkyl).

In certain embodiments, $L^2$ is —$SO_2((C_6)$aryl).

In certain embodiments, Q is CH.

In certain embodiments, Q is O.

In certain embodiments, Q is S.

In certain embodiments, Q is NH.

In certain embodiments, Q is a disulfide bond.

In certain embodiments, m is 0.

In certain embodiments, m is 1.

In certain embodiments, m is 2.

In certain embodiments, m is 3.

In certain embodiments, m is 4.

In certain embodiments, m is 5.

In certain embodiments, m is 6.

In certain embodiments, m is 7.

In certain embodiments, m is 8.

In certain embodiments, m is 9.

In certain embodiments, m is 10.

In certain embodiments, m is 11.

In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

In another embodiment, the invention encompasses Ionizable Lipids of the Invention of Formula VI:

Formula VI

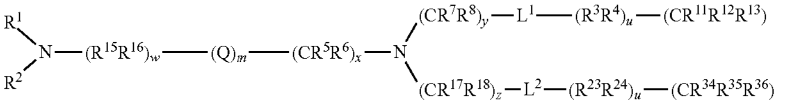

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryl oxy, optionally substituted $C_7$-$C_{10}$ aryl alkyl; optionally substituted $C_5$-$C_{10}$ heteroarylalkyl group, optionally substituted amine; or 10 and $R^2$ can together form cycloalkyl or heterocycloalkyl ring, wherein if Q is S or O the $R^1$ attached to the S or O is an electron pair;

wherein each $R^3$, $R^4$, $R^{23}$ and $R^{24}$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^{11}$, $R^{12}$, $R^{13}$, $R^{17}$, $R^{18}$, $R^{34}$, $R^{35}$, $R^{36}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, x, y, and z is independently an integer from 0-20;

wherein each Q is independently an atom selected from O, NH, S, or a disulfide bond;

wherein each of m is an integer from 0-4, preferably 0, 1, or 2; and wherein each of $L^1$ and $L^2$ is independently selected from the group consisting of —C(═O)—; OC(═O)—; —OC(═O)O—; —C(═O)O—; —C(═O)O(CR$^6$R$^7$)$_m$; —NH—C(═O)—; —C(═O)NH—; —SO—, —$SO_2$—; —$SO_3$—; —$NSO_2$—; —$SO_2$N—; —NH$((C_1\text{-}C_8)$alkyl); —N$((C_1\text{-}C_8)$alkyl$)_2$; —NH$((C_6)$aryl); —N$((C_6)$aryl$)_2$; —NHC(═O)NH—; —NHC(═O)O—; —OC(═O)NH—; —NHC(═O)NR$^1$—; —NHC(═O)O—; —OC(═O)NR$^1$—; —C(═O)R$^1$—; —CO$((C_1\text{-}C_8)$alkyl); —CO$((C_6)$aryl); —$CO_2((C_1\text{-}C_8)$alkyl); —$CO_2((C_6)$aryl); —$SO_2((C_1\text{-}C_8)$alkyl); and —$SO_2((C_6)$aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(═O)O—$C_1$-$C_{22}$ alkyl.

In a preferred embodiment, $R^3$ is substituted or unsubstituted —C(═O)O—$C_1$-$C_{22}$ alkenyl.

In a preferred embodiment, $R^3$ is substituted or unsubstituted —C(═O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(═O)O—$C_1$-$C_{22}$ alkyl.

In a preferred embodiment, $R^4$ is substituted or unsubstituted —C(═O)O—$C_1$-$C_{22}$ alkenyl.

In a preferred embodiment, $R^4$ is substituted or unsubstituted —C(═O)O—$C_1$-$C_{22}$ alkynyl.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{12}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.
In certain embodiments, w is 18.
In certain embodiments, w is 19.
In certain embodiments, w is 20.
In certain embodiments, x is 0.
In certain embodiments, x is 1.
In certain embodiments, x is 2.
In certain embodiments, x is 3.
In certain embodiments, x is 4.
In certain embodiments, x is 5.
In certain embodiments, x is 6.
In certain embodiments, x is 7.
In certain embodiments, x is 8.
In certain embodiments, x is 9.
In certain embodiments, x is 10.
In certain embodiments, x is 11.
In certain embodiments, x is 12.
In certain embodiments, x is 13.
In certain embodiments, x is 14.
In certain embodiments, x is 15.
In certain embodiments, x is 16.
In certain embodiments, x is 17.
In certain embodiments, x is 18.
In certain embodiments, x is 19.
In certain embodiments, x is 20.
In certain embodiments, y is 0.
In certain embodiments, y is 1.
In certain embodiments, y is 2.
In certain embodiments, y is 3.
In certain embodiments, y is 4.
In certain embodiments, y is 5.
In certain embodiments, y is 6.
In certain embodiments, y is 7.
In certain embodiments, y is 8.
In certain embodiments, y is 9.
In certain embodiments, y is 10.
In certain embodiments, y is 11.
In certain embodiments, y is 12.
In certain embodiments, y is 13.
In certain embodiments, y is 14.
In certain embodiments, y is 15.
In certain embodiments, y is 16.
In certain embodiments, y is 17.
In certain embodiments, y is 18.
In certain embodiments, y is 19.
In certain embodiments, y is 20.
In certain embodiments, z is 0.
In certain embodiments, z is 1.
In certain embodiments, z is 2.
In certain embodiments, z is 3.
In certain embodiments, z is 4.
In certain embodiments, z is 5.
In certain embodiments, z is 6.
In certain embodiments, z is 7.
In certain embodiments, z is 8.
In certain embodiments, z is 9.
In certain embodiments, z is 10.
In certain embodiments, z is 11.
In certain embodiments, z is 12.
In certain embodiments, z is 13.
In certain embodiments, z is 14.
In certain embodiments, z is 15.
In certain embodiments, z is 16.
In certain embodiments, z is 17.
In certain embodiments, z is 18.
In certain embodiments, z is 19.
In certain embodiments, z is 20.

In certain embodiments $L^1$ is a bond.
In certain embodiments, $L^1$ is —C(═O)—.
In certain embodiments, $L^1$ is —OC(═O)O—.
In certain embodiments, $L^1$ is —NH—C(═O)—.
In certain embodiments, $L^1$ is —SO—.
In certain embodiments, $L^1$ is —$SO_2$—.
In certain embodiments, $L^1$ is OC(═O).
In certain embodiments, $L^1$ is —C(═O)O—.
In certain embodiments, $L^1$ is —C(═O)NH—.
In certain embodiments, $L^1$ is —$SO_3$—.
In certain embodiments, $L^1$ is —$NSO_2$—.
In certain embodiments, $L^1$ is —$SO_2N$.
In certain embodiments, $L^1$ is —NH(($C_1$-$C_{22}$)alkyl).
In certain embodiments, $L^1$ is —N(($C_1$-$C_8$)alkyl)$_2$.
In certain embodiments, $L^1$ is —NH(($C_6$)aryl).
In certain embodiments, $L^1$ is —N(($C_6$)aryl)$_2$.
In certain embodiments, $L^1$ is dioxolopyrrolidine-dione.
In certain embodiments, $L^1$ is —C(═O)$R^1$—.
In certain embodiments, $L^1$ is —CO(($C_1$-$C_{22}$)alkyl).
In certain embodiments, $L^1$ is —CO(($C_6$)aryl).
In certain embodiments, $L^1$ is —$CO_2$(($C_1$-$C_{22}$)alkyl).
In certain embodiments, $L^1$ is —$CO_2$(($C_6$)aryl).
In certain embodiments, $L^1$ is —C(═O)O($CR^1R^2R^3$)
In certain embodiments, $L^1$ is —$SO_2$(($C_1$-$C_{22}$)alkyl).
In certain embodiments, $L^1$ is —$SO_2$(($C_6$)aryl).
In certain embodiments $L^2$ is a bond.
In certain embodiments, $L^2$ is —C(═O)—.
In certain embodiments, $L^2$ is —OC(═O)O—.
In certain embodiments, $L^2$ is —NH—C(═O)—.
In certain embodiments, $L^2$ is —SO—.
In certain embodiments, $L^2$ is —$SO_2$—.
In certain embodiments, $L^2$ is OC(═O).
In certain embodiments, $L^2$ is —C(═O)O—.
In certain embodiments, $L^2$ is —C(═O)NH—.
In certain embodiments, $L^2$ is —$SO_3$—.
In certain embodiments, $L^2$ is —$NSO_2$—.
In certain embodiments, $L^2$ is —$SO_2N$.
In certain embodiments, $L^2$ is —NH(($C_1$-$C_{22}$)alkyl).
In certain embodiments, $L^2$ is —N(($C_1$-$C_8$)alkyl)$_2$.
In certain embodiments, $L^2$ is —NH(($C_6$)aryl).
In certain embodiments, $L^2$ is —N(($C_6$)aryl)$_2$.
In certain embodiments, $L^2$ is dioxolopyrrolidine-dione.
In certain embodiments, $L^2$ is —C(═O)$R^1$—.
In certain embodiments, $L^2$ is —CO(($C_1$-$C_{22}$)alkyl).
In certain embodiments, $L^2$ is —CO(($C_6$)aryl).
In certain embodiments, $L^2$ is —$CO_2$(($C_1$-$C_{22}$)alkyl).
In certain embodiments, $L^2$ is —$CO_2$(($C_6$)aryl).
In certain embodiments, $L^2$ is —$SO_2$(($C_1$-$C_{22}$)alkyl).
In certain embodiments, $L^2$ is —$SO_2$(($C_6$)aryl).
In certain embodiments, Q is CH.
In certain embodiments, Q is O.
In certain embodiments, Q is S.
In certain embodiments, Q is NH.
In certain embodiments, Q is a disulfide bond.
In certain embodiments, m is 0.
In certain embodiments, m is 1.
In certain embodiments, m is 2.
In certain embodiments, m is 3.
In certain embodiments, m is 4.
In certain embodiments, m is 5.
In certain embodiments, m is 6.
In certain embodiments, m is 7.
In certain embodiments, m is 8.
In certain embodiments, m is 9.
In certain embodiments, m is 10.
In certain embodiments, m is 11.
In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

In another embodiment, the invention encompasses Ionizable Lipids of the Invention of Formula VII:

Formula VII

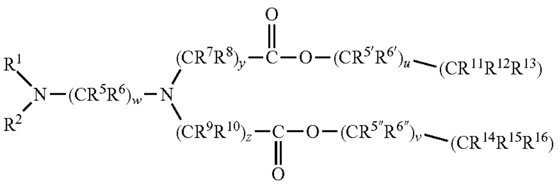

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycloalkyl or heteroaryl ring;

wherein each $R^5$, $R^6$, $R^{5'}$, $R^{6'}$, $R^{5''}$, and $R^{6''}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each $R^5$, $R^6$, $R^7$, $R^8$, $R^9$, $R^{10}$, $R^{11}$, $R^{12}$, $R^{13}$, $R^{14}$, $R^{15}$, and $R^{16}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, y, and z is independently an integer from 0-20;

wherein each Q is independently an atom selected from 0, NH, S, or a disulfide bond; and wherein each of $L^1$ and $L^2$ is independently selected from the group consisting of —C(=O)—; OC(=O)—; —OC(=O)O—; —C(=O)O—; —C(=O)O$(CR^5R^6R^7)_m$; —NH—C(=O)—; —C(=O)NH—; —SO—; —$SO_2$—; —$SO_3$—; —$NSO_2$—; —$SO_2N$—; —NH(($C_1$-$C_8$)alkyl); —N(($C_1$-$C_8$)alkyl$)_2$; —NH(($C_6$)aryl); —N(($C_6$)aryl$)_2$; —NHC(=O)NH—; —NHC(=O)O—; —OC(=O)NH—; —NHC(=O)$NR^1$—; —NHC(=O)O—; —OC(=O)$NR^1$—; —C(=O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(═O)—.

In certain embodiments, $L^1$ is —OC(═O)O—.

In certain embodiments, $L^1$ is —NH—C(═O)—.

In certain embodiments, $L^1$ is —SO—.

In certain embodiments, $L^1$ is —$SO_2$—.

In certain embodiments, $L^1$ is OC(═O).

In certain embodiments, $L^1$ is —C(═O)O—.

In certain embodiments, $L^1$ is —C(═O)NH—.

In certain embodiments, $L^1$ is —$SO_3$—.

In certain embodiments, $L^1$ is —$NSO_2$—.

In certain embodiments, $L^1$ is —$SO_2N$.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(═O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(═O)—.

In certain embodiments, $L^2$ is —OC(═O)O—.

In certain embodiments, $L^2$ is —NH—C(═O)—.

In certain embodiments, $L^2$ is —SO—.

In certain embodiments, $L^2$ is —$SO_2$—.

In certain embodiments, $L^2$ is OC(═O).

In certain embodiments, $L^2$ is —C(═O)O—.

In certain embodiments, $L^2$ is —C(═O)NH—.

In certain embodiments, $L^2$ is —$SO_3$—.

In certain embodiments, $L^2$ is —$NSO_2$—.

In certain embodiments, $L^2$ is —$SO_2N$.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(═O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$CO_2$($CR^1R^2R^3$).

In certain embodiments, $L^2$ is —$SO_2$(($C_1$-$C_{22}$)alkyl).

In certain embodiments, $L^2$ is —$SO_2$(($C_6$)aryl).

In certain embodiments, Q is CH.

In certain embodiments, Q is O.

In certain embodiments, Q is S.

In certain embodiments, Q is NH.

In certain embodiments, Q is a disulfide bond.

In certain embodiments, m is 0.

In certain embodiments, m is 1.

In certain embodiments, m is 2.

In certain embodiments, m is 3.

In certain embodiments, m is 4.

In certain embodiments, m is 5.

In certain embodiments, m is 6.

In certain embodiments, m is 7.

In certain embodiments, m is 8.

In certain embodiments, m is 9.

In certain embodiments, m is 10.

In certain embodiments, m is 11.

In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

In another embodiment, the invention encompasses Ionizable Lipids of the Invention of Formula VIII:

Formula VIII

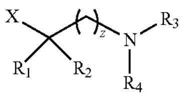

wherein $R_1$ and $R_2$ are each independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl or optionally substituted $C_5$-$C_{10}$ heteroarylalkyl group;

$R_3$ and $R_4$ are each independently optionally substituted $C_{10}$-$C_{22}$ alkyl, optionally substituted $C_{10}$-$C_{22}$ alkenyl, optionally substituted $C_{10}$-$C_{22}$ alkynyl, or together for a 3-7 membered heterocycloalkyl or heteroaryl ring;

X is OH, or $NR_1R_2$; and

Z is an integer from 0 to 5.

In certain embodiments, the ionizable lipid of Formula VIII is selected from the group consisting of:

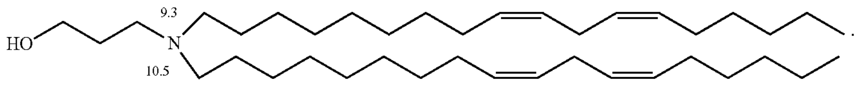

In certain embodiments, the ionizable lipid of Formula VIII is selected from the group consisting of:

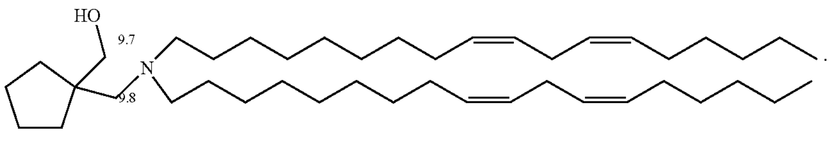 [SMILES: CCCCC/C=C\C/C=C\CCCCCCCCN(CCCCCCCC/C=C\C/C=C\CCCCC)CC1(CO)CCCC1]

In certain embodiments, the ionizable lipid of Formula VIII is selected from the group consisting of:

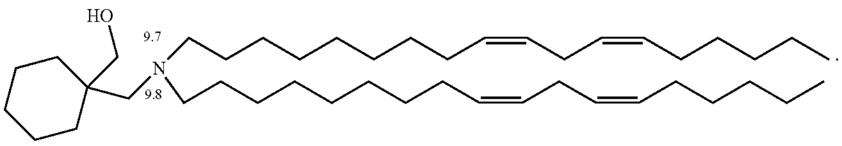 [SMILES: CCCCC/C=C\C/C=C\CCCCCCCCN(CCCCCCCC/C=C\C/C=C\CCCCC)CC1(CO)CCCCC1]

In certain embodiments, the ionizable lipid of Formula VIII is selected from the group consisting of:

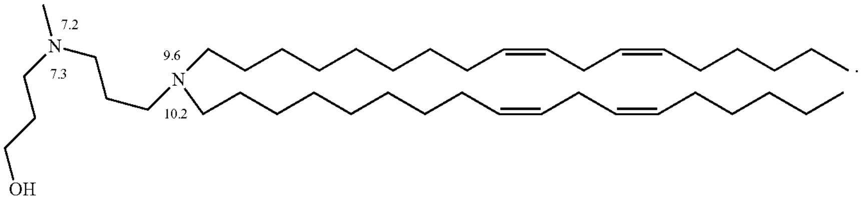 [SMILES: CCCCC/C=C\C/C=C\CCCCCCCCN(CCCCCCCC/C=C\C/C=C\CCCCC)CCCN(C)CCCO]

In certain embodiments, the ionizable lipid of Formula VIII is selected from the group consisting of:

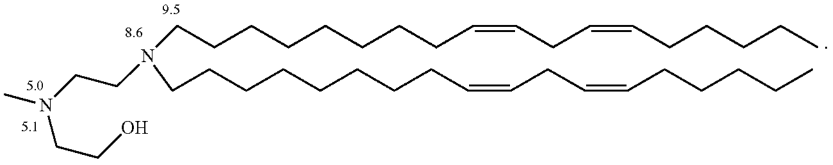 [SMILES: CCCCC/C=C\C/C=C\CCCCCCCCN(CCCCCCCC/C=C\C/C=C\CCCCC)CCN(C)CCO]

In certain embodiments, the ionizable lipid of Formula VIII is selected from the group consisting of:

6

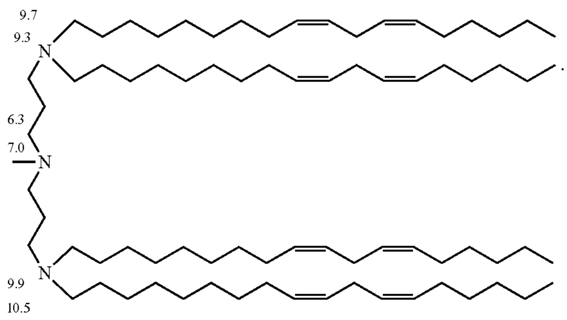

In certain embodiments, the ionizable lipid of Formula VIII is selected from the group consisting of:

7

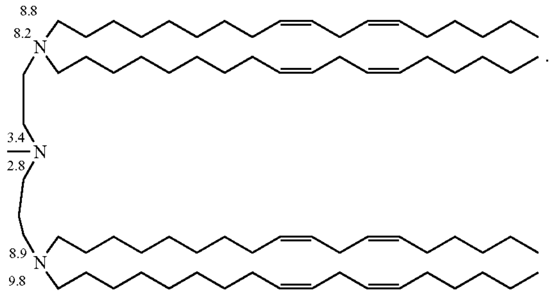

In certain embodiments, the ionizable lipid of Formula VIII is selected from the group consisting of:

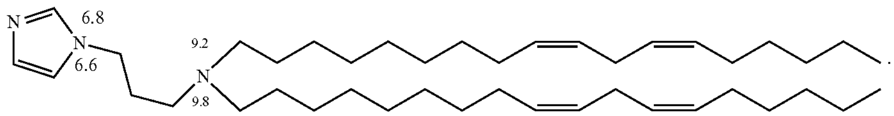 [SMILES: CCCCC/C=C\C/C=C\CCCCCCCCN(CCCCCCCC/C=C\C/C=C\CCCCC)CCCn1ccnc1]

In another embodiment, the invention encompasses Ionizable Lipids of the Invention of Formula IX:

Formula IX

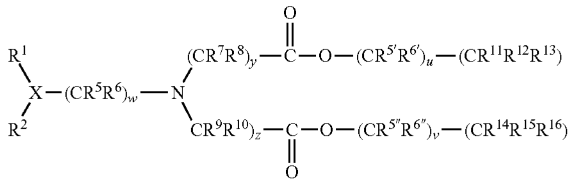

wherein each $R^1$ and each $R^2$ is independently selected from the group consisting of H, an electron pair, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycloalkyl or heteroaryl ring;

wherein each $R^5$, $R^6$, $R^{5'}$, $R^{6'}$, $R^{5''}$, and $R^{6''}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each $R^5$, $R^6$, $R^7$, $R^8$, $R^9$, $R^{10}$, $R^{11}$, $R^{12}$, $R^{13}$, $R^{14}$, $R^{15}$, and $R^{16}$ is is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, y, and z is independently an integer from 0-20;

wherein X is O, S, or N; and wherein each of $L^1$ and $L^2$ is independently selected from the group consisting of —C(═O)—; OC(═O)—; —OC(═O)O—; —C(═O)O—; —C(═O)O$(CR^5R^6R^7)_m$; —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl$)_2$; —NH(($C_6$)aryl); —N(($C_6$)aryl$)_2$; —NHC(═O)NH—; —NHC(═O)O—; —OC(═O)NH—; —NHC(═O)NR$^1$—; —NHC(═O)O—; —OC(═O)NR'—; —C(═O)R'—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(=O)—.

In certain embodiments, $L^1$ is —OC(=O)O—.

In certain embodiments, $L^1$ is —NH—C(=O)—.

In certain embodiments, $L^1$ is —SO—.

In certain embodiments, $L^1$ is —$SO_2$—.

In certain embodiments, $L^1$ is OC(=O).

In certain embodiments, $L^1$ is —C(=O)O—.

In certain embodiments, $L^1$ is —C(=O)NH—.

In certain embodiments, $L^1$ is —$SO_3$—.

In certain embodiments, $L^1$ is —$NSO_2$—.

In certain embodiments, $L^1$ is —$SO_2N$.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(═O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(═O)—.

In certain embodiments, $L^2$ is —OC(═O)O—.

In certain embodiments, $L^2$ is —NH—C(═O)—.

In certain embodiments, $L^2$ is —SO—.

In certain embodiments, $L^2$ is —$SO_2$—.

In certain embodiments, $L^2$ is OC(═O).

In certain embodiments, $L^2$ is —C(═O)O—.

In certain embodiments, $L^2$ is —C(═O)NH—.

In certain embodiments, $L^2$ is —$SO_3$—.

In certain embodiments, $L^2$ is —$NSO_2$—.

In certain embodiments, $L^2$ is —$SO_2$N.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(═O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$CO_2$($CR^1R^2R^3$).

In certain embodiments, $L^2$ is —$SO_2$(($C_1$-$C_{22}$)alkyl).

In certain embodiments, $L^2$ is —$SO_2$(($C_6$)aryl).

In certain embodiments, Q is CH.

In certain embodiments, X is O.

In certain embodiments, X is S.

In certain embodiments, X is N.

In certain embodiments, m is 0.

In certain embodiments, m is 1.

In certain embodiments, m is 2.

In certain embodiments, m is 3.

In certain embodiments, m is 4.

In certain embodiments, m is 5.

In certain embodiments, m is 6.

In certain embodiments, m is 7.

In certain embodiments, m is 8.

In certain embodiments, m is 9.

In certain embodiments, m is 10.

In certain embodiments, m is 11.

In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

"naLNP" as used herein refers to a nucleic acid payload carrying lipid nanoparticle made in accordance with the methods disclosed herein. naLNPs have significantly greater potency relative to a Reference LNP.

The "Reference LNP of refLNP" as used herein refers a lipid nanoparticle formed with one or more LNP lipids using a Reference LNP Manufacturing Method. In one embodiment, the Reference LNP is a 50-100 nm diameter LNP including a the nucleic acid and 4 lipids: an ionizable lipid with an amine group (50%), a zwitterionic helper lipid—1,2-distearoyl-sn-glycero-3-phosphocholine (DSPC) (10%), cholesterol (38.5%), and a pegylated lipid—1,2-dimyristoyl-rac-glycero-3-methoxypolyethylene glycol-2000 (DMG-PEG2000) (1.5%) (mole ratios in parentheses). The hydrophilic DMG-PEG forms the shell of the LNP.

"Reference LNPs" are defined by the fact that they are generated by a "Reference LNP Manufacturing Method."

In one embodiment, the "Reference Manufacturing Method" may be summarized as follows:

- Nucleic Acid Solution: Prepare mRNA at one reference nucleic acid concentration of less than 0.20 mg/ml in a buffer at one concentration and one pH, i.e. 50 mM citrate pH 5 or 25 mM sodium acetate pH 4, or 10-50 mM citrate pH 4.
- Lipid Solution: Prepare lipid mix in ethanol at one reference lipid concentration corresponding to the desired NP ratio (5.67) and/or lipid/mRNA weight ratio (10:1 to 30:1)
- Assemble refLNPs: Combining portions of the Nucleic Acid Solution and portions of the Lipid Solution result in a single mixing solution in a buffer.
- Dialyze refLNPs in the mixing solution to physiological pH.
- Measure refLNP size using light scattering
- Measure RNA encapsulation in the refLNPs using the Ribogreen assay
- Select refLNPs that have high encapsulation >70% and diameters from 50-100 nm "Mixing" as used herein preferably refers to turbulent mixing ("T-mix"), vortex mixing ("V-mix"), microfluidic mixing, or both. See for example mixing described in U.S. Pub. No. 20200306191.

In one embodiment, the Reference LNP Manufacturing Method is that described in Hassett et al., Mol. Ther.—Nucleic Acids 2019, 15, 1-11. In another embodiment, the Reference Manufacturing Method" is as described in U.S. App. Ser. No. 20190032087. In one embodiment, the reference method includes: (a) introducing a first stream comprising a therapeutic agent (e.g., nucleic acid) in a first solvent into a microchannel; wherein the microchannel has a first region adapted for flowing one or more streams introduced into the microchannel and a second region for mixing the contents of the one or more streams; (b) introducing a second stream comprising LNP-forming materials (e.g., reference LNP lipids) in a second solvent in the microchannel to provide first and second streams flowing under laminar flow conditions, wherein the lipid particle-forming materials comprise an ionizable lipid, and wherein the first and second solvents are the same or are not the same; (c) flowing the one or more first streams and the one or more second streams from the first region of the microchannel into the second region of the microchannel; and (d) mixing of the contents of the one or more first streams and the one or more second streams in the second region of the microchannel to provide a third stream comprising lipid particles with encapsulated therapeutic agents.

The contents of the first and second streams can be mixed by chaotic advection in microfluidic channels or by nanoprecipation in a T-mixer.

In one embodiment, mixing the contents of the one or more first streams and the one or more second streams comprises varying the concentration or relative mixing rates of the one or more first streams and the one or more second streams. In the above embodiment, unlike known methods, the method does not include a dilution after mixing.

To further stabilize the third stream containing the lipid particles with encapsulated therapeutic agents, the method can, but need not further include, comprising diluting the third stream with an aqueous buffer. In one embodiment, diluting the third stream includes flowing the third stream and an aqueous buffer into a second mixing structure.

In another embodiment, the aqueous buffer comprising lipid particles with encapsulated therapeutic agents is dialyzed to reduce the amount of the second solvent.

The first stream includes a therapeutic agent in a first solvent. Suitable first solvents include solvents in which the therapeutic agents are soluble and that are miscible with the second solvent. Suitable first solvents include aqueous buffers. Representative first solvents include citrate and acetate buffers. The first solvent can be water alone if the second solvent includes a protonation agent such as HCl to protonate the ionizable lipid.

The second stream includes lipid particle-forming materials in a second solvent. Suitable second solvents include solvents in which the ionizable lipids are soluble and that are miscible with the first solvent. Suitable second solvents include 1, 4-dioxane, tetrahydrofuran, acetone, acetonitrile, dimethyl sulfoxide, dimethylformamide, acids, and alcohols. Representative second solvents include aqueous ethanol at >50%.

In some embodiments, the lipid particles of the invention are advantageously formed in a microfluidic process that utilizes relatively rapid mixing and high flow rates. The rapid mixing provide lipid particles having the advantageous properties noted above including size, homogeneity, and encapsulation efficiency. Mixing rates used in the practice of the method of the invention range from about 100 .mu.sec to about 10 msec. Representative mixing rates include from about 1 to about 5 msec. Whereas hydrodynamic flow focusing methods operate at relatively low flow rates (e.g., 5 to 100 .mu.L/minute) with relatively low lipid volumes, the method of the invention operates at relatively high flow rates and relatively high lipid volumes. In certain embodiments, for methods that incorporate a single mixing region (i.e., mixer), the flow rate is about 1 to about 100 mL/min. For methods of the invention that utilize mixer arrays (e.g., 10 mixers), flow rates of 40 mL/minute are employed (for 100 mixers, flow rate 400 mL/min). Thus, the methods of the invention can be readily scaled to provide quantities of lipid particles necessary for demanding production requirements.

The inventive LNP compositions disclosed herein can include one or more biologically active agents including, but not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, and enzymatic nucleic acids. Various methods for loading biologically active agents into lipid compositions, such as liposomes and lipid nanoparticles are available in the art, including both passive and active loading methods. The exact method used may be chosen based on multiple factors that include, but are not limited to, e.g., the biologically active agent to be loaded, the storage method to be used once loaded, the size of the resulting particle, and the dosage regimen contemplated. Methods include, e.g., mechanical mixing of the drug and lipids at the time the liposomes are formed or reconstituted, dissolving all components in an organic solvent and concentrating them into a dry film, forming a pH or ion gradient to draw the active agent into the interior of the liposome, creating a transmembrane potential, and ionophore mediated loading. See, e.g., PCT Publication No. WO 95/08986, U.S. Pat. Nos. 5,837,282; 5,837,282, and 7,811,602.

The term "nucleic acids" refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate. In some embodiments, "nucleic acid" includes antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid" (messenger RNA, mRNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occurring or synthetic, and may be chemically modified. In one embodiment the biologically active agent is an RNAi agent, short interfering nucleic acid (siNA), short interfering RNA (siRNA), double-stranded RNA (dsRNA), micro-RNA (miRNA), or a short hairpin RNA (shRNA) molecule. In one embodiment the biologically active agent is a RNAi agent useful for mediating RNA interference (RNAi).

As used herein, the term "nucleic acid" is also meant to include any oligonucleotide or polynucleotide. Fragments containing up to 50 nucleotides are generally termed oligonucleotides, and longer fragments are called polynucleotides. In particular embodiments, oligonucleotides of the present invention are 20-50 nucleotides in length. In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases. Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose. The nucleic acid that is present in a lipid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, and triplex-forming oligonucleotides.

In another embodiment the biologically active agent is an mRNA. In one embodiment, the nucleic acid is an mRNA encoding a COVID-19 protein or peptide.

As used herein, the terms "Pyr" "Pyrd" and "PyrD" are used interchangeably and refer to a pyridine or pyridyl substituent.

"Potency" as referred to herein refers to the ability of an LNP to deliver a nucleic acid payload to a cell or tissue, where the LNP is internalized into the cell (or cells in a tissue) and released from the endosome to the cytoplasm whereupon the nucleic acid payload is released from the lipid and becomes bioavailable. Potency may be measured any number of ways known to those of skill in the art. For example, it may be measured in terms of cell uptake, nucleic acid payload transcription, nucleic acid payload translation, or production of a polypeptide encoded by the nucleic acid payload. Where an LNP's nucleic acid payload is meant to function in an gene expression inhibitory manner such as in for example in RNAi, LNP potency may be measured in terms of target gene 'knock down' through reduction of the target gene's transcription rate, the length of the gene target's mRNA transcripts half-life, or translation of the target gene's mRNA transcript. Additional assays for measuring potency depend on measuring LNP immunogenicity and LNP systemic distribution. All such assays and their permutations are well known in the art.

On one embodiment an experiment measuring LNP potency is conducted in parallel to a reference LNP. Such experiments may use a standardized nucleic acid payload such as for example a reporter gene. A reporter gene (often simply reporter) is a gene that researchers attach to a regulatory sequence of another gene of interest in bacteria, cell culture, animals, or plants. Such genes are called reporters because the characteristics they confer on organisms expressing them are easily identified and measured, or because they are selectable markers. Reporter genes may be used as an indication of whether a certain gene has been taken up by or expressed in the cell or organism population. Typical reporters genes are lacZ, cat, gfp, rfp, luc, which encode β-galactosidase, Chloramphenicol acetyltransferase, Green fluorescent protein, Red fluorescent protein, Luciferase enzyme, respectively, which can be used in respective histochemical, acetylation, fluorescent, spectrophotometric, and bioluminescence assays. All such assays and their permutations are well known in the art.

In one embodiment, LNP Potency is measured by Luciferase reporter activity in vitro or in vivo at a known dose or several doses. Relative LNP potency is determined by Luciferase activity measure in vitro or in vivo. See also for example, U.S. Pat. No. 10,221,127.

LNP Potency may also be measured in terms of a desired biological reaction to the nucleic acid payload including for example, a therapeutic or prophylactic effect or an impact on a mechanism of action leading thereto. In some embodiments, LNP potency is measured by the ability of an LNP carrying an mRNA encoding an immunogen, e.g., a polypeptide that to induces the immune system to make a secreted cognate IgG antibody after administration.

"Increase in LNP Potency" refers to the extent to which the inventive naLNP has greater potency than a Reference LNP. In certain embodiments, the inventive LNPs disclosed herein have an increase in LNP Potency that is about or at least a factor of 1.25, 1.50, 1.75, 2, 3, 4, 5, 6, 7, 8, 9, 10, 11, 12, 13, 14, 15, 16, 17, 18, 19, 20, 21, 22, 23, 24, 25, 26, 27, 28, 29 30, 35, 40, 45, 50, 60, 70, 80, 90, 100, 150, 200, 400, 500, 750, 1000, 10,000 greater than a Reference LNP in the same assay delivering the same nucleic acid cargo.

"Organic solvents" as used herein refers to a type of volatile organic compound (VOC). VOCs are organic chemicals which vaporize at room temperature and are typical in the art for dissolving certain materials and substances in the manufacture of pharmaceutical products. Organic solvents in manufacturing are typically used: aromatic compounds, e.g. benzene and toluene, alcohols, e.g., methanol or ethanol, esters and ethers, ketones, e.g., acetone, amines, nitrated and halogenated hydrocarbons.

As used herein, "Nitrogen-Phosphate or 'NP'" ratio is defined as the molar ratio of the ionizable lipid to the moles of phosphate on the nucleic acid backbone. It should be noted that that the moles are total moles in the Mixture Solution versus concentrations in the initial Nucleic Acid or Lipid Solutions which can be mixed at different volume ratios. Of note is the case of more than one amine per ionizable lipid. Often only one amine will be protonated under mixing conditions so that NP ratio is most naturally defined with one amine per ionizable lipid even when there are more than one, since electrostatic binding involves only the charged groups. However certain ionizable lipids can have two or more amines charged during mixing.

As used herein a "lipid/nucleic acid weight ratio" is weight ratios that may be used instead of NP ratio. Conversion between NP ratio and weight ratios involves molar mass of the ionizable lipid and of the nucleic acid divided by the number of bases for the molar mass per phosphate.

In one embodiment, the amount of nucleic acid is represented by the LNP mole ratio of the amine on the ionizable lipid to the phosphate groups on the nucleic acid backbone and is typically about 3 to about 6. In one embodiment, the pKa of the LNP is in the about 6 to about 7 range corresponding to the pH in the early endosome. A link between the pKa of ionizable lipid in the LNP and gene silencing efficiency has shown that an LNP pKa in the range of about 6 to about 7 produced more silencing for the ionizable lipid DLinDMA and was associated with promoting lipid structures that could disrupt the membrane of the endosome. The pKa of the LNP may be measured using the pH-dependence of fluorescence enhancement of the anionic dye TNS.

As used herein "cholesterol" refers to a biologically active organic compound with four rings arranged in a specific molecular configuration. The steroid core structure is typically composed of seventeen carbon atoms, bonded in four "fused" rings: three six-member cyclohexane rings (rings A, B and C) and one five-member cyclopentane ring (the D ring). Steroids vary by the functional groups attached to this four-ring core and by the oxidation state of the rings. Sterols are forms of steroids with a hydroxy group at position three and a skeleton derived from cholestane. Steroids can also be more radically modified, such as by changes to the ring structure, for example, cutting one of the rings. Cutting Ring B produces secosteroids one of which is vitamin D3. Examples include the lipid cholesterol, the sex hormones estradiol and testosterone, [4]:10-19 and the anti-inflammatory drug dexamethasone. Many of steroids are found in plants, animals and fungi. Steroids are preferably manufactured in cells from the sterols lanosterol (opisthokonts) or cycloartenol (plants). Lanosterol and cycloartenol are derived from the cyclization of the triterpene squalene. In some embodiments, the LNPs compositions disclosed herein contain a cholesterol derivative which is for example, dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3.beta.-[N—(N'N'-dimethylaminoethyl)carbamoyl cholesterol (DC-Chol), 24(S)-hydroxycholesterol, 25-hydroxycholesterol, 25(R)-27-hydroxycholesterol, 22-oxacholesterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5.alpha.-cholest-7-en-3.beta.-ol, 3,6,9-trioxaoctan-1-ol-cholesteryl-3e-ol, dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol, or fecosterol, or a salt or ester thereof. In some embodiments, the cholesterol or cholesterol derivative is cholesterol, cholesterol succinic acid, cholesterol sulfate, cholesterol hemisuccinate, cholesterol phthalate, cholesterol phosphate, cholesterol valerate, cholesterol acetate, cholesteryl oleate, cholesteryl linoleate, cholesteryl myristate, cholesteryl palmitate, cholesteryl arachidate, cholesteryl phosphorylcholine, and sodium cholate. Other exemplary steroid are disclosed in U.S. Publication No. 20200129445.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the LNP.

II. Methods of LNP Manufacture

The prior art has heretofore focused on the identity and structure of the ionizable lipid as the main parameter for determining LNP potency. Secondary parameters including discerning the influence of the other lipids like DSPE vs DSPC or different cholesterol analogues for cholesterol and the mole ratios of the 4 lipids.

Moreover, the prior art shows that the skilled artisan believed that buffer concentration should be high enough and pH low enough to highly protonate the ionizable lipid to encapsulate a maximum amount of mRNA (close to 100%) and that this will maximize LNP potency.

Furthermore, the prior art teaches that working with mixing solutions having high concentrations of nucleic acid and lipids leads to a range of technical problems including insolubility, undesired precipitation, poor mixing, generation of non-uniform LNP size and heterogenous nucleic acid encapsulation rates. Moreover, nucleic acid solutions, particularly reporter mRNA solutions having a concentration greater than 1 mg/ml are not commercially available. Even if high concentration solutions were commercially available, the performance of hundreds of high concentration mixes to test various concentrations would be cost prohibitive. In view of these prevailing assumptions, scientists involved in LNP manufacture focused on using mixing solutions having low concentrations of nucleic acid and lipid so as to avoid high testing costs, unwanted precipitation, LNP size heterogeneity, and LNP nucleic acid encapsulation heterogeneity, believing that mRNA dosages could be later adjusted by concentrating thusly made LNPs in solution during downstream processing steps. This does not however resolve the basic problem that this prior art procedure results in LNPs of low potency.

For example, heretofore, 0.5 ml of high concentration mRNA solution at a concentration of >2 mg/ml would have costed at least $1,500 per mix. To arrive at the naLNPs disclosed herein, a technician would have utilized >100 mixes at a cost of at least $150,000 merely for preparation of the Nucleic Acid Solution disclosed herein not accounting other costs. Aside from the expense of generating high concentration nucleic acid solutions, high concentrations were heretofore thought to cause insolubility, aggregation, precipitation and/or poor mixing.

Moreover, the Applicants determined that the use of high nucleic acid concentrations resulted in lower encapsulation rates, e.g., about 70% in a naLNP versus about 90% in the refLNP. However, the inventors surprisingly found that even with substantially lower encapsulation rates, the naLNPs disclosed herein had greater LNP potency than refLNPs.

Applicants have developed a highly controlled and reproducible in vitro FLuc assay that allows for the determination of naLNP potency by comparing the results of experiments under identical conditions (cell numbers, etc), internal recombinant quantilum standards, and the same refLNP from experiment to experiment.

The Applicants further submit that it was heretofore unknown that a non-protonated fraction of ionizable lipids increases endosomal release and/or a looser binding of mRNA for better endosomal release, and/or a more peripheral distribution of ionizable lipid or nucleic acid, e.g., mRNA, in the LNP.

Disclosed herein, however, is the unexpected finding that LNP potency is strongly affected by the absolute concentration of nucleic acid:lipid mix while maintaining constant NP or weight ratios.

The data provided herein demonstrate that both the absolute concentrations of nucleic acid at the time of mixing and buffer concentrations and pH strongly influence LNP potency and that these two influences interact. A significant variable in mediating this interaction is the protonation level of the ionizable lipid during mixing that should not be maximized to maximize encapsulation as previously believed. Rather, protonation level of the ionizable lipid should be at a level that maximizes LNP potency in accordance with the methods disclosed herein.

In general embodiments, the invention encompasses a enhanced method to manufacture a lipid nanoparticle, wherein the lipid nanoparticle delivery efficiency depends on ionizable lipid ionization and alkyl tail structure.

In certain embodiments, the LNPs with high delivery efficiency are critically important in the success of the current COVD-19 mRNA vaccines from BioNTech/Pfizer and Moderna. In certain embodiments, the LNPs in these vaccines contain 4 lipids, an ionizable lipid, the helper lipid DSPC, cholesterol, and a PEG lipid that self-assemble with the mRNA sequence into a nanoparticle with diameter of ~60 nm1. In certain embodiments, the protonated form of the ionizable lipid electrostatically binds the anionic phosphate backbone of the mRNA to encapsulate it in the LNP while DSPC forms a peripheral bilayer that contains the PEG-lipid tail with the hydrophilic PEG domain facing the aqueous medium. In certain embodiments, the role of the ionizable lipid is to facilitate endosomal release by protonating as the endosomal pH drops below 7 and then interacting with the endosomal membrane to open it and release the mRNA. In certain embodiments, the ionizable lipid in the LNP has a pKa in the 5 to 7.4 range to release the RNA prior to endosome-lysosome fusion. In certain embodiments, the alkyl tails of the ionizable lipid also need to be incompatible with the endosomal bilayer to destabilize it.

This latter requirement is achieved with the current ionizable lipids by a branched structure that is cone-shaped.

In certain embodiments, the invention also encompasses methods to rationally design LNP ionization for endosomal release by predicting the pKa of the LNP from the structure of the ionizable lipid. In certain embodiments, the pKa of the LNP is lower than the pKa of ionizable lipid due to the difference in proton solvation energy in the LNP compared to the aqueous phase. In certain embodiments, this allowed the rational design of a novel ionizable lipid (C2C4) that has 3 protonatable nitrogens providing increased endosomal protonation and mRNA translation. In certain embodiments, the C24LNP was found to be 10× superior to the MC3 LNP, the standard reference LNP, in terms of immunogenicity towards an mRNA-encoded SARS-CoV-2 spike protein, and resulted in greater protection against infection. In certain embodiments, the LNP rational design approach was expanded by developing models that use ionizable lipid structure to predict LNP ionization and the ability of the ionizable lipid to disrupt the endosomal membrane and release the mRNA.

In certain embodiments, the delivery efficiency depends on the mRNA-LNP manufacturing process. In certain embodiments, the mRNA-LNPs are manufactured using a microfluidic or a larger scale T-mixer through a self-assembly process where the 4 lipids in ethanol are mixed rapidly with the mRNA that is in a low pH buffer. In certain embodiments, the formation of the mRNA LNP occurs through electrostatic binding of the protonated cationic ionizable lipid with the anionic mRNA phosphate backbone followed by the lipids segregating from the aqueous phase to form the nanoparticle that is stabilized by the hydrophilic PEG interface. In certain embodiments, the many factors may be changed in the manufacturing process including but not limited to, the absolute and relative concentrations of the lipids and mRNA, the type of buffer, its concentration and pH, the ratio of the organic to aqueous phases, and the flow rate. We have discovered that increasing the absolute concentrations of the lipids and mRNA jointly, without changing relative concentrations, can increase the delivery efficiency of the resulting mRNA LNP typically by 4× (FIG. 34). In certain embodiments, the invention encompasses methods to increase these mixing concentrations, for example, by 6× to 75 mM total lipid and 1.5 mg/ml mRNA resulting in a 4× boost in delivery efficiency in vitro and in vivo at identical doses (FIG. 34B). By measuring the zeta potential increase from pH 7.4 to 5, we found these more potent LNPs to exhibit a 2 fold greater increase in zeta potential compared to those assembled under the standard conditions (FIG. 34C). Without being bound byt theory, this result indicates that the improved potency is partly due to a greater level of unprotonated ionizable lipid in the LNPs that increases endosomal protonation. In certain embodiments, the mRNA LNP assembly in a buffer-free environment. In certain embodiments, rather than use a low pH buffer in the mRNA solution to protonate the ionizable lipid upon mixing, the ionizable lipid is preprotonated by adding HCl to the lipid mix prior to mixing with mRNA in buffer-free water. In certain embodiments, TLC-MS and $^1$H NMR was used to verify that lipid degradation did not occur. In certain embodiments, using C24 ionizable lipid that has 3 nitrogens, and adding 0.25 protons per ionizable lipid, we protonated, on average, 1 nitrogen on every 4 lipids so that the protonated nitrogens are at a 1:1 ratio with the phosphates of mRNA (NP ratio was 4). In certain embodiments, the buffer-free assembly method produced yet higher potency in vivo, by 3× by IVIS for both IM and IV administration, compared to using a buffer, both using the high lipid and mRNA mixing concentrations. In certain embodiments, the buffer-free, high absolute lipid/mRNA concentration assembly method can therefore create LNPs that are 10× more potent than current manufacturing methods that use low concentrations and low pH buffers, yet does not change the composition of the final formulation. In certain embodiments, the preprotonation method more accurately targets a specific level of ionizable lipid protonation versus the buffer which requires convection and diffusion to contact and protonate the lipid that is an inherently fast and inhomogeneous process. In certain embodiments, the manufacturing process achieves high potency LNPs that are easily implemented at all manufacturing scales and with both microfluidic and T-mixing geometries.

In certain embodiments, the method of manufacture includes the steps of protonating the ionizable lipid prior to mixing with buffer free mRNA. In certain embodiments, the ionizable lipid can be protonated with HCL, DCL, weak acids, ethanol, water, or any solvent described herein. In certain embodiments, the protonation occurs alone prior to mixing with the other lipids or with an entire lipid mix.

In certain embodiments, hydrochloric acid is used for direct protonation of the ionizable lipid stock itself prior to the mixing with the other lipids into a lipid mix or to protonate the ionizable lipid once is already mixed in the lipid mix. This buffer-free pre-protonated ionizable lipid in the lipid mix is mixed after with the buffer-free mRNA solution. In certain embodiments, 100% protonation would mean that for each mole for ionizable lipid in solution, one mole of HCL will be added to protonate the nitrogen in the ionizable lipid. To protonate multiple nitrogen in multiproteic ionizable lipids, the corresponding moles of HCL are added to protonate each nitrogen.

In general embodiments, improved methods for making naLNPs disclosed herein may be summarized as follows:

Nucleic Acid Solution: Provide nucleic acids at a Nucleic Acid concentration in a buffer at a certain buffer concentration and at a certain Nucleic Acid Solution pH.

Lipid Solution: Provide lipids in an organic solvent at a Lipid Solution lipid concentration corresponding to the desired: i) Nitrogen-Phosphate ("NP") ratio; or ii) lipid/nucleic acid weight ratio.

Assemble naLNPs: Combine portions of the Nucleic Acid Solution and Lipid Solution into a Mixing Solution having a mixing buffer concentration and pH.

The skilled artisan will understand the certain steps in the inventive methods need not be performed in a certain order while other steps must be performed before others. Moreover, various parties might perform various steps of the overall method.

In some embodiments, the portions of the Nucleic Acid Solution and the Lipid Solution in the Mixing Solution are in volume ratio are about or at least 0.1:1, 0.2:1, 0.3:1, 0.4:1, 0.5:1, 0.6:1, 0.7:1, 0.8:1, 0.9:1, 1:1, 2:1, 3:2, 3:1, 4:1, 4:3, 5:1, 5:3, 5:4, 6:1, 6:5, 7:1, 8:1, 9:10, 10:1, 11:1, 12:1, 13:1, 14:1, 15:1, 16:1, 17:1, 18:1, 19:1, and 20:1.

LNPs made according to the method above may then be further processed for use according to methods well known in the art. In some embodiments, such further processing involves one or more of the following:

Bringing naLNPs to physiological pH, e.g., via dialysis between about 4 to about 24 hours, or alternatively via the use of tangential flow filtration and exchange buffers such as Repligen's KrosFlo® KR2i or KMPi Systems or Cytiva's ÄKTA Flux Tangential Flow Filtration System.

Measuring naLNP size, e.g., by light scattering.

Measuring RNA encapsulation, e.g., by Ribogreen assay.

Selecting naLNPs that have high encapsulation, e.g., at least or about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent encapsulation efficiency; or an average diameter at least or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 175, 200, 250, 300, 350, 400, 450, 500 nM; or having a minimum diameter of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nM and a maximum diameter of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 175, 200, 250, 300, 350, 400, 450, 500 nM, respectively.

In some embodiments, the Nucleic Acid Solution contains nucleic acids at a nucleic acid concentration of about or at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 milligrams/ml.

In some embodiments, the nucleic acids are present in about or at least 1, 2, 3, 4, 5, 6, 7, 8, 9, 10, 11, 12, 13, 14, 15, 16, 17, 18, 19, 20, or more molecular species each of which encode at about or at least 1, 2, 3, 4, 5, 6, 7, 8, 9, 10, 11, 12, 13, 14, 15, 16, 17, 18, 19, 20, or more open reading frames.

In some embodiments, the nucleic acid molecule can be about or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 50, 100, 200, 300, 400, 500, 750, 800, 1000, 2000, 3000, 4000, 5000, 6000, 7000, 8000, 9000, 10000, 11000, 15000, 20000, 30000, 40000, 50000, 75000, 100000 nucleotides in length.

In some embodiments, the Nucleic Acid Solution contains a buffer at a concentration of about or at least 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 175, 200, 250, 300, 350, 400, 450, 500 mM.

In some embodiments the buffer is salt buffer. In some embodiments, the buffering agent is citric acid, acetic acid, phosphate, and borate. In some embodiments, the buffer is potassium, magnesium, or sodium acetate. In other embodiments, the buffer may be citrate, MES, Histidine, ADA, ACES, PIPES, MOPSO, BES, HEPES, DIPSO, TEA, AMPD, Gly-Gly, TAPS, HEPBS, AMPD, TABS, AMP, CAPSO, CAPS, CABS, CHES, PBS, SSC, TAE, TBE, or TE and the like. See for example, "Acetate Buffer (pH 3.6 to 5.6) Preparation." AAT Bioquest, Inc, 29 Sep. 2020. Other suitable buffers are shown in the table below:

pKa Value and Buffer Range

| effective pH range | pKa 25° C. | buffer |
|---|---|---|
| 1.2-2.6 | 1.97 | maleate (pK1) |
| 1.7-2.9 | 2.15 | phosphate (pK1) |
| 2.2-3.6 | 2.35 | glycine (pK1) |
| 2.2-6.5 | 3.13 | citrate (pK1) |
| 2.5-3.8 | 3.14 | glycylglycine (pK1) |
| 2.7-4.2 | 3.40 | malate (pK1) |
| 3.0-4.5 | 3.75 | formate |
| 3.0-6.2 | 4.76 | citrate (pK2) |
| 3.2-5.2 | 4.21 | succinate (pK1) |
| 3.6-5.6 | 4.76 | acetate |
| 3.8-5.6 | 4.87 | propionate |
| 4.0-6.0 | 5.13 | malate (pK2) |
| 4.9-5.9 | 5.23 | pyridine |
| 5.0-6.0 | 5.33 | piperazine (pK1) |
| 5.0-7.4 | 6.27 | cacodylate |
| 5.5-6.5 | 5.64 | succinate (pK2) |
| 5.5-6.7 | 6.10 | MES |
| 5.5-7.2 | 6.40 | citrate (pK3) |
| 5.5-7.2 | 6.24 | maleate (pK2) |
| 5.5-7.4 | 1.70, 6.04, 9.09 | histidine |
| 5.8-7.2 | 6.46 | bis-tris |
| 5.8-8.0 | 7.20 | phosphate (pK2) |
| 6.0-12.0 | 9.50 | ethanolamine |
| 6.0-7.2 | 6.59 | ADA |
| 6.0-8.0 | 6.35 | carbonate (pK1) |
| 6.1-7.5 | 6.78 | ACES |
| 6.1-7.5 | 6.76 | PIPES |
| 6.2-7.6 | 6.87 | MOPSO |
| 6.2-7.8 | 6.95 | imidazole |
| 6.3-9.5 | 6.30, 9.00 | BIS-TRIS propane |
| 6.4-7.8 | 7.09 | BES |
| 6.5-7.9 | 7.14 | MOPS |
| 6.8-8.2 | 7.48 | HEPES |
| 6.8-8.2 | 7.40 | TES |
| 6.9-8.3 | 7.60 | MOBS |
| 7.0-8.2 | 7.52 | DIPSO |
| 7.0-8.2 | 7.61 | TAPSO |
| 7.0-8.3 | 7.76 | triethanolamine (TEA) |
| 7.0-9.0 | 0.91, 2.10, 6.70,9.32 | pyrophosphate |
| 7.1-8.5 | 7.85 | HEPPSO |
| 7.2-8.5 | 7.78 | POPSO |
| 7.4-8.8 | 8.05 | tricine |
| 7.5-10.0 | 8.10 | hydrazine |
| 7.5-8.9 | 8.25 | glycylglycine (pK2) |
| 7.5-9.0 | 8.06 | Trizma (tris) |
| 7.6-8.6 | 8.00 | EPPS, HEPPS |
| 7.6-9.0 | 8.26 | BICINE |
| 7.6-9.0 | 8.30 | HEPBS |
| 7.7-9.1 | 8.40 | TAPS |
| 7.8-9.7 | 8.80 | 2-amino-2-methyl-1,3-propanediol (AMPD) |
| 8.2-9.6 | 8.90 | TABS |
| 8.3-9.7 | 9.00 | AMPSO |
| 8.4-9.6 | 9.06 | taurine (AES) |
| 8.5-10.2 | 9.23, 12.74, 13.80 | borate |
| 8.6-10.0 | 9.50 | CHES |
| 8.7-10.4 | 9.69 | 2-amino-2-methyl-1-propanol (AMP) |
| 8.8-10.6 | 9.78 | glycine (pK2) |
| 8.8-9.9 | 9.25 | ammonium hydroxide |
| 8.9-10.3 | 9.60 | CAPSO |
| 9.5-11.1 | 10.33 | carbonate (pK2) |
| 9.5-11.5 | 10.66 | methylamine |
| 9.5-9.8 | 9.73 | piperazine (pK2) |
| 9.7-11.1 | 10.40 | CAPS |
| | 12.33 | phosphate (pK3) |
| 10.0-11.4 | 10.70 | CABS |
| 10.5-12.0 | 11.12 | piperidine |

-continued

| Buffer Range alphabetically | | |
|---|---|---|
| buffer | pKa 25° C. | effective pH range |
| ACES | 6.78 | 6.1-7.5 |
| Acetate | 4.76 | 3.6-5.6 |
| ADA | 6.59 | 6.0-7.2 |
| ammonium hydroxide | 9.25 | 8.8-9.9 |
| AMP (2-amino-2-methyl-1-propanol) | 9.69 | 8.7-10.4 |
| AMPD (2-amino-2-methyl-1,3-propanediol) | 8.80 | 7.8-9.7 |
| AMPSO | 9.00 | 8.3-9.7 |
| BES | 7.09 | 6.4-7.8 |
| BICINE | 8.26 | 7.6-9.0 |
| bis-tris | 6.46 | 5.8-7.2 |
| BIS-TRIS propane | 6.30, 9.00 | 6.3-9.5 |
| borate | 9.23, 12.74, 13.80 | 8.5-10.2 |
| CABS | 10.70 | 10.0-11.4 |
| cacodylate | 6.27 | 5.0-7.4 |
| CAPS | 10.40 | 9.7-11.1 |
| CAPSO | 9.60 | 8.9-10.3 |
| carbonate (pK1) | 6.35 | 6.0-8.0 |
| carbonate (pK2) | 10.33 | 9.5-11.1 |
| CHES | 9.50 | 8.6-10.0 |
| citrate (pK1) | 3.13 | 2.2-6.5 |
| citrate (pK2) | 4.76 | 3.0-6.2 |
| citrate (pK3) | 6.40 | 5.5-7.2 |
| DIPSO | 7.52 | 7.0-8.2 |
| EPPS, HEPPS | 8.00 | 7.6-8.6 |
| ethanolamine | 9.50 | 6.0-12.0 |
| formate | 3.75 | 3.0-4.5 |
| glycine (pK1) | 2.35 | 2.2-3.6 |
| glycine (pK2) | 9.78 | 8.8-10.6 |
| glycylglycine (pK1) | 3.14 | 2.5-3.8 |
| glycylglycine (pK2) | 8.25 | 7.5-8.9 |
| HEPBS | 8.30 | 7.6-9.0 |
| HEPES | 7.48 | 6.8-8.2 |
| HEPPSO | 7.85 | 7.1-8.5 |
| histidine | 1.70, 6.04, 9.09 | 5.5-7.4 |
| hydrazine | 8.10 | 7.5-10.0 |
| imidazole | 6.95 | 6.2-7.8 |
| malate (pK1) | 3.40 | 2.7-4.2 |
| malate (pK2) | 5.13 | 4.0-6.0 |
| maleate (pK1) | 1.97 | 1.2-2.6 |
| maleate (pK2) | 6.24 | 5.5-7.2 |
| MES | 6.10 | 5.5-6.7 |
| methylamine | 10.66 | 9.5-11.5 |
| MOBS | 7.60 | 6.9-8.3 |
| MOPS | 7.14 | 6.5-7.9 |
| MOPSO | 6.87 | 6.2-7.6 |
| phosphate (pK1) | 2.15 | 1.7-2.9 |
| phosphate (pK2) | 7.20 | 5.8-8.0 |
| phosphate (pK3) | 12.33 | |
| piperazine (pK1) | 5.33 | 5.0-6.0 |
| piperazine (pK2) | 9.73 | 9.5-9.8 |
| piperidine | 11.12 | 10.5-12.0 |
| PIPES | 6.76 | 6.1-7.5 |
| POPSO | 7.78 | 7.2-8.5 |
| propionate | 4.87 | 3.8-5.6 |
| pyridine | 5.23 | 4.9-5.9 |
| pyrophosphate | 0.91, 2.10, 6.70, 9.32 | 7.0-9.0 |
| succinate (pK1) | 4.21 | 3.2-5.2 |
| succinate (pK2) | 5.64 | 5.5-6.5 |
| TABS | 8.90 | 8.2-9.6 |
| TAPS | 8.40 | 7.7-9.1 |
| TAPSO | 7.61 | 7.0-8.2 |
| taurine (AES) | 9.06 | 8.4-9.6 |
| TES | 7.40 | 6.8-8.2 |
| tricine | 8.05 | 7.4-8.8 |
| triethanolamine (TEA) | 7.76 | 7.0-8.3 |
| Trizma (tris) | 8.06 | 7.5-9.0 |

In some embodiments, the Nucleic Acid Solution is at a pH of about or at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14.

In some embodiments, the Lipid Solution contains the organic solvent is benzene, toluene, alcohols, e.g., methanol, esters, ethers, ketones, e.g., acetone, amines, nitrated and/or halogenated hydrocarbons; or a combination thereof. In one embodiment the organic solvent is ethanol. Preferred solvents are volatile, non-toxic, and/or acceptable for administration to humans in trace amounts.

In some embodiments, the Lipid Solution contains a one or more lipids at a total concentration of about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 175, 200, 250, 300, 350, 400, 450, 500, 750, 800, 1000 mM.

In some embodiments, Mixing Solution has a mixing concentration of nucleic acid of about or at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 milligrams/ml.

In some embodiments, Mixing Solution has a mixing total concentration of lipids of about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 175, 200, 250, 300, 350, 400, 450, 500, 750, 800, 1000 mM In some embodiments, Mixing Solution has a mixing buffer concentration of about or at least 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 175, 200, 250, 300, 350, 400, 450, 500 mM.

In some embodiments, a buffer, e.g., a sodium acetate buffer, concentration in the Mixing Solution is optimized to maximize potency at any particular mixing concentration. For example, Example 13 shows that at 1.5 mg/ml of mRNA in the Nucleic Acid Solution, LNP potency increases 44% relative to a Reference LNP when reducing sodium acetate from 50 mM to 25 mM. At an mRNA concentration of 0.25 mg/ml in the Nucleic Acid Solution, reducing sodium acetate concentration from 25 mM to 10 mM increases LNP potency about 2.2×. The increase in mixing concentration and the optimized reductions in buffer concentration lead to encapsulation efficiency of ~70% which is lower than typically obtained in prior art methods wherein encapsulation was erroneously maximized as in the Example 10 by lowering mixing concentration and increasing buffer concentration. The LNPs made according to the methods disclosed herein are unexpectedly and significantly more potent (e.g. 5-10×) than LNPs made according to the Reference LNP Manufacturing Methods despite having a slightly lower encapsulation efficiency (e.g. 60-80% vs 80-100%).

In some embodiments, the Mixing Solution is at a pH of about or at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14.

In some embodiments the desired "Nitrogen-Phosphate or 'NP'" ratio is about: 1:100, 1:75, 1:50, 1-25, preferably 2:10, more preferably 3:6.

In some embodiments the desired") lipid/nucleic acid weight ratio is about: 1:1 to 1000:1, preferably 5:1-100:1, more preferably 10:1-30:1.

Figure 1A:
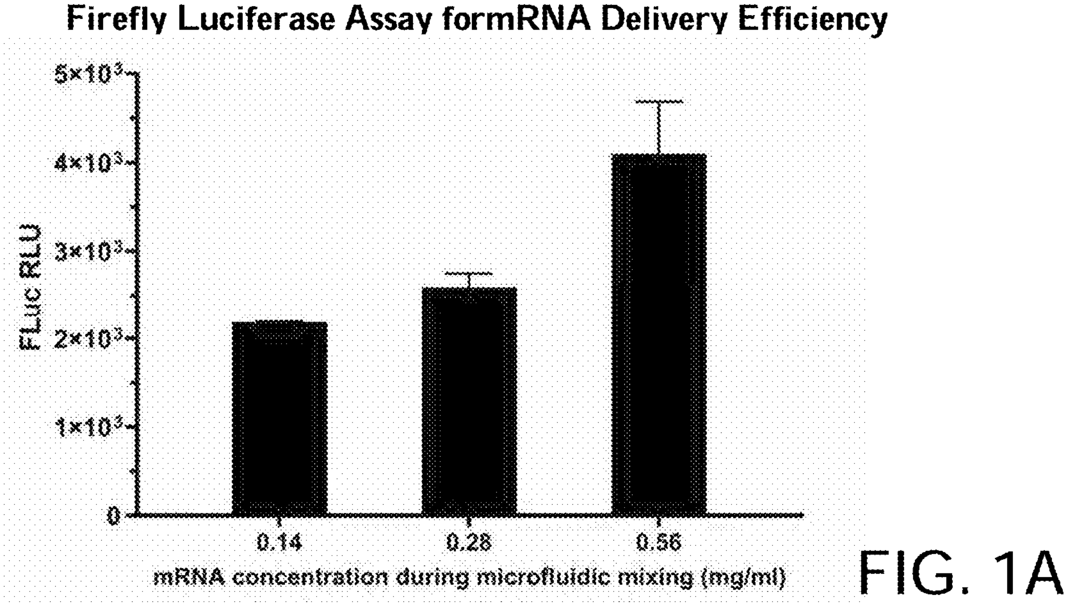
FIG. 1A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 1A correspond to procedure set forth in Example 1A.
Figure 1B:
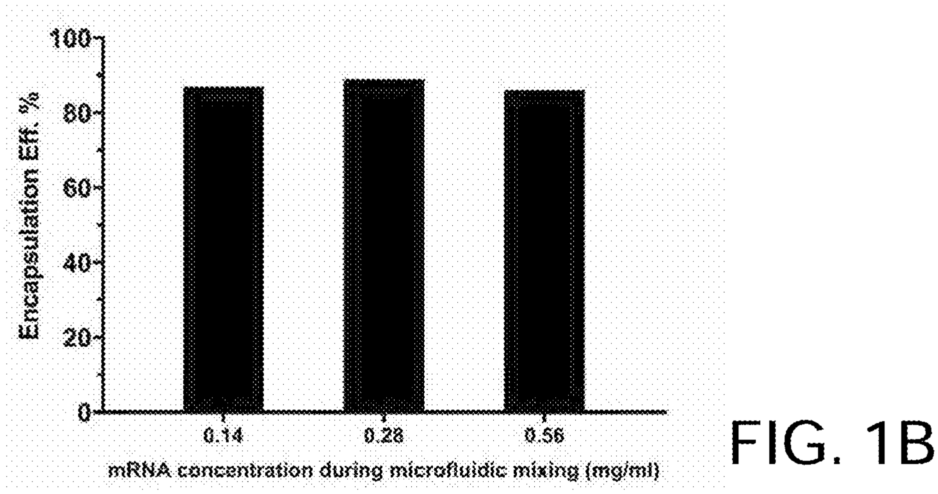
FIG. 1B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 1B correspond to procedure set forth in Example 1B.
Figure 1C:
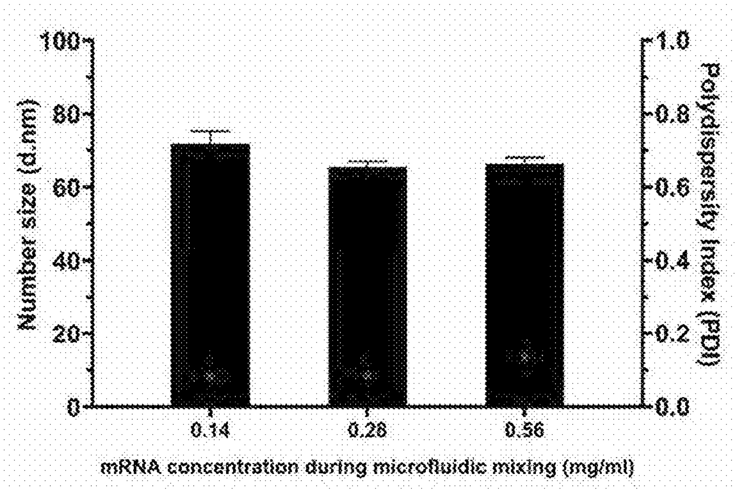
FIG. 1C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 1C correspond to procedure set forth in Example 1C.
Figure 2A:
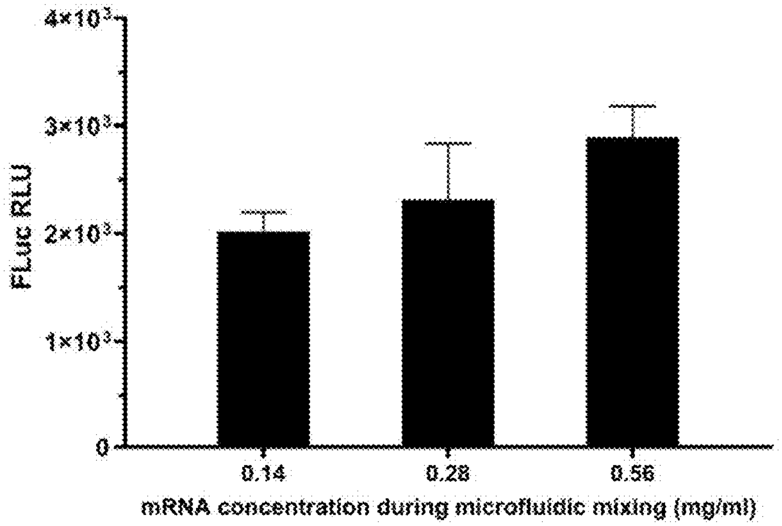
FIG. 2A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 2A correspond to procedure set forth in Example 2A.
Figure 2B:
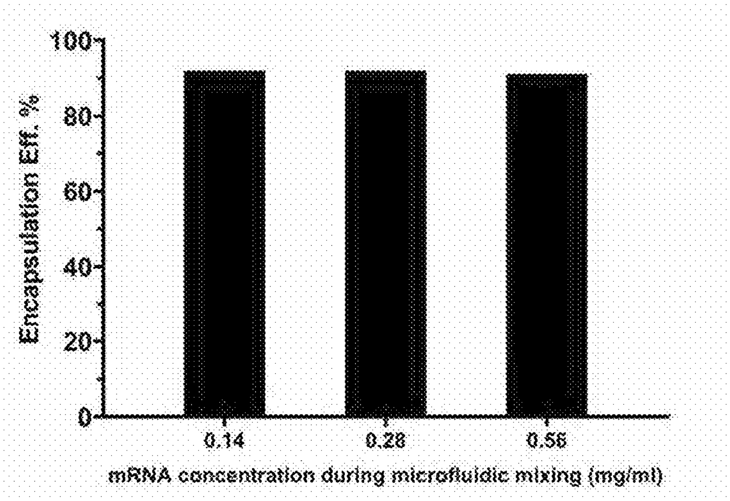
FIG. 2B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 2B correspond to procedure set forth in Example 2B.
Figure 2C:
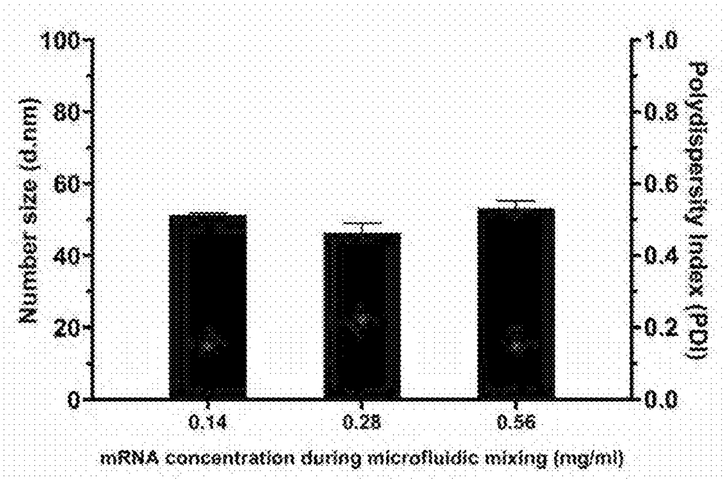
FIG. 2C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 2C correspond to procedure set forth in Example 2C.
Figure 3A:
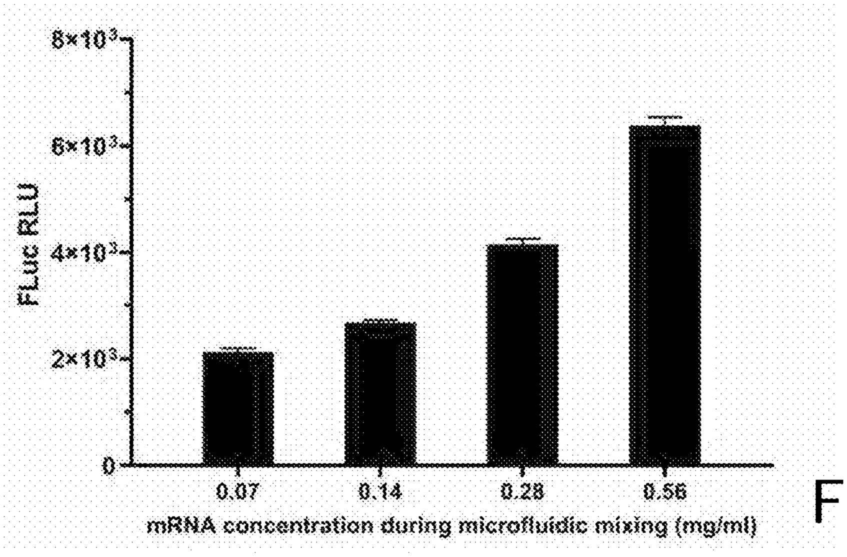
FIG. 3A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 3A correspond to procedure set forth in Example 3A.
Figure 3B:
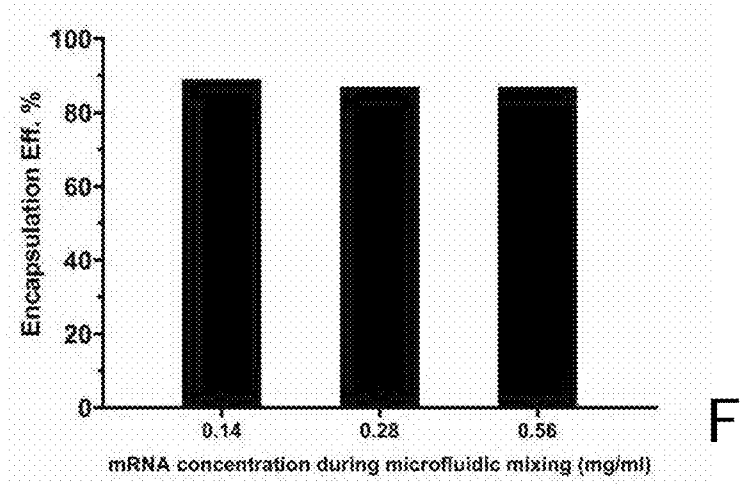
FIG. 3B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 3B correspond to procedure set forth in Example 3B.
Figure 3C:
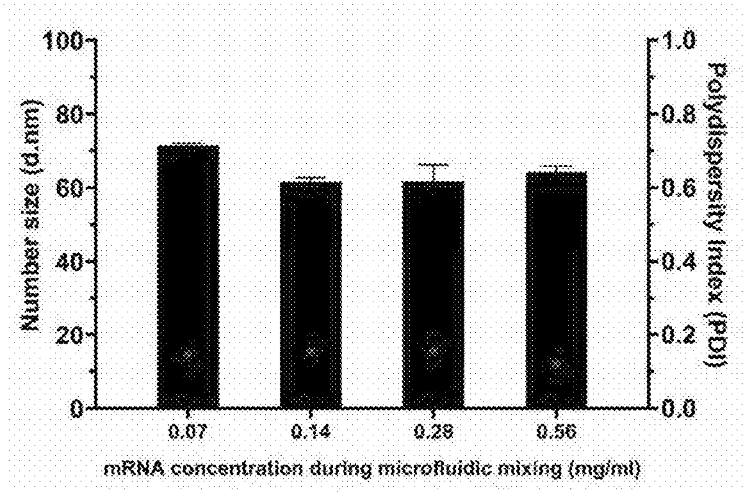
FIG. 3C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 3C correspond to procedure set forth in Example 3C.
Figure 3D:
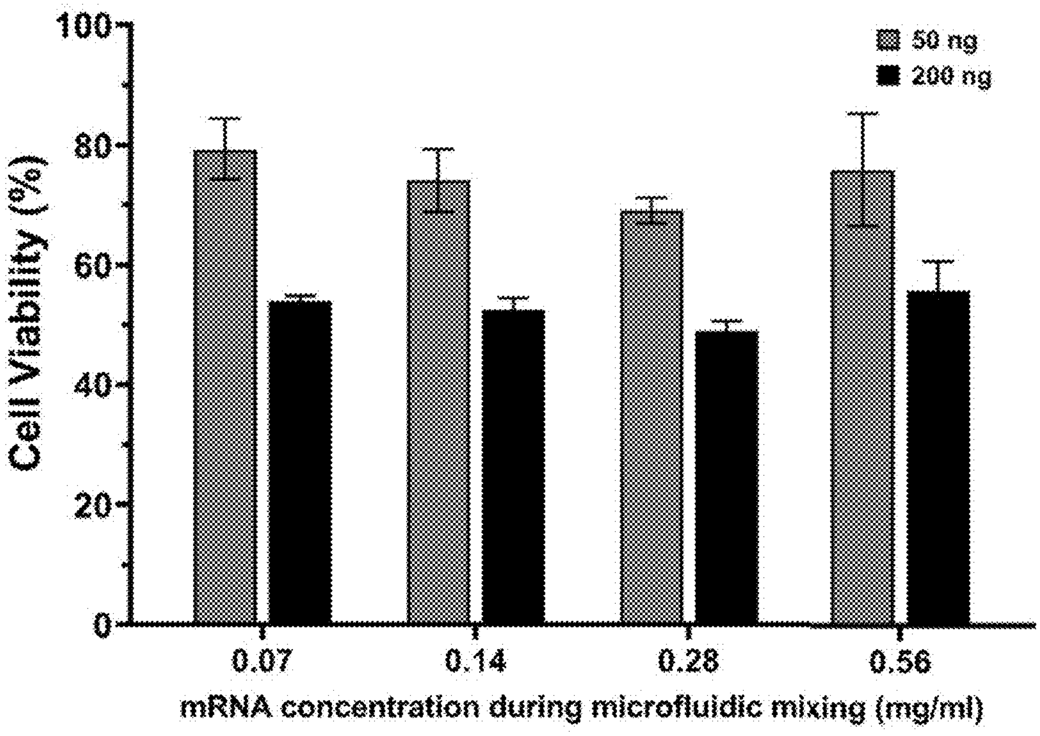
FIG. 3D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590). The embodiments illustrated in FIG. 3D correspond to procedure set forth in Example 3D.
Figure 4A:
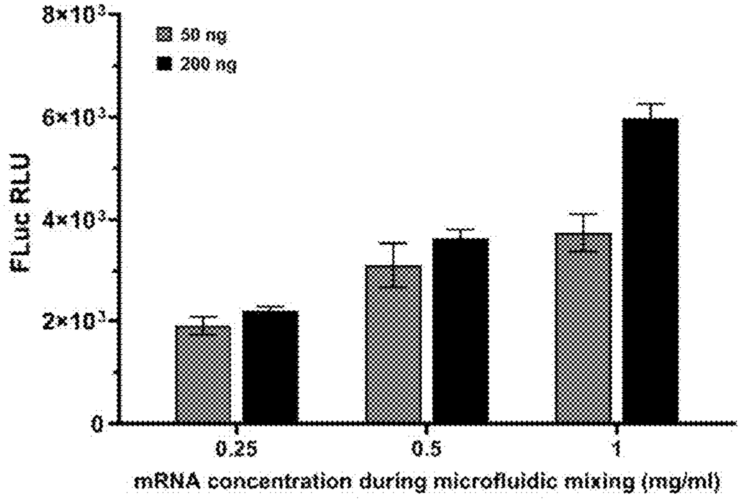
FIG. 4A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9x10-5 mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 4A correspond to procedure set forth in Example 4A.
Figure 4B:
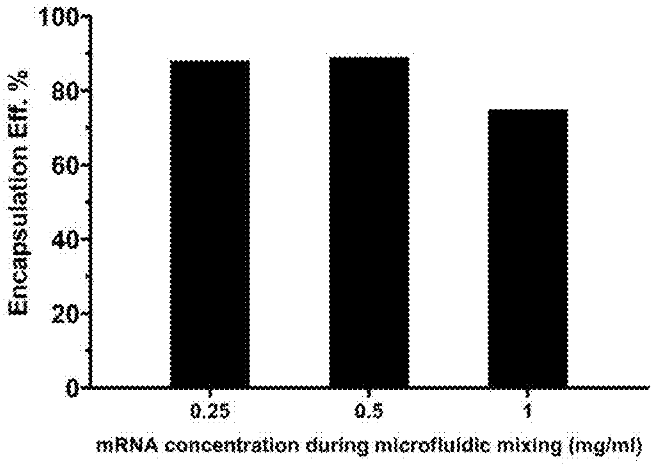
FIG. 4B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 4B correspond to procedure set forth in Example 4B.
Figure 4C:
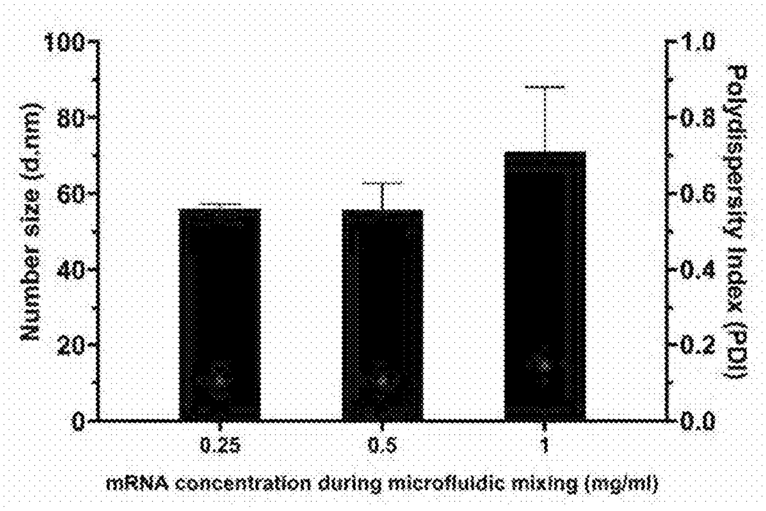
FIG. 4C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 4C correspond to procedure set forth in Example 4C.
Figure 4D:
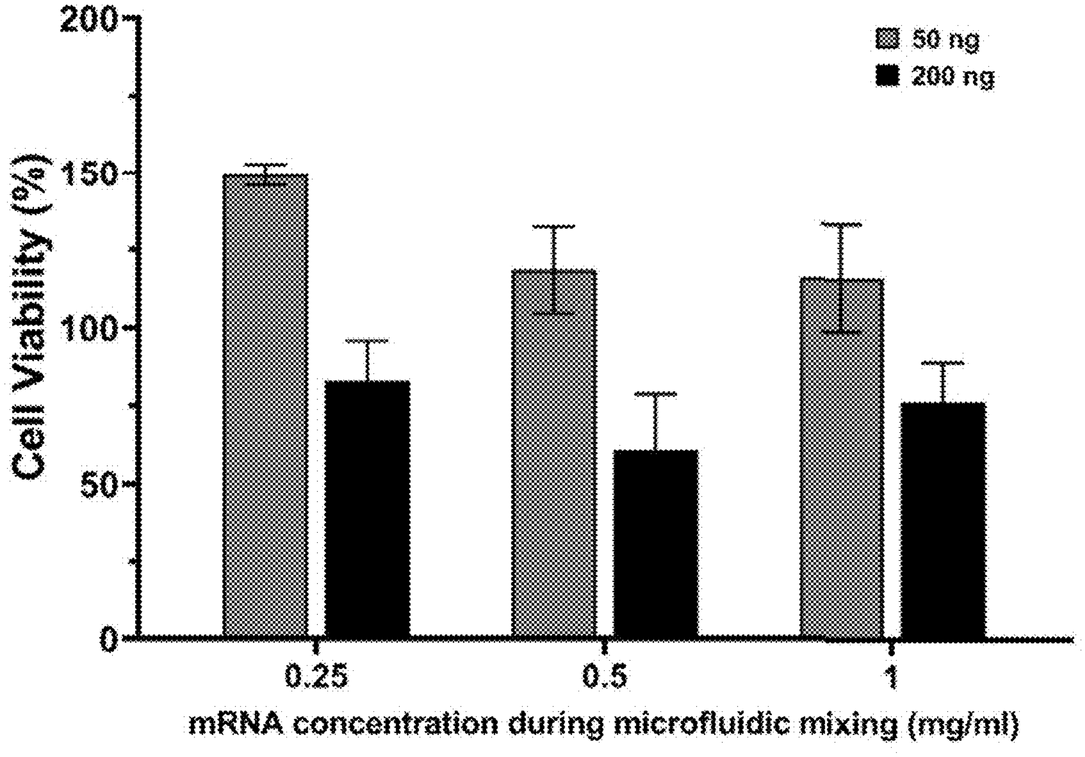
FIG. 4D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590). The embodiments illustrated in FIG. 4D correspond to procedure set forth in Example 4D
Figure 5A:
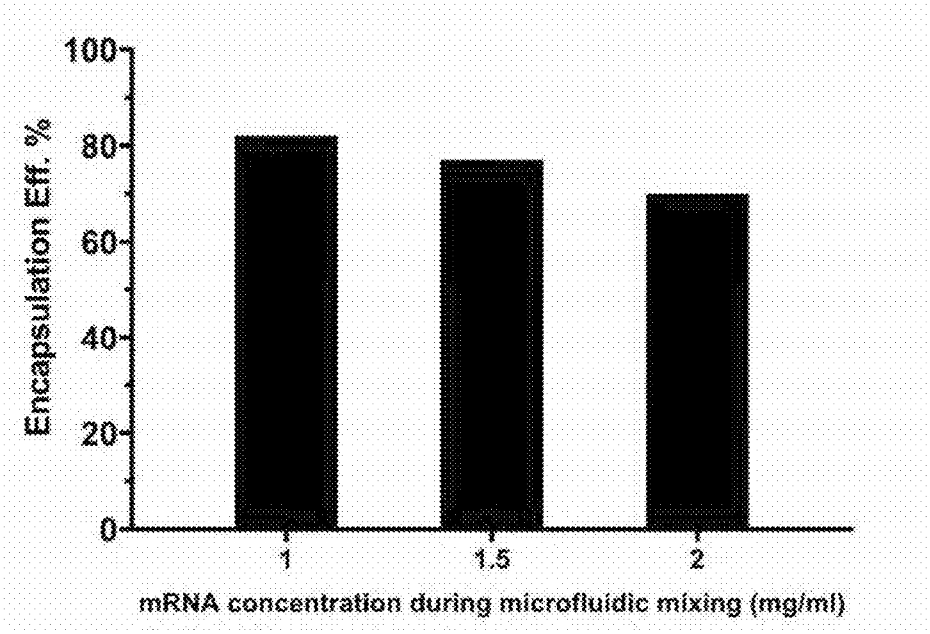
FIG. 5A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 5A correspond to procedure set forth in Example 5A.
Figure 5B:
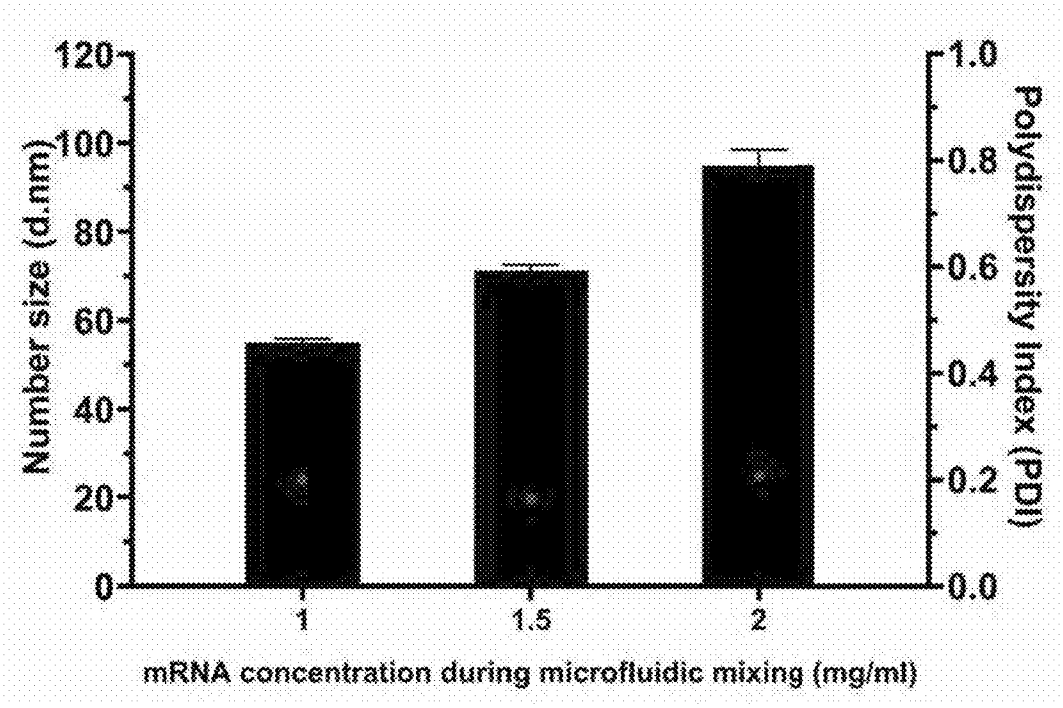
FIG. 5B: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 5B correspond to procedure set forth in Example 5B.
Figure 6A:
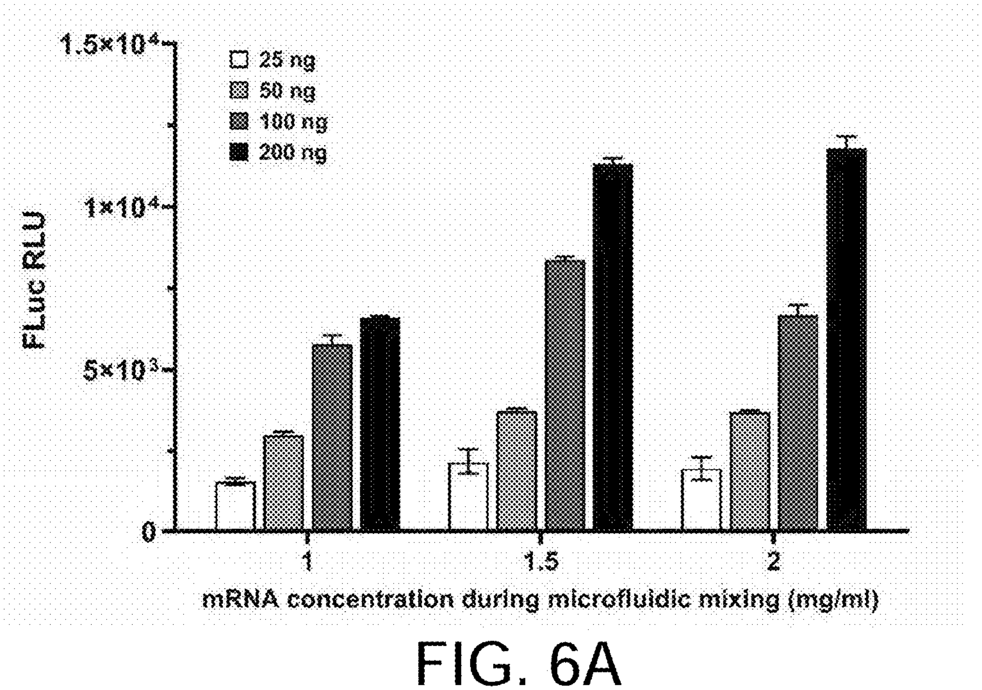
FIG. 6A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 6A correspond to procedure set forth in Example 6A.
Figure 6B:
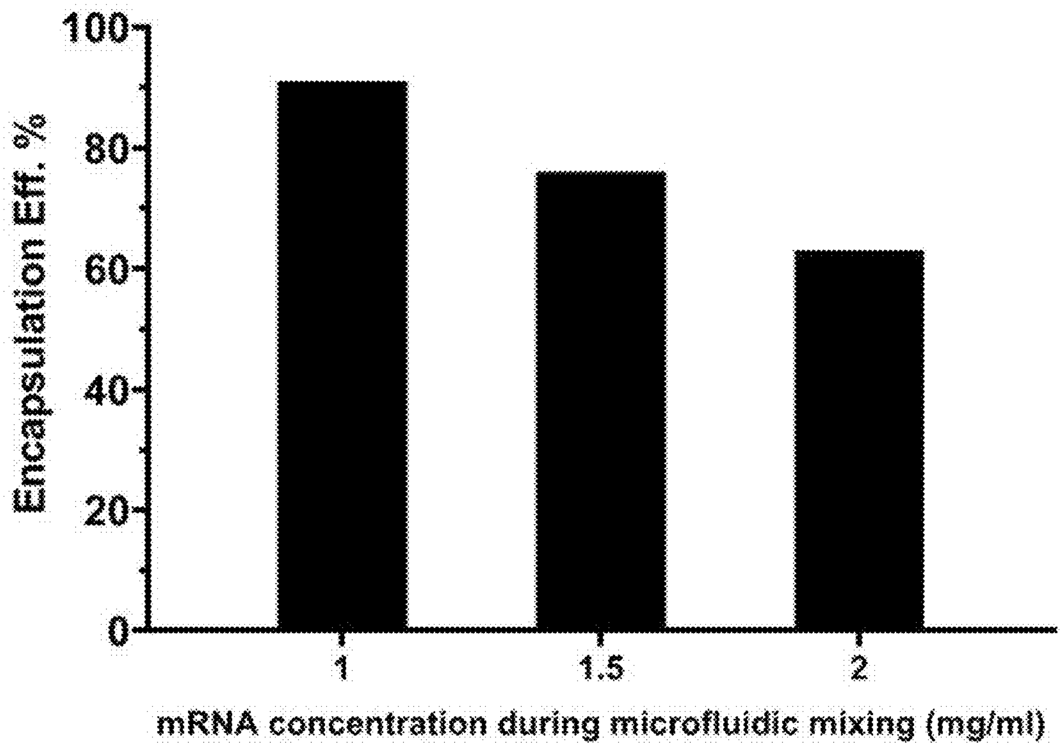
FIG. 6B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 6B correspond to procedure set forth in Example 6B.
Figures 6C, 6D:
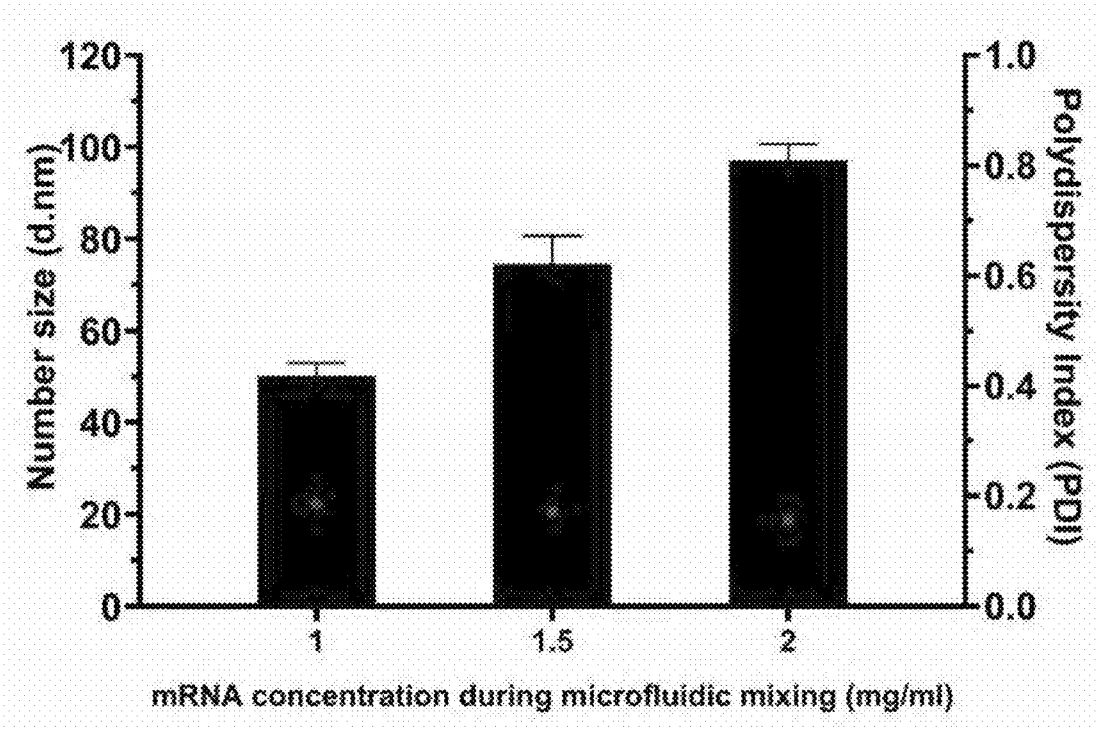
FIG. 6C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 6C correspond to procedure set forth in Example 6C.
FIG. 6D: pH measurements. Measurements were taken before and after dialysis against 1×DPBS pH7.4 for 4 hours. The embodiments illustrated in FIG. 6D correspond to procedure set forth in Example 6D.
Figure 7A:
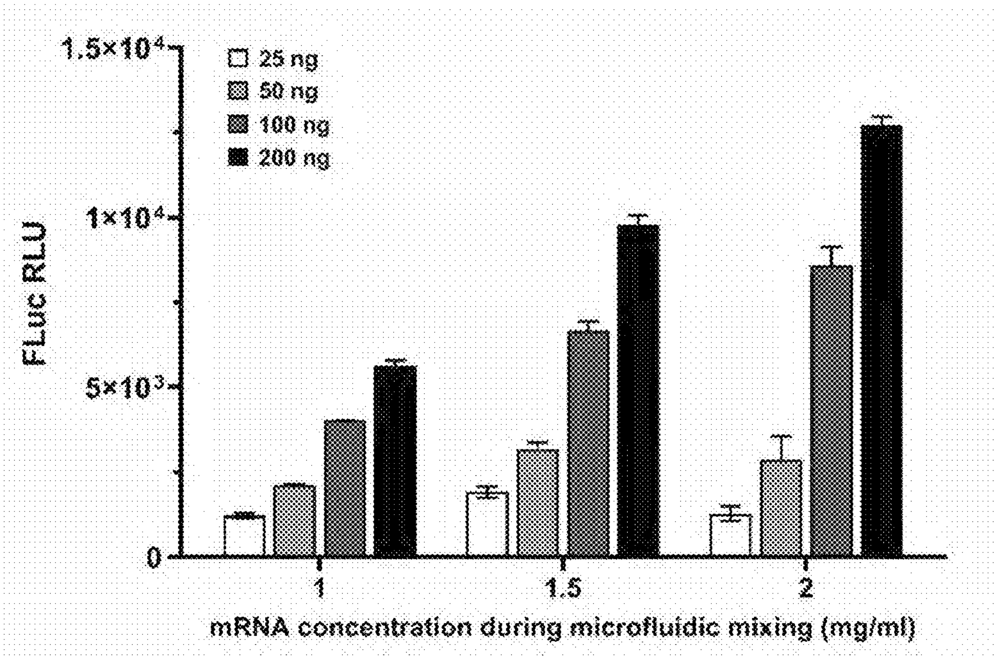
FIG. 7A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 7A correspond to procedure set forth in Example 7A.
Figure 7B:
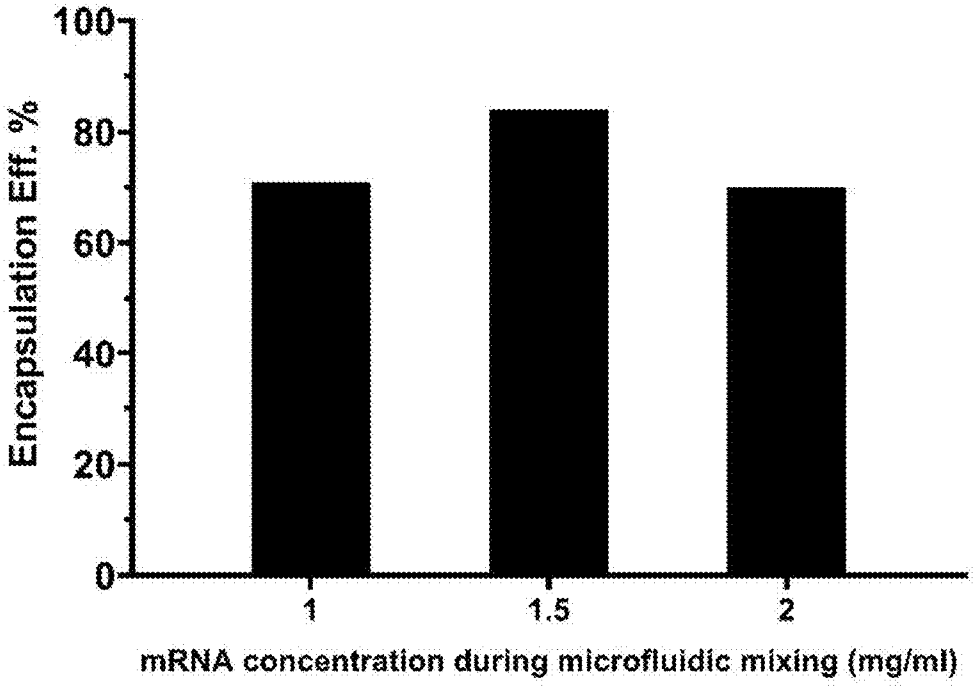
FIG. 7B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 7B correspond to procedure set forth in Example 7B.
Figures 7C, 7D:
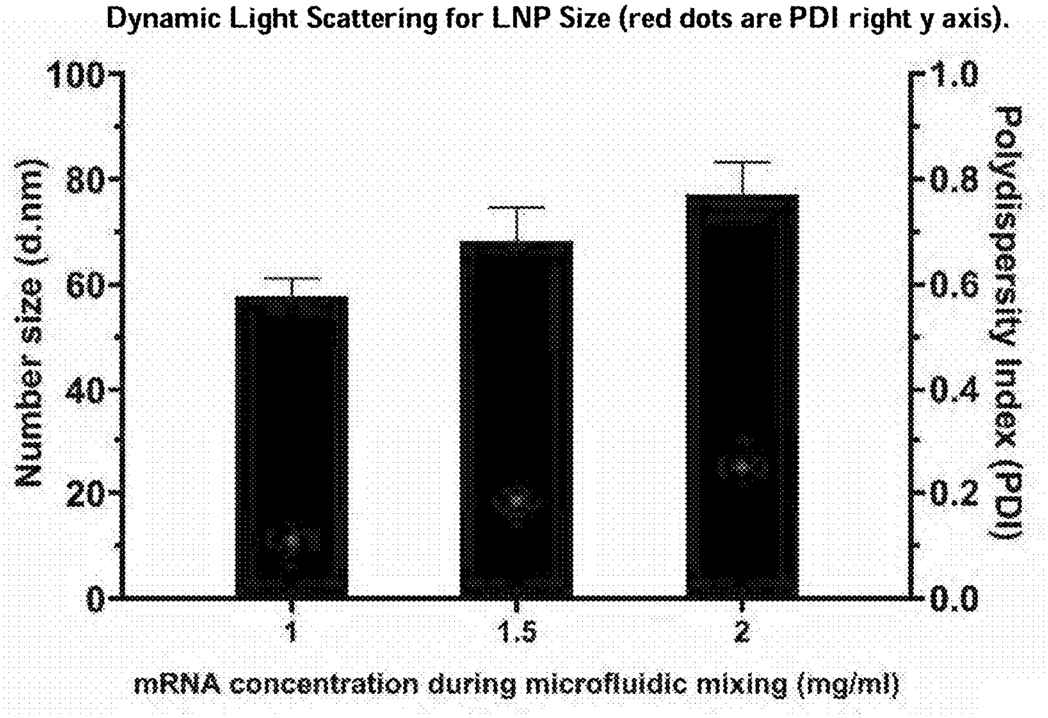
FIG. 7C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 7C correspond to procedure set forth in Example 7C.
FIG. 7D: pH measurements. Measurements were taken before and after dialysis against 1×DPBS pH7.4 for 4 hours. Note here in comparison to Example 6, these LNPs were formulated using 100 mM NaOAc. Increasing the concentration of Sodium Acetate Buffer in formulation keeps the pH lower due to higher buffer capacity, resulting in a lower pH before Dialysis for the LNPs. The embodiments illustrated in FIG. 7D correspond to procedure set forth in Example 7D.
Figure 8A:
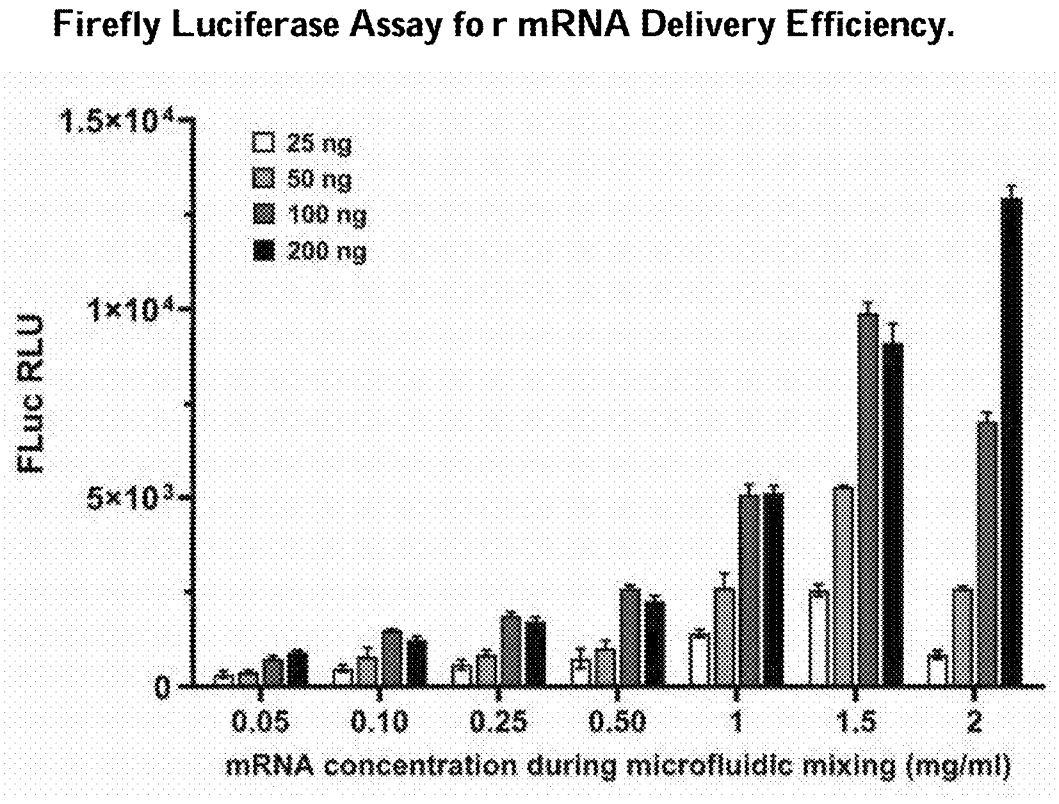
FIG. 8A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 8A correspond to procedure set forth in Example 8A.
Figure 8B:
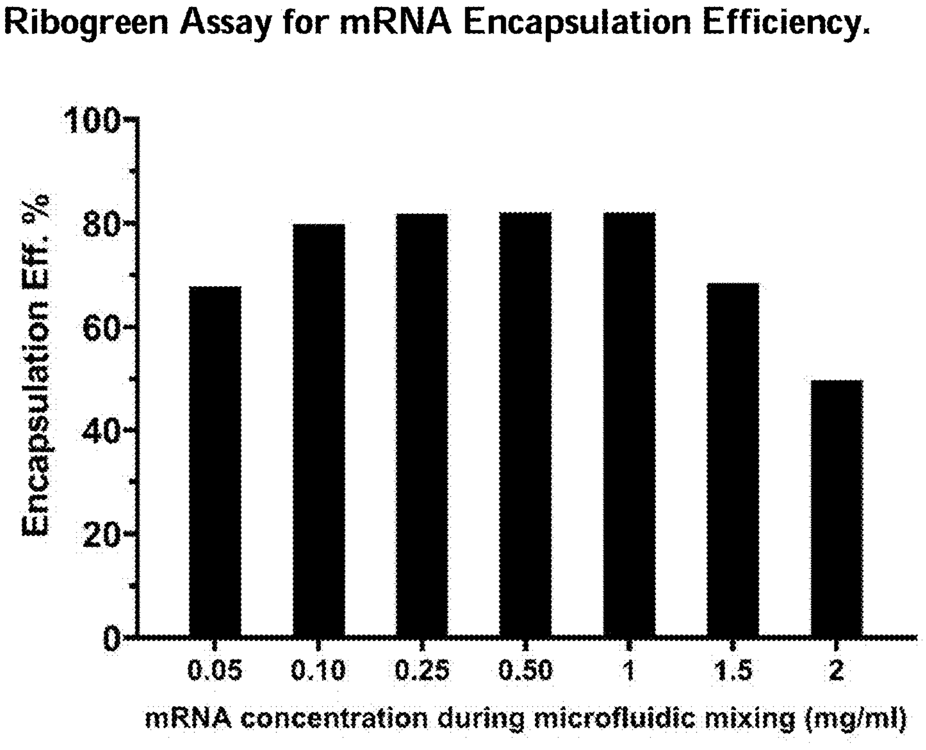
FIG. 8B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 8B correspond to procedure set forth in Example 8B.
Figure 8C:
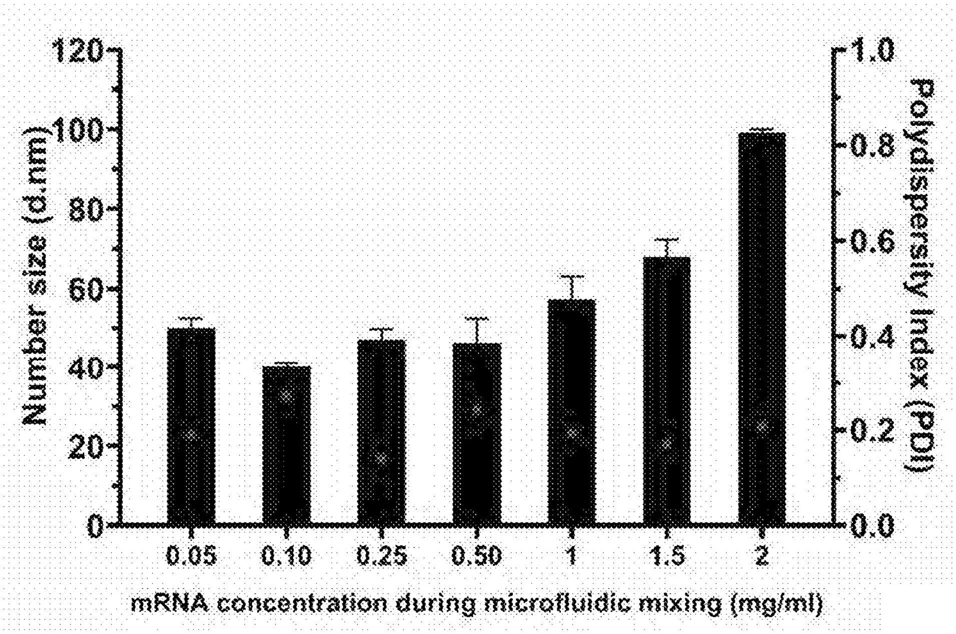
FIG. 8C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 8C correspond to procedure set forth in Example 8C.
Figure 8D:
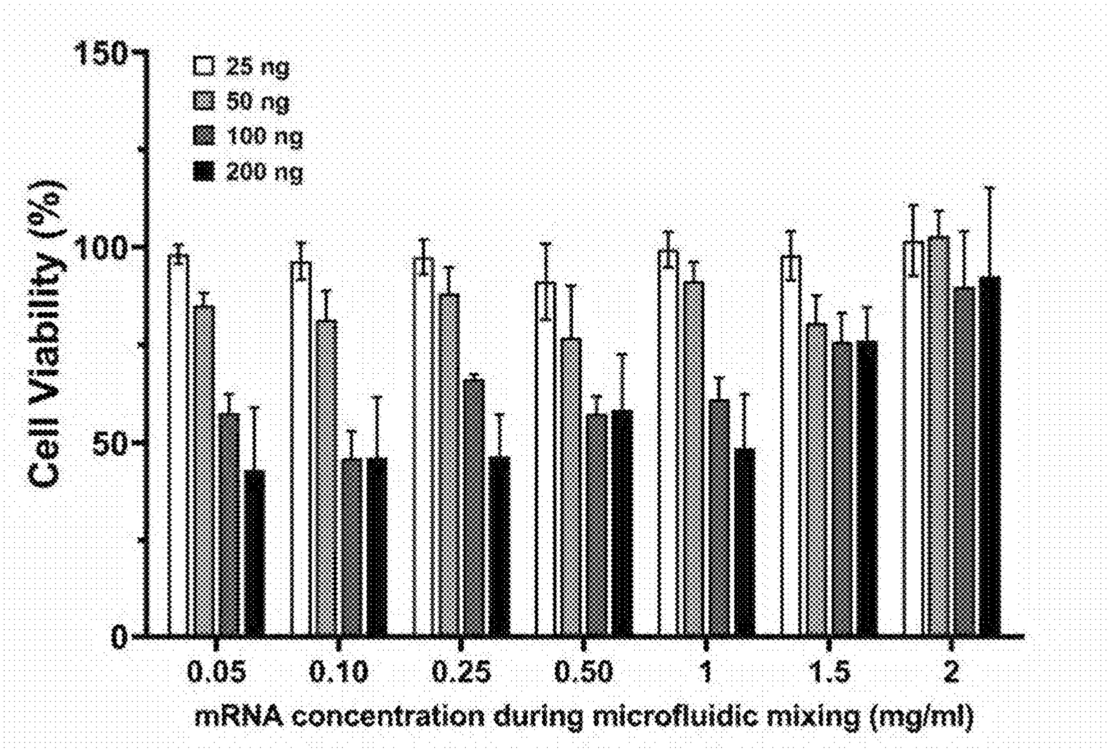
FIG. 8D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590). The embodiments illustrated in FIG. 8D correspond to procedure set forth in Example 8D.
Figure 9A:
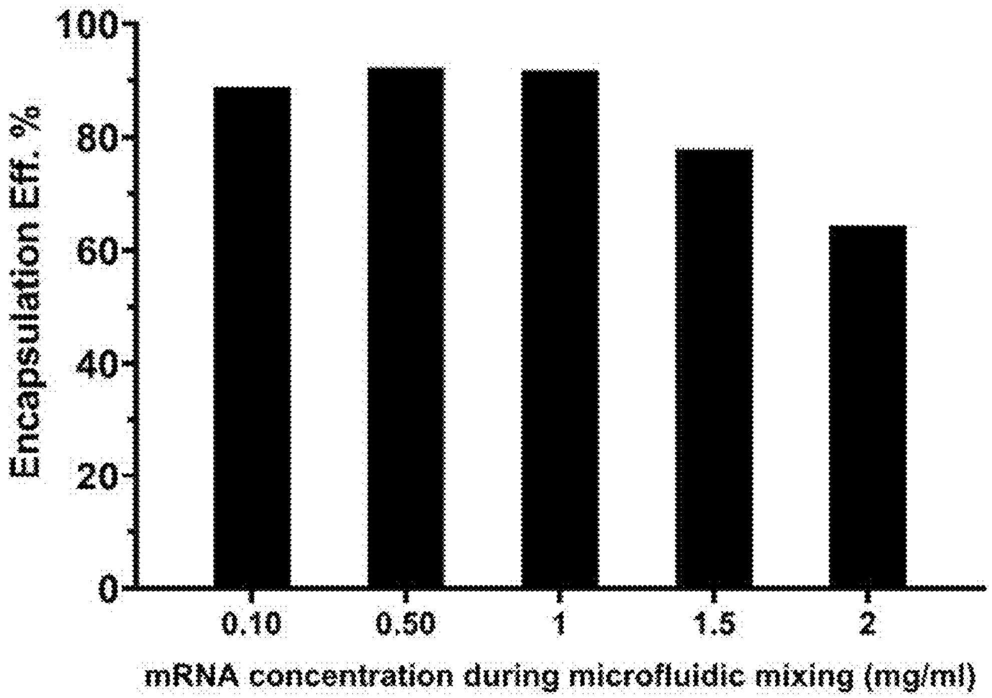
FIG. 9A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 9A correspond to procedure set forth in Example 9A.
Figure 9B:
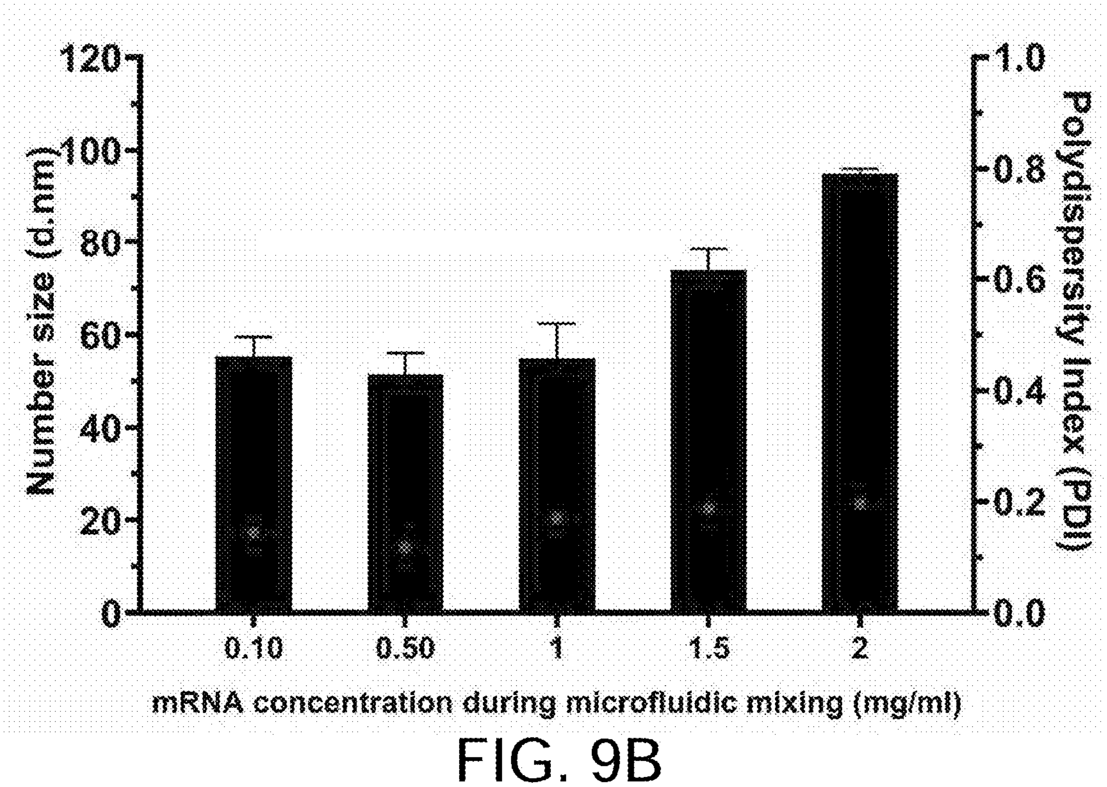
FIG. 9B: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 9B correspond to procedure set forth in Example 9B.
Figure 9C:
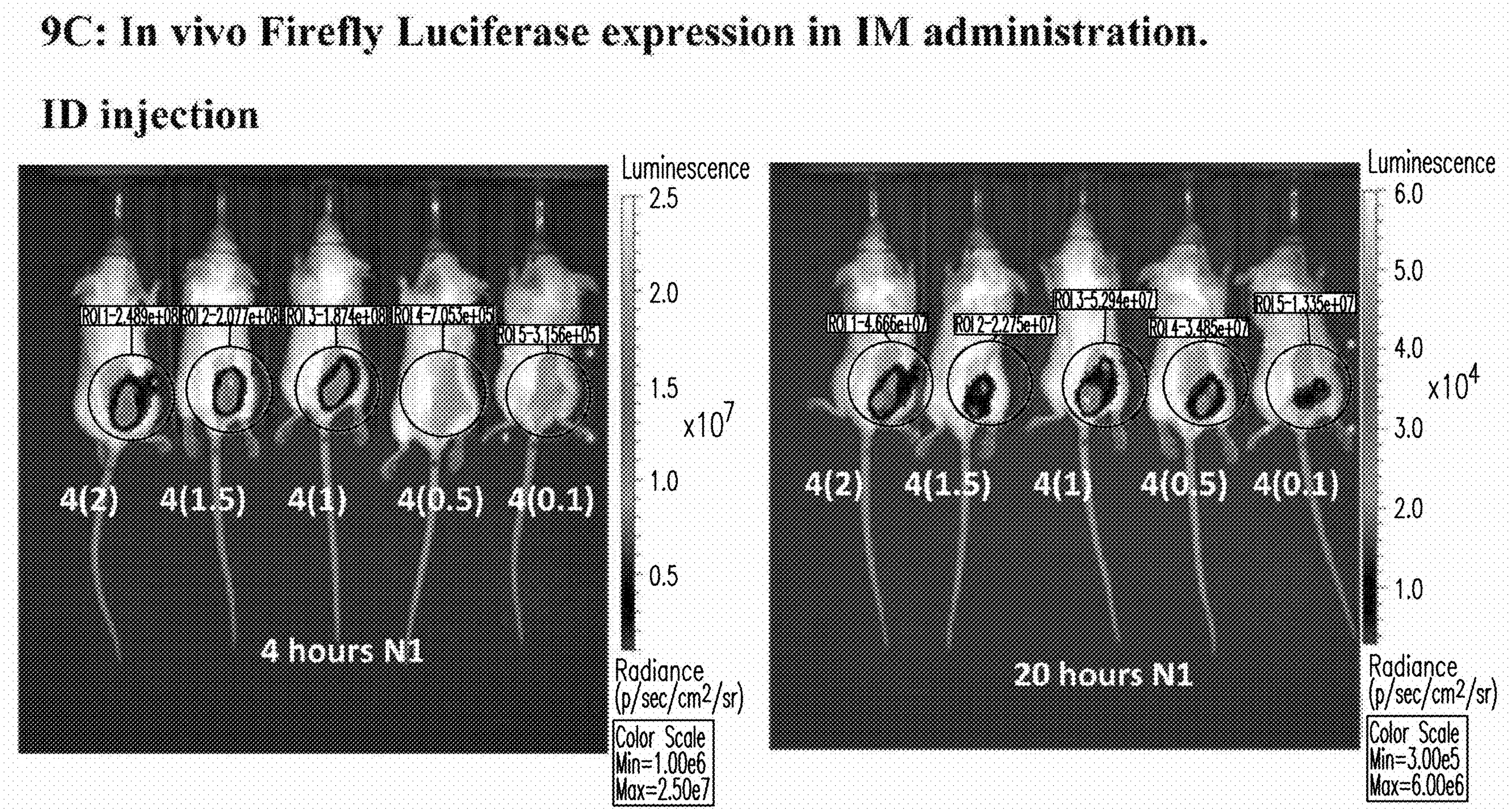
FIG. 9C: In vivo Firefly Luciferase expression after intradermal (I.D.) administration.
Figure 9D:
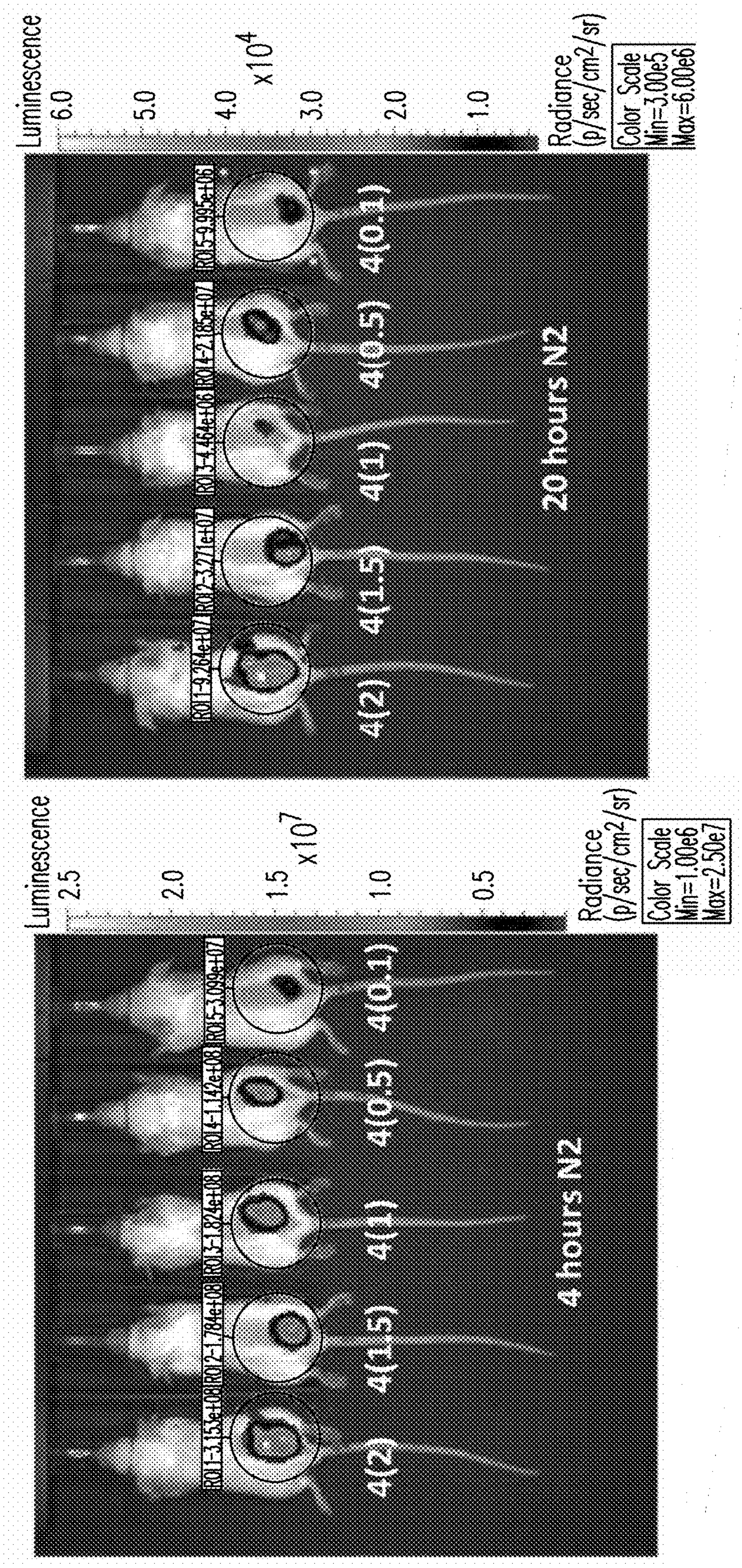
FIG. 9D illustrates in vivo Firefly Luciferase expression after intravenous (I.V.) administration.
Figure 9E:
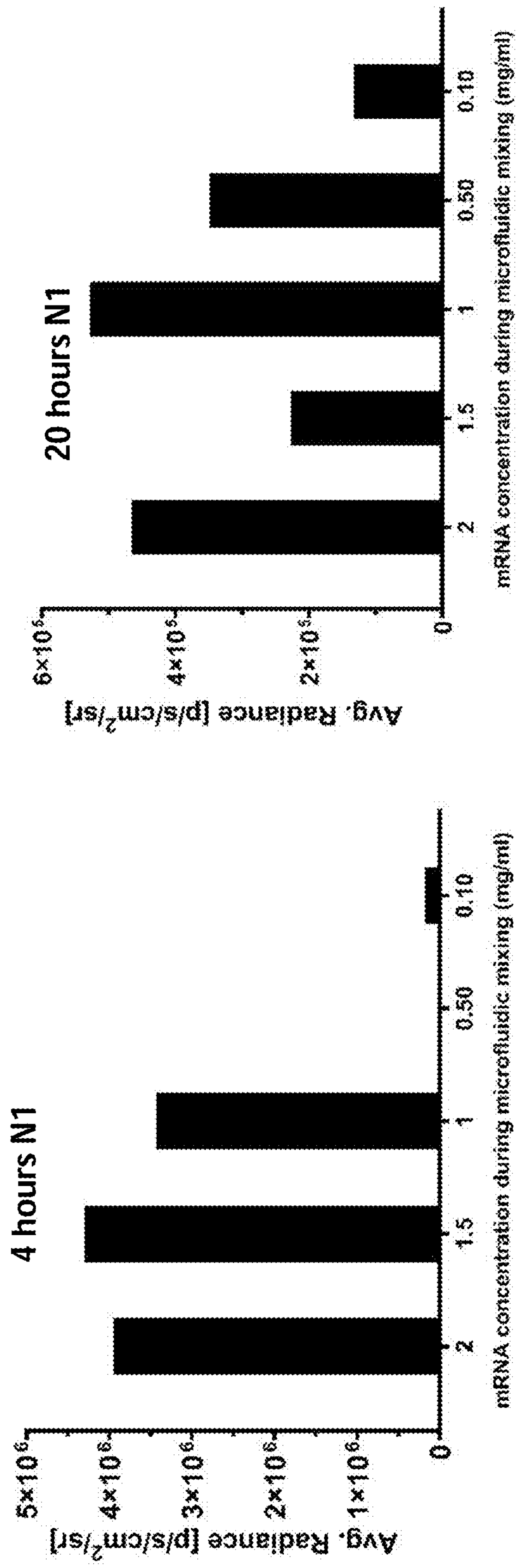
FIG. 9E illustrates average radiance after 4 hours and 20 hours.
Figure 9F:
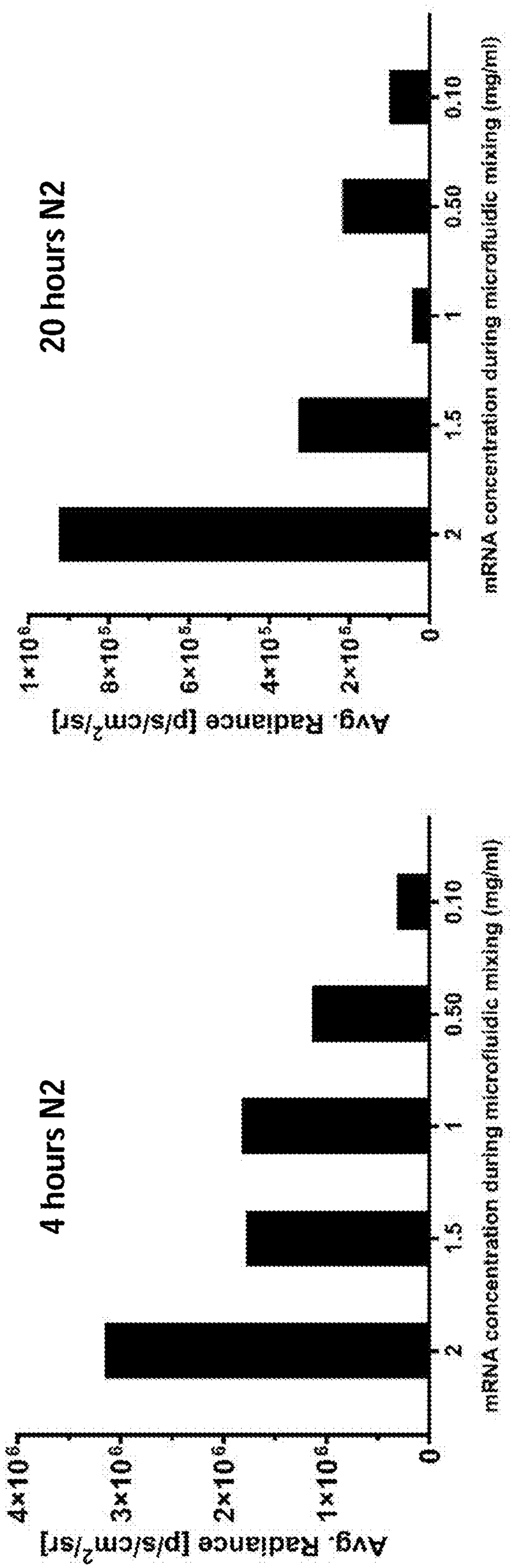
FIG. 9F illustrates average radiance after 4 hours and 20 hours.
Figure 9G:
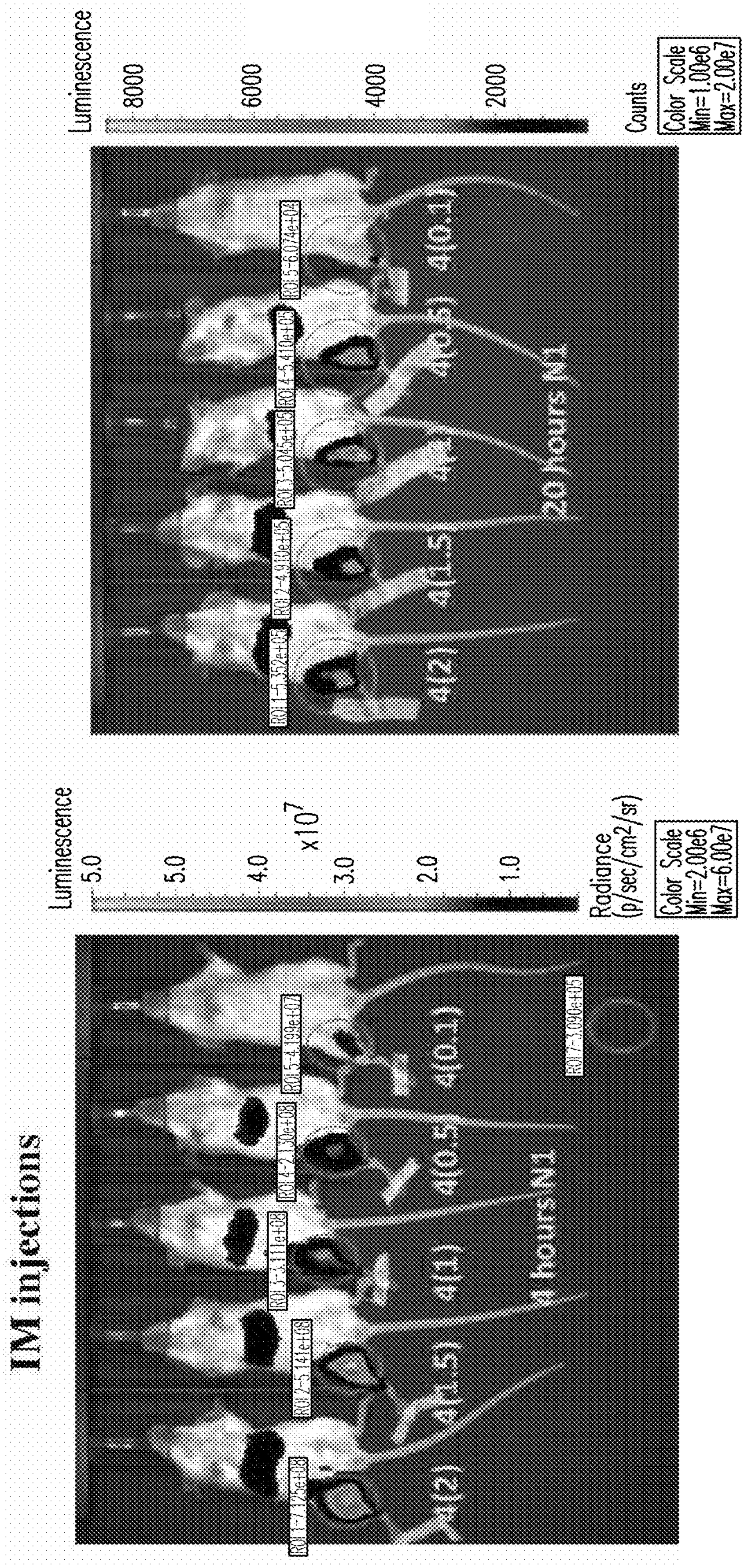
FIG. 9G and FIG. 9H illustrate in vivo Firefly Luciferase expression after intramuscular (I.M.)
Figure 9H:
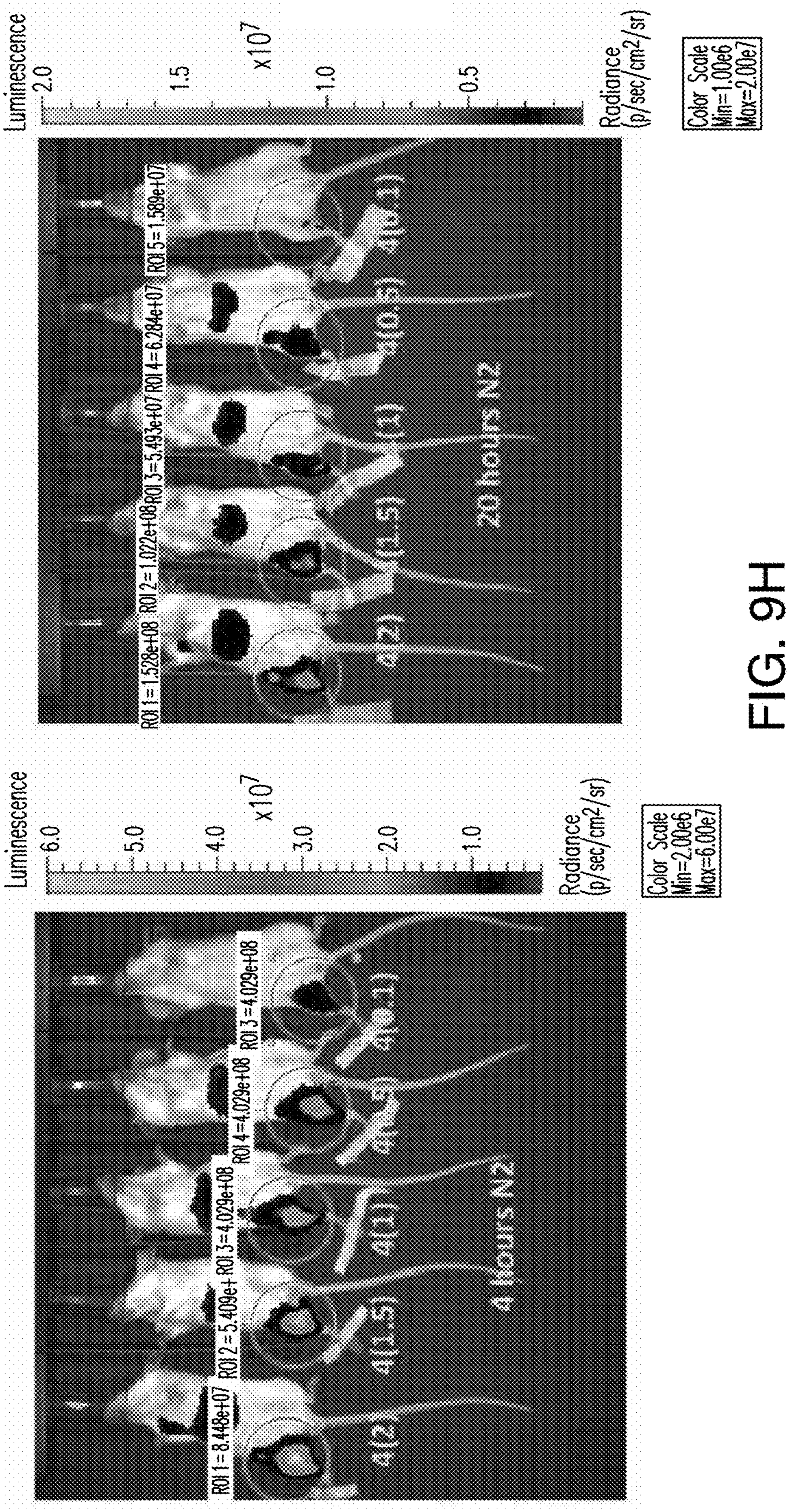
Figure 9I:
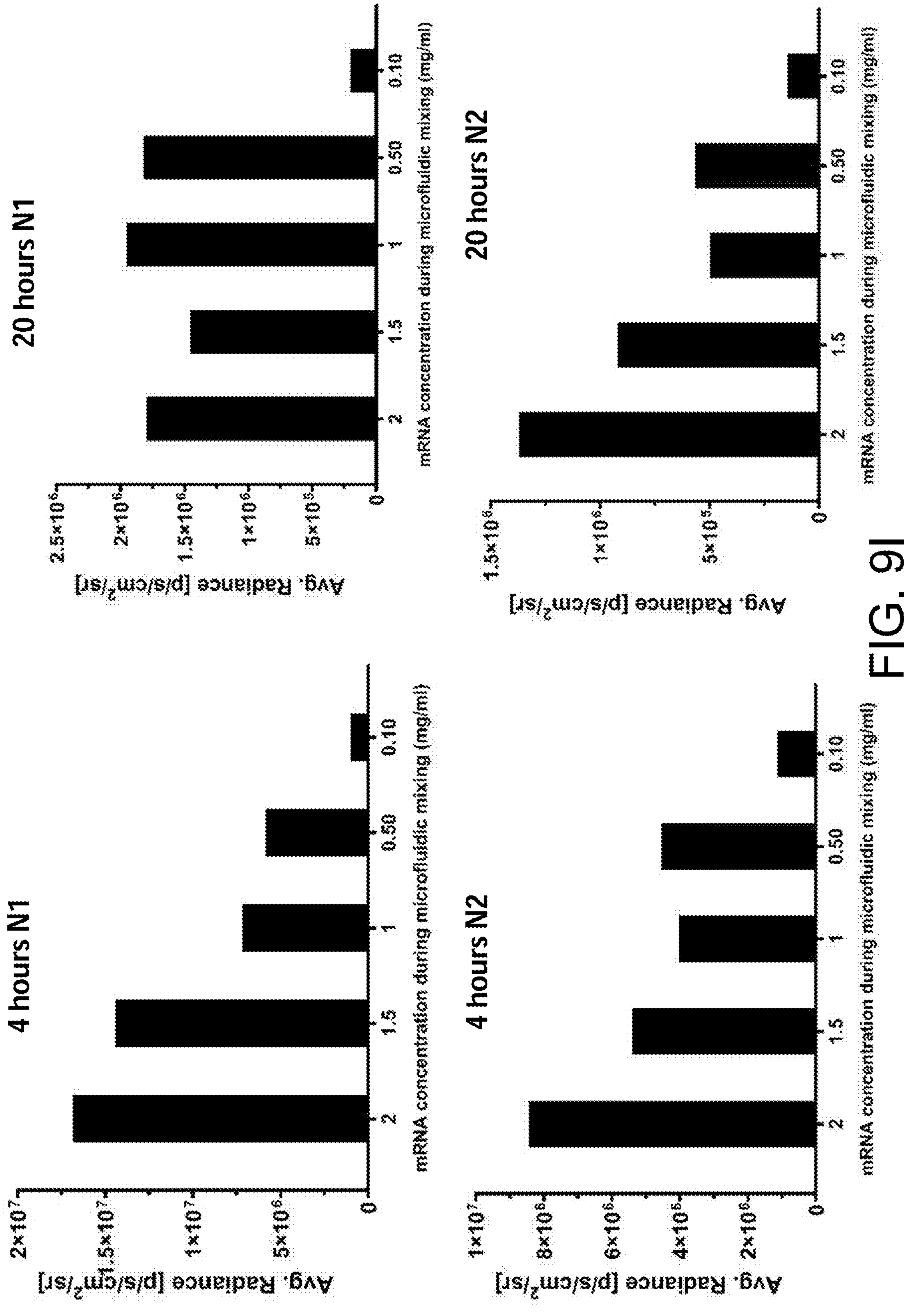
FIG. 9I illustrates average radiance after 4 hours and 20 hours.
Figure 9J:
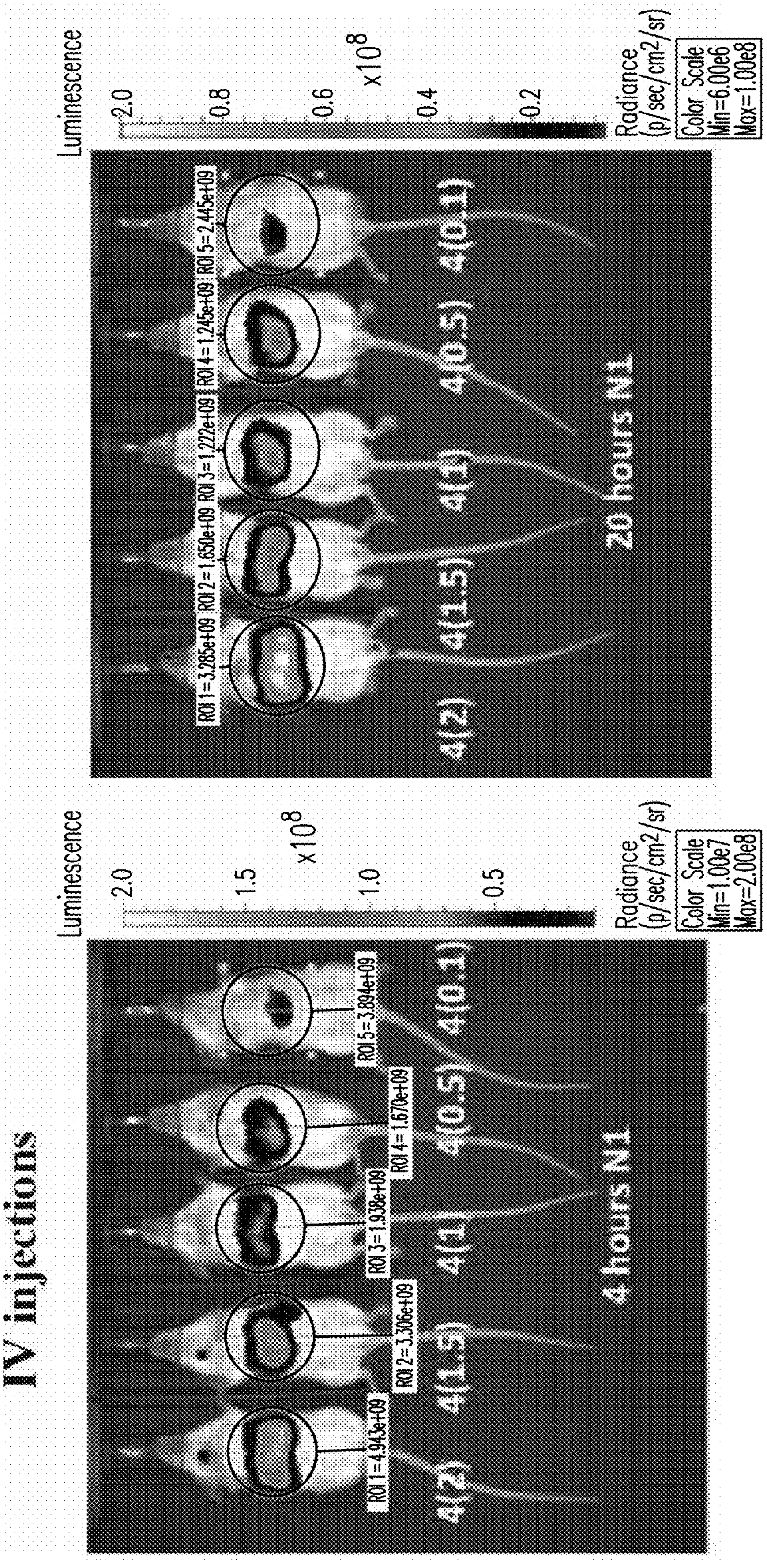
FIG. 9J and FIG. 9K illustrate in vivo Firefly Luciferase expression after intravenous (I.V.) administration.
Figure 9K:
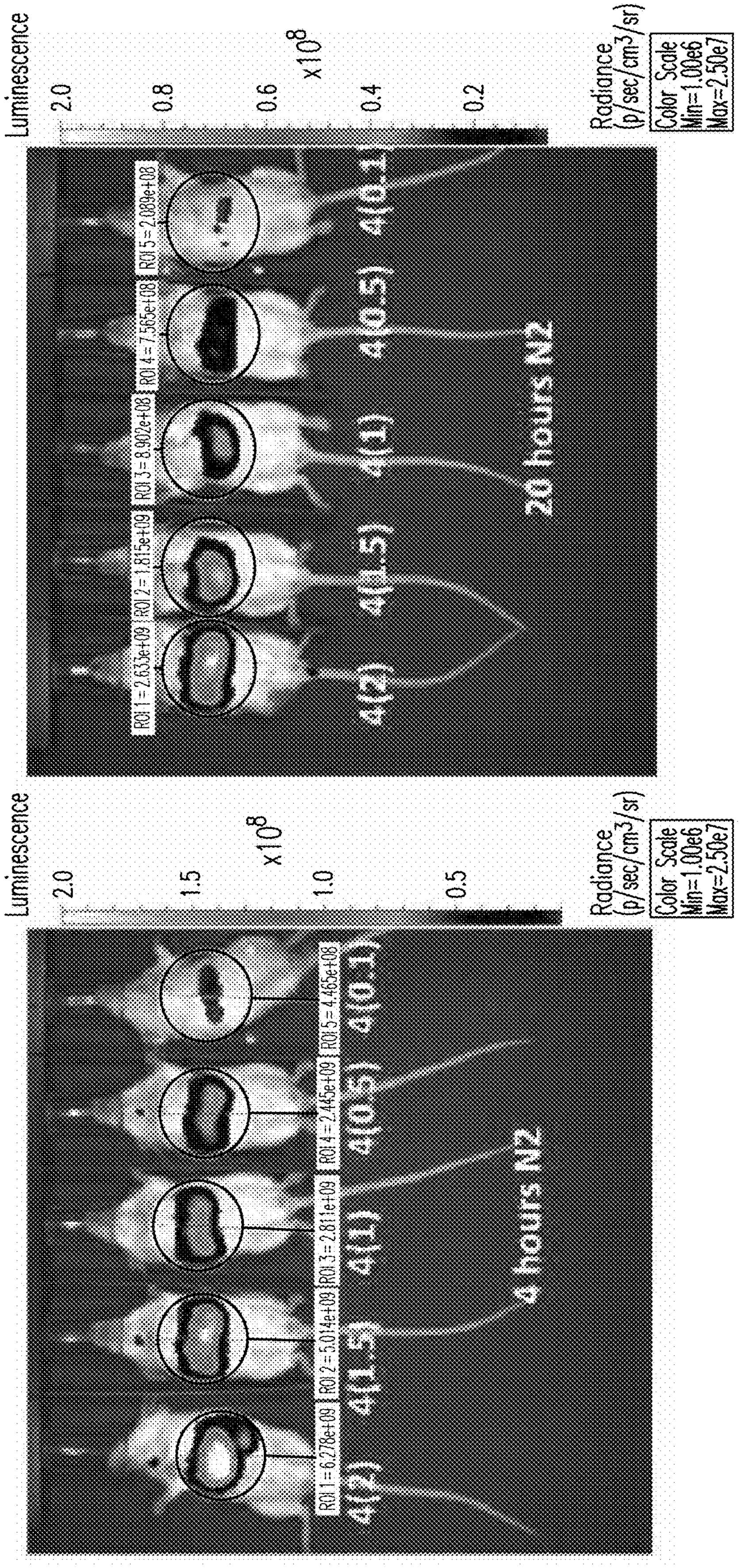
Figure 9L:
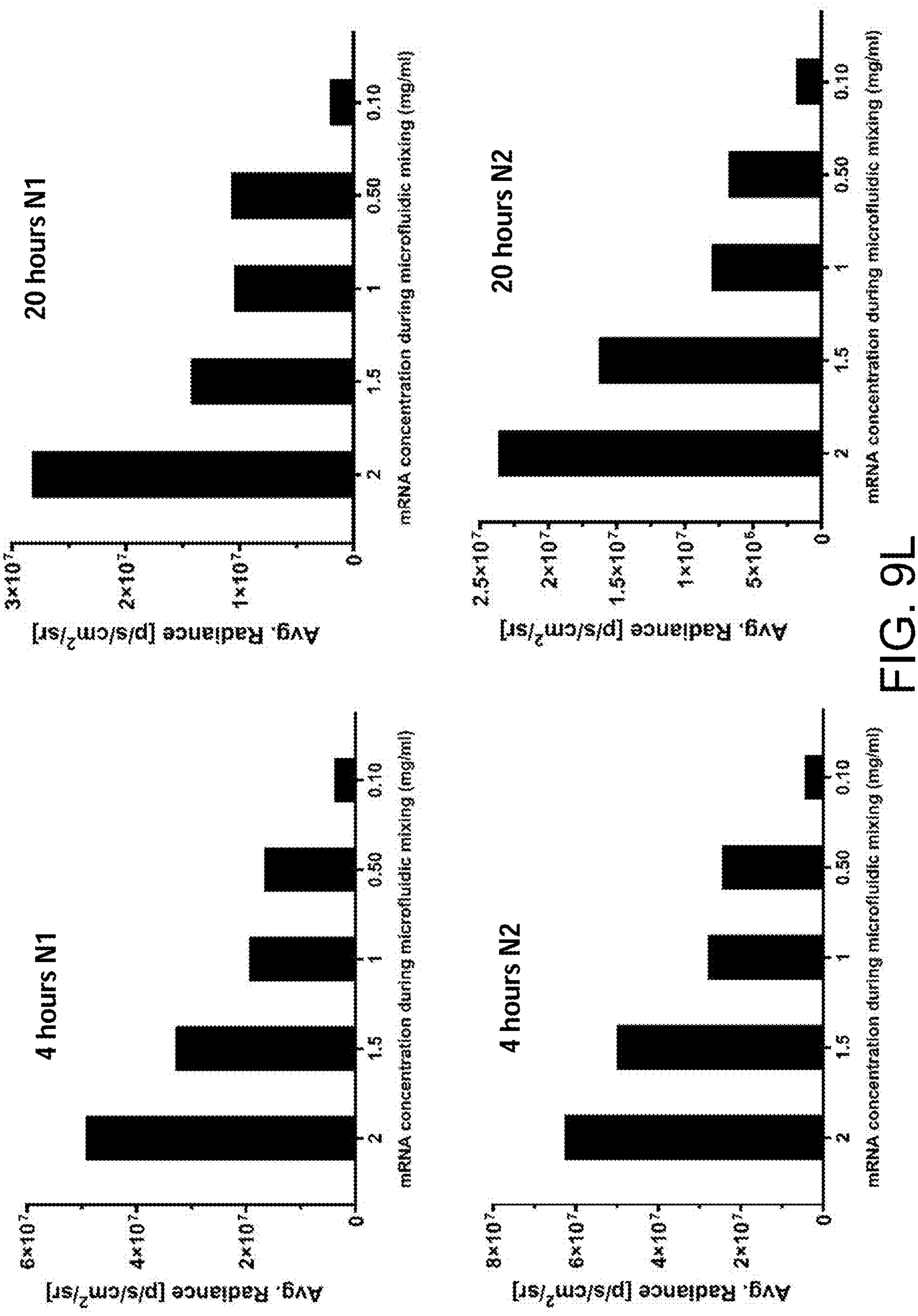
FIG. 9L illustrates average radiance after 4 hours and 20 hours.
Figure 9M:
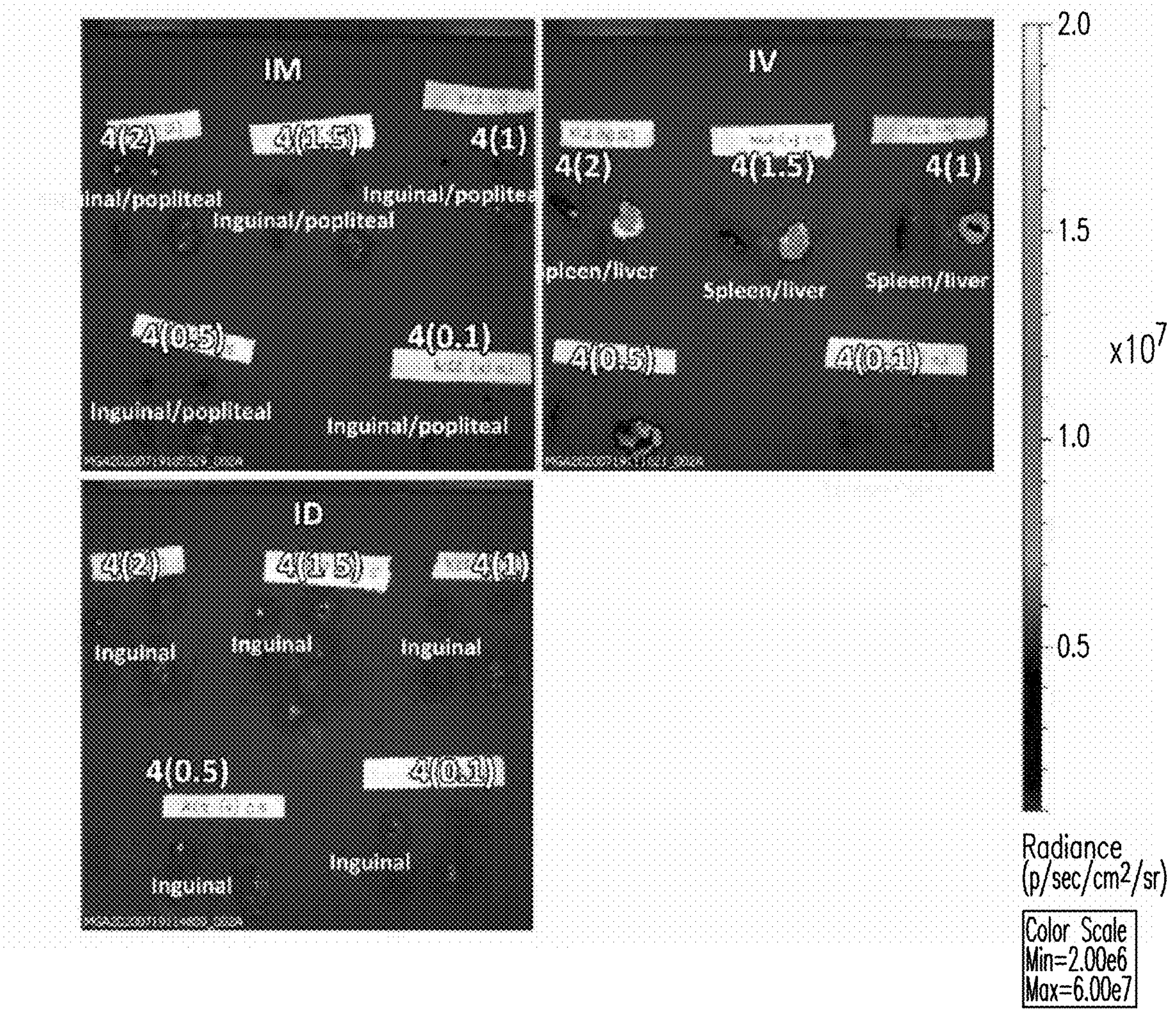
FIG. 9M illustrates ex vivo expression with all samples of Example 9.
Figure 9N:
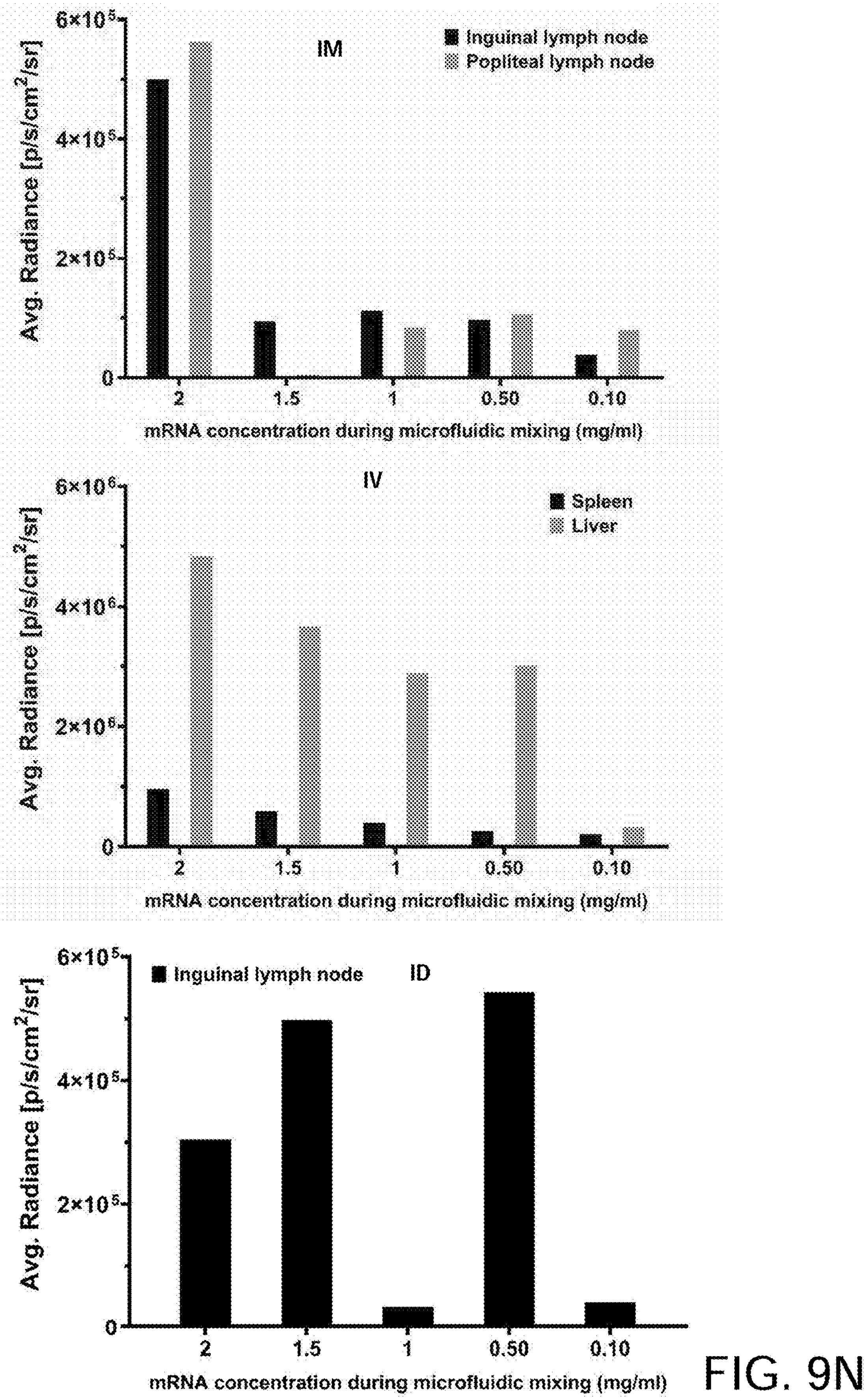
FIG. 9N illustrates average radiance after IM, IV, and ID administration.
Figure 10A:
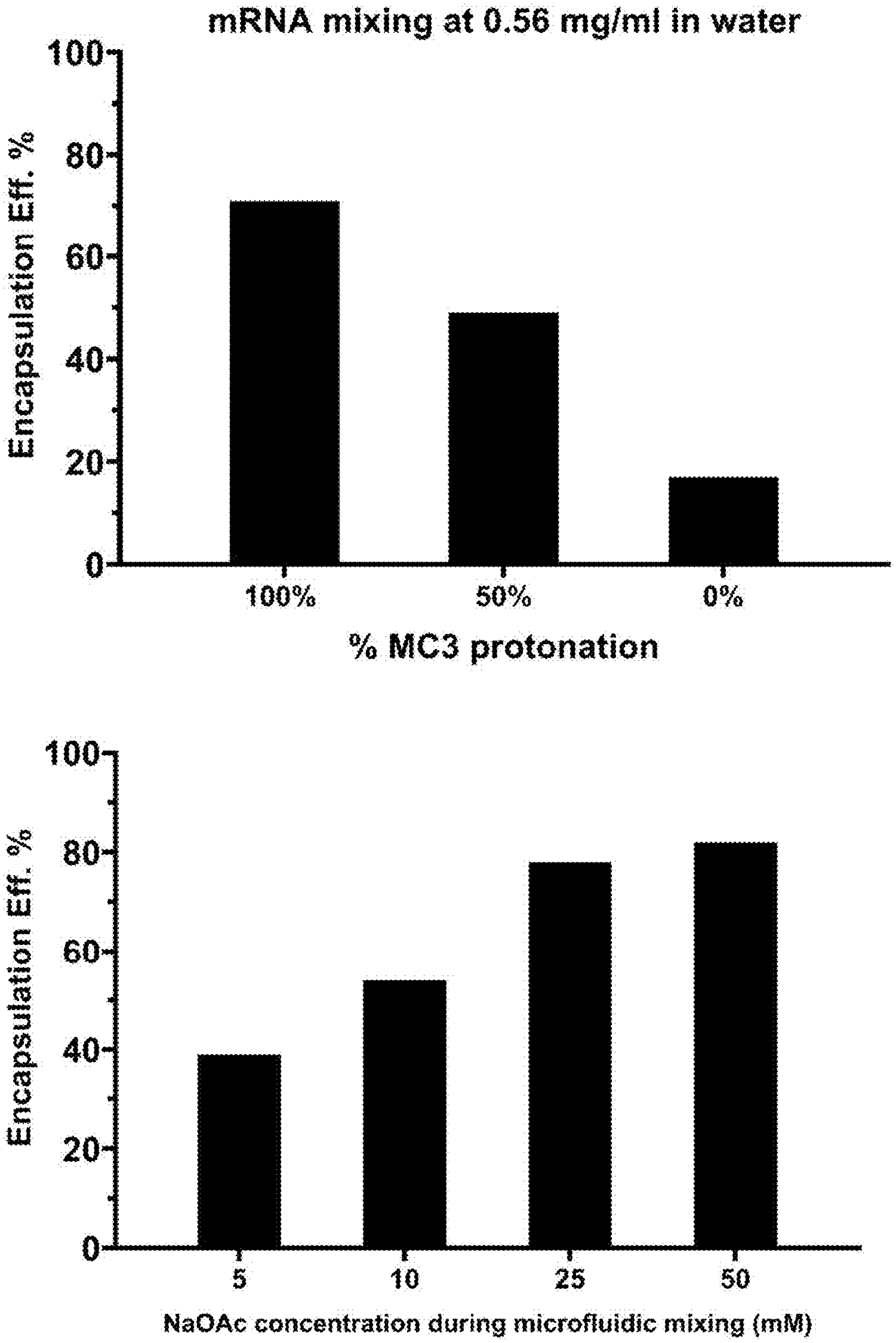
FIG. 10A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 10A correspond to procedure set forth in Example 10A.
Figure 10B:
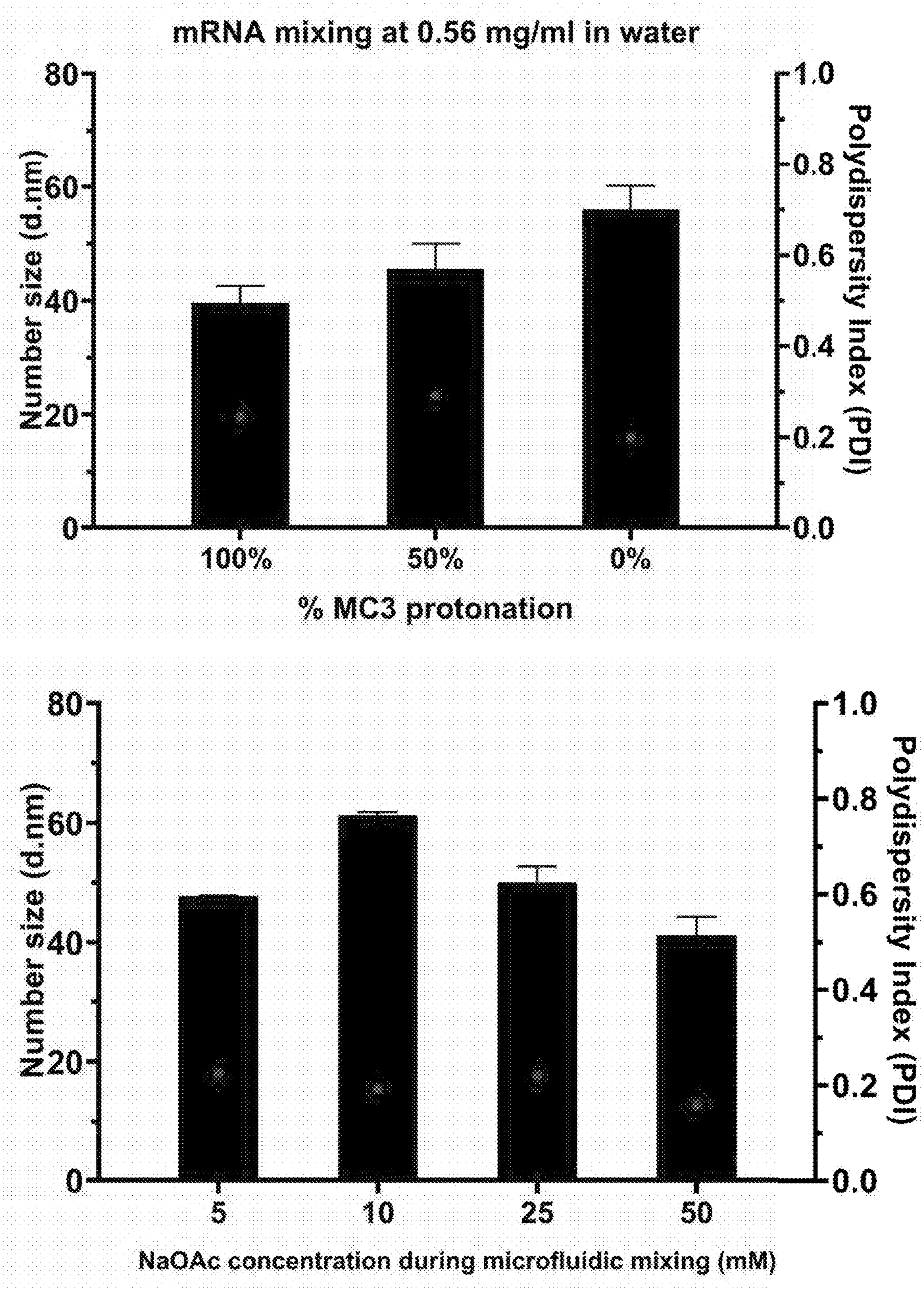
FIG. 10B: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 10B correspond to procedure set forth in Example 10B.
Figure 11A:
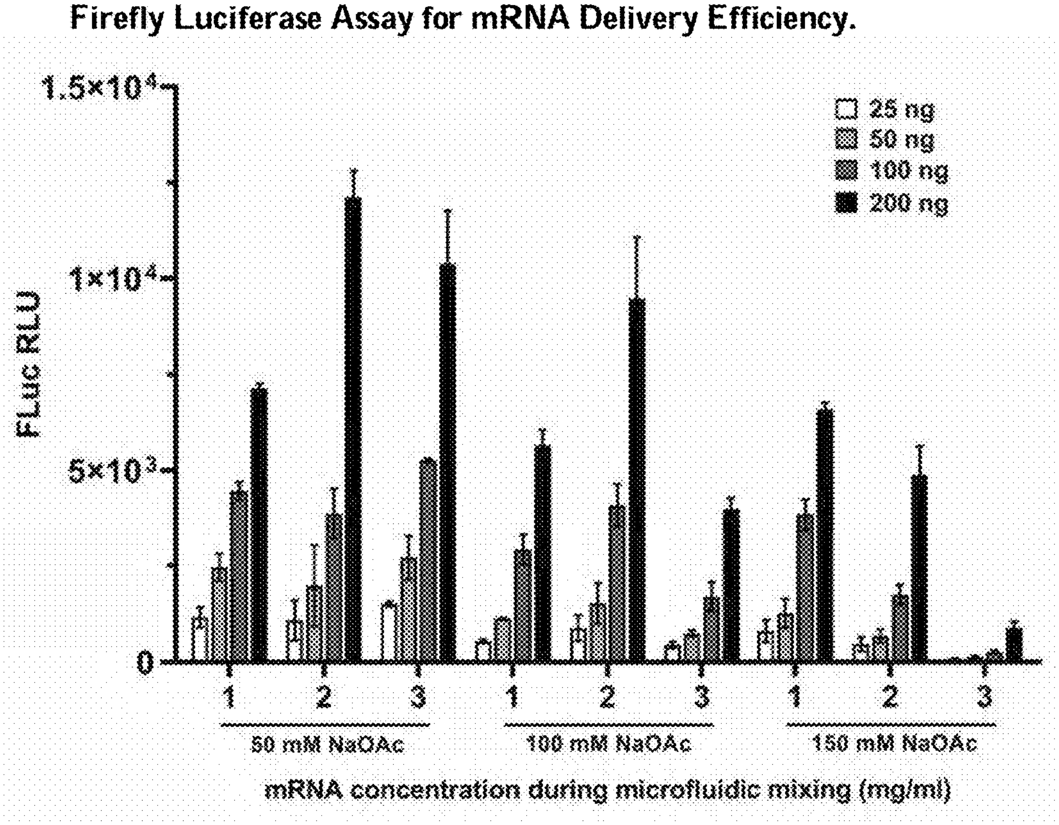
FIG. 11A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 11A correspond to procedure set forth in Example 11A.
Figure 11B:
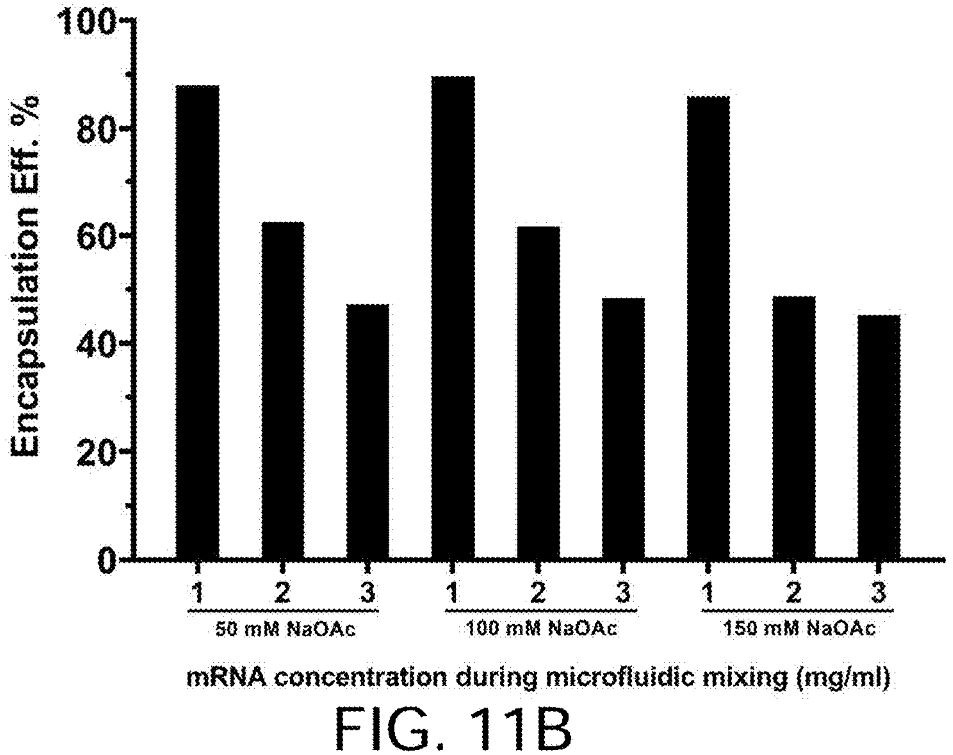
FIG. 11B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 11B correspond to procedure set forth in Example 11B.
Figures 11C, 11D:
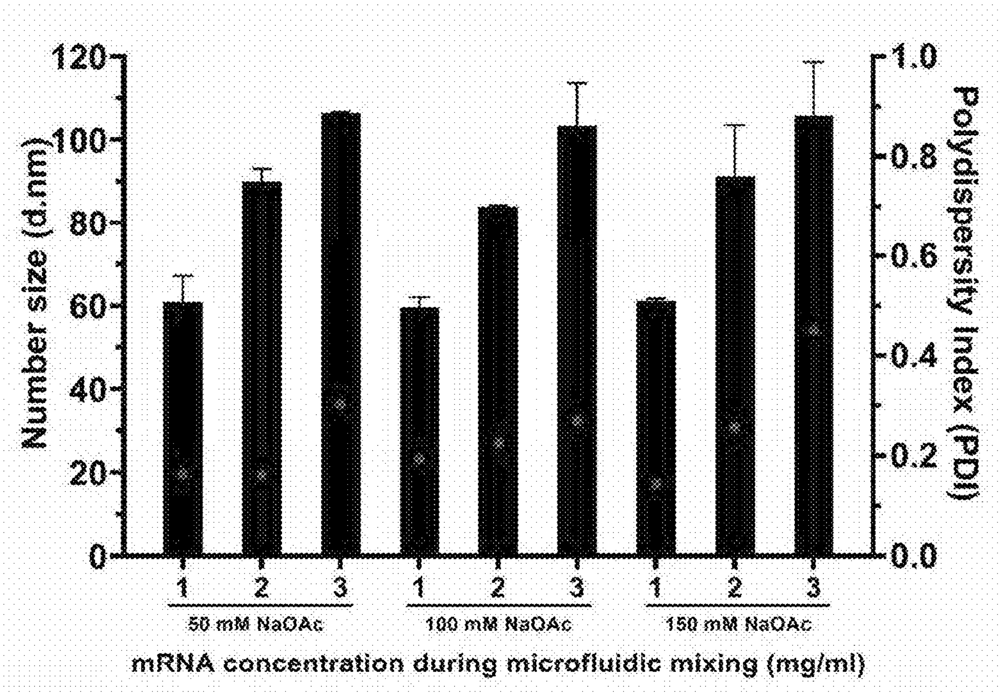
FIG. 11C: Dynamic Light Scattering for LNP Size (white dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 11C correspond to procedure set forth in Example 11C.
FIG. 11D: pH measurements. Measurements were taken before and after dialysis against 1×DPBS pH7.4 for 4 hours. The embodiments illustrated in FIG. 11D correspond to procedure set forth in Example 11D.
Figure 12A:
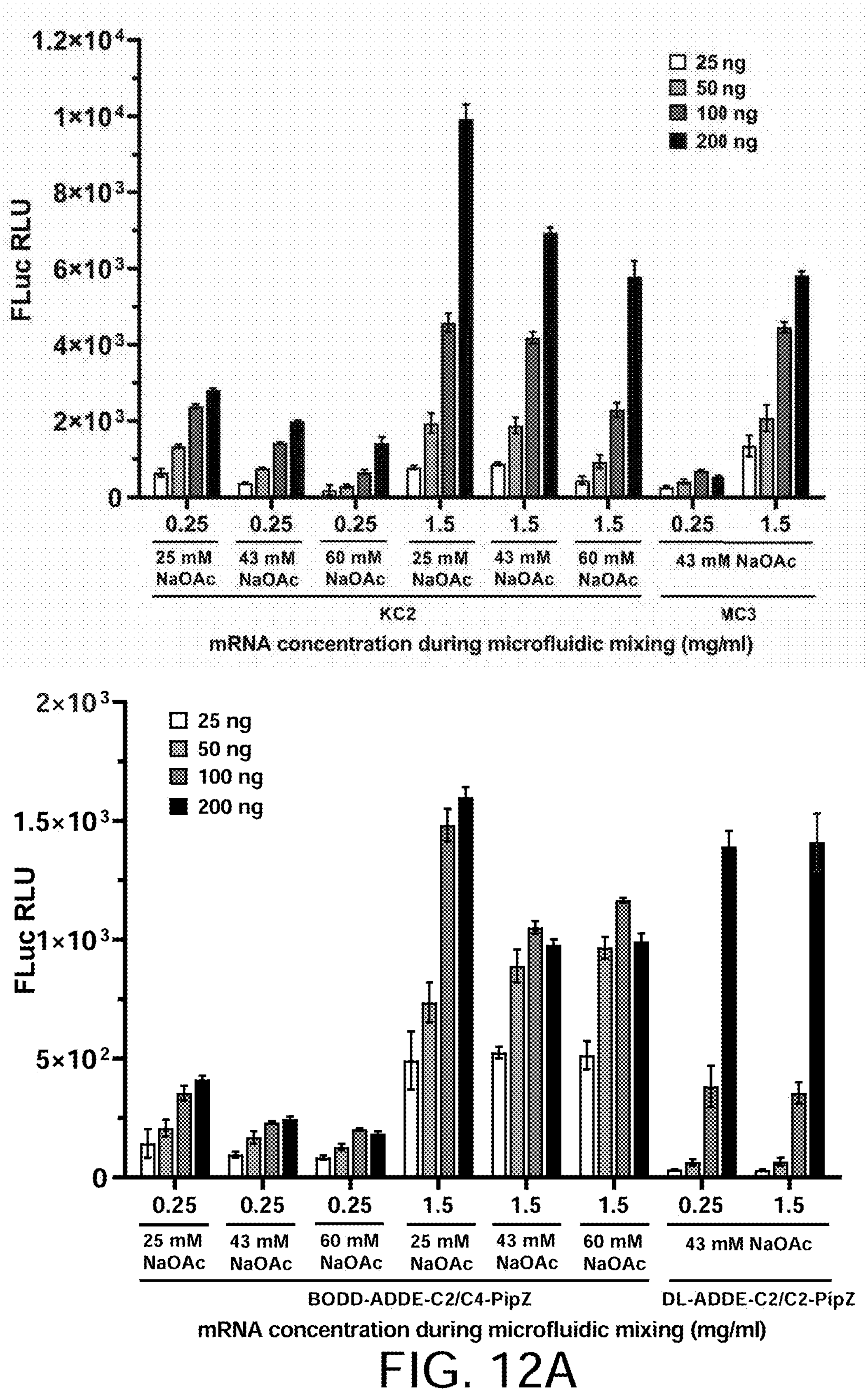
FIG. 12A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 12A correspond to procedure set forth in Example 12A.
Figure 12B:
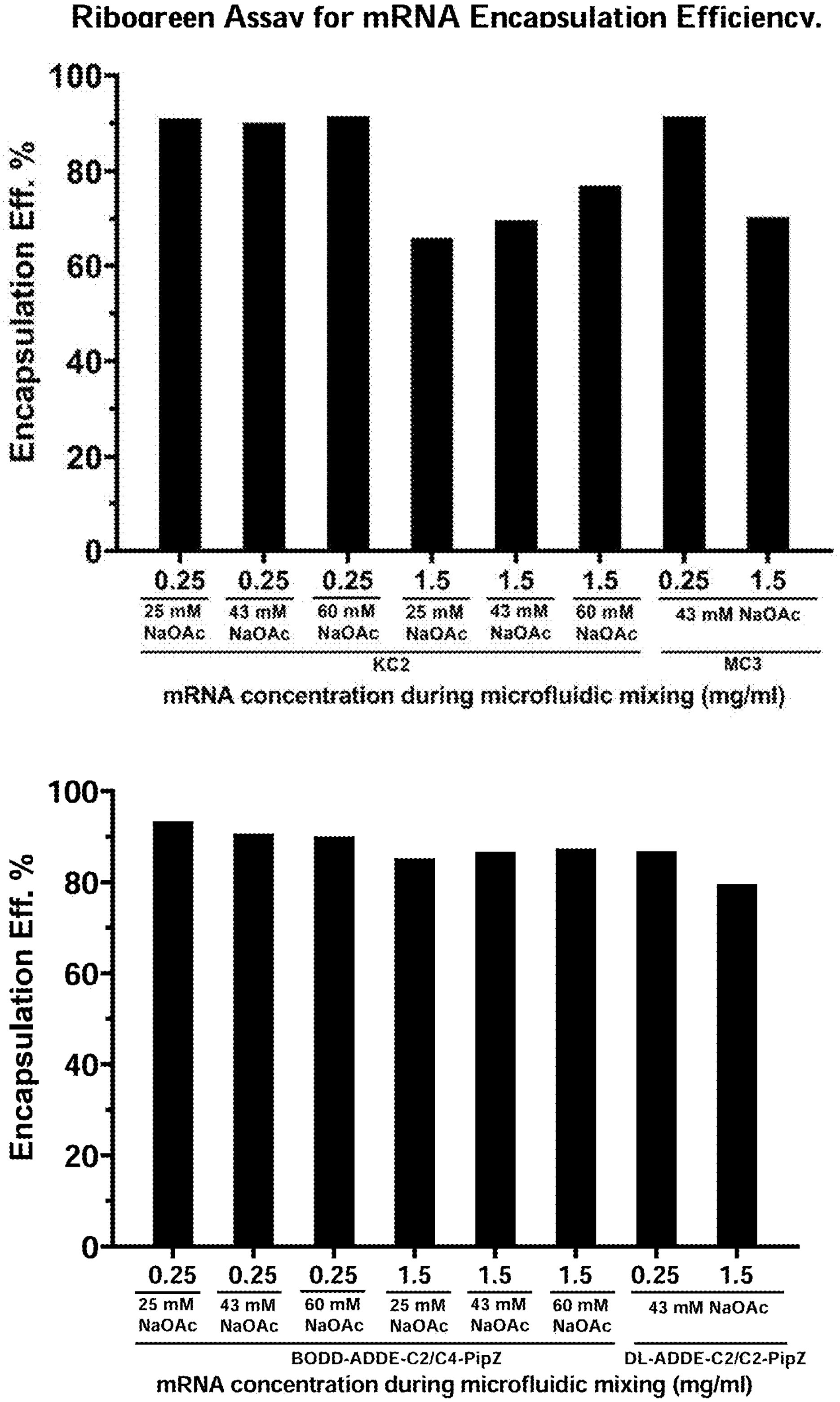
FIG. 12B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 12B correspond to procedure set forth in Example 12B.
Figure 12C:
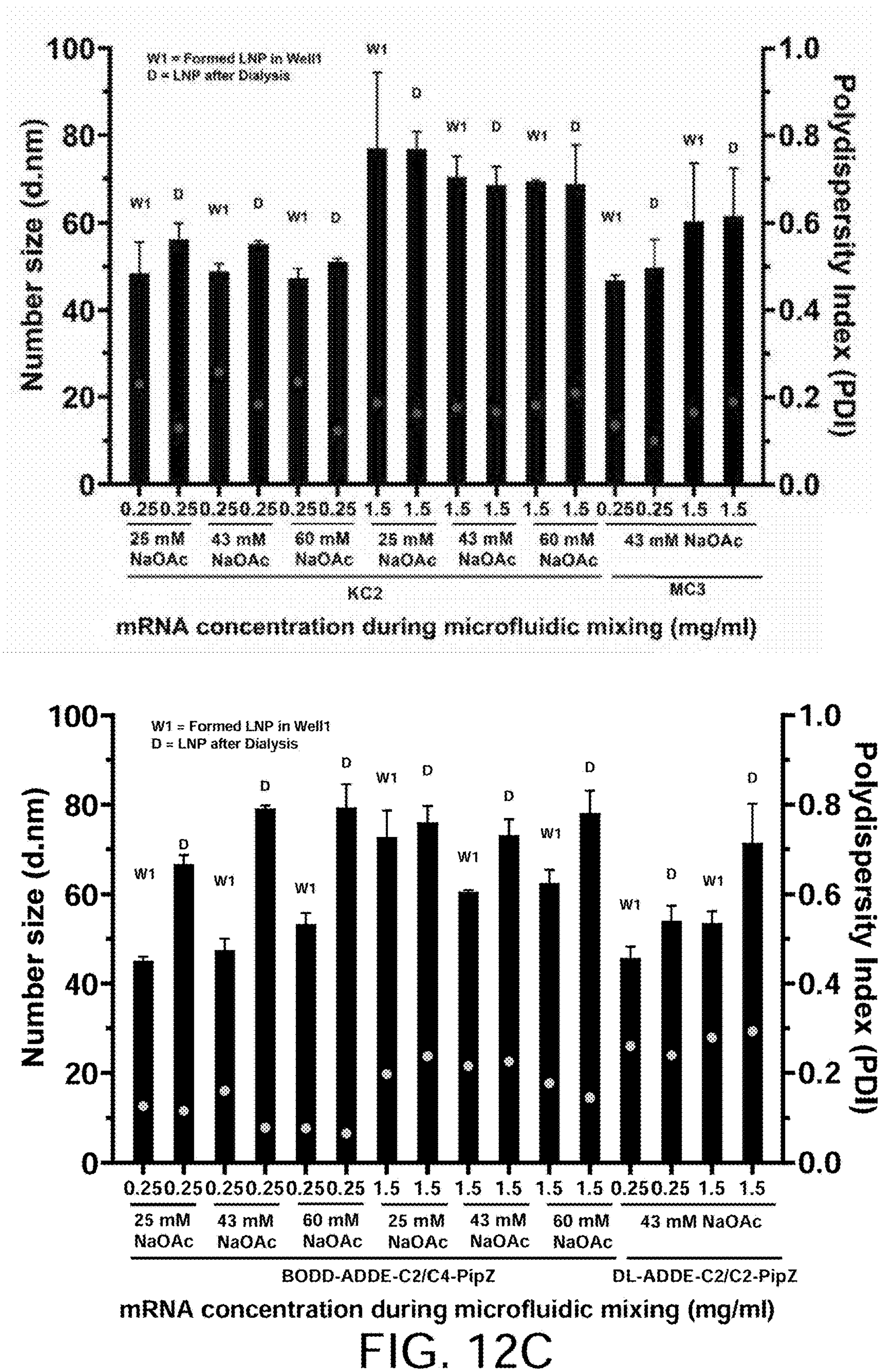
FIG. 12C: Dynamic Light Scattering for LNP Size (white dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 12C correspond to procedure set forth in Example 12C.
Figure 13A:
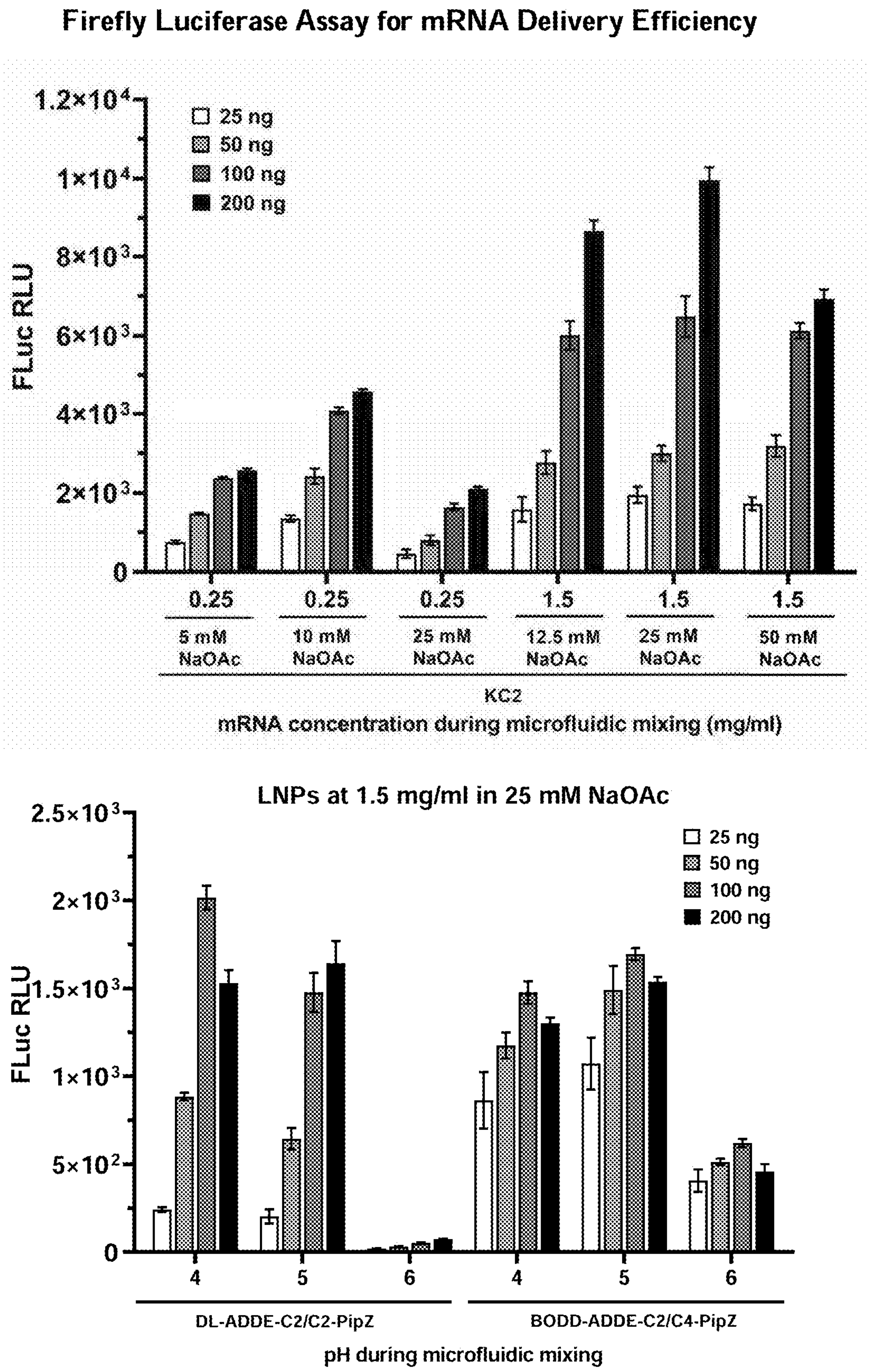
FIG. 13A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 13A correspond to procedure set forth in Example 13A.
Figure 13B:
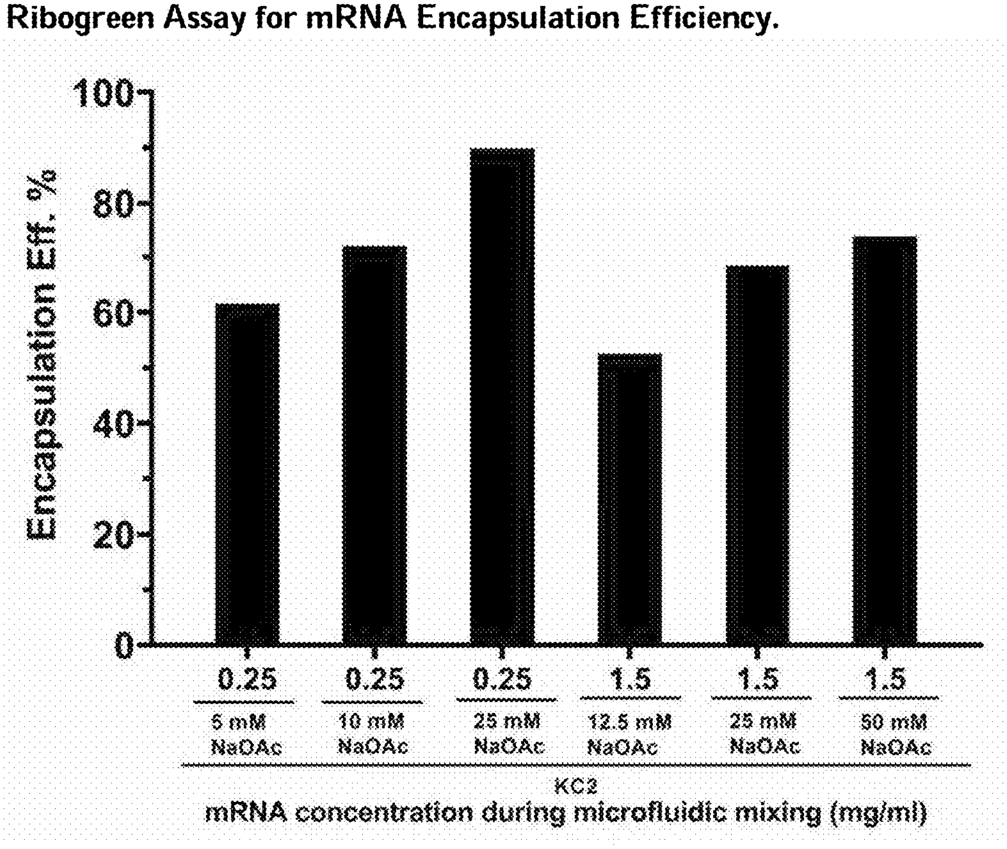
FIG. 13B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 13B correspond to procedure set forth in Example 13B.
Figure 13B:
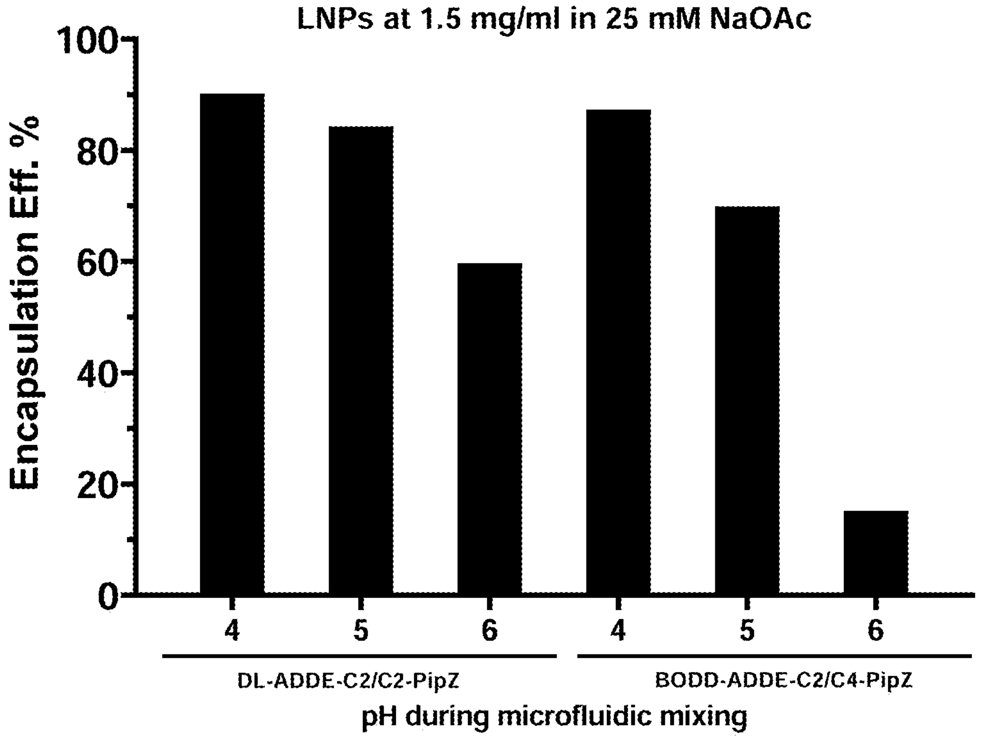
Figure 13C:
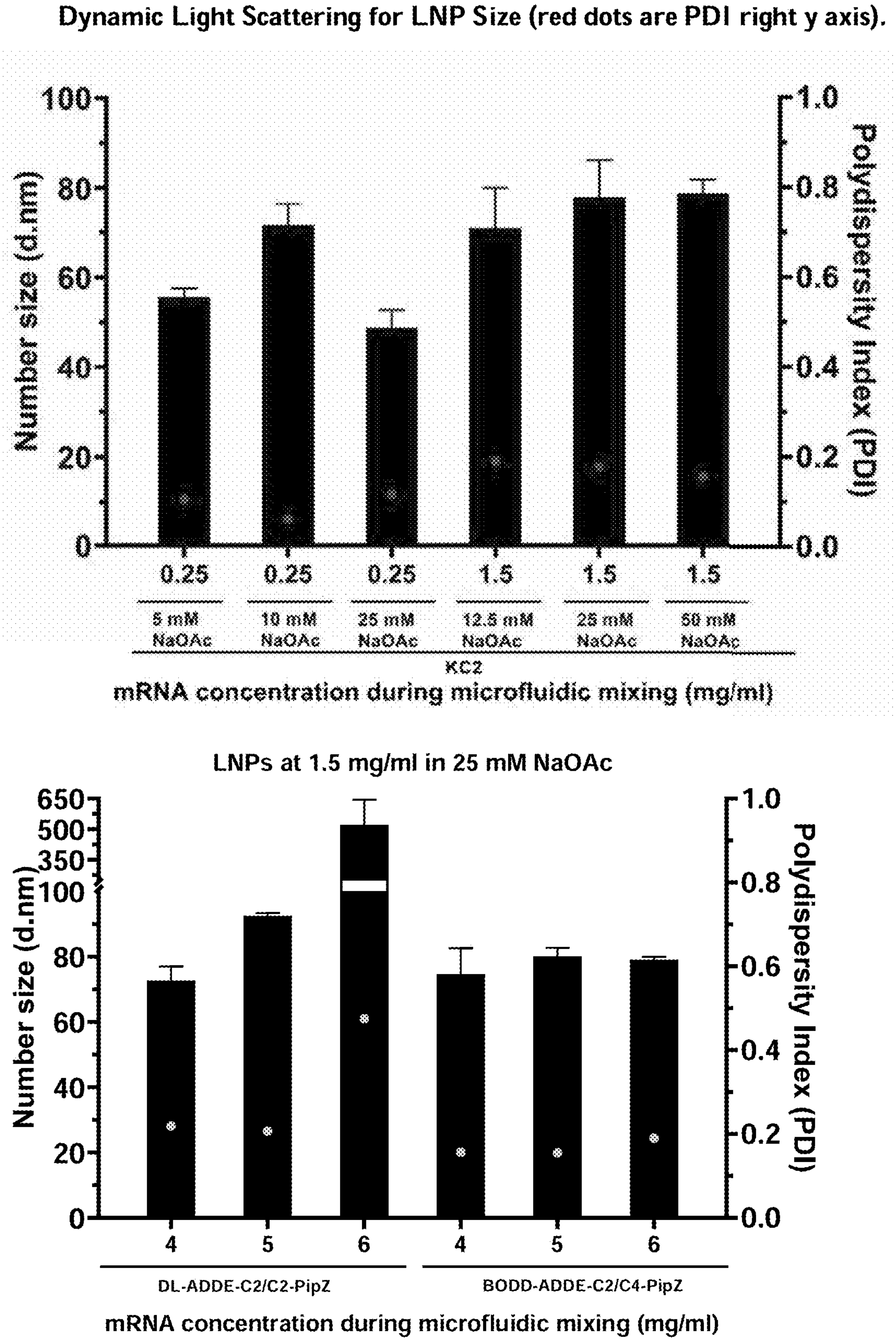
FIG. 13C: Dynamic Light Scattering for LNP Size (white dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 13C correspond to procedure set forth in Example 13C.
Figure 14A:
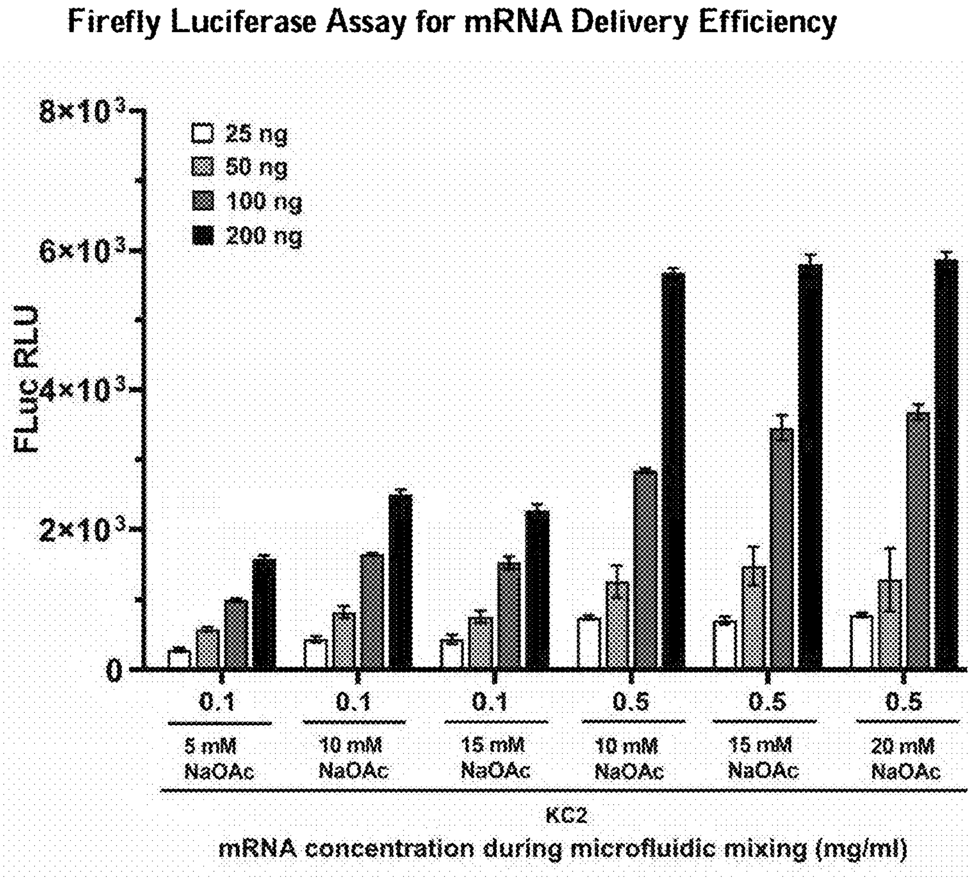
FIG. 14A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi- Mode Reader (Biotek) to read luminescence. The embodiments illustrated in FIG. 14A correspond to procedure set forth in Example 14A.
Figure 14A:
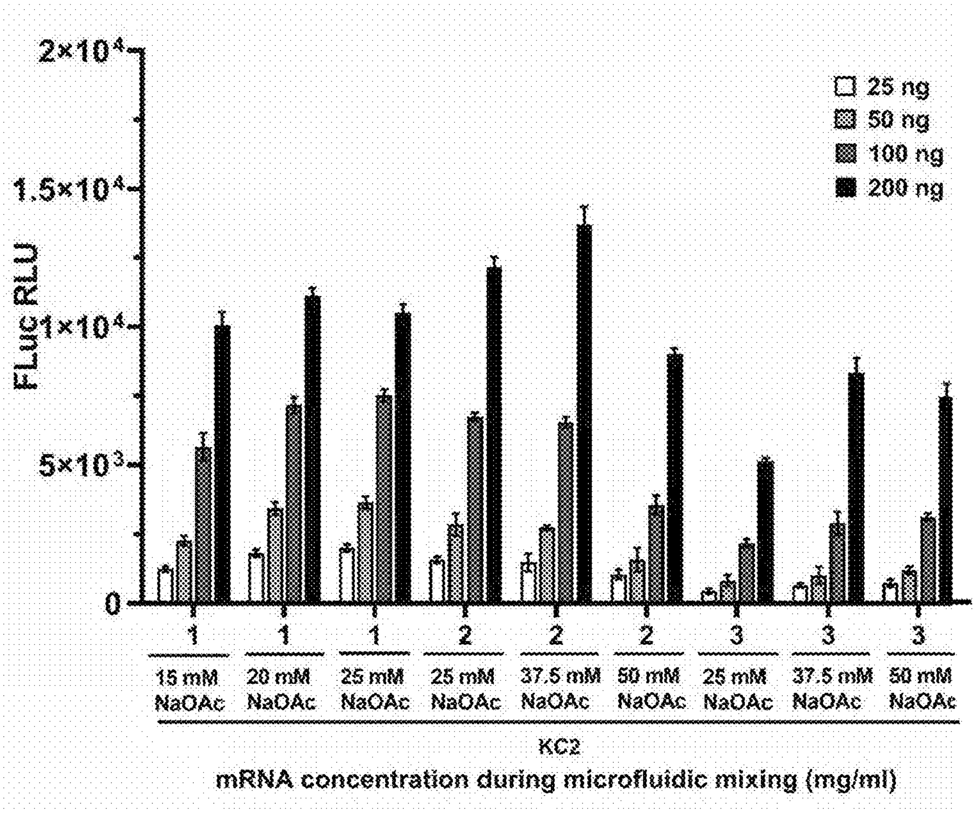
Figure 14B:
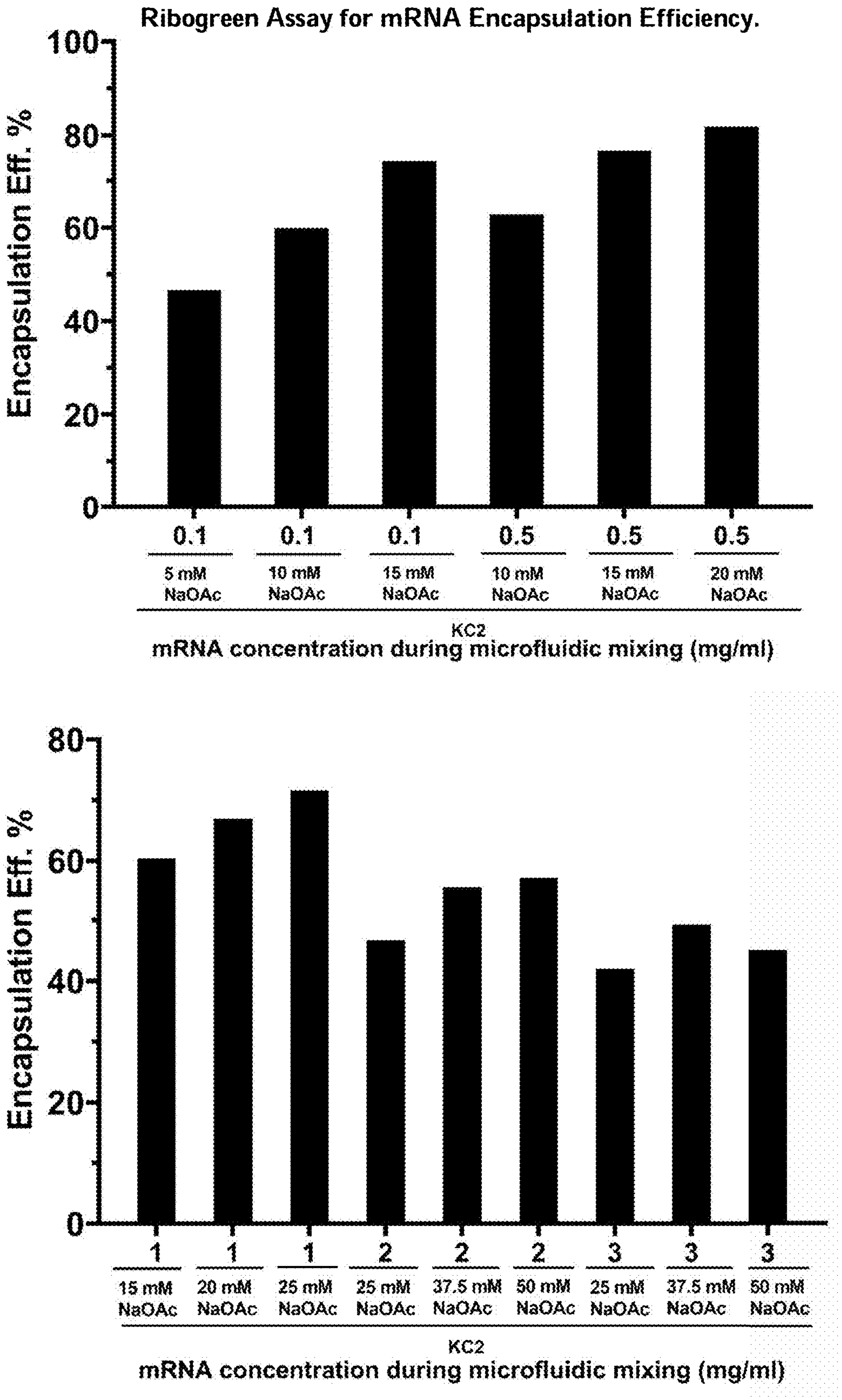
FIG. 14B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 14B correspond to procedure set forth in Example 14B.
Figure 14C:
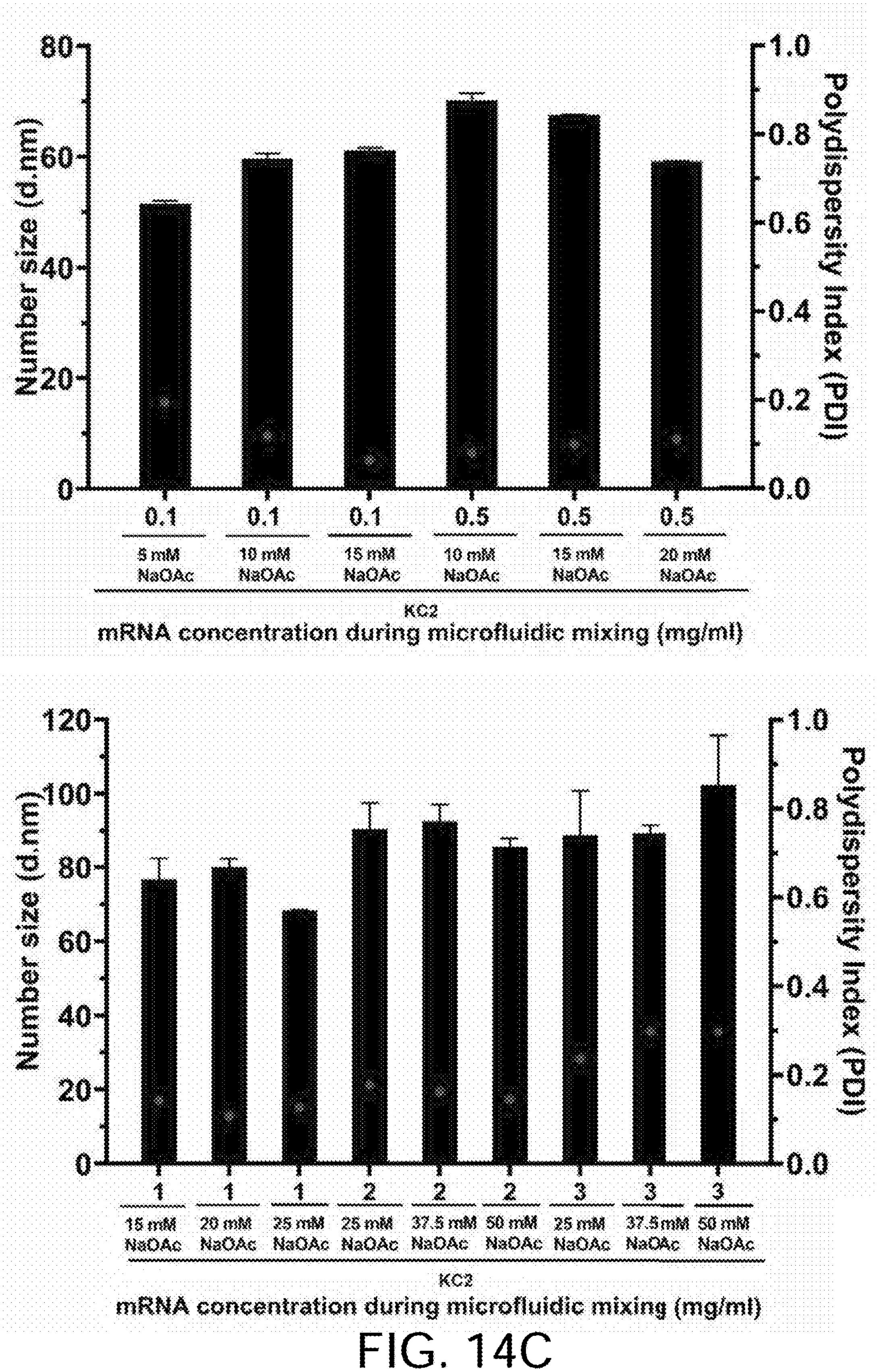
FIG. 14C: Dynamic Light Scattering for LNP Size (white dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 14C correspond to procedure set forth in Example 14C.
Figures 15A, 15B:
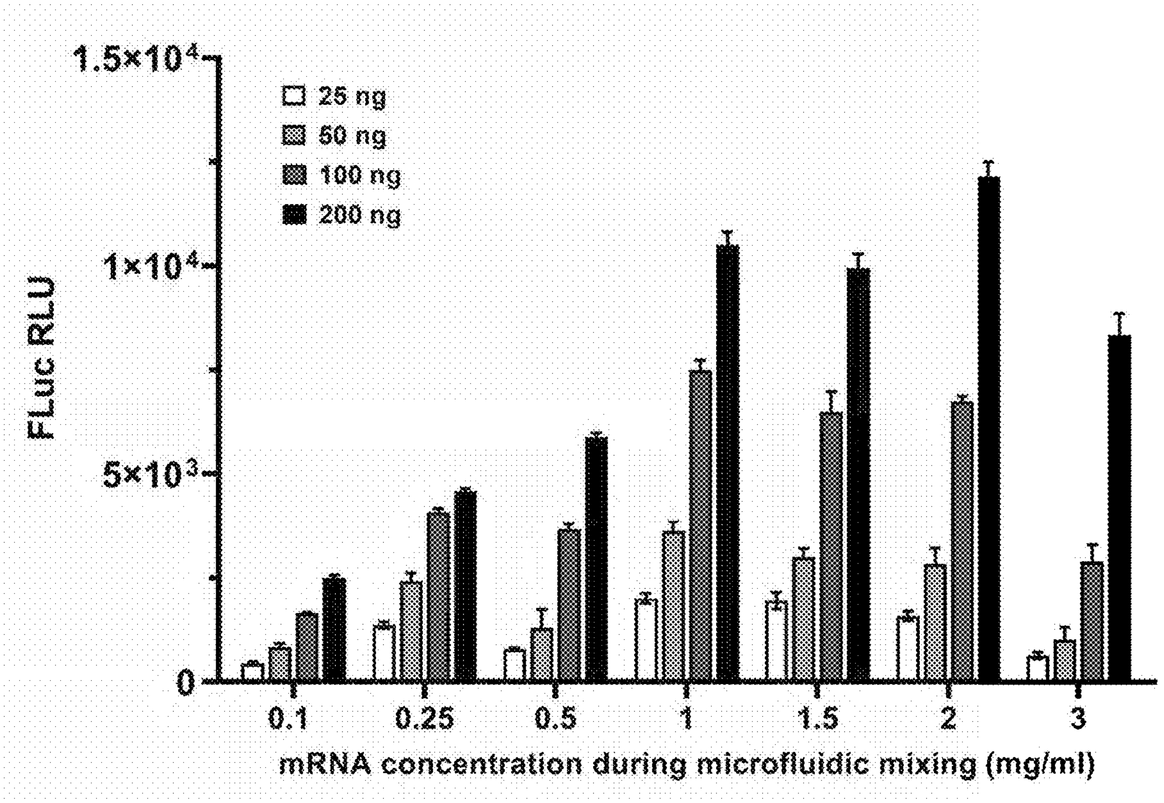
FIG. 15A: Table of initial mRNA concentration, initial lipid mix concentration, initial sodium acetate concentration that generates the highest potency for each particular initial mRNA concentration tested in Examples 13 and 14 (FIGS. 13 and 14). The embodiments illustrated in FIG. 15A correspond to the procedure set forth in Example 15A.
FIG. 15B. Firefly Luciferase Assay for mRNA Delivery Efficiency combining examples 13 and 14 for optimal sodium acetate concentration at each particular initial mRNA concentration. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The embodiments illustrated in FIG. 15B correspond to the procedure set forth in Example 15B.
Figure 15C:
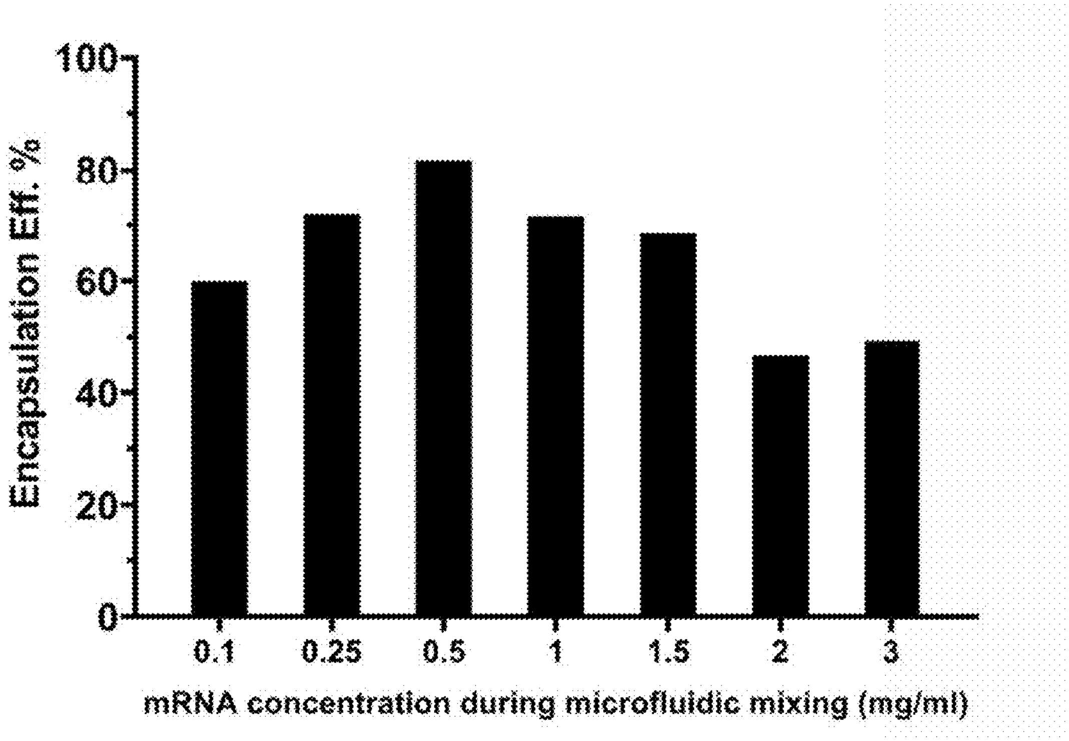
FIG. 15C: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528). The embodiments illustrated in FIG. 15C correspond to the procedure set forth in Example 15C.
Figure 15D:
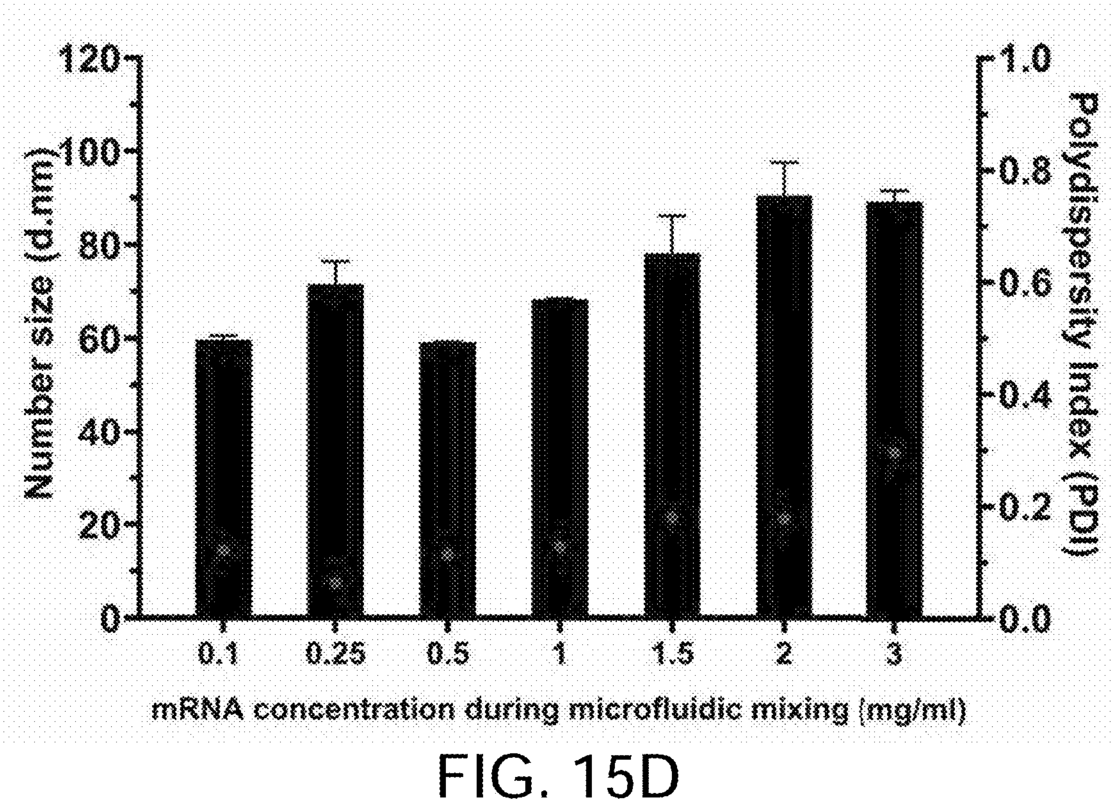
FIG. 15D: Dynamic Light Scattering for LNP Size (white dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The embodiments illustrated in FIG. 15D correspond to the procedure set forth in Example 15D.
Figure 16A:
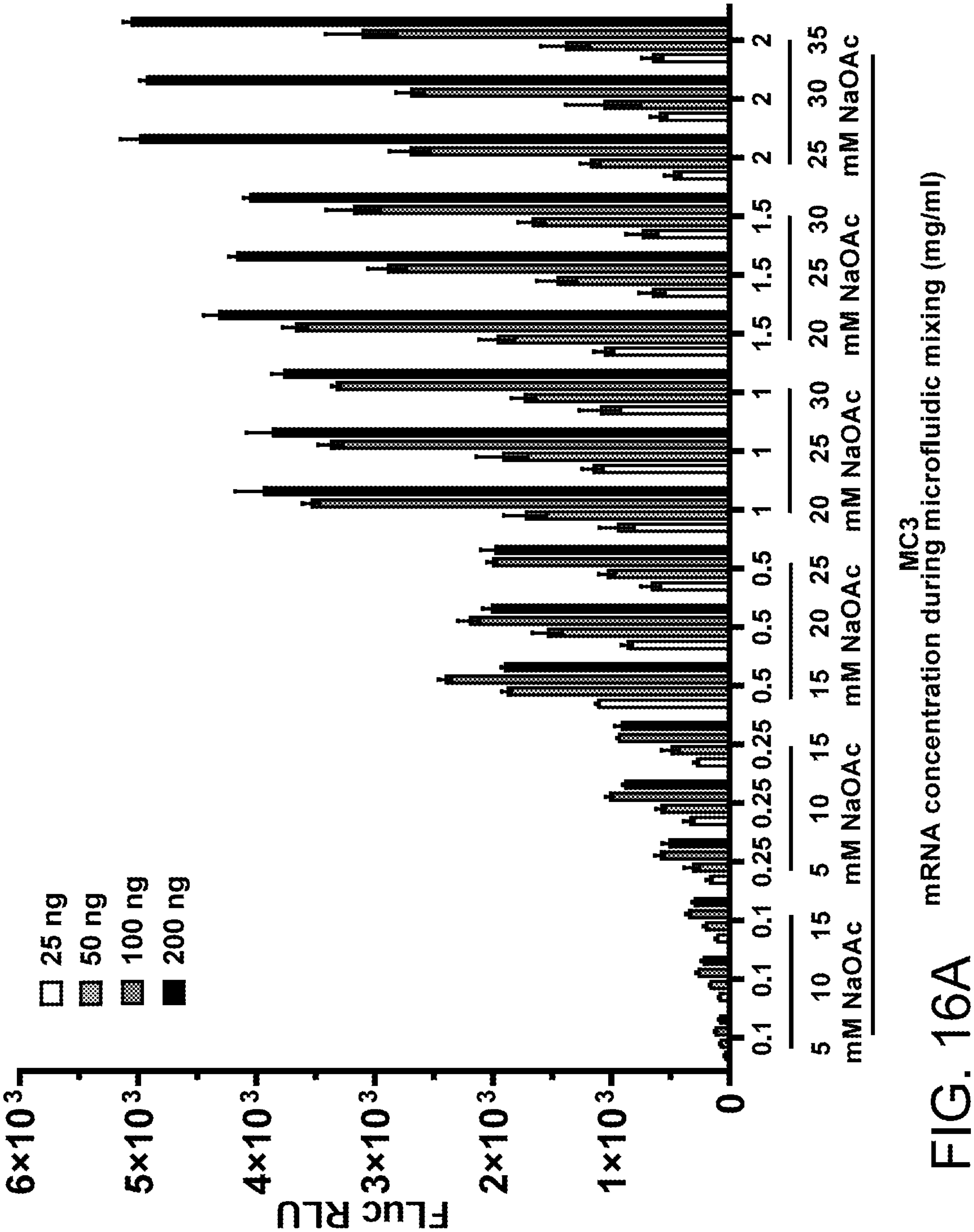
FIG. 16A: Firefly Luciferase Assay for mRNA Delivery Efficiency as set forth in Example 16.
Figure 16B:
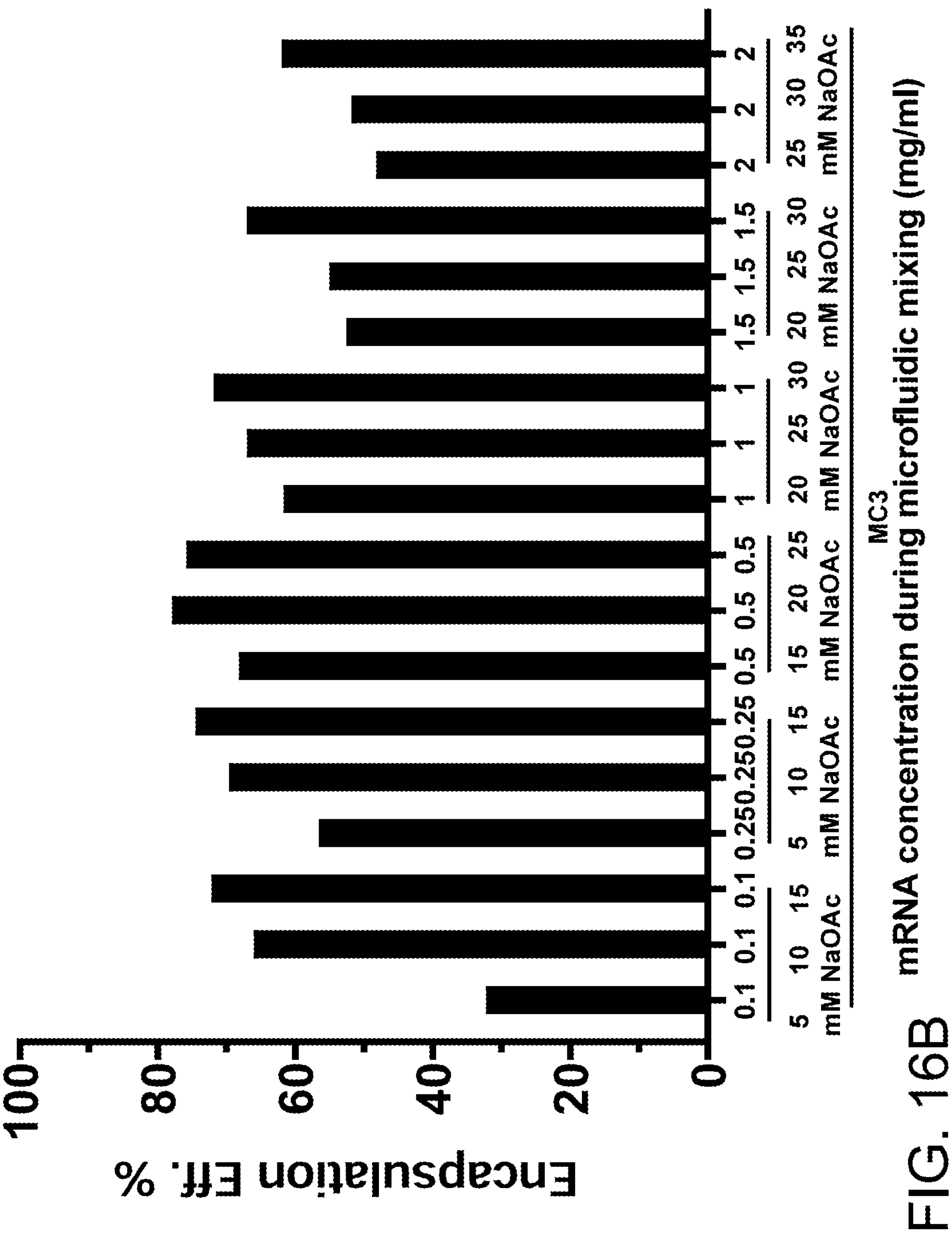
FIG. 16B: Ribogreen Assay for mRNA Encapsulation Efficiency as set forth in Example 16.
Figure 16C:
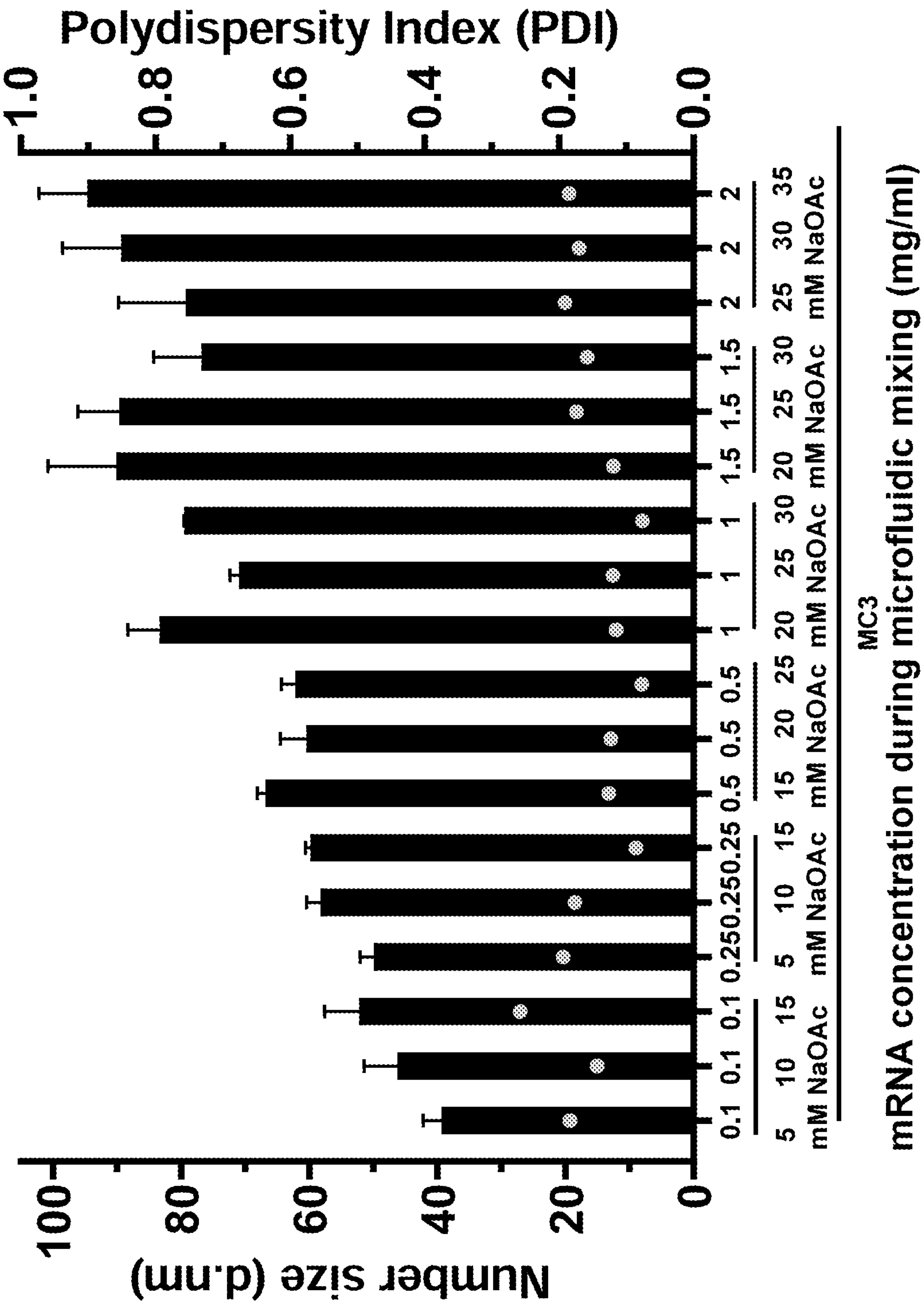
FIG. 16C: Dynamic Light Scattering for LNP Size (white dots are PDI right y axis) as set forth in Example 16.
Figure 17A:
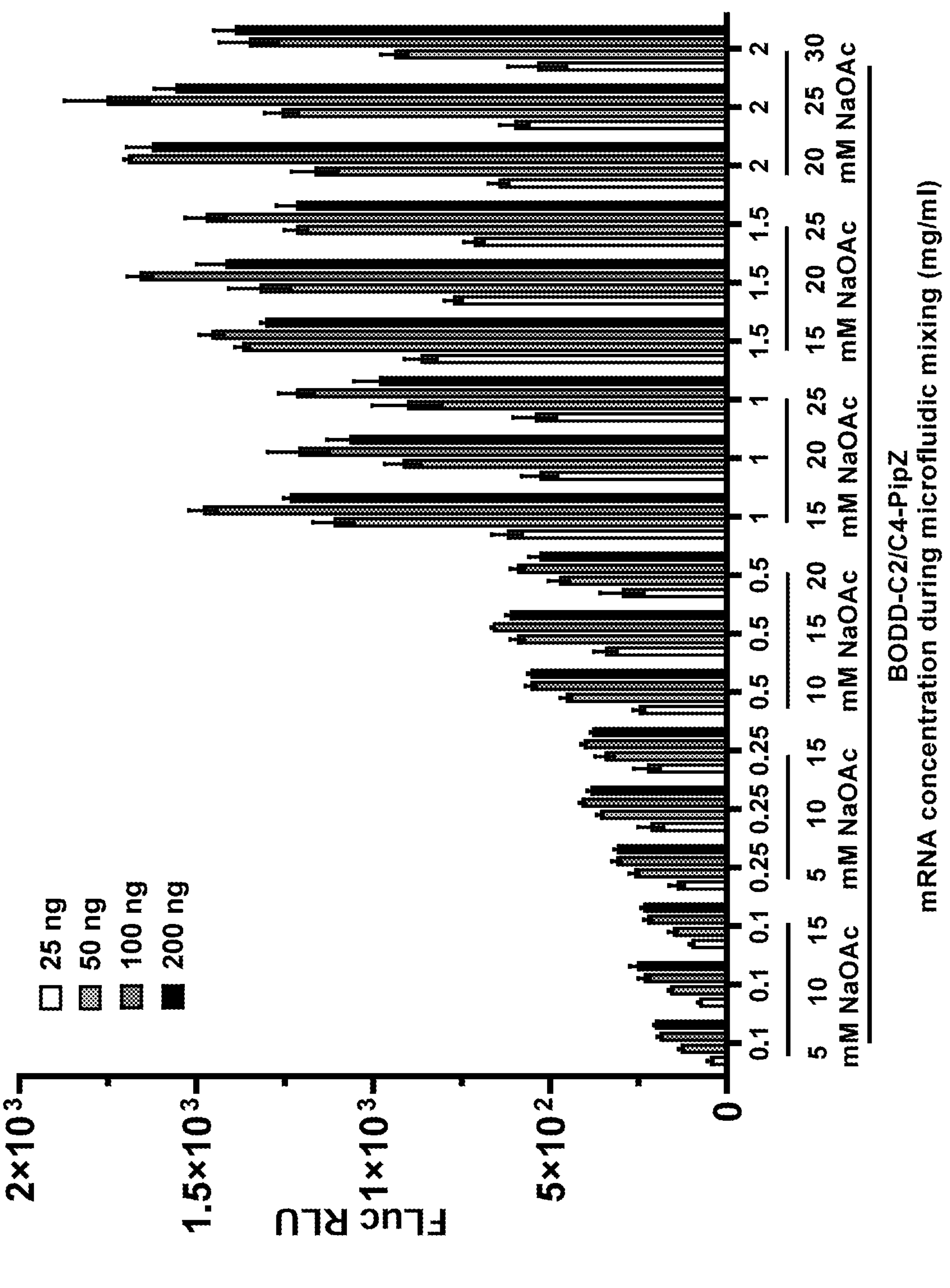
FIG. 17A: Firefly Luciferase Assay for mRNA Delivery Efficiency as set forth in Example 17.
Figure 17B:
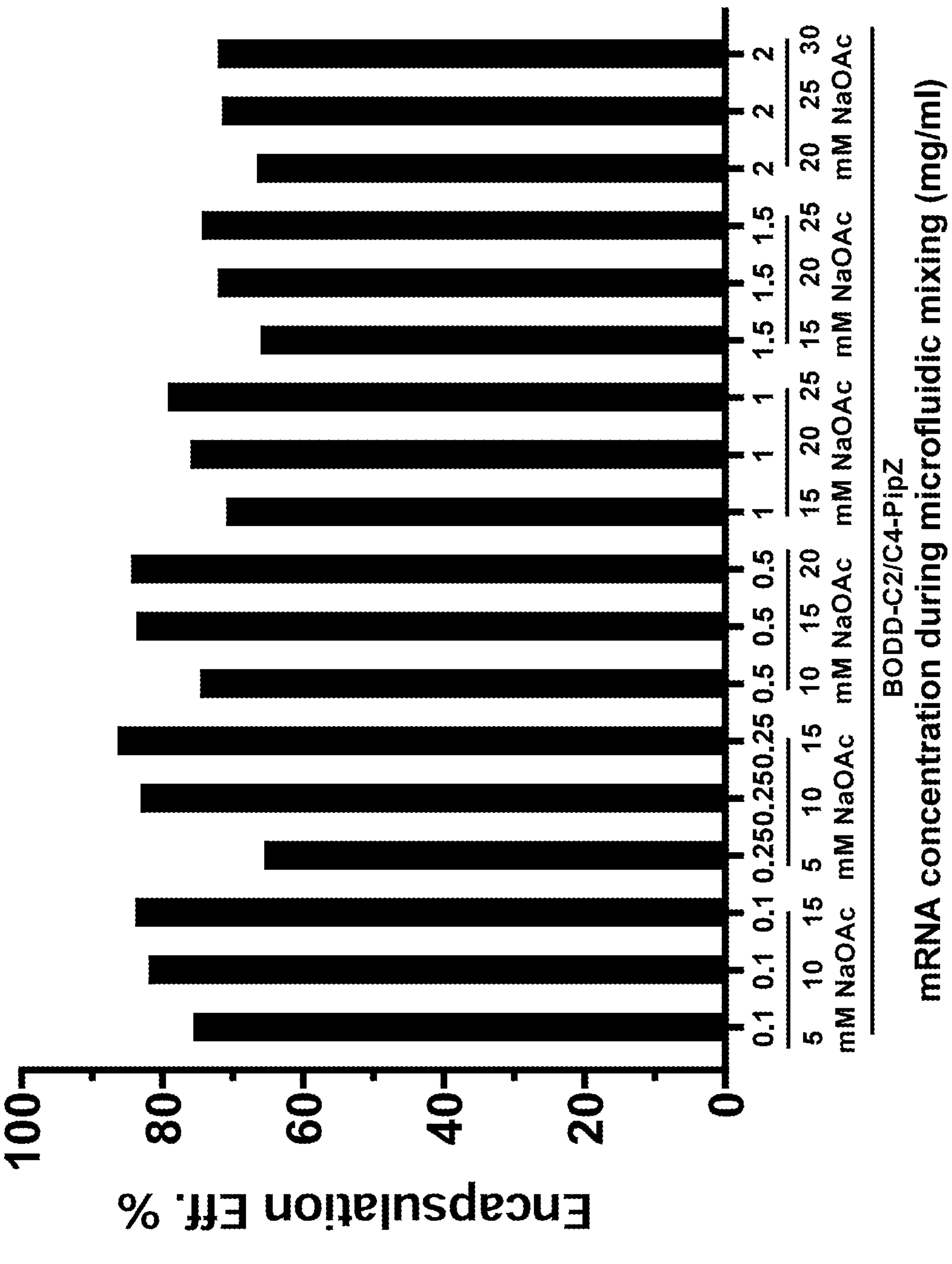
FIG. 17B: Ribogreen Assay for mRNA Encapsulation Efficiency as set forth in Example 17.
Figure 17C:
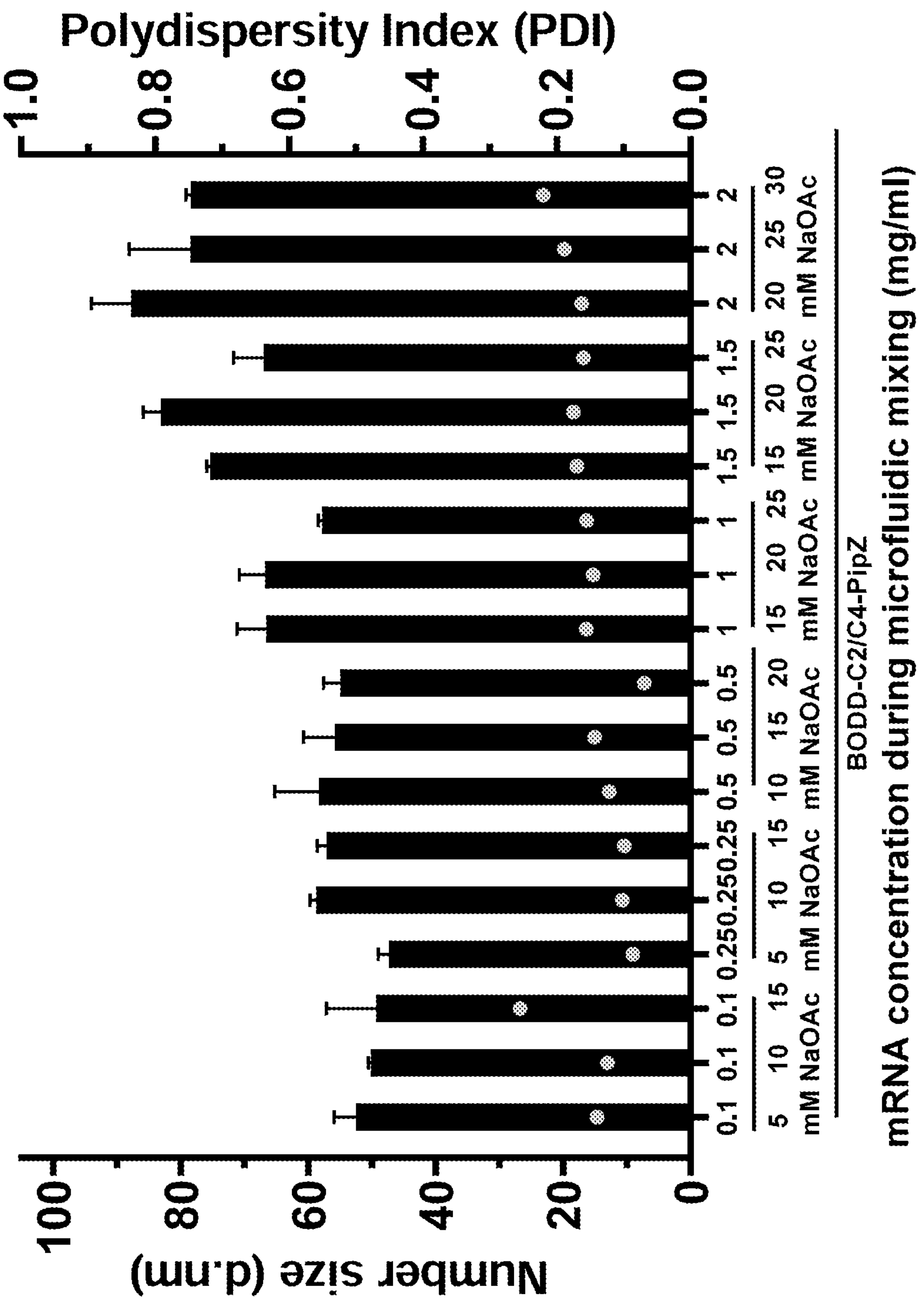
FIG. 17C: Dynamic Light Scattering for LNP Size (white dots are PDI right y axis) as set forth in Example 17.
Figure 18A:
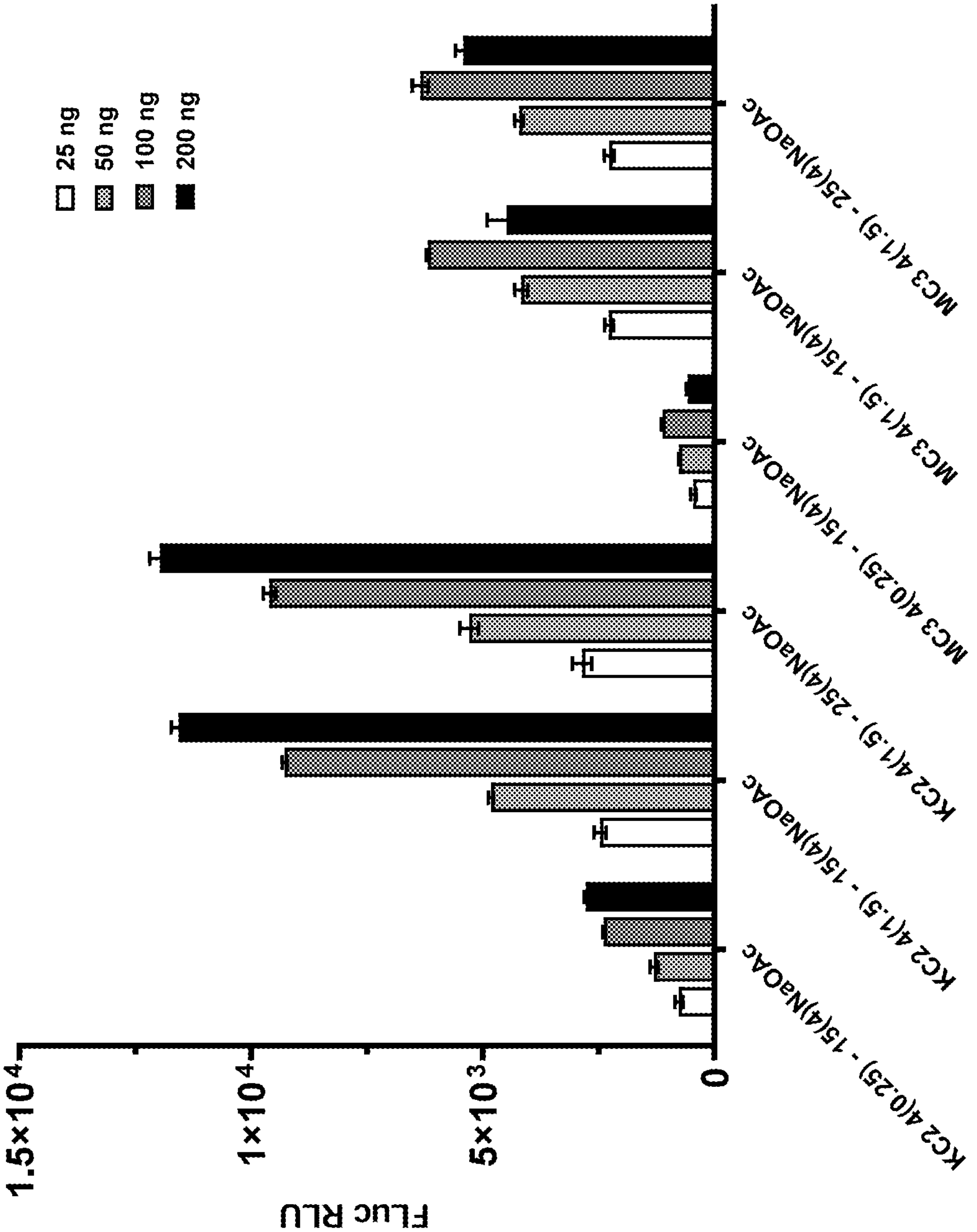
FIG. 18A: Firefly Luciferase Assay for mRNA Delivery Efficiency for known ionizable lipids as set forth in Example 18.
Figure 18B:
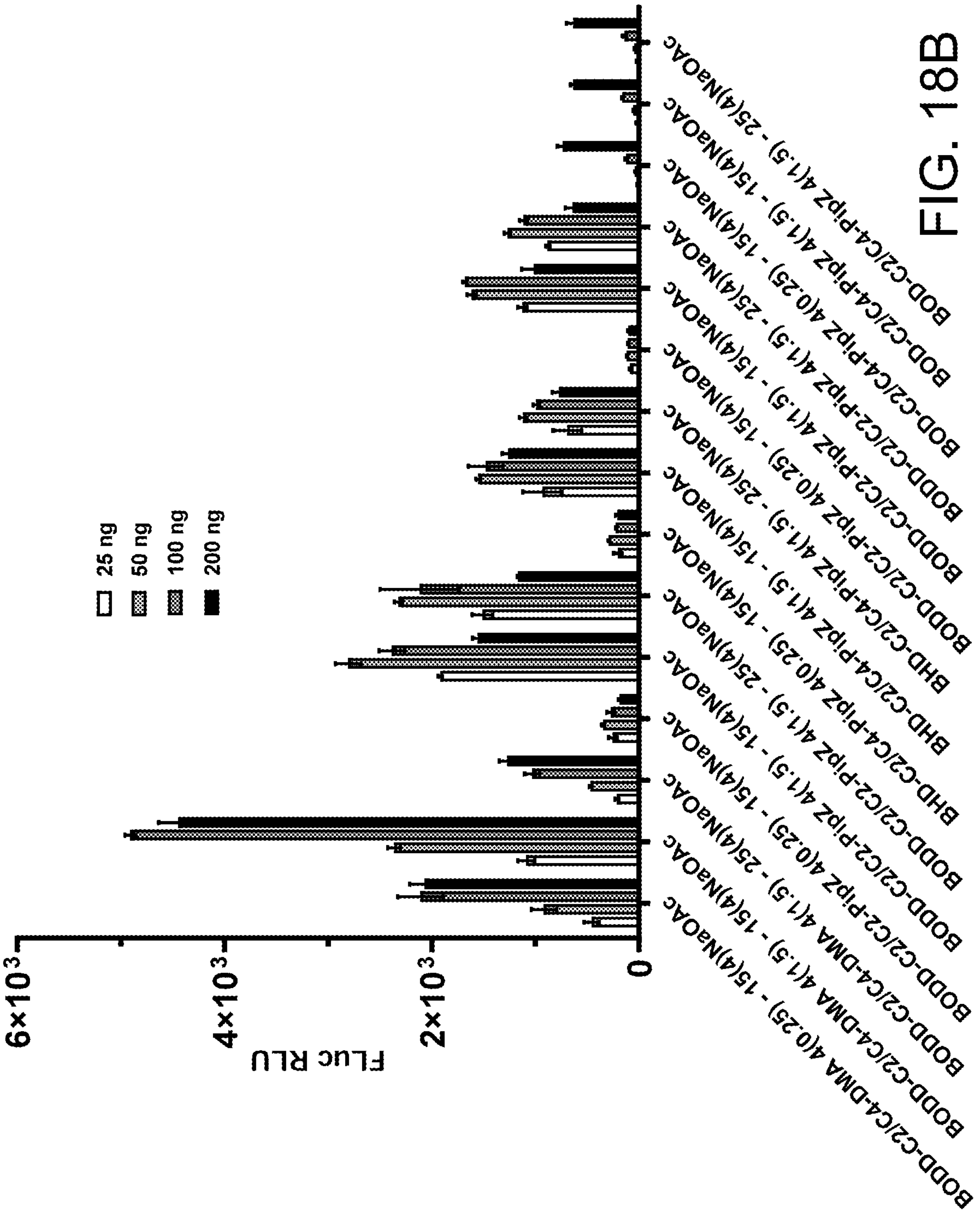
FIG. 18B: Firefly Luciferase Assay for mRNA Delivery Efficiency for illustrative ionizable lipids of the invention as set forth in Example 18.
Figure 18C:
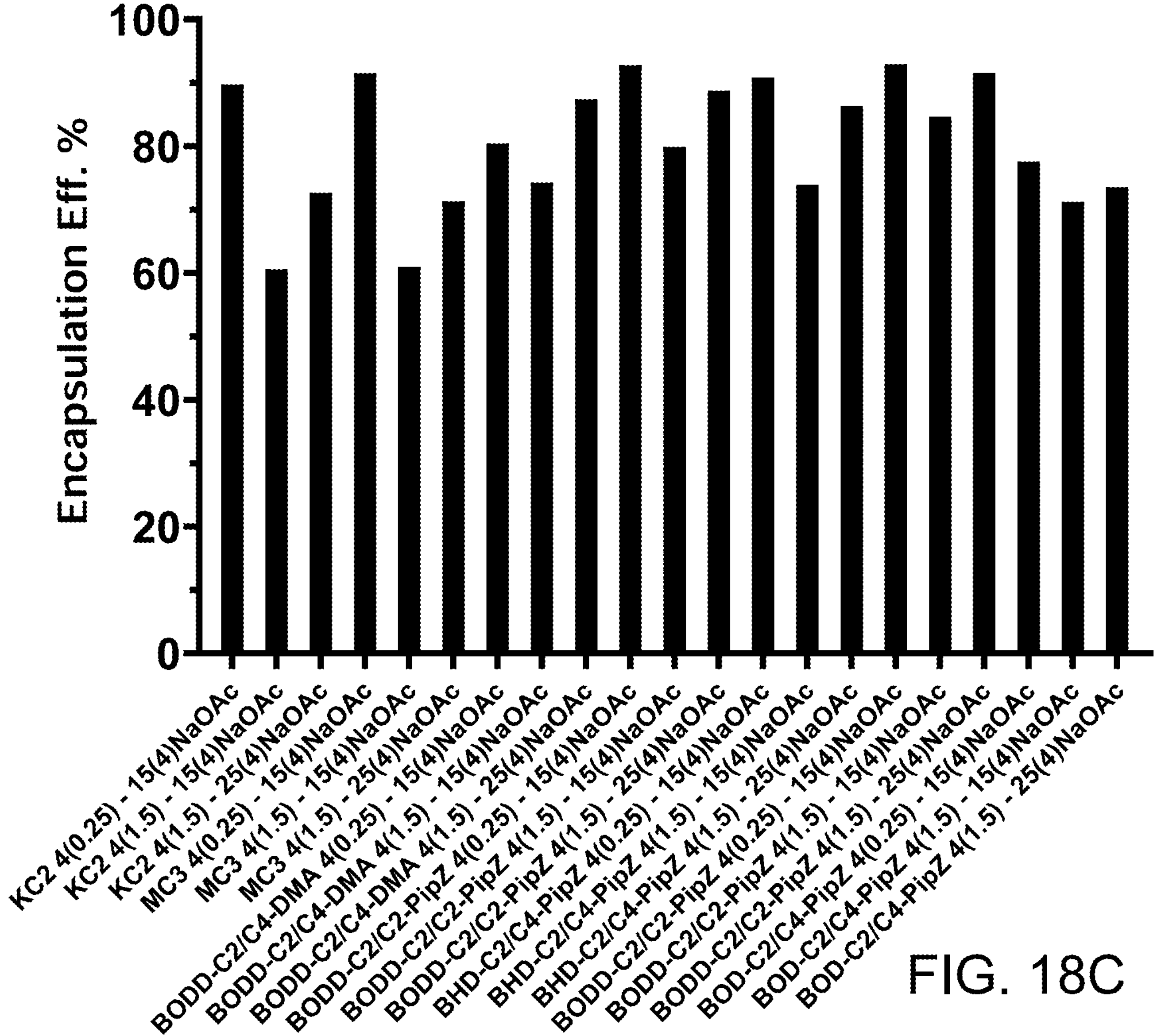
FIG. 18C: Ribogreen Assay for mRNA Encapsulation Efficiency as set forth in Example 18.
Figure 18D:
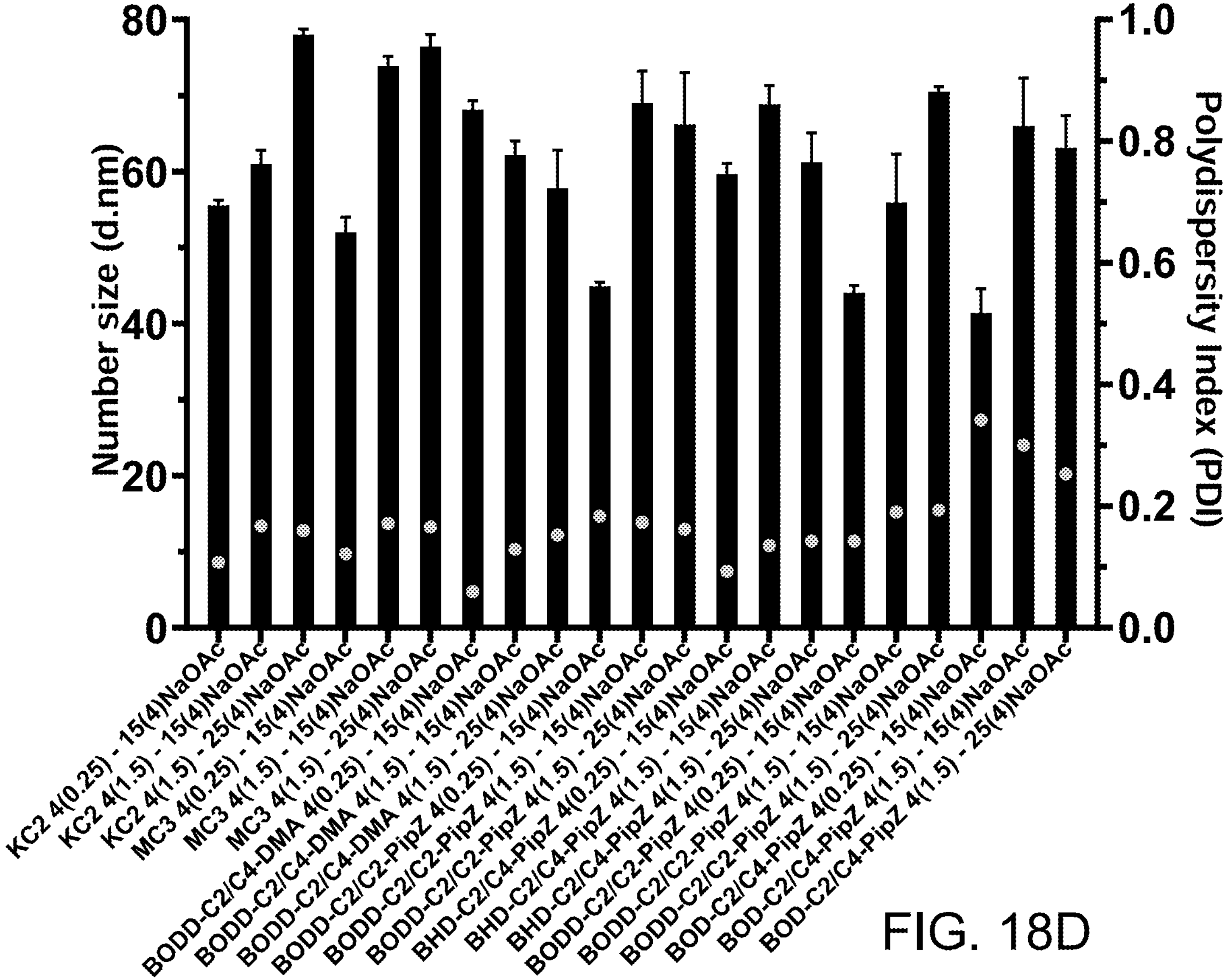
FIG. 18D: Dynamic Light Scattering for LNP Size (white dots are PDI right y axis) as set forth in Example 18.
Figure 19A:
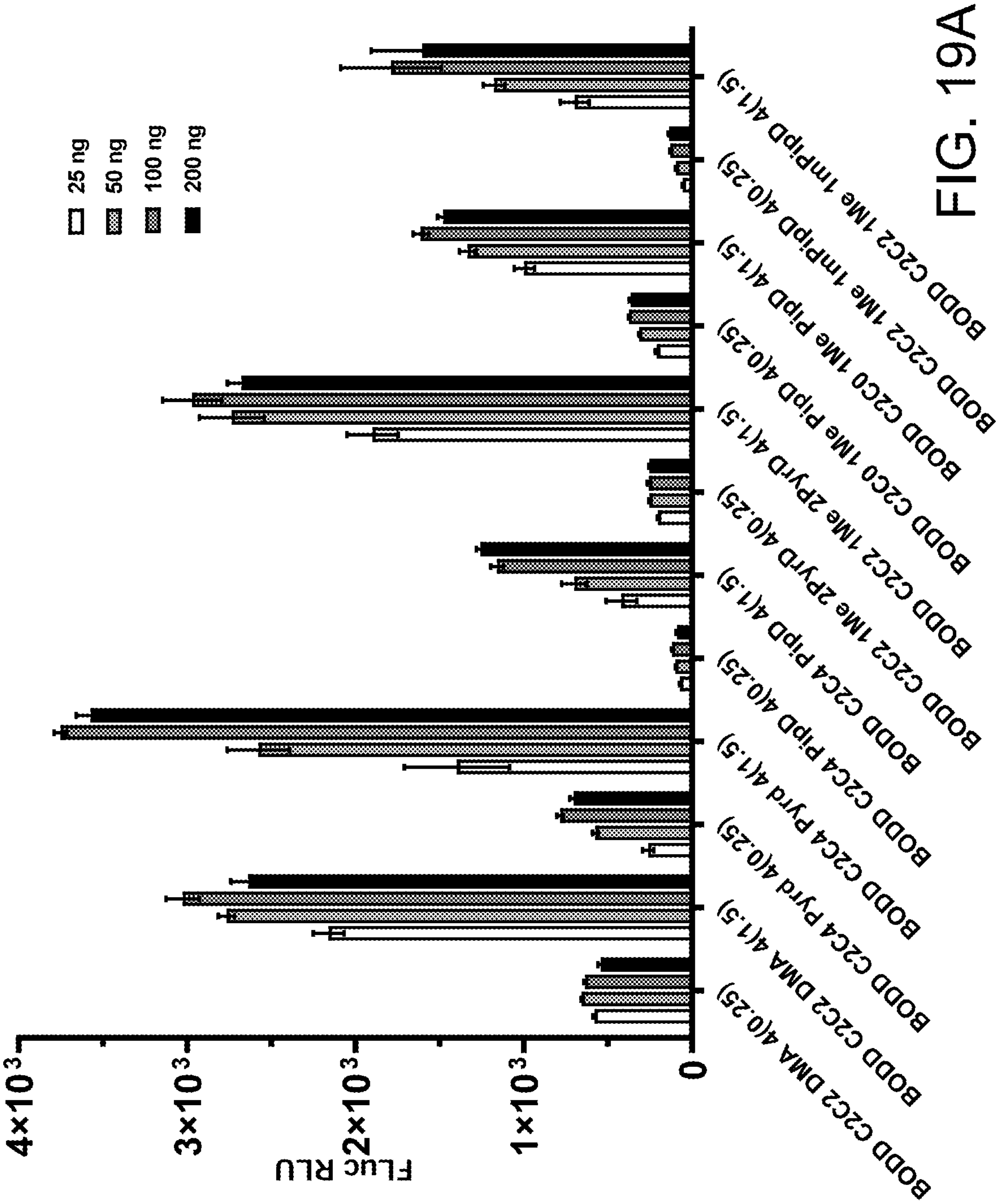
FIG. 19A: Firefly Luciferase Assay for mRNA Delivery Efficiency as set forth in Example 19.
Figure 19B:
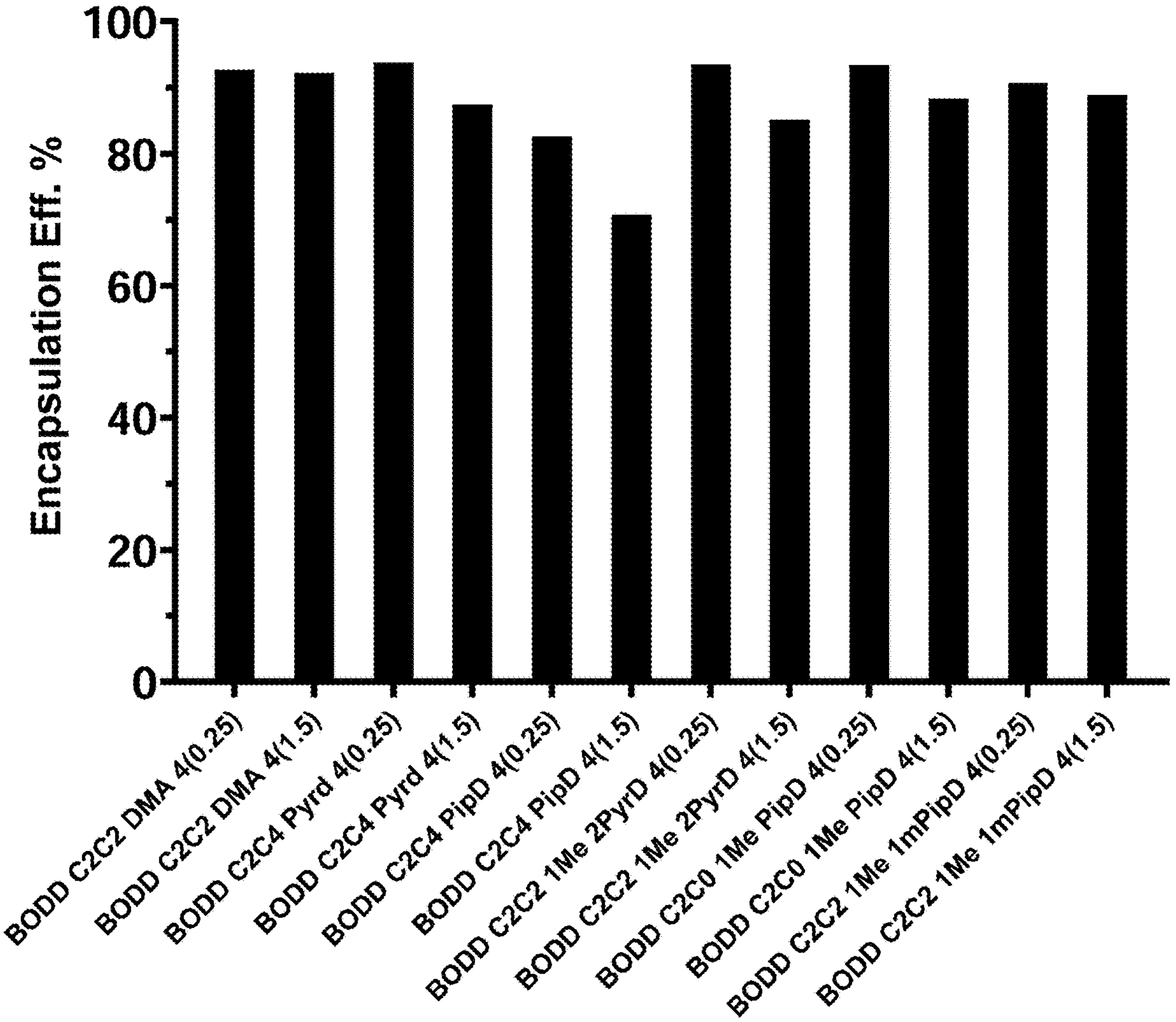
FIG. 19B: Ribogreen Assay for mRNA Encapsulation Efficiency as set forth in Example 19.
Figure 19C:
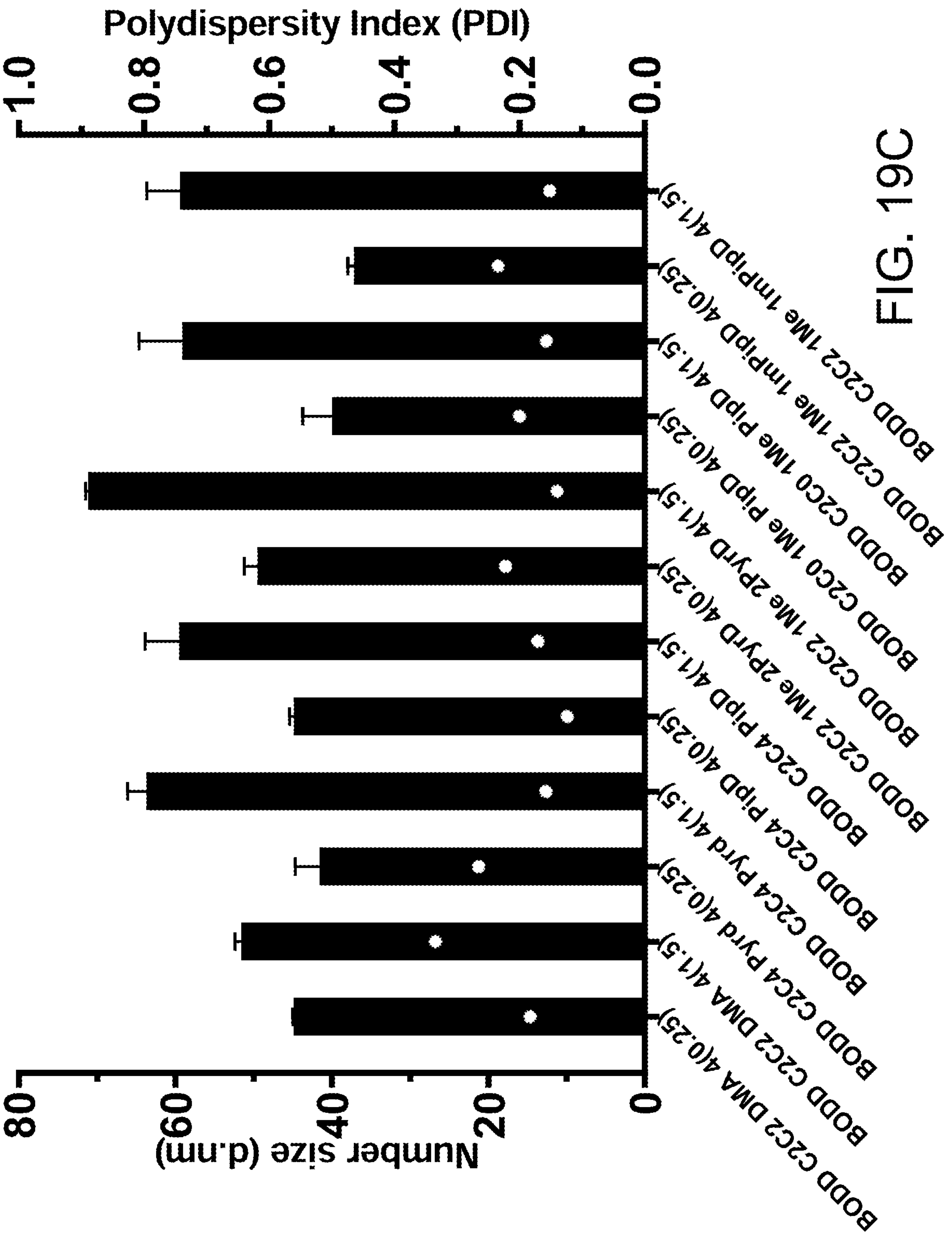
FIG. 19C: Dynamic Light Scattering for LNP Size (white dots are PDI right y axis) as set forth in Example 19.
Figure 20A:
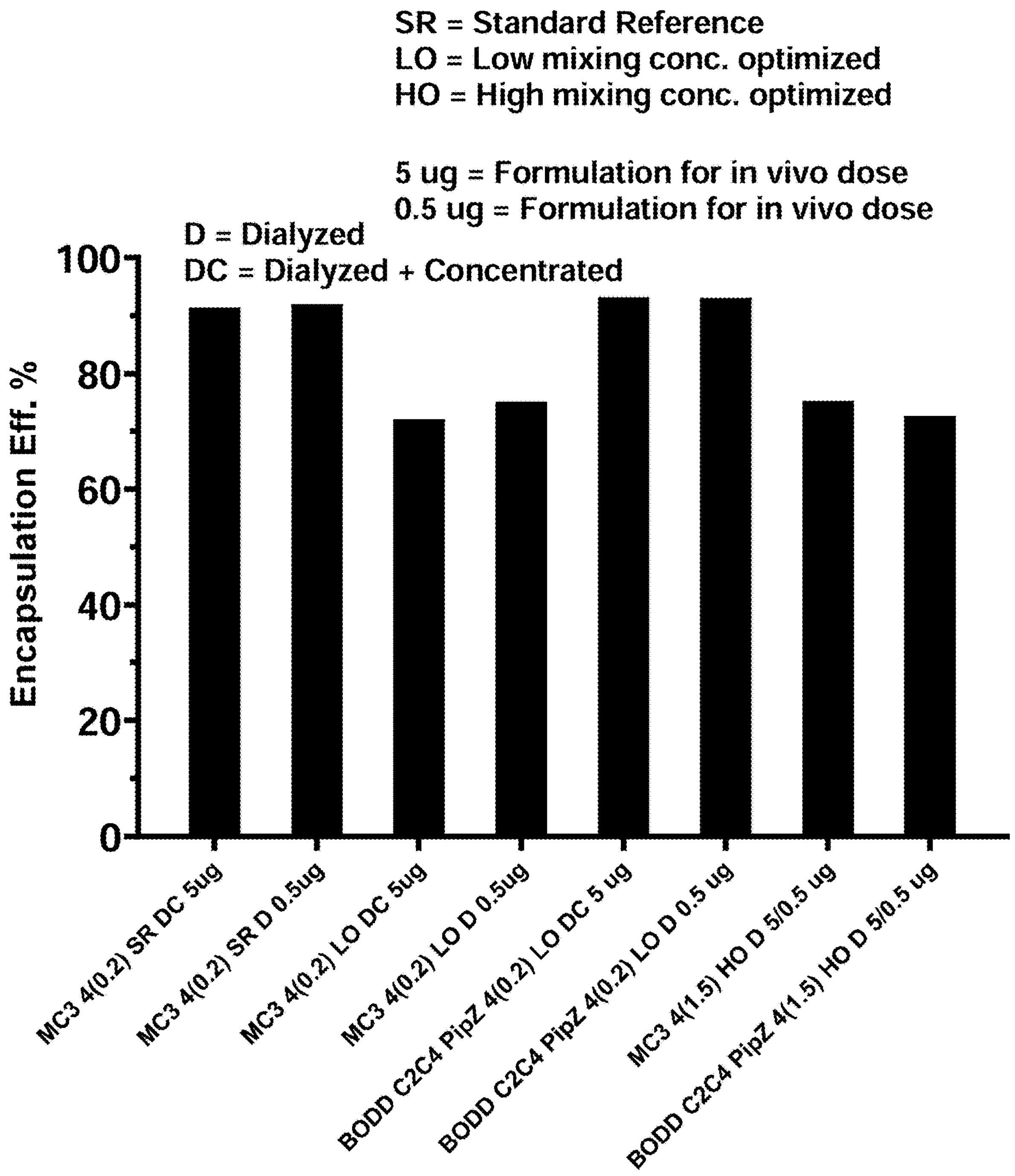
FIG. 20A: Ribogreen Assay for mRNA Encapsulation Efficiency as set forth in Example 20.
Figure 20B:
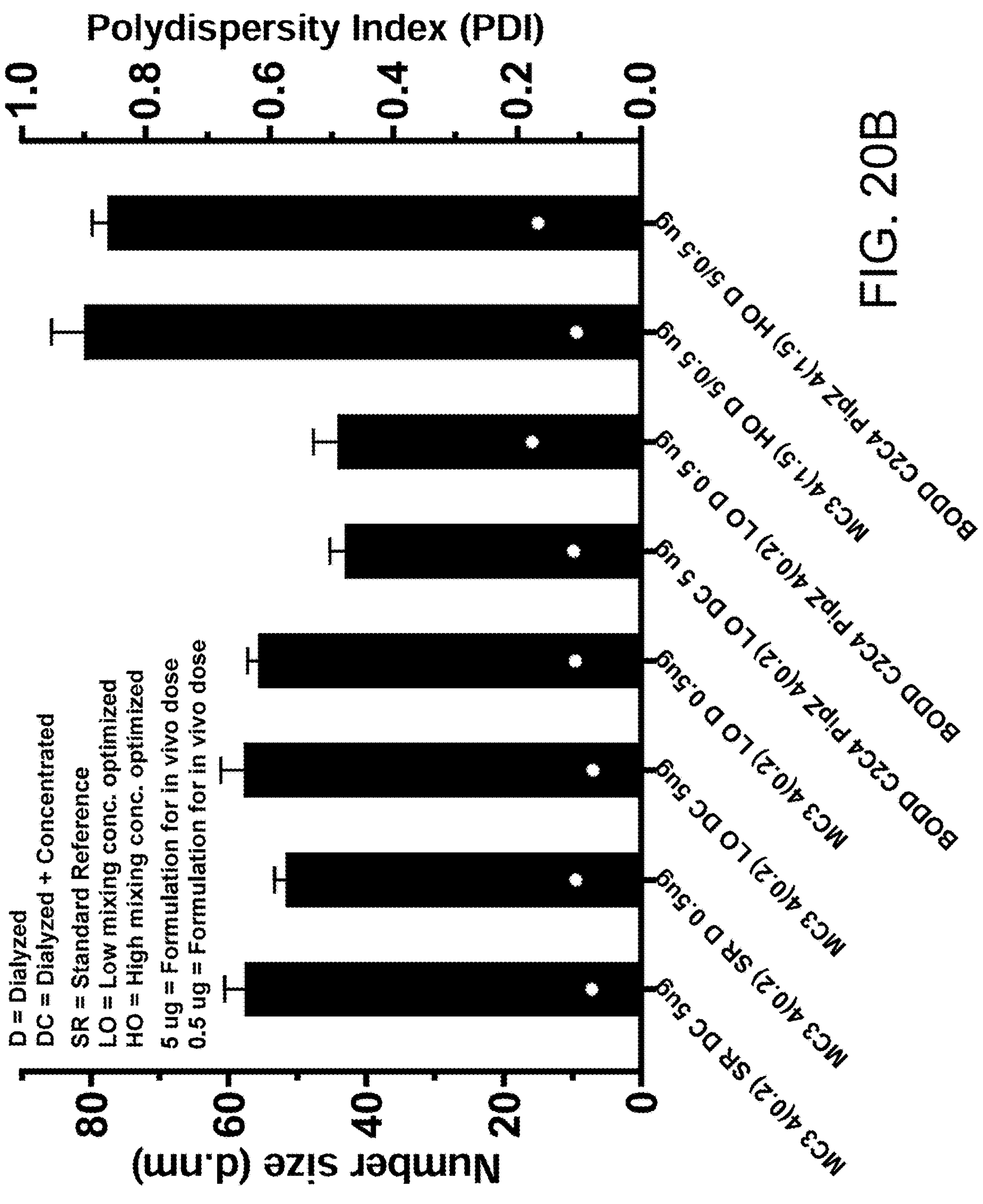
FIG. 20B: Dynamic Light Scattering for LNP Size (white dots are PDI right y axis) as set forth in Example 20.
Figure 20C:
FIG. 20C: In vivo Firefly Luciferase expression in IM administration after 4 hours as set forth in Example 20.
Figure 20D:
FIG. 20D: In vivo Firefly Luciferase expression in IM administration after 24 hours as set forth in Example 20.
Figure 20E:
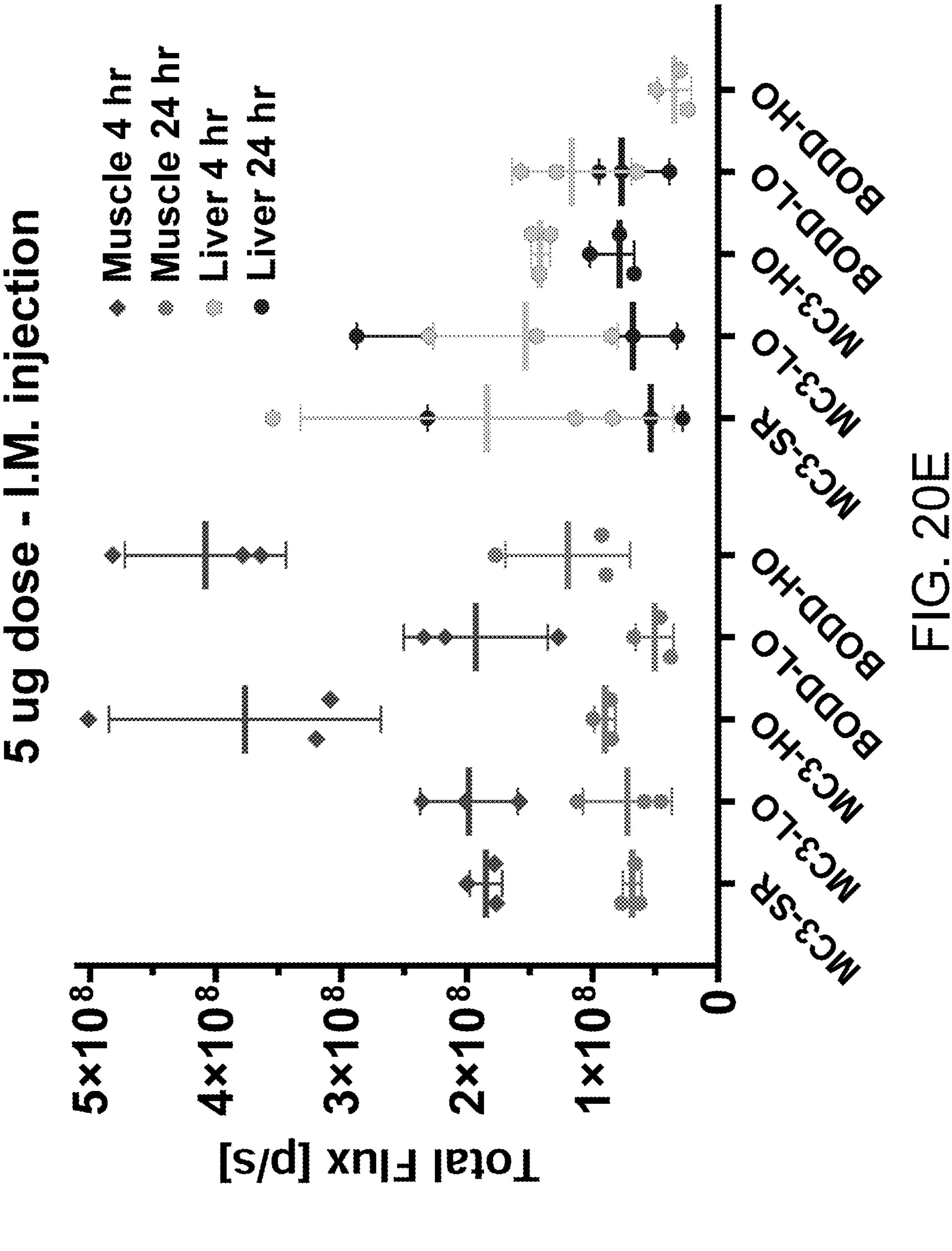
FIG. 20E: In vivo Firefly Luciferase expression in IM administration.
Figure 20F:
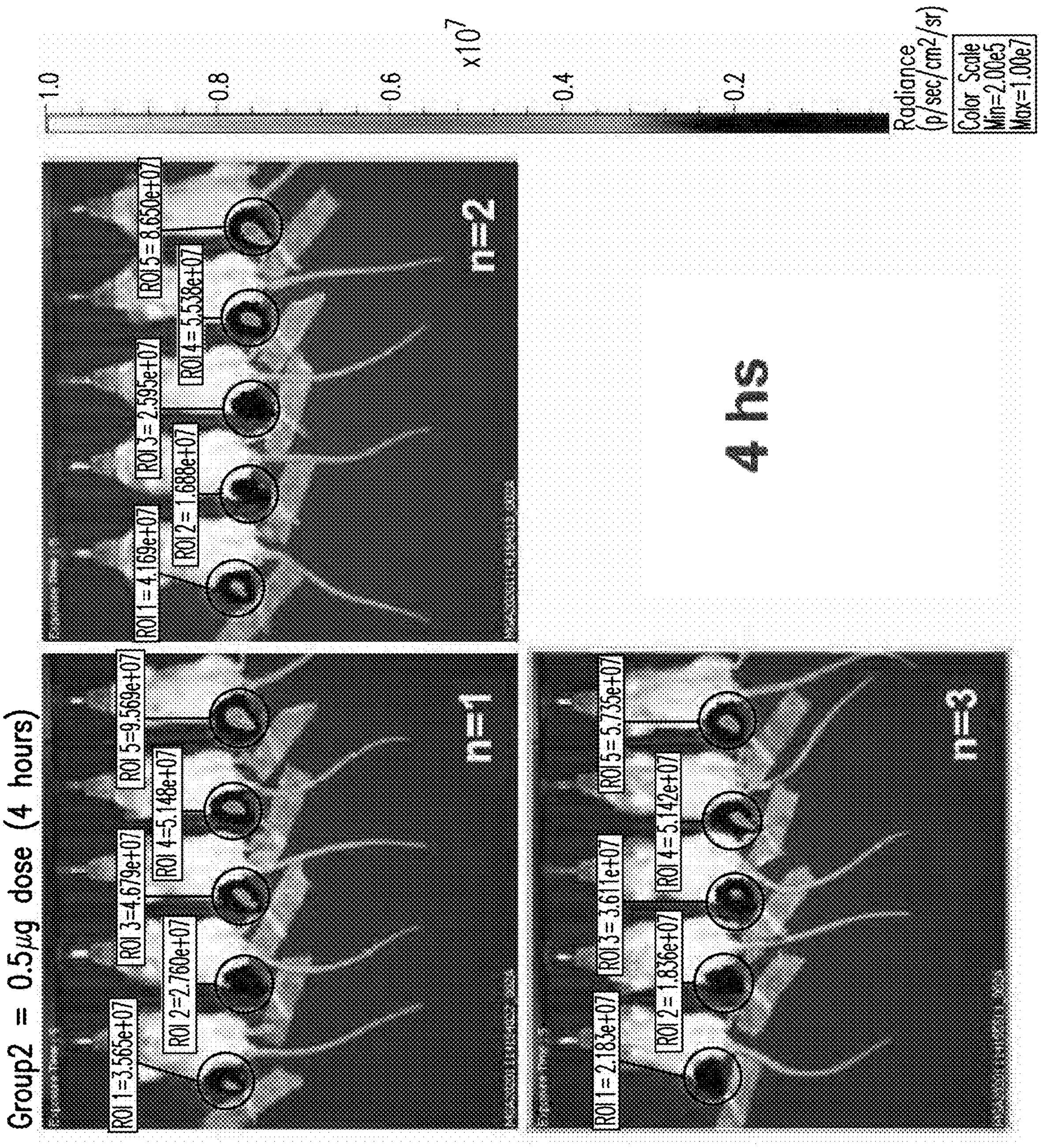
FIG. 20F: In vivo Firefly Luciferase expression in IM administration after 4 hours as set forth in Example 20.
Figure 20G:
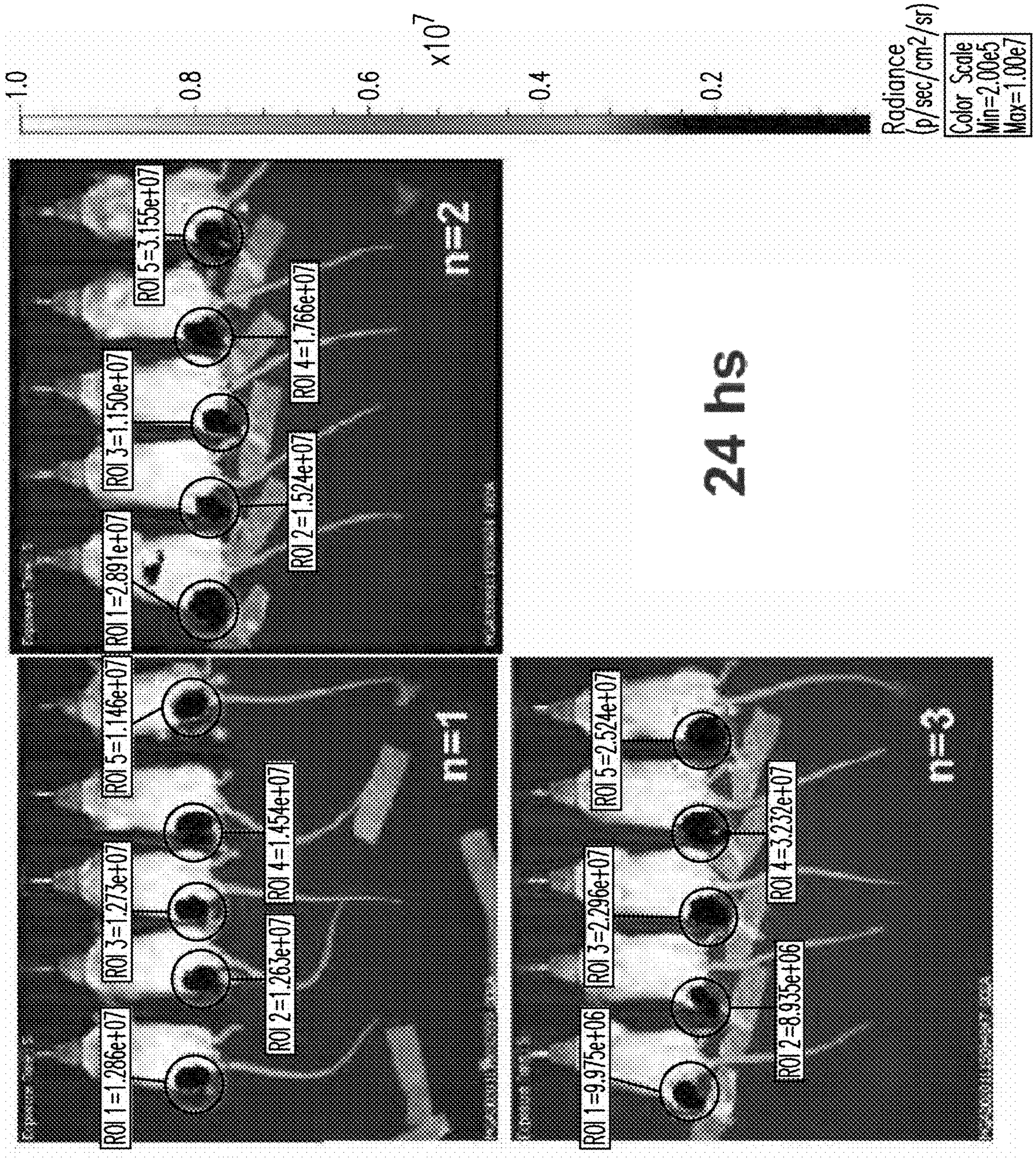
FIG. 20G: In vivo Firefly Luciferase expression in IM administration after 24 hours as set forth in Example 20.
Figure 20H:
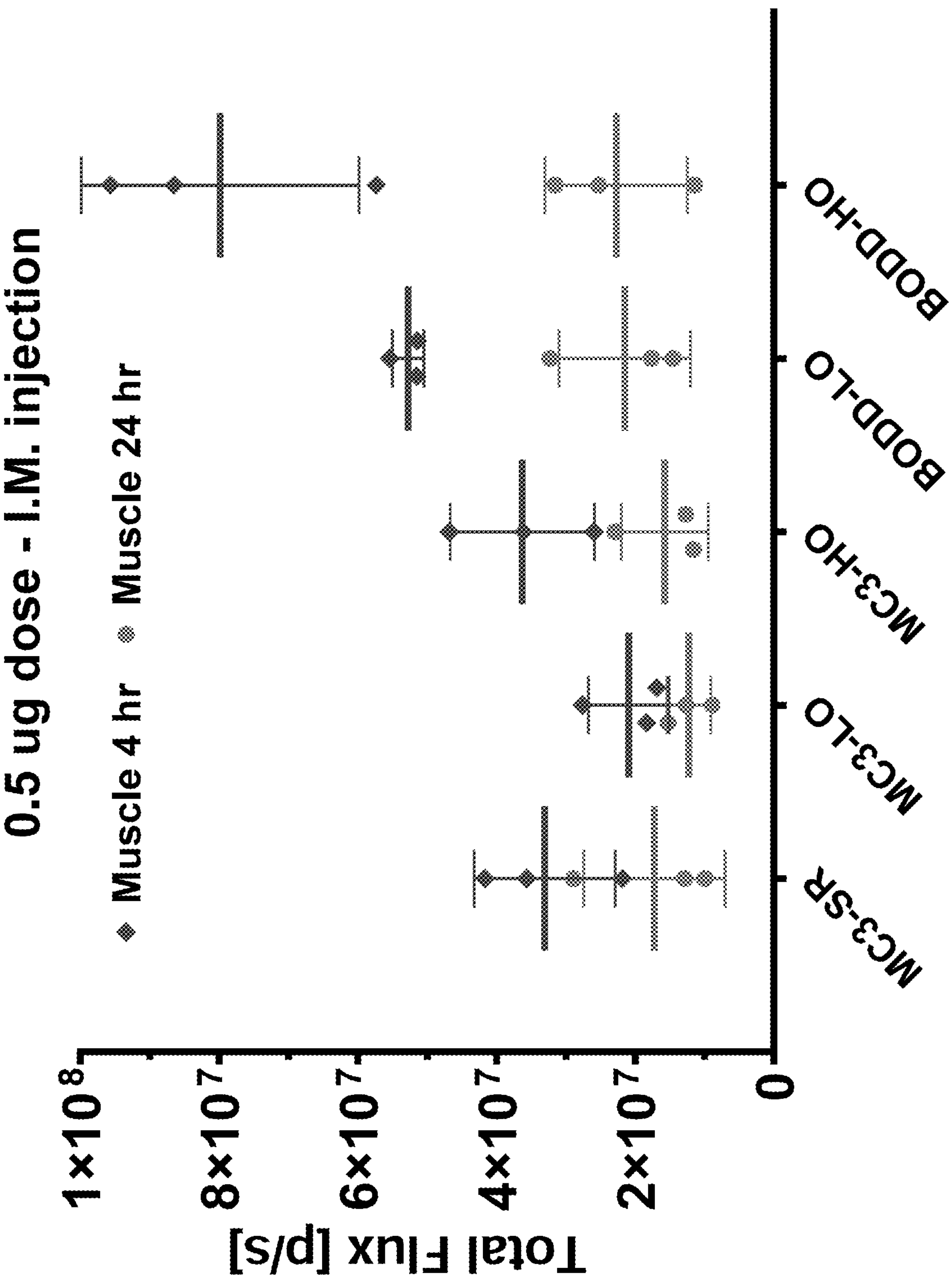
FIG. 20H: In vivo Firefly Luciferase expression in IM administration.
Figure 20I:
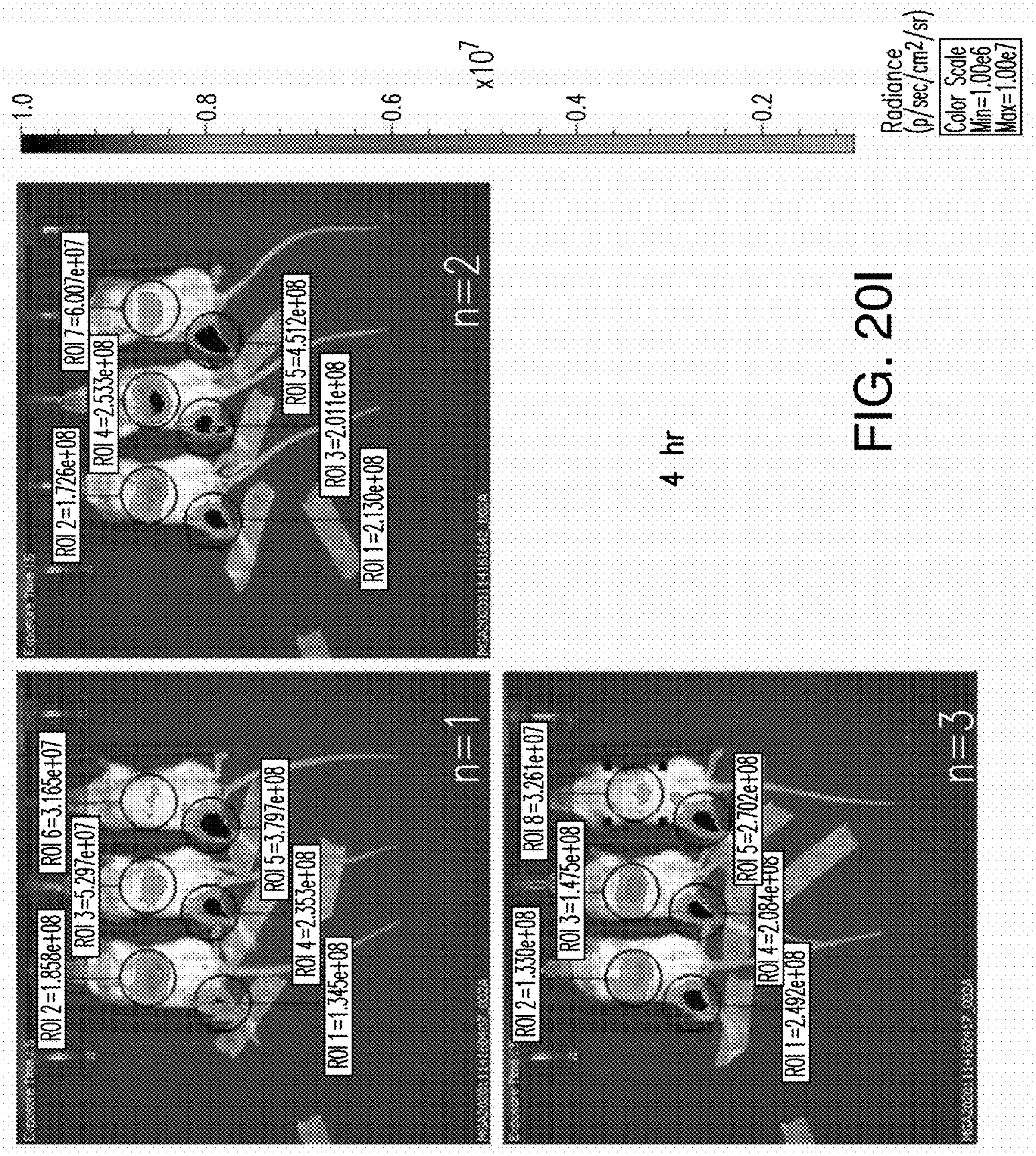
FIG. 20I: In vivo Firefly Luciferase expression in IM administration after 4 hours as set forth in Example 20.
Figure 20J:
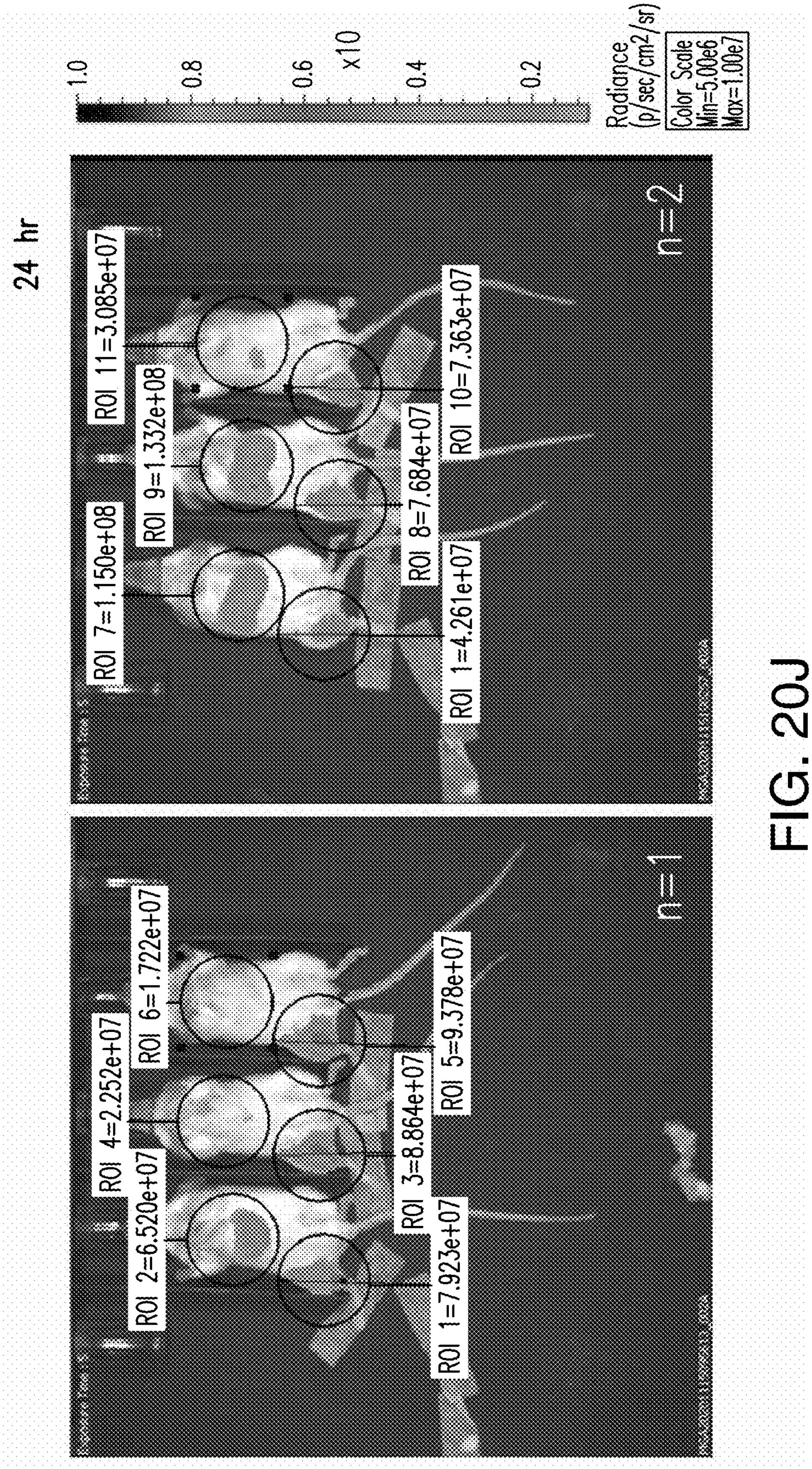
FIG. 20J: In vivo Firefly Luciferase expression in IM administration after 24 hours as set forth in Example 20.
Figure 20K:
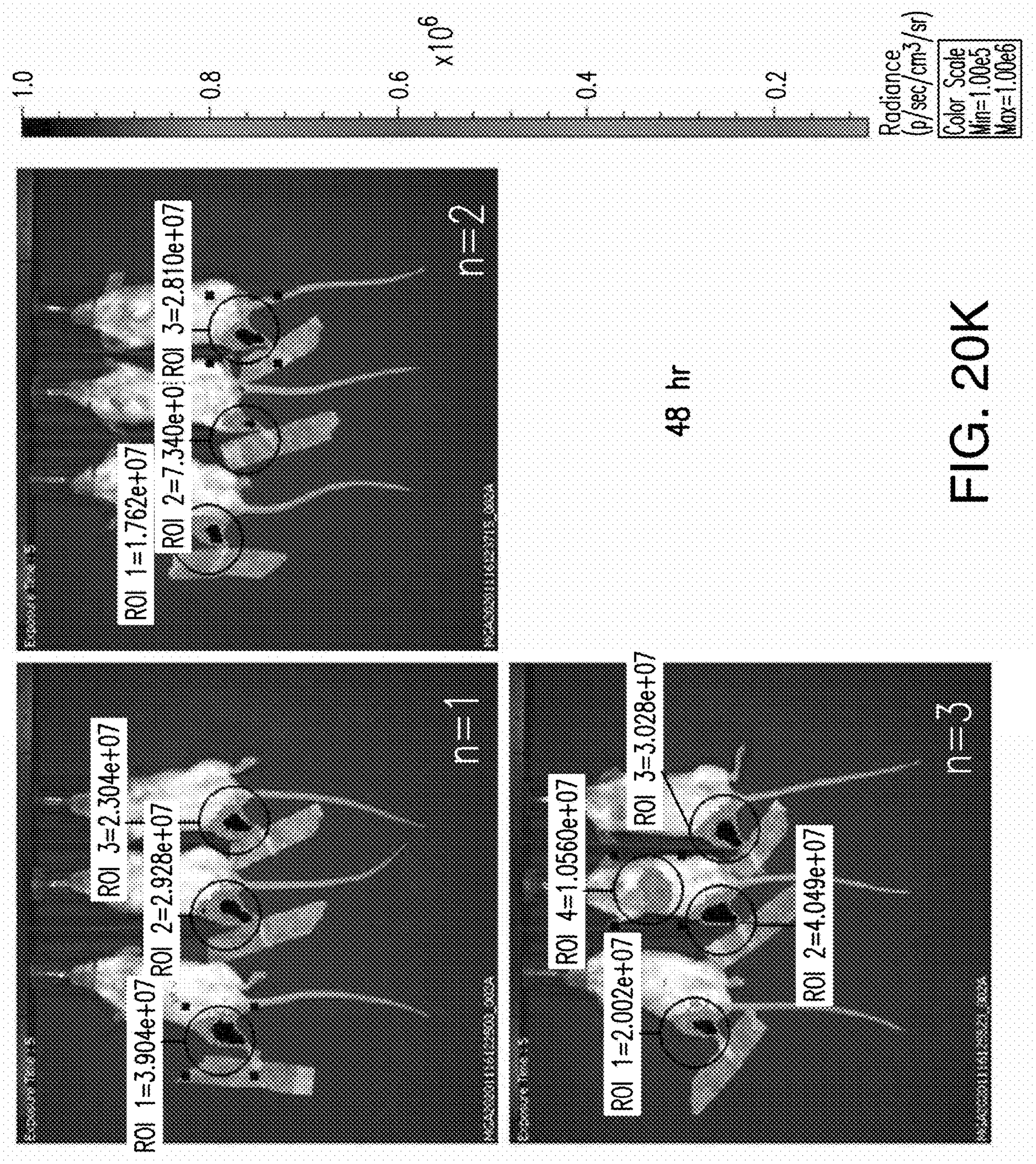
FIG. 20K: In vivo Firefly Luciferase expression in IM administration after 48 hours as set forth in Example 20.
Figure 20L:
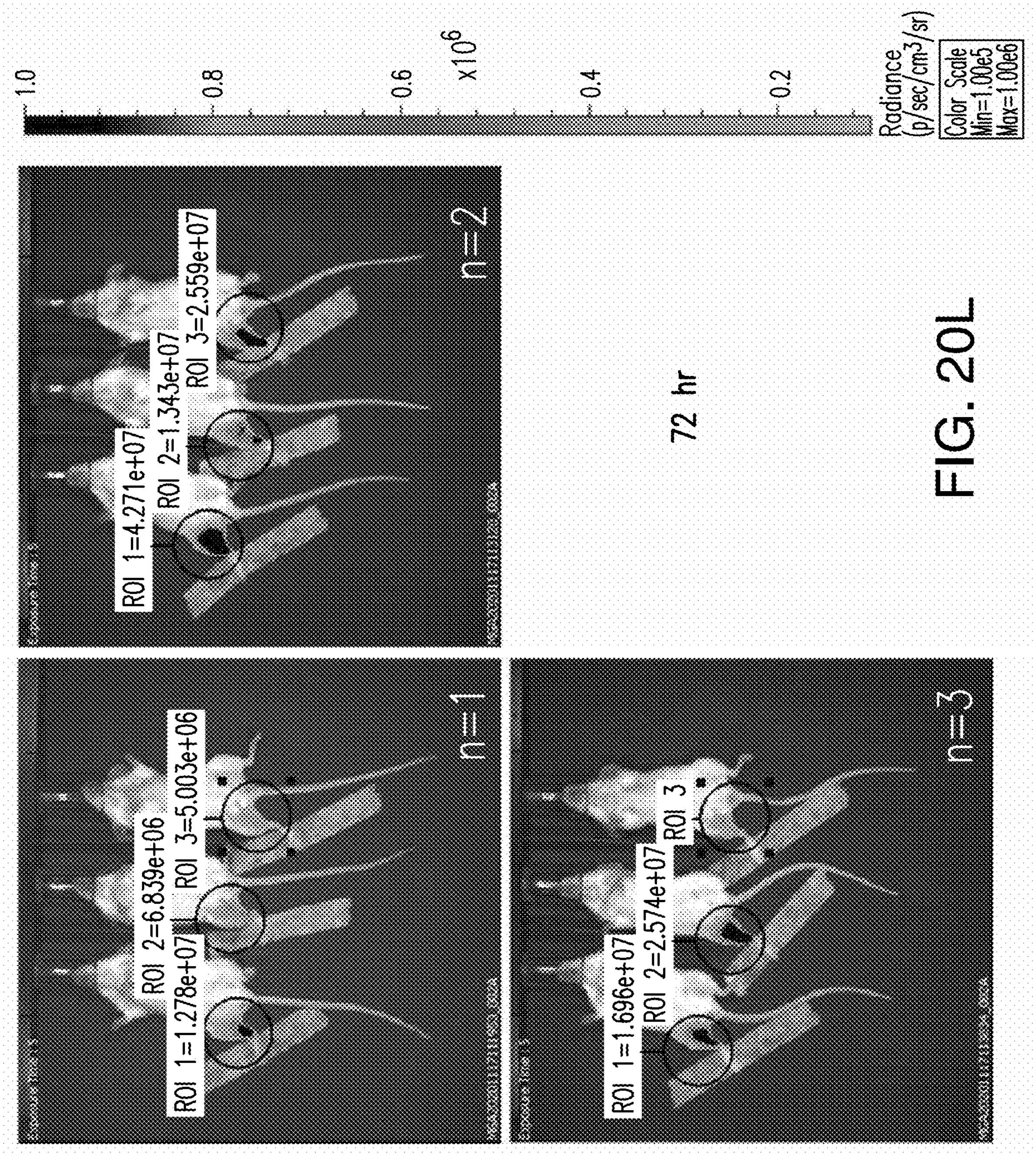
FIG. 20L: In vivo Firefly Luciferase expression in IM administration after 72 hours as set forth in Example 20.
Figure 20M:
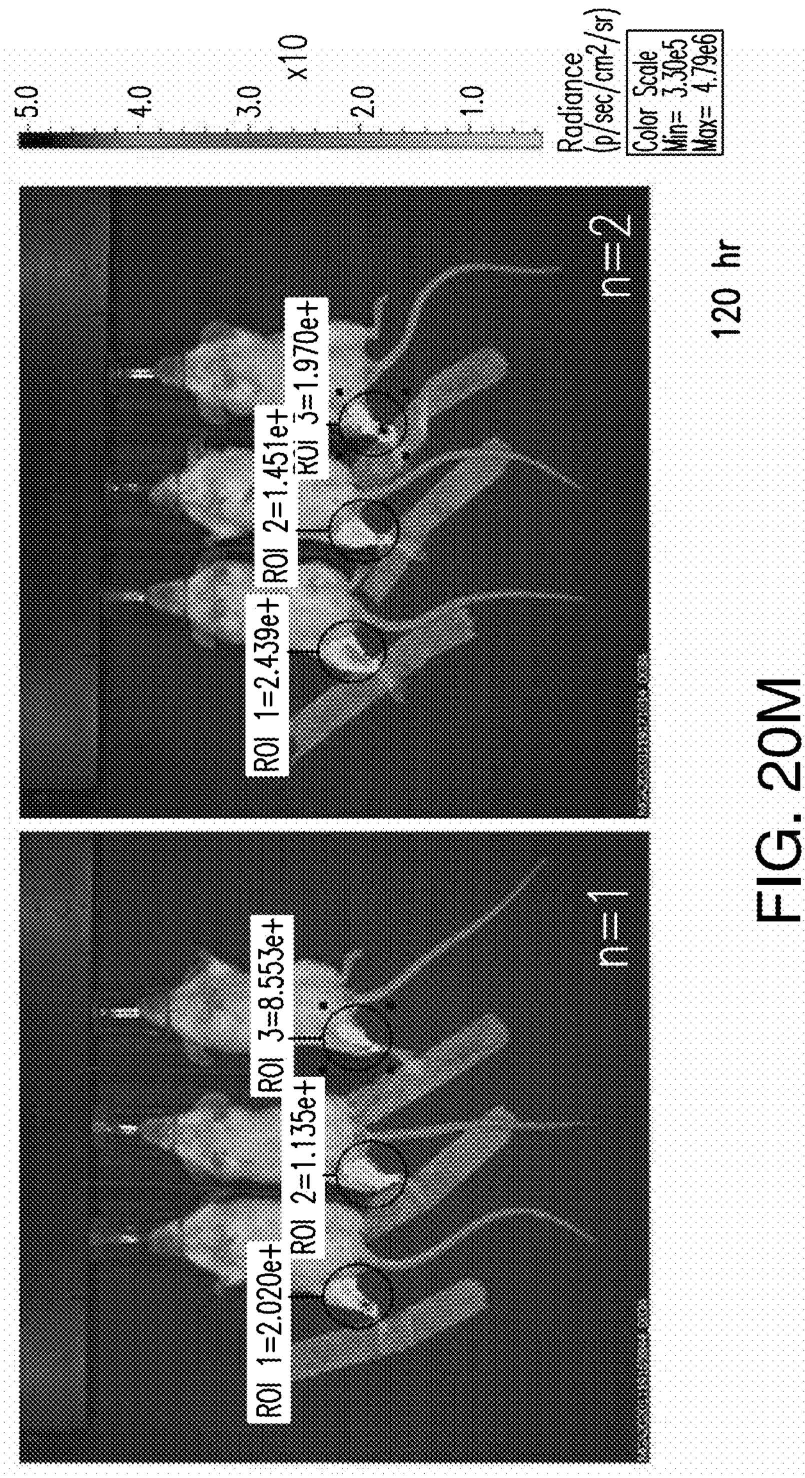
FIG. 20M: In vivo Firefly Luciferase expression in IM administration after 120 hours as set forth in Example 20.
Figure 20N:
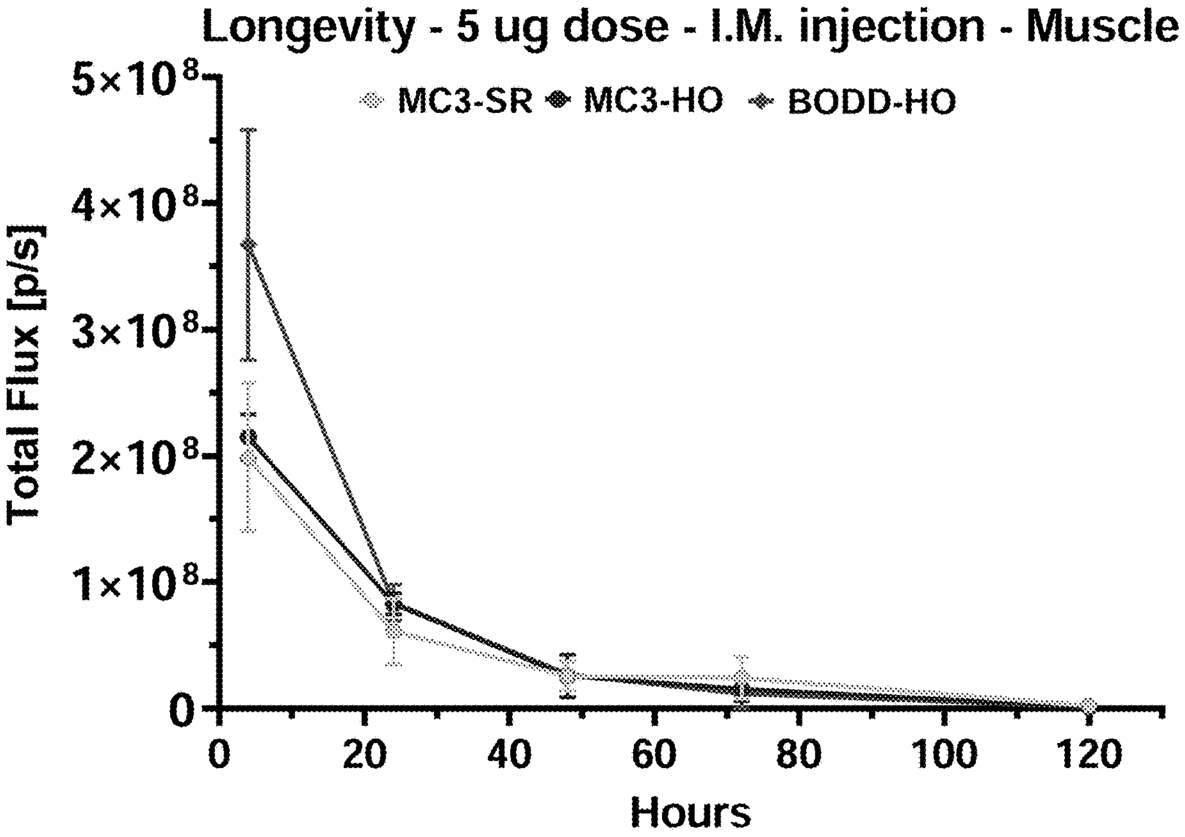
FIG. 20N: In vivo Firefly Luciferase expression in IM administration.
Figures 1, 21A:
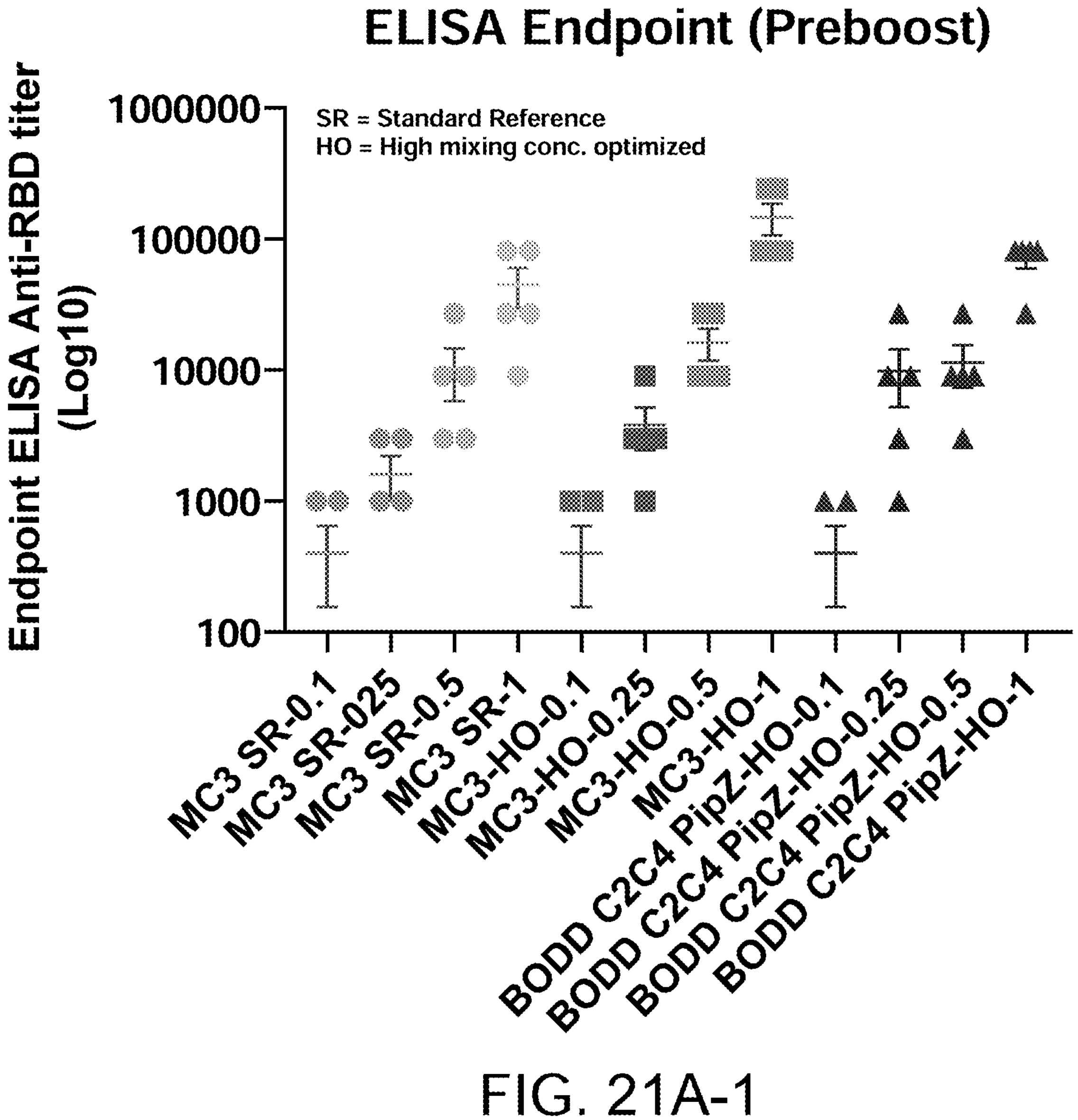
FIGS. 21A-1 and 21A-2: In vivo immunogenicity Endpoint ELISA Anti-RBD titers as set forth in Example 21.
Figures 2, 21A:
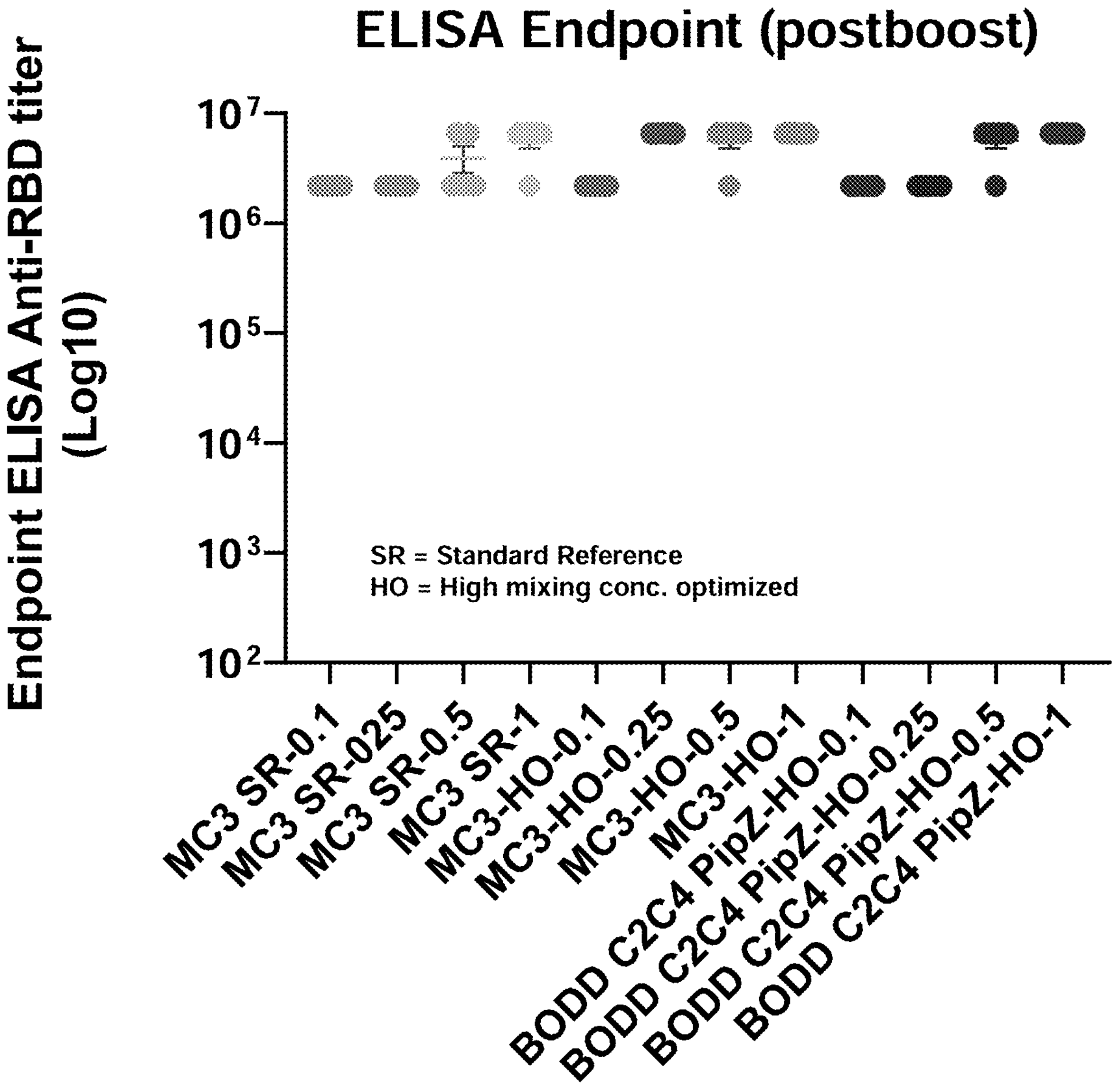
Figure 21B:
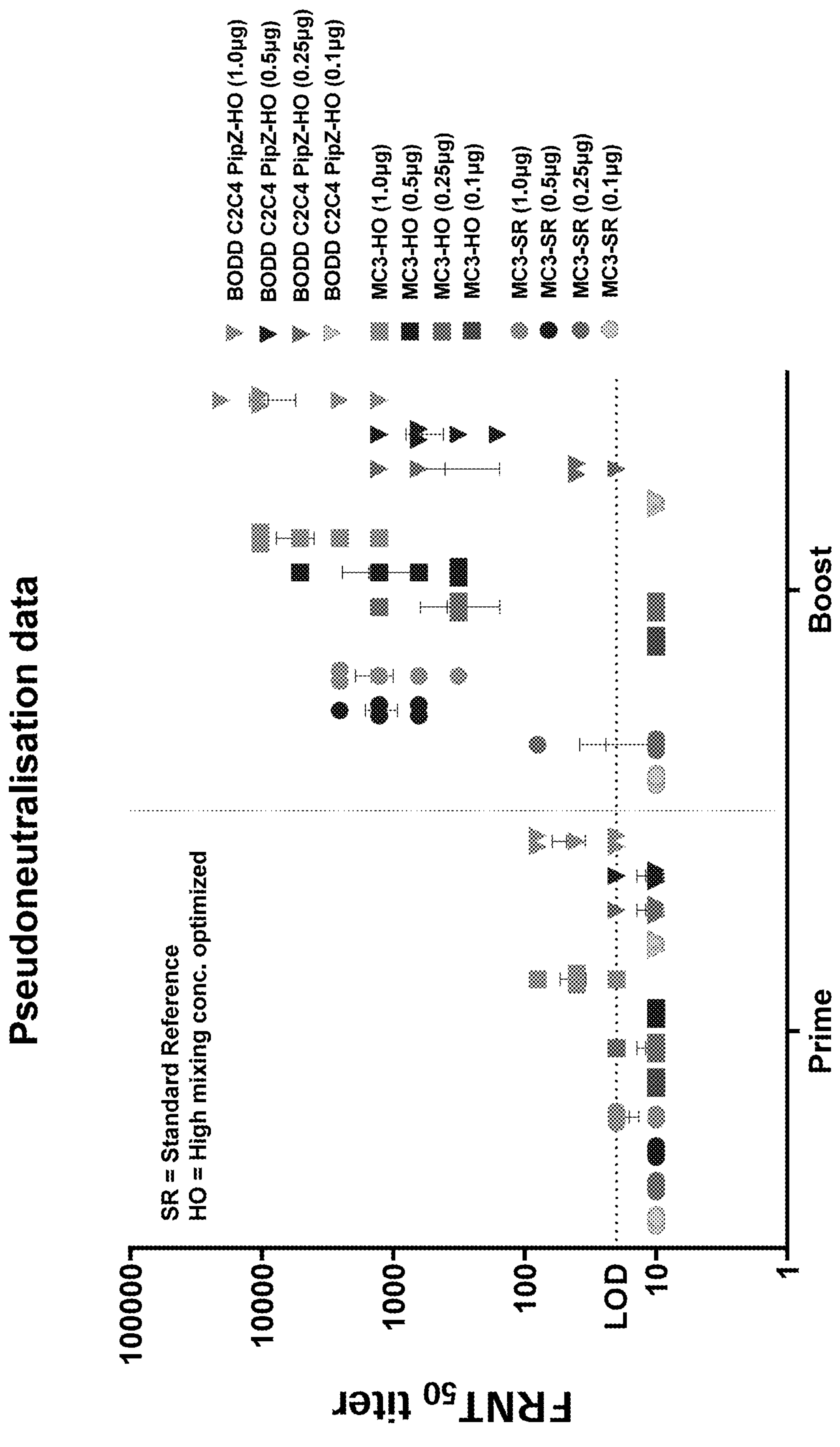
FIG. 21B: In vivo immunogenicity FRNT50 titer for Psuedoneutralisation assay as set forth in Example 21.
Figure 22A:
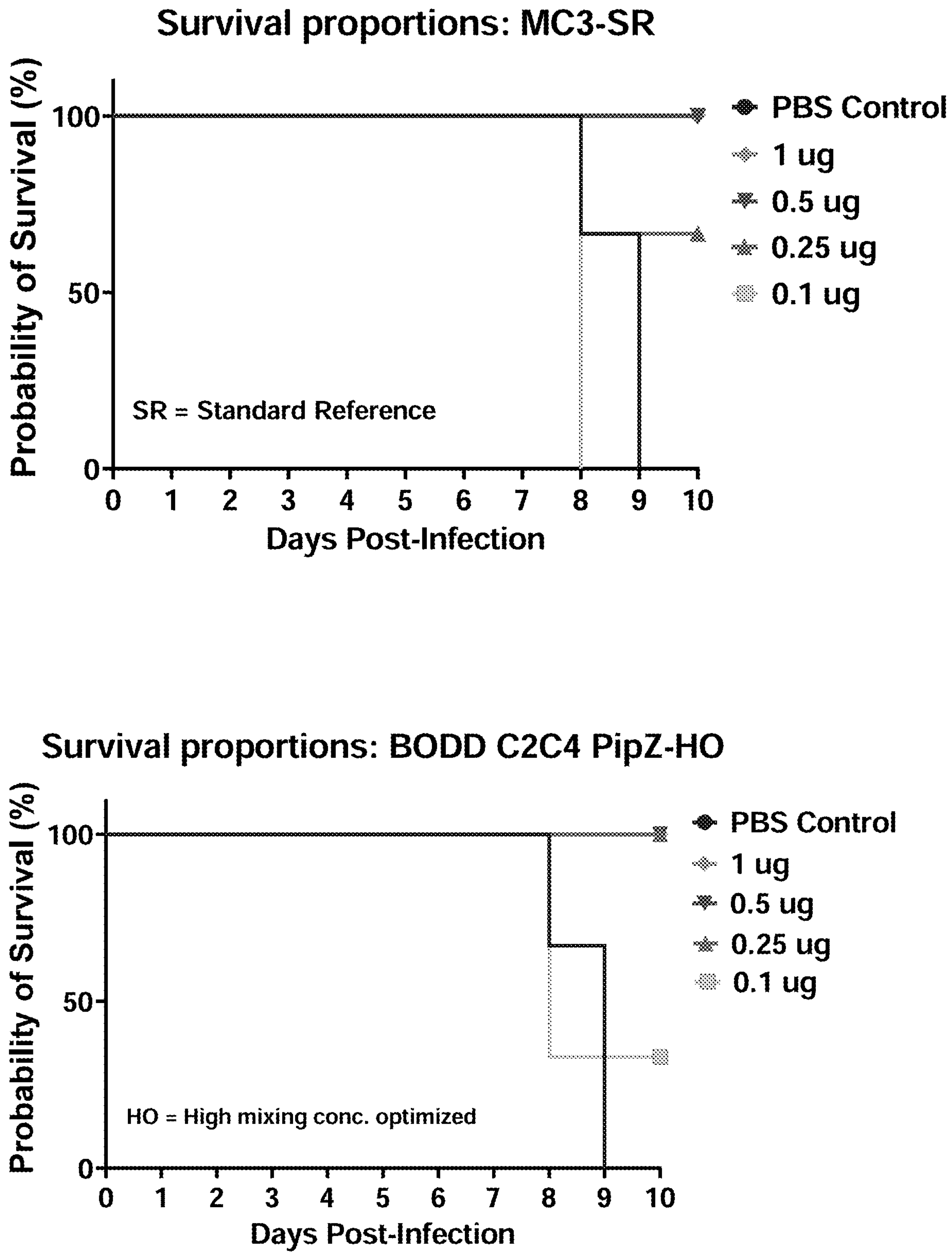
FIG. 22A: In vivo protection against viral challenge—Survival proportion, Weight and Temperature in Challenge model as set forth in Example 22.
Figure 22B:
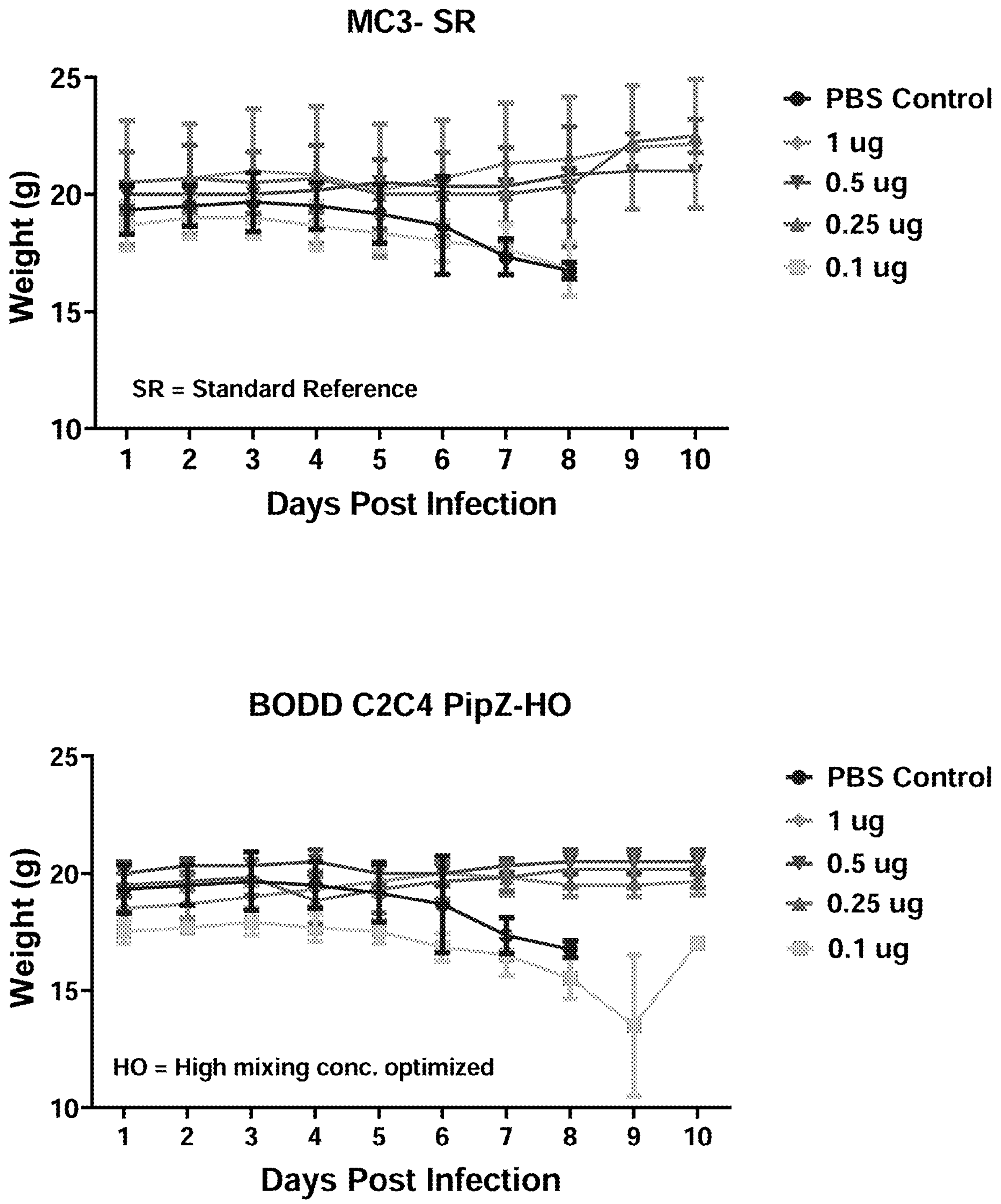
FIG. 22B: In vivo weight in Challenge model as set forth in Example 22.
Figure 22C:
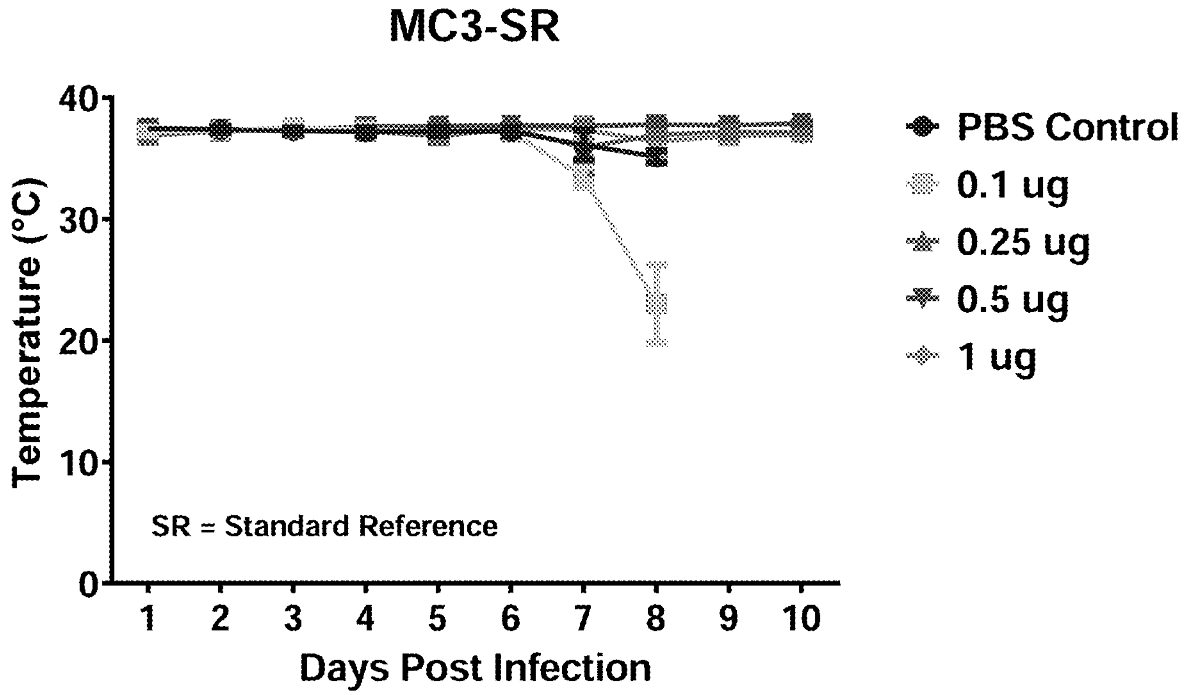
FIG. 22C: In vivo temperature in Challenge model as set forth in Example 22.
Figure 22C:
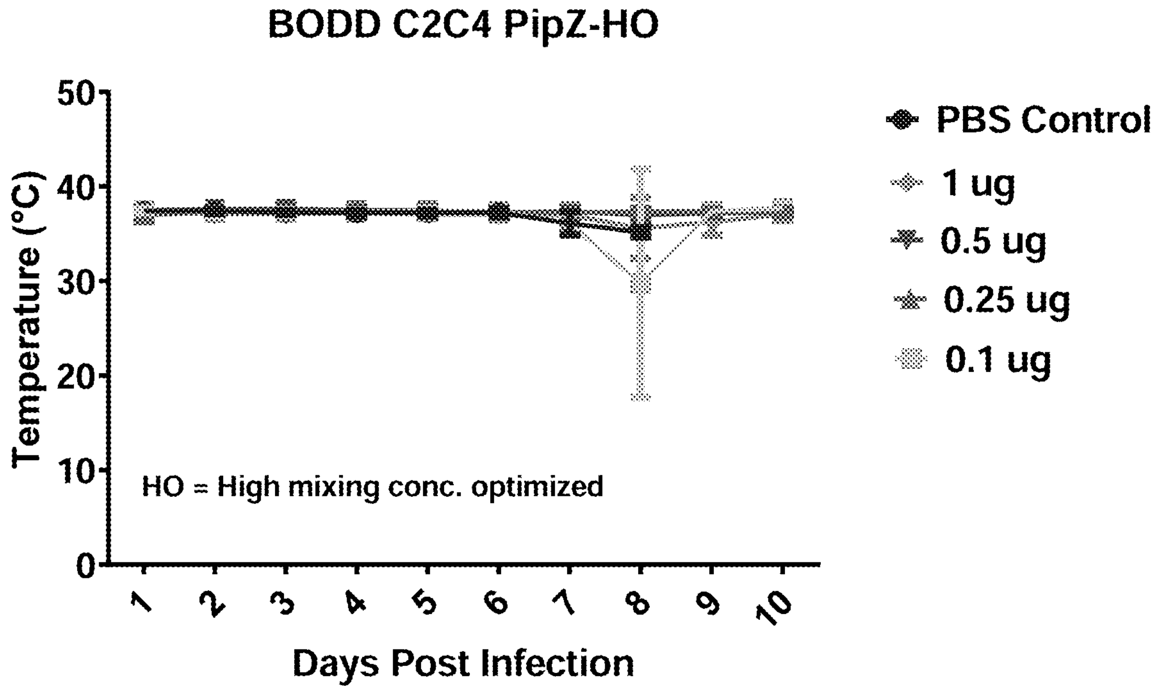
Figure 23A:
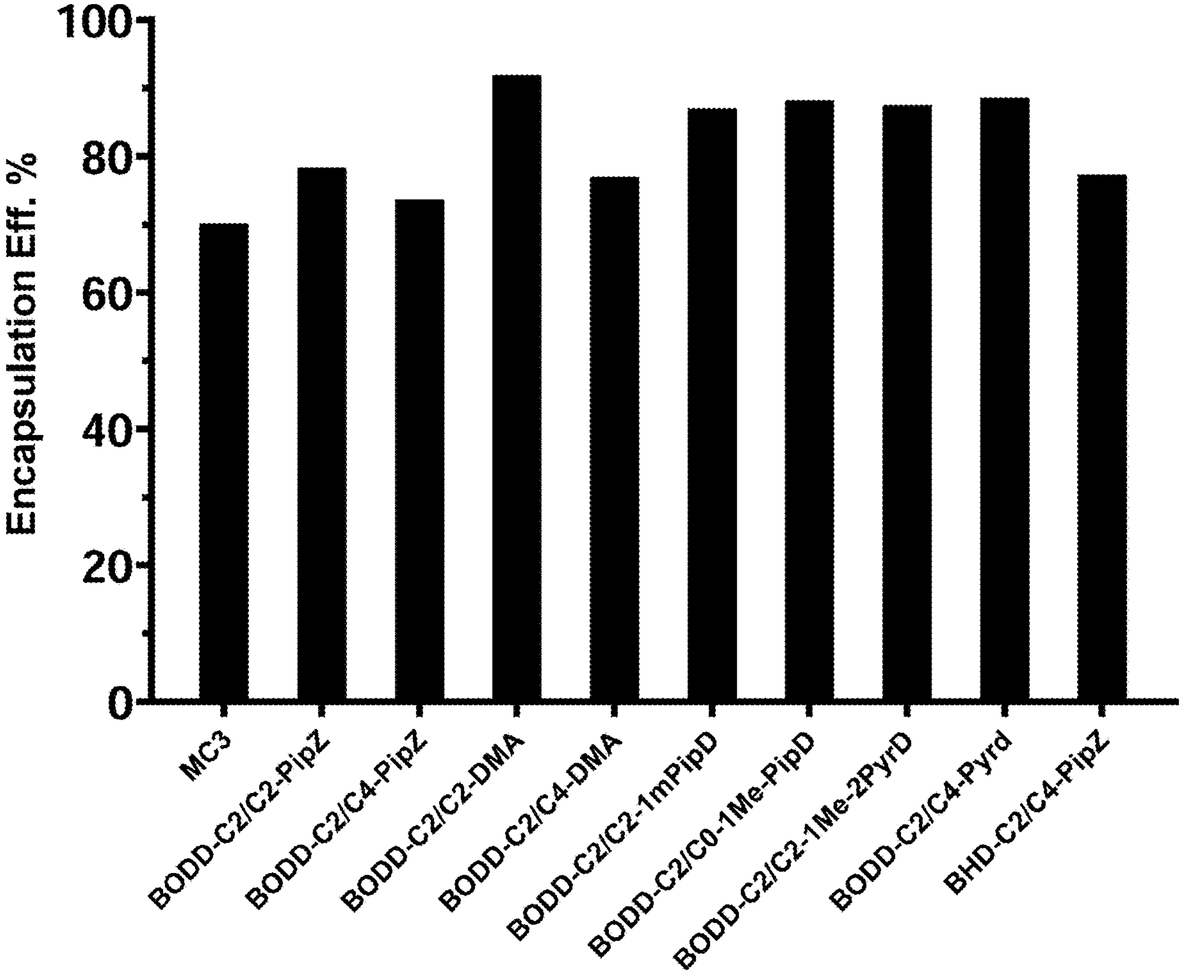
FIG. 23A: Ribogreen Assay for mRNA Encapsulation Efficiency as set forth in Example 23.
Figure 23B:
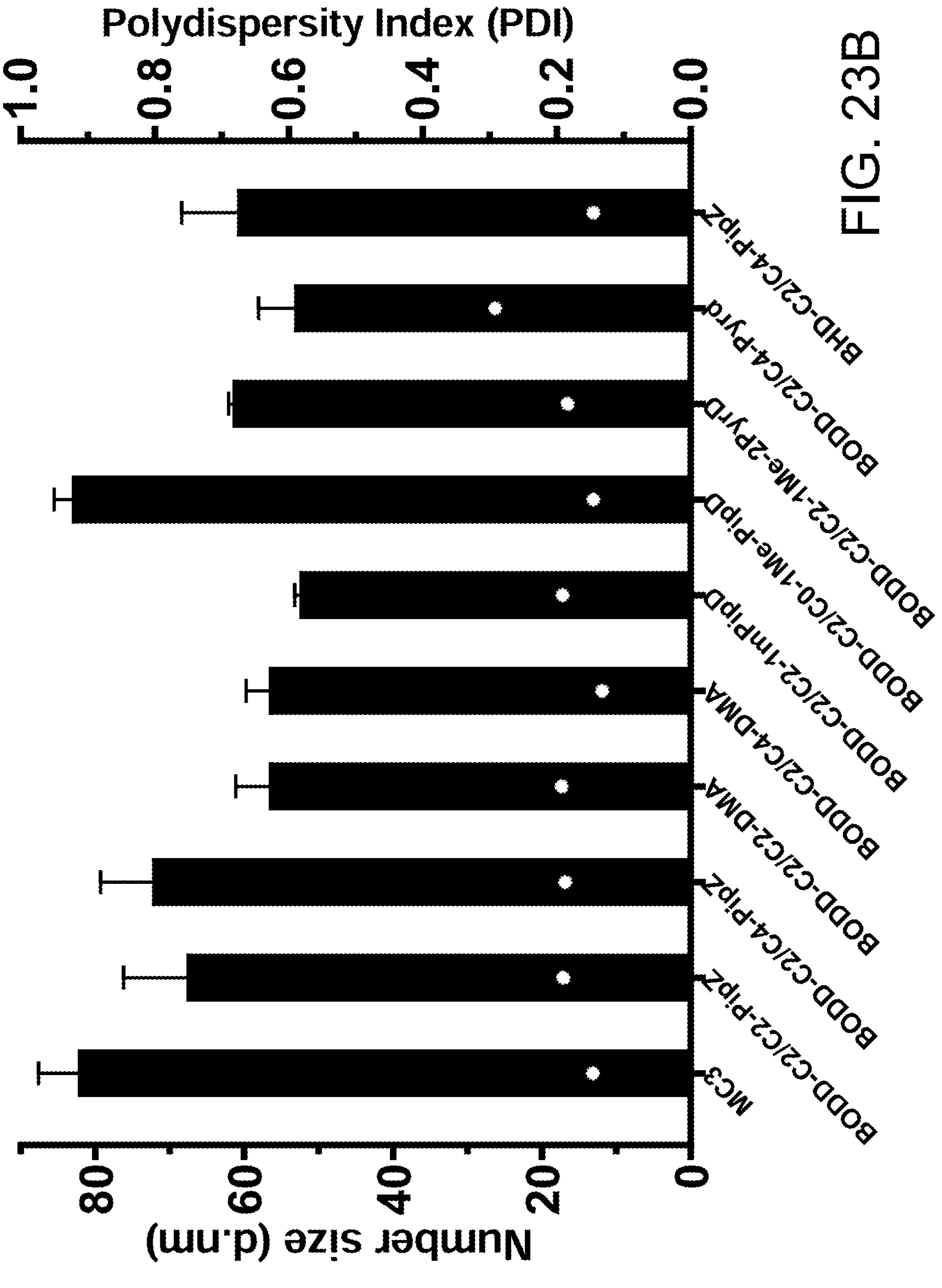
FIG. 23B: Dynamic Light Scattering for LNP Size (white dots are PDI right y axis) as set forth in Example 23.
Figure 23C:
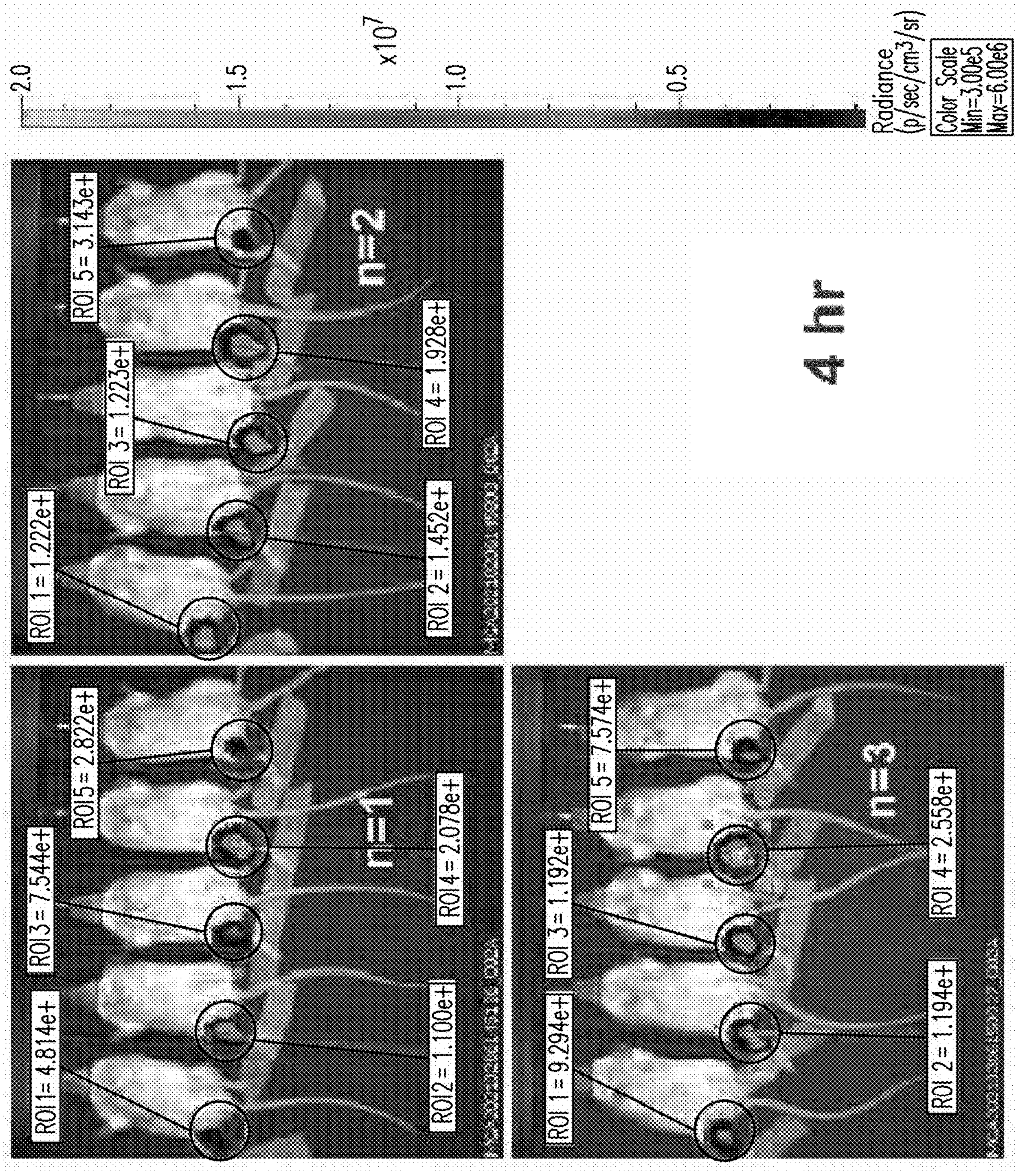
FIG. 23C and FIG. 23D: In vivo Firefly Luciferase expression in IM administration after 4 hours as set forth in Example 23.
Figure 23D:
Figure 23E:
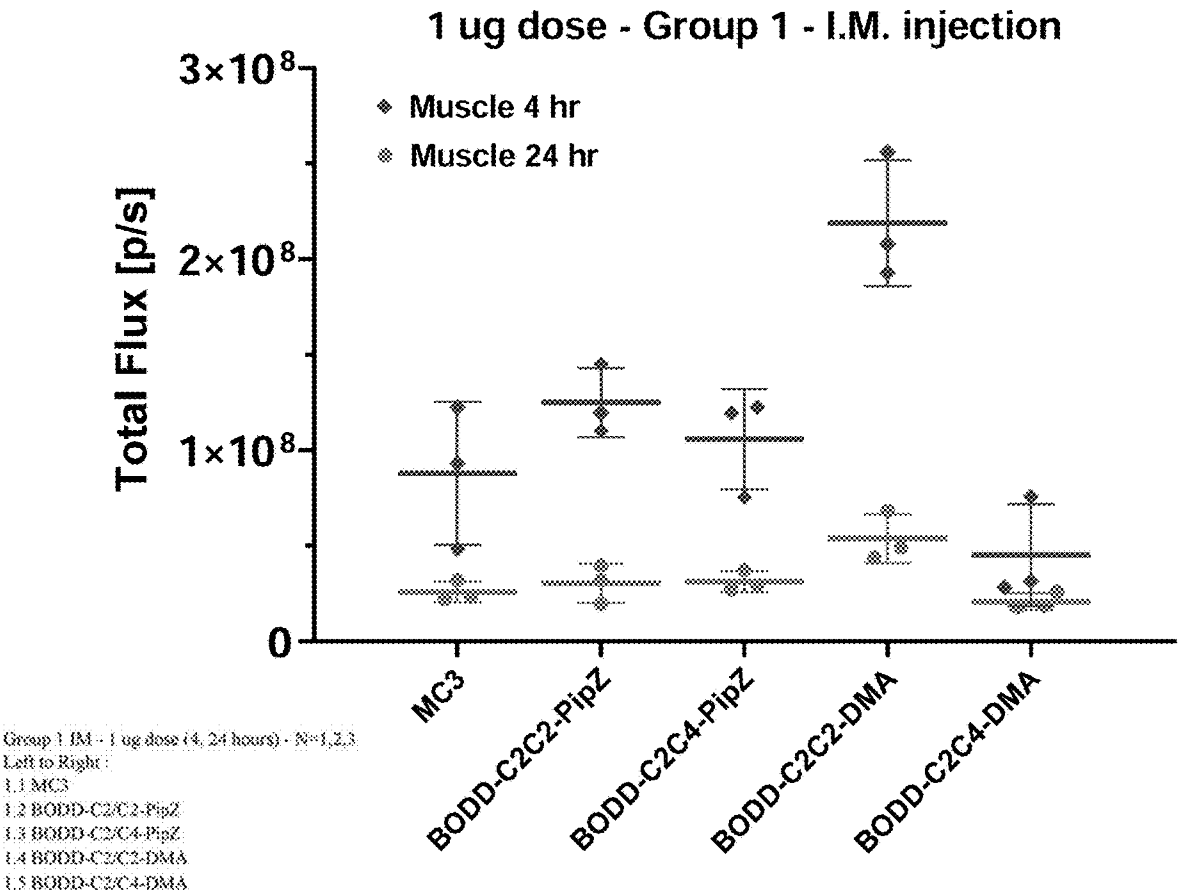
FIG. 23E: In vivo Firefly Luciferase expression in IM administration after 4 hours and 24 hours as set forth in Example 23.
Figure 23F:
FIG. 23F: In vivo Firefly Luciferase expression in IV administration after 4 hours as set forth in Example 23.
Figure 23G:
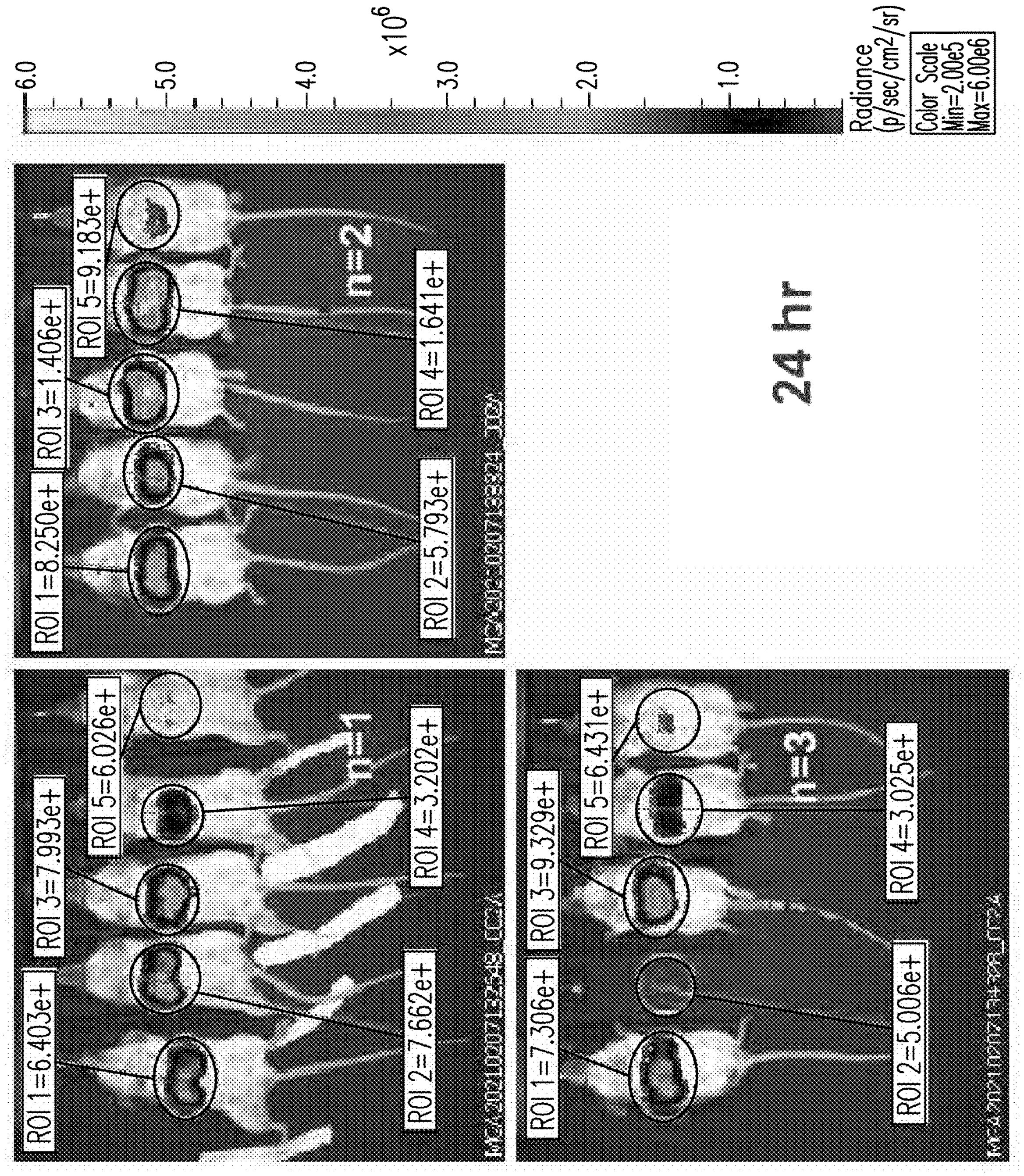
FIG. 23G: In vivo Firefly Luciferase expression in IV administration after 24 hours as set forth in Example 23.
Figure 23H:
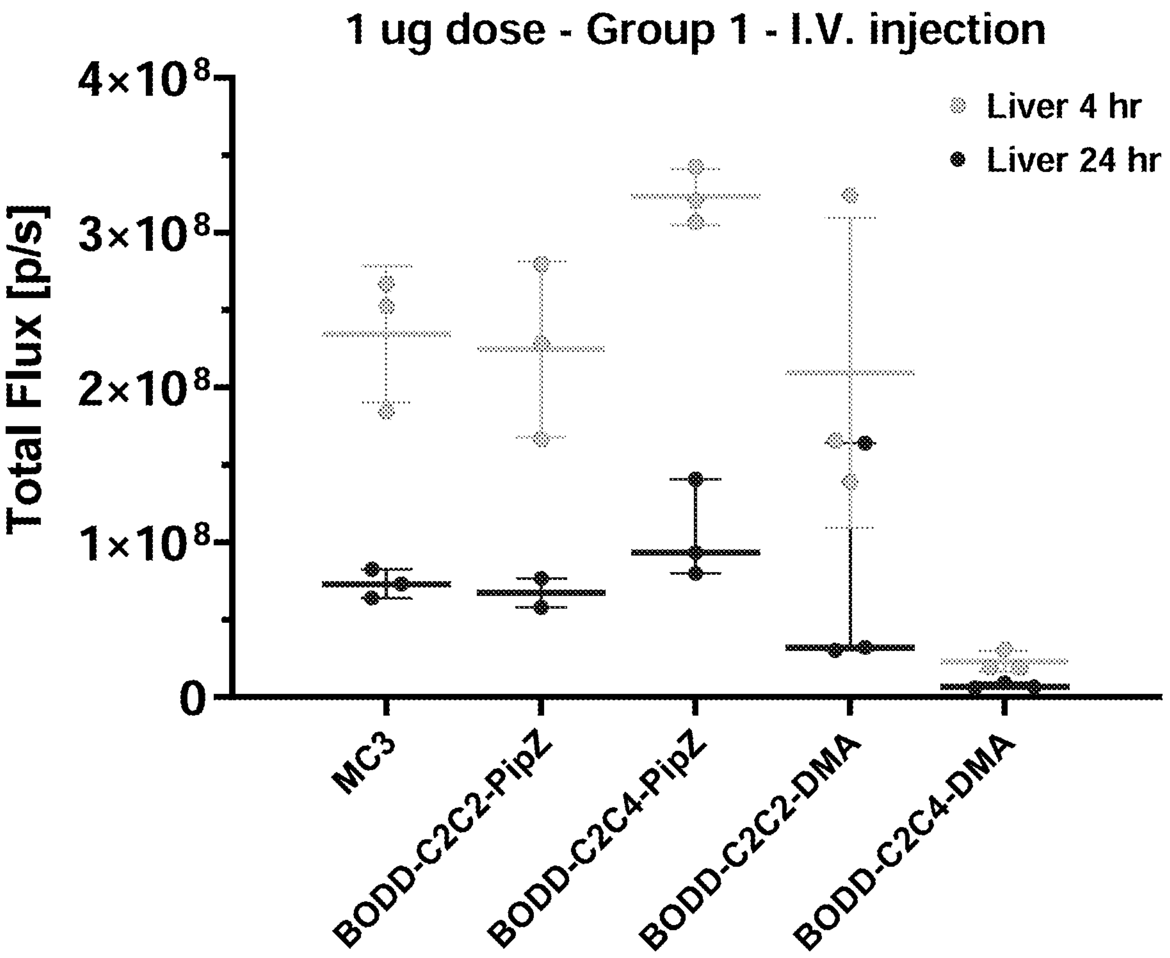
FIG. 23H: In vivo Firefly Luciferase expression in IV administration.
Figure 23I:
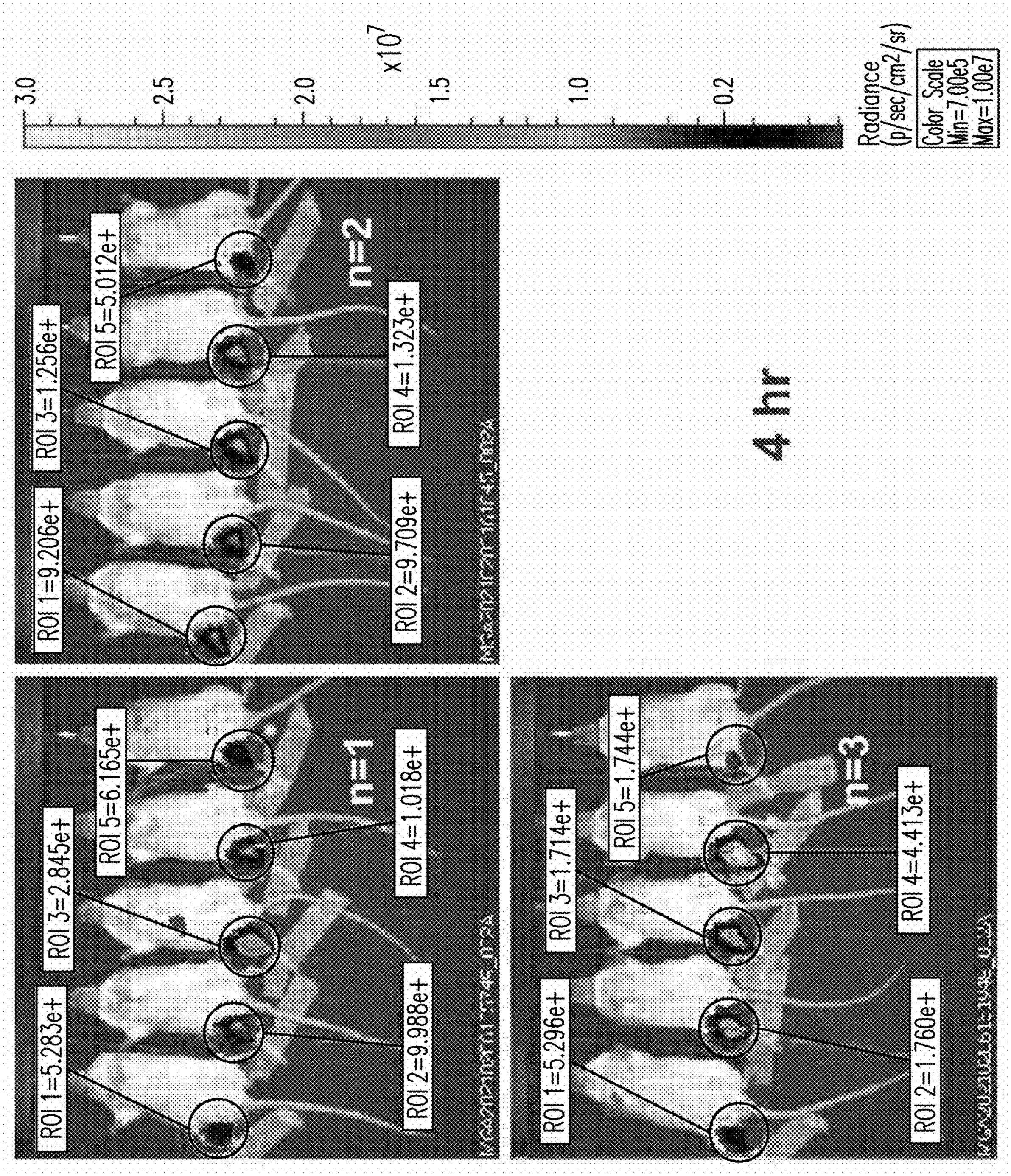
FIG. 23I: In vivo Firefly Luciferase expression in IM administration after 4 hours as set forth in Example 23.
Figure 23J:
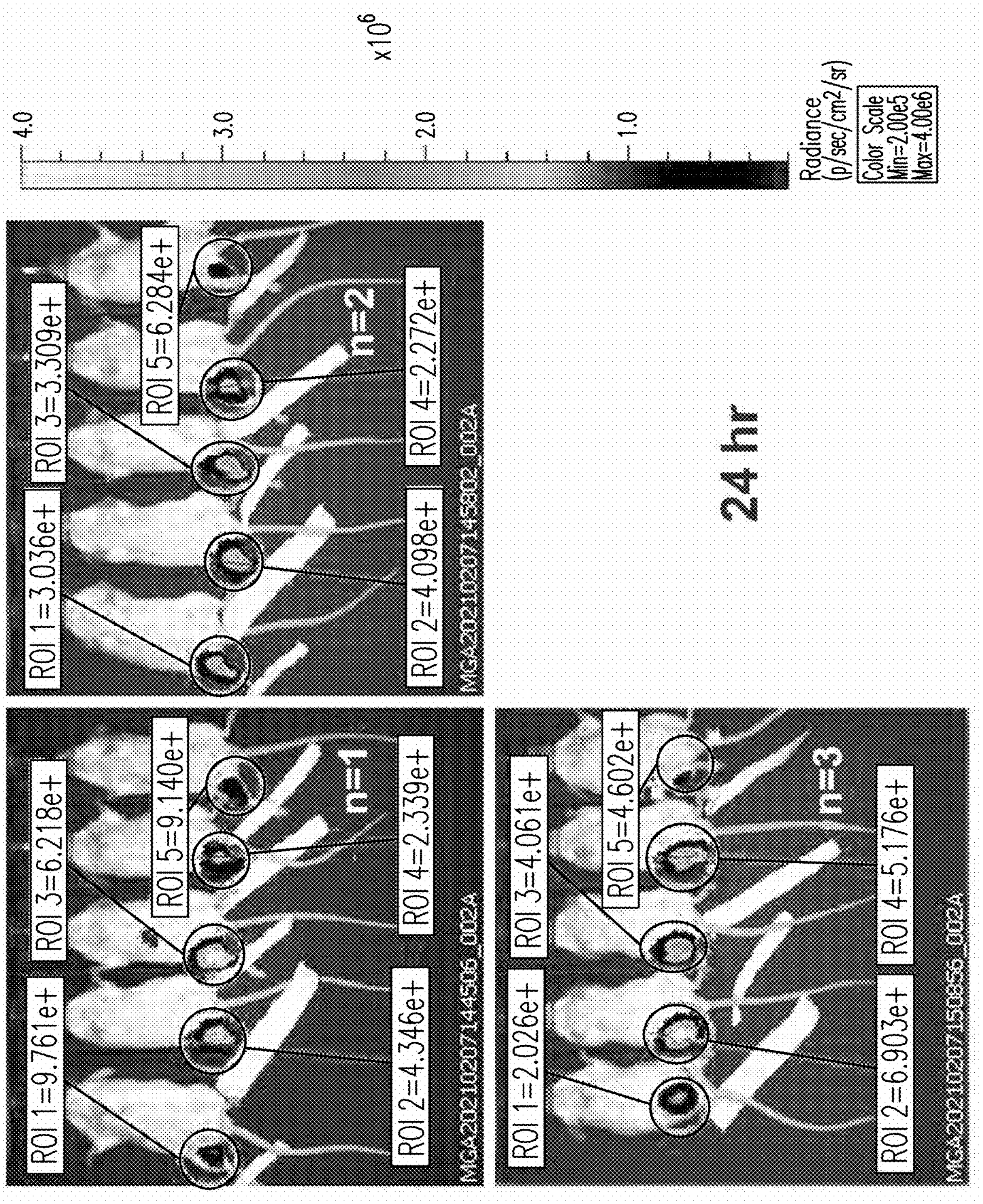
FIG. 23J: In vivo Firefly Luciferase expression in IM administration after 24 hours as set forth in Example 23.
Figure 23K:
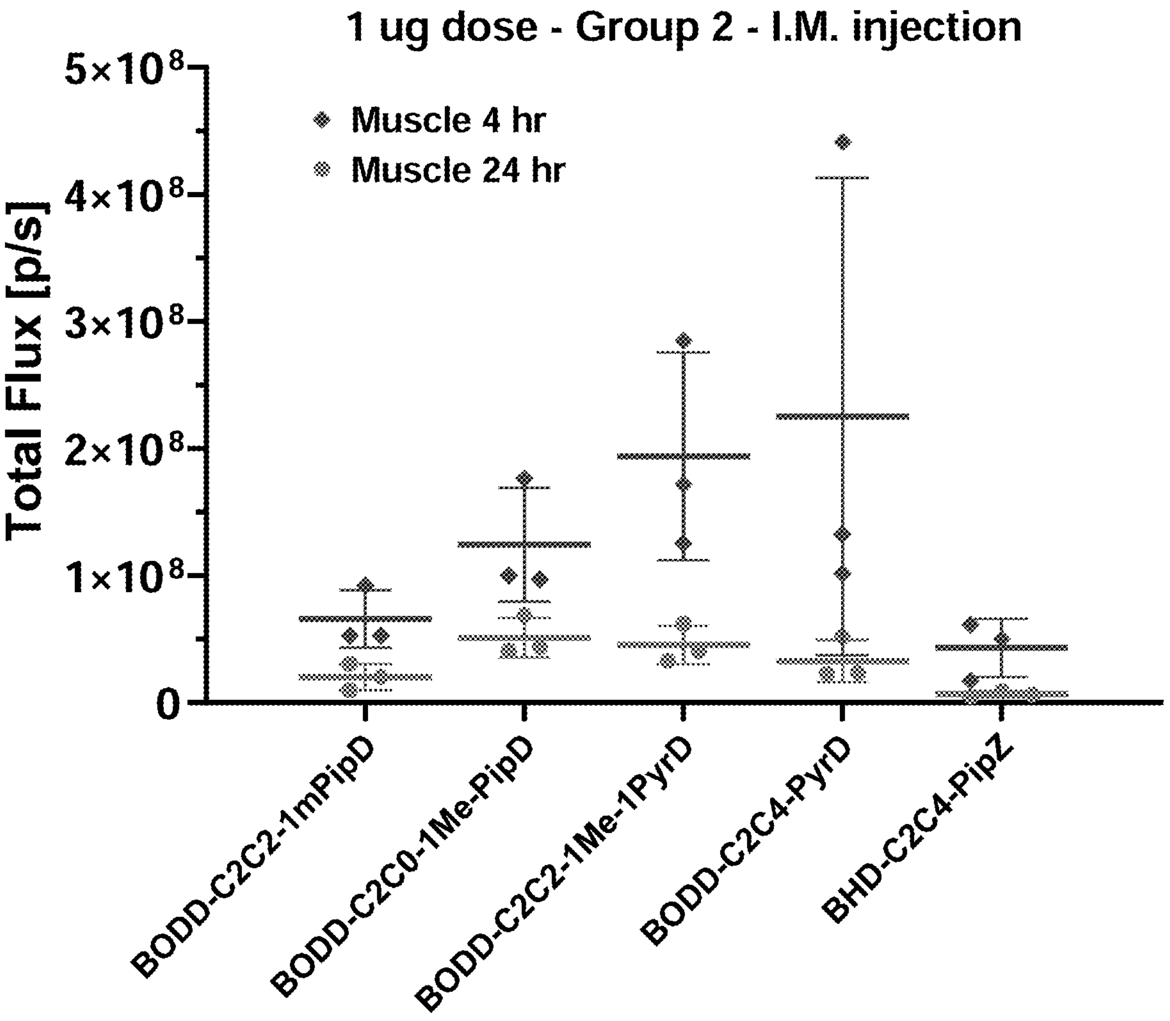
FIG. 23K: In vivo Firefly Luciferase expression in IM administration.
Figure 23L:
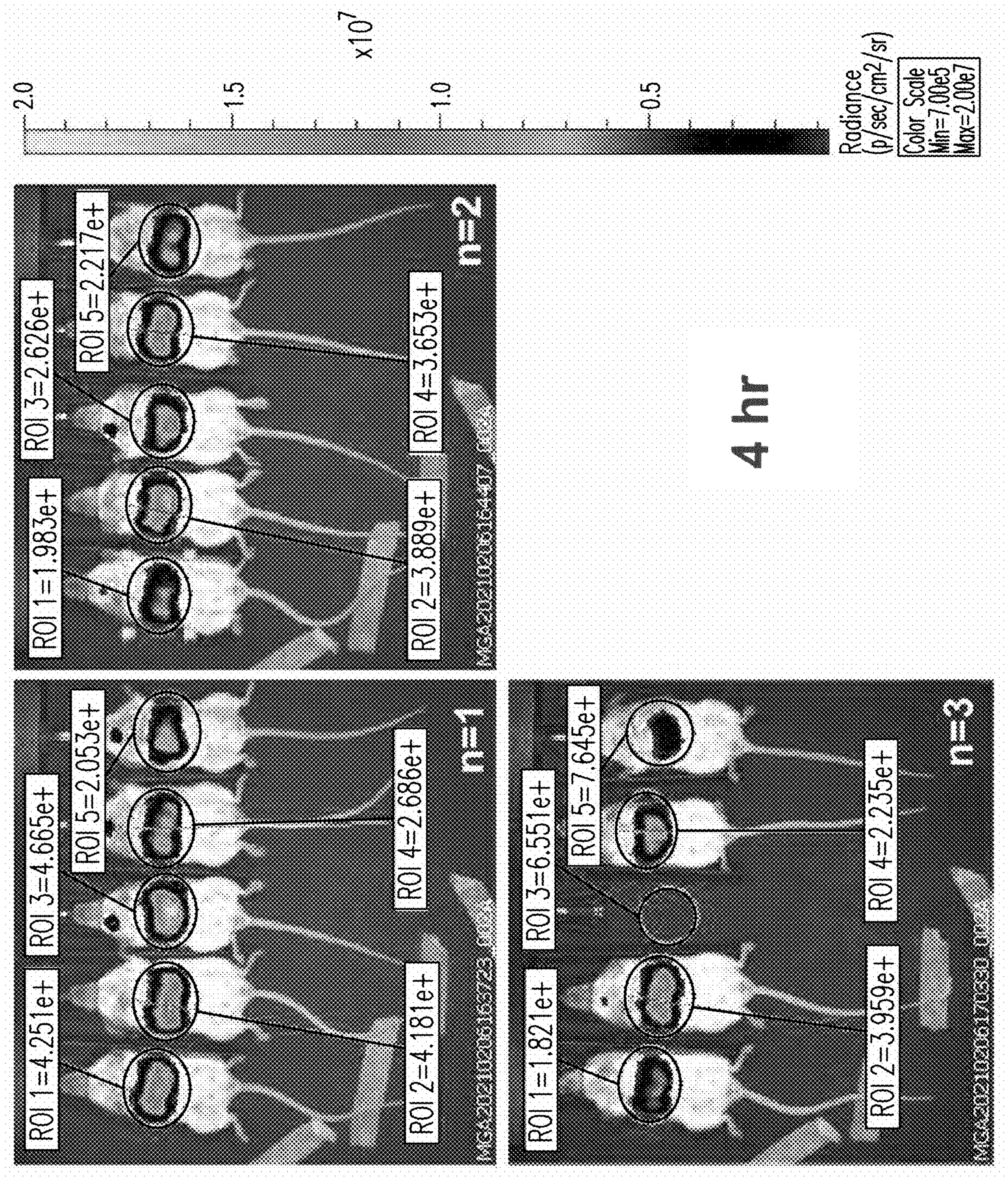
FIG. 23L: In vivo Firefly Luciferase expression in IV administration after 4 hours as set forth in Example 23.
Figure 23M:
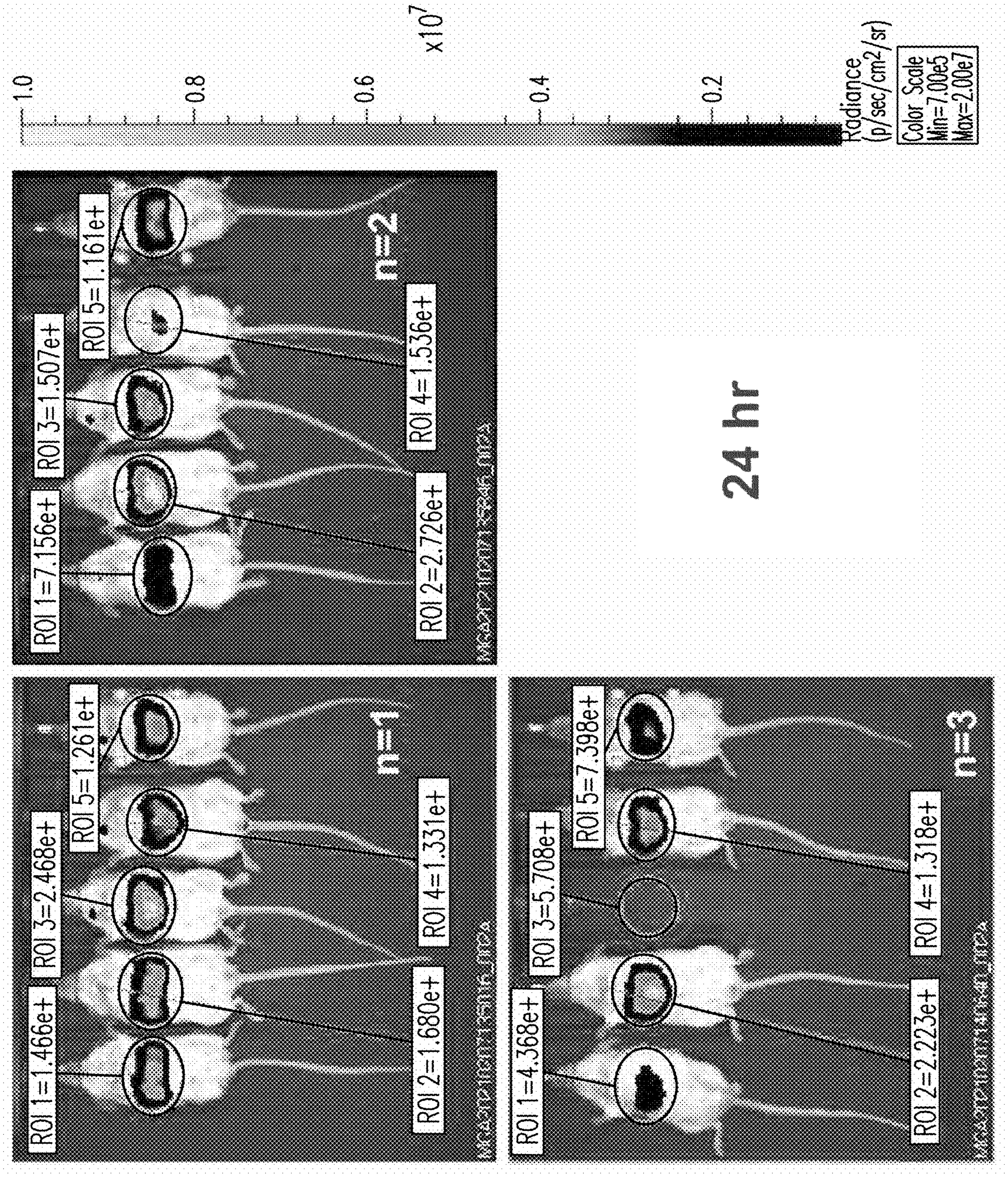
FIG. 23M: In vivo Firefly Luciferase expression in IV administration after 24 hours as set forth in Example 23.
Figure 23N:
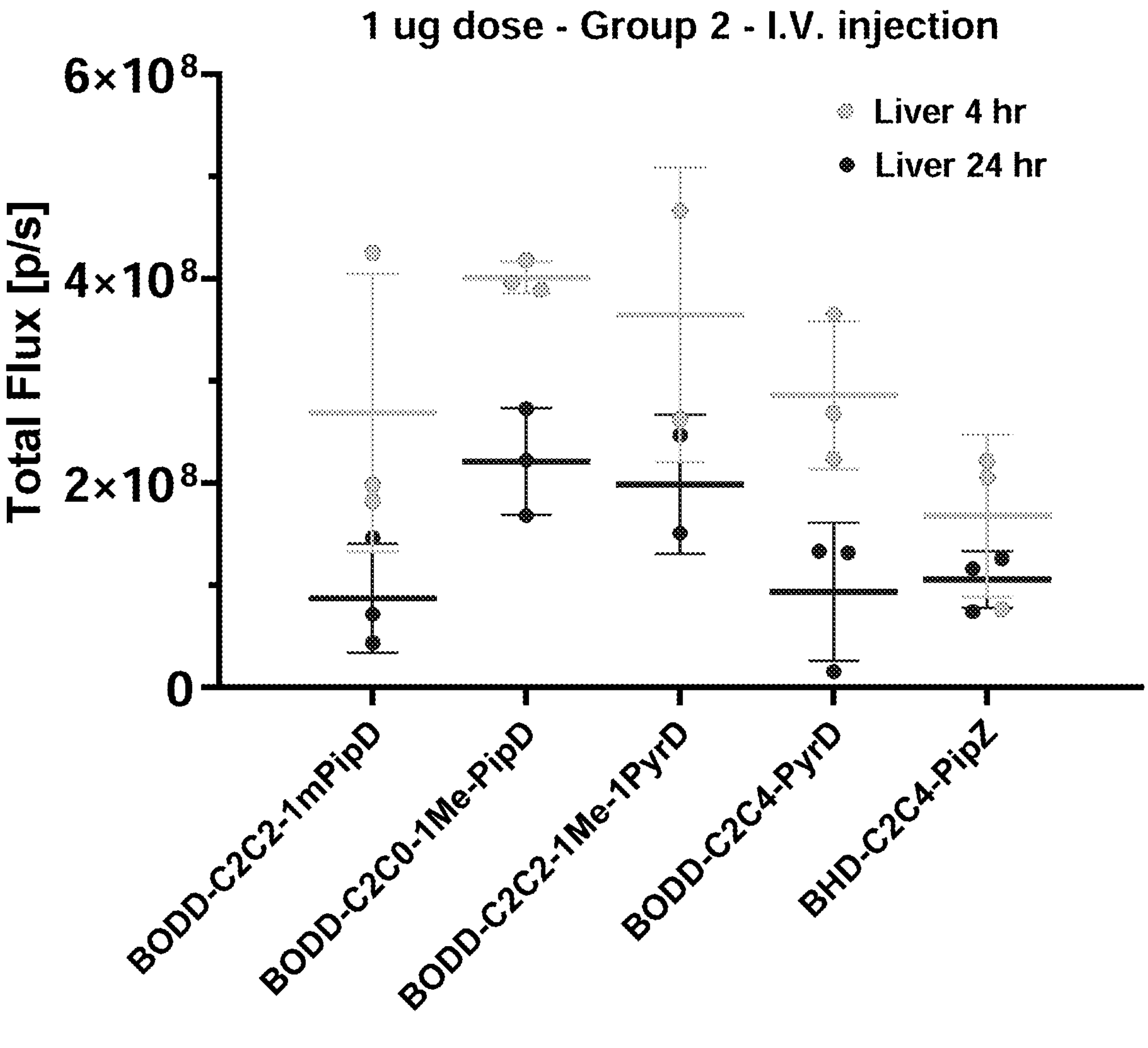
FIG. 23N: In vivo Firefly Luciferase expression in IV administration.
Figure 24A:
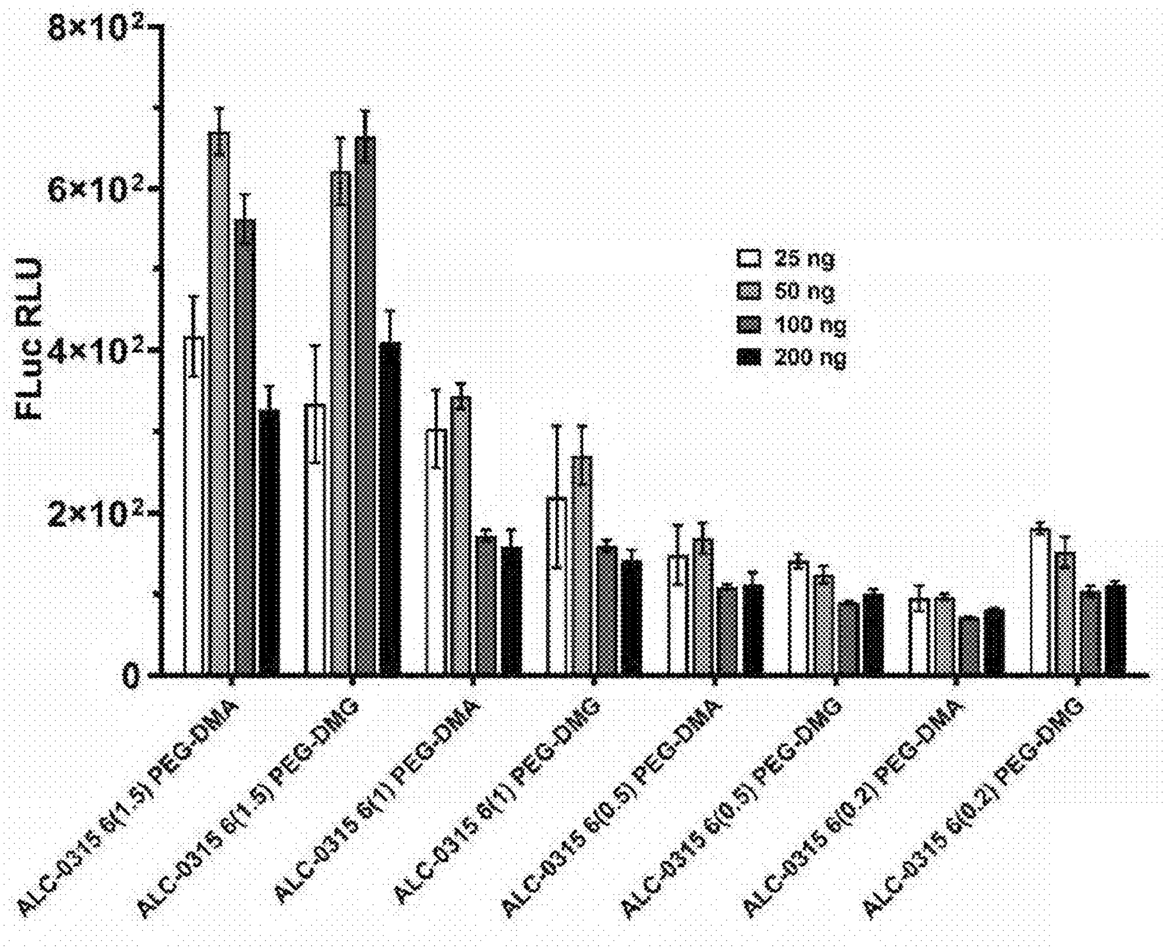
FIG. 24A: Firefly Luciferase Assay for mRNA Delivery Efficiency as set forth in Example 24.
Figure 24B:
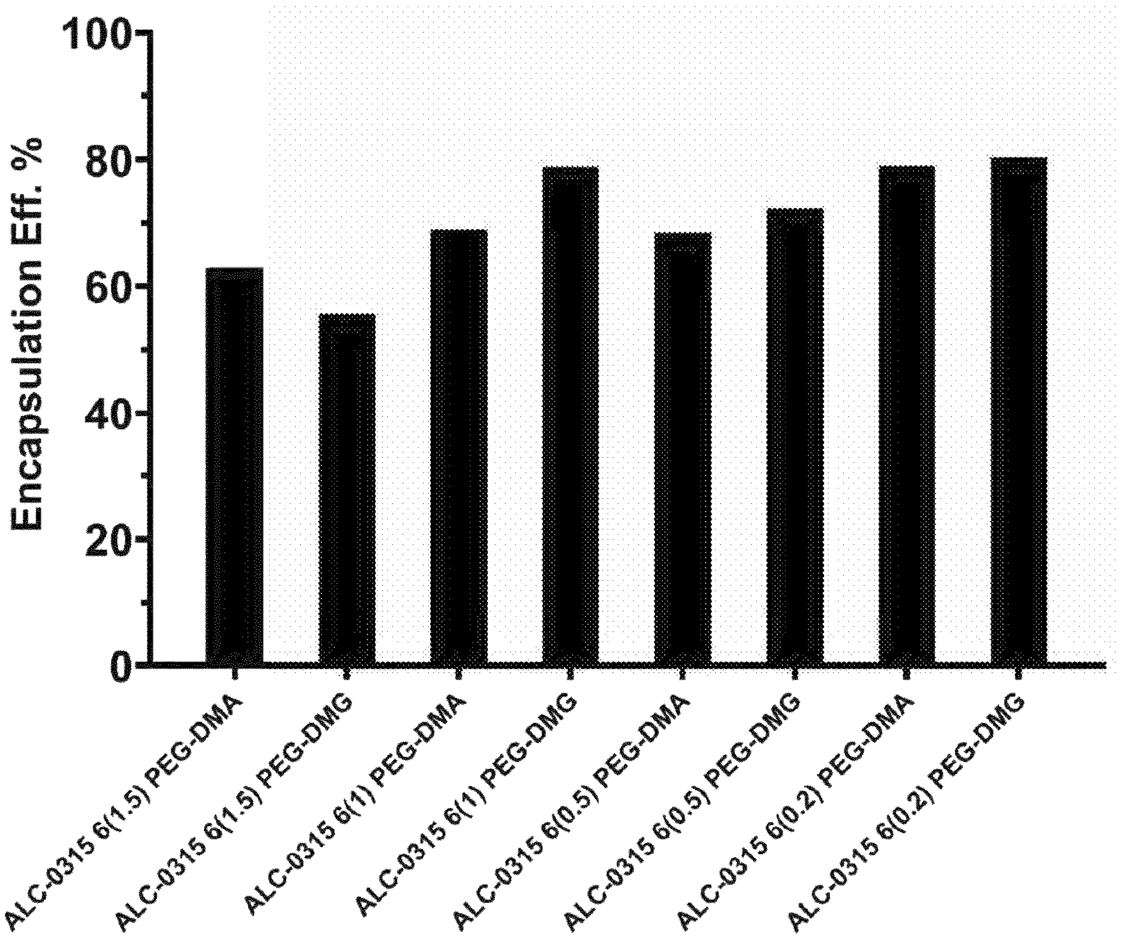
FIG. 24B: Ribogreen Assay for mRNA Encapsulation Efficiency as set forth in Example 24.
Figure 24C:
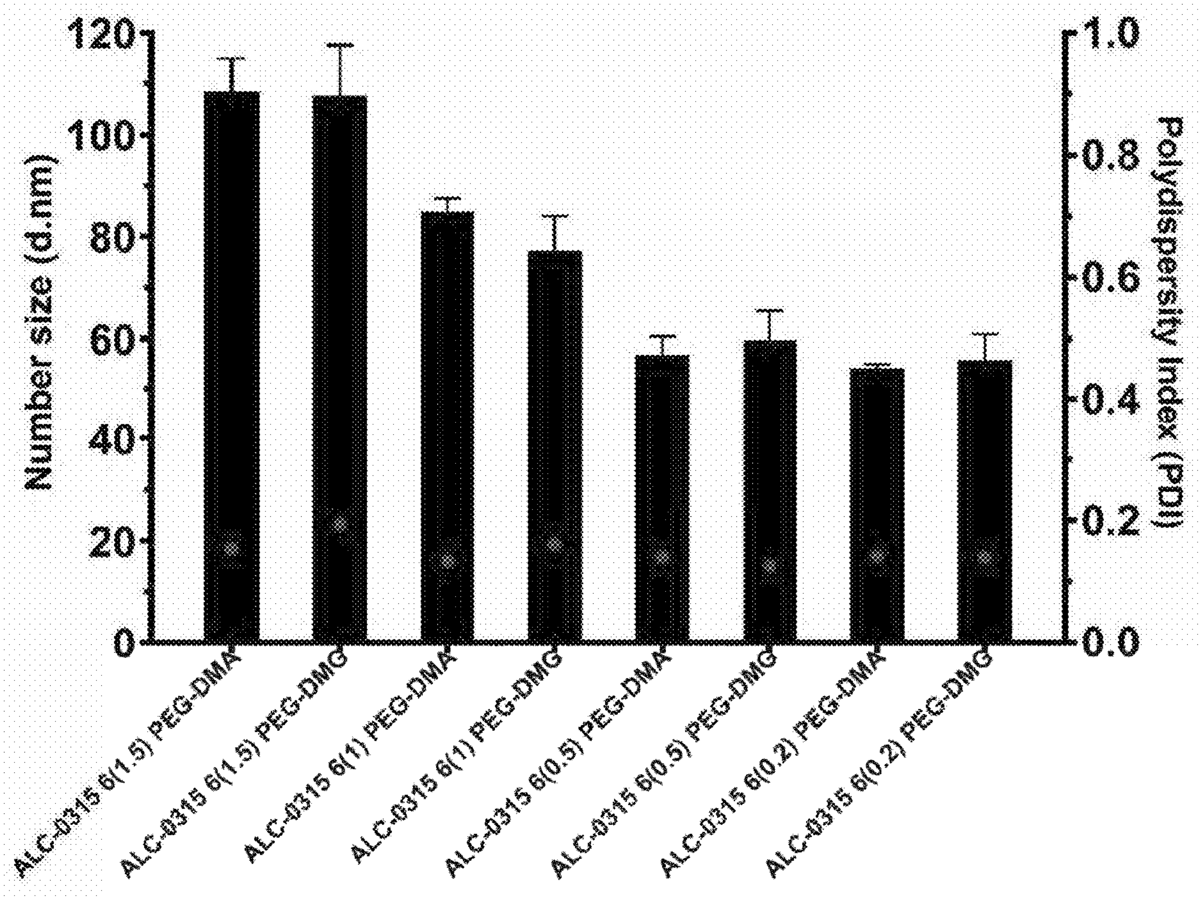
FIG. 24C: Dynamic Light Scattering for LNP Size (white dots are PDI right y axis) as set forth in Example 24.
Figure 25A:
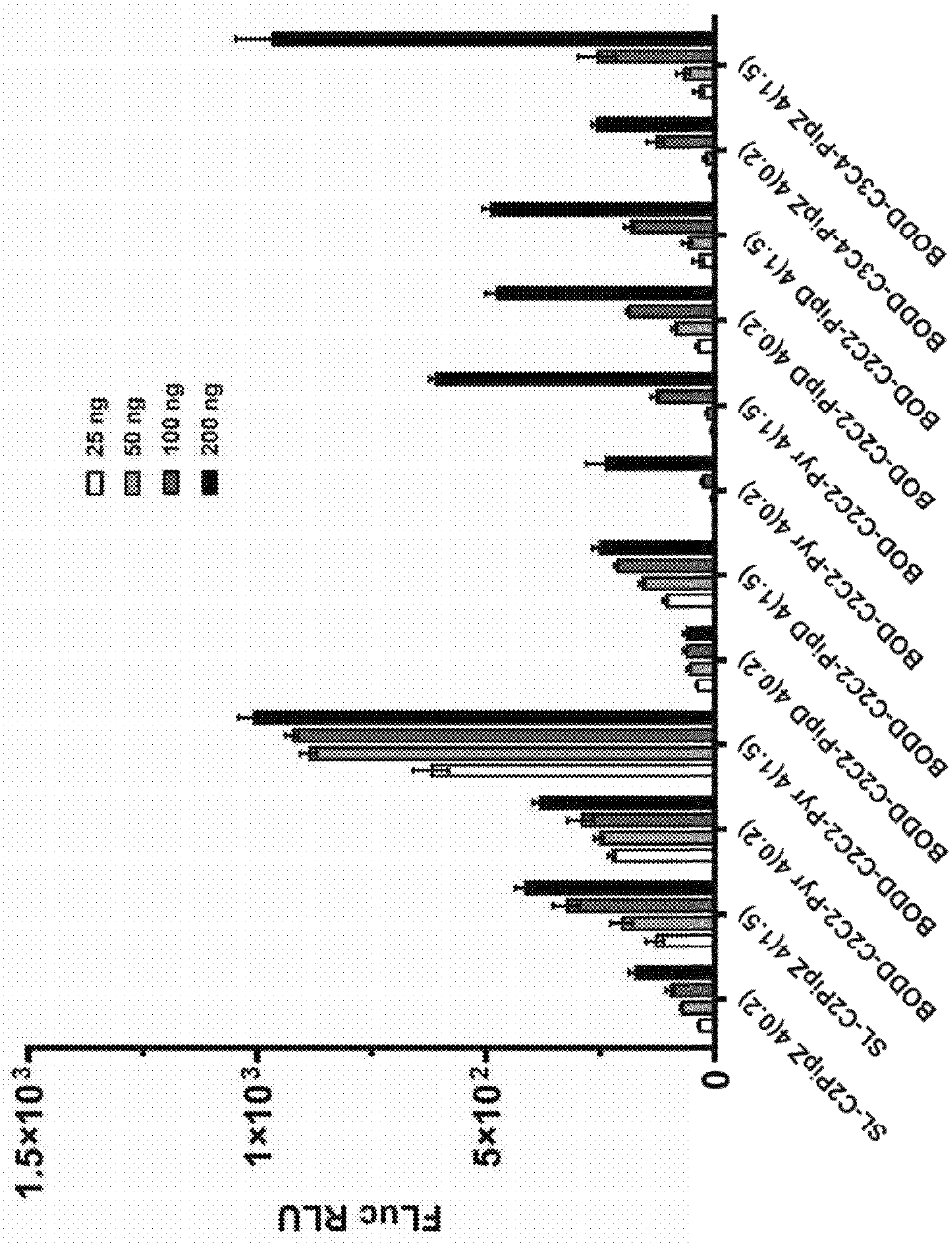
FIG. 25A and FIG. 25B: Firefly Luciferase Assay for mRNA Delivery Efficiency as set forth in Example 25.
Figure 25B:
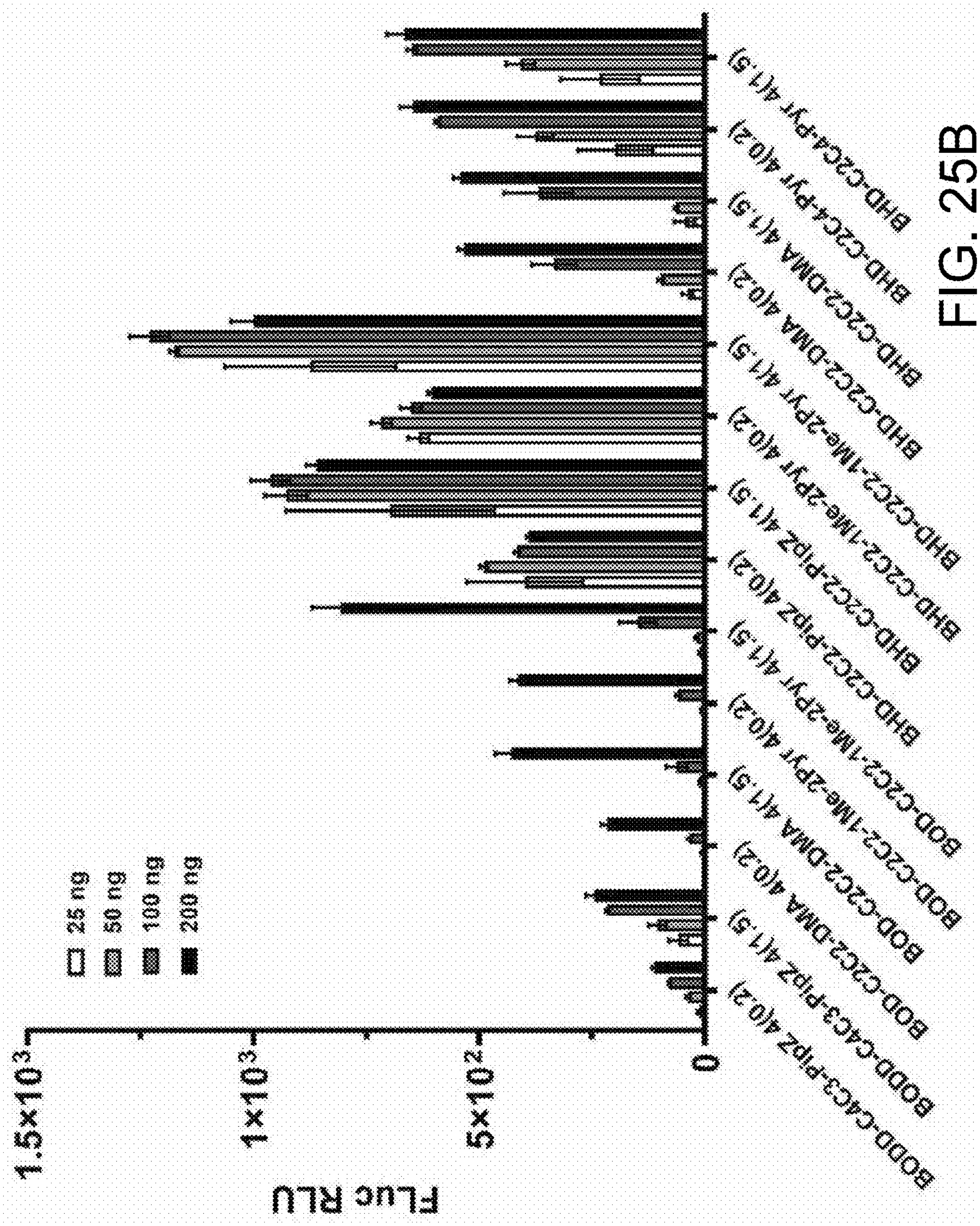
Figure 25C:
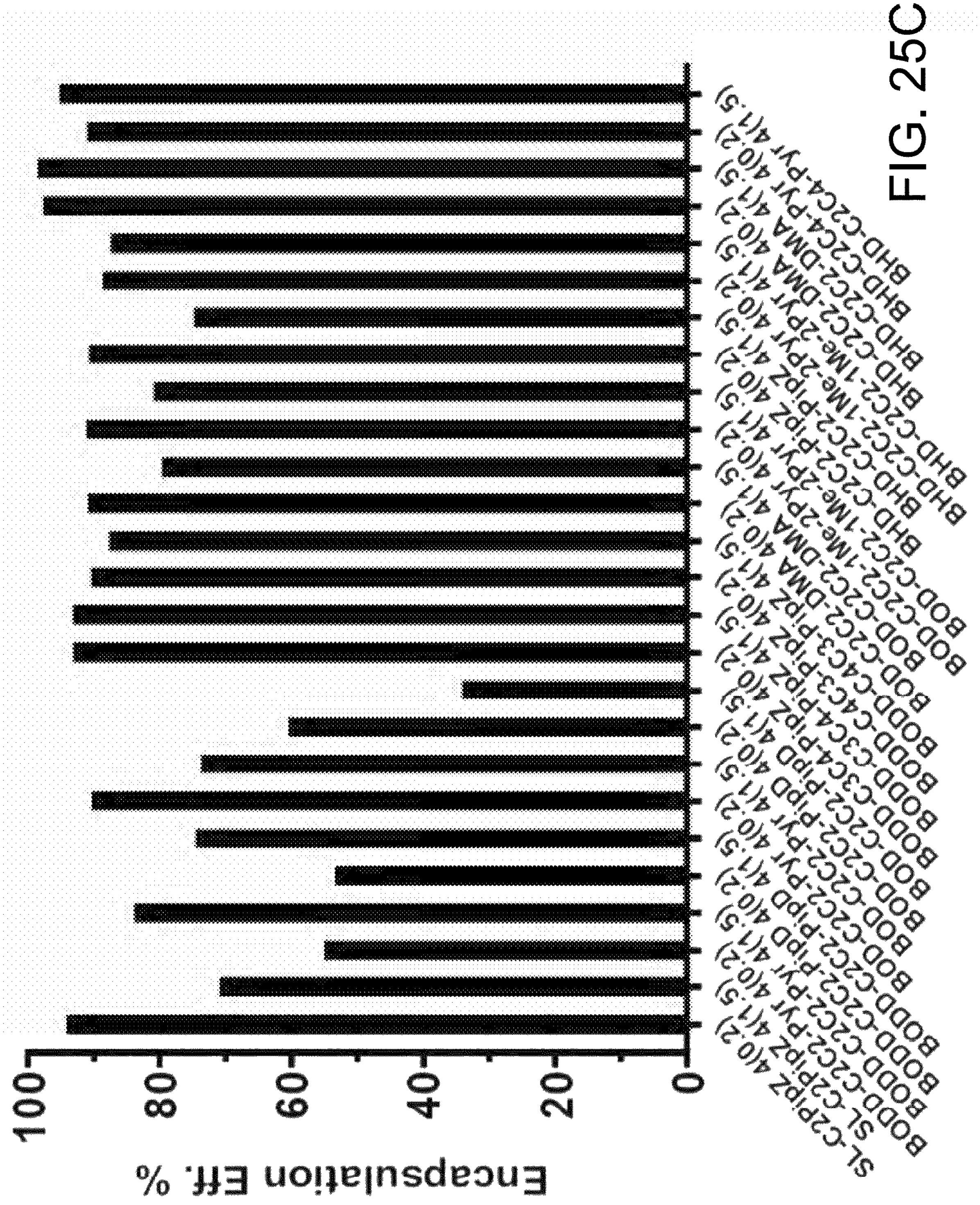
FIG. 25C: Ribogreen Assay for mRNA Encapsulation Efficiency as set forth in Example 25.
Figure 25D:
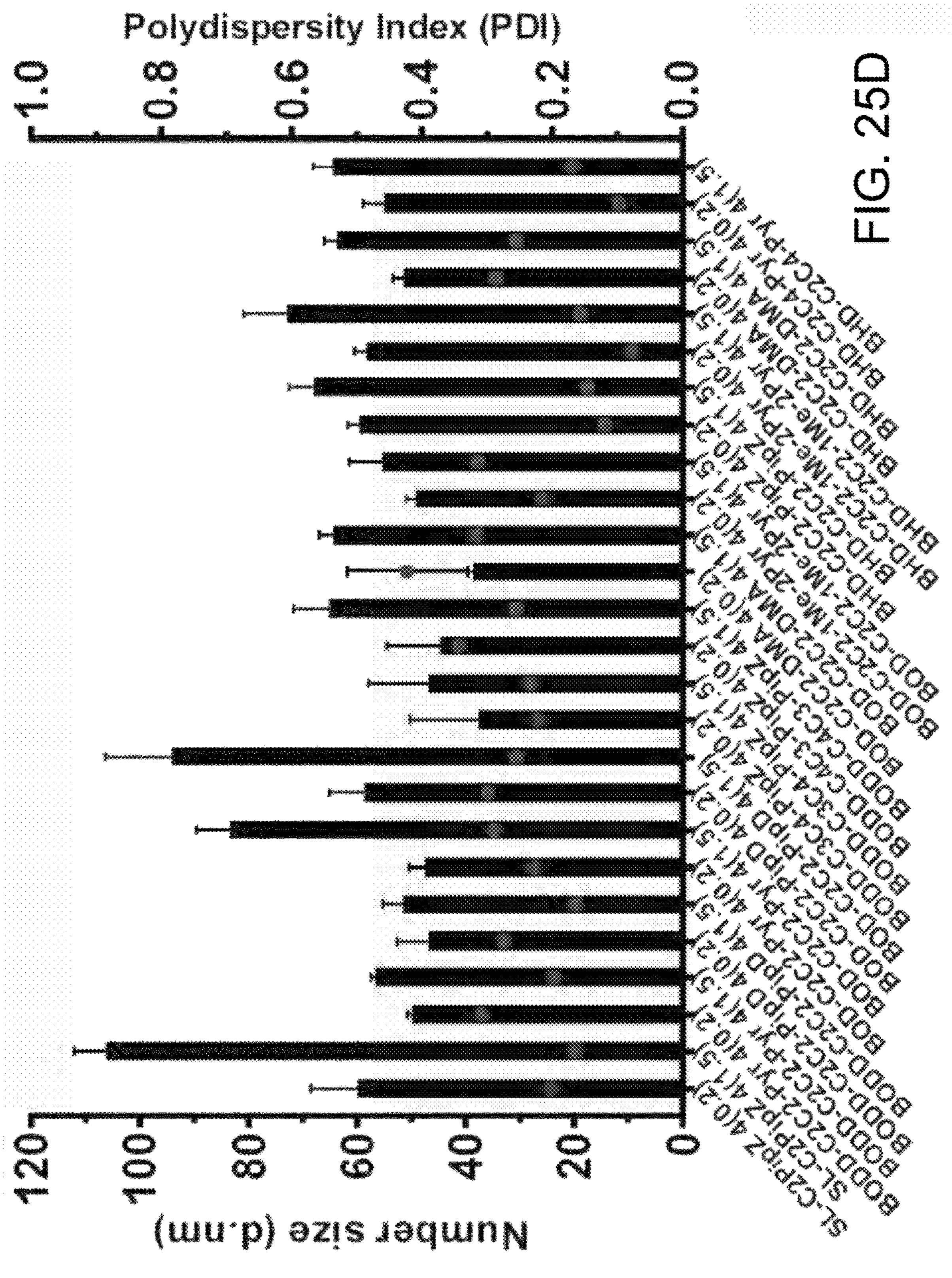
FIG. 25D: Dynamic Light Scattering for LNP Size (white dots are PDI right y axis) as set forth in Example 25.
Figure 26A:
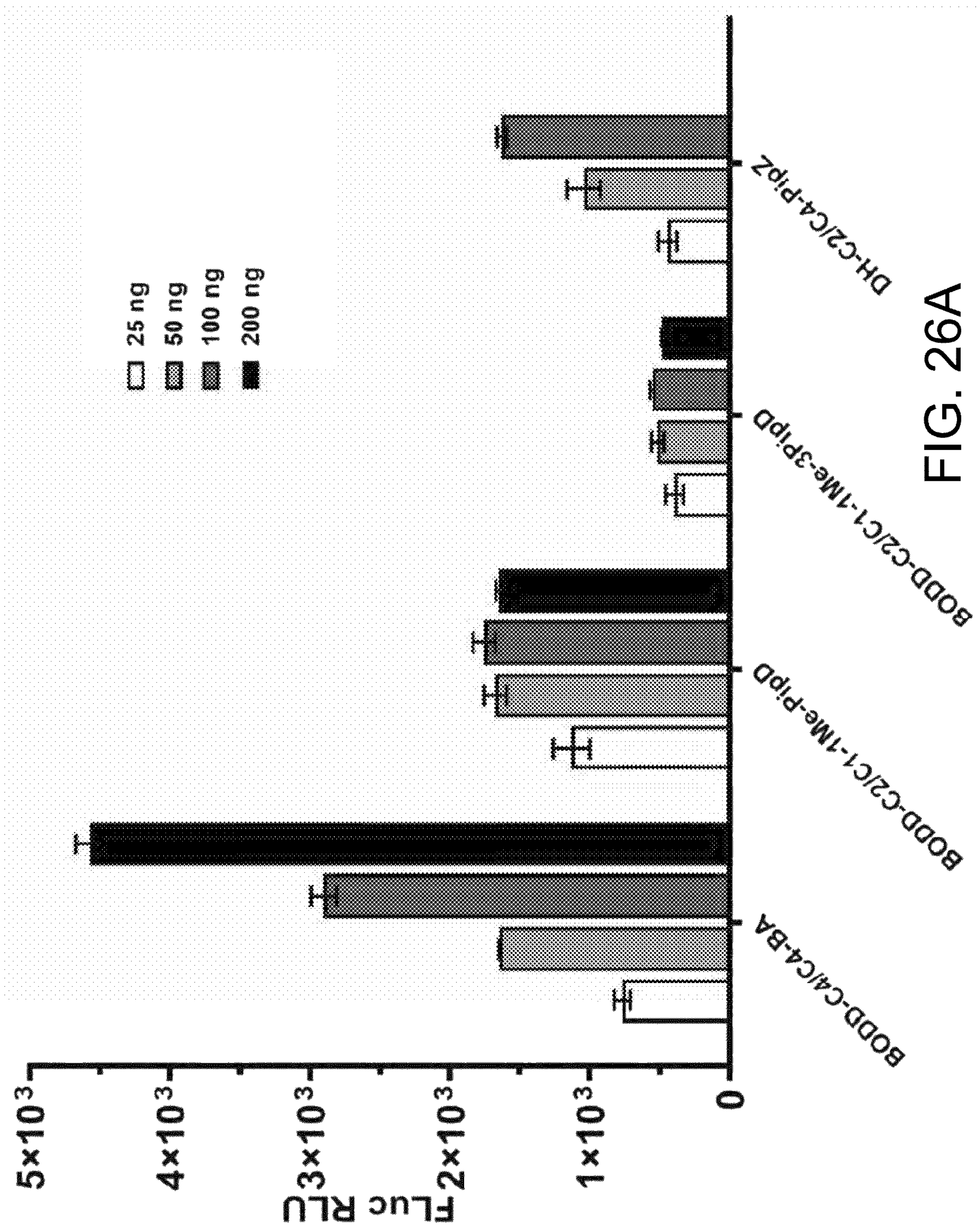
FIG. 26A: Firefly Luciferase Assay for mRNA Delivery Efficiency as set forth in Example 26.
Figure 26B:
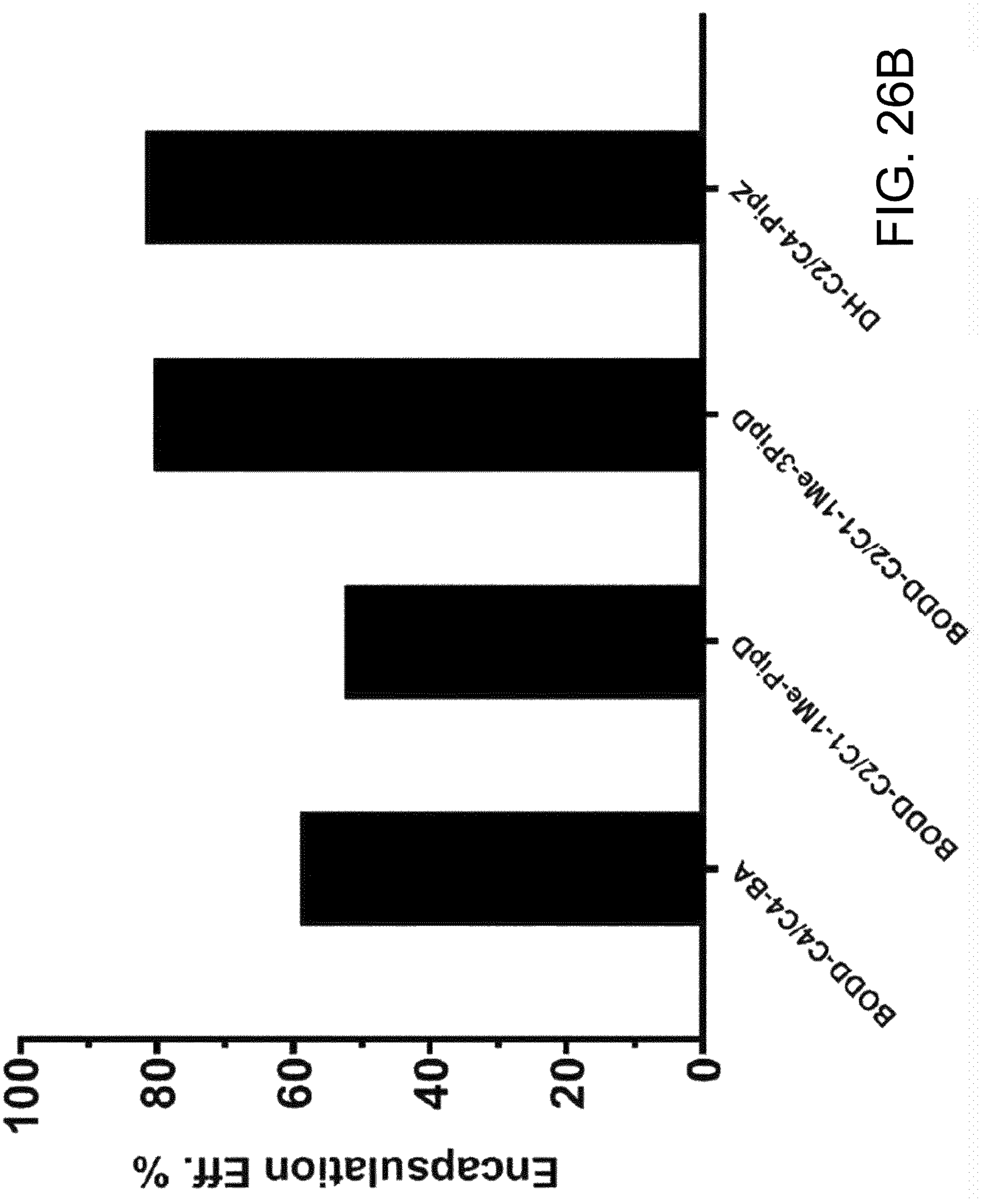
FIG. 26B: Ribogreen Assay for mRNA Encapsulation Efficiency as set forth in Example 26.
Figure 26C:
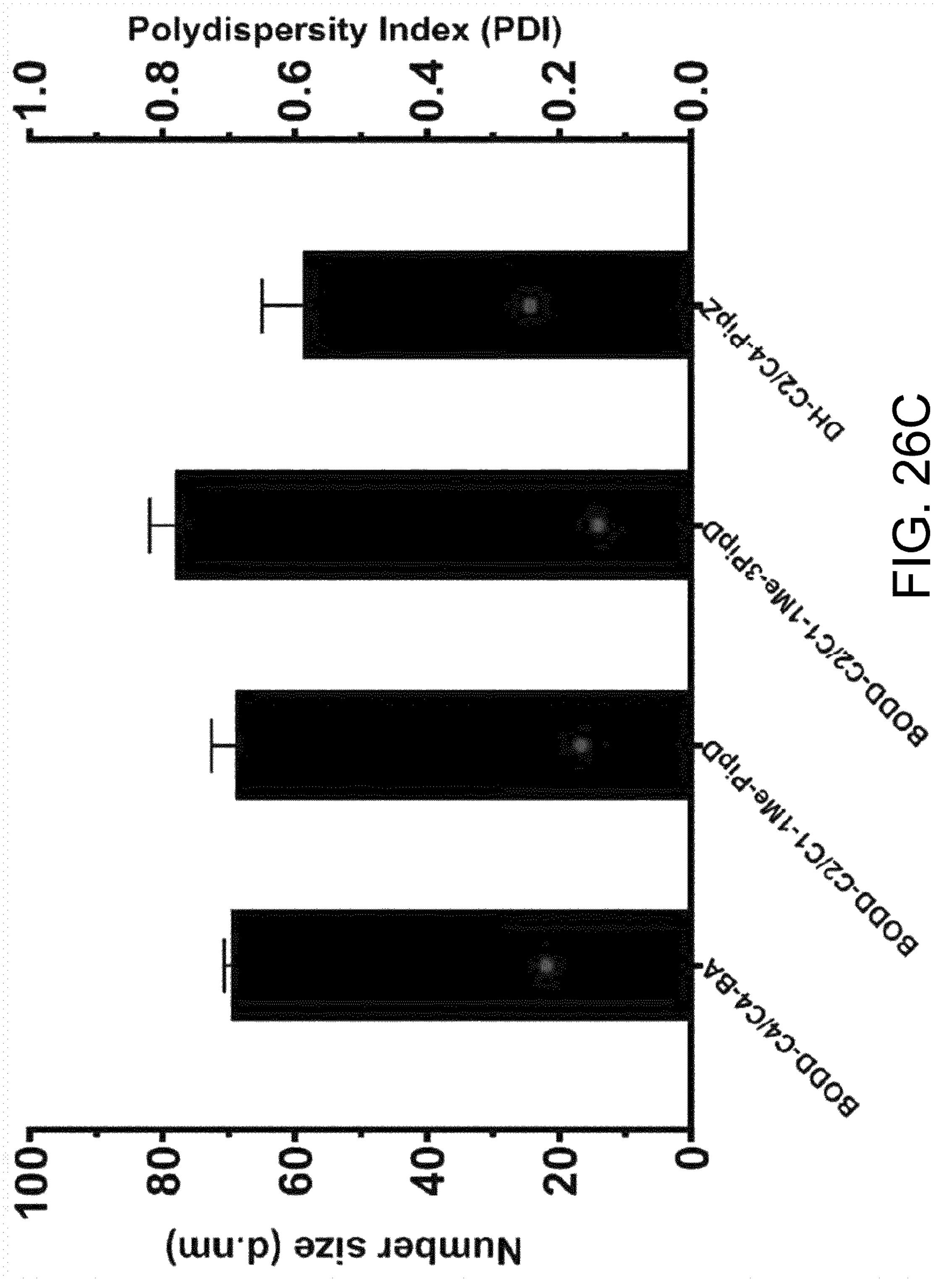
FIG. 26C: Dynamic Light Scattering for LNP Size (white dots are PDI right y axis) as set forth in Example 26.

In some embodiments, increasing the mRNA concentration in the Nucleic Acid Solution from 0.05 mg/ml mRNA to 1.5 mg/ml mRNA at a constant NP ratio 4 all in 50 mM sodium acetate pH 4 leads to a about 10× increase in LNP potency comparing 1.5 mg/ml to 0.05 mg/ml mixing concentration tested at the same doses in cells (FIG. 8A) and in animals (FIG. 9C IM and IV administration). The low mRNA concentration in the range 0.05 mg/ml-0.1 mg/ml LNPs represents LNPs made according to the Reference LNP Manufacturing Method. Preferably, the inventive methods have mixing taking place at about or above 0.20 mg/ml of mRNA, at which point a large increase in LNP potency is observed.

One embodiment, a Methods of Manufacture is as set for the below:

- Nucleic Acid Solution: Prepare mRNA at several concentrations in the range 0.05 to 3 mg/ml in a single buffer, e.g. 25 mM sodium acetate buffer at pH 4. As a general guideline, the buffer choice and pH here should be chosen to obtain a pH during mixing that is about 1 point below the pKa of the LNP being produced in order to obtain about 70% encapsulation. For example, KC2 or MC3 that have pKa=~6.5 mixed at 75 mM Total Lipid Concentration (37.5 mM KC2 or MC3 concentration) with mRNA at 1.5 mg/ml in 25 mM NaOAc at pH 4 to produce NP 4 results in a mixing pH of 5.5 in the Mixing Solution composed of 1 mg/ml mRNA (3.1 mM phosphate groups), 12.5 mM KC2 and 16.7 mM Sodium Acetate in 33% ethanol (ETOH), 67% H2O when 2 volumes of Nucleic Acid Solution are mixed with 1 volume of Lipid solution.
- Lipid Solution: Prepare the lipid mix in ethanol or another suitable solvent at several concentrations corresponding to the desired NP ratio or lipid/mRNA weight ratio for each of the mRNA solutions described immediately above in relation to the Nucleic Acid Solution preparation.
- Assemble naLNPs at the above multiple mixing concentrations with mRNA in a single buffer type, concentration and pH.
- Bringing naLNPs to physiological pH.
- Measure naLNP size using light scattering
- Measure RNA encapsulation in the naLNPs using the Ribogreen assay
- Accept naLNPs that have encapsulation >40%
- Measure Luciferase activity in vitro or in vivo at a known dose or several doses.
- Relative naLNP potency versus refLNPs is determined by Luciferase activity measured in vitro or in vivo.

In another embodiment naLNP potency may be optimized at any given mixing concentration by changing the pH of mixing and protonation level of the ionizable lipid during mixing by adjusting the mRNA buffer type, concentration and pH:

- Nucleic Acid Solution: Prepare mRNA at one concentration (i.e. in the above range 0.05 to 3 mg/ml) in a range of buffer types (sodium acetate, sodium citrate etc), buffer concentrations (1-100 mM) and pH (3-7). For any particular mixing concentration, the buffers chosen should produce encapsulation efficiencies spanning the range of 40-90% which could correspond approximately to the protonation level (40-90%) of the ionizable lipid which in turn is determined by the pH of the 33% ETOH/67% $H_2O$ buffer and thus the buffer type, concentration and pH.
- Lipid Solution: Prepare the lipid mix in ethanol or another suitable solvent at a concentration corresponding to the desired NP ratio or lipid/mRNA weight ratio for the mRNA solutions described in immediately above in relation to the Nucleic Acid Solution preparation.
- Assemble naLNPs in the multiple buffers above with a single mixing concentration.
- Bringing naLNPs to physiological pH.
- Measure naLNP size using light scattering
- Measure RNA encapsulation in the naLNPs using the Ribogreen assay
- Accept naLNPs that have encapsulation >40%
- Measure Luciferase activity in vitro or in vivo at a known dose or several doses.
- Relative naLNP potency is determined by Luciferase activity measured in vitro or in vivo.

For any particular naLNP formulation a potency increase of at least or about 10× relative to ref LNPs create by the Reference LNP Manufacturing Methods can be obtained by appropriate optimization of concentrations in the Nucleic Acid Solution and Lipid Solution and therefore the Mixing Solution and the mRNA buffer concentration and pH in accordance with the method disclosed herein.

In some embodiments, the buffer is missing entirely from the Nucleic Acid Solution solution and the ionizable lipids are protonated directly by controlled addition of an acid, e.g., HCl, to the Lipid Solution lipid mix as shown in Example 10. The latter will achieve a defined level of protonation in the lipid mix prior to mixing with mRNA in water and can lead to similar levels of encapsulation (70%) as that found to be optimal using sodium acetate.

In one embodiment the combining of the two liquids is by mixing. For example, the mixing is by microfluidic mixing by chaotic advection. In another embodiment, T-junction mixing can be used at larger scales resulting in similar LNPs.

Microfluidic devices provide an ability to controllably and rapidly mix fluids at the nanoliter scale with precise control over temperature, residence times, and solute concentrations. Controlled and rapid microfluidic mixing has been previously applied in the synthesis of inorganic nanoparticles and microparticles and can outperform macroscale systems in large scale production of nanoparticles. Microfluidic two-phase droplet techniques have been applied to produce monodisperse polymeric microparticles for drug delivery or to produce large vesicles for the encapsulation of cells, proteins, or other biomolecules. In some embodiments, the use of hydrodynamic flow focusing, a common microfluidic technique to provide rapid mixing of reagents, to create monodisperse liposomes of controlled size is used. This technique has also proven useful in the production of polymeric nanoparticles where smaller, more monodisperse particles were obtained, with higher encapsulation of small molecules as compared to bulk production methods.

In one embodiment, at least or about 1, 2, 3, 4, 5, 6, 7, 8, 9, 10, 11, 12, 13, 14, 15, or more lipids are solubilized in an organic solvent such as ethanol, while the nucleic acid is in a pH 3-6, preferably 4 acetic acid buffer. These two streams meet in a common microfluidic channel and are forced to mix in several milliseconds before being ejected into an aqueous recipient well. Two events occur while mixing: 1) the initially neutral ionizable lipid contacts the low pH buffer and becomes protonated at the same time as mixing with the anionic mRNA thus forming electrostatic bonds between the cationic lipid and anionic nucleic acid; and 2) the lipids become insoluble in the predominantly aqueous buffer and encapsulate the mRNA. The pH in the final well containing PBS is typically 6-6.5 due to the mixture of acetic acid, PBS and ionizable lipid, all of which are buffers with a certain buffer capacity and initial pH.

In some embodiments, the naLNPs are dialyzed against PBS to raise the pH to about 7.4 and remove ethanol. LNP assembly continues during dialysis as the ionizable lipid with an LNP pKa near 6.5 becomes gradually neutralized to pH 7.4 and thereby less soluble triggering a fusion of the LNPs that increases size and transforms an aqueous electron lucent core to an electron dense core containing predominantly the ionizable lipid and nucleic acid.

The total amount of lipid provided by the invention in the composition being administered is, in one embodiment, from about 2 to about 100 mg lipid per mg biologically active agent (e.g. RNA), in another embodiment from about 5 to about 25 mg lipid per mg biologically active agent (e.g. RNA), in another embodiment from about 7 to about 25 mg lipid per mg biologically active agent (e.g. RNA) and in one embodiment from about 10 to about 20 mg lipid per mg biologically active agent (e.g. RNA).

Pharmaceutical Compositions and Methods

The LNPs of the present invention may be used to deliver a therapeutic or prophylactic agent to a cell, in vitro or in vivo. In particular embodiments, the therapeutic agent is a nucleic acid, which is delivered to a cell using nucleic acid-lipid particles of the present invention. The methods and compositions may be readily adapted for the delivery of any suitable therapeutic agent for the treatment of any disease or disorder that would benefit from such treatment.

In certain embodiments, the present invention provides methods for introducing a nucleic acid into a cell. Preferred nucleic acids for introduction into cells are mRNA, siRNA, miRNA, immune-stimulating oligonucleotides, DNA plasmids, antisense and ribozymes. These methods may be carried out by contacting the particles or compositions of the present invention with the cells for a period of time sufficient for intracellular delivery to occur.

Nucleic acids for use with this invention may be prepared according to any available technique. For mRNA, the primary methodology of preparation is, but not limited to, enzymatic synthesis (also termed in vitro transcription) which currently represents the most efficient method to produce long sequence-specific mRNA. In vitro transcription describes a process of template-directed synthesis of RNA molecules from an engineered DNA template comprised of an upstream bacteriophage promoter sequence (e.g. including but not limited to that from the T7, T3 and SP6 coliphage) linked to a downstream sequence encoding the gene of interest. Template DNA can be prepared for in vitro transcription from a number of sources with appropriate techniques which are well known in the art including, but not limited to, plasmid DNA and polymerase chain reaction amplification (see Linpinsel, J. L and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012)

Transcription of the RNA occurs in vitro using the linearized DNA template in the presence of the corresponding RNA polymerase and adenosine, guanosine, uridine and cytidine ribonucleoside triphosphates (rNTPs) under conditions that support polymerase activity while minimizing potential degradation of the resultant mRNA transcripts. In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs. The methodology for in vitro transcription of mRNA is well known in the art. (see, e.g. Losick, R., 1972, In vitro transcription, Ann Rev Biochem v.41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y. Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference).

The desired in vitro transcribed mRNA is then purified from the undesired components of the transcription or associated reactions (including unincorporated rNTPs, protein enzyme, salts, short RNA oligos etc). Techniques for the isolation of the mRNA transcripts are well known in the art. Well known procedures include phenol/chloroform extraction or precipitation with either alcohol (ethanol, isopropanol) in the presence of monovalent cations or lithium chloride. Additional, non-limiting examples of purification procedures which can be used include size exclusion chromatography (Lukaysky, P. J. and Puglisi, J. D., 2004, Large-scale preparation and purification of polyacrylamide-free RNA oligonucleotides, RNA v.10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Furthermore, while reverse transcription can yield large quantities of mRNA, the products can contain one or more aberrant RNA impurities associated with undesired polymerase activity which may need to be removed from the full-length mRNA preparation. These include short RNAs that result from abortive transcription initiation as well as double-stranded RNA (dsRNA) generated by RNA-dependent RNA polymerase activity, RNA-primed transcription from RNA templates and self-complementary 3' extension. It has been demonstrated that these contaminants with dsRNA structures can lead to undesired immunostimulatory activity through interaction with various innate immune sensors in eukaryotic cells that function to recognize specific nucleic acid structures and induce potent immune responses. This in turn, can dramatically reduce mRNA translation since protein synthesis is reduced during the innate cellular immune response. Therefore, additional techniques to remove these dsRNA contaminants have been developed and are known in the art including but not limited to scaleable HPLC purification (see e.g. Kariko, K., Muramatsu, H., Ludwig, J. and Weissman, D., 2011, Generating the optimal mRNA for therapy: HPLC purification eliminates immune activation and improves translation of nucleoside-modified, protein-encoding mRNA, Nucl Acid Res, v. 39 e142; Weissman, D., Pardi, N., Muramatsu, H., and Kariko, K., HPLC Purification of in vitro transcribed long RNA in Synthetic Messenger RNA and Cell Metabolism Modulation in Methods in Molecular Biology v.969 (Rabinovich, P. H. Ed), 2013). HPLC purified mRNA has been reported to be translated at much greater levels, particularly in primary cells and in vivo.

A significant variety of modifications have been described in the art which are used to alter specific properties of in vitro transcribed mRNA and improve its utility. These include but are not limited to modifications to the 5' and 3' termini of the mRNA. Endogenous eukaryotic mRNA typically contain a cap structure on the 5'-end of a mature molecule which plays an important role in mediating binding of the mRNA Cap Binding Protein (CBP), which is in turn responsible for enhancing mRNA stability in the cell and efficiency of mRNA translation. Therefore, highest levels of protein expression are achieved with capped mRNA transcripts. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group.

Multiple distinct cap structures can be used to generate the 5'-cap of in vitro transcribed synthetic mRNA. 5'-capping of synthetic mRNA can be performed co-transcriptionally with chemical cap analogs (i.e. capping during in vitro transcription). For example, the Anti-Reverse Cap Analog (ARCA) cap contains a 5'-5'-triphosphate guanine-guanine linkage where one guanine contains an N7 methyl group as well as a 3'-O-methyl group. However, up to 20% of transcripts remain uncapped during this co-transcriptional process and the synthetic cap analog is not identical to the 5'-cap structure of an authentic cellular mRNA, potentially reducing translatability and cellular stability. Alternatively, synthetic mRNA molecules may also be enzymatically capped post-transcriptionally. These may generate a more authentic 5'-cap structure that more closely mimics, either structurally or functionally, the endogenous 5'-cap which have enhanced binding of cap binding proteins, increased half life, reduced susceptibility to 5' endonucleases and/or reduced 5' decapping. Numerous synthetic 5'-cap analogs have been developed and are known in the art to enhance mRNA stability and translatability (see e.g. Grudzien-Nogalska, E., Kowalska, J., Su, W., Kuhn, A. N., Slepenkov, S. V., Darynkiewicz, E., Sahin, U., Jemielity, J., and Rhoads, R. E., Synthetic mRNAs with superior translation and stability properties in Synthetic Messenger RNA and Cell Metabolism Modulation in Methods in Molecular Biology v.969 (Rabinovich, P. H. Ed), 2013).

On the 3'-terminus, a long chain of adenine nucleotides (poly-A tail) is normally added to mRNA molecules during RNA processing. Immediately after transcription, the 3' end of the transcript is cleaved to free a 3' hydroxyl to which poly-A polymerase adds a chain of adenine nucleotides to the RNA in a process called polyadenylation. The poly-A tail has been extensively shown to enhance both translational efficiency and stability of mRNA (see Bernstein, P. and Ross, J., 1989, Poly (A), poly (A) binding protein and the regulation of mRNA stability, Trends Bio Sci v. 14 373-377; Guhaniyogi, J. And Brewer, G., 2001, Regulation of mRNA stability in mammalian cells, Gene, v. 265, 11-23; Dreyfus, M. And Regnier, P., 2002, The poly (A) tail of mRNAs: Bodyguard in eukaryotes, scavenger in bacteria, Cell, v.111, 611-613).

Poly (A) tailing of in vitro transcribed mRNA can be achieved using various approaches including, but not limited to, cloning of a poly (T) tract into the DNA template or by post-transcriptional addition using Poly (A) polymerase. The first case allows in vitro transcription of mRNA with poly (A) tails of defined length, depending on the size of the poly (T) tract, but requires additional manipulation of the template. The latter case involves the enzymatic addition of a poly (A) tail to in vitro transcribed mRNA using poly (A) polymerase which catalyzes the incorporation of adenine residues onto the 3'termini of RNA, requiring no additional manipulation of the DNA template, but results in mRNA with poly(A) tails of heterogenous length. 5'-capping and 3'-poly (A) tailing can be performed using a variety of commercially available kits including, but not limited to Poly (A) Polymerase Tailing kit (EpiCenter), mMESSAGE mMACHINE T7 Ultra kit and Poly (A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. It is well known in the art that pathogenic DNA and RNA can be recognized by a variety of sensors within eukaryotes and trigger potent innate immune responses. The ability to discriminate between pathogenic and self DNA and RNA has been shown to be based, at least in part, on structure and nucleoside modifications since most nucleic acids from natural sources contain modified nucleosides In contrast, in vitro synthesized RNA lacks these modifications, thus rendering it immunostimulatory which in turn can inhibit effective mRNA translation as outlined above. The introduction of modified nucleosides into in vitro transcribed mRNA can be used to prevent recognition and activation of RNA sensors, thus mitigating this undesired immunostimulatory activity and enhancing translation capacity (see eg. Kariko, K. And Weissman, D. 2007, Naturally occurring nucleoside modifications suppress the immunostimulatory activity of RNA: implication for therapeutic RNA development, Curr Opin Drug Discov Devel, v.10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v.969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Nonimmunogenic Vector With Increased Translational Capacity and Biological Stability, Mol Ther v.16, 1833-1840. The modified nucleosides and nucleotides used in the synthesis of modified RNAs can be prepared monitored and utilized using general methods and procedures known in the art. A large variety of nucleoside modifications are available that may be incorporated alone or in combination with other modified nucleosides to some extent into the in vitro transcribed mRNA (see eg. US2012/0251618). In vitro synthesis of nucleoside-modified mRNA have been reported to have reduced ability to activate immune sensors with a concomitant enhanced translational capacity.

Other components of mRNA which can be modified to provide benefit in terms of translatability and stability include the 5' and 3' untranslated regions (UTR). Optimization of the UTRs (favorable 5' and 3' UTRs can be obtained from cellular or viral RNAs), either both or independently, have been shown to increase mRNA stability and translational efficiency of in vitro transcribed mRNA (see eg. Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v.969 (Rabinovich, P. H. Ed), 2013).

In addition to mRNA, other nucleic acid payloads may be used for this invention. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with this invention commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc) allows those bacteria containing the plasmid of interest to selective grow in antibiotic-containing cultures. Methods of isolating plasmid DNA are widely used and well known in the art (see, e.g. Heilig, J., Elbing, K. L. and Brent, R (2001) Large-Scale Preparation of Plasmid DNA. Current Protocols in Molecular Biology. 41:11:1.7:1.7.1-1.7.16; Rozkov, A., Larsson, B., Gillstrom, S., Bjornestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197, 553B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

Typical applications include using well known procedures to provide intracellular delivery of siRNA to knock down or silence specific cellular targets. Alternatively, applications include delivery of DNA or mRNA sequences that code for therapeutically useful polypeptides or gene editing components. In this manner, therapy is provided for genetic diseases by supplying deficient or absent gene products. Methods of the present invention may be practiced in vitro, ex vivo, or in vivo. For example, the compositions of the present invention can also be used for delivery of nucleic acids to cells in vivo, using methods which are known to those of skill in the art.

The delivery of siRNA by a lipid particle of the invention and its effectiveness in silencing gene expression is described below.

For in vivo administration, the pharmaceutical compositions are preferably administered parenterally (e.g., intraarticularly, intravenously, intraperitoneally, subcutaneously, or intramuscularly). In particular embodiments, the pharmaceutical compositions are administered intravenously or intraperitoneally by a bolus injection. Other routes of administration include topical (skin, eyes, mucus membranes), oral, pulmonary, intranasal, sublingual, rectal, and vaginal.

In one embodiment, the present invention provides a method of modulating the expression of a target polynucleotide or polypeptide. These methods generally comprise contacting a cell with a LNP of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In a further aspect, the invention provides a pharmaceutical composition comprising a lipid particle of the invention and a pharmaceutically acceptable carrier or diluent. Representative pharmaceutically acceptable carriers or diluents include solutions for intravenous injection (e.g., saline or dextrose). The composition can take the form of a cream, ointment, gel, suspension, or emulsion.

As used herein, "treatment" includes ameliorative, curative and prophylactic treatment. As used herein, a "patient" means an animal, preferably a mammal, preferably a human, in need of treatment.

The term "therapeutically effective amount" refers to the amount of the compound of the invention and the biologically active agent (e.g. the therapeutic compound) needed to treat or ameliorate a targeted disease or condition.

The term "immunologically effective amount" refers to the amount of the compound of the invention and of RNA which encodes an immunogen needed to elicit an immune response which recognizes the immunogen (e.g. in the context of a pathogen). The term "immunogen" refers to any substance or organism that provokes an immune response when introduced into the body. The phrase "RNA which encodes an immunogen" refers to a polynucleotide, such as a messenger RNA or a replicon (e.g., self-replicating RNA), that when administered to a cell or organism is capable of being translated into a polypeptide according to the codon sequence of such RNA.

By "proliferative disease" as used herein is meant any disease, condition, trait, genotype or phenotype characterized by unregulated cell growth or replication as is known in the art. In one embodiment, the proliferative disease is cancer. In one embodiment, the proliferative disease is a tumor. In one embodiment, the proliferative disease includes, but are not limited to, e.g., liquid tumors such as, e.g., leukemias, e.g., acute myelogenous leukemia (AML), chronic myelogenous leukemia (CML), acute lymphocytic leukemia (ALL), multiple myeloma, and chronic lymphocytic leukemia; and solid tumors, e.g., AIDS related cancers such as Kaposi's sarcoma; breast cancers; bone cancers; brain cancers; cancers of the head and neck, non-Hodgkins lymphoma, adenoma, squamous cell carcinoma, laryngeal carcinoma, gallbladder and bile duct cancers, cancers of the retina, cancers of the esophagus, gastrointestinal cancers, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, endometrial sarcoma, multidrug resistant cancers. In one embodiment, the proliferative disease includes neovascularization associated with tumor angiogenesis, macular degeneration (e.g. wet/dry age-related macular degeneration), corneal neovascularization, diabetic retinopathy, neovascular glaucoma, myopic degeneration. In one embodiment, the proliferative disease includes restenosis and polycystic kidney disease.

By "autoimmune disease" as used herein is meant any disease, condition, trait, genotype or phenotype characterized by autoimmunity as is known in the art. Autoimmune diseases include, but are not limited to, e.g., multiple sclerosis, diabetes mellitus, lupus, scleroderms, fibromyalgia, transplantation rejection (e.g. prevention of allograft rejection), pernicious anemia, rheumatoid arthritis, systemic lupus erythematosus, dermatomyositis, myasthenia gravis, lupus erythematosus, multiple sclerosis, and Grave's disease.

By "infectious disease" is meant any disease, disorder or condition associated with an infectious agent, such as a virus, bacteria, fungus, prion or parasite. The invention can be used to actively or passively immunize against pathogens which cause infectious disease. Examples of such pathogens are given below.

By "neurologic disease" is meant any disease, disorder, or condition affecting the central or peripheral nervous system. Neurologic diseases include, but are not limited to, diseases or disorders of either the peripheral or the central nervous system including, e.g., Alzheimer's Disease, Aneurysm, Brain Injury, Carpal Tunnel Syndrome, Cerebral Aneurysm, Chronic Pain, Creutzfeldt-Jakob Disease, Epilepsy, Huntington's Disease, Meningitis, Seizure Disorders, and other neurologic diseases, disorders and syndromes.

By "respiratory disease" is meant any disease or condition affecting the respiratory tract. Respiratory diseases include, but are not limited to, e.g., asthma, chronic obstructive pulmonary disease (COPD), allergic rhinitis, sinusitis, allergies, impeded respiration, respiratory distress syndrome, cystic fibrosis, pulmonary hypertension or vasoconstriction and emphysema.

By "cardiovascular disease" is meant and disease or condition affecting the heart and vasculature. Cardiovascular diseases include, but are not limited to, e.g., coronary heart disease (CHD), cerebrovascular disease (CVD), aortic stenosis, peripheral vascular disease, myocardial infarction (heart attack), arrhythmia, ischemia, and congestive heart failure.

By "ocular disease" as used herein is meant any disease, condition, trait, genotype or phenotype of the eye and related structures. Ocular diseases include, but are not limited to, e.g., cystoid macular edema, diabetic retinopathy, lattice degeneration, retinal vein occlusion, retinal artery occlusion, macular degeneration (e.g. age related macular degeneration such as wet AMD or dry AMD), toxoplasmosis, retinitis pigmentosa, conjunctival laceration, corneal laceration, glaucoma, and the like.

By "metabolic disease" is meant any disease or condition affecting metabolic pathways. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes obesity, insulin resistance, and diabetes (e.g. type I and/or type II diabetes).

By "dermatological disease" is meant any disease or condition of the skin, dermis, or any substructure therein such as a hair, a follicle, etc. Dermatological diseases, disorders, conditions, and traits can include psoriasis, ectopic dermatitis, skin cancers such as melanoma and basal cell carcinoma, hair loss, hair removal and alterations in pigmentation.

By "auditory disease" is meant any disease or condition of the auditory system, including the ear, such as the inner ear, middle ear, outer ear, auditory nerve, and any substructures therein. Auditory diseases, disorders, conditions, and traits can include hearing loss, deafness, tinnitus, vertigo, balance and motion disorders.

By "regenerative disease" is meant any disease or condition where insufficient cell or tissue generation or regeneration in vivo or in vitro prevents the establishment or restoration of proper organ function before or after injury, prevents or slows wound healing or resolution of ulcerative lesions, accelerates ageing, or prevents effective cell-based therapy. The term "messenger ribonucleic acid" (messenger RNA, mRNA) refers to a ribonucleic acid (RNA) molecule that mediates the transfer of genetic information to ribosomes in the cytoplasm, where it serves as a template for protein synthesis. It is synthesized from a DNA template during the process of transcription. See, The American Heritage®. Dictionary of the English Language, Fourth Edition (Updated in 2009). Houghton Mifflin Company.

In eukaryotes, mRNA is transcribed in vivo at the chromosomes by the cellular enzyme RNA polymerase. During or after transcription in vivo, a 5' cap (also termed an RNA cap, an RNA 7-methylguanosine cap, or an RNA m7G cap) is added in vivo to the 5' end of the mRNA. The 5' cap is terminal 7-methylguanosine residue that is linked through a 5'-5'-triphosphate bond to the first transcribed nucleotide. In addition, most eukaryotic mRNA molecules have a polyadenylyl moiety ("poly(A) tail") at the 3' end of the mRNA molecule. In vivo, the eukaryotic cell adds the poly(A) tail after transcription, often at a length of about 250 adenosine residues (SEQ ID NO: 1). Thus, a typical mature eukaryotic mRNA has a structure that begins at the 5' end with an mRNA cap nucleotide followed by a 5' untranslated region (5'UTR) of nucleotides, then an open reading frame that begins with a start codon which is an AUG triplet of nucleotide bases, that is the coding sequence for a protein, and that ends with a stop codon that may be a UAA, UAG, or UGA triplet of nucleotide bases, then a 3' untranslated region (3'UTR) of nucleotides and ending with a polyadenosine tail. While the features of the typical mature eukaryotic mRNA are made naturally in a eukaryotic cell in vivo, the same or structurally and functionally equivalent features can be made in vitro using the methods of molecular biology. Accordingly, any RNA having the structure similar to a typical mature eukaryotic mRNA can function as a mRNA and is within the scope of the term "messenger ribonucleic acid".

The mRNA molecule is generally of a size that it can be encapsulated in a lipid nanoparticle of the invention. While the size of a mRNA molecule varies in nature depending upon the identity of the mRNA species that encodes for a particular protein, an average size for a mRNA molecule is average mRNA size is 500-10,000 bases.

DNA can exist in at least two forms, which have different sizes. The first form of DNA is a very large-sized polymer called a chromosome. A chromosome contains the genetic information for many or most of the proteins in a cell and also contains information whereby the cell can control the replication of the DNA molecule. A bacterial cell may contain one or more chromosome. A eukaryotic cell usually contains more than one cell chromosome, each chromosome, The second form of DNA is a shorter sized form. Many DNA molecules of the second form are of a size that it can be encapsulated in a lipid nanoparticle of the invention. Some of these shorter forms of DNA can be of a size to usefully encode for proteins. Examples of these second, shorter, useful forms of DNA include plasmids and other vectors. For a fuller description, see, Alberts B et al. (2007) Molecular Biology of the Cell, Fifth Edition, Garland Science.

A plasmid is a small DNA molecule that is physically separate from, and can replicate independently of, chromosomal DNA within a cell. Plasmids commonly exist in vivo as small circular, double-stranded DNA molecules. In nature, plasmids carry genes that can be transcribed and translated to proteins that may benefit survival of an organism (e.g. antibiotic resistance). In nature, plasmids can frequently be transmitted from one organism to another by horizontal gene transfer. Artificial or recombinant plasmids are widely used in molecular biology, serving to permit the replication of recombinant DNA sequences and the expression of useful proteins within host organisms. Plasmid sizes can vary from about 1 to over 25 kilobase pairs. A recombinant plasmid can be recombinantly made to be of a size that it can be encapsulated in a lipid nanoparticle of the invention.

In molecular biology, a vector is a DNA molecule used as a vehicle to artificially carry genetic material from one cell or from a biochemical reaction in vitro into another cell, where the DNA can be replicated and/or expressed. A vector containing foreign DNA is termed recombinant. Among the types of useful vectors are plasmids and viral vectors. Insertion of a vector into the target cell is usually called transformation for bacterial cells, transfection for eukaryotic cells, although insertion of a viral vector is often called transduction.

Viral vectors are generally recombinant viruses carrying modified viral DNA or RNA that has been rendered noninfectious, but that still contain viral promoters and also the transgene, thus allowing for translation of the transgene through a viral promoter. Viral vectors, in some embodiments, are designed for permanent incorporation of the insert into the host genome (integrate), and thus leave distinct genetic markers in the host genome after incorporating the transgene. A viral vector can be recombinantly made to be of a size that it can be encapsulated in a lipid nanoparticle of the invention.

The term “short interfering nucleic acid” (siNA) as used herein refers to any nucleic acid molecule capable of inhibiting or down regulating gene expression or viral replication by mediating RNA interference (RNAi) or gene silencing in a sequence-specific manner. It includes short interfering RNA (siRNA), microRNA (miRNA), short interfering oligonucleotides and chemically-modified short interfering nucleic acid molecules. siRNAs are responsible for RNA interference, the process of sequence-specific post-transcriptional gene silencing in animals and plants. siRNAs are generated by ribonuclease III cleavage from longer double-stranded RNA (dsRNA) which are homologous to, or specific to, the silenced gene target.

The term “RNA interference” (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al., 2005, Nature Chemical Biology, 1, 216-222.

The term “RNAi inhibitor” is any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g., up-regulate or down-regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term “RNAi inhibitor” is used interchangeably with the term “siNA” in various embodiments herein.

The term “enzymatic nucleic acid” as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 JAMA 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186; 5,741,679; 5,589,332; 5,871,914; and PCT publication Nos. WO 00/24931, WO 00/26226, WO 98/27104, and WO 99/29842.

The term "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

III. Pharmaceutical Formulation of LNP Compositions

For pharmaceutical use, the LNP compositions of the invention may be administered by enteral or parenteral routes, including intravenous, intramuscular, subcutaneous, transdermal, airway (aerosol), oral, intranasal, rectal, vaginal, buccal, nasopharangeal, gastrointestinal or sublingual administration. The administration may be systemic (e.g., IV) or local (e.g., IM, SC, TD, intranasal, or topical). Topical administration may involve, e.g., catheterization, implantation, osmotic pumping, direct injection, dermal/transdermal application, stenting, ear/eye drops or portal vein administration. The compounds of formula (I) should be assessed for their biopharmaceutical properties, such as solubility and solution stability (across pH), permeability, etc., in order to select the most appropriate dosage form and route of administration for treatment of the proposed indication.

The compositions of the invention will generally, but not necessarily, be administered as a formulation in association with one or more pharmaceutically acceptable excipients. The term "excipient" includes any ingredient other than the compound(s) of the invention, the other lipid component(s) and the biologically active agent. An excipient may impart either a functional (e.g. drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include: diluents, e.g. lactose, dextrose, sucrose, mannitol, sorbitol, cellulose and/or glycine; lubricants, e.g. silica, talcum, stearic acid, its magnesium or calcium salt and/or polyethyleneglycol; binders, e.g. magnesium aluminum silicate, starch paste, gelatin, tragacanth, methylcellulose, sodium carboxymethylcellulose and/or polyvinyl pyrrolidone; disintegrants, e.g. starches, agar, alginic acid or its sodium salt, or effervescent mixtures; and/or absorbants, colorants, flavors and/or sweeteners.

In some embodiments, the naLNPs stored frozen and thawed before use. In some embodiments, that are stable at 4° C. for up to 2 weeks. In some embodiments they are in various cryopreservation solutions containing various sugars for freezing that remain at the time of injection.

The excipient may be an aqueous solution carrier which may optionally contain a buffer (e.g. a PBS buffer) and/or a sugar.

A thorough discussion of pharmaceutically acceptable excipients is available in Gennaro, Remington: The Science and Practice of Pharmacy 2000, 20th edition (ISBN: 0683306472).

The compositions of the invention may be administered orally. Oral administration may involve swallowing, so that the compound enters the gastrointestinal tract, and/or buccal, lingual, or sublingual administration by which the compound enters the blood stream directly from the mouth.

The compositions of the invention can be administered parenterally. The compounds and compositions of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycaprolactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, e.g., by lyophilisation, may readily be accomplished using standard pharmaceutical techniques well known to the skilled person.

The solubility of the compounds and compositions used in the preparation of parenteral solutions may be increased by the use of appropriate formulation techniques, such as the incorporation of co-solvents and/or solubility-enhancing agents such as surfactants, micelle structures and cyclodextrins.

The compositions of the invention can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebuliser contains a solution or suspension of the compound(s) of the invention comprising, e.g., ethanol, aqueous ethanol, or a suitable alternative agent for dispersing, solubilising, or extending release of the compositions of the invention, a propellant(s) as solvent and an optional surfactant, such as sorbitan trioleate, oleic acid, or an oligolactic acid.

Prior to use in a dry powder or suspension formulation, the composition is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, e.g., from gelatin or hydroxypropylmethylcellulose), blisters and cartridges for use in an inhaler or insufflator may be formulated to contain a powder mix of the compound or composition of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, e.g., PGLA. Modified release formulations include delayed-, sustained-, pulsed-, controlled-, targeted and programmed release.

Suitable formulations for transdermal application include a therapeutically effective amount of a compound or composition of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Lipid compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Lipid compositions of the invention can be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Suitable formulations for use in the present invention can be found, e.g., in Remington's Pharmaceutical Sciences, Mack Publishing Company, Philadelphia, Pa., 17.sup.th Ed. (1985). Often, compositions will comprise a solution of the lipid nanoparticles suspended in an acceptable carrier, such as an aqueous carrier.

In one embodiment, this invention provides for a pharmaceutical composition (i.e. formulation) comprising a lipid composition of the invention and a pharmaceutically acceptable carrier or excipient. In another embodiment at least one other lipid component is present in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is a RNA or DNA.

For immunization purposes a composition will generally be prepared as an injectable and will be administered by injection (e.g. by intramuscular injection).

The invention also provides a delivery device (e.g. syringe, nebuliser, sprayer, inhaler, dermal patch, etc.) containing a composition of the invention. This device can be used to administer a pharmaceutical composition to a subject e.g. to a human for immunization.

IV. Cells and Organs Targeted by the Pharmaceutical Compositions

The compounds, compositions, methods and uses of the invention can be used to deliver a biologically active agent to one or more of the following in a patient: the liver or liver cells (e.g. hepatocytes); a kidney or kidney cells; a tumor or tumor cells; the CNS or CNS cells (Central Nervous System, e.g. brain and/or spinal cord); the PNS or PNS cells (Peripheral Nervous System); a lung or lung cells; the vasculature or vascular cells; the skin or skin cells (e.g. dermis cells and/or follicular cells); an eye or ocular cells (e.g. macula, fovea, cornea, retina), and an ear or cells of the ear (e.g. cells of the inner ear, middle ear and/or outer ear).

The compounds, compositions, methods and uses of the invention can also be used to deliver a biologically active agent (e.g. RNA which encodes an immunogen) to cells of the immune system.

In one embodiment, the compounds, compositions, methods and uses of the invention are for delivering a biologically active agent to liver cells (e.g. hepatocytes). In one embodiment, the compounds, compositions, methods and uses of the invention are for delivering a biologically active agent to a tumor or to tumor cells (e.g. a primary tumor or metastatic cancer cells). In another embodiment, the compounds, compositions, methods and uses are for delivering a biologically active agent to the skin adipose, muscle and lymph nodes (i.e. sc dosing).

For delivery of a biologically active agent to the liver or liver cells, in one embodiment a composition of the invention is contacted with the liver or liver cells of the patient as is generally known in the art, such as via parental administration (e.g. intravenous, intramuscular, subcutaneous administration) or local administration (e.g. direct injection, portal vein injection, catheterization, stenting), to facilitate delivery.

For delivery of a biologically active agent to the kidney or kidney cells, in one embodiment a composition of the invention is contacted with the kidney or kidney cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to a tumor or tumor cells, in one embodiment a composition of the invention is contacted with the tumor or tumor cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to the CNS or CNS cells (e.g. brain cells and/or spinal cord cells), in one embodiment a composition of the invention is contacted with the CNS or CNS cells (e.g. brain cells and/or spinal cord cells) of the patient as is generally known in the art, such as via parental administration (e.g. intravenous, intramuscular, subcutaneous administration) or local administration (e.g. direct injection, catheterization, stenting, osmotic pump administration (e.g. intrathecal or ventricular)), to facilitate delivery.

For delivery of a biologically active agent to the PNS or PNS cells, in one embodiment a composition of the invention is contacted with the PNS or PNS cells of the patient as is generally known in the art, such as via parental administration (e.g. intravenous, intramuscular, subcutaneous administration) or local administration (e.g. direct injection), to facilitate delivery.

For delivery of a biologically active agent to a lung or lung cells, in one embodiment a composition of the invention is contacted with the lung or lung cells of the patient as is generally known in the art, such as via parental administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a composition of the invention is contacted with the vasculature or vascular cells of the patient as is generally known in the art, such as via parental administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a composition of the invention is contacted with the skin or skin cells (e.g. dermis cells and/or follicular cells) of the patient as is generally known in the art, such as via parental administration (e.g. intravenous, intramuscular, subcutaneous administration) or local administration (e.g. direct dermal application, iontophoresis), to facilitate delivery.

For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient as is generally known in the art, such as via parental administration (e.g. intravenous, intramuscular, subcutaneous administration) or local administration (e.g. direct injection, intraocular injection, periocular injection, subretinal, iontophoresis, use of eyedrops, implants), to facilitate delivery.

For delivery of a biologically active agent to an ear or cells of the ear (e.g. cells of the inner ear, middle ear and/or outer ear), in one embodiment composition of the invention is contacted with the ear or cells of the ear (e.g. cells of the inner ear, middle ear and/or outer ear) of the patient as is generally known in the art, such as via parental administration (e.g. intravenous, intramuscular, subcutaneous administration) or local administration (e.g. direct injection), to facilitate delivery.

For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA. Such immune cells can include macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. (e.g. see WO2012/006372).

V. Immunization According to the Invention

For immunization purposes, in some embodiments, the invention encompasses delivering an mRNA that encodes an immunogen. The immunogen elicits an immune response which recognizes the immunogen, and so can be used to provide immunity against a pathogen, or against an allergen, or against a tumor antigen. Immunizing against disease and/or infection caused by a pathogen is preferred.

In certain embodiments the naLNPs have adjuvant characteristics. For example, the naLNPs disclosed herein can have specific T follicular helper cell adjuvant activity that leading to potent antibody responses. An asymmetric ionizable lipid LNP may act as a strong Th2-biased adjuvant when delivered with protein subunit antigens. In some embodiments, naLNP mRNA vaccines disclosed herein drive a Tfh-biased response that stimulates the proliferation of Tfh and germinal center B cells and a potent long-lived neutralizing antibody response.

The RNA is delivered with a lipid composition of the invention (e.g. formulated as an LNP). In some embodiments, the invention utilizes liposomes within which immunogen-encoding RNA is encapsulated. Encapsulation within LNPs can protect RNA from RNase digestion. The encapsulation efficiency does not have to be 100%. Presence of external RNA molecules (e.g. on the exterior surface of liposome) or "naked" RNA molecules (RNA molecules not associated with an LNP) is acceptable. Preferably, for a composition comprising liposomes and RNA molecules, at least half of the RNA molecules (e.g., at least 50%, at least 55%, at least 60%, at least 65%, at least 70%, at least 75%, at least 80%, at least 85%, at least 90%, or at least 95% of the RNA molecules) are encapsulated in the naLNPs.

RNA molecules may also be complexed with LNPs. For example, it is not necessary that the lipid forms liposomes (with aqueous core) only. Some lipid nanoparticles may comprise a lipid core (e.g., the composition may comprise a mixture of liposomes and nanoparticles with a lipid core). In such cases, the RNA molecules may be encapsulated by LNPs that have an aqueous core, and complexed with the LNPs that have a lipid core by non-covalent interactions (e.g., ionic interactions between negatively charged RNA and cationic lipid). Encapsulation and complexation with LNPs (whether with a lipid or aqueous core) can protect RNA from RNase digestion. The encapsulation/complexation efficiency does not have to be 100%. Presence of "naked" RNA molecules (RNA molecules not associated with a liposome) is acceptable. Preferably, for a composition comprising a population of LNPs and a population of RNA molecules, at least half of the population of RNA molecules (e.g., at least 50%, at least 55%, at least 60%, at least 65%, at least 70%, at least 75%, at least 80%, at least 85%, at least 90%, or at least 95% of the RNA molecules) are either encapsulated in LNPs, or complexed with LNPs.

VI. RNA Molecules in the Pharmaceutical Compositions

After in vivo administration of an immunization composition, the delivered RNA is released and is translated inside a cell to provide the immunogen in situ. In certain embodiments, the RNA is plus ("+") stranded, so it can be translated by cells without needing any intervening replication steps such as reverse transcription. It may also bind to TLR7 receptors expressed by immune cells, thereby initiating an adjuvant effect. Additionally, or alternatively, the RNA may bind other receptors such as RIG I, MDAS, or RIG I and MDAS.

In certain embodiments, the RNA is a self-replicating RNA. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus, in certain embodiments, a (+) strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is a huge amplification in the number of the introduced replicon RNAs and so the encoded immunogen becomes a major polypeptide product of the host cells.

One suitable system for achieving self-replication is to use an alphavirus-based RNA replicon. These (+) stranded replicons are translated after delivery to a cell to give of a replicase (or replicase-transcriptase). The replicase is translated as a polyprotein which auto cleaves to provide a replication complex which creates genomic (−) strand copies of the (+) strand delivered RNA. These (−) strand transcripts can themselves be transcribed to give further copies of the +stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc. Mutant or wild-type viruses sequences can be used e.g. the attenuated TC83 mutant of VEEV has been used in replicons.

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non structural replicase polyprotein, in particular embodiments, a self-replicating RNA molecule of the invention does not encode alphavirus structural proteins. Thus a particular self replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. One open reading frame encodes a replicase, e.g., the first, (5') open reading frame; the other open reading frame encodes an immunogen, e.g., the second, (3') open reading frame. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths, but they are typically 5000-25000 nucleotides long e.g. 8000-15000 nucleotides, or 9000-12000 nucleotides. Thus the RNA is longer than seen in siRNA or conventional mRNA delivery. In some embodiments, the self-replicating RNA is greater than about 2000 nucleotides, such as greater than about: 9000, 12000, 15000, 18000, 21000, 24000, or more nucleotides long An RNA molecule may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

An RNA molecule may have a 3' poly A tail. It may also include a poly A polymerase recognition sequence (e.g. AAUAAA) near its 3' end.

An RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT transcribed RNA can function efficiently as a substrate for its self-encoded replicase.

As discussed in WO2011/005799, the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first 1, 2 or 3 5' ribonucleotides may be methylated at the 2' position of the ribose.

An RNA used with the invention for immunization purposes ideally includes only phosphodiester linkages between nucleosides, but in some embodiments it can contain phosphoramidate, phosphorothioate, and/or methylphosphonate linkages.

The invention includes embodiments where multiple species of RNAs are formulated with a lipid composition provided by the invention, such as 2, 3, 4, 5, 6, 7, 8, 9, 10, or more species of RNA, including different classes of RNA (such as mRNA, siRNA, self-replicating RNAs, and combinations thereof).

VII. Immunogens

RNA molecules used with the invention for immunization purposes, in some embodiments, encode a polypeptide immunogen. In these embodiments, after administration, the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognizes the corresponding pathogen (or allergen or tumor) polypeptide, but in some embodiments the polypeptide may act as a mimotope to elicit an immune response which recognizes a saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from an mRNA, then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

In certain embodiments, polypeptide immunogens (e.g., 1, 2, 3, 4, 5, 6, 7, 8, 9, 10, or more immunogens) may be used, either alone or together with a RNA molecule, such as a self-replicating RNA, encoding one or more immunogens (either the same or different as the polypeptide immunogens).

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in Giuliani et al. (2006) Proc Natl Acad Sci USA 103(29):10834-9.

*Streptococcus pneumoniae*: useful polypeptide immunogens are disclosed in WO2009/016515. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in WO02/34771 and WO2005/032582.

*Moraxella catarrhalis.*

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in WO2010/119343, such as a hemolysin, esxA, esxB, ferrichrome-binding protein (sta006) and/or the sta011 lipoprotein.

*Clostridium tetani*: the typical immunogen is tetanus toxoid.

*Cornynebacterium diphtheriae*: the typical immunogen is diphtheria toxoid.

*Haemophilus influenzae*: Useful immunogens include, but are not limited to, the polypeptides disclosed in WO2006/110413 and WO2005/111066.

*Pseudomonas aeruginosa*

*Streptococcus agalactiae*: useful immunogens include, but are not limited to, the polypeptides disclosed in WO02/34771.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in WO2005/002619). LcrE (WO2006/138004) and HtrA (WO2009/109860) are two preferred immunogens.

*Chlamydia pneumoniae*: Useful immunogens include, but are not limited to, the polypeptides disclosed in WO02/02606.

*Helicobacter pylori*: Useful immunogens include, but are not limited to, CagA, VacA, NAP, and/or urease (WO03/018054).

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in WO2006/091517 and WO2008/020330. Useful MNEC immunogens are disclosed in WO2006/089264. A useful immunogen for several *E. coli* types is AcfD (WO2009/104092).

*Bacillus anthracis*

*Yersinia pestis*: Useful immunogens include, but are not limited to, those disclosed in WO2007/049155 and WO2009/031043.

*Staphylococcus epidermis*

*Clostridium perfringens* or *Clostridium botulinums*

*Legionella pneumophila*

*Coxiella burnetiid*

*Brucella*, such as *B. abortus, B. canis, B. melitensis, B. neotomae, B. ovis, B. suis, B. pinnipediae.*

*Francisella*, such as *F. novicida, F. philomiragia, F. tularensis*

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Rickettsia*

*Listeria monocytogenes*

*Vibrio cholerae*

*Salmonella typhi*

*Borrelia burgdorferi*

*Porphyromonas gingivalis*

*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: immunogens include, but are not limited to, those derived from Orthopoxvirus such as Variola vera, including but not limited to, Variola major and Variola minor.

Picornavirus: immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: immunogens include, but are not limited to, those derived from an

Orthobunyavirus, such as California encephalitis virus, a Phlebovirus, such as Rift Valley Fever virus, or a Nairovirus, such as Crimean-Congo hemorrhagic fever virus.

Heparnavirus: immunogens include, but are not limited to, those derived from a

Heparnavirus, such as hepatitis A virus (HAV).

Filovirus: immunogens include, but are not limited to, those derived from a Filovirus, such as an Ebola virus (including a Zaire, Ivory Coast, Reston or Sudan ebolavirus) or a Marburg virus.

Togavirus: immunogens include, but are not limited to, those derived from a Togavirus, such as a Rubivirus, an Alphavirus, or an Arterivirus. This includes rubella virus.

Flavivirus: immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: immunogens include, but are not limited to, those derived from a Pestivirus, such as Bovine viral diarrhea (BVDV), Classical swine fever (CSFV) or Border disease (BDV).

Hepadnavirus: immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: immunogens include, but are not limited to, those derived from a Rhabdovirus, such as a Lyssavirus (e.g. a Rabies virus) and Vesiculovirus (VSV).

Caliciviridae: immunogens include, but are not limited to, those derived from Calciviridae, such as Norwalk virus (Norovirus), and Norwalk-like Viruses, such as Hawaii Virus and Snow Mountain Virus.

Coronavirus: immunogens include, but are not limited to, those derived from COVID-19, a SARS coronavirus, avian infectious bronchitis (IBV), Mouse hepatitis virus (MHV), SARS, MERS, and Porcine transmissible gastroenteritis virus (TGEV). In addition, immunogens from bat and pangolin coronaviruses with pandemic potential can be used. The coronavirus immunogen may be a spike polypeptide or other virus proteins. Specific Coronavirus epitopes are comprehensively analyzed and described in Shrock et al, Science, Sep. 29, 2020 which is incorporated herein by reference.

Retrovirus: immunogens include, but are not limited to, those derived from an Oncovirus, a Lentivirus (e.g. HIV-1 or HIV-2) or a Spumavirus.

Reovirus: immunogens include, but are not limited to, those derived from an Orthoreovirus, a Rotavirus, an Orbivirus, or a Coltivirus.

Parvovirus: immunogens include, but are not limited to, those derived from Parvovirus B19.

Herpesvirus: immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: immunogens include those derived from serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), land-locked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and Sorghum, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), VVT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Me1-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

VIII. Vaccine Compositions

A pharmaceutical composition of the invention, particularly one useful for immunization, may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Such agonist(s) can, in some embodiments, be encapsulated with the RNA inside LNPs, or encapsulated or complexed with LNPs, but in other embodiments they are unencapsulated or uncomplexed. In some embodiments, adjuvants are for example: montanide ISA-51 (Seppic Inc., Fairfield, N.J., United States of America); QS-21 (Aquila Biopharmaceuticals. Inc., Framingham, Mass., United States of America); Arlacel A; oeleic acid; tetanus helper peptides (such as but not limited to QYIKANSKFIGITEL (SEQ ID NO: 2) and/or AQYIKANSKFIGITEL (SEQ ID NO: 3); GM-CSF; cyclophosamide; *bacillus* Calmette-Guerin (BCG); *Corynbacterium parvum*; levamisole, azimezone; isoprinisone; dinitrochlorobenezene (DNCB); keyhole limpet hemocyanin (KLH); Freunds adjuvant (complete and incomplete); mineral gels; aluminum hydroxide (Alum); lysolecithin; pluronic polyols; polyanions; peptides; oil emulsions; nucleic acids (such as but not limited to soluble-stranded RNAs; dsRNA) dinitrophenol; diphtheria toxin (DT); toll-like receptor (TLR; such as but not limited to TLR3, TLR4, TLR7, TLR8, and/or TLR9) agonists (including but not limited to endotoxins such as lipopolysaccharide (LPS); monophosphoryl lipid A (MPL); and/or polyinosinic-polycytidylic acid (poly-ICLC/HILTONOL®; Oncovir, Inc., Washington, D.C., United States of America); IMO-2055; glucopyranosyl lipid A (GLA); QS-21 (a saponin extracted from the bark of the *Quillaja saponaria* tree, also known as the soap bark tree or Soapbark); resiquimod (a TLR7/8 agonist); CDX-1401 (a fusion protein consisting of a fully human monoclonal antibody with specificity for the dendritic cell receptor DEC-205 linked to the NY-ESO-1 tumor antigen); Juvaris' Cationic Lipid-DNA Complex; Vaxfectin; and combinations thereof. In one embodiment, adjuvants using heterogeneous monophosphoryl Lipid A (MPL) derived from *Salmonella minnesota* R595 are used to induce Th-1 type immune responses to heterologous proteins in animal and human vaccines. Exemplary monophosphoryl Lipid A type adjuvants are shown below:

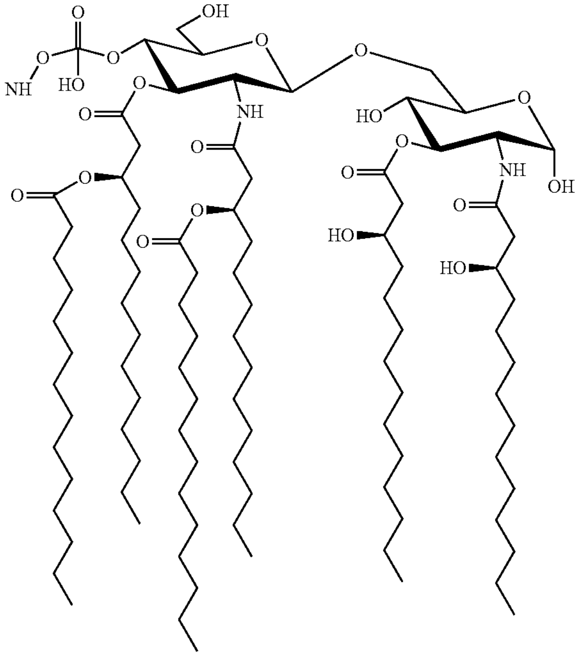

PHAD®

-continued

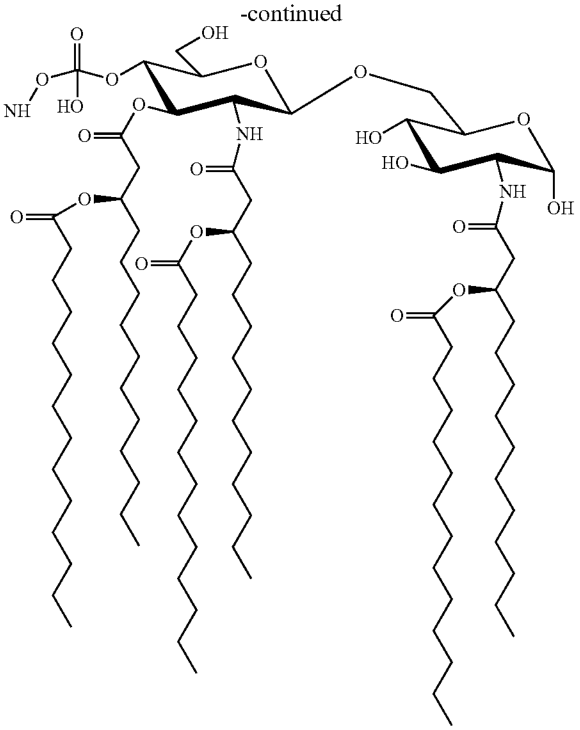

3D(6A)-PHAD®

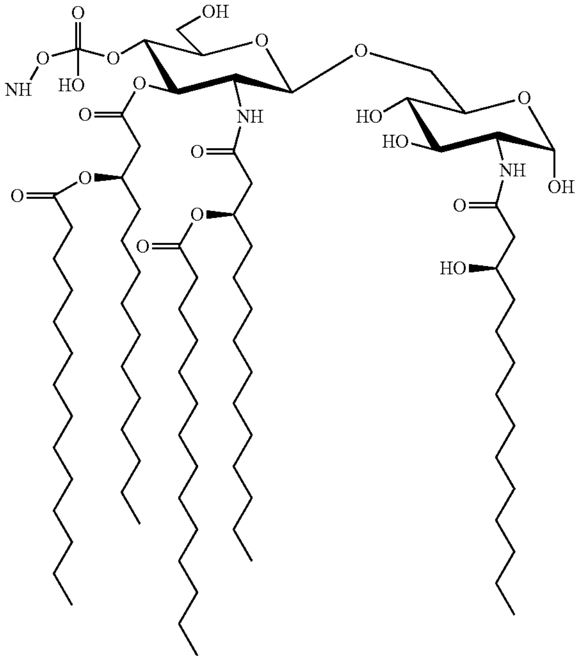

3D-PHAD®

Pharmaceutical compositions of the invention may have an osmolality of about or at least 100, 150, 175, 200, 250, 275, 300, 325, 350, 375, 400, 425, 450, 475, 500 mOsm/kg. In some embodiments, osmolality between about 200 mOsm/kg and 400 mOsm/kg, e.g. between about 240-360 mOsm/kg, or between about 290-310 mOsm/kg.

Pharmaceutical compositions of the invention may include one or more preservatives, such as thiomersal or 2 phenoxyethanol. Mercury-free compositions can be made and preservative-free vaccines can be prepared.

Compositions comprise an immunologically effective amount of lipid compositions described herein (e.g., liposomes and LNPs), as well as any other components, as needed. Immunologically effective amount refers to the amount administered to an individual, either in a single dose or as part of a series, is effective for treatment (e.g., prophylactic immune response against a pathogen). This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The compositions of the invention will generally be expressed in terms of the amount of RNA per dose. A preferred dose has .ltoreq.100 .mu.g RNA (e.g. from 10-100 .mu.g, such as about 10 .mu.g, 25 .mu.g, 50 .mu.g, 75 .mu.g or 100 .mu.g), but expression can be seen at much lower levels e.g. .ltoreq.1.mu.g/dose, .ltoreq.100 ng/dose, .ltoreq.10 ng/dose, .ltoreq.1 ng/dose, etc.

The invention also provides a delivery device (e.g. syringe, nebuliser, sprayer, inhaler, dermal patch, etc.) containing a pharmaceutical composition of the invention. This device can be used to administer the composition to a vertebrate subject.

Methods of Treatment and Medical Uses

LNP-formulated RNA and pharmaceutical compositions described herein are for in vivo use for inducing an immune response against an immunogen of interest.

The invention provides a method for inducing an immune response in a vertebrate comprising administering an effective amount of the liposome-formulated or LNP-formulated RNA, or pharmaceutical composition, as described herein. The immune response is preferably protective and preferably involves antibodies and/or cell-mediated immunity. The compositions may be used for both priming and boosting purposes. Alternatively, a prime-boost immunization schedule can be a mix of RNA and the corresponding polypeptide antigen (e.g., RNA prime, protein boost).

The invention also provides a liposome, LNP, or pharmaceutical composition for use in inducing an immune response in a vertebrate. The invention also provides the use of a liposome, LNP, or pharmaceutical composition in the manufacture of a medicament for inducing an immune response in a vertebrate.

By inducing an immune response in the vertebrate by these uses and methods, the vertebrate can be protected against various diseases and/or infections e.g. against bacterial and/or viral diseases as discussed above. The liposomes, LNPs, and compositions are immunogenic, and are more preferably vaccine compositions. Vaccines according to the invention may either be prophylactic (i.e. to prevent infection) or therapeutic (i.e. to treat infection) but will typically be prophylactic.

The vertebrate is preferably a mammal, such as a human or a large veterinary mammal (e.g. horses, cattle, deer, goats, pigs). As used herein "large mammal" refers to mammals having a typical or average adult weight of at least 5 kg, preferably at least 7 kg. Such large mammals can include, for example, humans, non-human primates, dogs, pigs, cattle, deer, goats, and is meant to exclude small mammals, such as mice, rats, guinea pigs, and other rodents.

Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus, a human patient may be less than 1 year old, less than 5 years old, 1-5 years old, 5-15 years old, 15-55 years old, or at least 55 years old. Preferred patients for receiving the vaccines are the elderly (e.g. .gtoreq.50 years old, .gtoreq.60 years old, and preferably .gtoreq.65 years), the young (e.g. ltoreq.5 years old), hospitalized patients, healthcare workers, armed service and military personnel, pregnant women, the chronically ill, or immunodeficient patients. The vaccines are not suitable solely for these groups, however, and may be used more generally in a population. Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; intraglossal injection is not typically used for immunization purposes. Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to induce systemic and/or mucosal immunity, preferably to elicit an enhanced systemic and/or mucosal immunity.

Dosage can be by a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organization's Expanded Program on Immunization ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter. The data and disclosure of each of Examples 1A-33E correspond to FIGS. 1A-33E.

Example 1: Increasing Concentrations of Lipids from 6 to 27 mM and mRNA from 0.14 to 0.56 mg/ml Increases LNP Delivery Efficiency in Vitro (Study TRANS-10)

Summary: LNPs were formulated using total lipid concentration of 6 to 27 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively), then serial dilutions were done to reach 6 to 27 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 1 mg/mL. Fluc mRNA stock was diluted in serial dilutions from a higher concentration solution to lower concentrations to reach 0.14 to 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 200 ng and 12K HEK293 cells were transfected with the same 200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 2: Increasing Concentrations of Lipids from 6 to 27 mM and mRNA from 0.14 to 0.56 mg/ml Increases LNP Delivery Efficiency In Vitro (Study TRANS-12)

Summary: LNPs were formulated using total lipid concentration of 6 to 27 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively), then serial dilutions were done to reach 6 to 27 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 1 mg/mL. Fluc mRNA stock was diluted in serial dilutions from a higher concentration solution to lower concentrations to reach 0.14 to 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 200 ng and 12K HEK293 cells were transfected with the same 200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 3: Increasing Concentrations of Lipids from 3 to 27 mM and mRNA from 0.07 to 0.56 mg/ml Increases LNP Delivery Efficiency In Vitro (Study TRANS-14)

Summary: LNPs were formulated using total lipid concentration of 3 to 27 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively), then serial dilutions were done to reach 3 to 27 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 1 mg/mL. Fluc mRNA stock at 1 mg/ml was diluted in serial dilutions from a higher concentration solution to lower concentrations to reach 0.07 to 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 200 ng and 12K HEK293 cells were transfected with the same 50-200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590).

Example 4: Increasing Concentrations of Lipids from 12.5 to 50 mM and mRNA from 0.25 to 1 mg/ml Increases LNP Delivery Efficiency In Vitro (Study TRANS-16)

Summary: LNPs were formulated using total lipid concentration of 12.5 to 50 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively), then serial dilutions were done to reach 12.5 to 50 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/mL. Fluc mRNA stock was diluted in serial dilutions from a higher concentration solution to lower concentrations to reach 0.25 to 1 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr LNPs were then diluted so that 32 ul contained 200 ng and 12K HEK293 cells were transfected with the same 50-200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^{7}$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590).

Example 5: Increasing Concentrations of Lipids from 50 to 100 mM and mRNA from 1 to 2 mg/ml Increases LNP Delivery Efficiency (Study LNP-14 Part II)

Summary: LNPs were formulated using total lipid concentration of 50 to 100 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). To prepare 75 mM total lipid concentration (37.5/7.5/28.88/1.13 mM respectively), KC2 and Cholesterol were mixed first, same for DSPC and PEG to solubilize both solutions in ethanol before combining them to reach 75 mM. To prepare 100 mM total lipid concentration (50/10/38.5/1.5 mM respectively), KC2 and Cholesterol were mixed first, same for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/mL. Fluc mRNA stock was diluted in serial dilutions from a higher concentration solution to lower concentrations to reach 1 to 2 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr.

A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

B: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 6: Increasing Concentrations of Lipids from 50 to 100 mM and mRNA from 1 to 2 mg/ml Increases LNP Delivery Efficiency In Vitro (Study TRANS-25)

Summary: LNPs were formulated using total lipid concentration of 50 to 100 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). To prepare 75 mM total lipid concentration (37.5/7.5/28.88/1.13 mM respectively), KC2 and Cholesterol were mixed first, same for DSPC and PEG to solubilize both solutions in ethanol before combining them to reach 75 mM. To prepare 100 mM total lipid concentration (50/10/38.5/1.5 mM respectively), KC2 and Cholesterol were mixed first, same for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. Fluc mRNA stock was diluted in serial dilutions from a higher concentration solution to lower concentrations to reach 1 to 2 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 200 ng and 12K HEK293 cells were transfected with the same 25-200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: pH measurements. Measurements were taken before and after dialysis against 1×DPBS pH7.4 for 4 hours.

| Sample | pH before Dialysis | pH after Dialysis |
|---|---|---|
| 1 mg/ml | 6.05 | 7.38 |
| 1.5 mg/ml | 6.43 | 7.32 |
| 2 mg/ml | 6.5 | 7.29 |

Example 7: Increasing Concentrations of Lipids from 50 to 100 mM and mRNA from 1 to 2 mg/ml Increases LNP Delivery Efficiency In Vitro (Study TRANS-26)

Summary: LNPs were formulated using total lipid concentration of 50 to 100 mM comprised of KC2/DSPC/Cholesterol/PEG-DMG (50:10:38.5:1.5 mol %). Each one of the lipids were solubilized in ethanol until a clear solution was observed. The four lipids were combined to get 100 mM total lipid concentration (25/5/19.25/0.75 mM respectively). To prepare 75 mM total lipid concentration (37.5/7.5/28.88/1.13 mM respectively), KC2 and Cholesterol were mixed first, same for DSPC and PEG to solubilize both solutions in ethanol before combining them to reach 75 mM. To prepare 100 mM total lipid concentration (50/10/38.5/1.5 mM respectively), KC2 and Cholesterol were mixed first, same for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. Fluc mRNA stock was diluted in serial dilutions from a higher concentration solution to lower concentrations to reach 1 to 2 mg/ml in 100 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 200 ng and 12K HEK293 cells were transfected with the same 25-200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^{7}$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: pH measurements. Measurements were taken before and after dialysis against 1×DPBS pH7.4 for 4 hours. Note here in comparison to Example 6, these LNPs were formulated using 100 mM NaOAc. Increasing the concentration of Sodium Acetate Buffer in formulation keeps the pH lower due to higher buffer capacity, resulting in a lower pH before Dialysis for the LNPs.

| Sample | pH before Dialysis | pH after Dialysis |
|---|---|---|
| 1 mg/ml | 5.1 | 7.22 |
| 1.5 mg/ml | 5.29 | 7.31 |
| 2 mg/ml | 5.41 | 7.42 |

Example 8: Increasing Concentrations of Lipids from 2.5 to 100 mM and mRNA from 0.05 to 2 mg/ml Increases LNP Delivery Efficiency In Vitro (Study TRANS-27)

Summary: LNPs were formulated using total lipid concentration of 2.5 to 100 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) then serial dilutions were done to reach 2.5 to 50 mM. To prepare 75 mM total lipid concentration (37.5/7.5/28.88/1.13 mM respectively), KC2 and Cholesterol were mixed first, same for DSPC and PEG to solubilize both solutions in ethanol before combining them to reach 75 mM. To prepare 100 mM total lipid concentration (50/10/38.5/1.5 mM respectively), KC2 and Cholesterol were mixed first, same for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. Fluc mRNA stock was diluted in serial dilutions from a higher concentration solution to lower concentrations to reach 0.05 to 2 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same 200 ng dose but manufactured at different concentrations in the microfluidic mixer. Increased mixing concentration results in increased delivery efficiency at the same dose, suggesting concentrations during mixing influence LNP structure and thereby efficiency of delivery. This finding is significant for commercial manufacturing of mRNA vaccines.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590).

E: pH measurements. Measurements were taken before and after dialysis against 1×DPBS pH7.4 for 4 hours.

| Sample | pH before Dialysis | pH after Dialysis |
|---|---|---|
| 0.05 mg/ml | 6.09 | 7.31 |
| 0.1 mg/ml | 6.12 | 7.35 |

-continued

| Sample | pH before Dialysis | pH after Dialysis |
|---|---|---|
| 0.25 mg/ml | 6.44 | 7.33 |
| 0.5 mg/ml | 6.53 | 7.4 |
| 1 mg/ml | 6.65 | 7.42 |
| 1.5 mg/ml | 6.67 | 7.41 |
| 2 mg/ml | 6.08 | 7.35 |

Example 9: Increasing Concentrations of Lipids from 5 to 100 mM and mRNA from 0.1 to 2 mg/ml Increases LNP Delivery Efficiency In Vivo (Study In Vivo-3)

Summary: LNPs were formulated using total lipid concentration of 5 to 100 mM comprised of KC2/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) then serial dilutions were done to reach 5 to 50 mM. To prepare 75 mM total lipid concentration (37.5/7.5/28.88/1.13 mM respectively), KC2 and Cholesterol were mixed first, same for DSPC and PEG to solubilize both solutions in ethanol before combining them to reach 75 mM. To prepare 100 mM total lipid concentration (50/10/38.5/1.5 mM respectively), KC2 and Cholesterol were mixed first, same for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. Fluc mRNA stock was diluted in serial dilutions from a higher concentration solution to lower concentrations to reach 0.1 to 2 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 24 µl Lipid Mix and 48 µl mRNA solution were mixed on Setting 5 and ejected into 72 µl 1×DPBS pH 7.4. The formed LNPS were then diluted into an additional 144 µl 1×DPBS pH 7.4. LNPs were then dialyzed against 1×DPBS pH 7.4 for 4×1 hr. LNPs were concentrated in order to inject 5 ug of encapsulated mRNA in 50 ul for an intramuscular administration. Increased mixing concentration results in increased delivery efficiency at the same dose, suggesting concentrations during mixing influence LNP structure and thereby efficiency of delivery. This finding is significant for commercial manufacturing of mRNA vaccines.

A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

B: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

C: In vivo Firefly Luciferase expression in IM administration. 5 ug of encapsulated mRNA were injected in mice in intramuscular (I.M.), intradermal (ID.) and intravenous (I.V.) injections. ROIs were calculated using the IVIS system. Imaging were performed at 4 and 20 hours.

Example 10: Direct Protonation of Ionizable Lipid and Mixing with mRNA in Water Encapsulates mRNA. Increasing Concentrations of Sodium Acetate (NaOAc) Buffer at p114 Increases mRNA Encapsulation (Study LNP-6 Part II)

Summary: LNPs were formulated using total lipid concentration of 27.74 mM comprised of MC3/DSPC/Cholesterol/PEG-DMG (50:10:38.5:1.5 mol %). Each one of the lipids were solubilized in ethanol until a clear solution was observed. MC3 stocks were protonated at 0%, 50%, and 100% total amines using 1M HCl by calculating the moles of amines on the ionizable lipid and adding 0%, 50%, 100% of that in moles of HCl. The four lipids were combined to get 50 mM total lipid concentration (25/5/19.25/0.75 mM respectively). Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 1 mg/ml. Fluc mRNA stock was to reach 0.56 mg/ml in water, 5, 10, 25, and 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. The results show that direct protonation of the ionizable lipid using HCl mixed with mRNA in water with no buffer results in similar levels of mRNA encapsulation as mixing in sodium acetate buffer at pH4. Additionally, when mixing in sodium acetate buffer at pH4, a concentration of 25 mM sodium acetate was required to maximize mRNA encapsulation. This criteria of maximal encapsulation is used in all prior art to determine buffer concentration and mixing conditions. The current invention show that such a procedure does not maximize LNP potency since buffer concentration needs to be optimized in addition to absolute mixing concentrations to maximize LNP potency.

A: Ribogreen Assay for mRNA Encapsulation Efficiency. 1× TE Buffer and Triton Buffer (2% v/v in ix TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

B: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

C: pH measurements. Measurements were taken before dialysis.

| Sample | pH before Dialysis |
|---|---|
| MC3 100% protonation 0.56 mg/ml in water | 7.16 |
| MC3 50% protonation 0.56 mg/ml in water | 7.35 |
| MC3 0% protonation 0.56 mg/ml in water | 7.5 |
| MC3 0.56 mg/ml in 5 mM NaOAc | 7.34 |
| MC3 0.56 mg/ml in 10 mM NaOAc | 7.21 |
| MC3 0.56 mg/ml in 25 mM NaOAc | 6.84 |
| MC3 0.56 mg/ml in 50 mM NaOAc | 6.29 |

Example 11: Increasing Concentrations of Lipids from 50 to 150 mM and mRNA from 1 to 3 mg/ml Increases LNP Delivery Efficiency at Low Concentrations of Sodium Acetate. Increasing Sodium Acetate Concentration Above 50 mM Reduces LNP Potency at all Concentrations In Vitro (Study TRANS-32)

Summary: LNPs were formulated using total lipid concentration of 50 to 120 mM comprised of KC2/DSPC/

Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). To prepare 100 mM total lipid concentration (50/10/38.5/1.5 mM respectively), KC2 and Cholesterol were mixed first, same for DSPC and PEG to solubilize both solutions in ethanol before combining them to reach 100 mM. To prepare 150 mM total lipid concentration (75/15/57.75/2.25 mM respectively), KC2 and Cholesterol were mixed first, same for DSPC and PEG to solubilize both solutions in ethanol before combining them to reach 150 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.4 mg/ml. Fluc mRNA stock was diluted in serial dilutions from a higher concentration solution to lower concentrations to reach 1 to 3 mg/ml in 50, 100, and 150 mM Sodium acetate (NaOAc) buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer. Increased mixing concentration results in increased delivery efficiency at the same dose only at the lowest NaOAc concentration of 50 mM. Higher NaOAc concentrations reduce LNP potency and more so at the higher mixing concentrations.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: pH measurements. Measurements were taken before and after dialysis against 1×DPBS pH7.4 for 4 hours.

| Sample | pH before Dialysis after dilution | pH after Dialysis |
|---|---|---|
| LNP 1 mg/ml in 50 mM NaOAc pH4 | 6.09 | 7.51 |
| LNP 2 mg/ml in 50 mM NaOAc pH4 | 6.29 | 7.47 |
| LNP 3 mg/ml in 50 mM NaOAc pH4 | 6.56 | 7.52 |
| LNP 1 mg/ml in 100 mM NaOAc pH4 | 5.14 | 7.5 |
| LNP 2 mg/ml in 100 mM NaOAc pH4 | 5.34 | 7.49 |
| LNP 3 mg/ml in 100 mM NaOAc pH4 | 5.73 | 7.49 |
| LNP 1 mg/ml in 150 mM NaOAc pH4 | 4.79 | 7.45 |
| LNP 2 mg/ml in 150 mM NaOAc pH4 | 4.9 | 7.45 |
| LNP 3 mg/ml in 150 mM NaOAc pH4 | 5.01 | 7.47 |

Example 12: Increasing Concentrations of Lipids from 12.5 to 75 mM and mRNA from 0.25 to 1.5 mg/ml Increases LNP Delivery Efficiency in Vitro for Ionizable Lipids KC2, MC3 and BOD-ADDE-$C_2$/$C_4$-PipZ. Lowering Sodium Acetate Concentration can Increase LNP Potency while Lowering mRNA Encapsulation (Study TRANS-33)

Summary: LNPs were formulated using total lipid concentration of 12.5 and 75 mM comprised of several ionizable (KC2/MC3/DL-ADDE-C2C2-PipZ/BODD-ADDE-C2C4-PipZ)/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) then serial dilutions were done to reach 12.5 mM. To prepare 75 mM total lipid concentration (37.5/7.5/28.88/1.13 mM respectively), KC2/MC3/DL-ADDE-C2C2-PipZ/BODD-ADDE-C2C4-PipZ and Cholesterol were mixed first, same for DSPC and PEG to solubilize both solutions in ethanol before combining them to reach 75 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.4 mg/ml. Fluc mRNA stock was diluted in serial dilutions from a higher concentration solution to lower concentrations to reach 0.25 and 1.5 mg/ml in 25, 43, and 60 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into Well 1 (W1 in size graphs) containing 48 μl 1×DPBS pH 7.4. The formed LNPS were then diluted into an additional 96 μl 1× DPBS pH 7.4 (D in size graphs). LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer. KC2, MC3, and BODD-ADDE-C2C4-PipZ ionizable lipids demonstrated a large increase in potency when mixed at the higher concentration 1.5 mg/ml vs the lower concentration 0.25 mg/ml while DL-ADDE-C2C2-PipZ did not. The latter lipid has a much higher pKa in the LNP (~7.5) vs the first 3 (~6.5) so that it would be more highly protonated during mixing potentially indicating that ideal mixing conditions including pH and protonation were not achieved for this lipid. KC2, MC3, and BODD-ADDE-C2C4-PipZ LNPs also increased potency when sodium acetate concentration was reduced from 60 mM to 25 mM and could reduce mRNA encapsulation while DL-ADDE-C2C2-PipZ did not show either effect.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: pH measurements. Measurements were taken before (Well1) and after dialysis against 1×DPBS pH7.4 for 4 hours.

| Sample | pH before Dialysis from Well1 | pH after Dialysis |
|---|---|---|
| KC2 1.5 mg/ml in 43 mM NaOAc pH4 | 5.29 | 7.4 |
| MC3 1.5 mg/ml in 43 mM NaOAc pH4 | 5.34 | 7.4 |
| C2C2PipZ 1.5 mg/ml in 43 mM NaOAc pH4 | 5.98 | 7.38 |
| BODDC2C4PipZ 1.5 mg/ml in 43 mM NaOAc pH4 | 5.85 | 7.42 |
| KC2 0.25 mg/ml in 43 mM NaOAc pH4 | 4.85 | 7.4 |
| MC3 0.25 mg/ml in 43 mM NaOAc pH4 | 4.84 | 7.38 |
| C2C2PipZ 0.25 mg/ml in 43 mM NaOAc pH4 | 4.84 | 7.39 |
| BODDC2C4PipZ 0.25 mg/ml in 43 mM NaOAc pH4 | 4.82 | 7.35 |
| KC2 1.5 mg/ml in 60 mM NaOAc pH4 | 5.09 | 7.4 |
| BODDC2C4PipZ 1.5 mg/ml in 60 mM NaOAc pH4 | 5.07 | 7.41 |
| KC2 1.5 mg/ml in 25 mM NaOAc pH4 | 6.33 | 7.35 |
| BODDC2C4PipZ 1.5 mg/ml in 25 mM NaOAc pH4 | 6.33 | 7.38 |
| KC2 0.25 mg/ml in 60 mM NaOAc pH4 | 4.64 | 7.31 |
| BODDC2C4PipZ 0.25 mg/ml in 60 mM NaOAc pH4 | 4.67 | 7.32 |
| KC2 0.25 mg/ml in 25 mM NaOAc pH4 | 5.45 | 7.35 |
| BODDC2C4PipZ 0.25 mg/ml in 25 mM NaOAc pH4 | 5.45 | 7.39 |

Example 13: Increasing Concentrations of Lipids from 12.5 to 75 mM and mRNA from 0.25 to 1.5 mg/ml Increases LNP Delivery Efficiency In Vitro. Further Optimizing the Sodium Acetate Concentration at any Particular Mixing Concentration Results in Further Increased LNP Potency. (Study TRANS-34)

Summary: LNPs were formulated using total lipid concentration of 12.5 to 75 mM comprised of several ionizable (KC2/DL-ADDE-C2C2-PipZ/BODD-ADDE-C2C4-PipZ)/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) then serial dilutions were done to reach 12.5 mM. To prepare 75 mM total lipid concentration (37.5/7.5/28.88/1.13 mM respectively), KC2/DL-ADDE-C2C2-PipZ/BODD-ADDE-C2C4-PipZ and Cholesterol were mixed first, same for DSPC and PEG to solubilize both solutions in ethanol before combining them to reach 75 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.4 mg/ml. Fluc mRNA stock was diluted in serial dilutions from a higher concentration solution to lower concentrations to reach 0.25 to 1.5 mg/ml in 5, 10, 12.5, 25, and 50 mM Sodium acetate buffer pH 4, 5 or 6, keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer. LNP potency increases at the higher versus lower mixing concentration but can be increase further at each concentration by adjusting sodium acetate concentration. For example at 1.5 mg/ml of mRNA LNP potency further increases 44% when reducing sodium acetate from 50 mM to 25 mM. At an mRNA concentration of 0.25 mg/ml reducing sodium acetate concentration from 25 mM to 10 mM increases potency 2.2×. The increase in mixing concentration and the optimized reductions in buffer concentration lead to encapsulation efficiency of ~70% that is lower than typically obtained in prior art where encapsulation was erroneously maximized by lowering mixing concentration and increasing buffer concentration. We also found that increasing pH from 4 to 5 increases potency for BODD-ADDE-C2C4-PipZ. DL-ADDE-C2C2-PipZ behaved differently for reasons explained in Example 12.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: pH measurements. Measurements were taken before (Well1) and after dialysis against 1×DPBS pH7.4 for 4 hours.

| Sample | pH before Dialysis after dilution | pH after Dialysis |
|---|---|---|
| KC2 0.25 mg/ml in 5 mM NaOAc pH4 | 7.18 | 7.39 |
| KC2 0.25 mg/ml in 10 mM NaOAc pH4 | 7.04 | 7.4 |
| KC2 0.25 mg/ml in 25 mM NaOAc pH4 | 6.53 | 7.44 |
| KC2 1.5 mg/ml in 12.5 mM NaOAc pH4 | 6.98 | 7.39 |
| KC2 1.5 mg/ml in 25 mM NaOAc pH4 | 6.68 | 7.38 |
| KC2 1.5 mg/ml in 50 mM NaOAc pH4 | 6.03 | 7.32 |
| C2C2PipZ 1.5 mg/ml in 25 mM NaOAc pH4 | 6.88 | 7.4 |
| BODDC2C4PipZ 1.5 mg/ml in 25 mM NaOAc pH4 | 6.76 | 7.45 |
| C2C2PipZ 1.5 mg/ml in 25 mM NaOAc pH5 | 7.22 | 7.4 |
| BODDC2C4PipZ 1.5 mg/ml in 25 mM NaOAc pH5 | 7.14 | 7.49 |
| C2C2PipZ 1.5 mg/ml in 25 mM NaOAc pH6 | 7.64 | 7.48 |
| BODDC2C4PipZ 1.5 mg/ml in 25 mM NaOAc pH6 | 7.38 | 7.46 |

Example 14: Increasing Concentrations of Lipids from 5 to 150 mM and mRNA from 0.1 to 3 mg/ml Increases LNP Delivery Efficiency In Vitro Optimization of Sodium Acetate Concentration at any Particular Mixing Concentration Results in Further Increased LNP Potency (TRANS-35)

Summary: LNPs were formulated using total lipid concentration of 5 to 150 mM comprised of ionizable KC2/DSPC/Cholesterol/PEG-DMG (50:10:38.5:1.5 mol %). Each one of the lipids were solubilized in ethanol until a clear solution was observed. The four lipids were combined to achieve 50 mM total lipid concentration (25/5/19.25/0.75 mM respectively) then serial dilutions were done to reach 5 mM. To prepare 75 mM total lipid concentration (37.5/7.5/28.88/1.13 mM respectively), KC2 and Cholesterol were mixed first, and similarly for DSPC and PEG to solubilize both solutions in ethanol before combining them to reach 75 mM. To prepare 100 mM total lipid concentration (50/10/38.5/1.5 mM respectively), KC2 and Cholesterol were mixed first, and similarly for DSPC and PEG to solubilize both solutions in ethanol before combining them to reach 100 mM. To prepare 150 mM total lipid concentration (75/15/57.75/2.25 mM respectively), KC2 and Cholesterol were mixed first, and similarly for DSPC and PEG to solubilize both solutions in ethanol before combining them to reach 150 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.4 mg/ml. Fluc mRNA stock was diluted in serial dilutions from a higher concentration solution to lower concentrations to reach 0.1 to 3 mg/ml in 10, 20, 25, and 37.5 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPs were then diluted into an additional 96 μl 1×DPBS pH 7.4. LNPs were then dialyzed against 1×DPBS pH 7.4 for 4×1 hr. LNPs were finally diluted so that 32 ul contained 25-200 ng and 12K HEK293 cells were transfected with the same dose but manufactured at different concentrations in the microfluidic mixer. LNP potency increases at the higher versus lower mixing concentration. Each mixing concentration potency was optimized by adjusting sodium acetate concentration. For example at 1.5 mg/ml of mRNA LNP potency further increases 44% when reducing sodium acetate from 50 mM to 25 mM. At an mRNA concentration of 0.25 mg/ml reducing sodium acetate concentration from 25 mM to 10 mM increases potency 2.2×.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 15: Increasing Concentrations of Lipids from 5 to 150 mM and mRNA from 0.1 to 3 mg/ml Increases LNP Delivery Efficiency In Vitro. Optimization of Sodium Acetate Concentration at any Particular Mixing Concentration Results in Further Increased LNP Potency. (TRANS-34/35)

Summary: LNPs were formulated using total lipid concentration of 5 to 150 mM comprised of ionizable KC2/DSPC/Cholesterol/PEG-DMG (50:10:38.5:1.5 mol %). Each one of the lipids were solubilized in ethanol until a clear solution was observed. The four lipids were combined to achieve 50 mM total lipid concentration (25/5/19.25/0.75 mM respectively) then serial dilutions were done to reach 5 mM. To prepare 75 mM total lipid concentration (37.5/7.5/28.88/1.13 mM respectively), KC2 and Cholesterol were mixed first, and similarly for DSPC and PEG to solubilize both solutions in ethanol before combining them to reach 75 mM. To prepare 100 mM total lipid concentration (50/10/38.5/1.5 mM respectively), KC2 and Cholesterol were mixed first, and similarly for DSPC and PEG to solubilize both solutions in ethanol before combining them to reach 100 mM. To prepare 150 mM total lipid concentration (75/15/57.75/2.25 mM respectively), KC2 and Cholesterol were mixed first, and similarly for DSPC and PEG to solubilize both solutions in ethanol before combining them to reach 150 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.4 mg/ml. Fluc mRNA stock was diluted in serial dilutions from a higher concentration solution to lower concentrations to reach 0.1 to 3 mg/ml in 10, 20, 25, and 37.5 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPs were then diluted into an additional 96 μl 1×DPBS pH 7.4. LNPs were then dialyzed against 1×DPBS pH 7.4 for 4×1 hr. LNPs were finally diluted so that 32 ul contained 25-200 ng and 12K HEK293 cells were transfected with the same dose but manufactured at different concentrations in the microfluidic mixer. LNP potency increases at the higher versus lower mixing concentration. Each mixing concentration potency was optimized by adjusting sodium acetate concentration. For example at 1.5 mg/ml of mRNA LNP potency further increases 44% when reducing sodium acetate from 50 mM to 25 mM. At an mRNA concentration of 0.25 mg/ml reducing sodium acetate concentration from 25 mM to 10 mM increases potency 2.2×.

A. Optimal Concentration of Sodium Acetate at pH 4 for Highest Potency at Each mRNA Concentration

| mRNA concentration (mg/ml) | Lipid mix concentration (mM) | Sodium Acetate pH 4 concentration (mM) |
|---|---|---|
| 0.1 | 5 | 10 |
| 0.25 | 12.5 | 10 |
| 0.5 | 25 | 20 |
| 1 | 50 | 25 |
| 1.5 | 75 | 25 |
| 2 | 100 | 25 |
| 3 | 150 | 37.5 |

B. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

C: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

D: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 16: Increasing Concentrations of Lipids from 5 to 100 mM and mRNA from 0.1 to 2 mg/ml Increases LNP Delivery Efficiency In Vitro. Optimization of Sodium Acetate Concentration at any Particular Mixing Concentration Results in Further Increased LNP Potency. (TRANS-36)

Summary: LNPs were formulated using total lipid concentration of 5 to 100 mM comprised of the ionizable MC3/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) then serial dilutions were done to reach 5 mM. To prepare 75 mM total lipid concentration (37.5/7.5/28.88/1.13 mM respectively), MC3 and Cholesterol were mixed first, and similarly for DSPC and PEG to solubilize both solutions in ethanol before combining them to reach 75 mM. To prepare 100 mM total lipid concentration (50/10/38.5/1.5 mM respectively), MC3 and Cholesterol were mixed first, and similarly for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.6 mg/ml. Fluc mRNA stock was diluted in serial dilutions from a higher concentration solution to lower concentrations to reach 0.1 to 2 mg/ml in 5-35 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were finally diluted so that 32 ul contained 25-200 ng and 12K HEK293 cells were transfected with the same dose but manufactured at different concentrations in the microfluidic mixer. LNP potency increases at the higher versus lower mixing concentration. Each mixing concentration potency was optimized by adjusting sodium acetate concentration.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 17: Increasing Concentrations of Lipids from 5 to 100 mM and mRNA from 0.1 to 2 mg/ml Increases LNP Delivery Efficiency in Vitro. Optimization of Sodium Acetate Concentration at any Particular Mixing Concentration Results in Further Increased LNP Potency. (TRANS-37)

Summary: LNPs were formulated using total lipid concentration of 5 to 100 mM comprised of ionizable BODD-C2/C4-PipZ/DSPC/Cholesterol/PEG-DMG (47:13:37:2 mol %). Each one of the lipids were solubilized in ethanol until a clear solution was observed. The four lipids were combined to get 50 mM total lipid concentration (24/6.5/18.5/1 mM respectively) then serial dilutions were done to reach 5 mM. To prepare 75 mM total lipid concentration (36/9.75/27.75/1.5 mM respectively), the ionizable and Cholesterol were mixed first, and similarly for DSPC and PEG to solubilize both solutions in ethanol before combining them to reach 75 mM. To prepare 100 mM total lipid concentration (48/13/37/2 mM respectively), the ionizable and Cholesterol were mixed first, and similarly for DSPC and PEG to solubilize both solutions in ethanol before combining them to reach 100 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.1 to 2 mg/ml in 5-30 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were finally diluted so that 32 ul contained 25-200 ng and 12K HEK293 cells were transfected with the same dose but manufactured at different concentrations in the microfluidic mixer. LNP potency increases at the higher versus lower mixing concentration. Each mixing concentration potency was optimized by adjusting sodium acetate concentration.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 18: Increasing Concentrations of Lipids from 12.5 to 75 mM and mRNA from 0.25 to 1.5 mg/ml Increases LNP Delivery Efficiency in Vitro. Optimization of Sodium Acetate Concentration at any Particular Mixing Concentration Results in Further Increased LNP Potency. (TRANS-41)

Summary: LNPs were formulated using total lipid concentration of 12.5-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 12.5 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.25-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 19: Increasing Concentrations of Lipids from 12.5 to 75 mM and mRNA from 0.25 to 1.5 mg/ml Increases LNP Delivery Efficiency In Vitro. Optimization of Sodium Acetate Concentration at any Particular Mixing Concentration Results in Further Increased LNP Potency. (TRANS-43)

Summary: LNPs were formulated using total lipid concentration of 12.5-75 mM comprised of several ionizable/DSPC/Cholesterol/PEG-DMG (47:13:37:2 mol %). Each one of the lipids were solubilized in ethanol until a clear solution was observed. The four lipids were combined to get 75 mM total lipid concentration then serial dilutions were done to reach 12.5 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.25-1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 20: Increasing Concentrations of Lipids from 10 to 75 mM and mRNA from 0.2-1.5 mg/ml Increases LNP Delivery Efficiency In Vivo. Optimization of Sodium Acetate Concentration at any Particular Mixing Concentration Results in Further Increased LNP Potency. (InVivo-7)

Summary: LNPs were formulated using total lipid concentration of 10-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 10 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

B: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

C: In vivo Firefly Luciferase expression in IM administration. 0.5-5 ug of total mRNA was injected in mice in intramuscular (I.M.) injections. Luciferin was administrated intraperitoneally at 4 hours post-injection and luciferase expression monitored by live animal imaging at 4 and 24 hours. ROIs were calculated using the IVIS system.

Example 21: Increasing Concentrations of Lipids from 10 to 75 mM and mRNA from 0.2-1.5 mg/ml Increases Immunogenicity when Delivering a SARS-CoV-2 Immunogen (In Vivo 8)

Summary: LNPs were formulated using total lipid concentration of 10-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 10 mM. Codon optimized 2019-nCoV Wuhan S-2P (Covid) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A: In vivo immunogenicity Endpoint ELISA Anti-RBD titers. 0.1, 0.25, 0.5, 1 ug of total mRNA was injected in mice in intramuscular (I.M.) injections. Pre boost and Post boost (after 3 weeks) shown below.

B: In vivo immunogenicity FRNT50 titer for Psuedoneutralisation assay. 0.1, 0.25, 0.5, 1 ug of total mRNA was injected in mice in intramuscular (I.M.) injections. Pre boost and Post boost (after 3 weeks) shown below.

Example 22: Increasing Concentrations of Lipids from 10 to 75 mM and mRNA from 0.2-1.5 mg/ml Increases Protection Against Lethal Challenge when Delivering a SARS-CoV-2 Immunogen (In Vivo 9) in a Challenge Model where Proprietary BODD C2C4 PipZ is 100% Protective Using 0.25 Ug and MC3 Standard Reference is 100% Protective Using 0.5 Ug Summary: LNPs were formulated using total lipid concentration of 10-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 10 mM. Codon optimized 2019-nCoV Wuhan S-2P (Covid) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A: In vivo protection against viral challenge—Survival proportion, Weight and Temperature in Challenge model. 0.1, 0.25, 0.5, 1 ug of total mRNA was injected in mice in intramuscular (I.M.) injections Pre boost and Post boost (after 5 weeks). The challenge used with the Italian strain at $5\times10^4$ PFU.

B: In vivo weight and temperature in Challenge model. 0.1, 0.25, 0.5, 1 ug of total mRNA was injected in mice in intramuscular (I.M.) injections Pre boost and Post boost (after 5 weeks). The challenge used with the Italian strain at $5\times10^4$ PFU.

Example 23: High Concentrations of Lipids (77 mM) and mRNA (1.5 mg/ml) Produces High LNP Delivery Efficiency In Vivo. (InVivo-10)

Summary: LNPs were formulated using total lipid concentration of 77 mM comprised of several ionizable/DSPC/Cholesterol/PEG-DMG (47:13:37:2 mol %). Each one of the lipids were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

B: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

C: In vivo Firefly Luciferase expression in IM and IV administration. 1 ug of total mRNA was injected in mice in intramuscular (I.M.) and Intravenous (I.V.) injections. Luciferin was administrated intraperitoneally at 4 hours post-injection and luciferase expression monitored by live animal imaging at 4 and 24 hours. ROIs were calculated using the IVIS system.

Example 24: Increasing Concentrations of Lipids from ~46 to ~420 mM and mRNA from 0.2 to 1.5 mg/ml for Rapid Microfluidic Mixing Increases LNP Delivery Efficiency In Vitro. PEG-DMG was Tested Comparing PEG-DMA. (TRANS-47)

Summary: LNPs were formulated using total lipid concentration of ~12-~120 mM comprised of ALC-0315 ionizable/DSPC/Cholesterol/PEG-DMG (46:9.4:42.9:1.7 mol %), and each one of the lipids were solubilized in ethanol until a clear solution was observed. The four lipids were combined to obtain ~120 mM total lipid concentration. Different stocks for lower total lipid concentration up to ~16 mM were prepared independently. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 0.2-1.5 mg/ml in 25 mM Sodium acetate buffer pH 4 keeping the NP ratio constant at 6, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 25: Increasing Concentrations of Lipids from 10.2 to 77 mM and mRNA from 0.2 to 1.5 mg/ml for Rapid Microfluidic Mixing Increases LNP Delivery Efficiency In Vitro. (TRANS-49)

Summary: LNPs were formulated using total lipid concentration of 10.2-77 mM comprised of several ionizable lipids and DSPC/Cholesterol/PEG-DMG (47:13:37:2 mol %). Each one of the lipids were solubilized in ethanol until a clear solution was observed. The four lipids were combined to obtain 77 mM total lipid concentration then serial dilutions were done to reach 10.2 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 26: High Concentrations of Lipids (77 mM) and mRNA (1.5 mg/ml) for Rapid Microfluidic Mixing Results in High LNP Delivery Efficiency in Vitro. (TRANS-52)

Summary: LNPs were formulated using total lipid concentration of 77 mM comprised of several ionizables and DSPC/Cholesterol/PEG-DMG (47:13:37:2 mol %). Each one of the lipids were solubilized in ethanol until a clear solution was observed. The four lipids were combined to obtain 77 mM total lipid concentration. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 0.88 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 27: Increasing Concentrations of Lipids from ~10 to ~77 mM and mRNA from 0.2 to 1.5 mg/ml for Rapid Microfluidic Mixing Shows LNP Delivery Efficiency In Vitro at Different Sodium Acetate Concentrations. Directly Protonating the Ionizable Lipid Prior to Mixing with mRNA in Water without any Buffer Improved Delivery Efficiency In Vivo in IM and IV Injections. (InVivo-12 v.2)

Summary: BODD C2/C4 PipZ (C24 PipZ) LNPs were formulated using total lipid concentration of 77 mM along with DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration and diluted to −10 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 1.5 mg/ml in 15-50 mM Sodium acetate buffer pH 4 keeping the NP ratio constant at 4, prior to mixing in the Spark NanoAssmblr (Precision NanoSystems), which allows high reproducibility in formulations using a microfluidic mixing technology. Also, mRNA was diluted in water and lipid mixes protonated at different levels 200%-25% to be mixed later at same conditions described above. 16 µl Lipid Mix and 341 mRNA solution were mixed on Setting 3 and ejected into 48 µl 1×DPBS pH 7.4. The formed LNPS were then diluted into an additional 96 µl 1×DPBS pH 7.4. LNPs were then dialyzed against Sucrose Buffer pH 7.5 for 6×1 hr. LNPs were kept frozen at −80 C for In Vivo injections. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in Sucrose Buffer pH 7.5 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.1 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: In vivo and ex vivo Firefly Luciferase expression in IM administration for LNPs mixed at 1.5 mg/ml. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging.

E: In vivo and ex vivo Firefly Luciferase expression in IV administration for LNPs mixed at 1.5 mg/ml. 1 ug of total mRNA was injected in mice in intravascular (I.V.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging.

Example 28: LNP/18PA Mixed at Total Lipid 74 mM and mRNA to 1.5 mg/ml for Rapid Microfluidic Mixing Shows Reduced Liver Expression and Increase Spleen Expression after IV Injections. (TRANS-55)

Summary: MC3 were formulated using total lipid concentration of 74 mM with DSPC/Cholesterol/PEG-DMG (50:10:38.5:1.5 mol %). Dual lipid stocks (ionizable/Cholesterol, DSPC/PEG-DMG) were solubilized in ethanol until a clear solution was observed. The four lipids were combined to get 77 mM total lipid concentration. Lipid mixes was mixed with 18PA lipid to be at 0%, 15% and 30% total lipid. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 1.5 mg/ml in 25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against Sucrose Buffer pH 7.5 for 6×1 hr. LNPs were kept frozen at −80 C for In Vivo injections. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. However the presence of anionic 18PA likely increases background signal. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in Sucrose Buffer pH 7.5 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in Sucrose at 25° C. with viscosity of 1.1 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: In vivo and ex vivo Firefly Luciferase expression in IM administration for LNPs mixed at 1.5 mg/ml. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging.

E: In vivo and ex vivo Firefly Luciferase expression in IV administration for LNPs mixed at 1.5 mg/ml. 1 ug of total mRNA was injected in mice in intravascular (I.V.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging.

Example 29: New Lipids at ~25 mM Mixed with mRNA at 0.5 mg/ml for Rapid Microfluidic Mixing Shows High LNP Delivery Efficiency In Vitro. (TRANS-59)

Summary: LNPs were formulated using total lipid concentration of ~25 mM comprised of several ionizable/DSPC/Cholesterol/PEG-DMG (47:13:37:2 mol %). Each one of the lipids were solubilized in ethanol until a clear solution was observed. The four lipids were combined to get ~25 mM total lipid concentration. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 0.5 mg/ml in 25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer.

Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in Sucrose Buffer pH 7.5 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in Sucrose at 25° C. with viscosity of 1.1 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 30: Assembly of LNPs with Total Lipid Concentrations 77 mM and mRNA Concentration 1.5 mg/ml for Rapid Microfluidic Mixing Shows LNP Delivery Efficiency In Vivo. (InVivo-11)

Summary: LNPs were formulated using total lipid concentration of 77 mM comprised of several ionizable-lipids and DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 20 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: In vivo Firefly Luciferase expression of the Injection site in IM administration. 1 ug of total mRNA was injected in mice in intramuscular (I.M.) injections. Luciferin was administrated intraperitoneally at 4 hours post-injection and luciferase expression monitored by live animal imaging of the injection site at 4 hours. ROIs were calculated using the IVIS system.

B: Ex Vivo Firefly Luciferase expression in IM administration. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging.

Example 31: Assembly of LNPs with Total Lipid Concentrations 77 mM and mRNA Concentration 1.5 mg/ml for Rapid Microfluidic Mixing Shows LNP Delivery Efficiency In Vivo. (InVivo-13)

Summary: LNPs were formulated using total lipid concentration of 77 mM comprised of several ionizable lipids and DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against Sucrose Buffer pH 7.5 for 6×1 hr. Frozen LNPs were kept at −80 C for In Vivo injections. LNPs were then diluted so that 32 ul contained 25-200 ng and 12K HEK293 cells were transfected with the same dose but manufactured at different concentrations in the microfluidic mixer.

A: In vivo Firefly Luciferase expression of the injection sites in IM administration. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system.

B: Ex Vivo Firefly Luciferase expression in IM administration. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging.

Example 32: Concentrations of Lipids of ~77 mM and mRNA at 1.5 mg/ml in Rapid Microfluidic Mixing Shows LNP Delivery Efficiency In Vitro at Different Sodium Acetate Concentrations. Directly Protonating the Ionizable Lipid Prior to Mixing with mRNA in Water without any Buffer Results in Improved Delivery Efficiency In Vitro (TRANS-54 v.1)

Summary: BODD C2/C4 PipZ (C24 PipZ) LNPs were formulated using total lipid concentration of 77 mM along with DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 1.5 mg/ml in 15-50 mM Sodium acetate buffer pH 4 keeping the NP ratio constant at 4, prior to mixing in the Spark NanoAssmblr (Precision NanoSystems), which allows high reproducibility in formulations using a microfluidic mixing technology. Also, mRNA was diluted in water and lipid mixes protonated at different levels 200%-25% to be mixed later at same conditions described above. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9x10-5 mg/ml to 4.88x10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence.

B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 0.88 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

Example 33: Increasing Concentrations of Lipids from ~10 to ~77 mM and mRNA from 0.2 to 1.5 mg/ml for Rapid Microfluidic Mixing Shows LNP Delivery Efficiency In Vitro at Different Sodium Acetate Concentrations. Directly Protonating the Ionizable Lipid Prior to Mixing with mRNA in Water without any Buffer Results in Improved Delivery Efficiency In Vivo in IM and IV Injections. (TRANS-54 v.2/InVivo-12 v.1)

Summary: BODD C2/C4 PipZ (C24 PipZ) LNPs were formulated using total lipid concentration of 77 mM along with DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration and diluted to −10 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 1.5 mg/ml in 15-50 mM Sodium acetate buffer pH 4 keeping the NP ratio constant at 4, prior to mixing in the Spark NanoAssmblr (Precision NanoSystems), which allows high reproducibility in formulations using a microfluidic mixing technology. Also, mRNA was diluted in water and lipid mixes protonated at different levels 200%-25% to be mixed later at same conditions described above. 16 μl Lipid Mix and 341 mRNA solution were mixed on Setting 3 and ejected into 48 μl 1×DPBS pH 7.4. The formed LNPS were then diluted into an additional 96 μl 1×DPBS pH 7.4. LNPs were then dialyzed against Sucrose Buffer pH 7.5 for 6×1 hr. LNPs were kept frozen at −80 C for In Vivo injections. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of 3.9×10-5 mg/ml to 4.88×10-3 mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence B: Ribogreen Assay for mRNA Encapsulation Efficiency. 1× TE Buffer and Triton Buffer (2% v/v in 1× TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1× TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1× TE Buffer and added to each well in a ratio 1:1. Microplates were immediately introduced into the Cytation 5 Cell Imaging Multi-Mode Reader (Biotek) to read Fluorescence (Ex485/Em528).

C: Dynamic Light Scattering for LNP Size (red dots are PDI right y axis). Dialyzed LNPs were diluted to 6.25 ng/ul in Sucrose Buffer pH 7.5 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.1 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution.

D: In vivo Firefly Luciferase expression in IM administration for LNPs mixed at 1.5 mg/ml. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system.

E: In vivo Firefly Luciferase expression in IV administration for LNPs mixed at 1.5 mg/ml. 1 ug of total mRNA was injected in mice in intravascular (I. V.) injections. Luciferin was administrated intraperitoneally at 4 hours post-injection and luciferase expression monitored by live animal imaging at 4 hours. ROIs were calculated using the IVIS system.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art-thus, to the extent an element is described in one or more references known to the person having ordinary skill in the art, they may be excluded from the claimed invention by, inter alia, a negative proviso or disclaimer of the feature or combination of features.

What is claimed is:

1. A method for making a lipid nanoparticle comprising a nucleic acid ("naLNP") comprising:

a. Providing a nucleic acid solution comprising at least one nucleic acid at a nucleic acid concentration from about 1 to about 3 mg/ml;

b. Providing a lipid solution comprising at least one lipid at a lipid concentration from about 50 mM to about 100 mM; and c. Combining a portion of the nucleic acid solution and a portion of the lipid solution to create a mixing solution comprising a mixing nitrogen-phosphate ratio and a lipid:nucleic acid ratio; and d. Optionally adjusting the pH in the final mixed solution to physiological pH to obtain a pH-adjusted mixing solution; and e. Obtaining the naLNPs from the mixed solution; and wherein the naLNPs have a greater potency than a reference lipid nanoparticle ("refLNP"), wherein the refLNP comprises the at least one lipid and the at least one nucleic acid and is made by a reference LNP manufacturing method.

2. The method of claim 1, wherein the portion nucleic acid solution and the portion of the lipid solution are combined in step (c) in volume ratio selected from the group consisting of 1:1, 2:1, 3:1, 4:1, 5:1, 6:1 and 7:1.

3. The method according to claim 1, wherein the naLNPs have an average diameter in the range of about 40 to about 150 nanometers.

4. The method according to claim 1, wherein the naLNPs have an average diameter in the range of about 50 to about 100 nanometers.

5. The method according to claim 1, wherein the naLNPs have a nucleic acid encapsulation efficiency of about 40% to about 100%.

6. The method according to claim 1, wherein the naLNPs have a nucleic acid encapsulation efficiency of about 50% to about 85%.

7. The method according to claim 1, wherein the naLNPs have a nucleic acid encapsulation efficiency of about 60% to about 85%.

8. The method according to claim 1, wherein the naLNPs have a nucleic acid encapsulation efficiency of about 68% to about 83%.

9. The method of claim 1, wherein the naLNP has a lower nucleic acid encapsulation rate less than the refLNP.

10. The method of claim 1, wherein the at least one nucleic acid is DNA or RNA.

11. The method of claim 1, wherein the at least one nucleic acid is RNA.

12. The method of claim 1, wherein the at least one nucleic acid is mRNA.

13. The method of claim 1, wherein the at least one nucleic acid is mRNA encoding at least one open reading frame.

14. The method of claim 1, wherein the at least one nucleic acid is mRNA encoding at least one open reading frame encoding an immunogen.

15. The method of claim 1, wherein the nucleic acid solution comprises a buffer.

16. The method of claim 1, wherein the lipid solution comprises an organic solvent selected from the group consisting of methanol, ethanol, acetone, benzene and toluene.

17. The method of claim 1, wherein the at least one lipid in the lipid solution is selected from the group consisting of Formula I, Formula II, Formula III, Formula IV and combinations thereof.

18. The method of claim 1, wherein the mixing solution has a pH that is about 0 to about 2 units of pH below the pKa of the lipid in the refLNP.

19. The method of claim 1, wherein the mixing solution has a pH that is about 0.5 to about 1.5 units of pH below the pKa of the lipid in the refLNP.

20. The method of claim 1, wherein the mixing solution has a pH that is about 0.75 to about 1.25 units of pH below the pKa of the lipid in the refLNP.

21. The method of claim 1, wherein the mixing solution nitrogen-phosphate ratio is at least or about 2 to at least or about 10.

22. The method of claim 1, wherein the mixing solution lipid: nucleic acid weight ratio is at least or about 1:1, 2:1, 3:1, 4:1, 5:1, 6:1, 7:1, 8:1, 9:1, 10:1, 11:1, 12:1, 15:1, 17:1, 18:1, 20:1, 25:1, 30:1, 35:1, 40:1 or 50:1.

23. The method of claim 1, wherein the refLNP is made using a reference nucleic acid concentration less than 0.21 mg/ml.

24. The method of claim 1, wherein the refLNP is made using a reference lipid concentration less than 10.5 mM.

25. The method of claim 1, wherein the refLNP is made using a reference nucleic acid concentration less than 0.21 mg/ml and a reference lipid concentration less than 10.5 mM.

26. The method of claim 1, wherein the potency is about 1.5 times more than the refLNP.

27. The method of claim 1, wherein the potency is about 2 times more than the refLNP.

28. The method of claim 1, wherein the potency is about 3 times more than the refLNP.

29. The method of claim 1, wherein the potency is about 4 times more than the refLNP.

30. The method of claim 1, wherein the potency is at least or about 5 times more than the refLNP.

31. The method of claim 1, wherein the potency is at least or about 6 times more than the refLNP.

32. The method of claim 1, wherein the potency is at least or about 7 times more than the refLNP.

33. The method of claim 1, wherein the potency is at least or about 8 times more than the refLNP.

34. The method of claim 1, wherein the potency is at least or about 9 times more than the refLNP.

35. The method of claim 1, wherein the potency is at least or about 10 times more than the refLNP.

36. The method of claim 1, wherein the potency is at least or about 11 times more than the refLNP.

37. The method of claim 1, wherein the potency is at least or about 12 times more than the refLNP.

38. The method of claim 1, wherein the potency is at least or about 13 times more than the refLNP.

39. The method of claim 1, wherein the potency is at least or about 14 times more than the refLNP.

40. The method of claim 1, wherein the potency is at least or about 15 times more than the refLNP.

41. The method of claim 1, wherein the potency is at least or about 20 times more than the refLNP.

42. The method of claim 1, wherein the potency is at least or about 25 times more than the refLNP.

43. The method of claim 1, wherein the potency is at least or about 50 times more than the refLNP.

44. The method of claim 1, wherein the lipid concentration in the lipid solution is about 75 mM.

45. The method of claim 1, wherein the nucleic acid concentration in the nucleic acid solution is about 1.5 mg/mL.

* * * * *